US012600714B2

(12) United States Patent
Xie et al.

(10) Patent No.: US 12,600,714 B2
(45) Date of Patent: Apr. 14, 2026

(54) SUBSTITUTED PYRAZINECARBOXAMIDE COMPOUNDS FOR TREATING DISEASES RELATED TO EGFR MUTATION

(71) Applicant: WIGEN BIOMEDICINE TECHNOLOGY (SHANGHAI) CO., LTD., Shanghai (CN)

(72) Inventors: Yuli Xie, Shanghai (CN); Yingming Wu, Shanghai (CN); Houxing Fan, Shanghai (CN); Lihui Qian, Shanghai (CN)

(73) Assignee: WIGEN BIOMEDICINE TECHNOLOGY (SHANGHAI) CO., LTD., Shanghai (CN)

( * ) Notice: Subject to any disclaimer, the term of this patent is extended or adjusted under 35 U.S.C. 154(b) by 679 days.

(21) Appl. No.: 17/917,435

(22) PCT Filed: Jun. 1, 2021

(86) PCT No.: PCT/CN2021/097583

§ 371 (c)(1),
(2) Date: Oct. 6, 2022

(87) PCT Pub. No.: WO2021/244505

PCT Pub. Date: Dec. 9, 2021

(65) Prior Publication Data

US 2023/0167099 A1 Jun. 1, 2023

(30) Foreign Application Priority Data

Jun. 1, 2020 (CN) ......................... 202010486394.1
Sep. 10, 2020 (CN) ......................... 202010947590.4
May 27, 2021 (CN) ......................... 202110587528.3

(51) Int. Cl.

| | |
|---|---|
| ***C07D 405/14*** | (2006.01) |
| ***C07D 401/14*** | (2006.01) |
| ***C07D 405/12*** | (2006.01) |
| ***C07D 409/14*** | (2006.01) |
| ***C07D 413/14*** | (2006.01) |
| ***C07D 417/14*** | (2006.01) |

(Continued)

(52) U.S. Cl.
CPC ......... *C07D 405/14* (2013.01); *C07D 401/14* (2013.01); *C07D 405/12* (2013.01);
(Continued)

(58) Field of Classification Search
None
See application file for complete search history.

(56) References Cited

FOREIGN PATENT DOCUMENTS

CN 102421761 A 4/2012
CN 104080774 A 10/2014
(Continued)

OTHER PUBLICATIONS

Machine Translation of CN 10408774 A, Translated by Patent Translate Espacenet.org on Jun. 12, 2025. Claims Only. (Year: 2014).*

(Continued)

*Primary Examiner* — Jennifer A Berrios
*Assistant Examiner* — Sophia Reilly
(74) *Attorney, Agent, or Firm* — SZDC Law PC

(57) ABSTRACT

The present invention relates to a compound as represented by general formula (1), and a preparation method therefor, and the use of the compound as represented by general formula (1) and an isomer, a crystal form, a pharmaceutically acceptable salt, a hydrate or a solvate thereof as an EGFR inhibitor in the preparation of a drug against EGFR-related diseases, such as tumors.

(1)

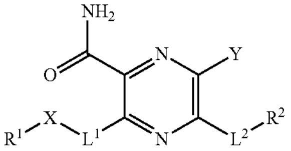

11 Claims, 1 Drawing Sheet

(51) Int. Cl.

| | |
|---|---|
| ***C07D 471/04*** | (2006.01) |
| ***C07D 471/10*** | (2006.01) |
| ***C07D 487/04*** | (2006.01) |
| ***C07D 491/107*** | (2006.01) |
| ***C07D 519/00*** | (2006.01) |

(52) U.S. Cl.

CPC ......... *C07D 409/14* (2013.01); *C07D 413/14* (2013.01); *C07D 417/14* (2013.01); *C07D 471/04* (2013.01); *C07D 471/10* (2013.01); *C07D 487/04* (2013.01); *C07D 491/107* (2013.01); *C07D 519/00* (2013.01); *C07B 2200/05* (2013.01)

(56) References Cited

FOREIGN PATENT DOCUMENTS

| | | | |
|---|---|---|---|
| CN | 107207468 | A | 9/2017 |
| CN | 107709315 | A | 2/2018 |
| EP | 2428508 | A1 | 3/2012 |
| EP | 2805940 | A1 | 11/2014 |
| WO | 0076980 | A1 | 12/2000 |
| WO | 03045924 | A1 | 6/2003 |
| WO | 2010128659 | A1 | 11/2010 |
| WO | 2013108754 | A1 | 7/2013 |
| WO | 2016121777 | A1 | 8/2016 |
| WO | 2018103663 | A1 | 6/2018 |

OTHER PUBLICATIONS

Lynch et. al. “Activating Mutations in the Epidermal Growth Factor Receptor Underlying Responsiveness of NonâSmall-Cell Lung Cancer to Gefitinib” N Engl J Med 2004, 350, 21, 2129-2139. DOI: 10.1056/NEJMoa040938 (Year: 2004).*

Voldborg et. al. “Epidermal growth factor receptor (EGFR) and EGFR mutations, function and possible role in clinical trials” Annals of Oncology 1997, 8, 12, 1197-1206. DOI: 10.1023/A:1008209720526 (Year: 1997).*

* cited by examiner

SUBSTITUTED PYRAZINECARBOXAMIDE COMPOUNDS FOR TREATING DISEASES RELATED TO EGFR MUTATION

The present application is the National Stage Application of PCT/CN2021/097583, filed on Jun. 1, 2021, which claims priority to Chinese Patent Application No. CN202010486394.1 filed on Jun. 1, 2020, Chinese Patent Application No. CN202010947590.4 filed on Sep. 10, 2020 and Chinese Patent Application No. CN202110587528.3 filed on May 27, 2021, which are incorporated herein by reference in their entirety.

TECHNICAL FIELD

The present invention relates to the field of pharmaceutical chemistry, and particularly to a pyrazine compound, a method for preparing the same and use of the compound as an EGFR inhibitor in preparing an antitumor medicament.

BACKGROUND

Lung cancer is one of common malignant tumors, with about 1.6 million new cases of lung cancer worldwide each year and about 1.4 million deaths each year. Among them, non-small cell lung cancer (NSCLC) accounts for about 80%-85% of the total number of lung cancers (*Nature,* 2018, 553:446-454).

EGFR family is a group of protein kinases, which are responsible for transducing mitogenic signals and play important roles in growth and development. Extensive analysis and study of in vitro tumor cells, animal models and human tumor samples indicate that the mutation of EGFR family members may cause the progression of tumors in human and is one of the important causes of the development and progression of many cancers. Targeting EGFR mutant proteins and inhibiting their activity are thus important means for treating related tumors.

Studies showed that EGFR gene mutations can be found in about 12% to 47% of non-small cell lung cancers. In non-small cell lung cancer, the two most common EGFR gene mutations are exon 19 deletion (del19) and L858R missense mutation in exon 21. These two mutations result in sustained activation of the EGFR proteins independent of ligands. Although NSCLC patients with Del19 or L858R mutations in EGFR proteins are more sensitive to the targeted therapy with EGFR protein kinase inhibitors (EGFR TKIs), such as erlotinib, gefitinib, afatinib or osimertinib, demonstrating a high (around 60%-85%) objective response rate (ORR) in clinical practice, this response usually does not last long enough and most patients using first- or second-generation EGFR TKIs would experience disease progression at about 11 months. Analysis of drug resistance showed that in about 50%-70% of drug-resistant patients, the molecular mechanism of drug resistance is the acquisition of a second mutation, T790M mutation (T790M+), in EGFR gene (*Cancer discov.* 2012, 2:872-5). This secondary mutation causes the loss of inhibitory activities of the first- and second-generation EGFR TKIs against mutant tumor cells.

Osimertinib, a third-generation covalent EGFR TKI, is developed to treat tumors with EGFR del19 and L858R mutations with or without T790M mutation. Although osimertinib has a high response rate despite the drug resistance induced by T790M mutation, drug resistance would eventually occur in about 70% of the patients and the disease will progress after about 10 months (*Lung Cancer.* 2017, 108: 228-231). Studies on the molecular mechanism of drug resistance to third-generation EGFR TKIs showed that in about 20%-40% of patients who received osimertinib and had relapse, one of the major mechanisms of drug resistance is the acquisition of a third mutation, C797S mutation, in EGFR gene. Moreover, patients with EGFR del19/L858R T790M C797S mutant would no longer respond to first-, second-, or third-generation EGFR TKIs after the treatment with the third-generation EGFR TKI. In 2015, Thress et al. first reported an analysis of resistance to osimertinib based on 15 patients and found that about 40% of the drug resistance was caused by C797S mutation (*Nature Medicine,* 2015, 21:560-562). On the American Society of Clinical Oncology (ASCO) annual meeting in 2017, Piotrowska and Caicun Zhou each reported an analysis of drug resistance in 23 patients and 99 patients, respectively, and both analyses showed that about 22% of the drug resistance was caused by C797S mutation. Therefore, targeted inhibition of EGFR del19/L858R T790M C797S mutation can overcome the resistance to osimertinib. However, at present, there is no EGFR TKI on the market capable of inhibiting EGFR del19/L858R T790M C797S mutant, and it is thus urgent to study and discover a fourth-generation EGFR TKI to meet this clinical need.

EGFR del19/L858R T790M C797S mutant, a new EGFR mutant occurred after the treatment with third-generation EGFR TKIs, has not been adequately interpreted. At present, only a few fourth-generation EGFR TKIs have been reported to inhibit the EGFR del19/L858R T790M C797S mutant. For example, Boehringer Ingelheim reported a class of macrocyclic compounds BI-4020 with anti-EGFR del19/L858R T790M C797S mutant activity and anti-tumor activity in vivo (*J. Med. Chem.* 2019, 62:10272-10293). Patent No. WO2019/015655 reported a class of aryl-phosphorus-oxygen compounds with anti-EGFR del19/L858R T790M C797S mutant activity and anti-tumor activity in vivo. A general formula A and a representative compound B (Example 41) thereof are shown in the following structures (refer to the invention for the definitions of the symbols in the formula):

BI-4020

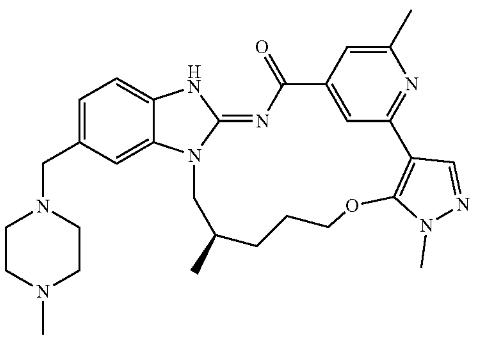

-continued

A

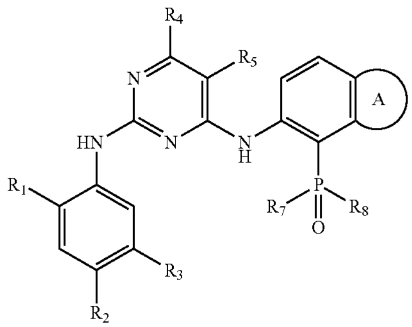

B

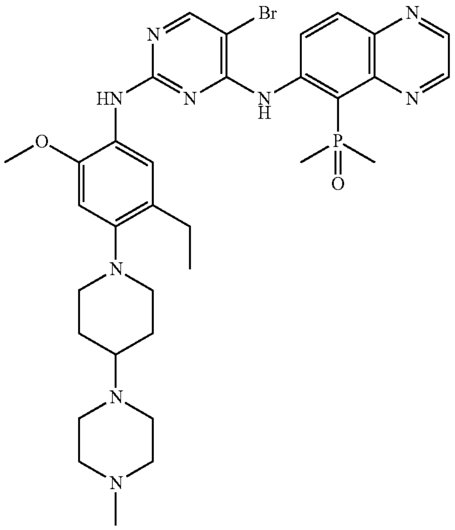

At present, there is an urgent need to explore and discover compounds with good EGFR del19/L858R T790M C797S mutant activity.

SUMMARY

The present invention aims to provide a compound of general formula (1), or an isomer, a crystalline form, a pharmaceutically acceptable salt, a hydrate or a solvate thereof:

(1)

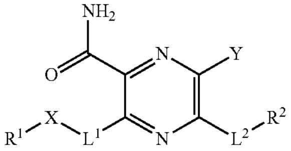

wherein, in general formula (1):

Y is a 3-11 membered heterocycloalkyl, a C6-C14 aryl or a 5-10 membered heteroaryl, wherein the heterocycloalkyl, the aryl and the heteroaryl may be optionally substituted with one or more of the following groups: —H, a halogen, $—R^4$, $—OR^4$, $—(CH_2)_nOR^4$, $—(CH_2)_nNR^4R^5$, $—NR^4R^5$, —CN, $—C(O)NR^4R^5$, $—NR^5C(O)R^4$, $—NR^5S(O)_2R^4$, $—S(O)_pR^4$, $—S(O)_2NR^4R^5$ and $—O—CH_2—O—$;

$L^1$ is —O— or —NH—;

X is a C6-C14 arylene or a 5-11 membered heteroarylene, wherein the arylene and the heteroarylene may be optionally substituted with one or more of the following groups: —H, a halogen, a C1-C6 alkyl, a C3-C6 cycloalkyl, a C1-C6 alkoxy and a C1-C6 haloalkoxy;

$R^1$ is —H, halogen, $—(CH_2)_nNR^6R^7$, $—NR^6R^7$, $—O(CH_2)_mNR^6R^7$, $—N(R^5)(CH_2)_mNR^6R^7$, a C1-C6 alkoxy, $—CH_2$-3-15 membered heterocycloalkyl or a 3-15 membered heterocycloalkyl, wherein the alkoxy and the heterocycloalkyl may be optionally substituted with one or more of the following groups: —H, $—R^4$, $—(CH_2)_nR^6R^7$, $—NR^6R^7$, $—O(CH_2)_mNR^6R^7$, $—N(R^5)(CH_2)_mNR^6R^7$ and $—R^3$;

$L^2$ is —O—, —NH— or a chemical bond;

$R^2$ is a C1-C6 alkyl, a C3-C14 cycloalkyl, a C6-C14 aryl, a 3-4 membered heterocycloalkyl,

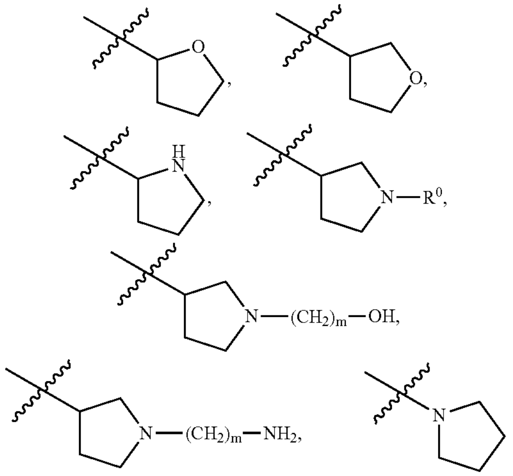

or a 6-11 membered heterocycloalkyl; wherein the alkyl, the cycloalkyl, the aryl, the heterocycloalkyl,

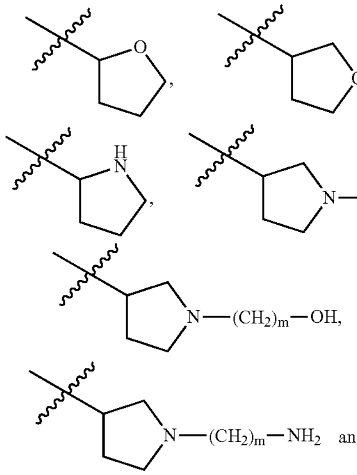

and

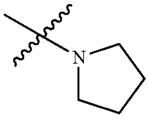

may be optionally substituted with one or more of the following groups: —H, a halogen, $—R^4$, $—(CH_2)_nOR^4—$, $—(CH_2)_nNR^4R^5—$, $—OR^4$, $—NR^4R^5$, —CN, $—C(O)NR^4R^5$, $—NR^5C(O)R^4$, $—NR^5S(O)_2R^4$, $—S(O)_pR^4$ and $—S(O)_2NR^4R^5$;

$R^3$ is a 3-11 membered heterocycloalkyl, wherein the heterocycloalkyl may be optionally substituted with one or more of the following groups: —H, —$CD_3$, —$R^4$, —$OR^4$ and —$NR^4R^5$;

$R^4$ and $R^5$ are each independently —H, a C1-C6 alkyl or a C3-C14 cycloalkyl;

$R^6$ and $R^7$ are each independently —H, a C1-C6 alkyl or a C3-C14 cycloalkyl, or $R^6$ and $R^7$ form a 3-11 membered heterocycloalkyl along with N atoms connected thereto, wherein the heterocycloalkyl may be optionally substituted with one or more of the following groups: —H, —$CD_3$, a halogen, —$R^4$ and —$OR^4$;

$R^0$ is a C1-C6 alkyl or a C3-C14 cycloalkyl; and p is an integer of 0, 1 or 2, n is an integer of 0, 1, 2 or 3, and m is an integer of 1, 2 or 3.

In another preferred embodiment, in general formula (1), Y is a 5-6 membered heterocycloalkyl, phenyl or a 5-9 membered heteroaryl, wherein the heterocycloalkyl, the phenyl and the heteroaryl may be optionally substituted with one or more of the following groups: —H, —F, —Cl, —Br, —CN, —OH, —$OCH_3$, —$NH_2$, —$N(CH_3)_2$, —$NHCOCH_3$, —$NHSO_2CH_3$, —$CH_3$, —$CONH_2$, —$CH_2OH$ and —O—$CH_2$—O—.

In another preferred embodiment, in general formula (1), Y is:

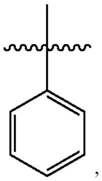,
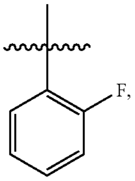
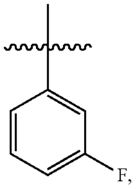
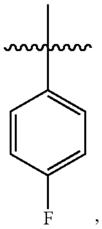,

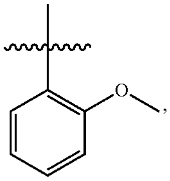,
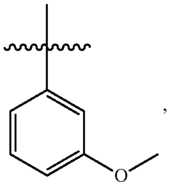,
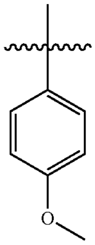,

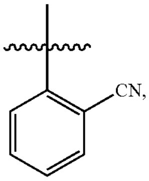
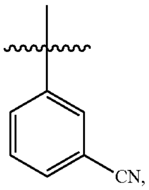
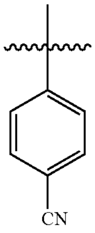,

-continued

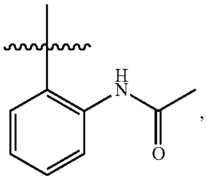,
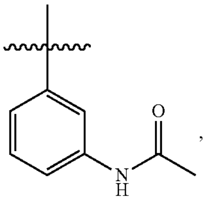,
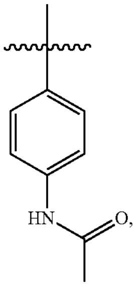

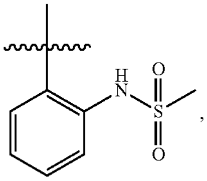,
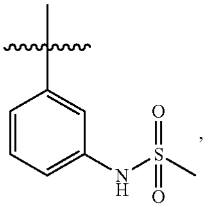,
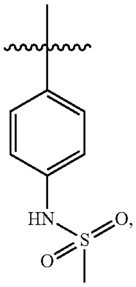

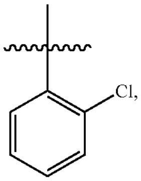
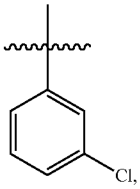
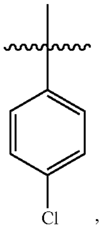,
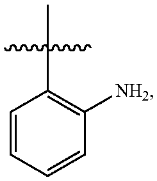

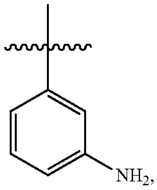
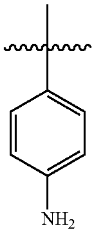,
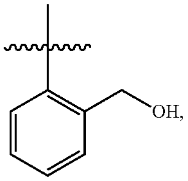

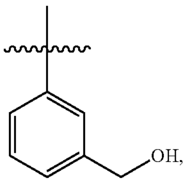
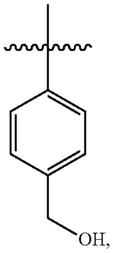
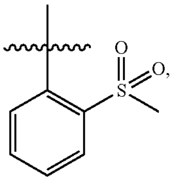

-continued
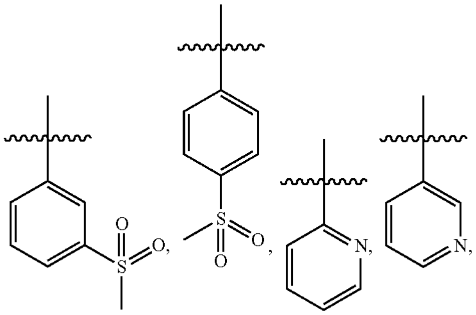
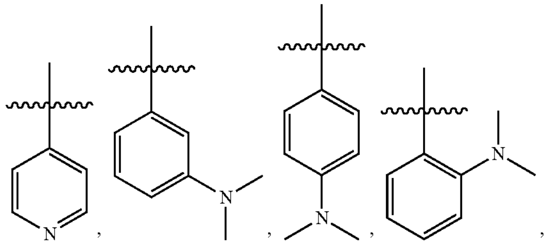
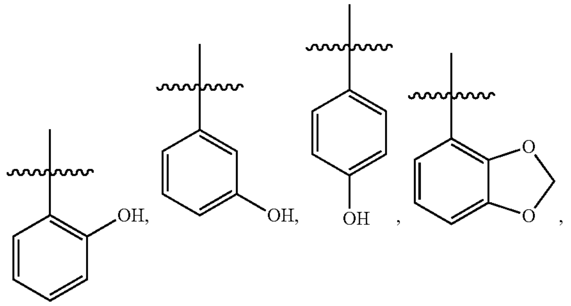
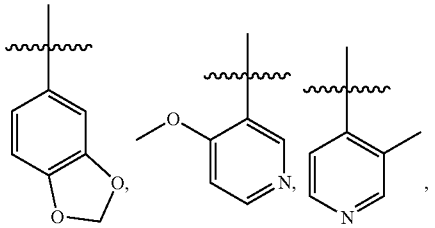
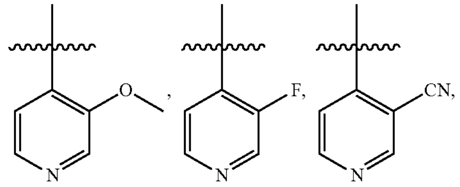
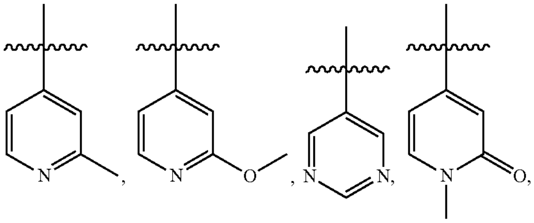
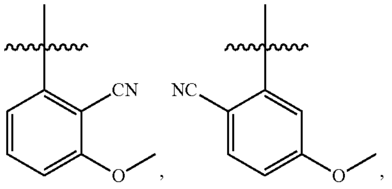
-continued
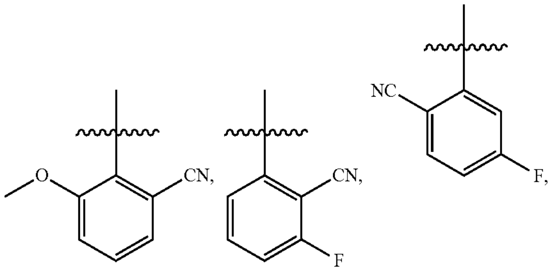
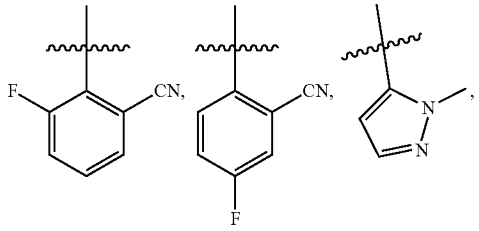
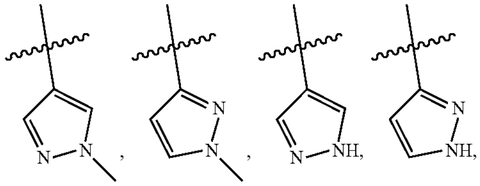
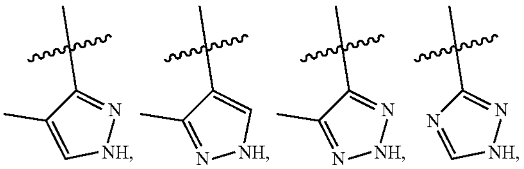
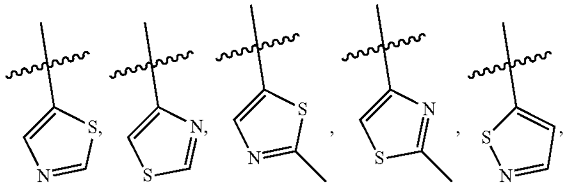
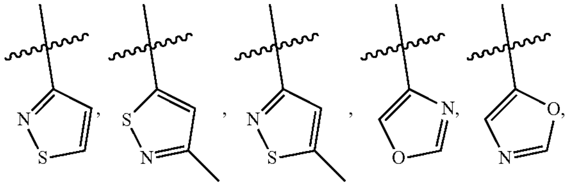
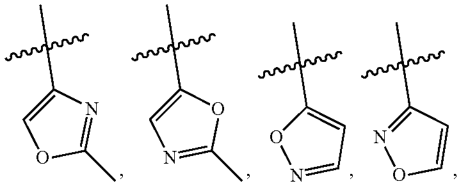
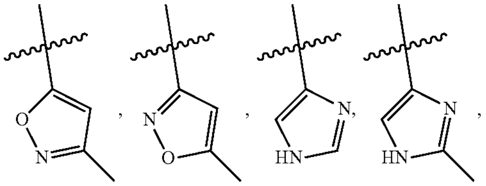

-continued
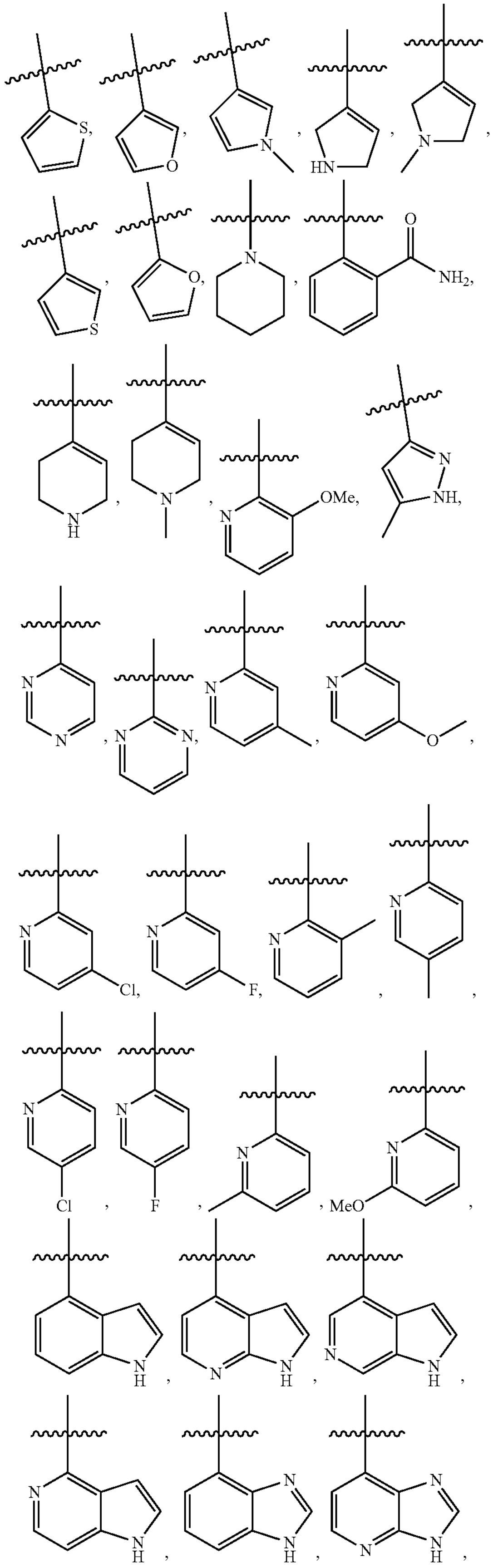
-continued
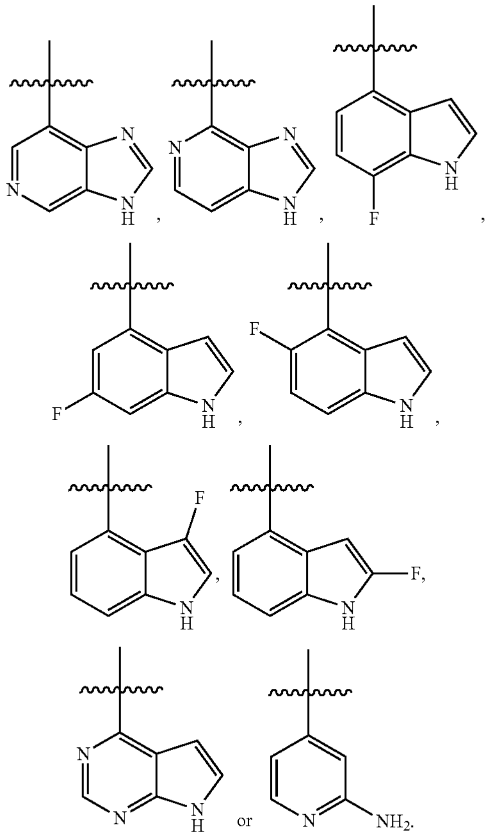
or
In another preferred embodiment, in general formula (1), X is phenylene or a 6-membered heteroarylene, wherein the phenylene and heteroarylene may be optionally substituted with one or more of the following groups: —H, —F, —$CH_3$, —$CH_2CH_3$, —$CH(CH_3)_2$,
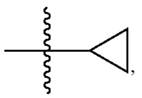
—$OCH_3$, —$OCF_2H$ and —$OCF_3$.
In another preferred embodiment, in general formula (1), X is:
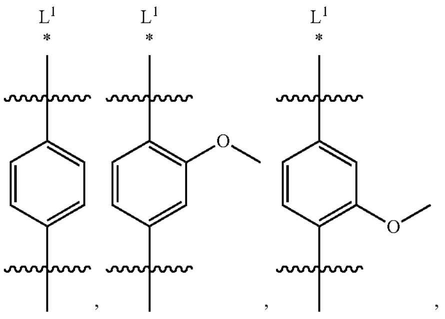

-continued
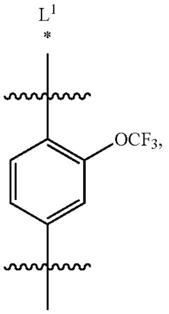
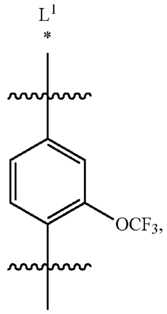
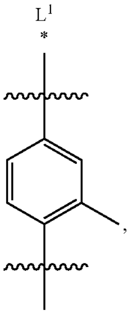
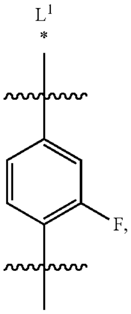
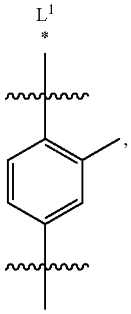
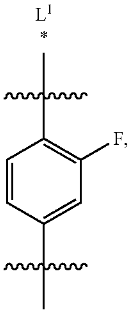
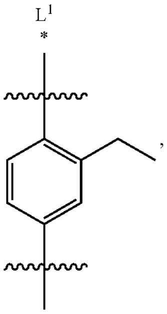
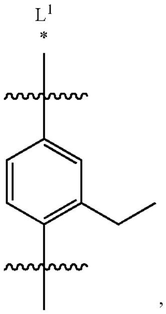
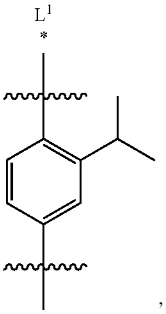
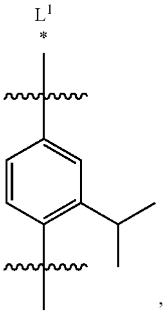
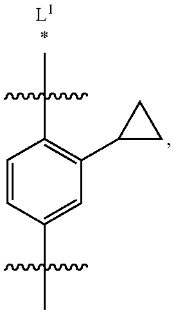
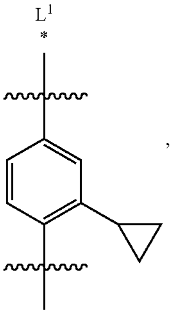
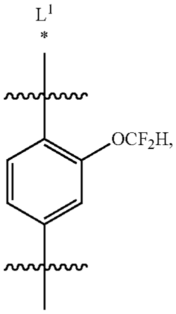
-continued
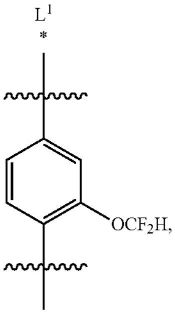
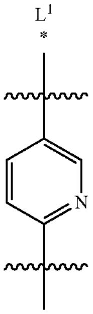
or
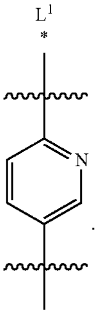
.
In another preferred embodiment, in general formula (1), $R_1$ is: —H, —$N(CH_3)_2$, —$CH_2$-6-11 membered heterocycloalkyl or a 6-11 membered heterocycloalkyl, wherein the heterocycloalkyl is
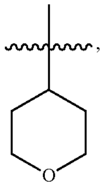,
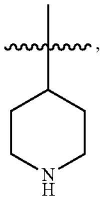,
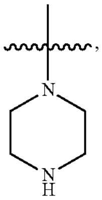,
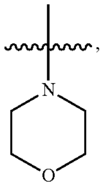,
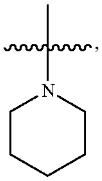,
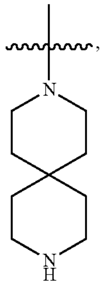,
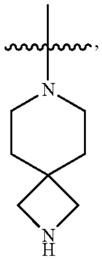,
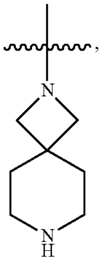,
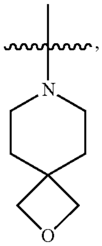,
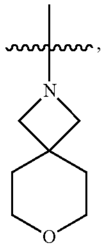,
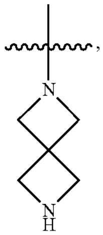,
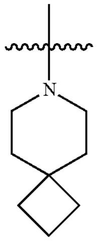
or
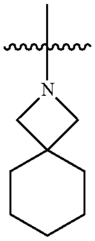
and may be optionally substituted with one or more of the following groups:
—H, —$CH_3$, 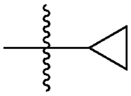, —$N(CH_3)_2$, -continued
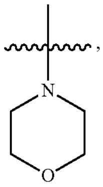, 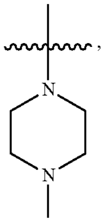, 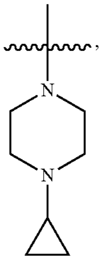, 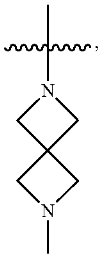,
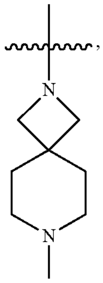, 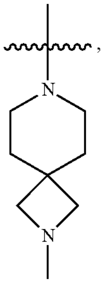, 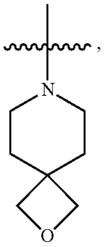,
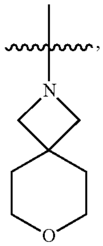, 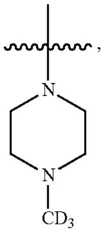, and —$CD_3$.
In another preferred embodiment, in general formula (1), $R^1$ is:
—H, —$(N(CH_3)_2)$, 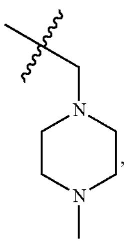, 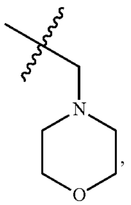,
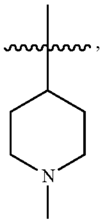, 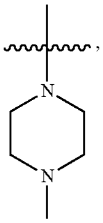, 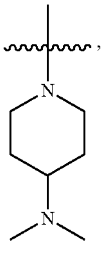,
-continued
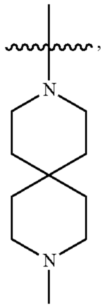, 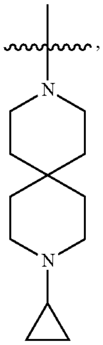, 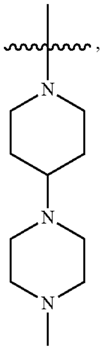,
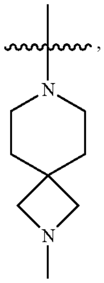, 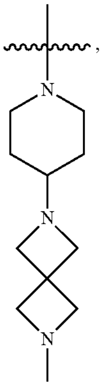, 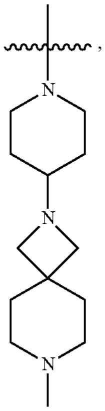,
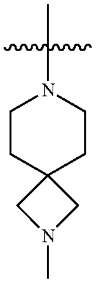 or 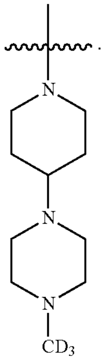.
In another preferred embodiment, in general formula (1), when $L^2$ is —NH—, $R^2$ is:
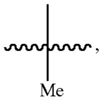, 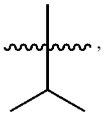, 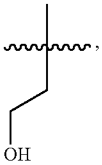, 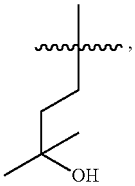,
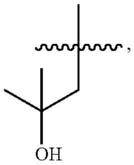, 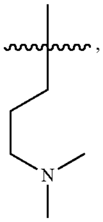, 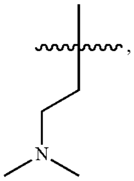, -continued
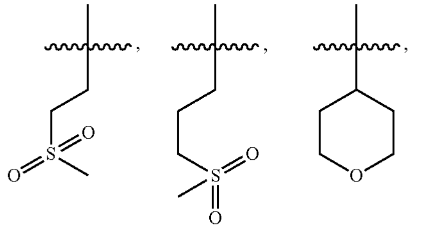
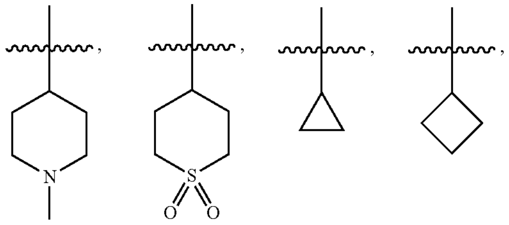
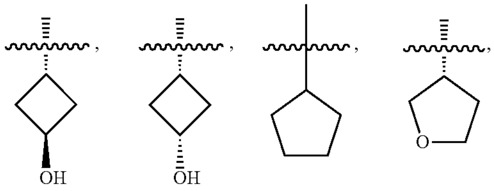
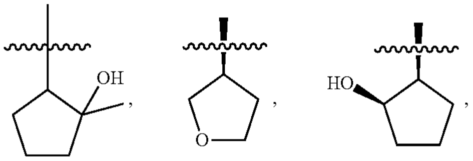
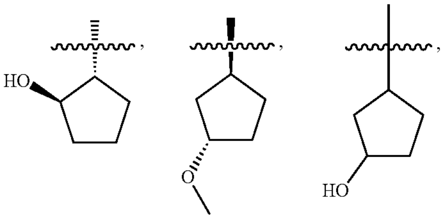
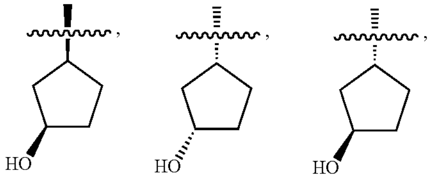
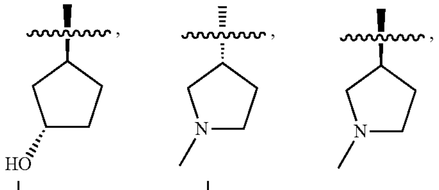
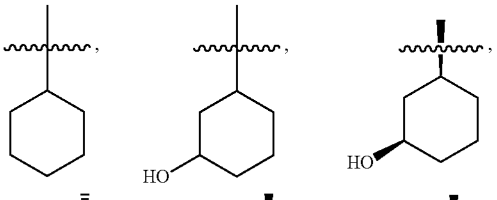
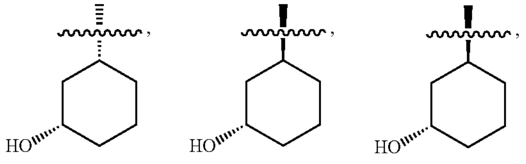
-continued
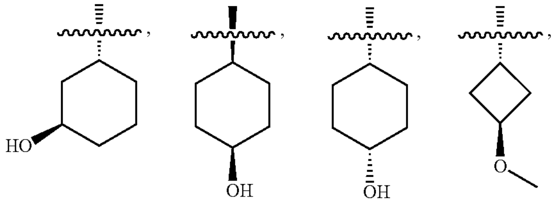
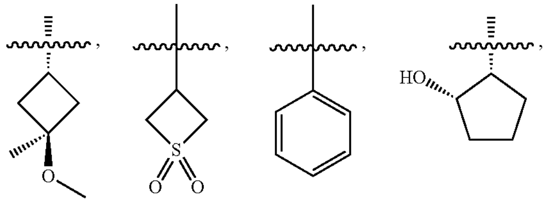
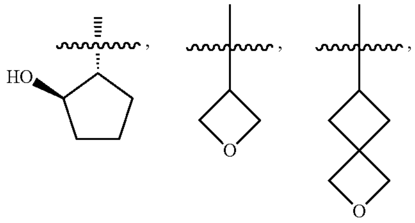
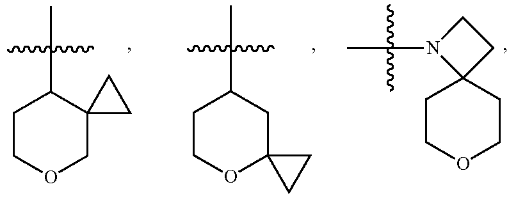
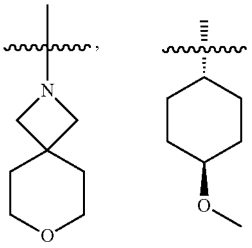
or
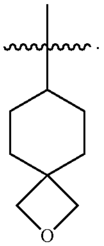
In another preferred embodiment, in general formula (1), when $L^2$ is —O—, $R^2$ is:
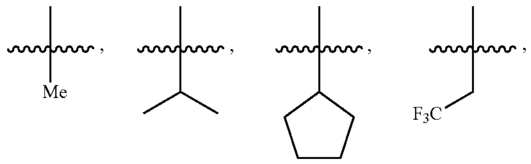
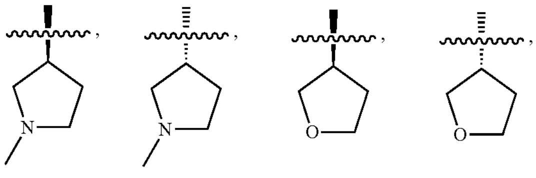

-continued
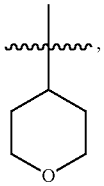
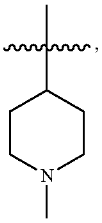
or
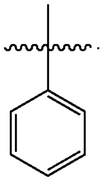
In another preferred embodiment, in general formula (1), when $L^2$ is a chemical bond, $R^2$ is:
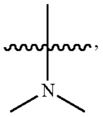
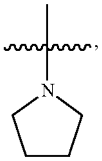
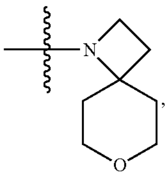
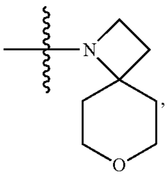
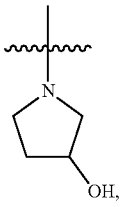
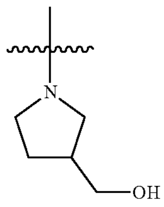
or
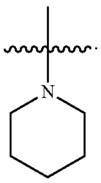
In various embodiments, representative compounds of the present invention have one of the following structures:
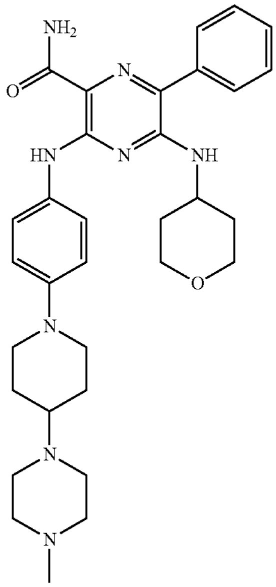
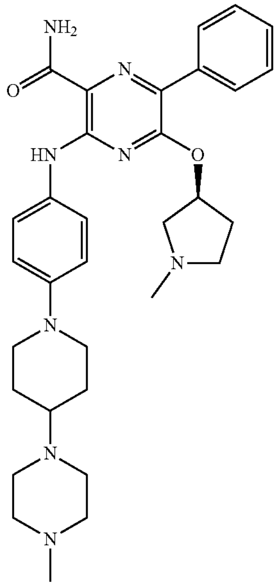
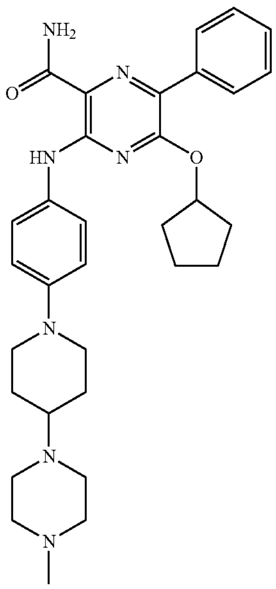
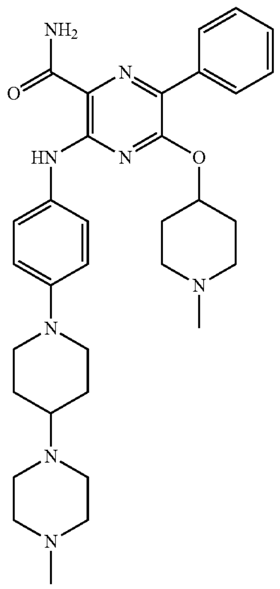

-continued
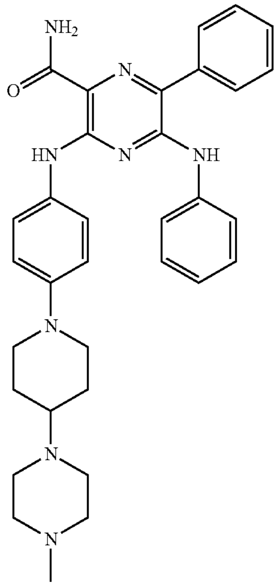
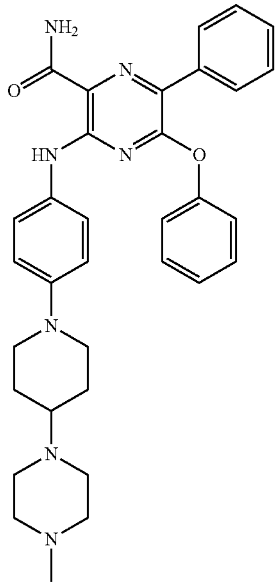
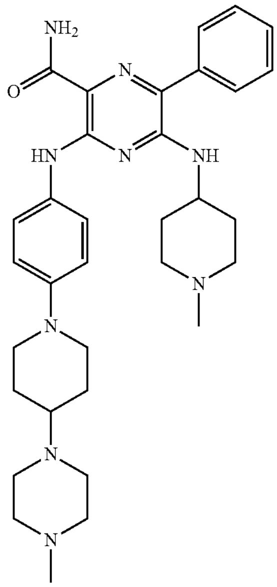
-continued
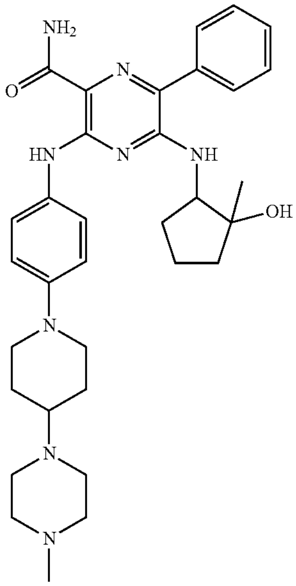
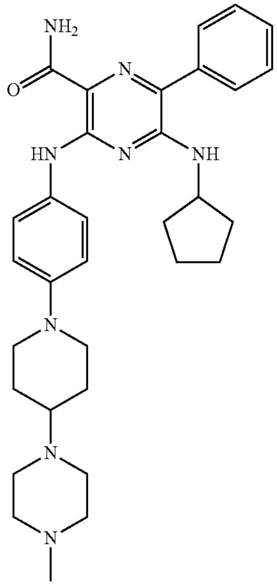
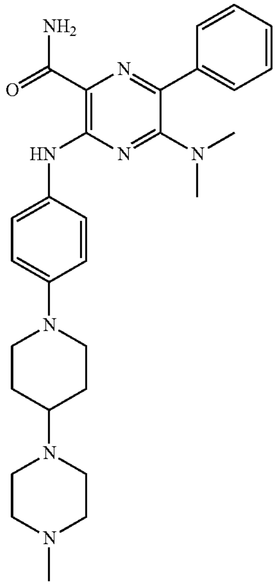

-continued
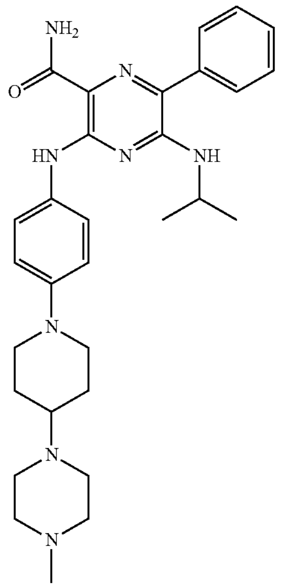
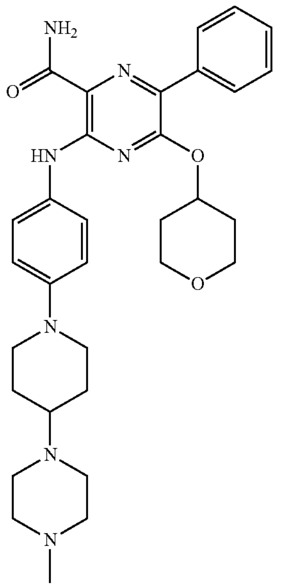
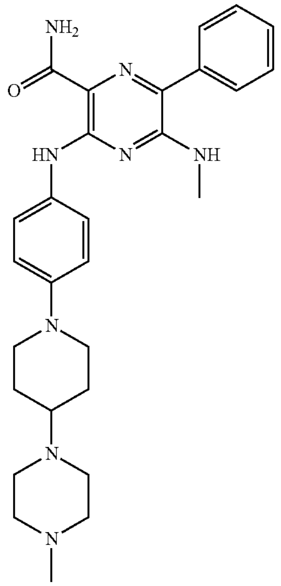
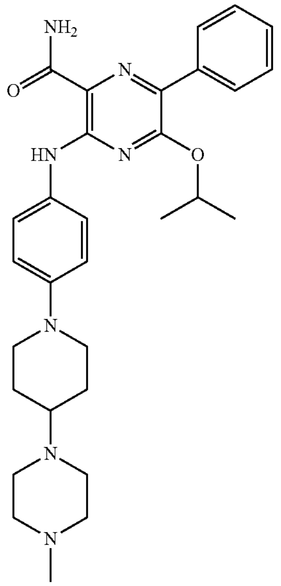
-continued
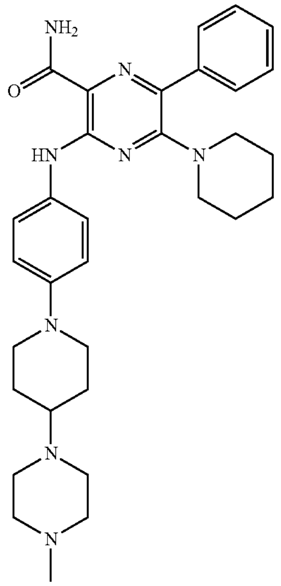
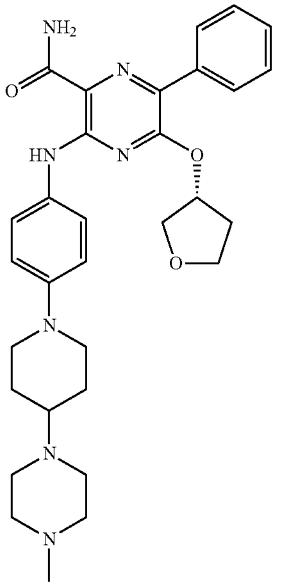
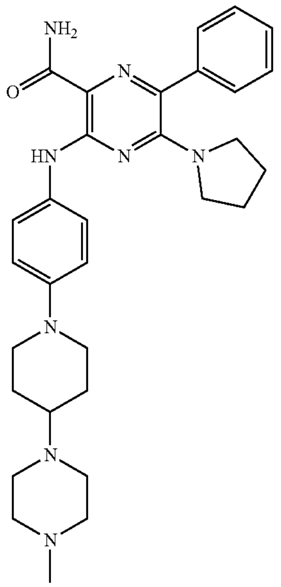
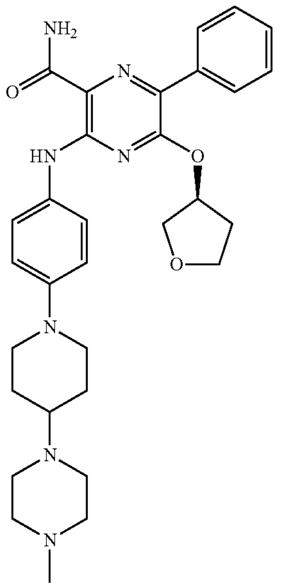

-continued
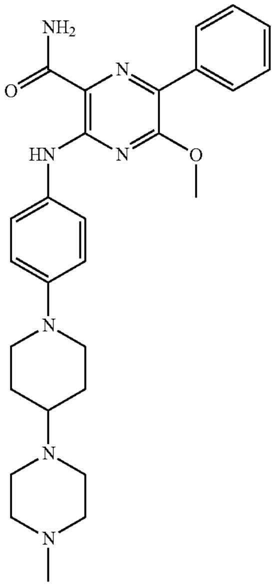
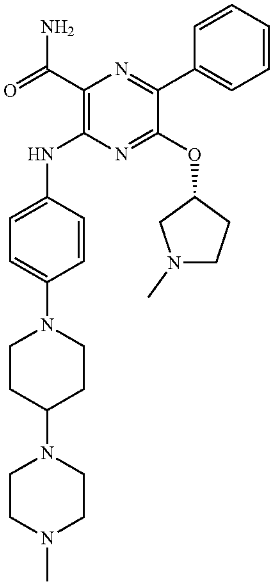
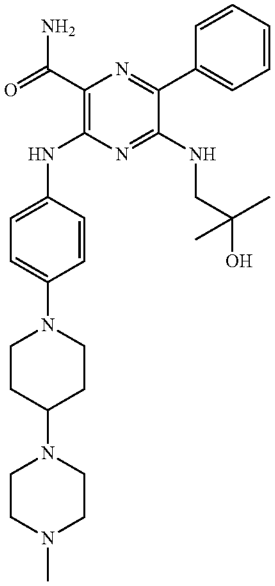
-continued
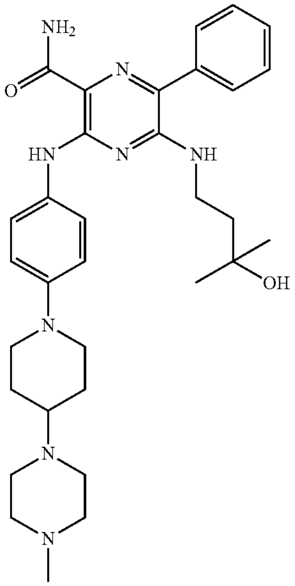
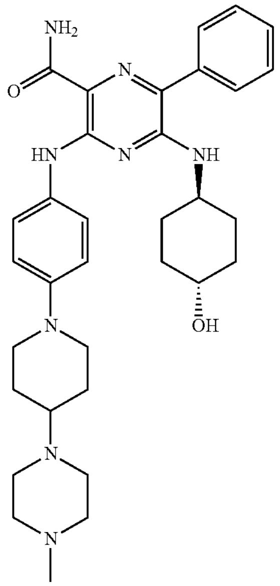
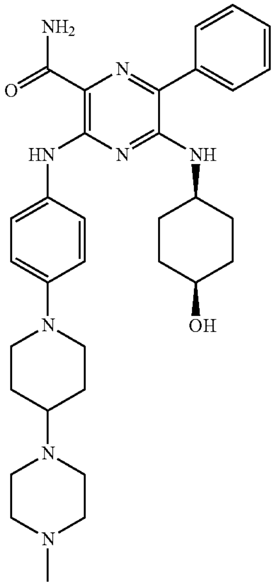
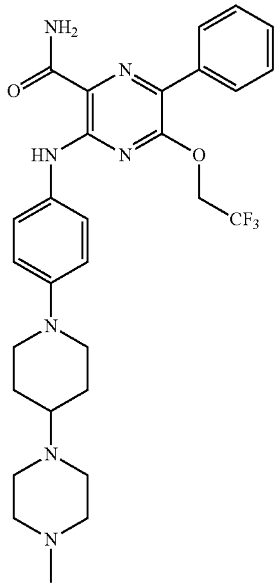

-continued
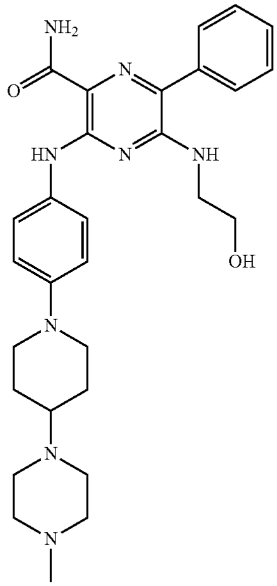
-continued
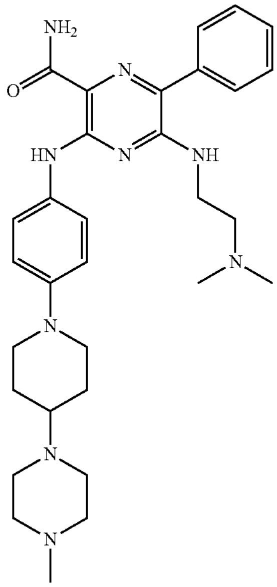
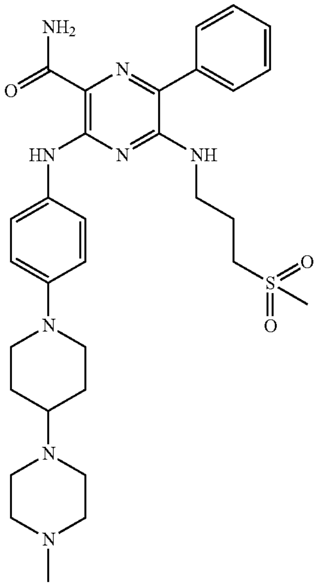
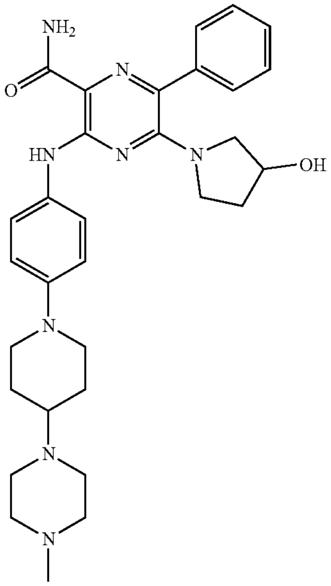

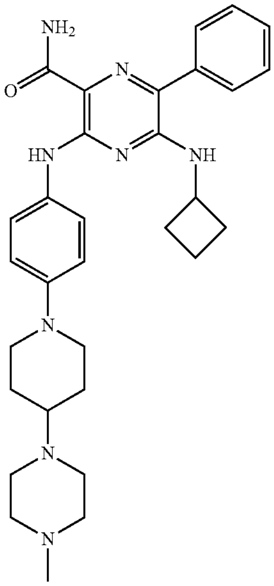
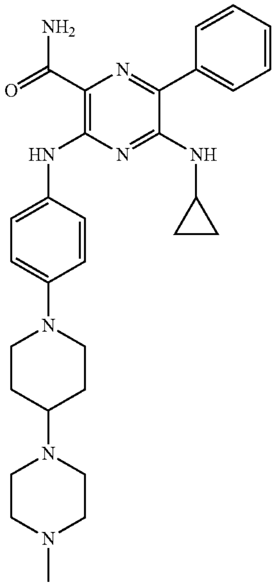
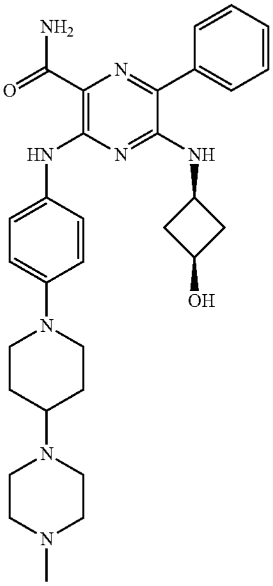
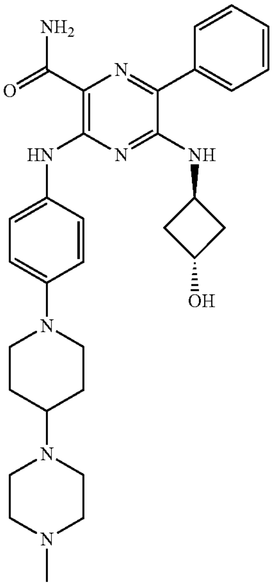
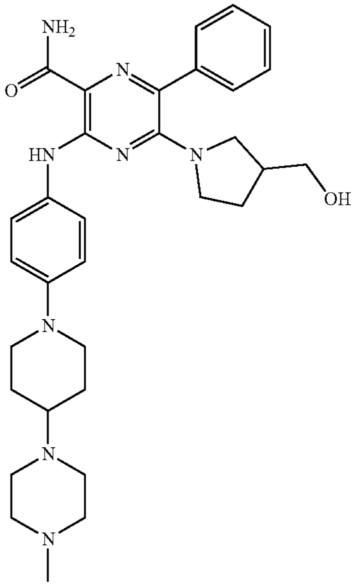

-continued
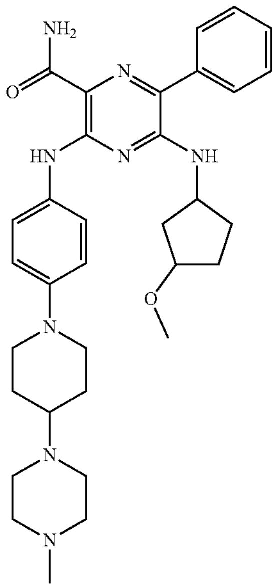
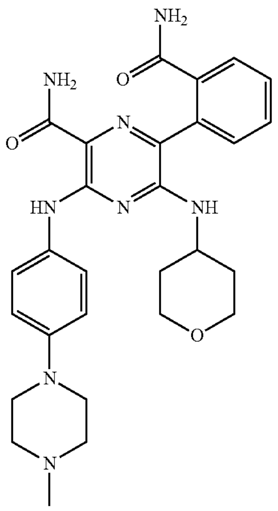
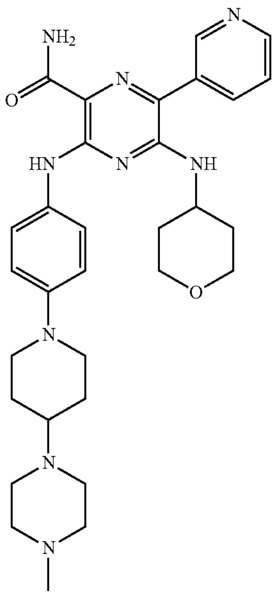
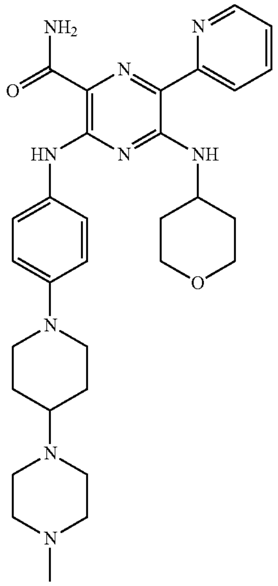
-continued
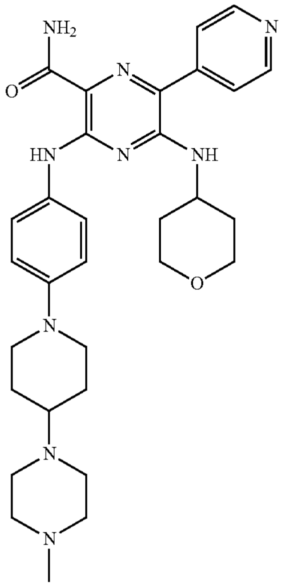
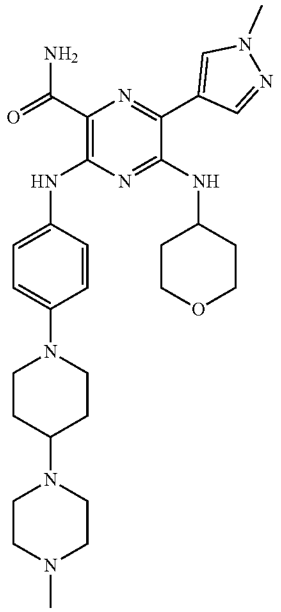
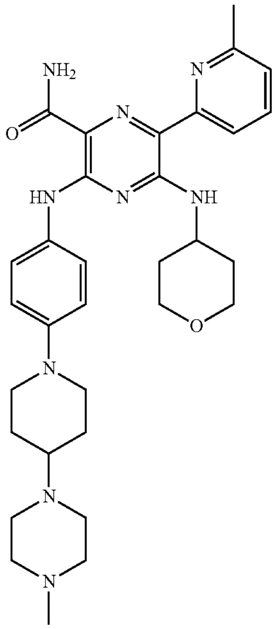
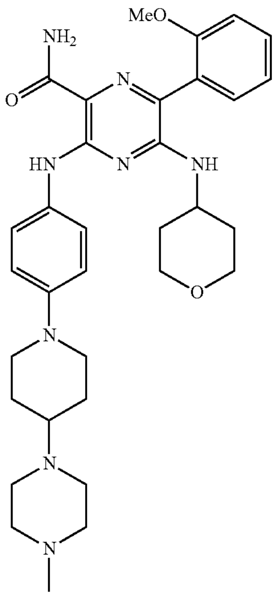

-continued
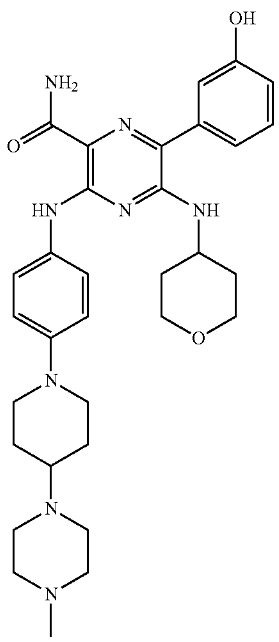
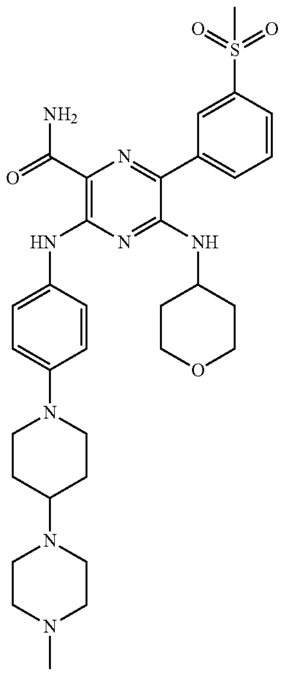
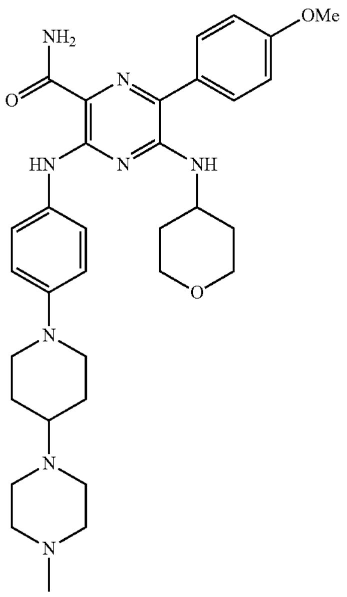
-continued
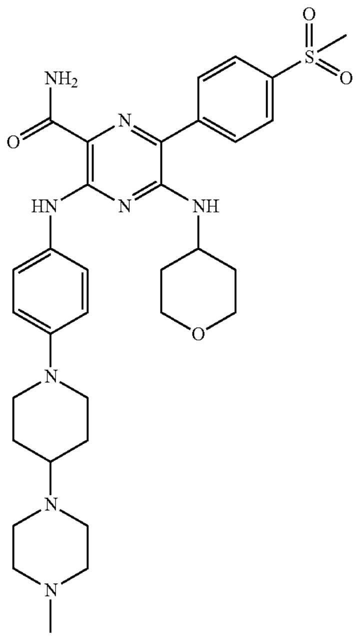
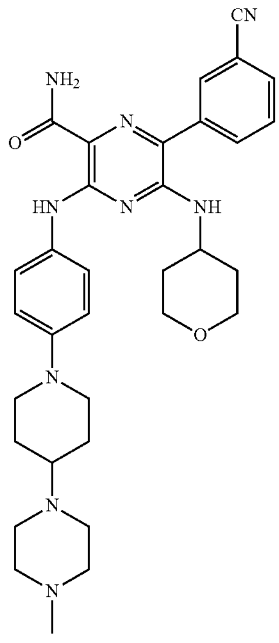
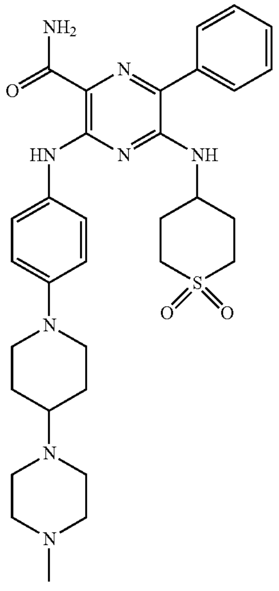

-continued
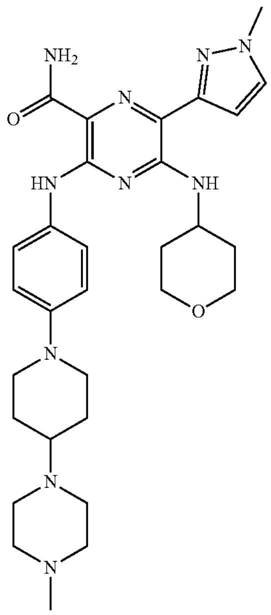
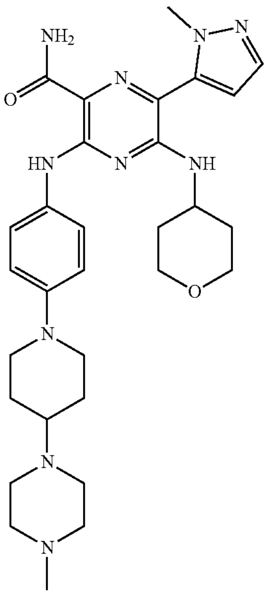
-continued
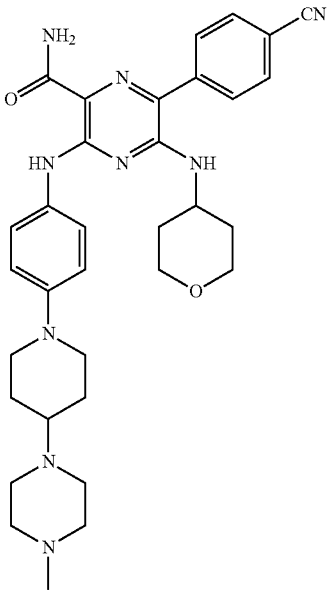
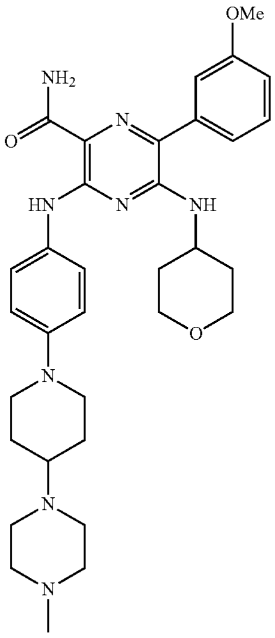
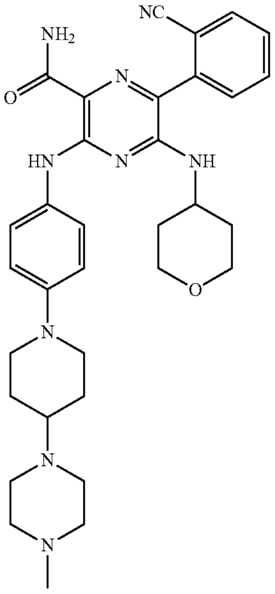
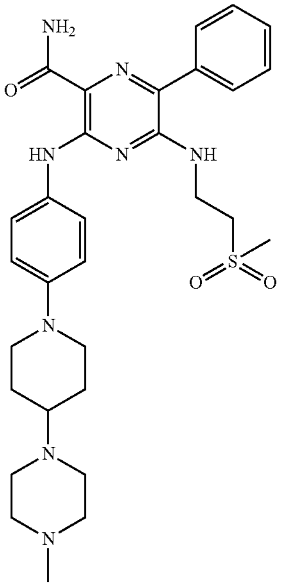
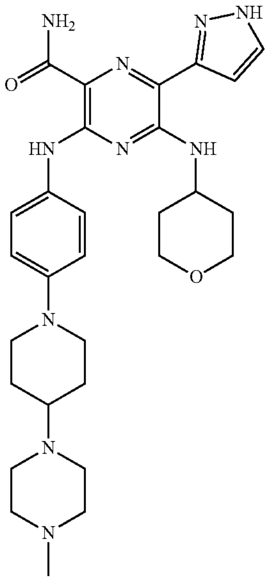

-continued
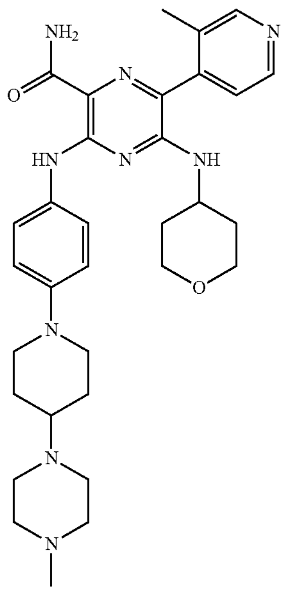
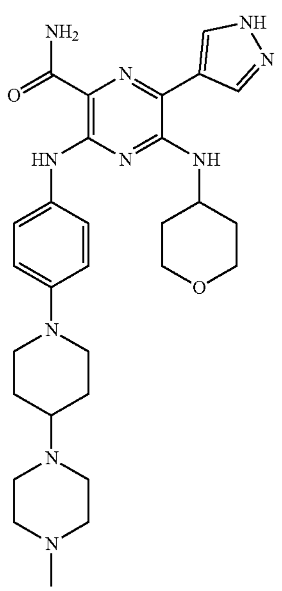
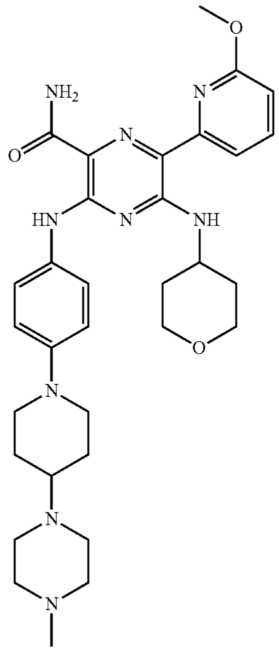
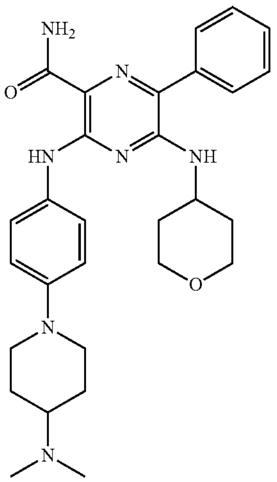
-continued
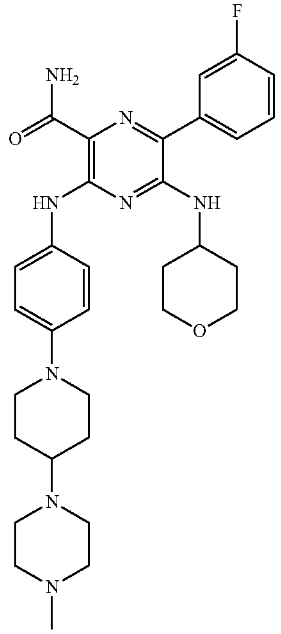
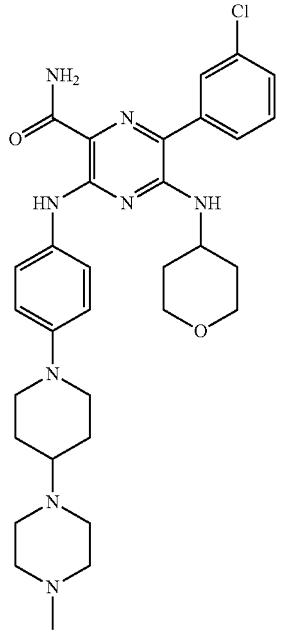
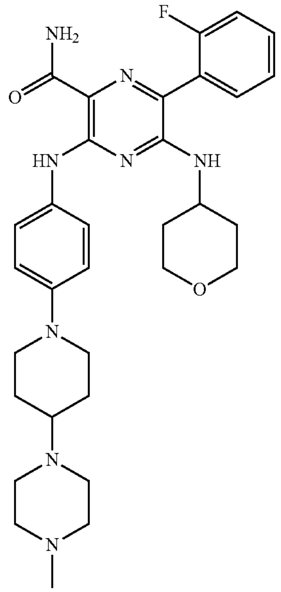
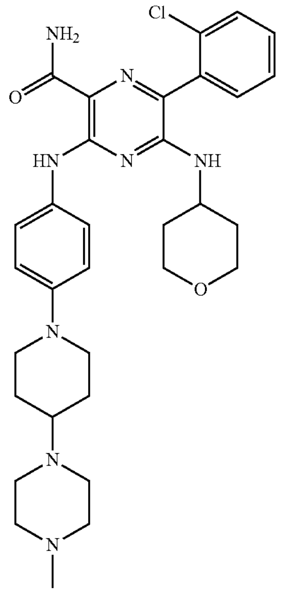

-continued
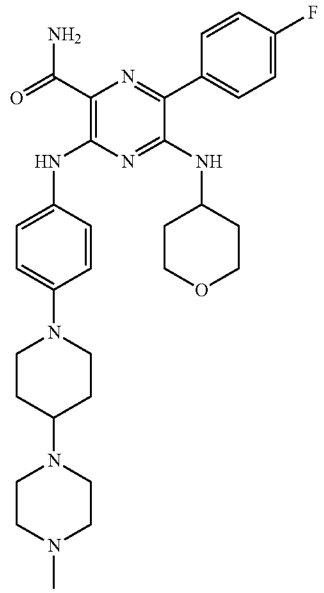
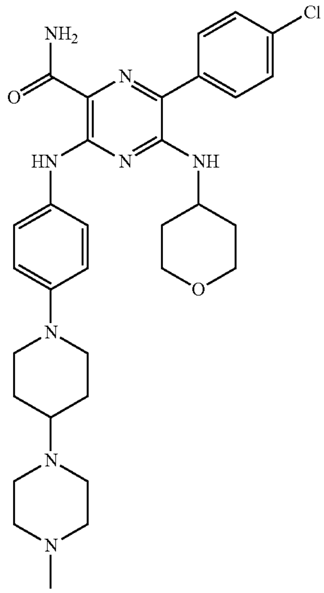
-continued
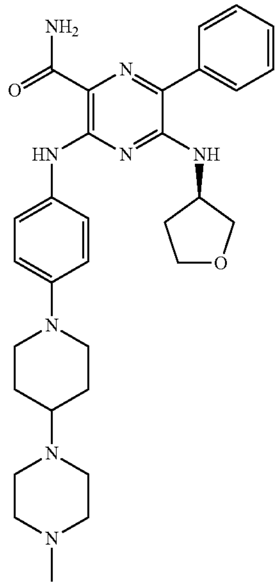
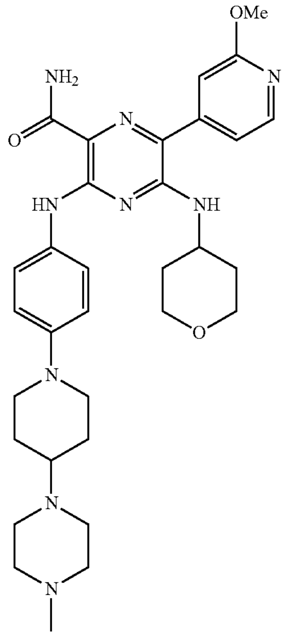

-continued
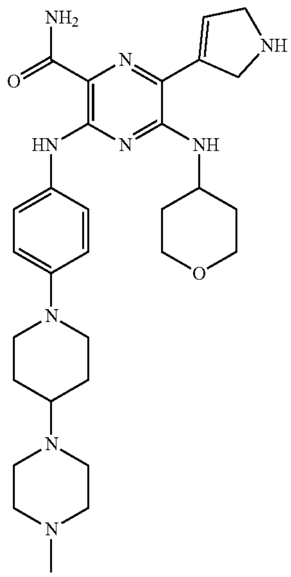
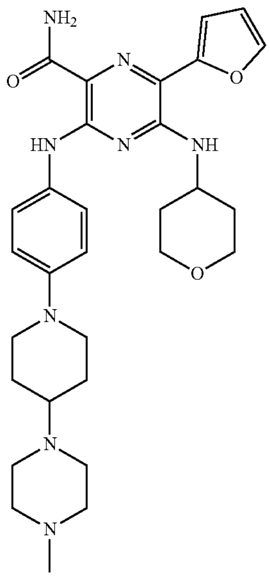
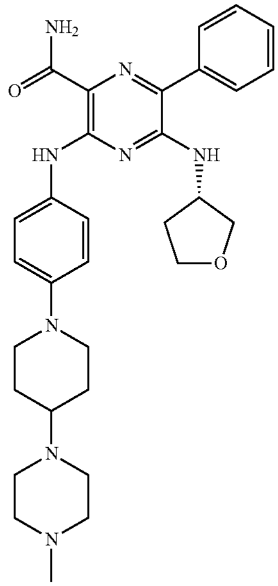
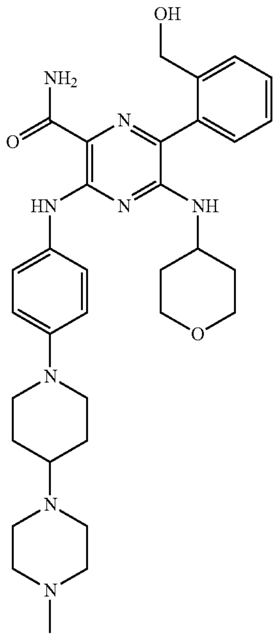
-continued
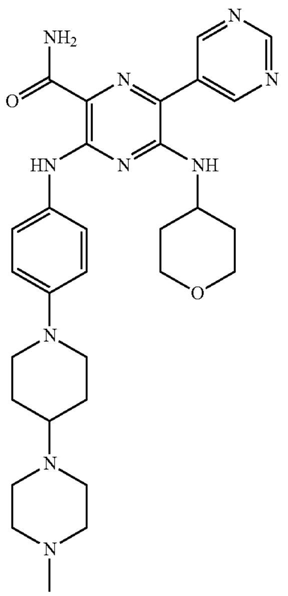
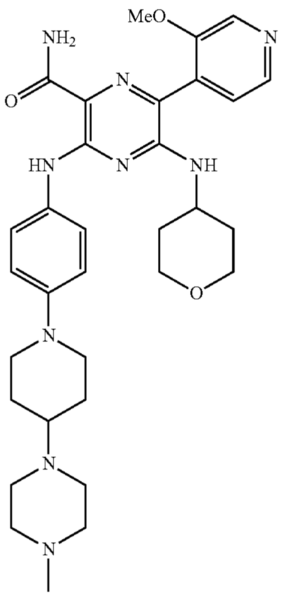
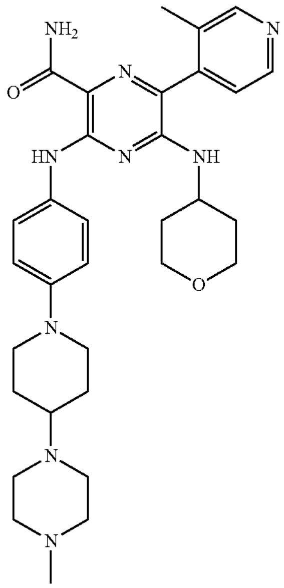
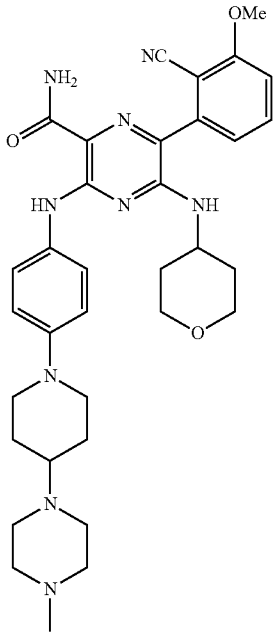

-continued
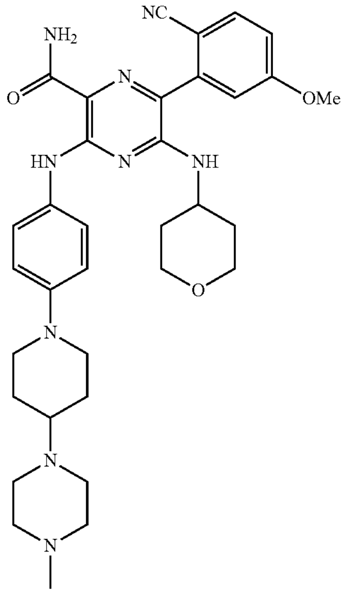
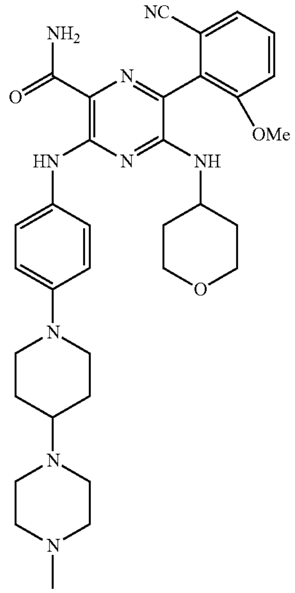
-continued
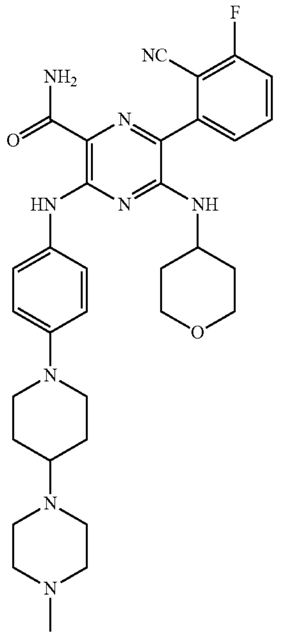
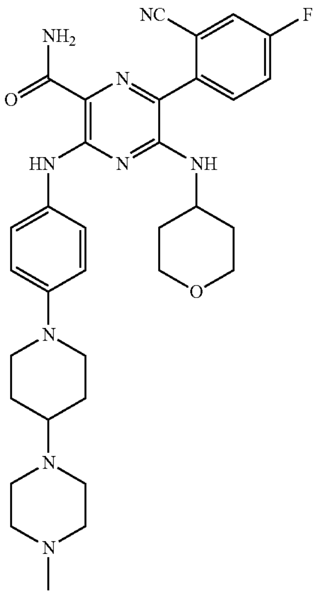

-continued
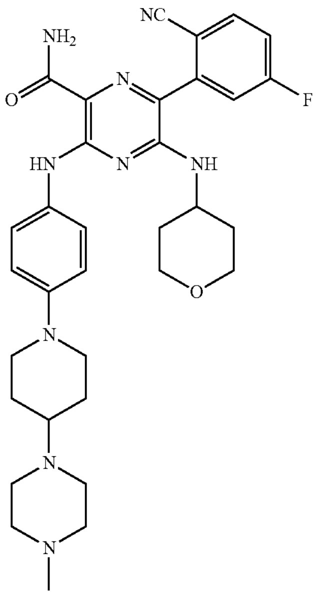
-continued
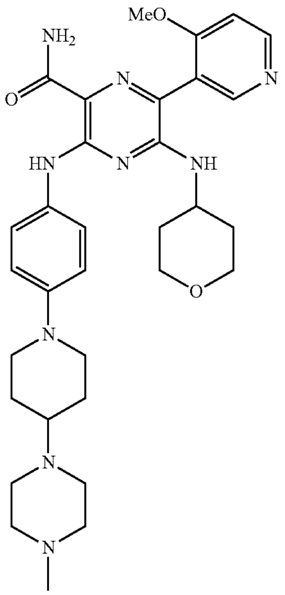
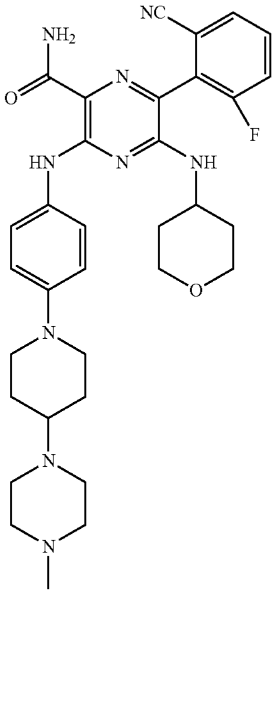
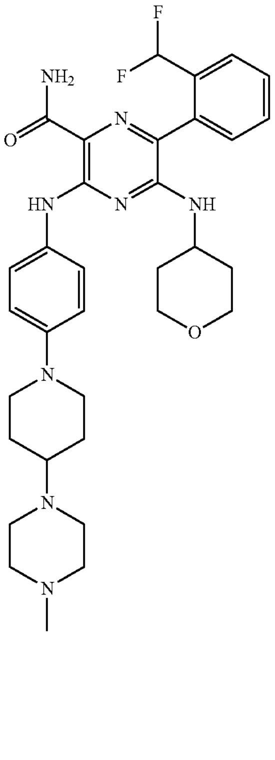
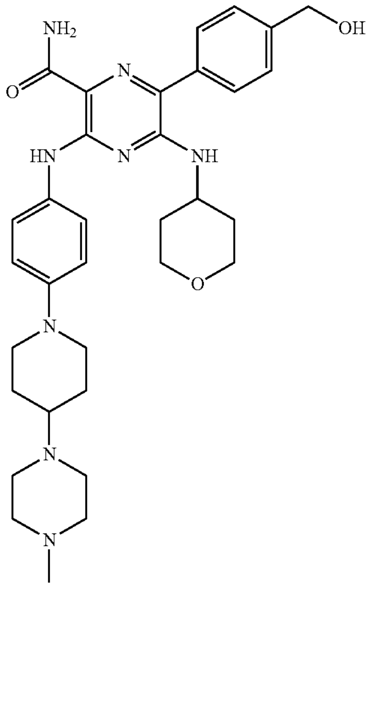

-continued
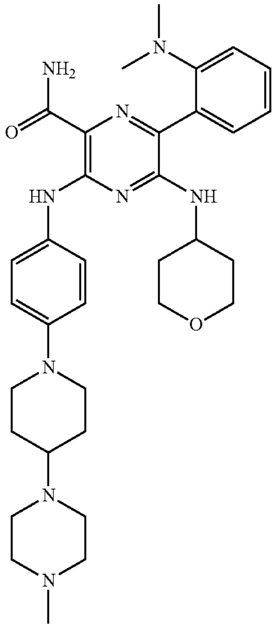
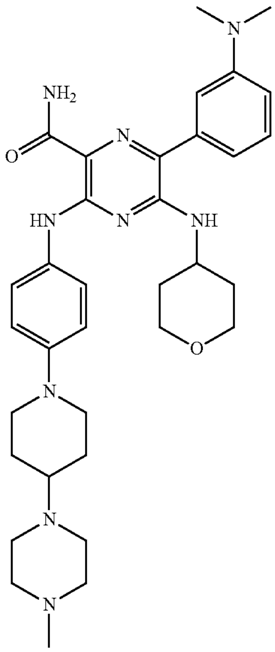
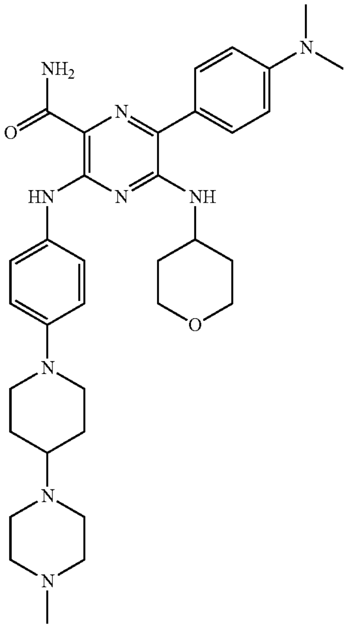
-continued
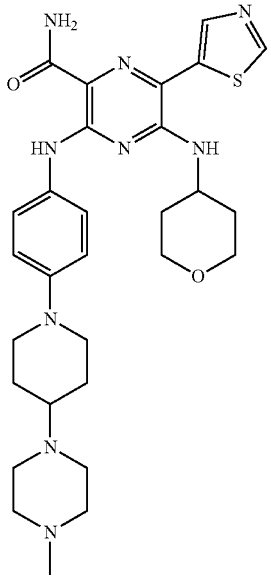
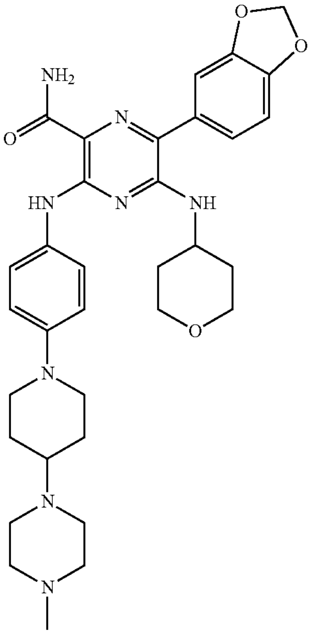

-continued
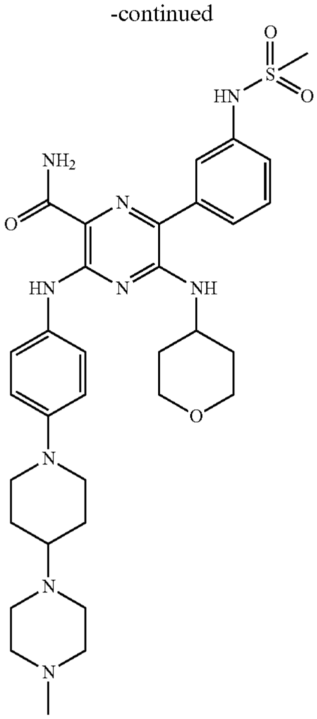
-continued
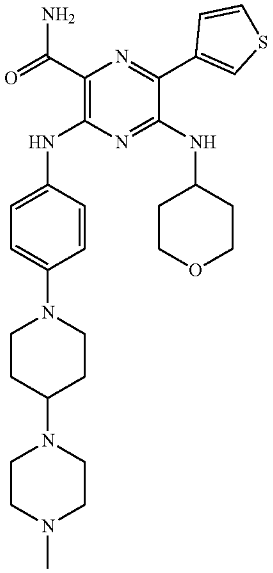
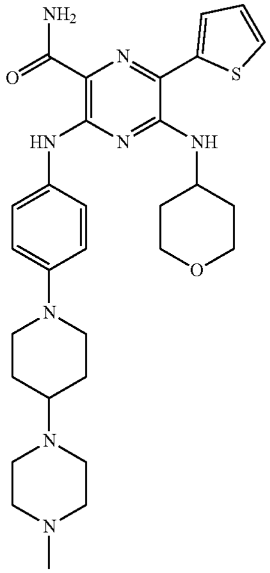
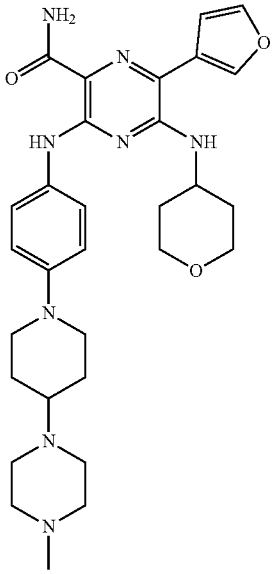
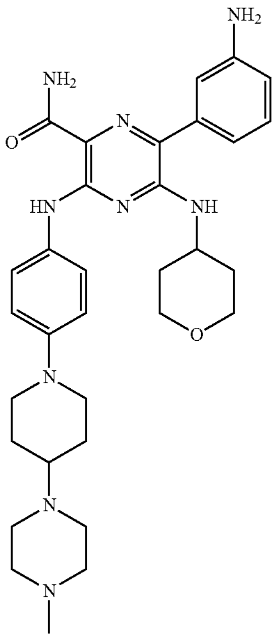
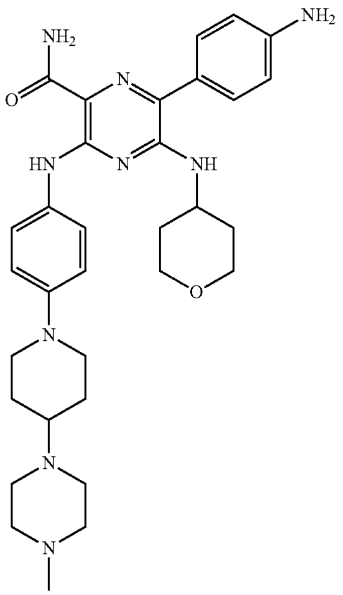

-continued
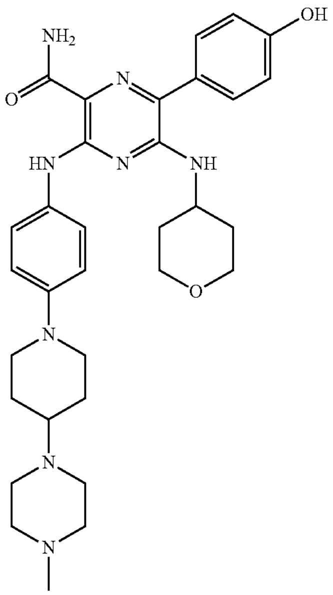
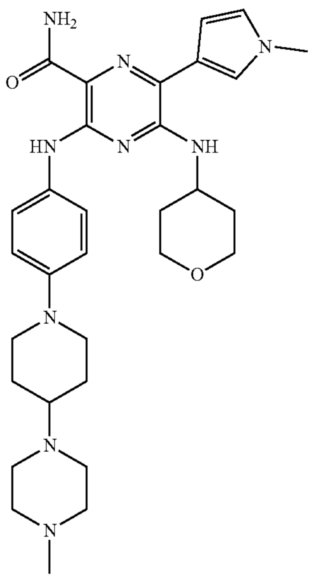
-continued
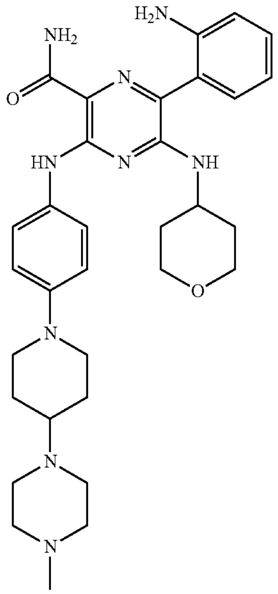
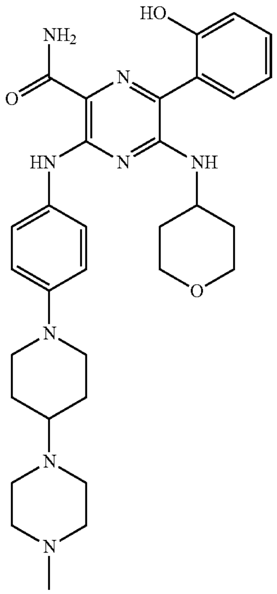
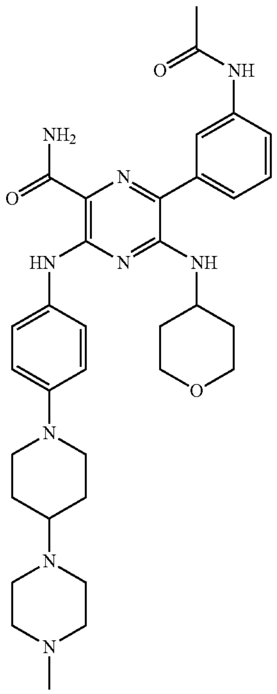

-continued
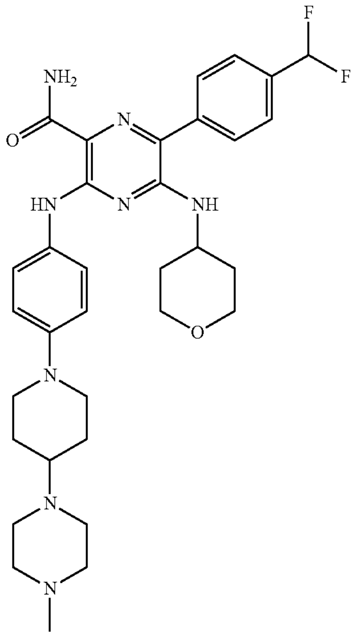
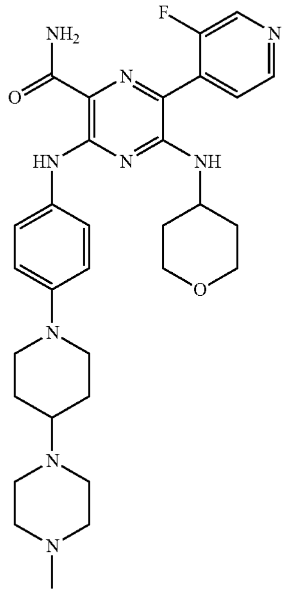
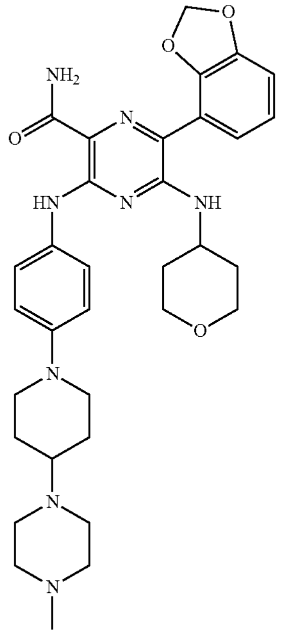
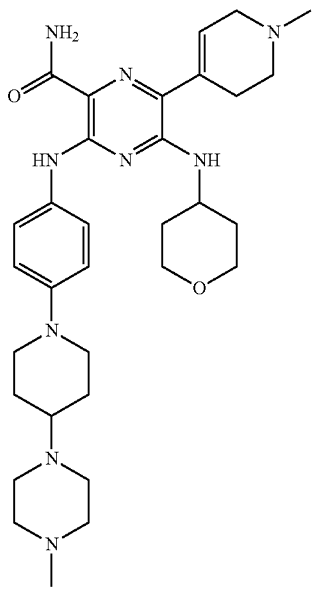
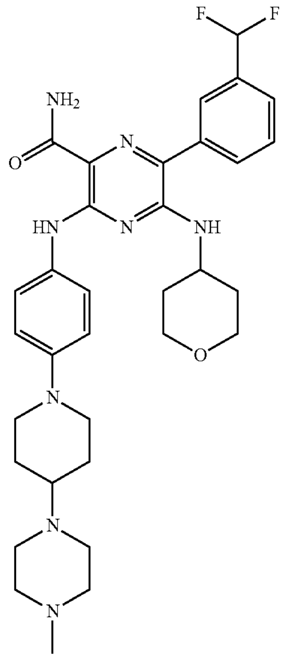

-continued
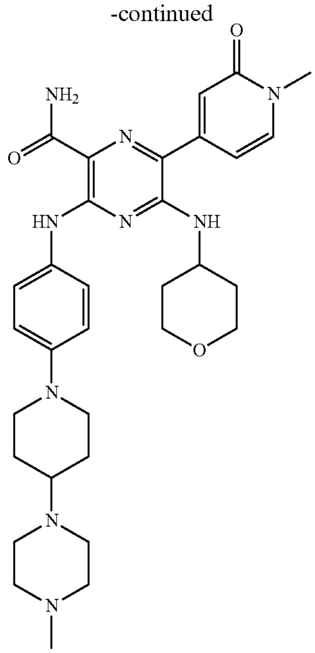
-continued
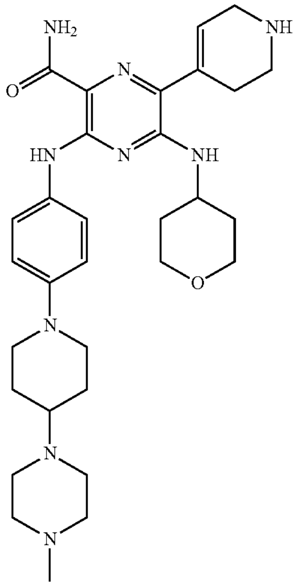
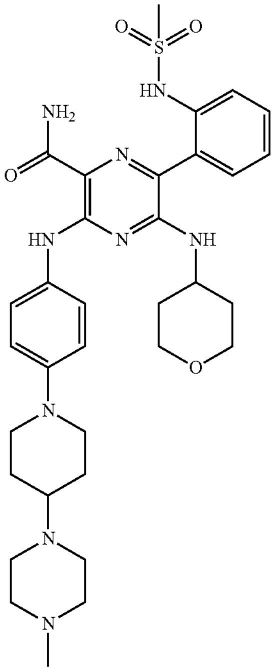
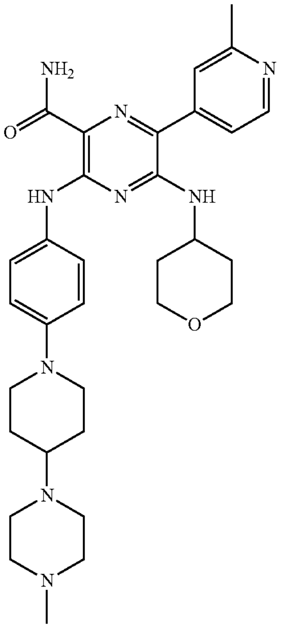
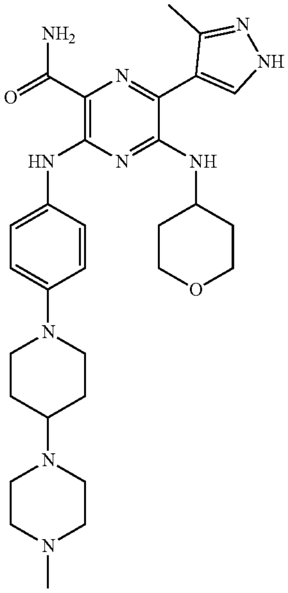

-continued
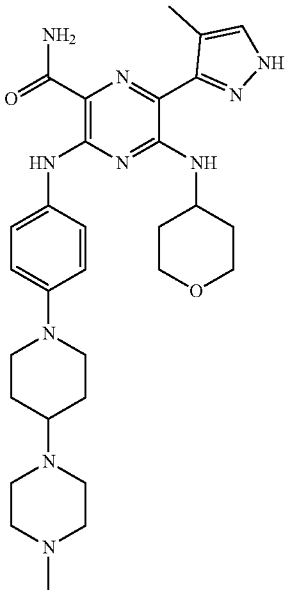
-continued
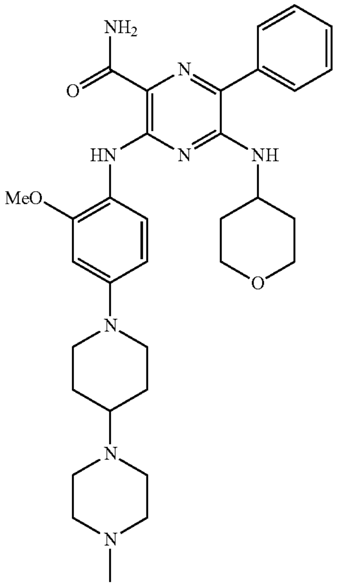
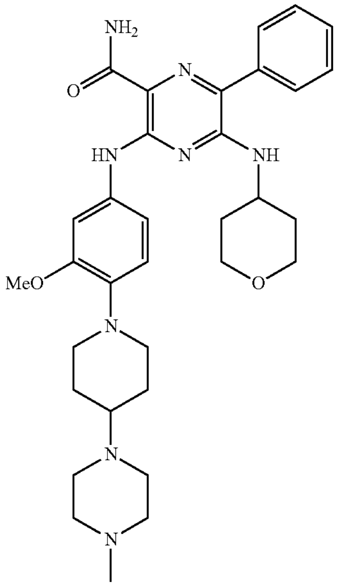
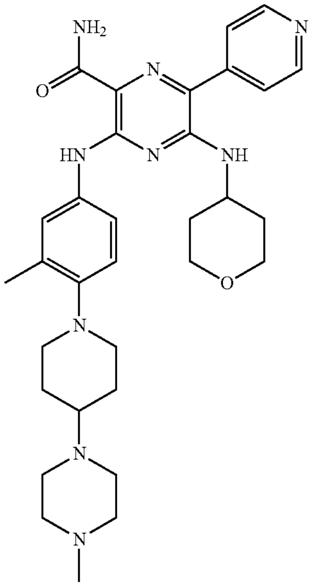

-continued
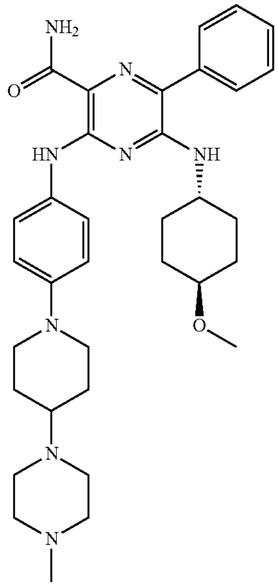
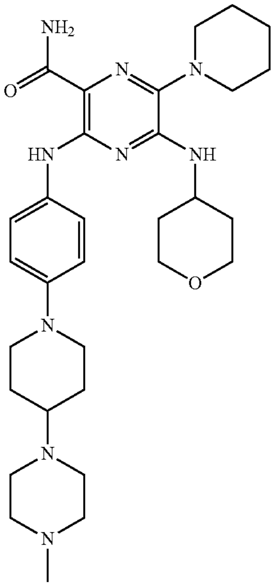
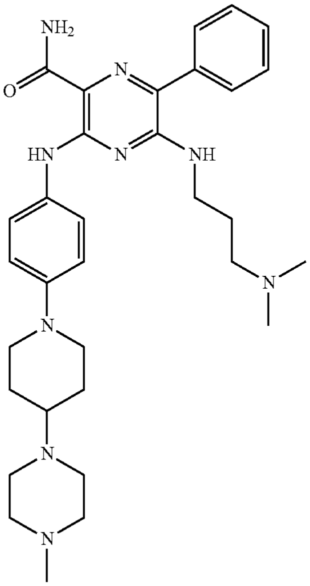
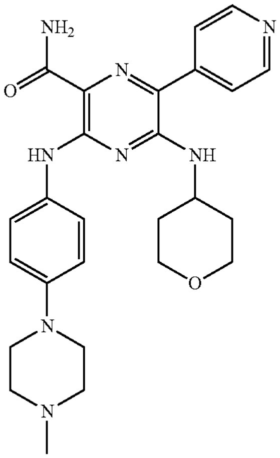
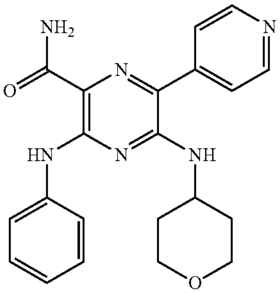
-continued
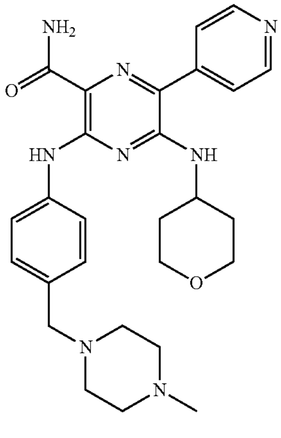
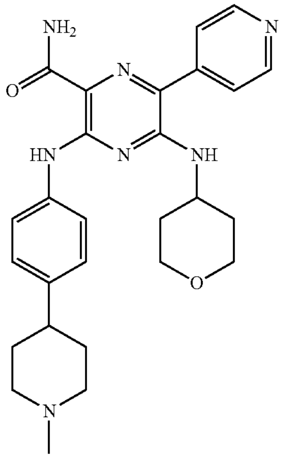
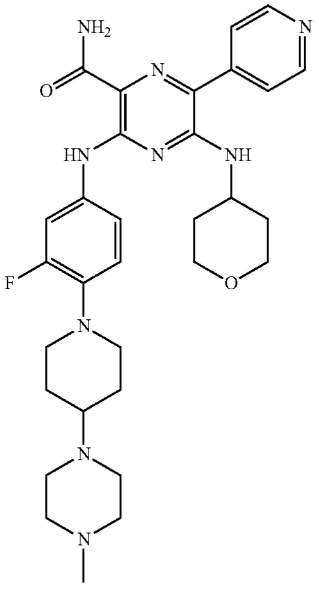
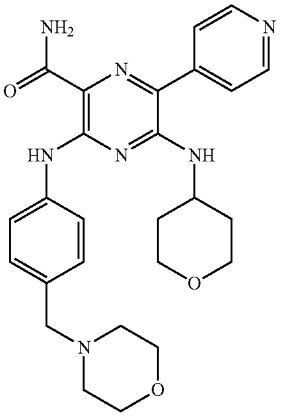

-continued
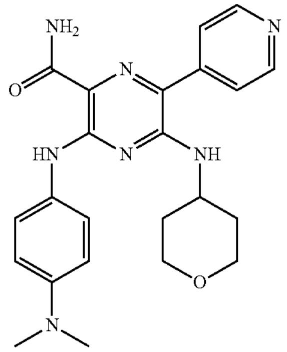
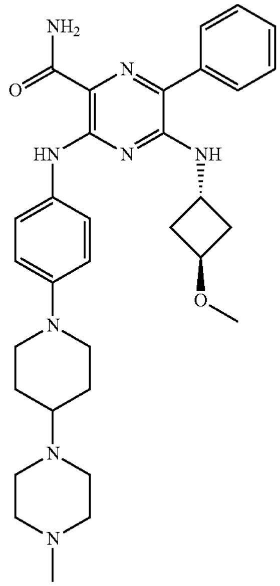
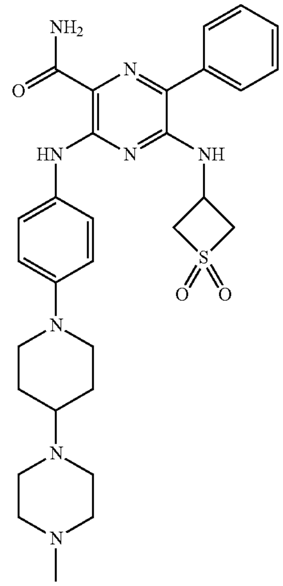
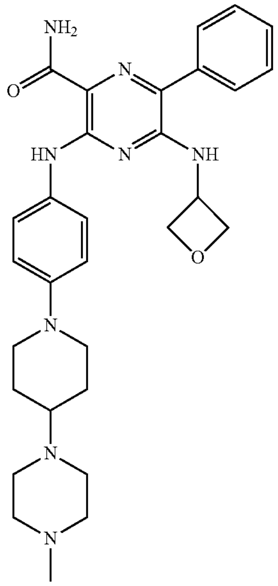
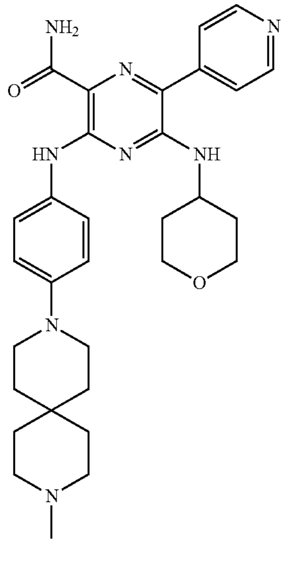
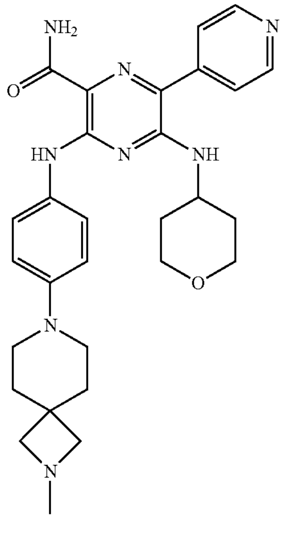
-continued
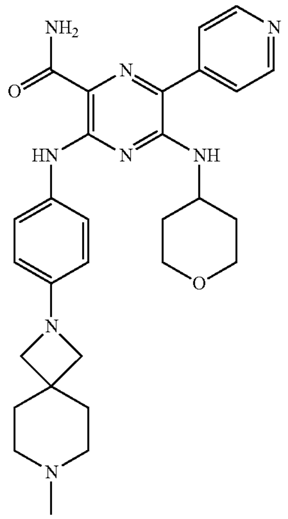
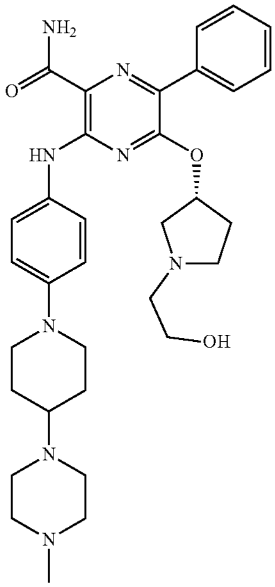
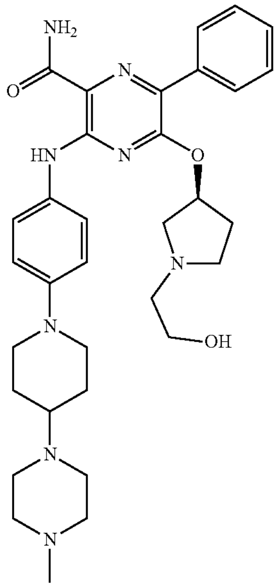
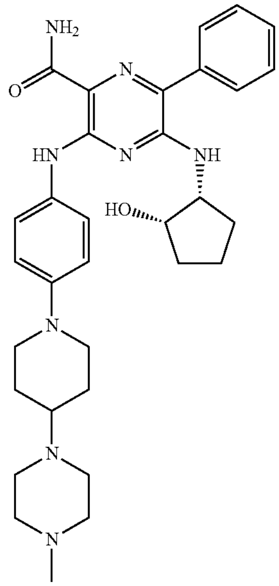
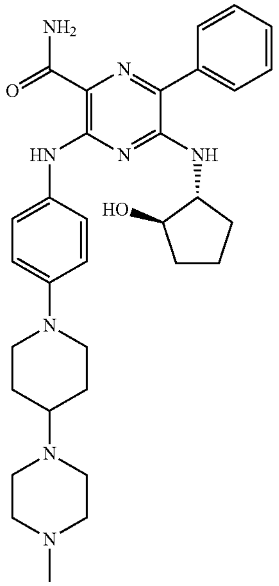

-continued
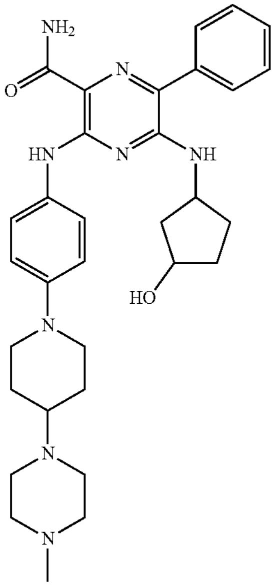
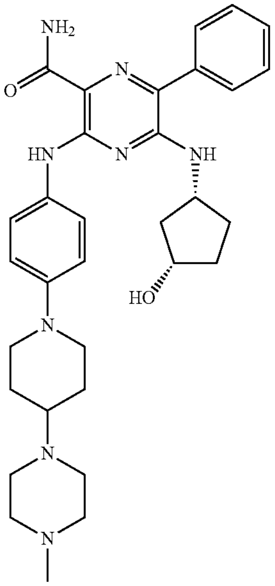
-continued
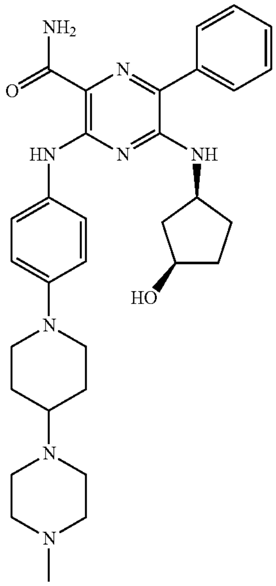
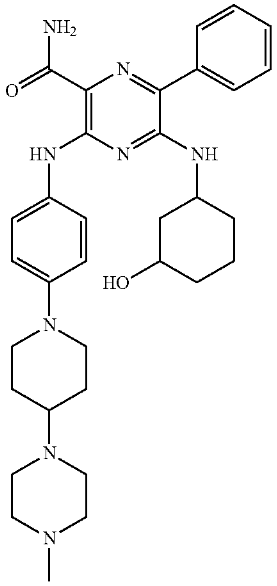
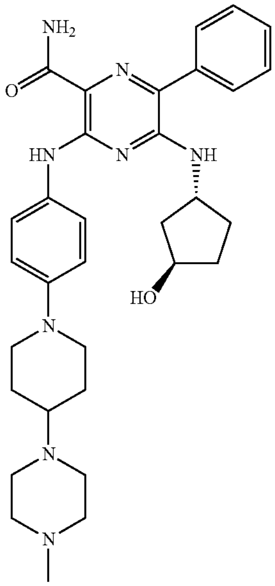
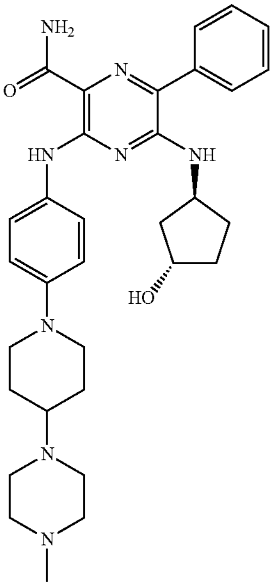
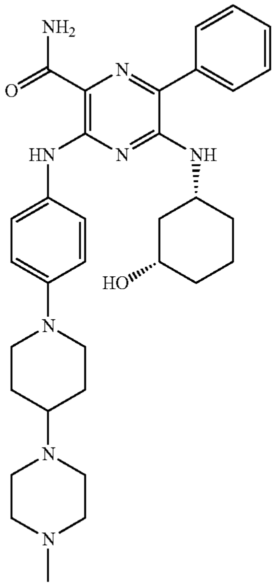
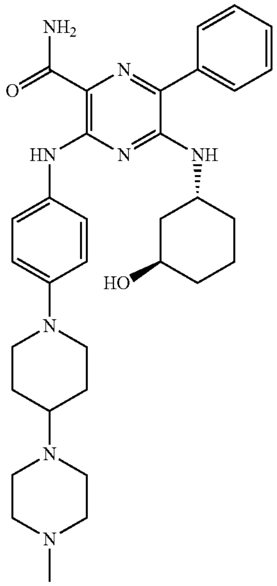

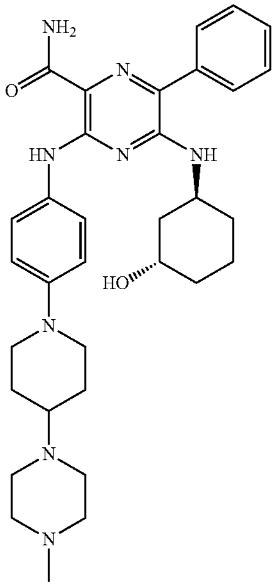
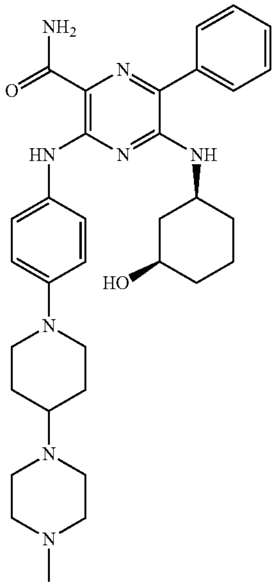
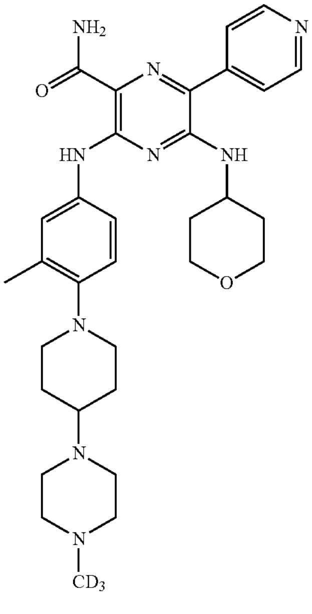
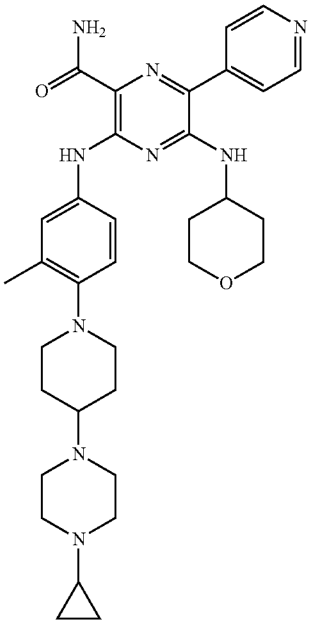
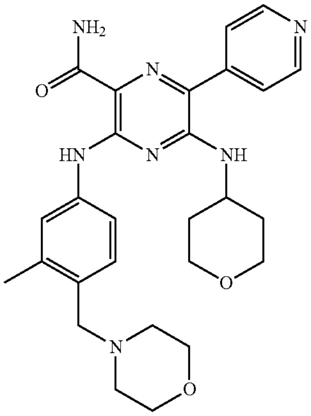
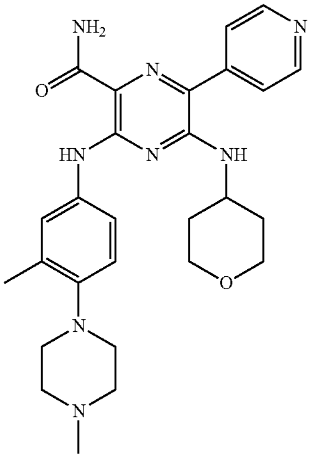

-continued
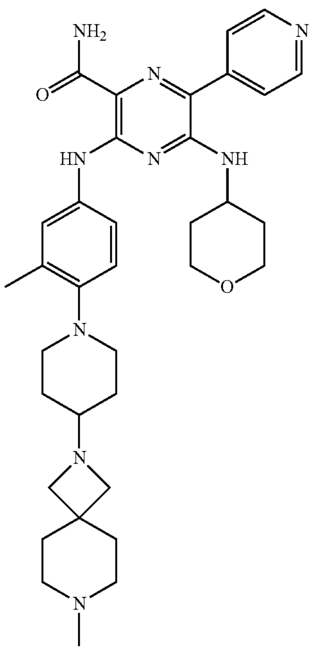
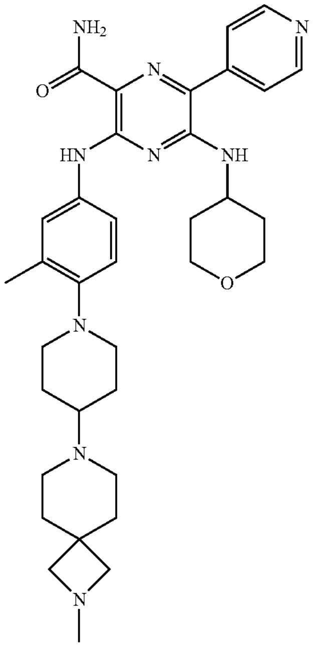
-continued
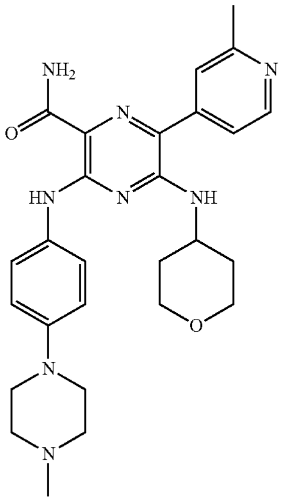
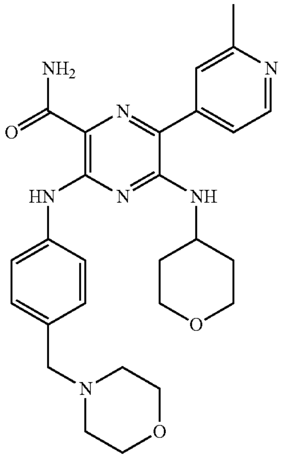
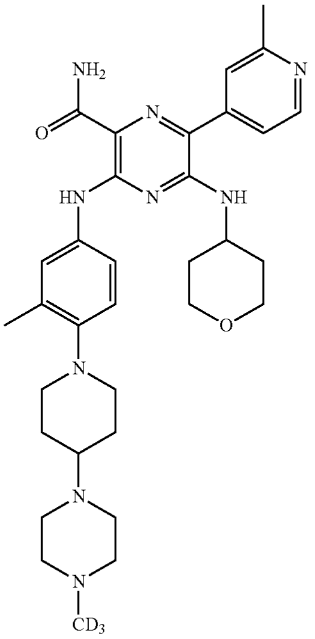

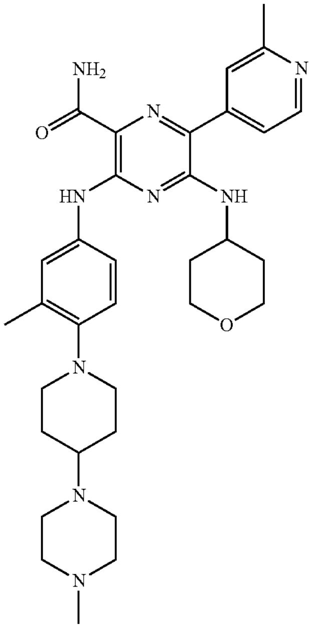
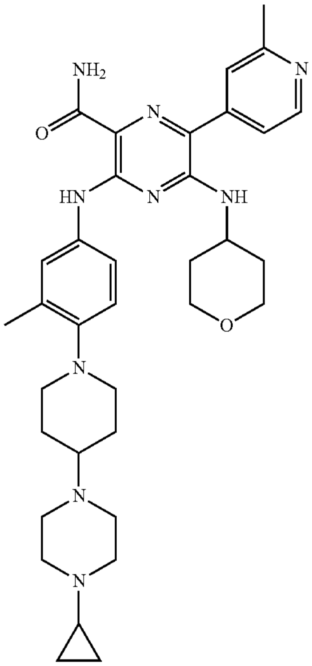
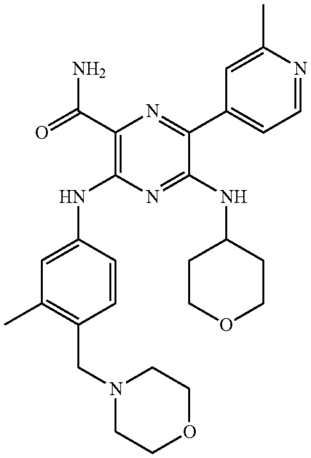
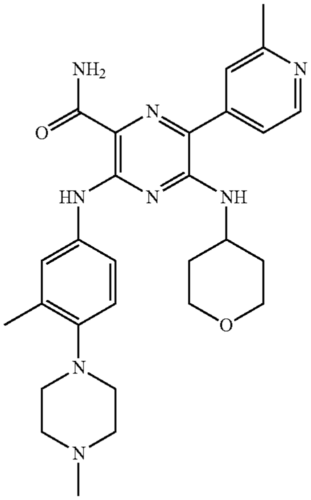
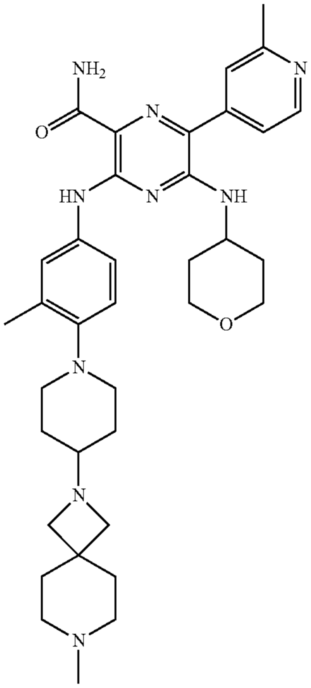

-continued
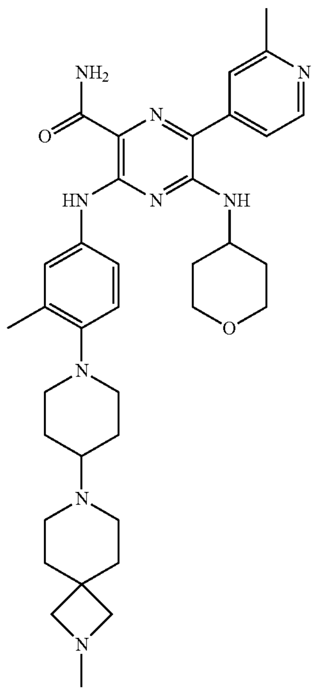
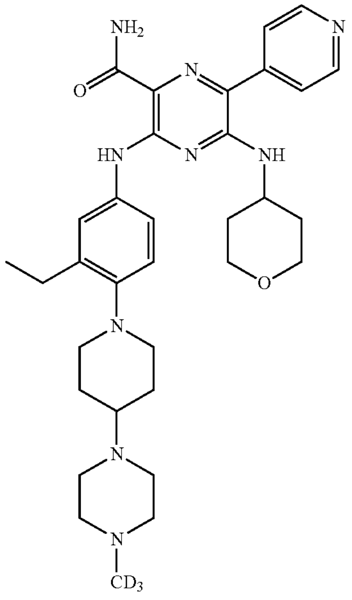
-continued
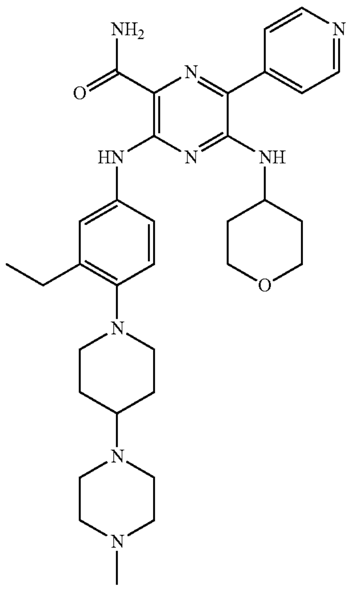
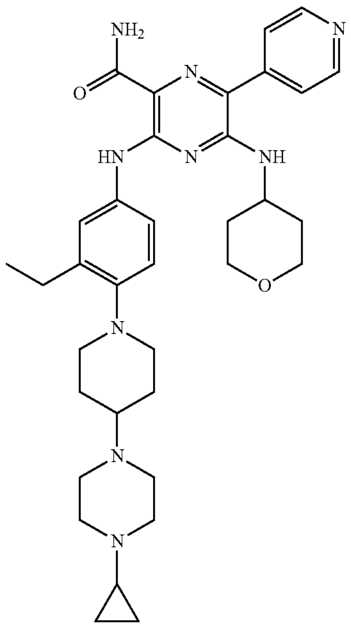
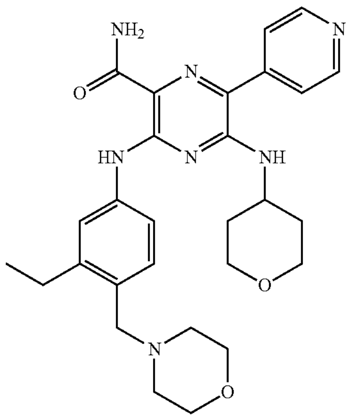

-continued
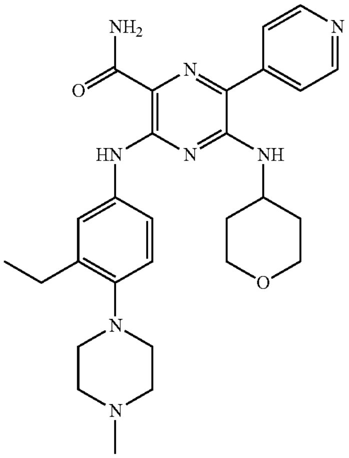
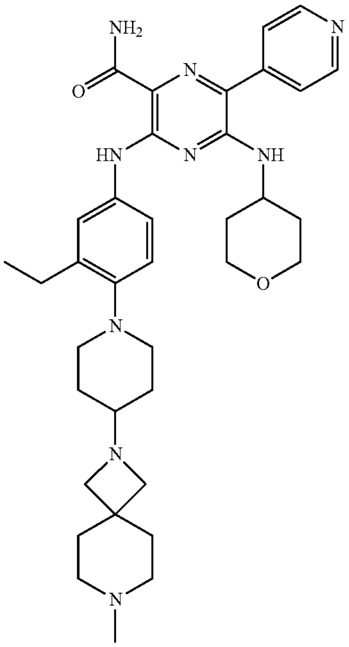
-continued
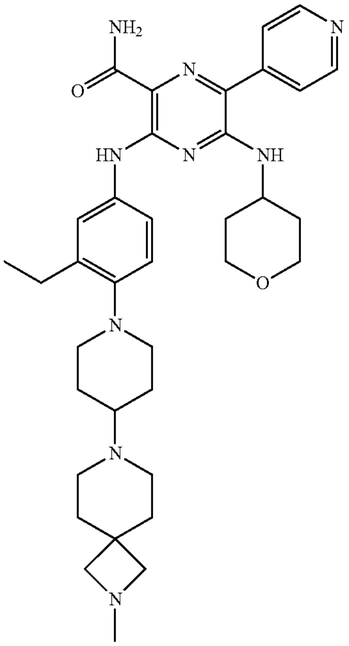
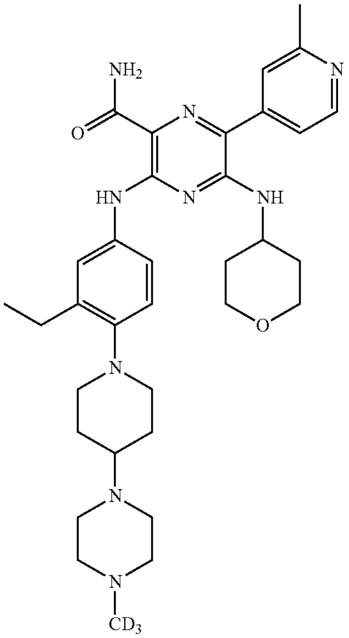

-continued
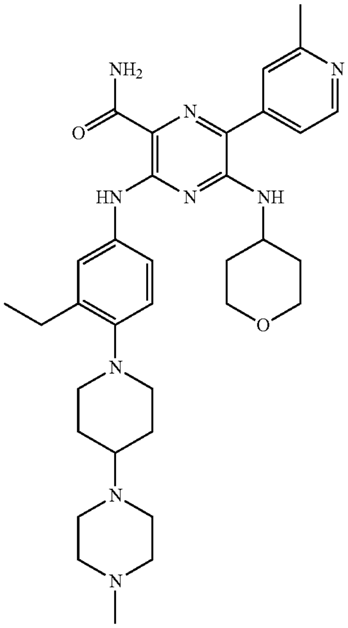
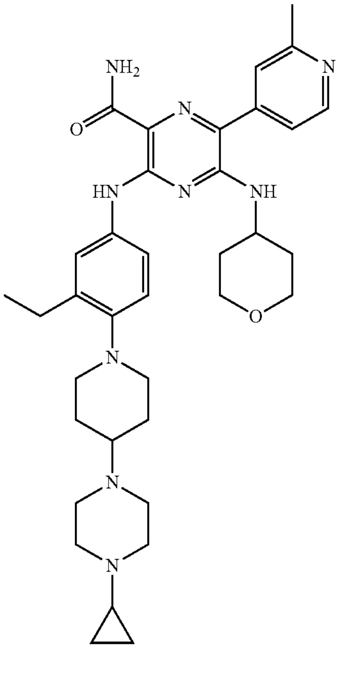
-continued
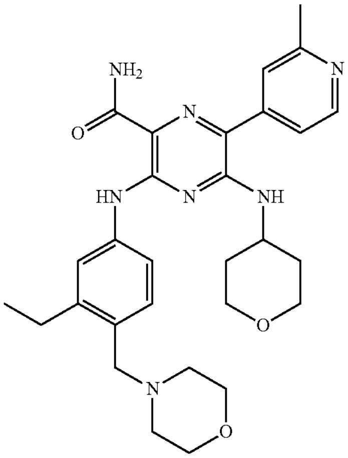
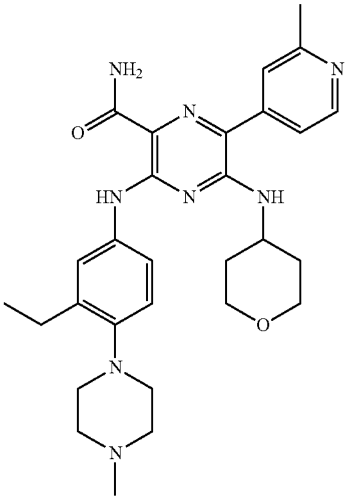
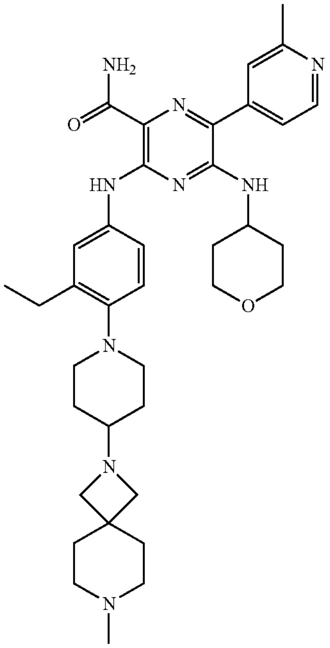

-continued
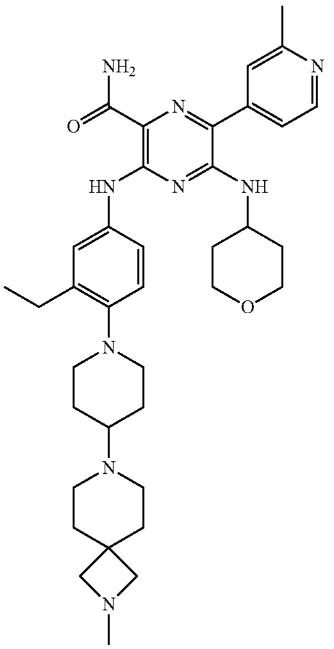
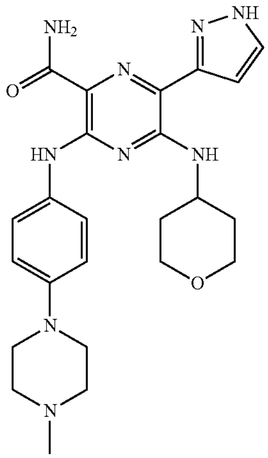
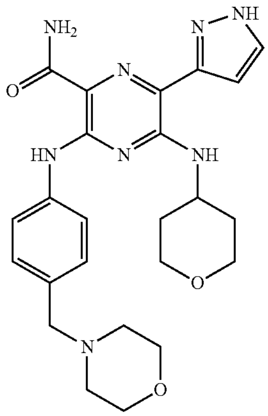
-continued
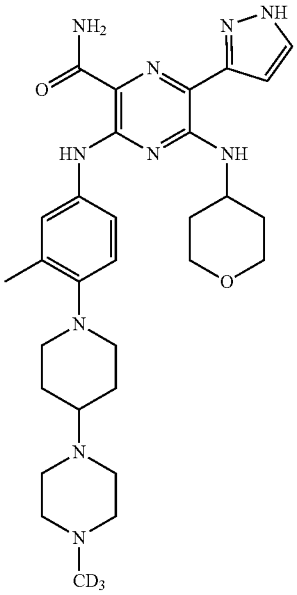
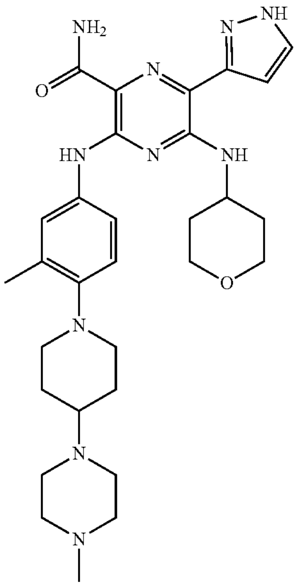

-continued
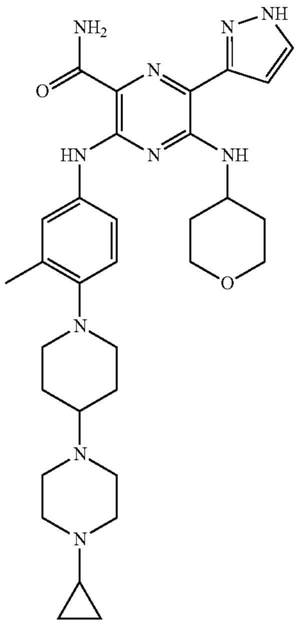
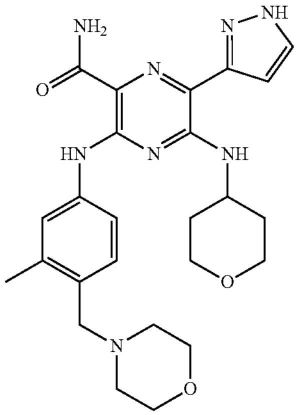
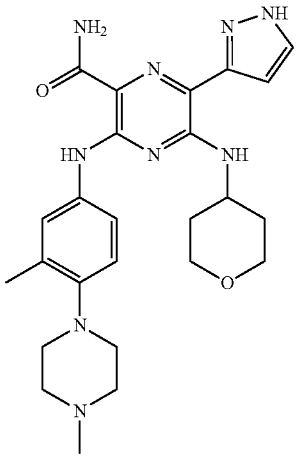
-continued
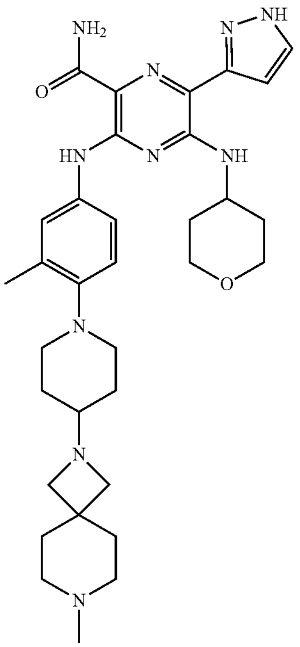
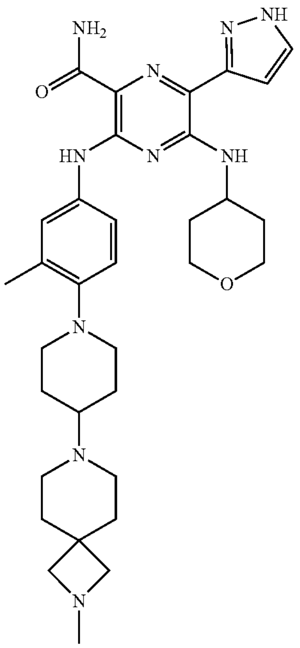

-continued
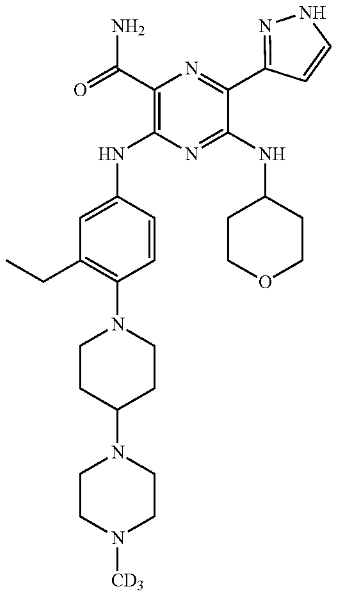
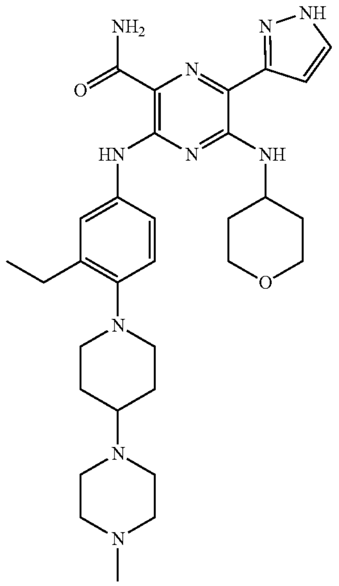
-continued
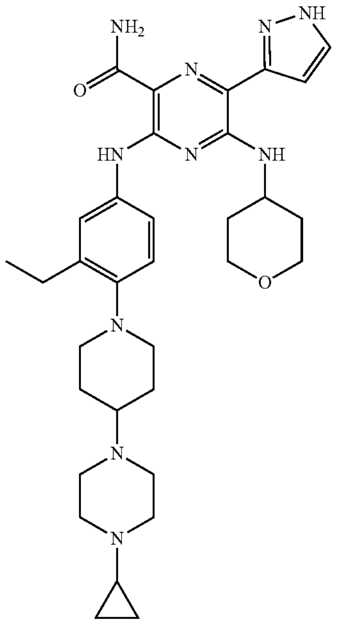
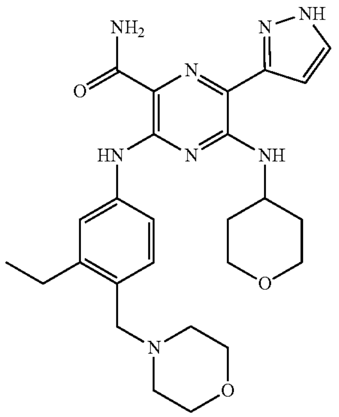
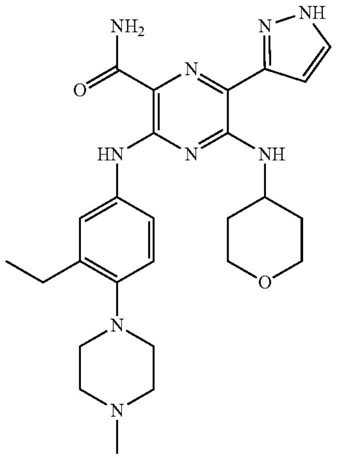

-continued
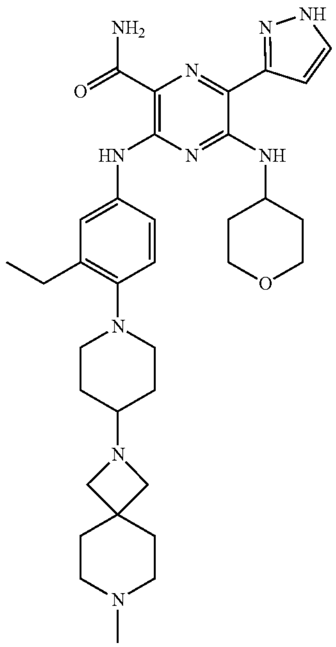
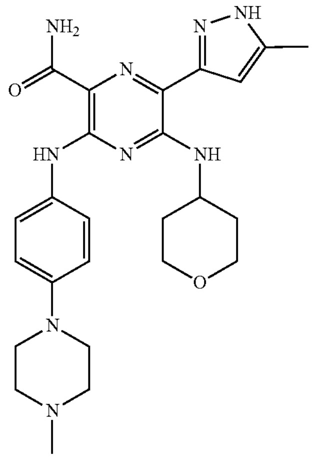
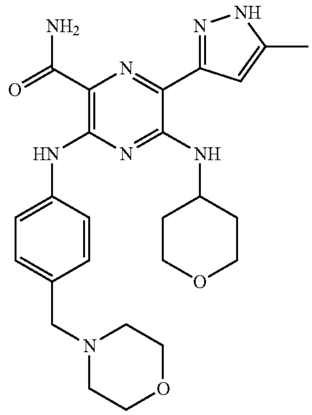
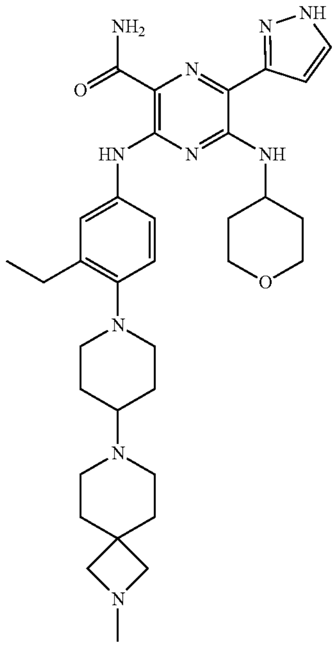
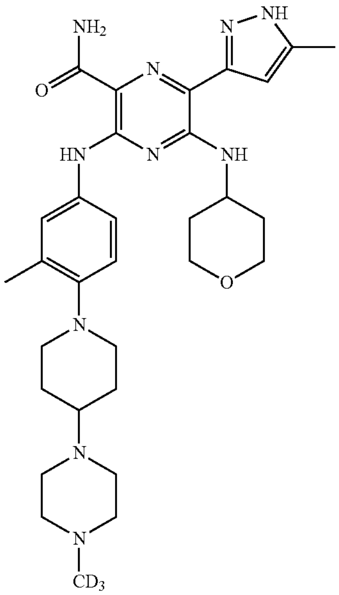

-continued
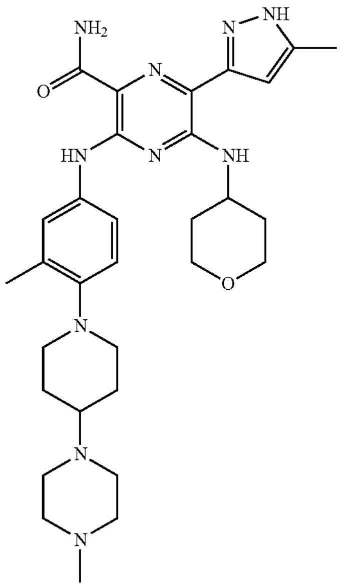
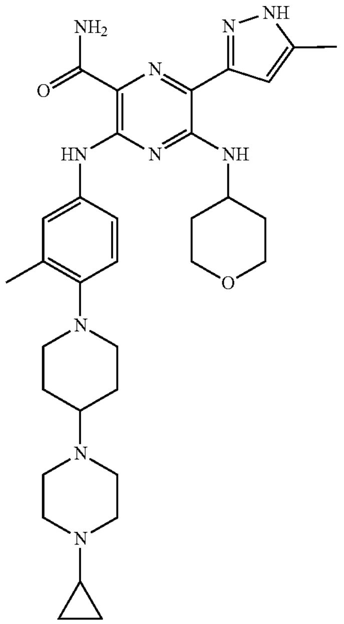
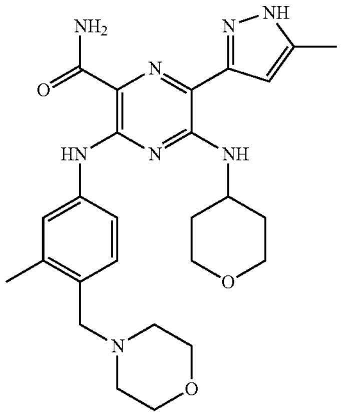
-continued
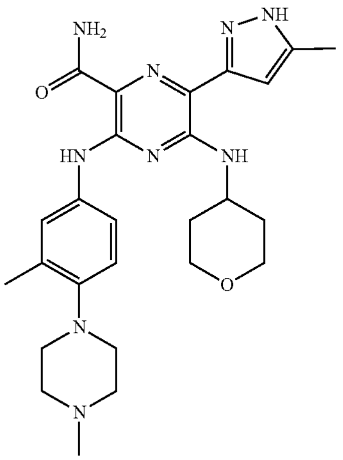
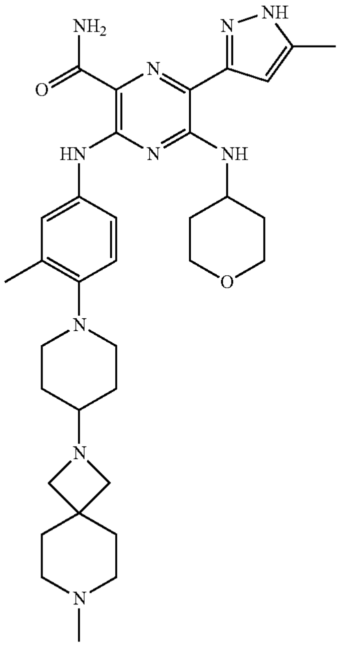

-continued
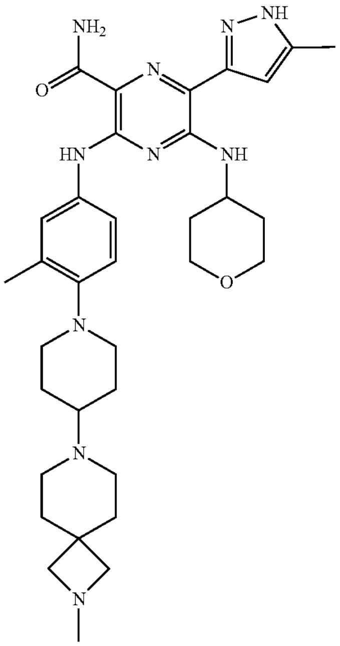
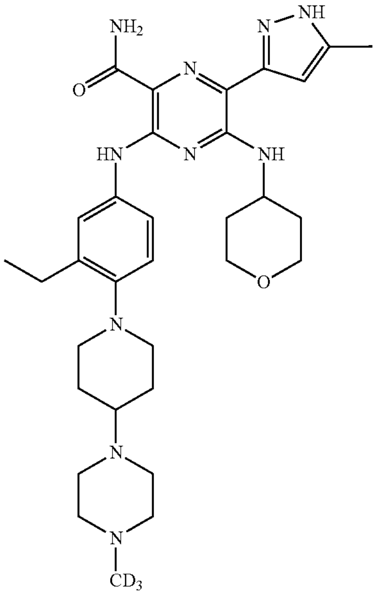
-continued
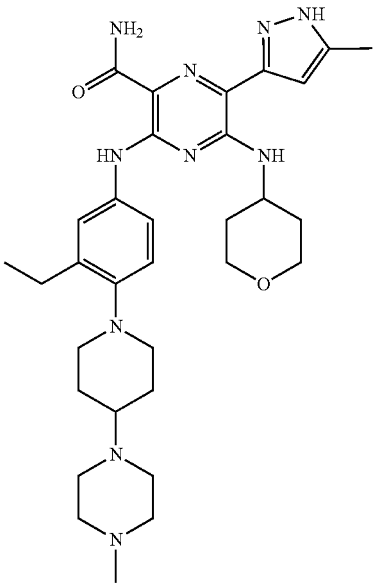
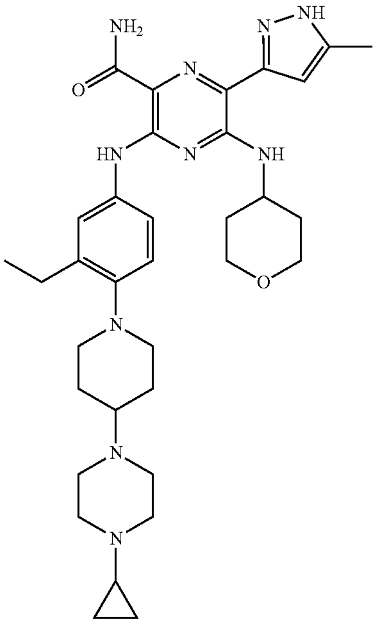
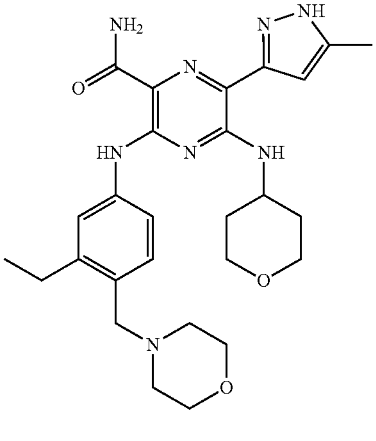

-continued
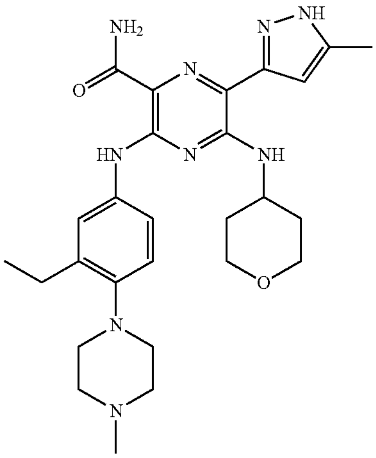
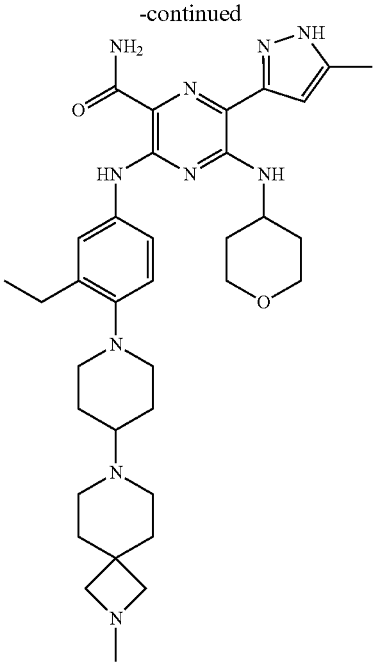
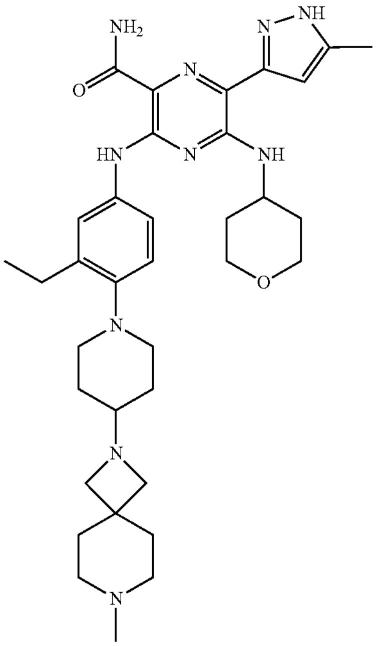
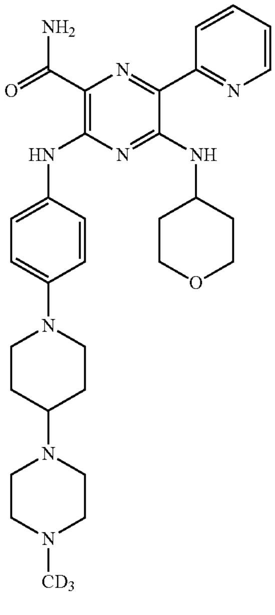

-continued
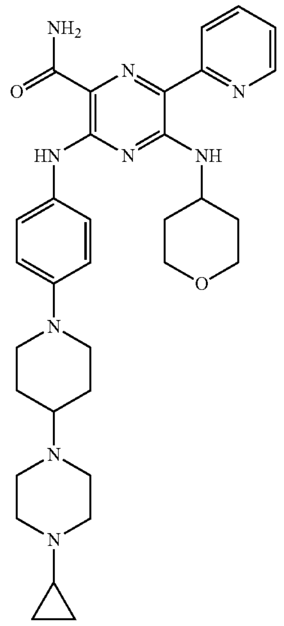
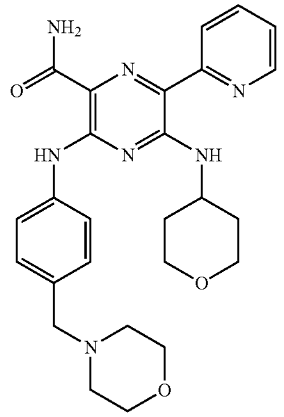
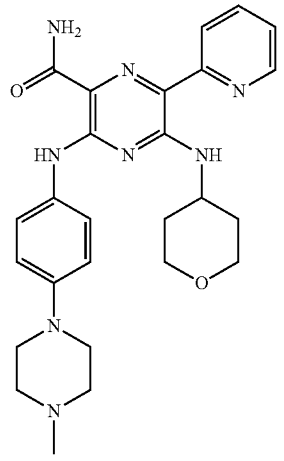
-continued
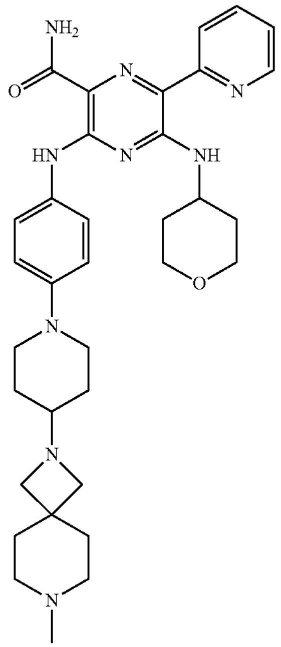
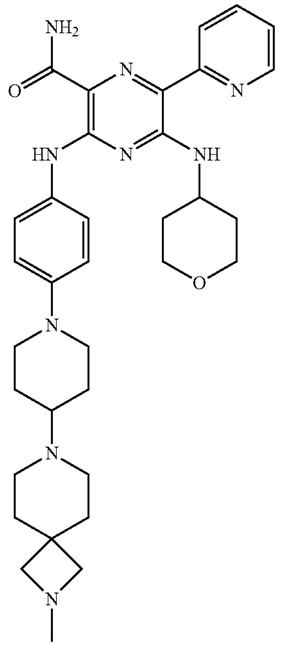

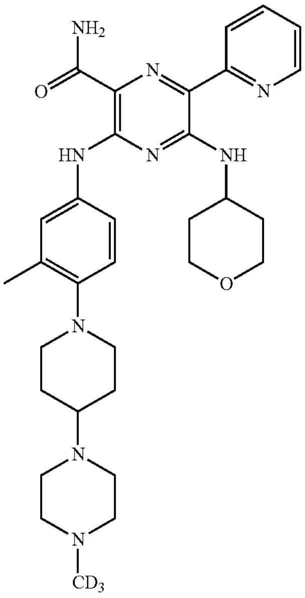
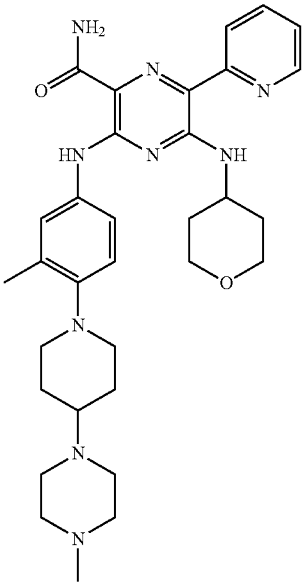
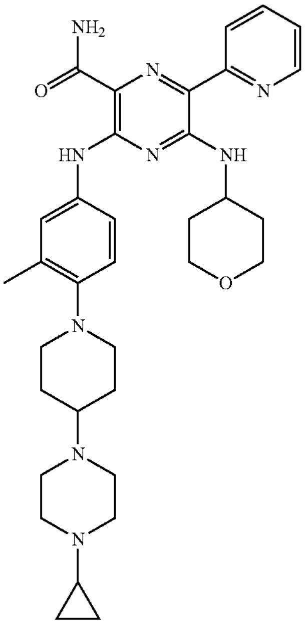
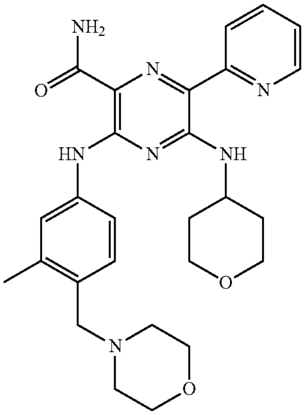
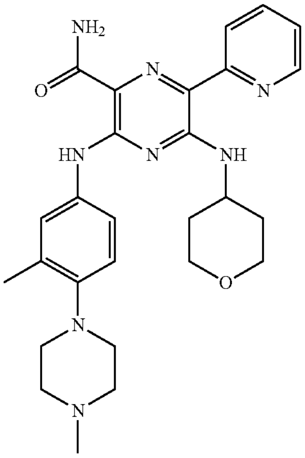

-continued
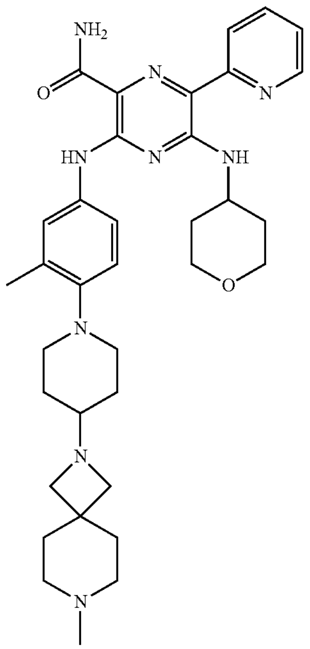
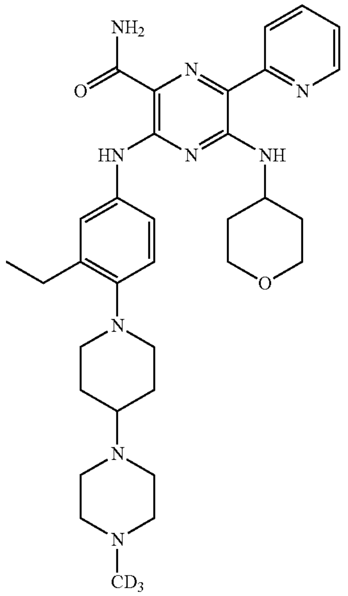
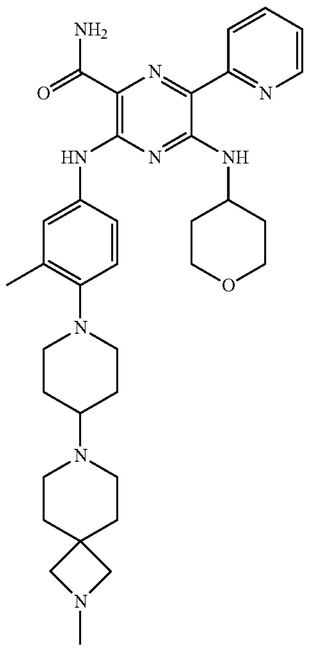
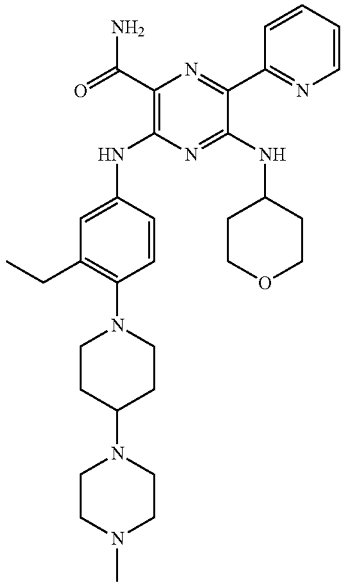
-continued

-continued
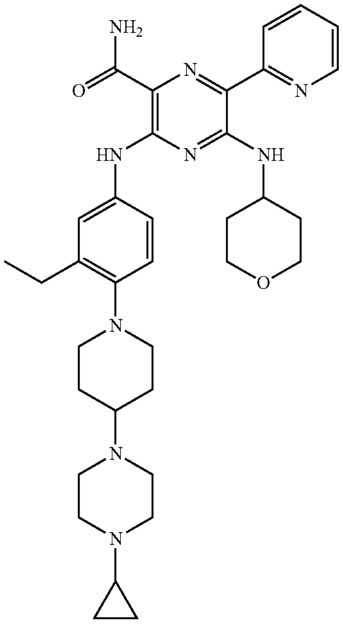
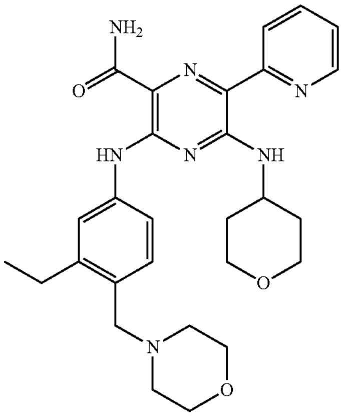
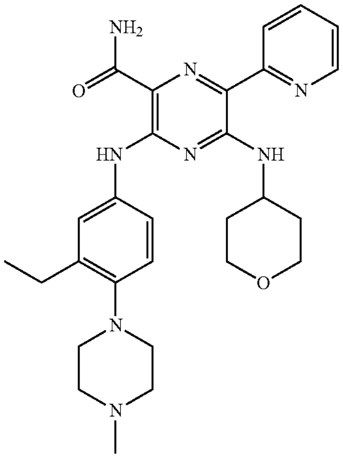
-continued
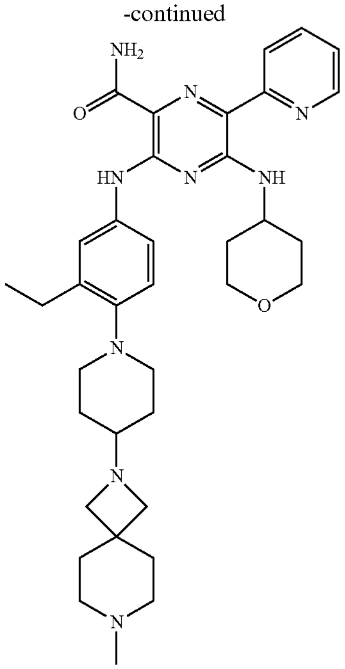
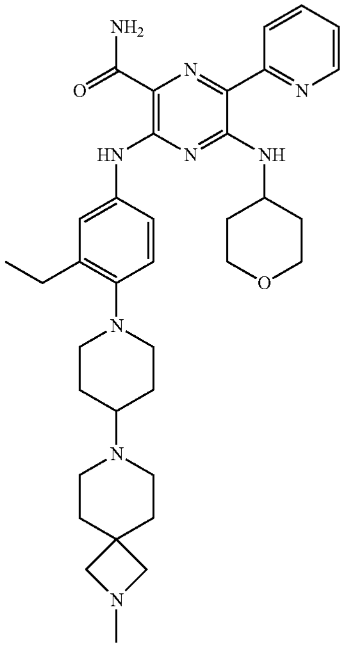

-continued
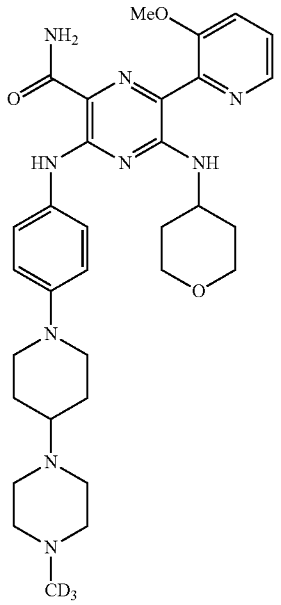
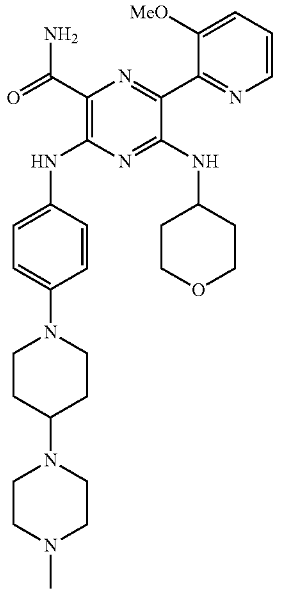
-continued
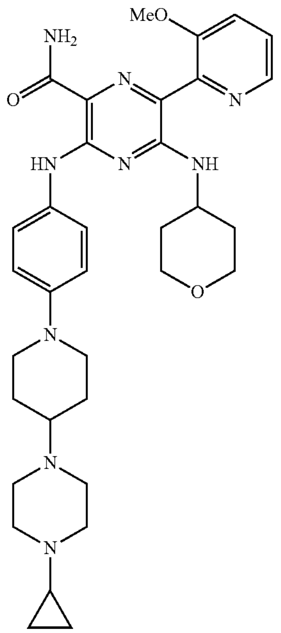
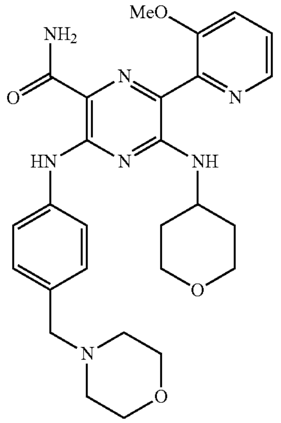
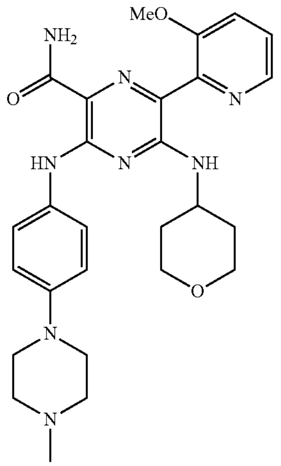

-continued
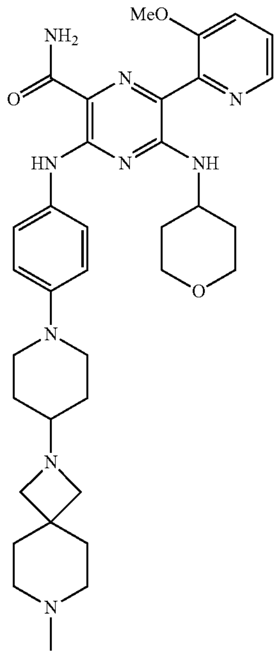
-continued
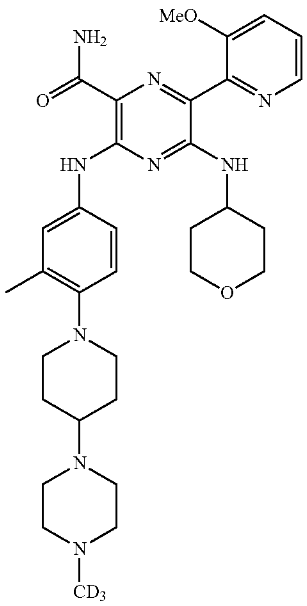
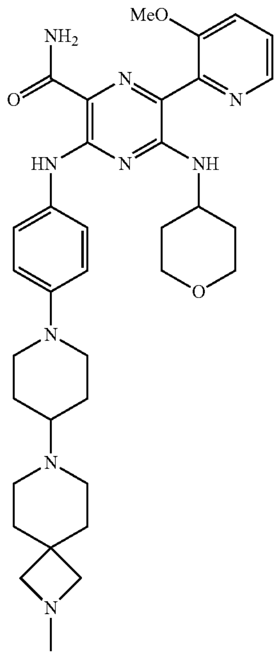
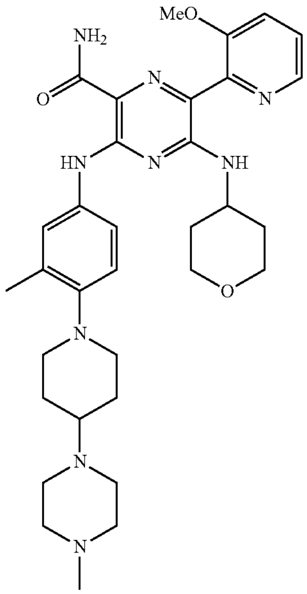

-continued
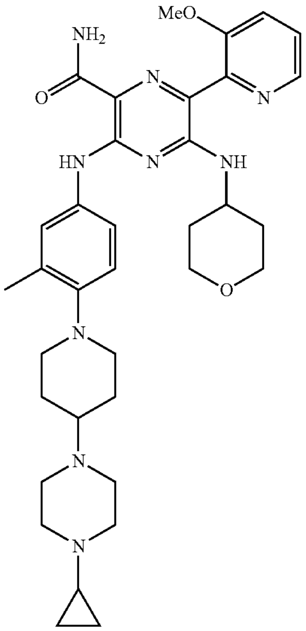
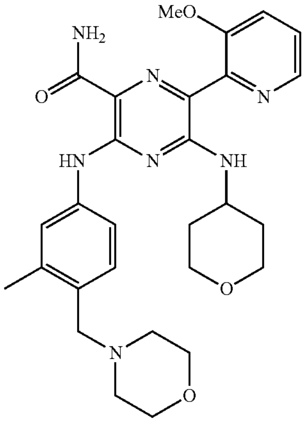
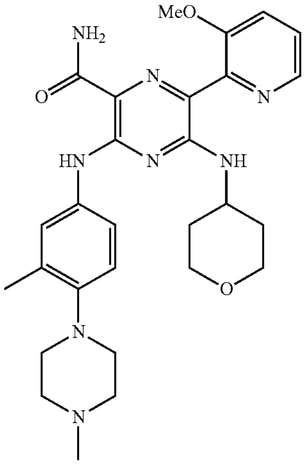
-continued
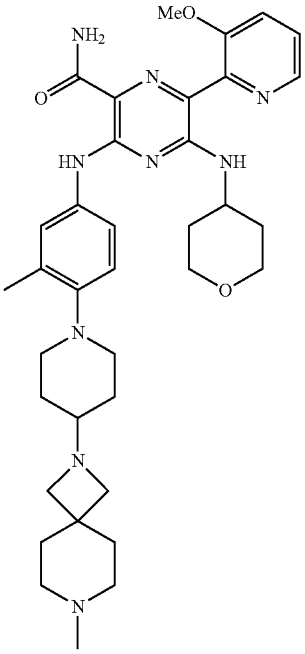
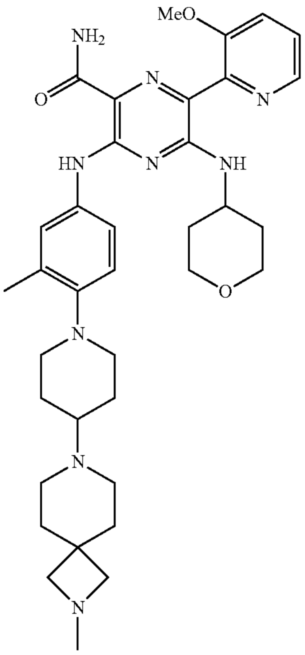

-continued
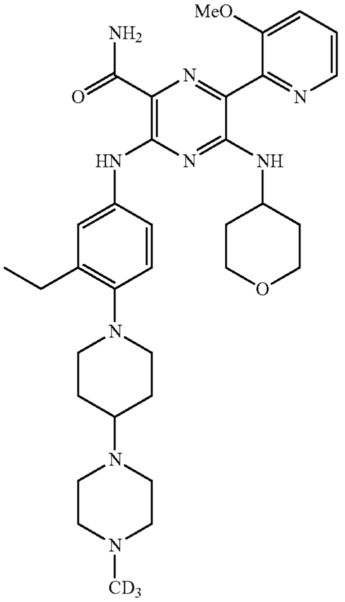
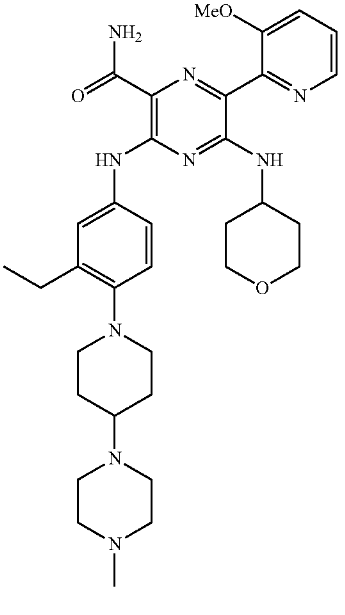
-continued
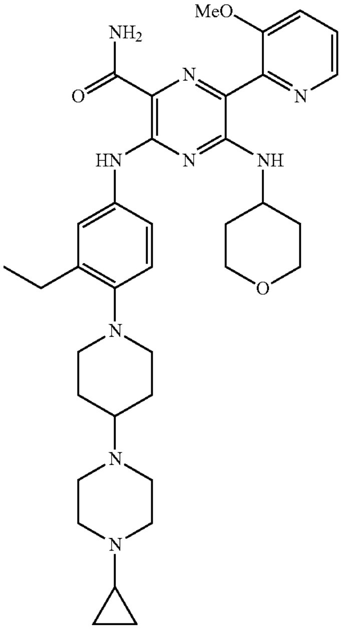
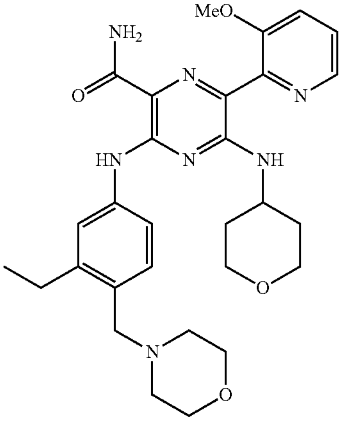
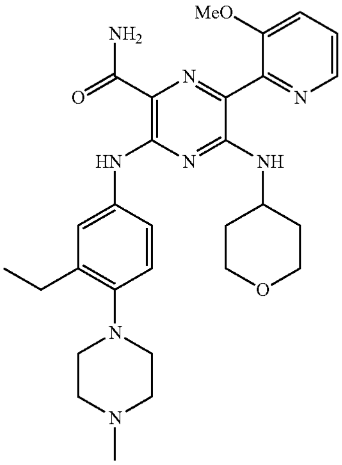

-continued
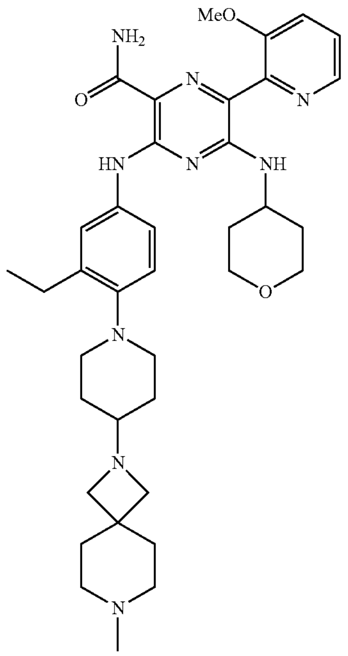
-continued
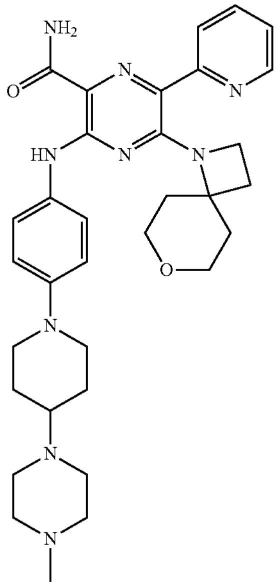
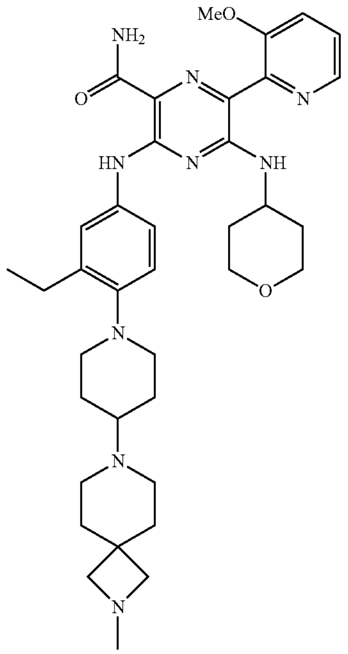
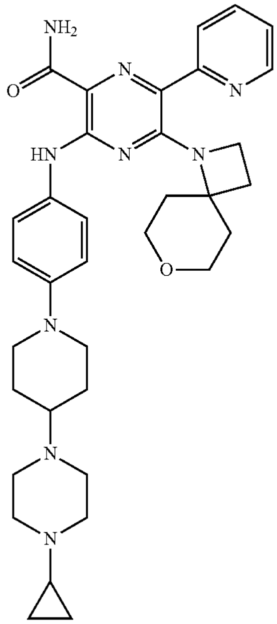

-continued
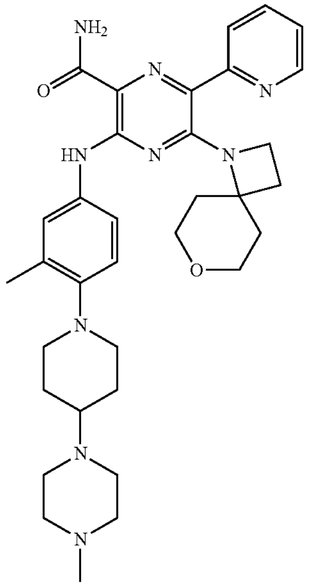
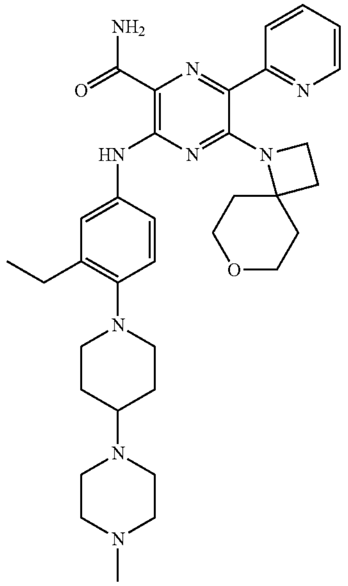
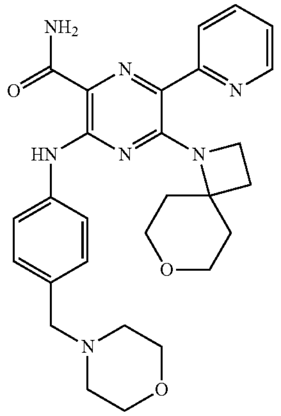
-continued
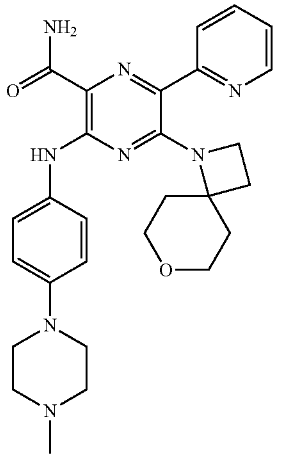
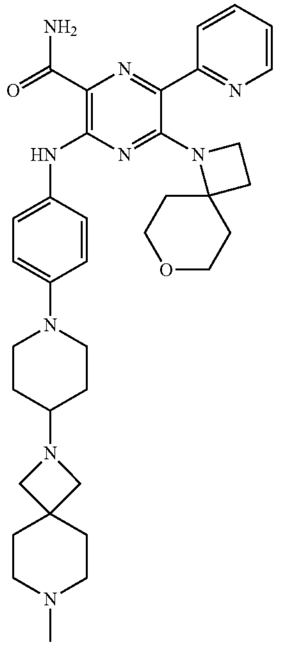

-continued
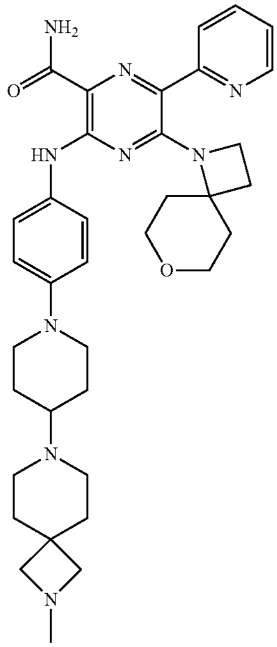
-continued
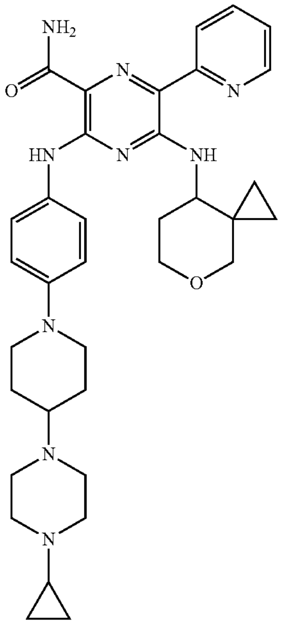
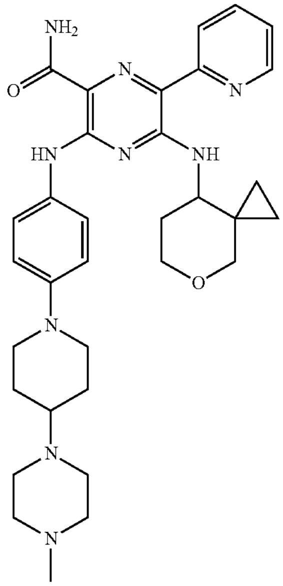
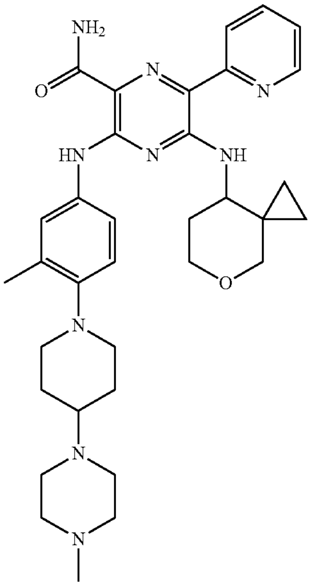

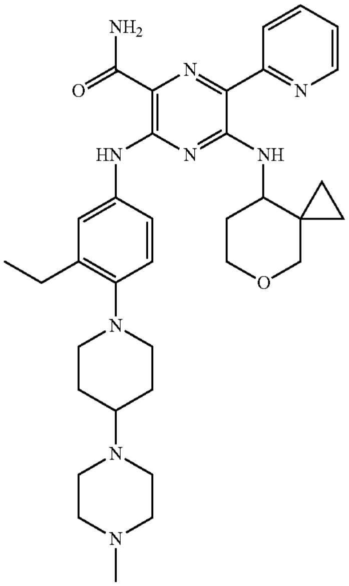
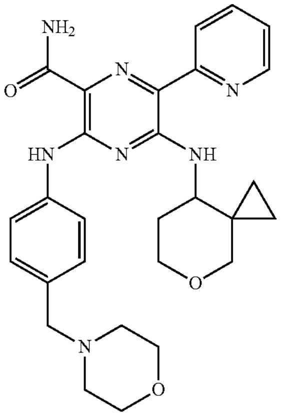
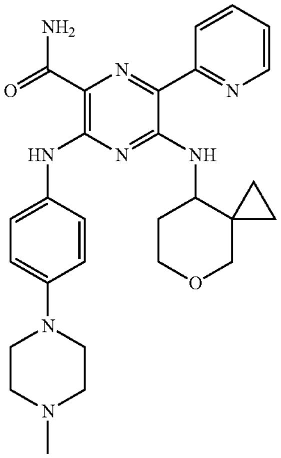
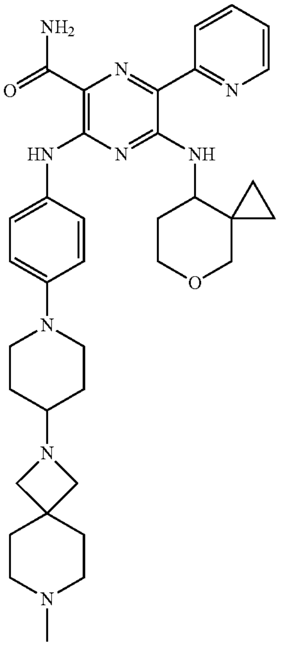
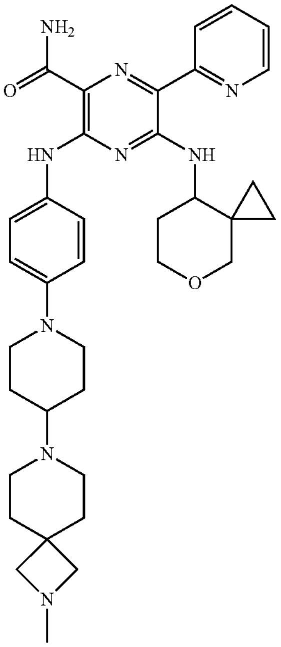

-continued
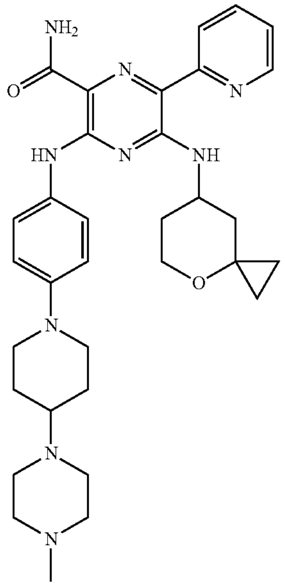
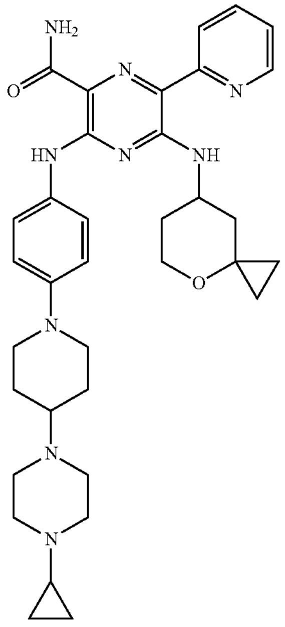
-continued
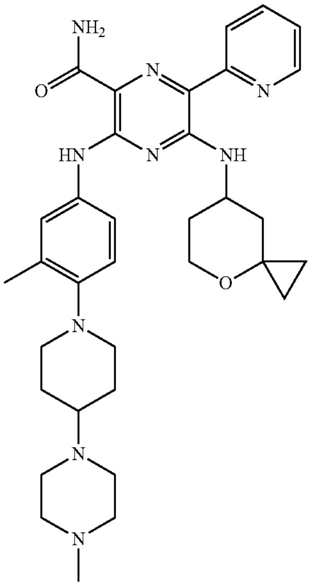
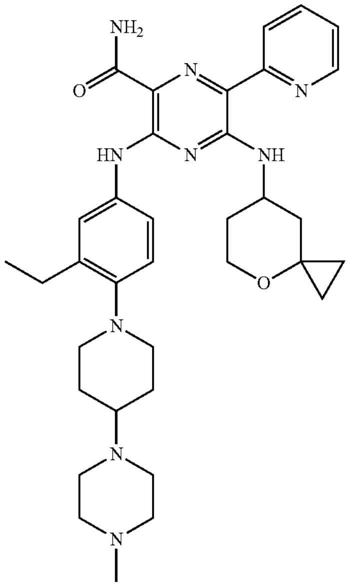
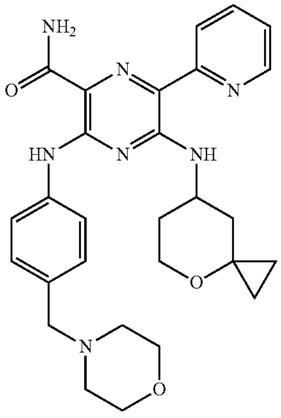

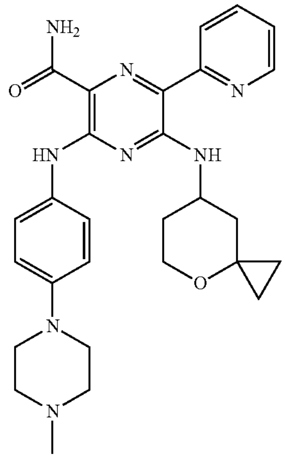
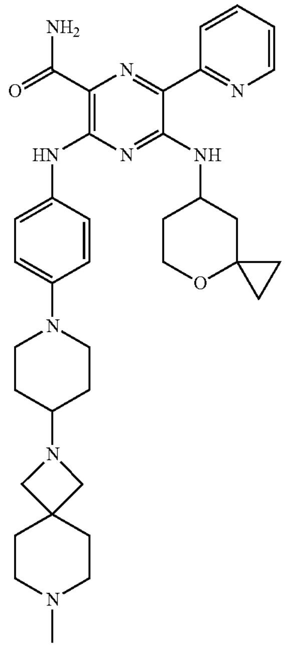
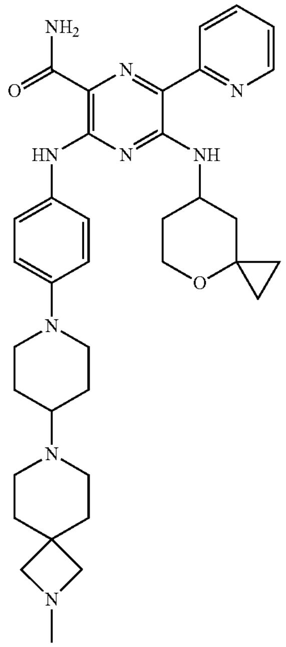
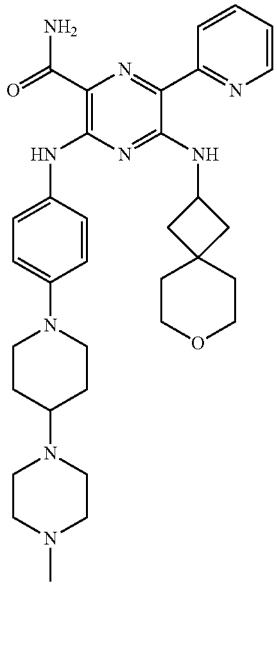

-continued
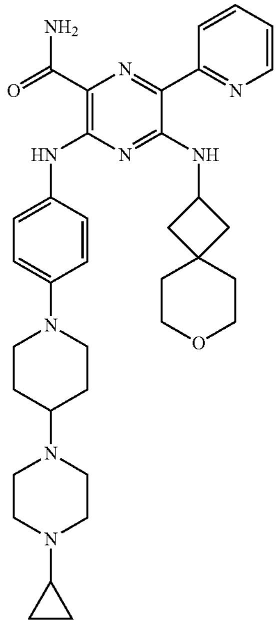
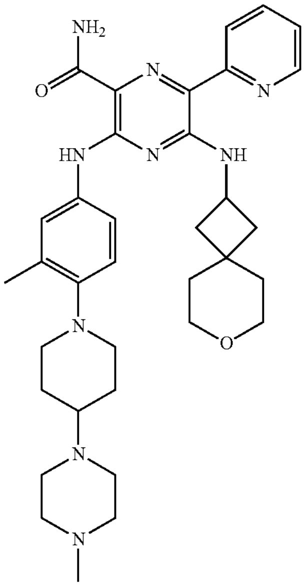
-continued
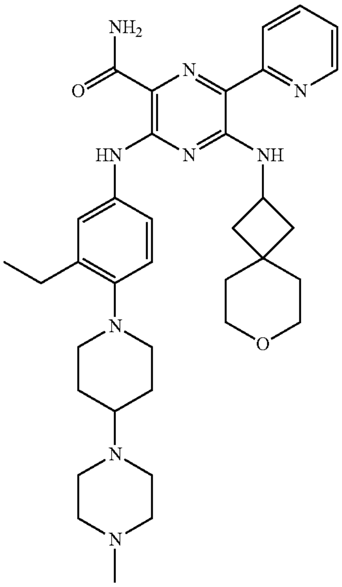
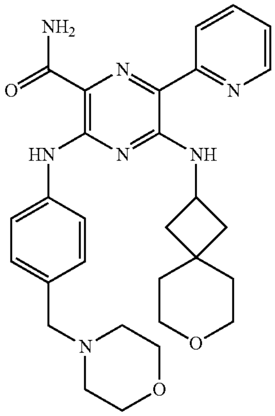
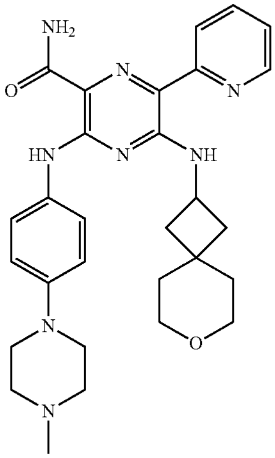

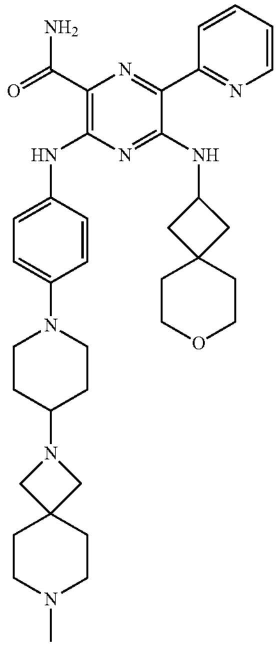
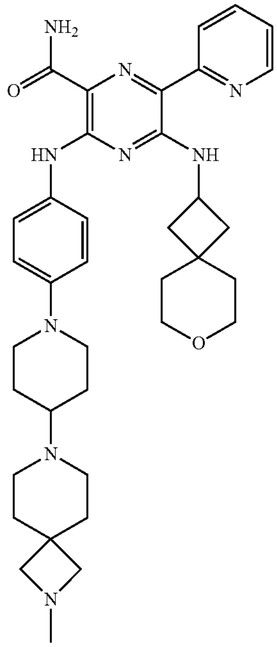
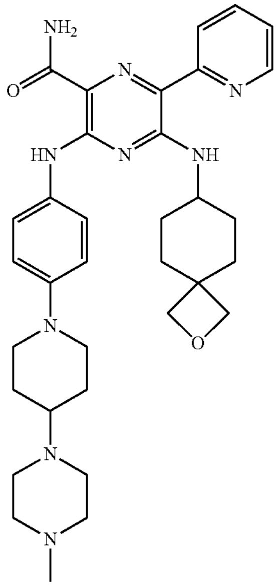
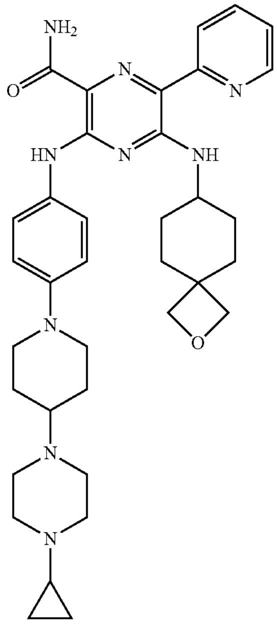

-continued
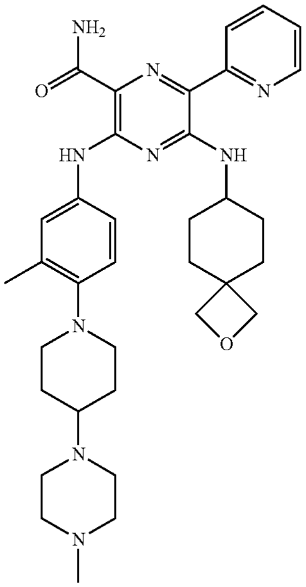
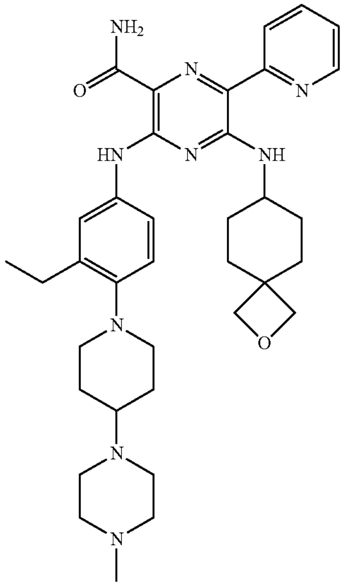
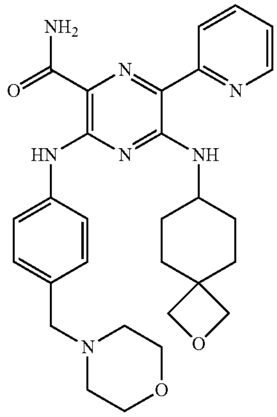
-continued
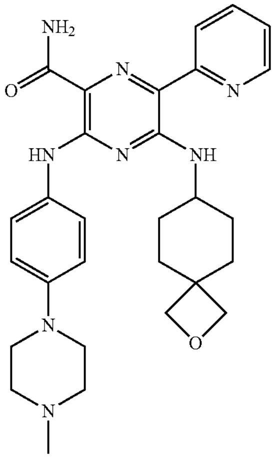
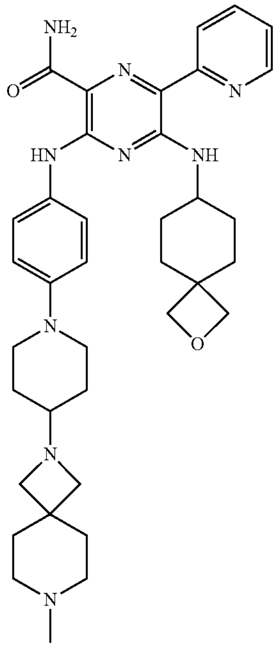

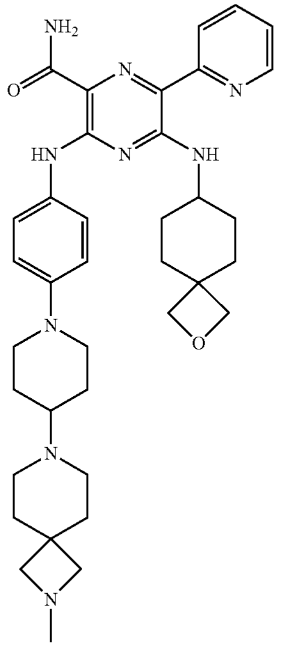
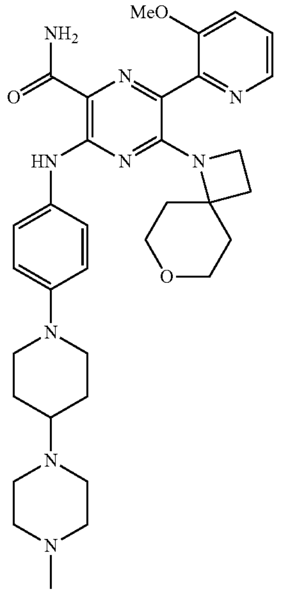
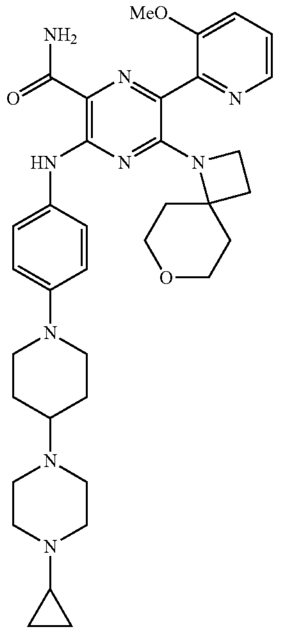
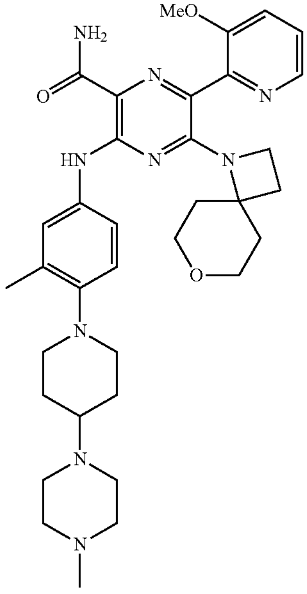

-continued
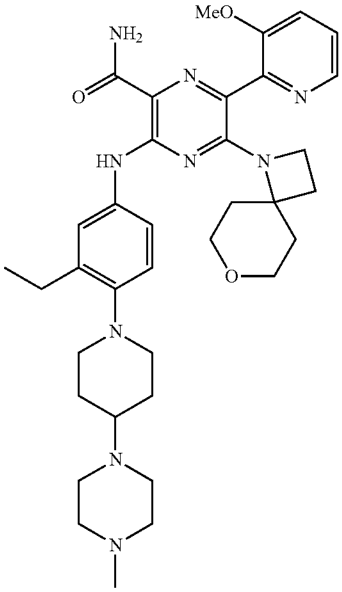
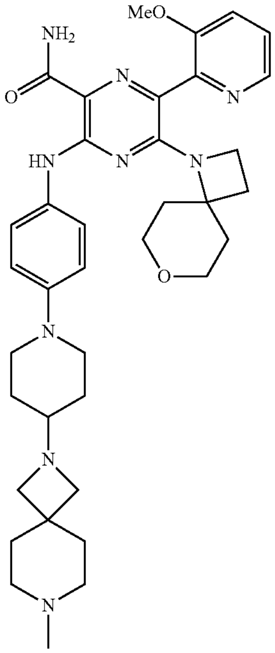
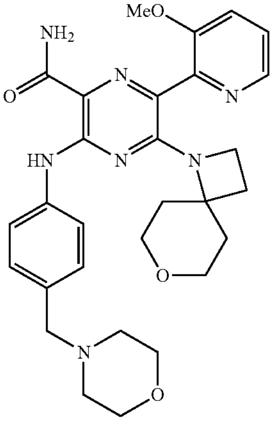
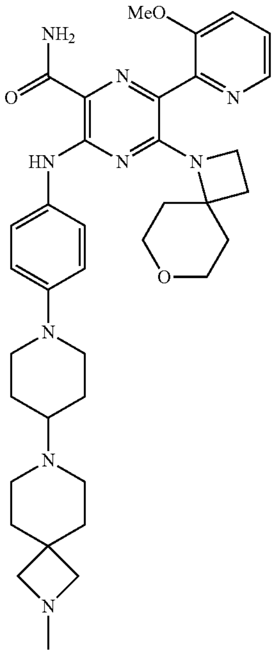
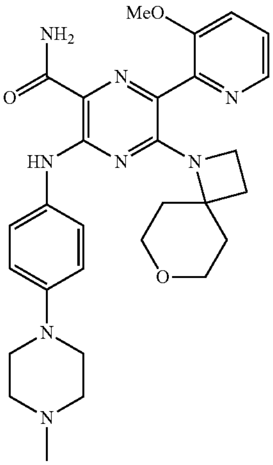
-continued -continued
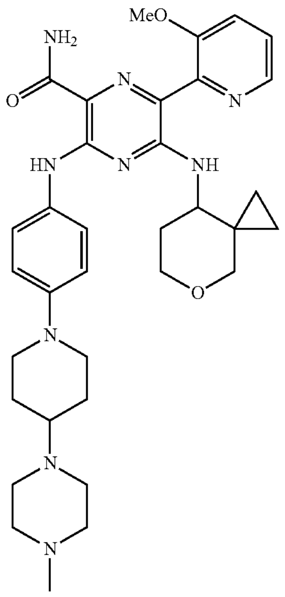
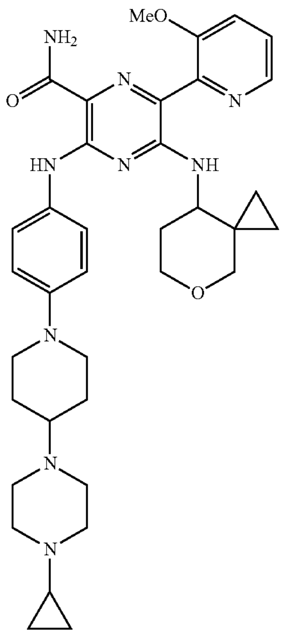
-continued
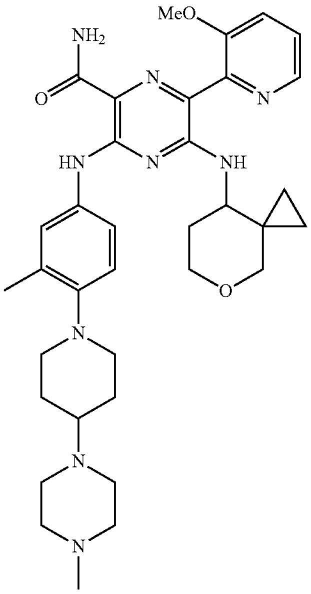
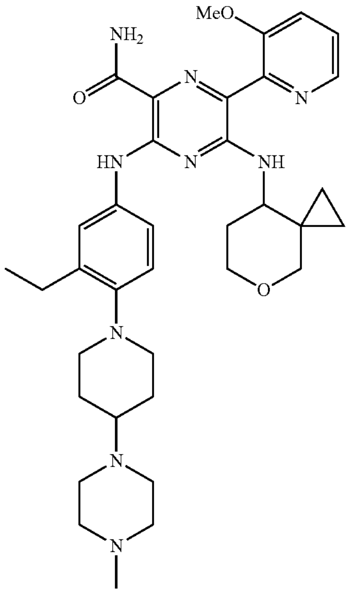
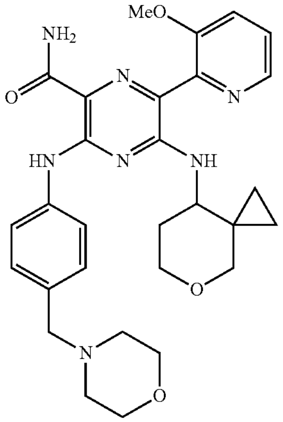

-continued
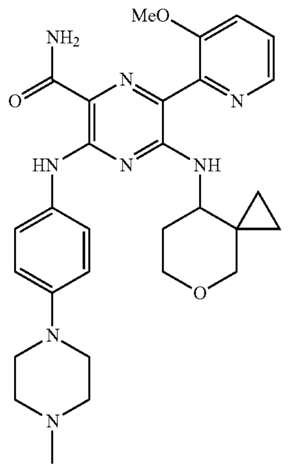
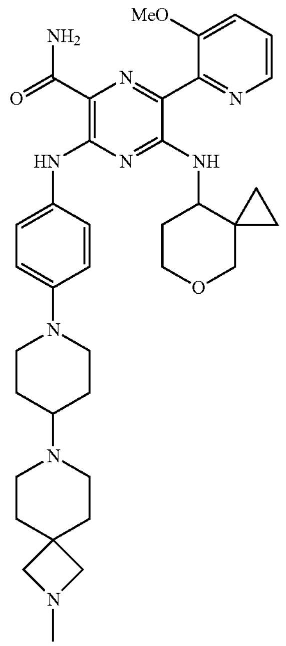
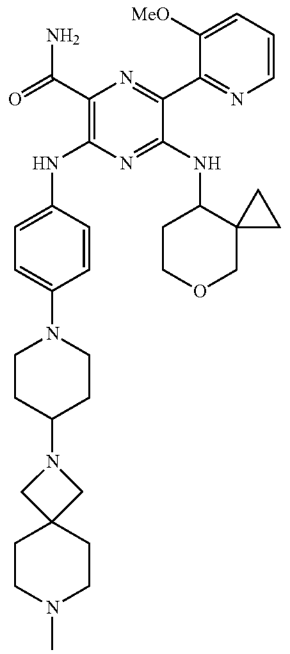
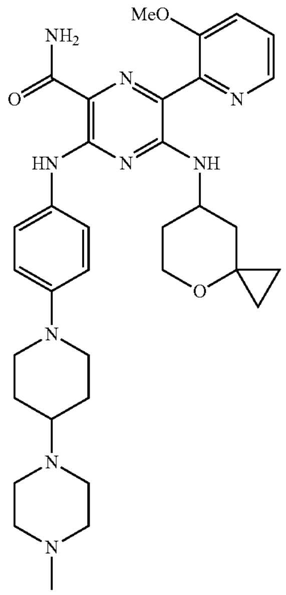

-continued
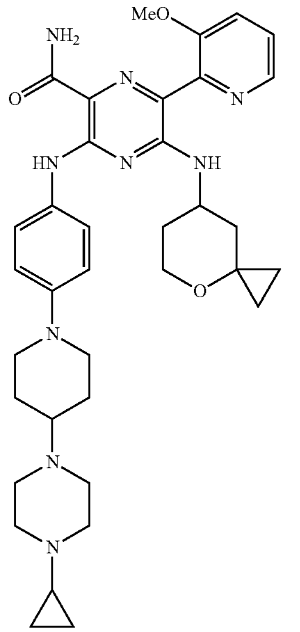
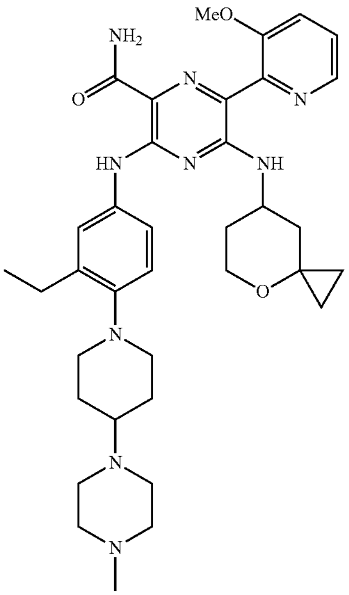
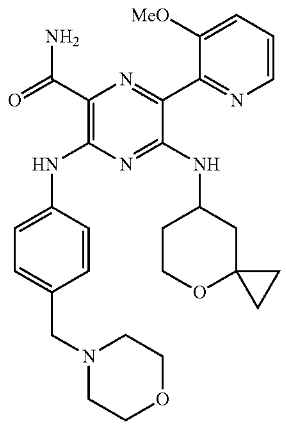
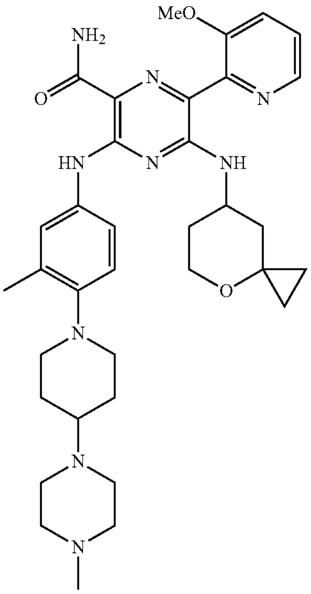
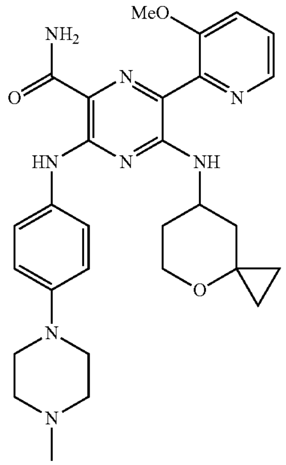

-continued
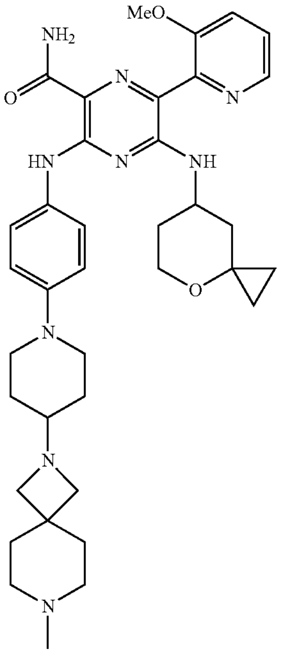
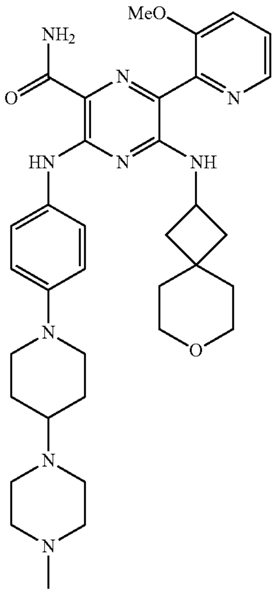
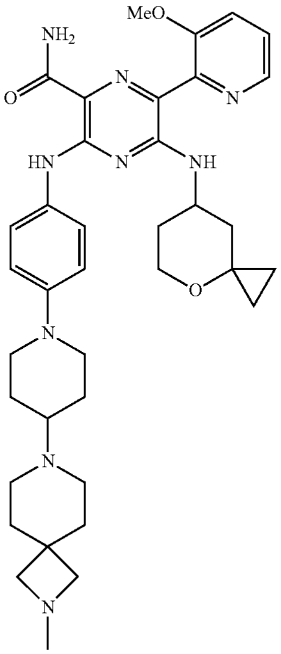
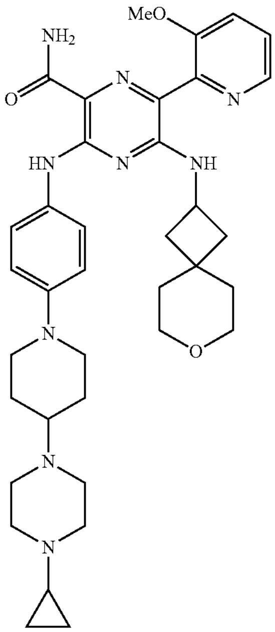

-continued
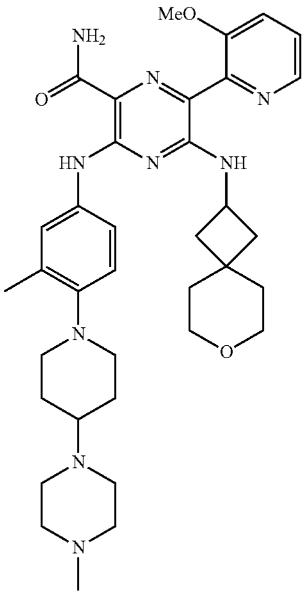
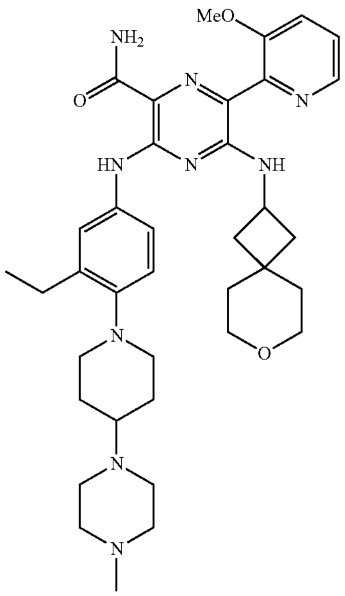
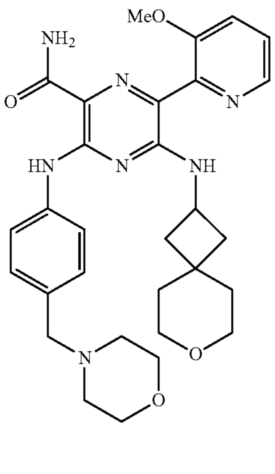
-continued
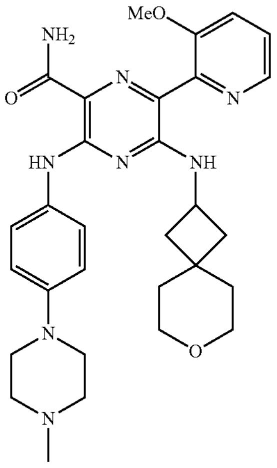
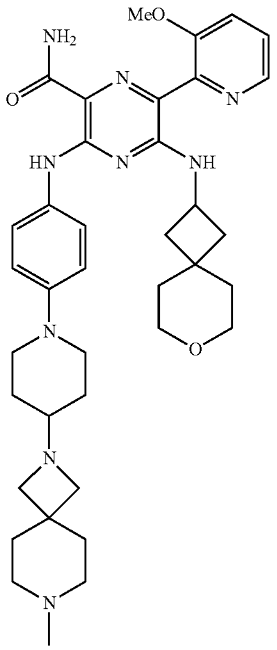

-continued
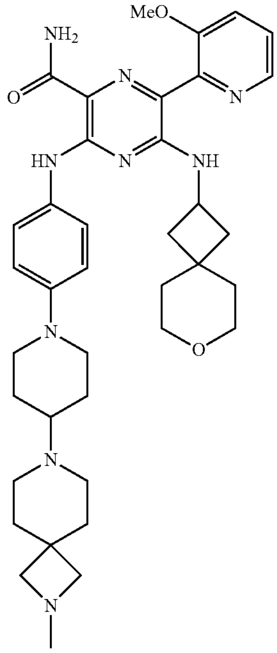
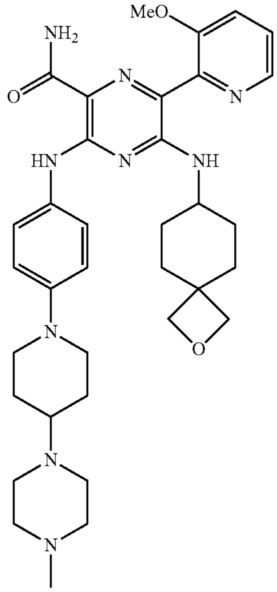
-continued
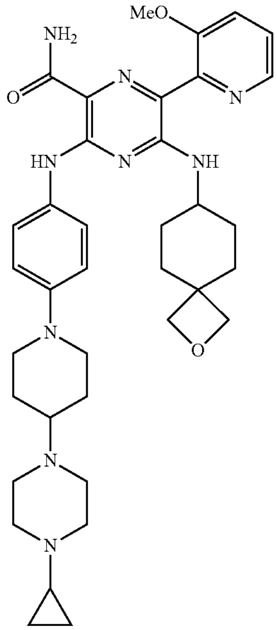
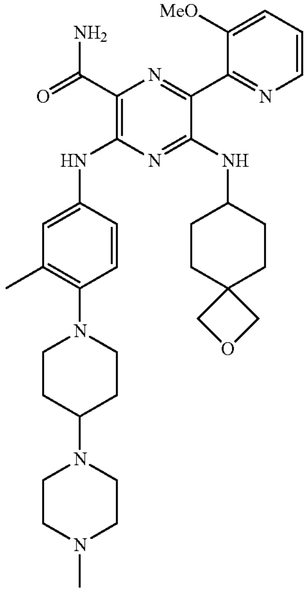

-continued
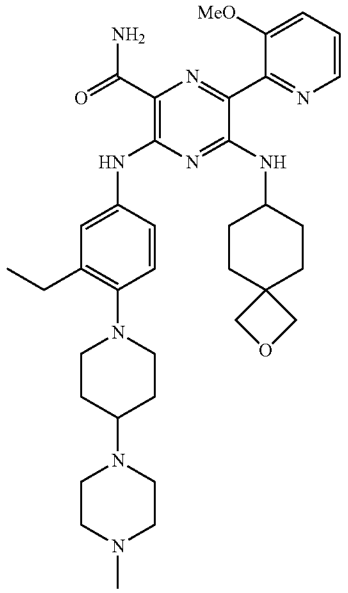
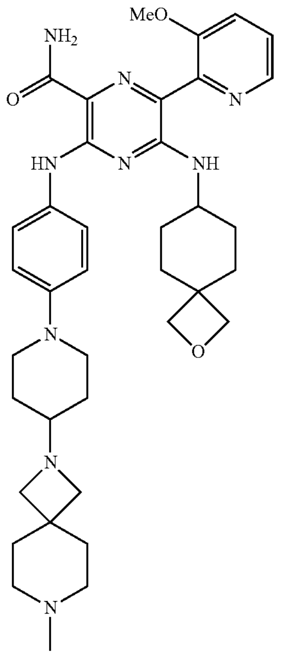
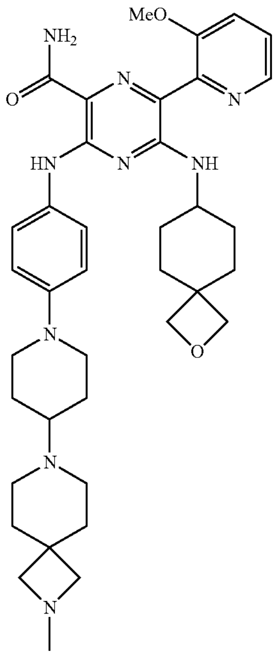
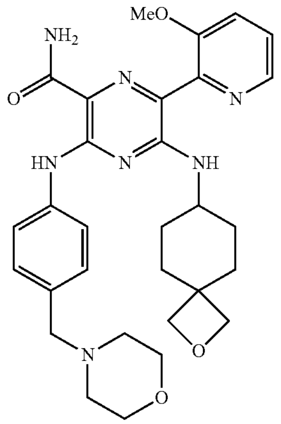
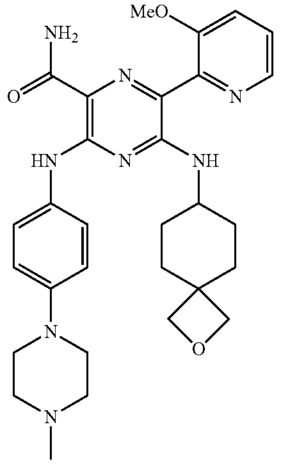
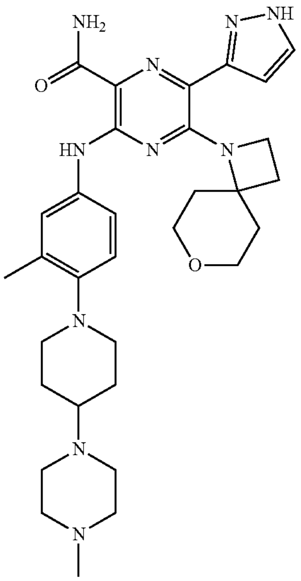

-continued
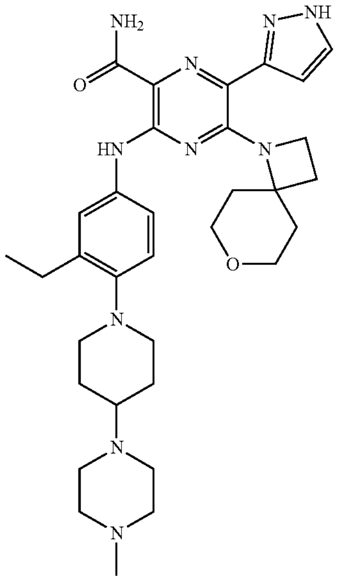
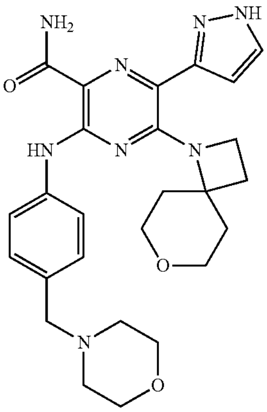
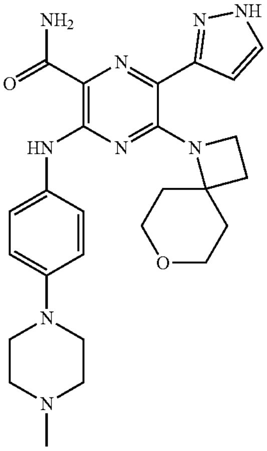
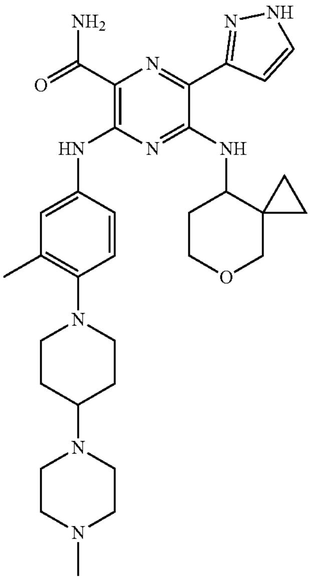
-continued
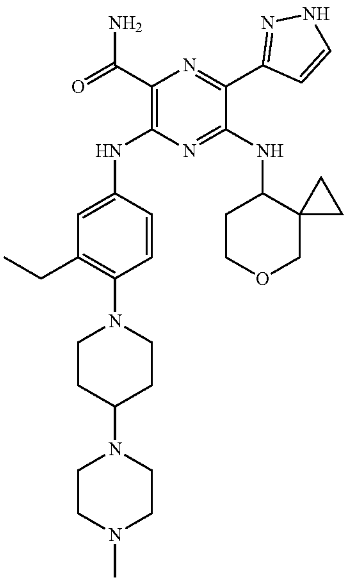
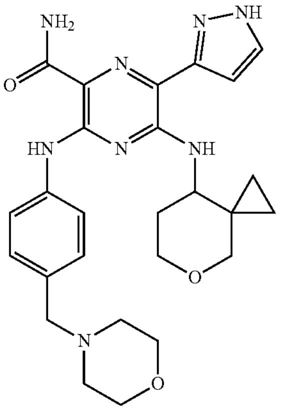
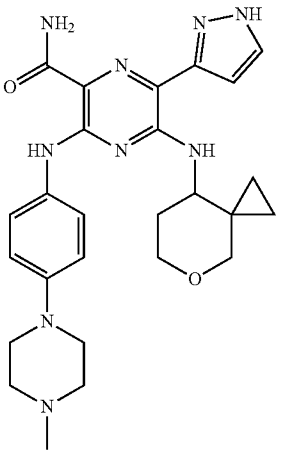

-continued
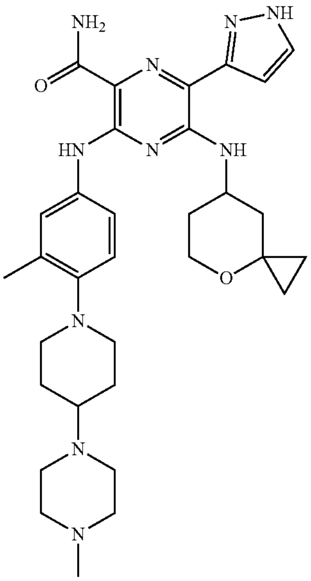
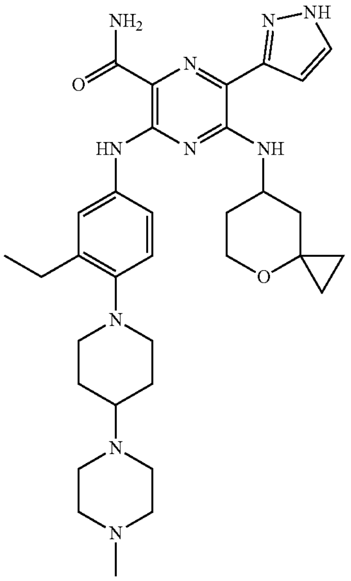
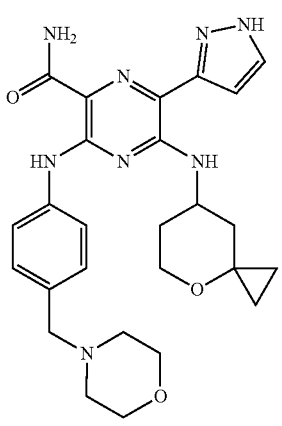
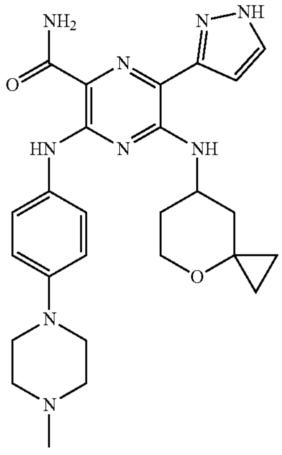
-continued
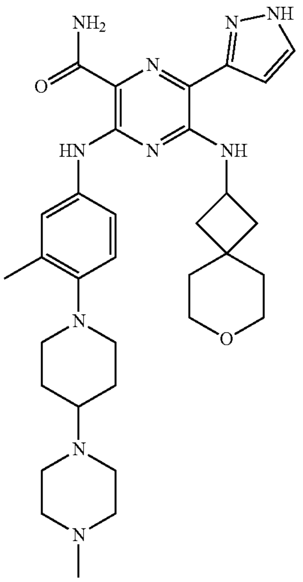
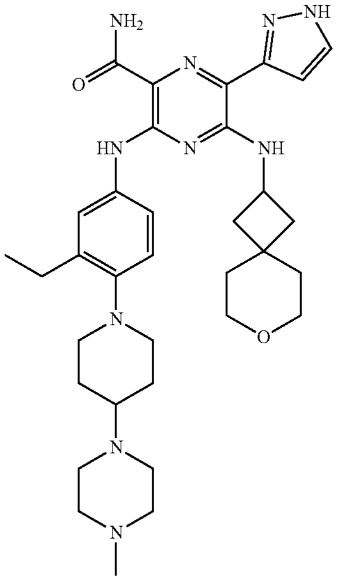
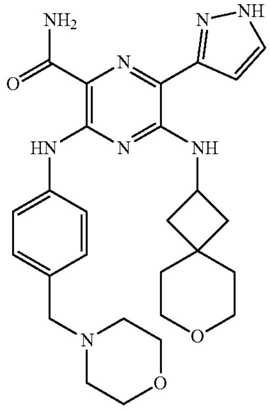
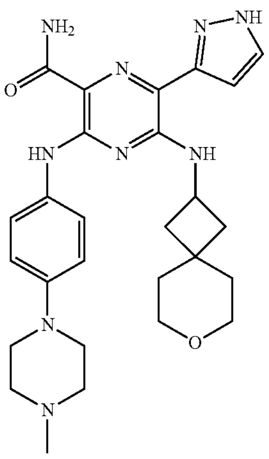

-continued
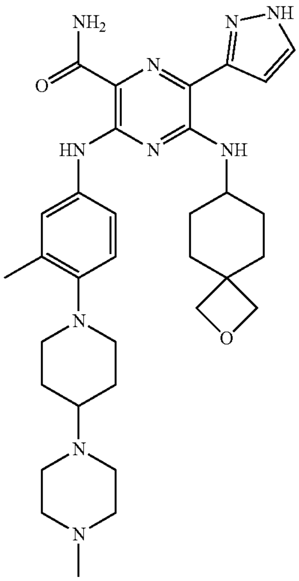
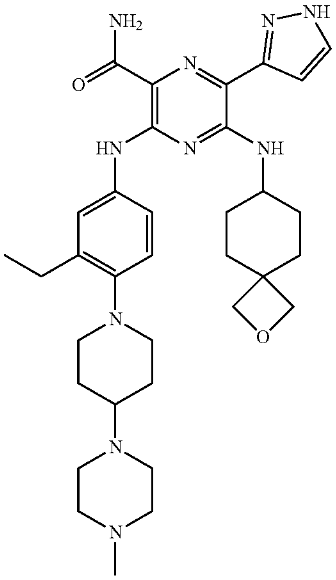
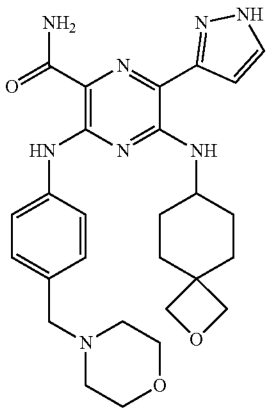
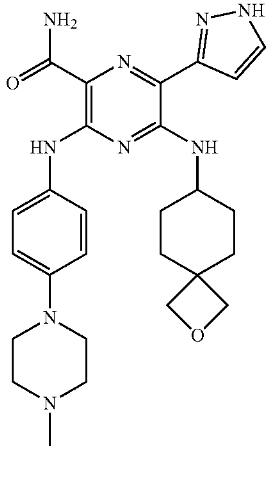
-continued
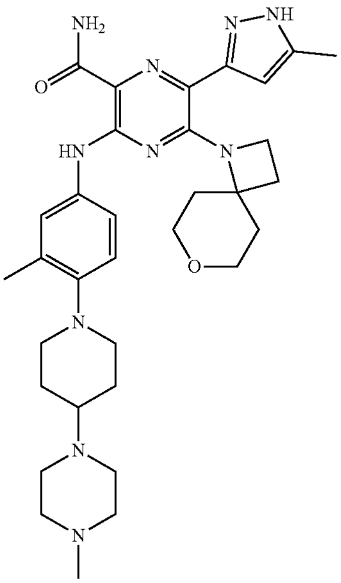
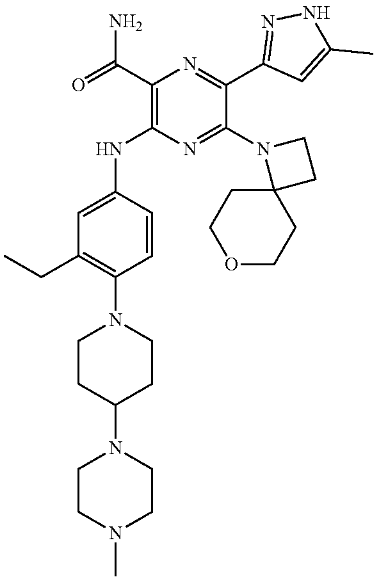
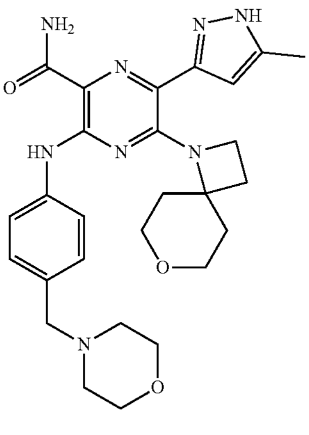

-continued
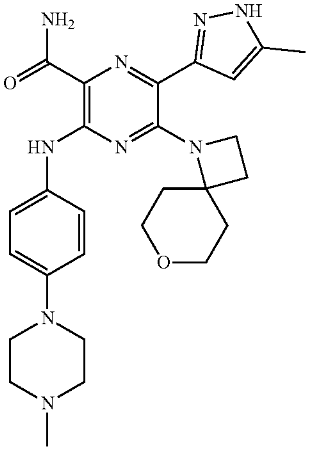
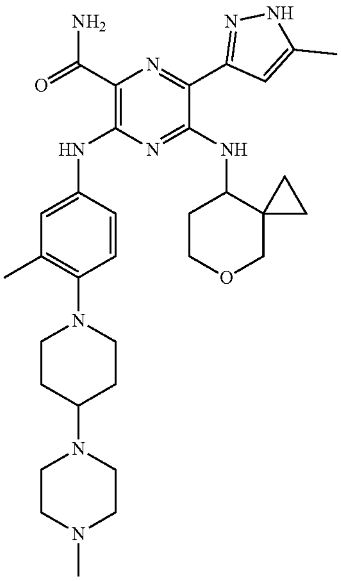
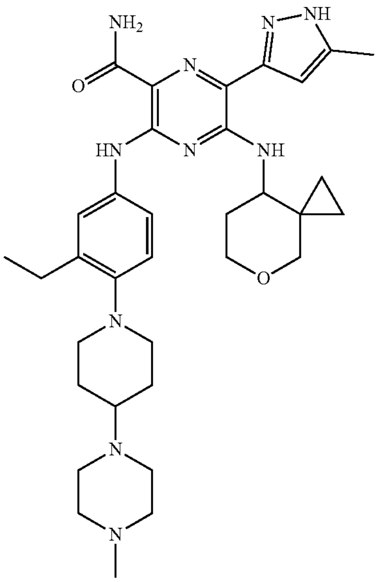
-continued
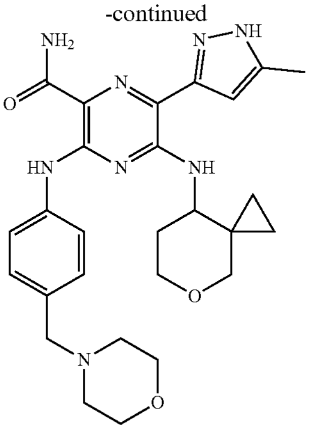
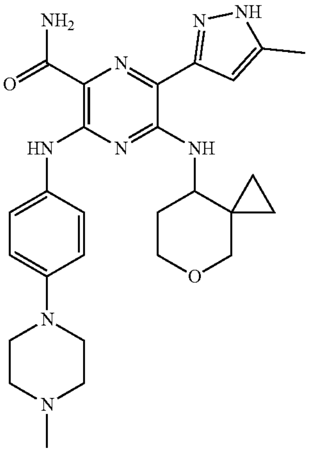
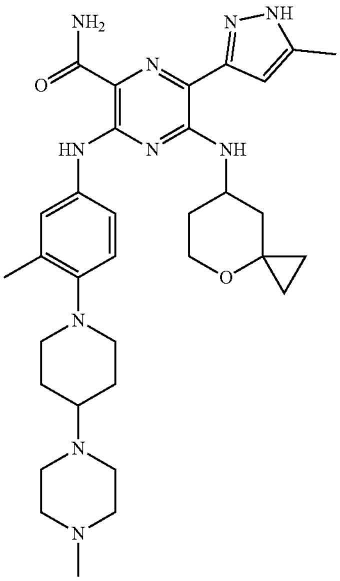

-continued
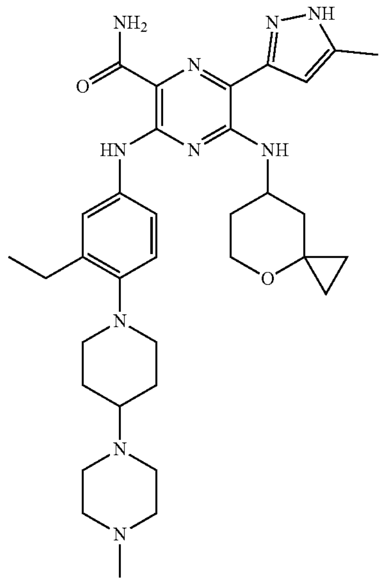
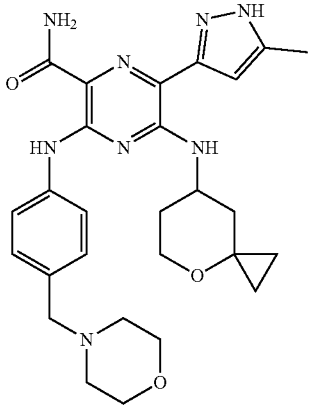
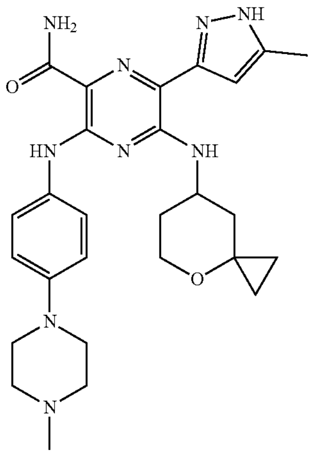
-continued
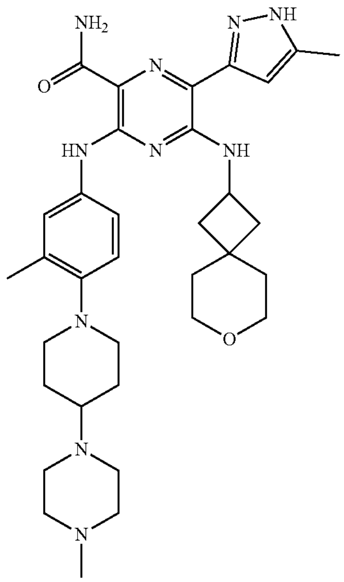
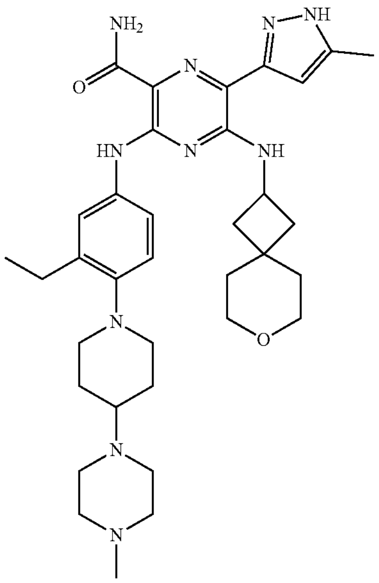
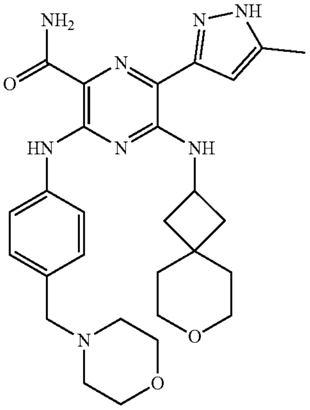

-continued
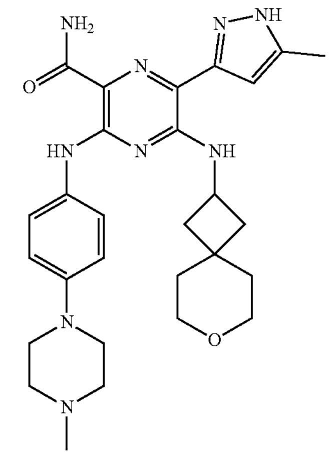
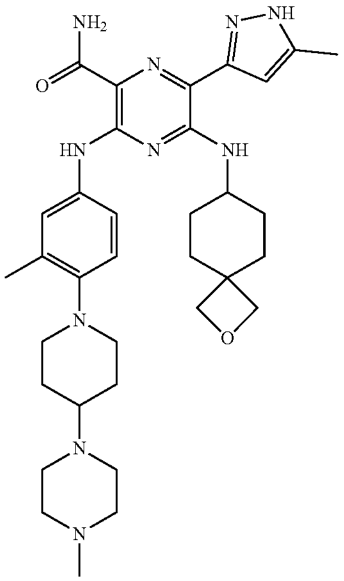
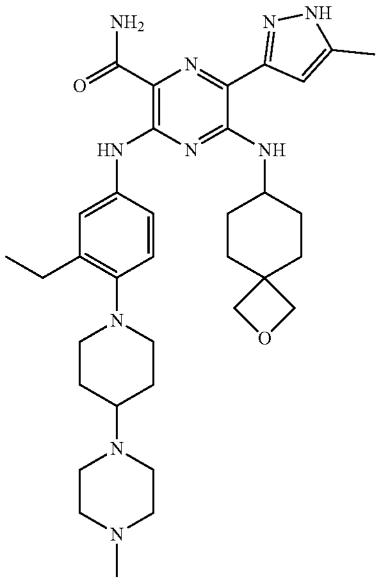
-continued
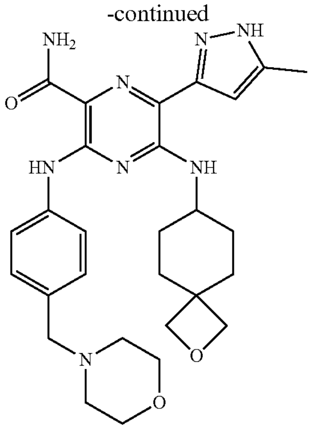
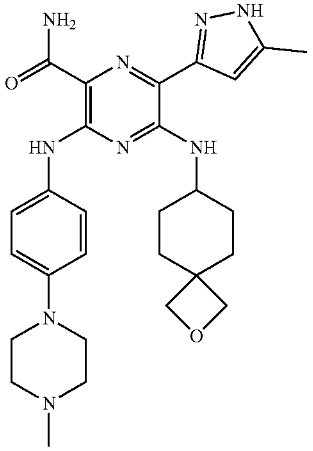
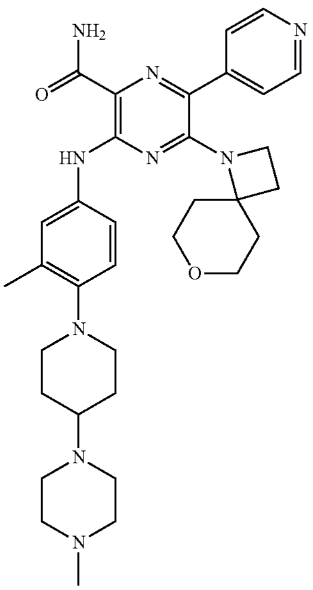

-continued
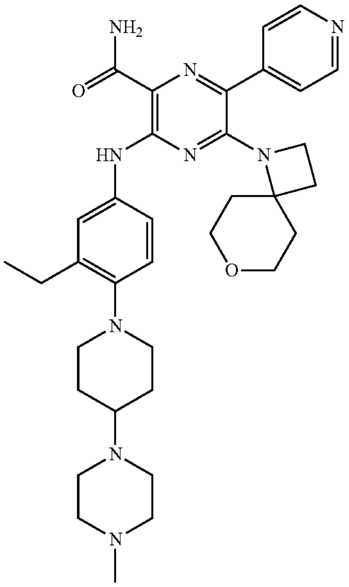
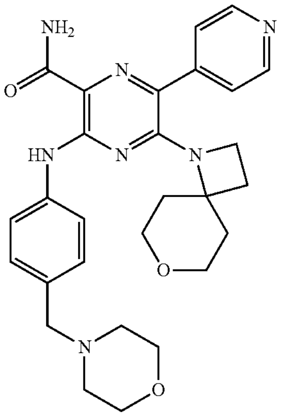
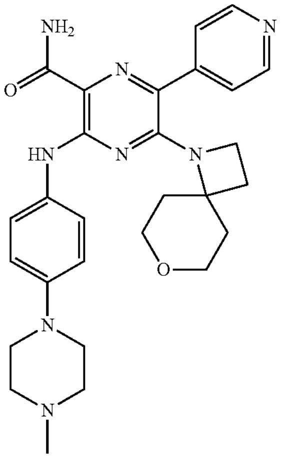
-continued
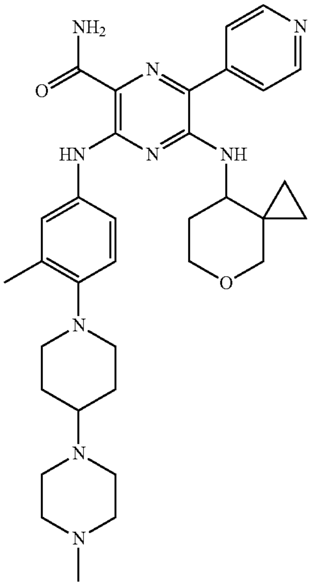
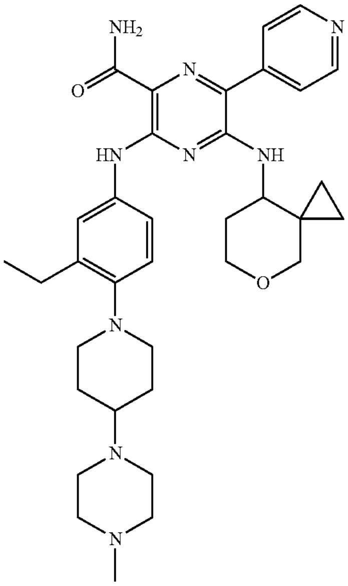
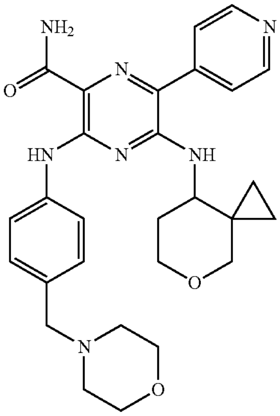

-continued
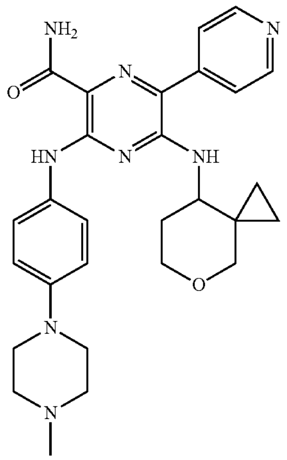
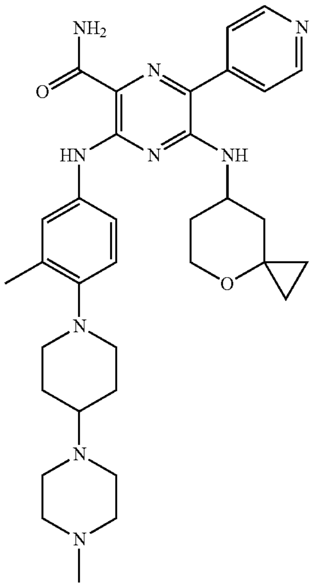
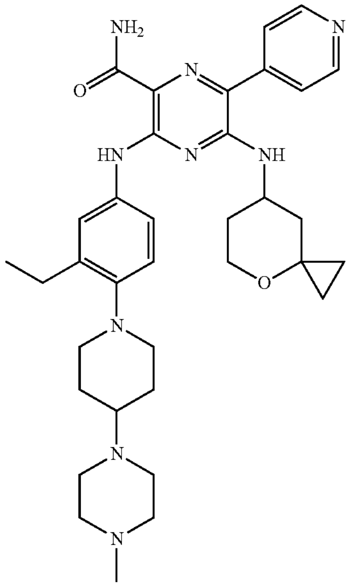
-continued
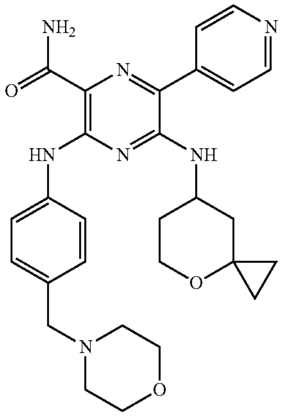
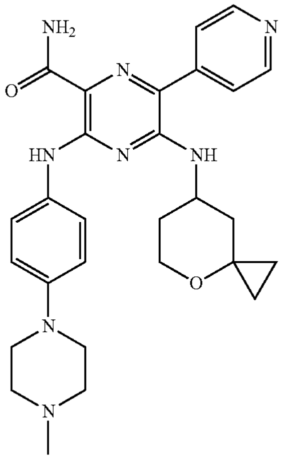
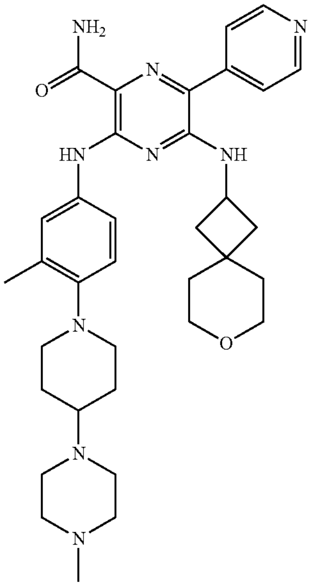

-continued
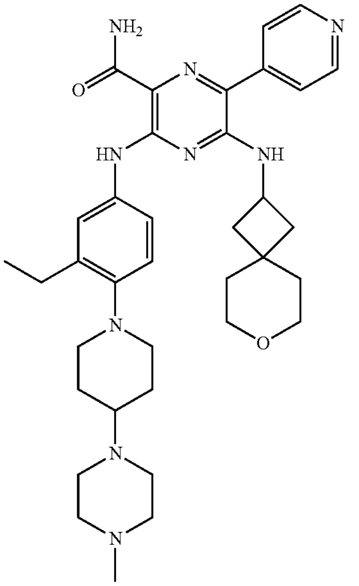
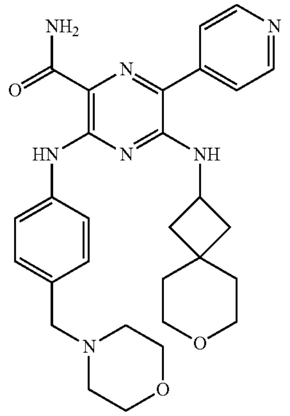
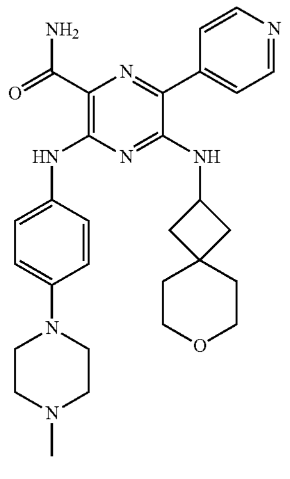
-continued
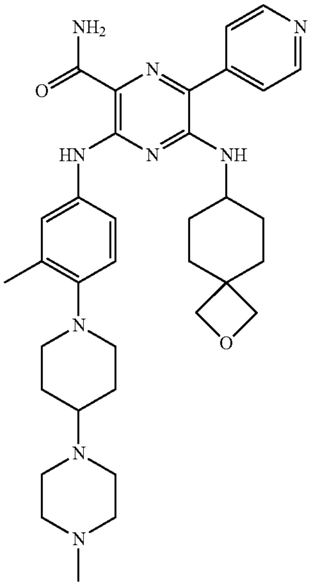
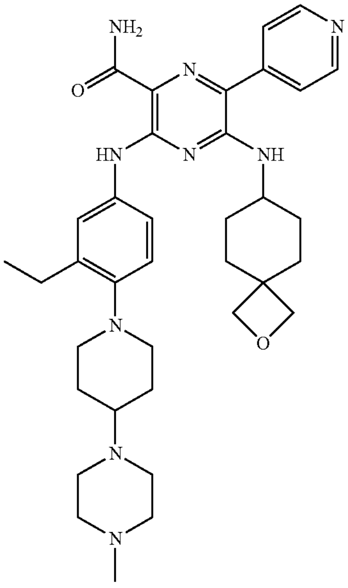
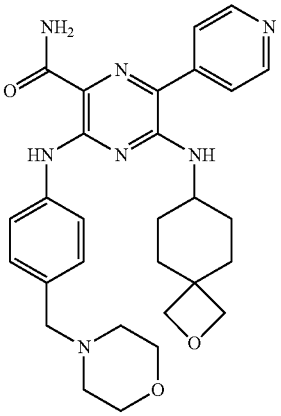

-continued
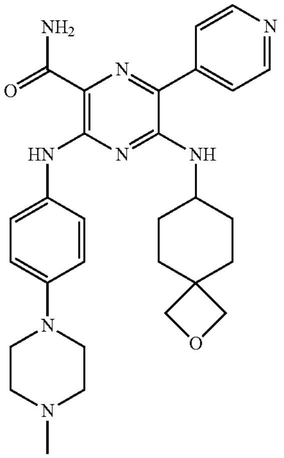
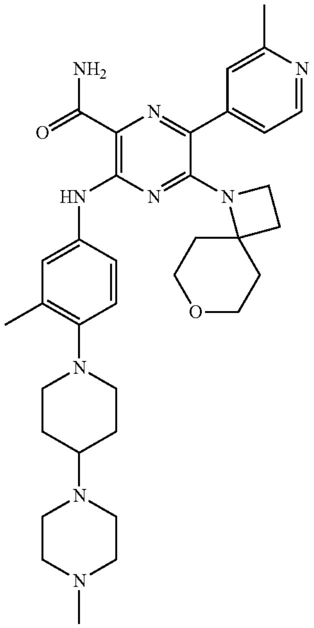
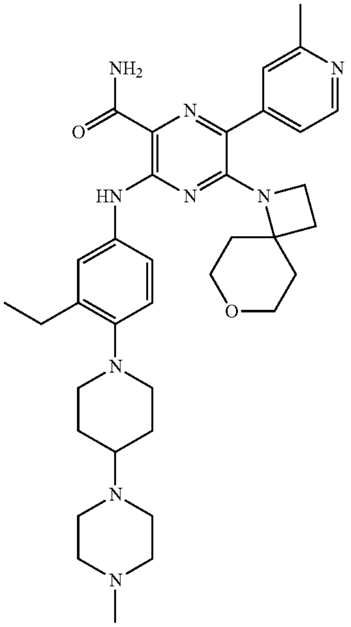
-continued
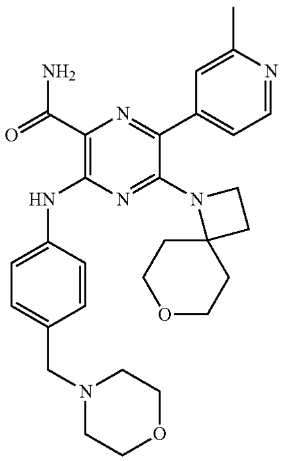
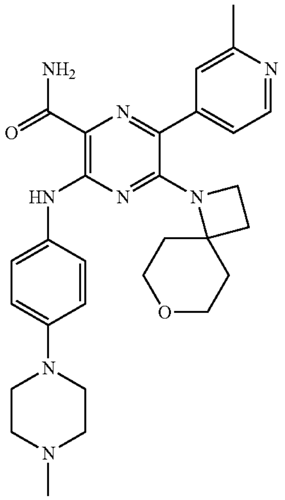
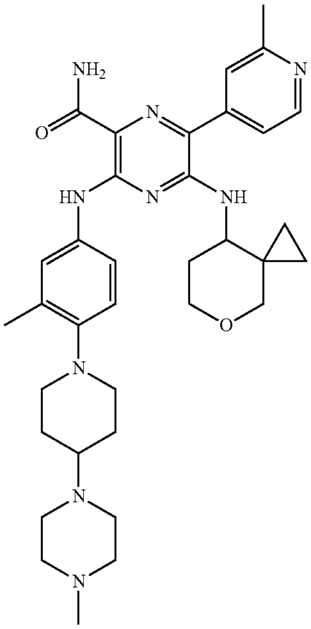

-continued
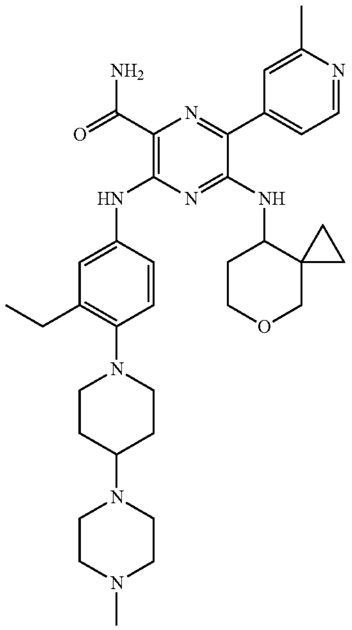
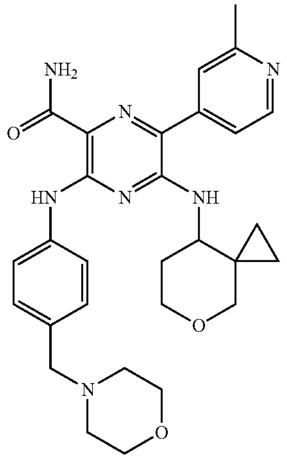
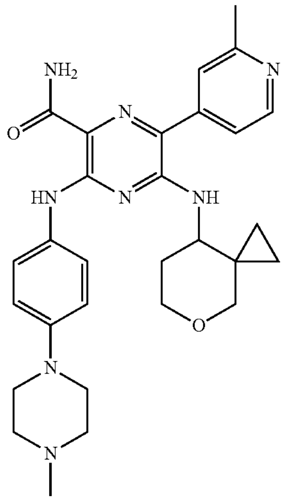
-continued
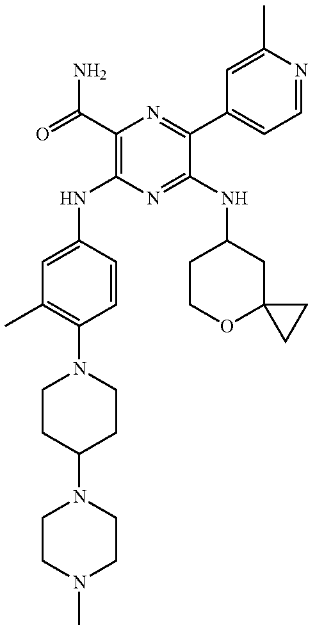
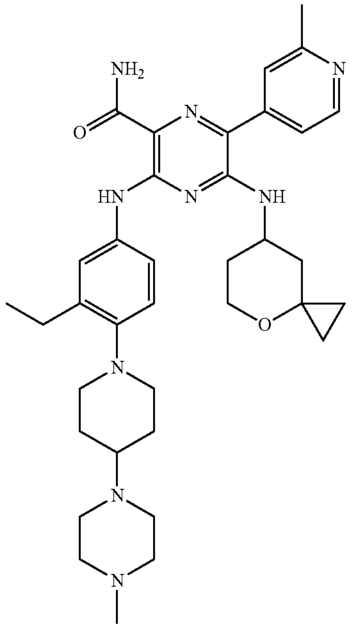
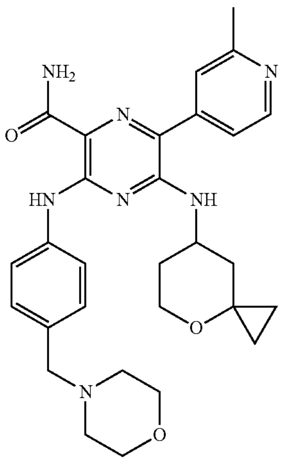

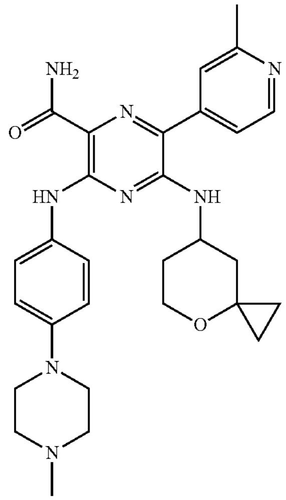
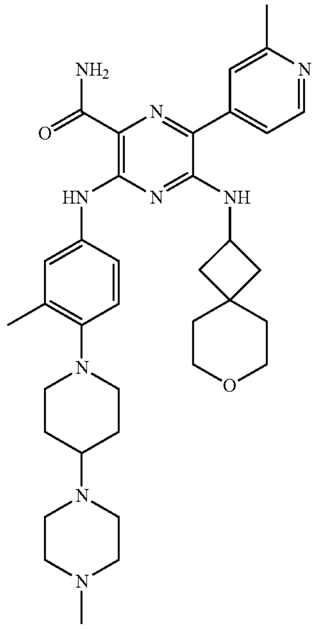
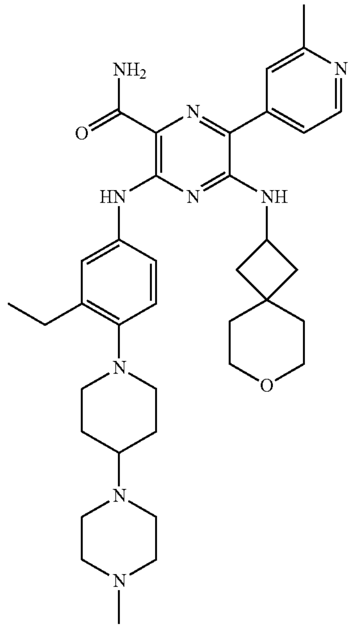
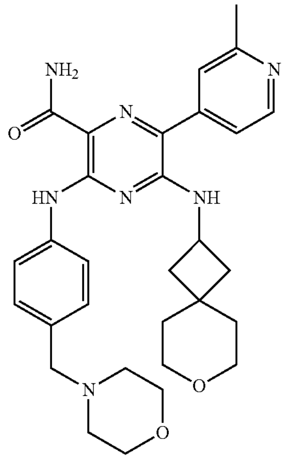
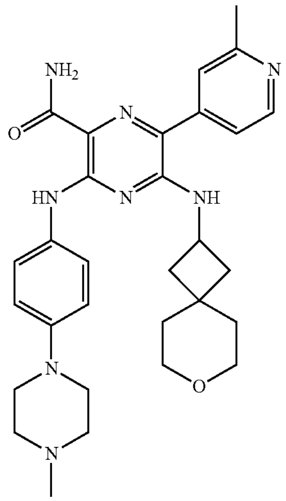

-continued
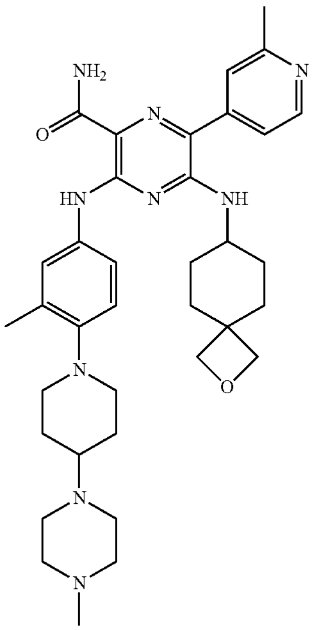
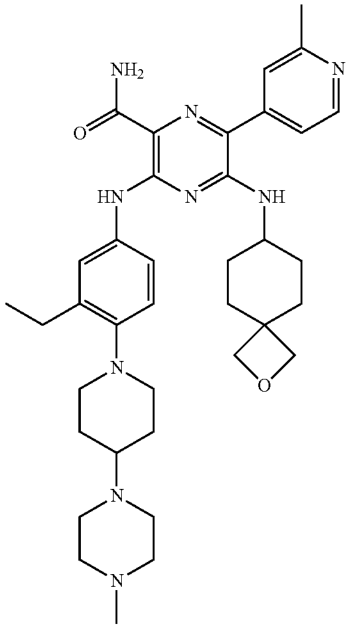
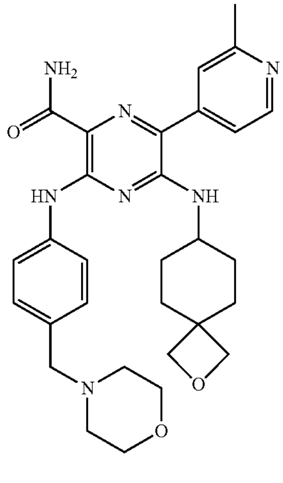
-continued
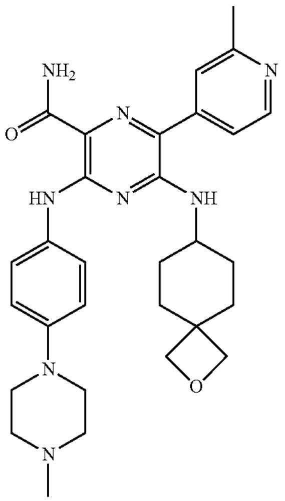
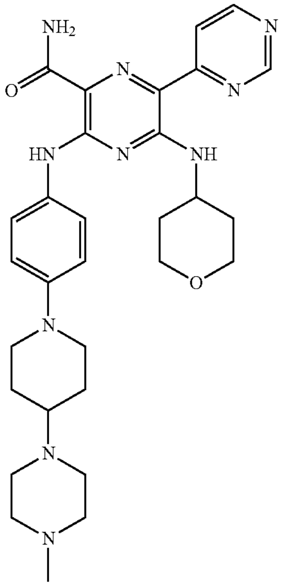
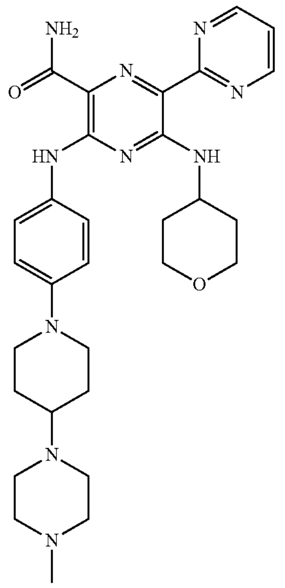

-continued
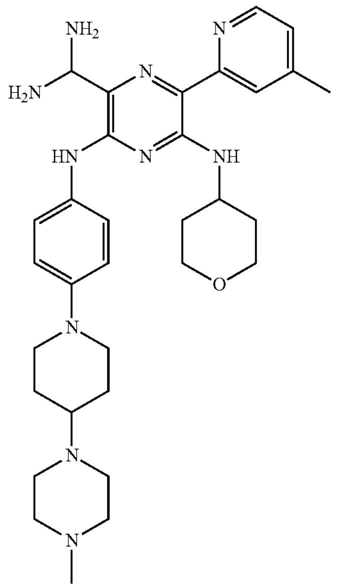
-continued
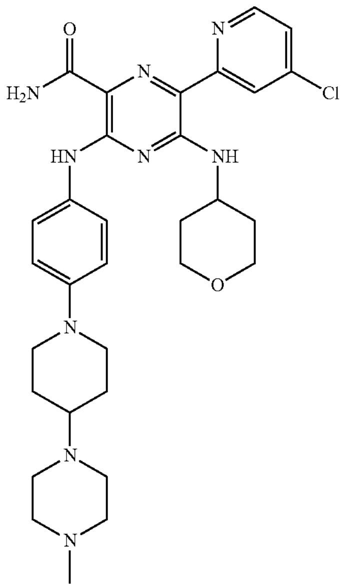
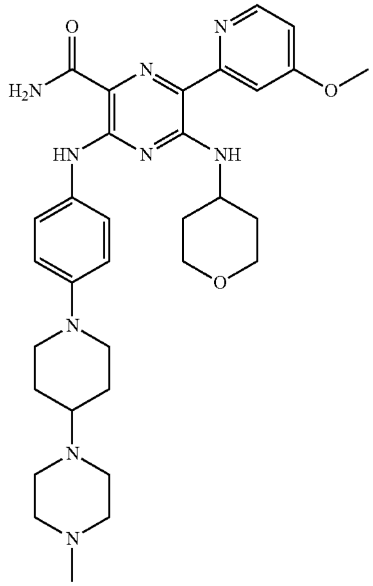
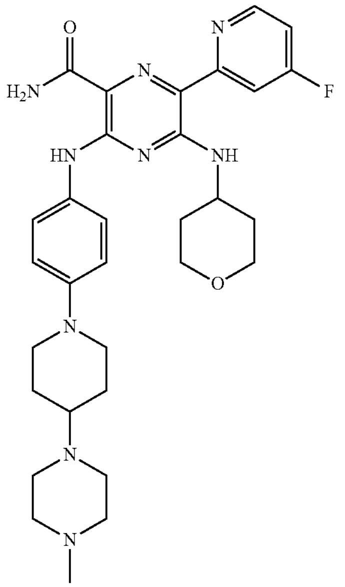

-continued
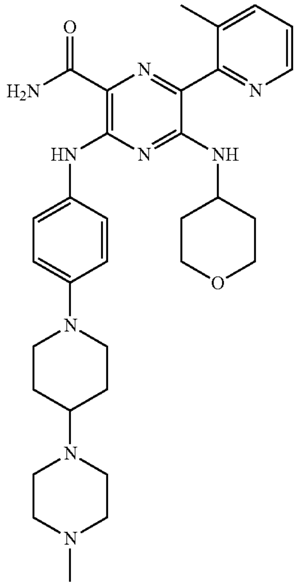
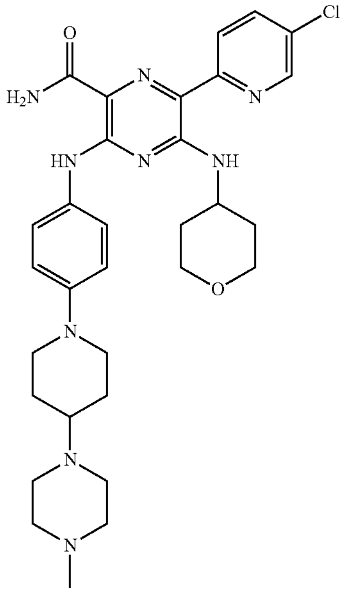
-continued
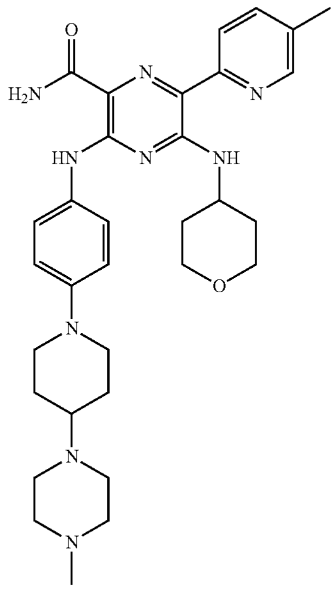
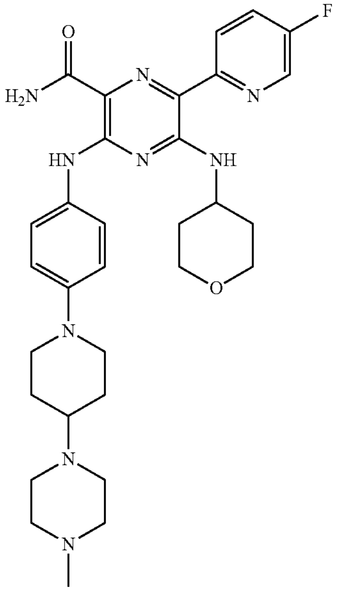

-continued
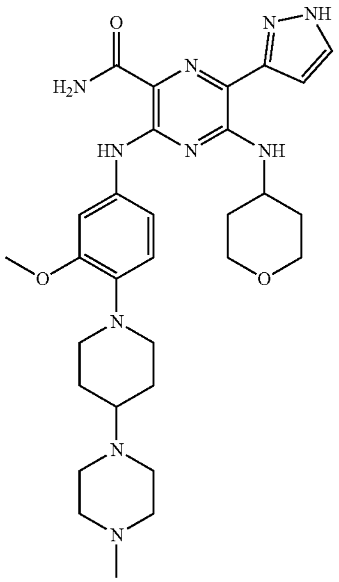
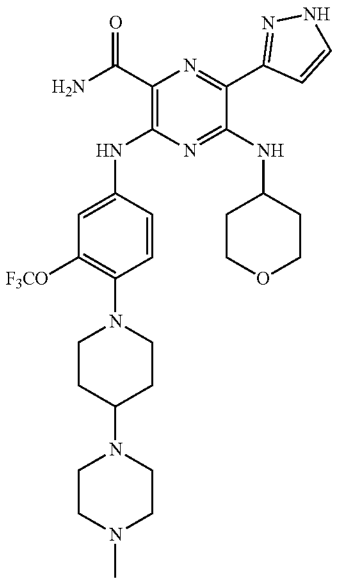
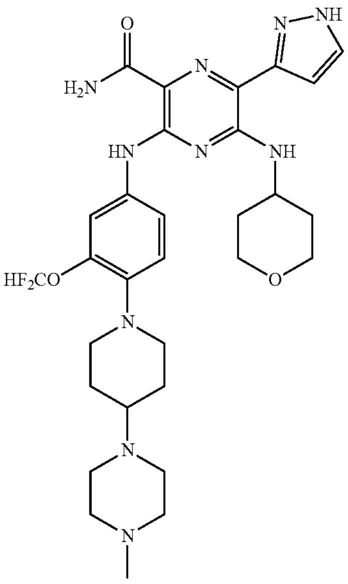
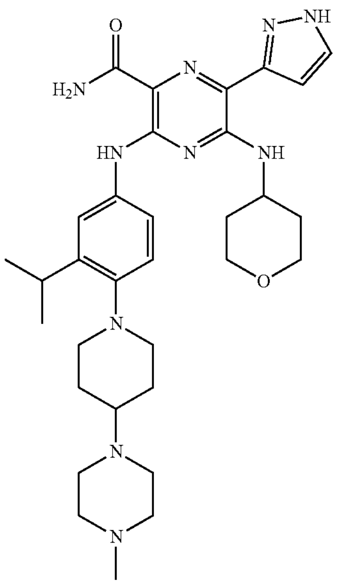

-continued
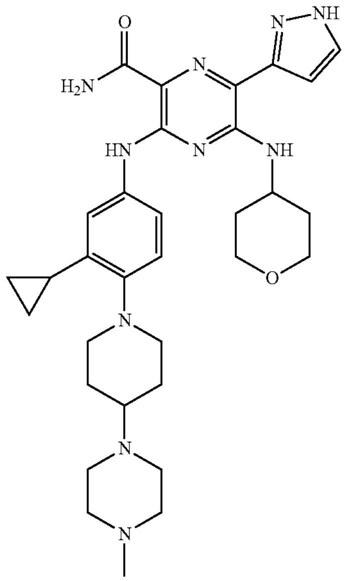
-continued
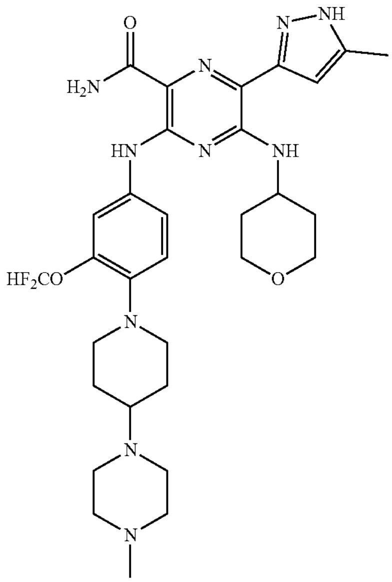
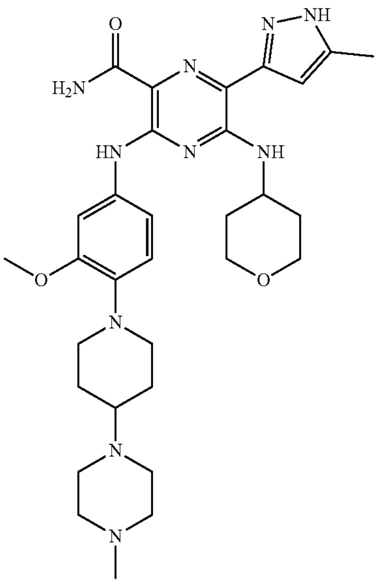
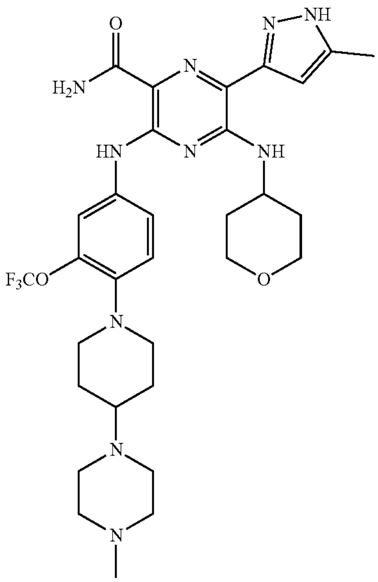

-continued
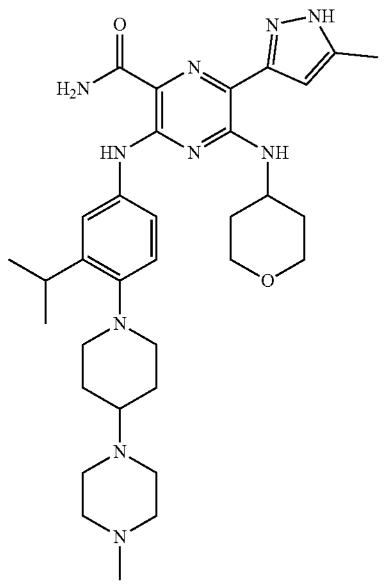
-continued
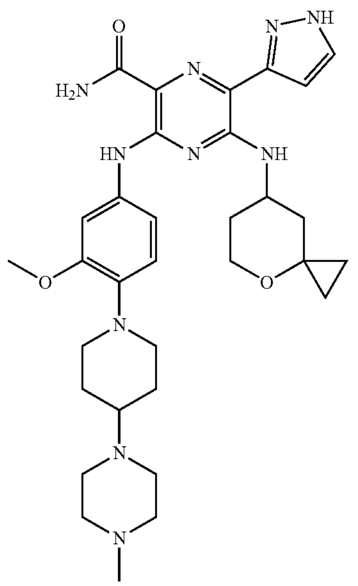
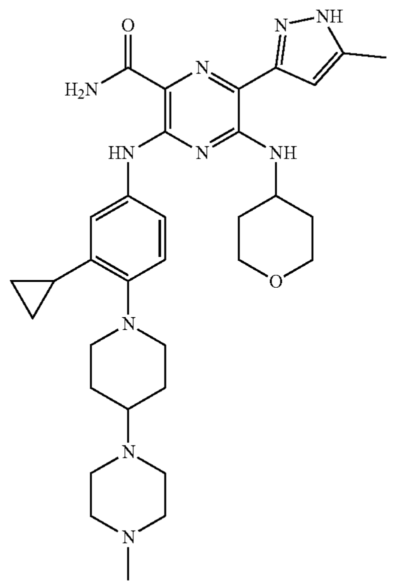
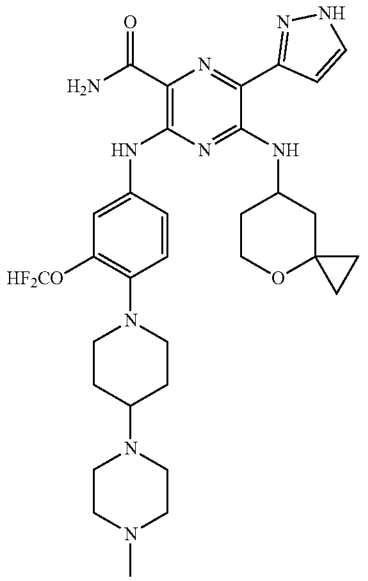

-continued
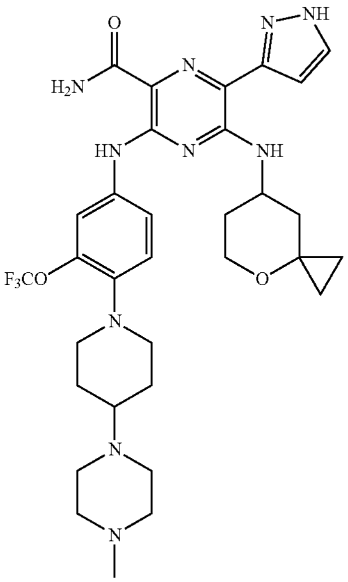
-continued
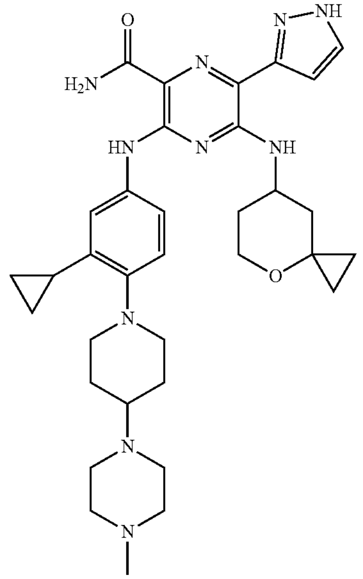
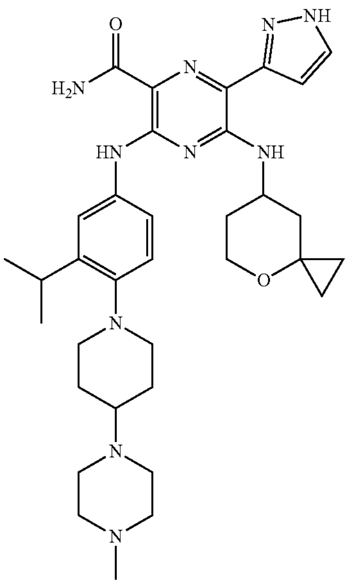
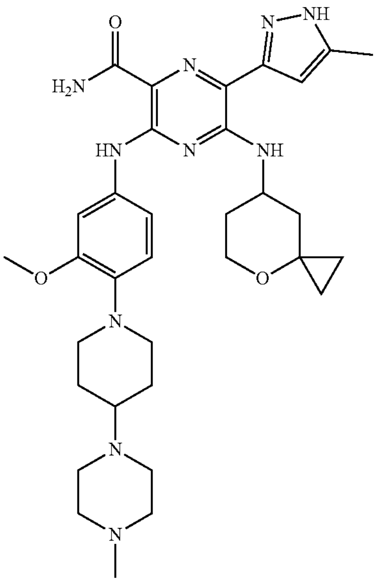

-continued
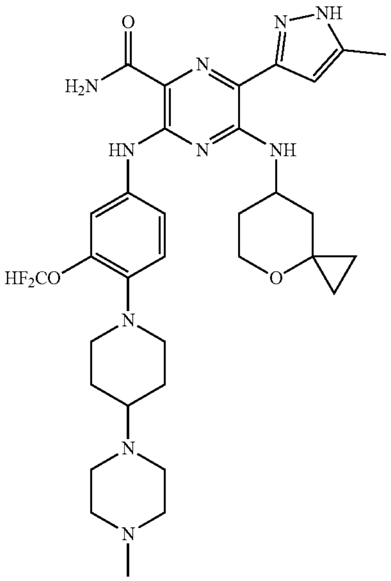
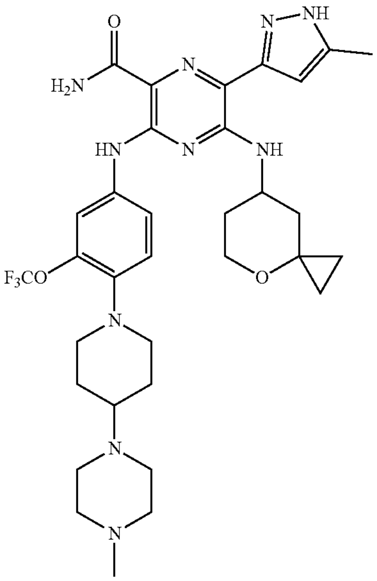
-continued
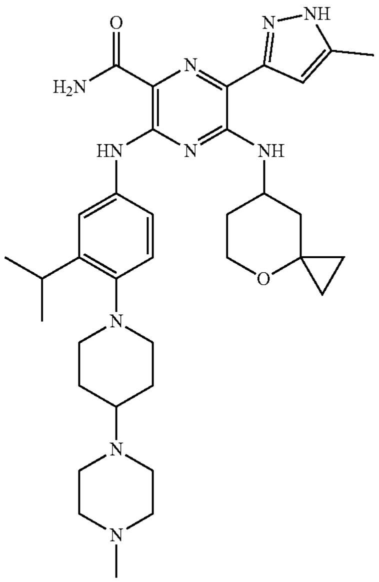
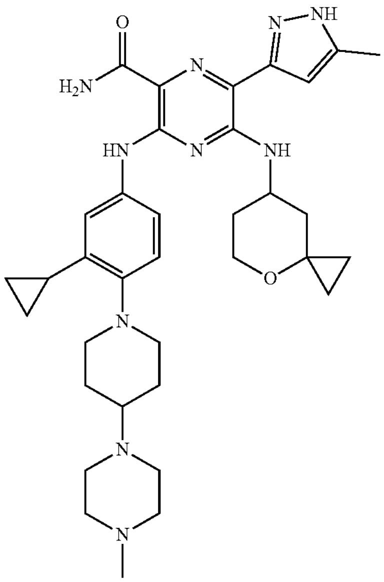

-continued
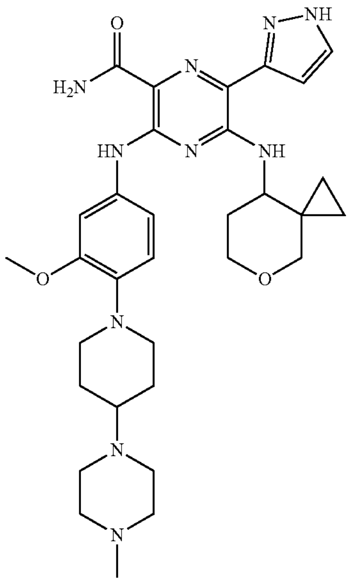
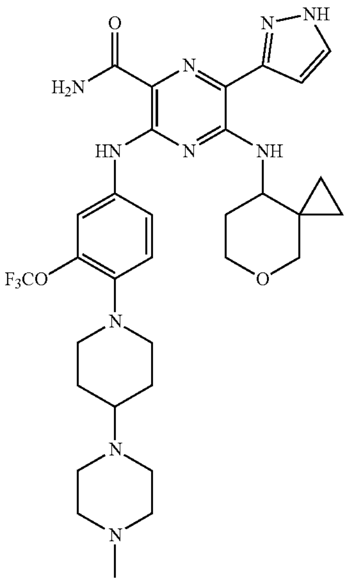
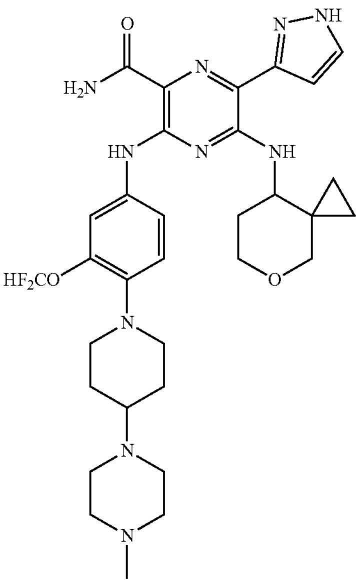
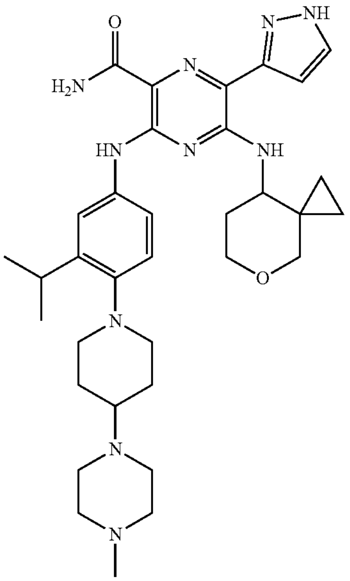
-continued

-continued
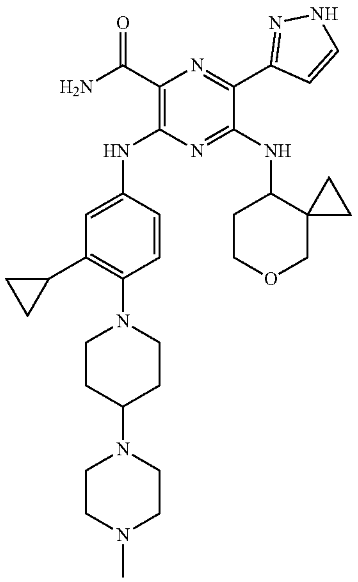
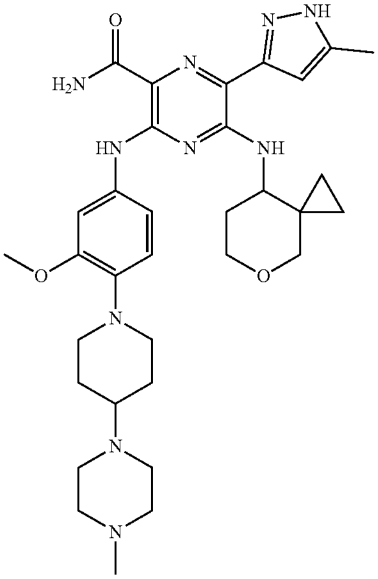
-continued
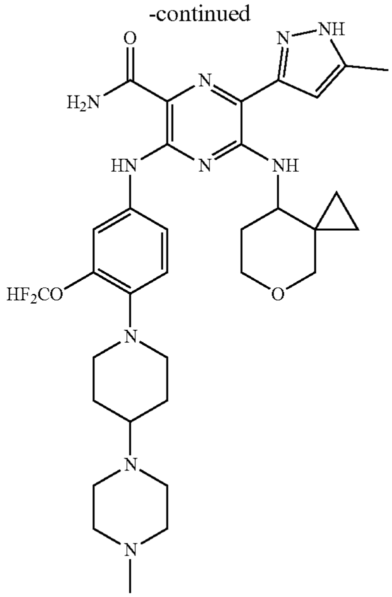
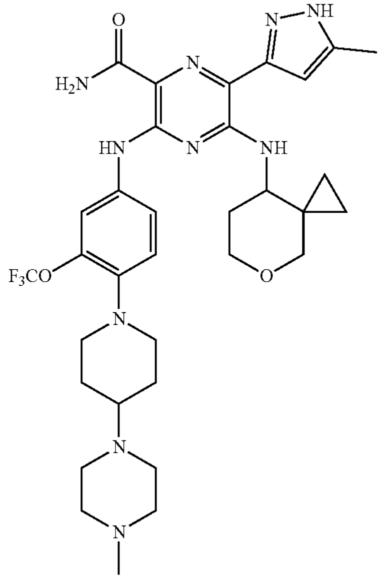
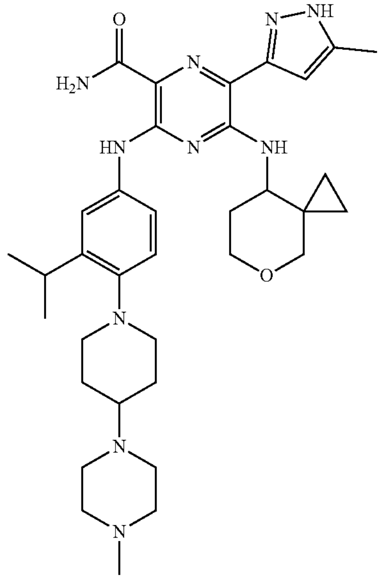

-continued
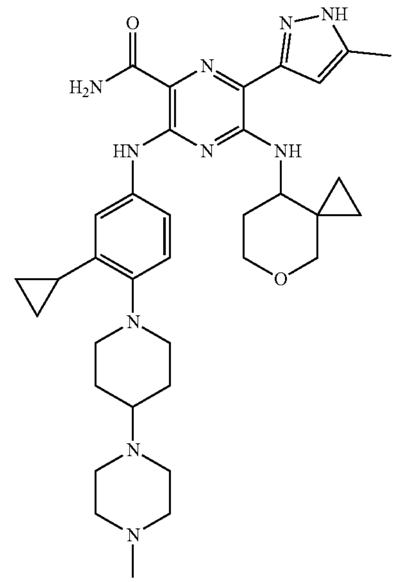
-continued
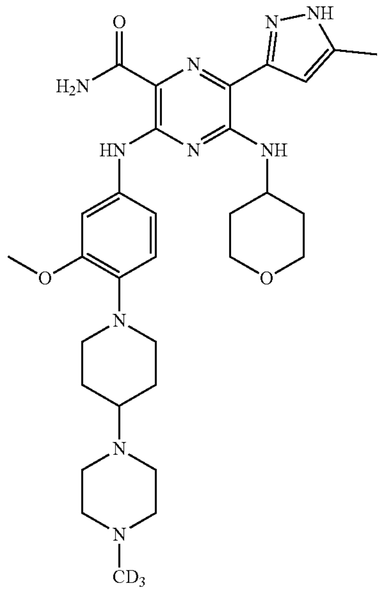
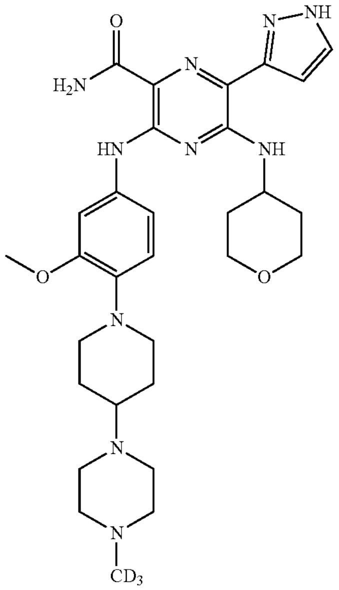
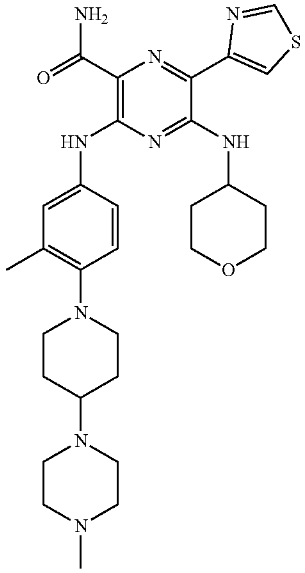

-continued
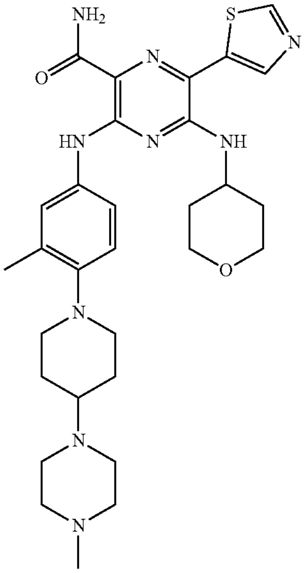
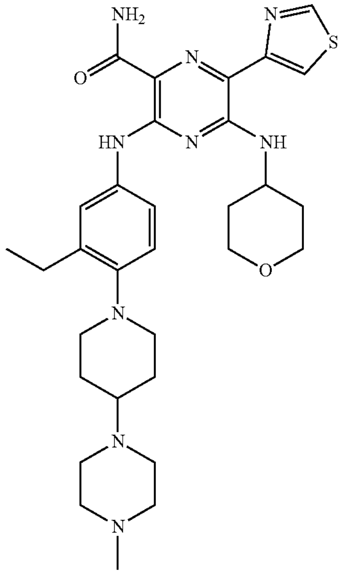
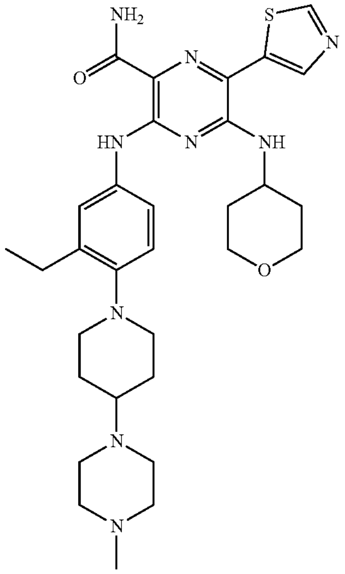
-continued
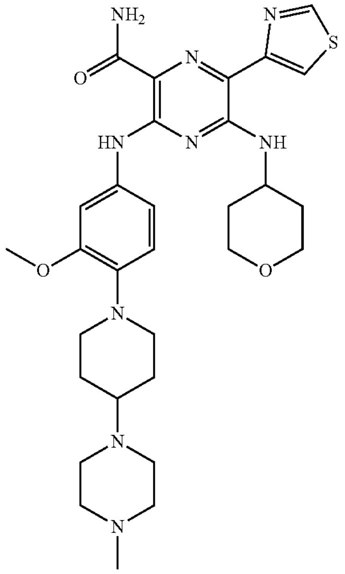
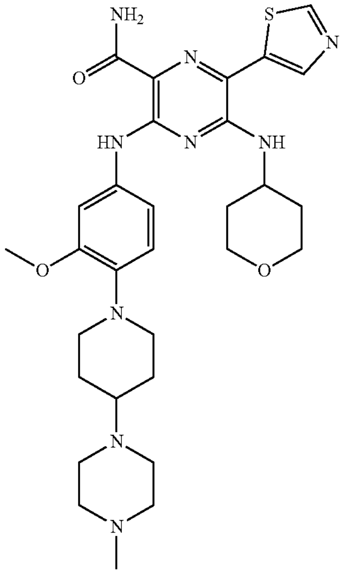

-continued
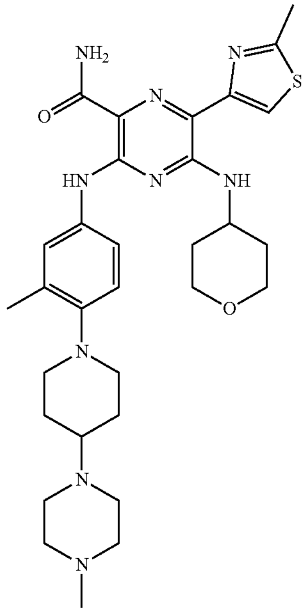
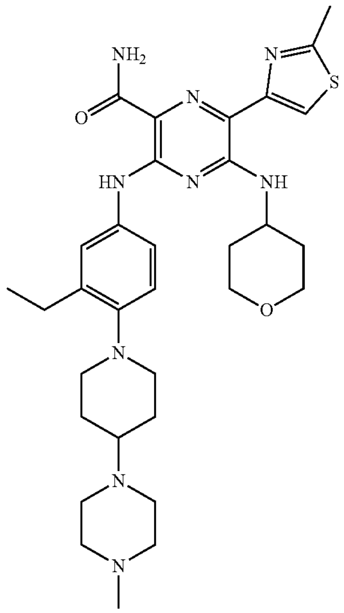
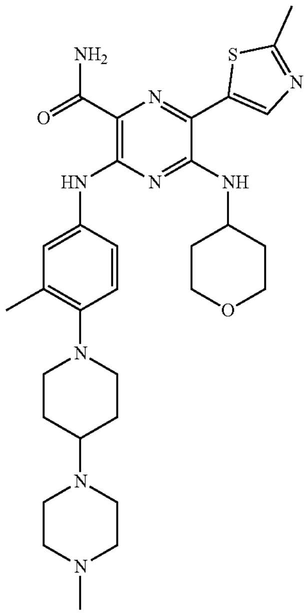
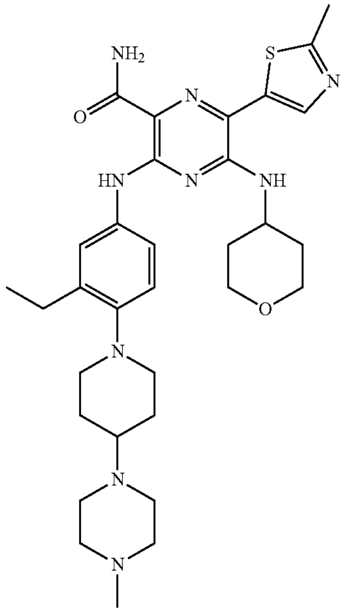

-continued
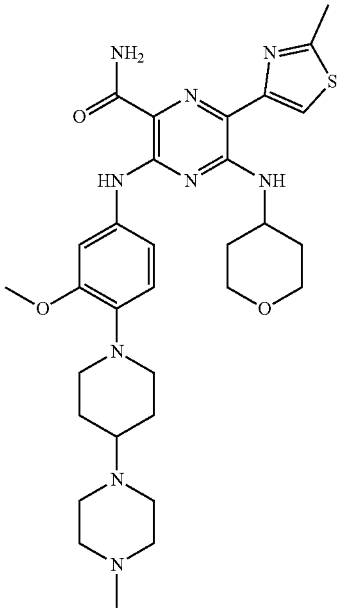
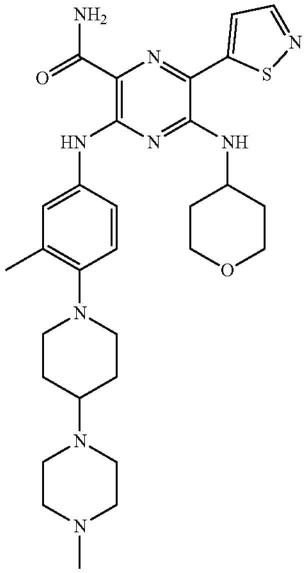
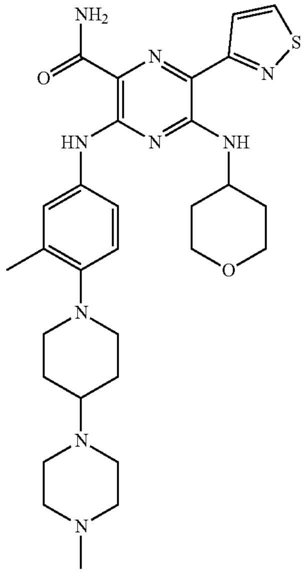
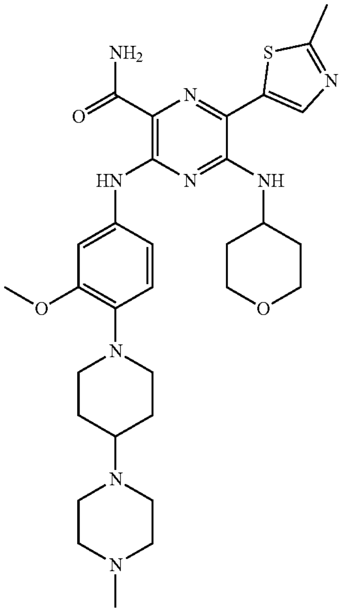
-continued
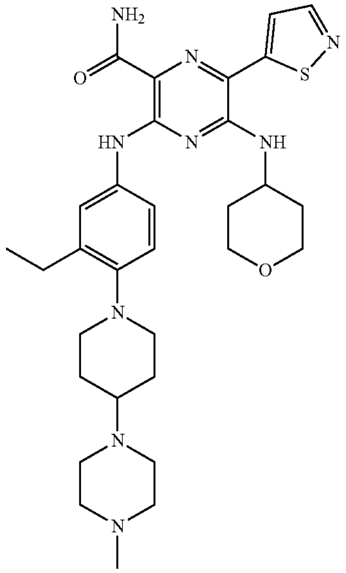

-continued
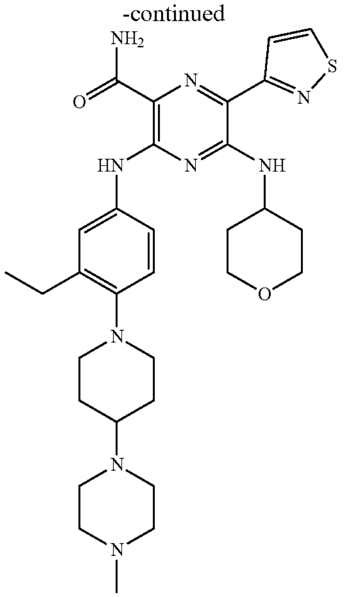
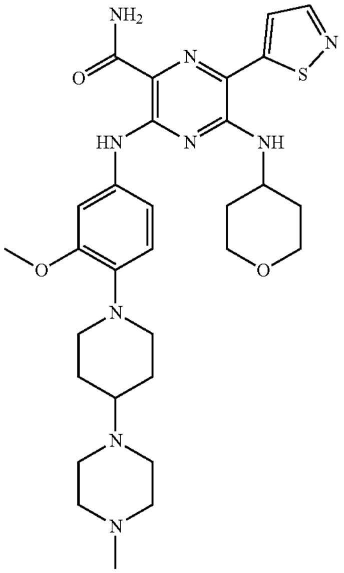
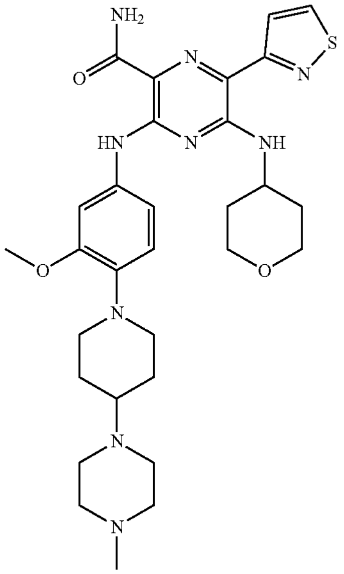
-continued
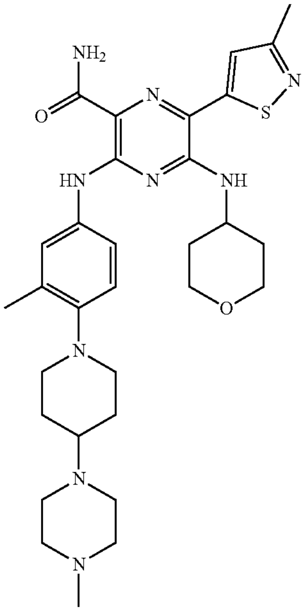
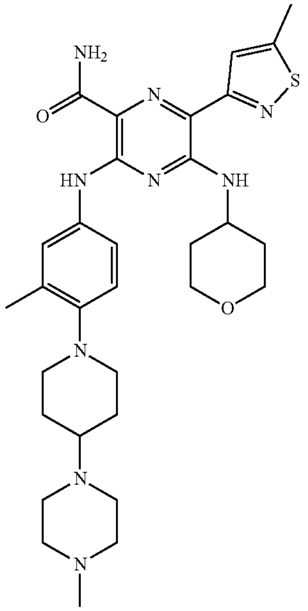

-continued
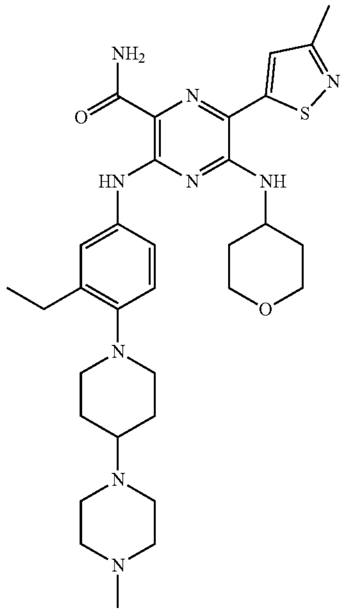
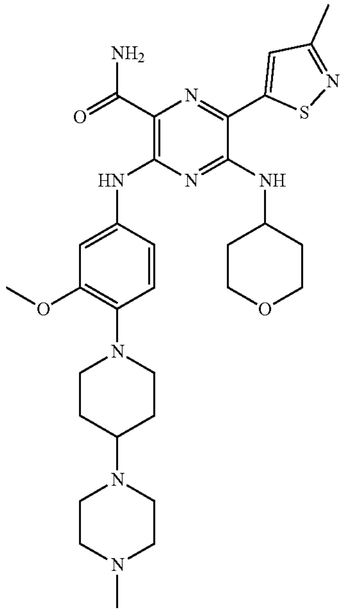
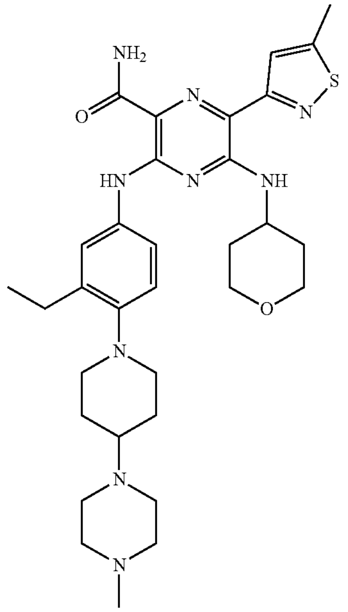
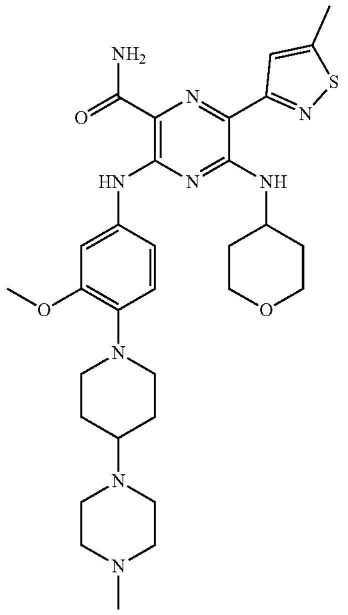

-continued
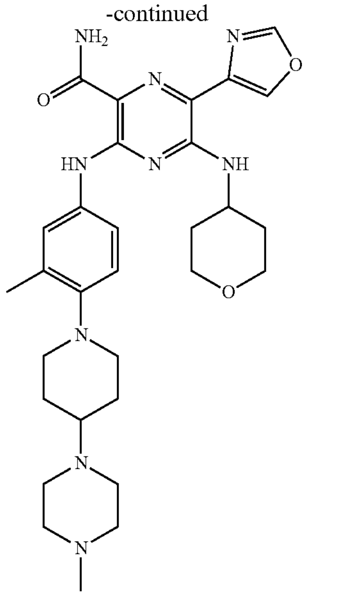
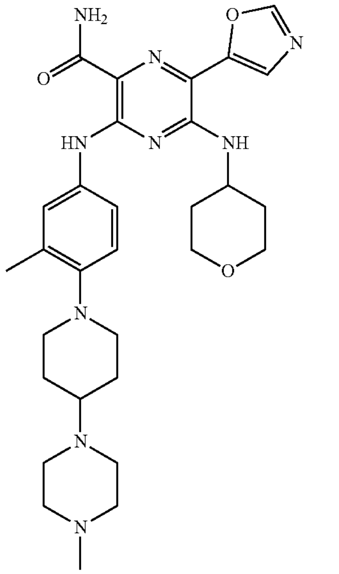
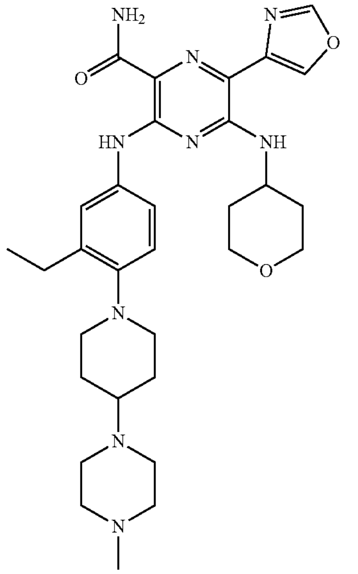
-continued
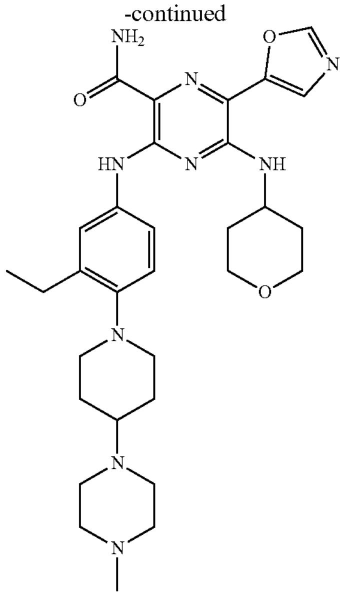
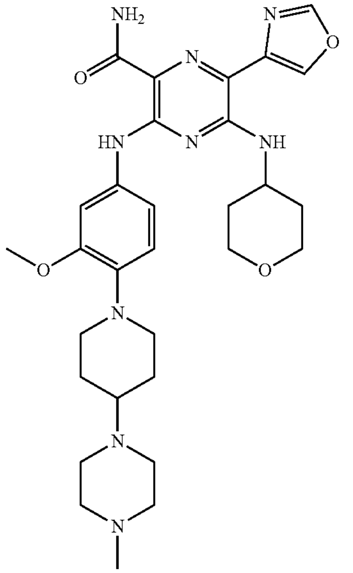
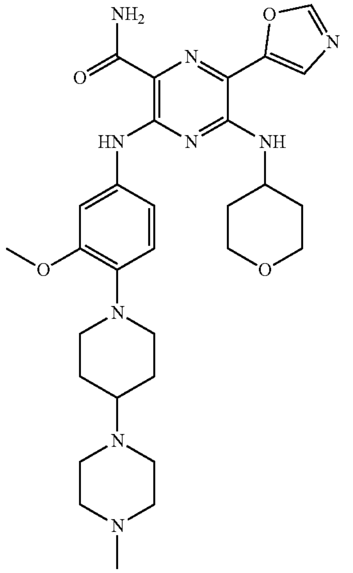

-continued
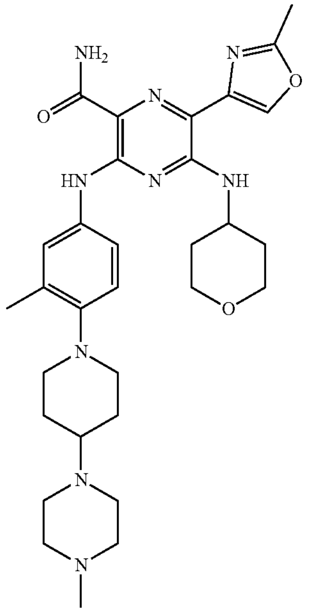
-continued
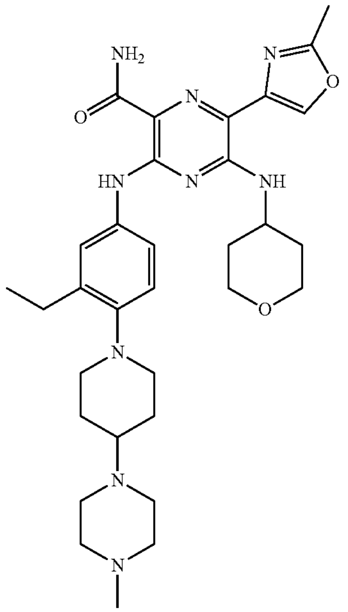
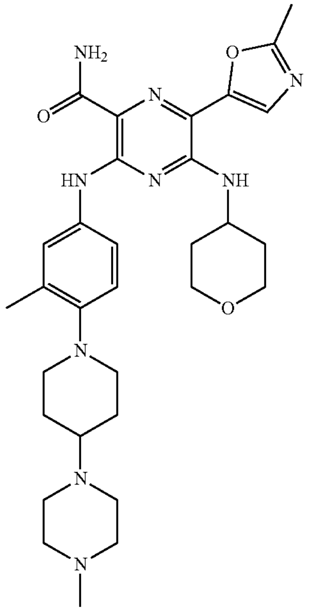
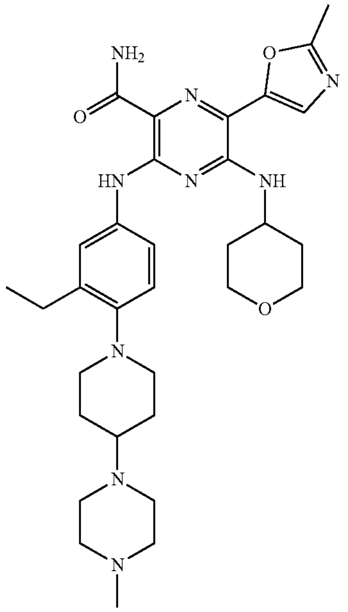

-continued
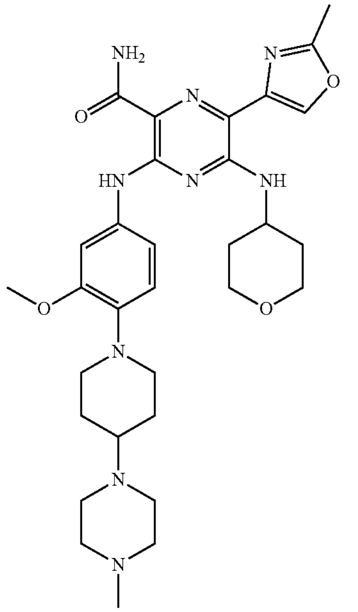
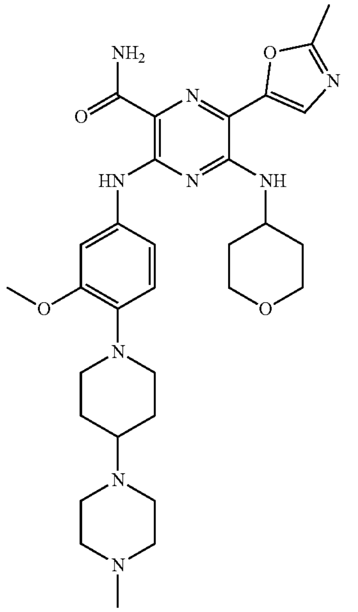
-continued
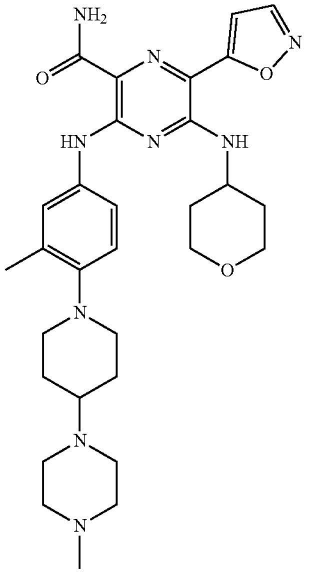
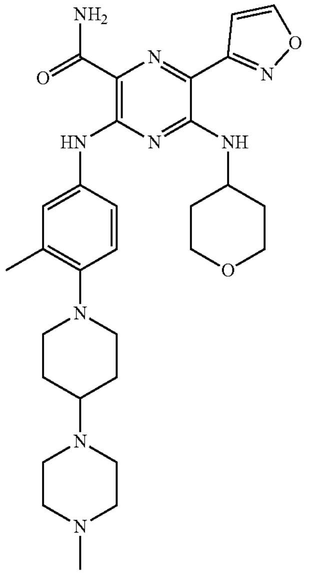
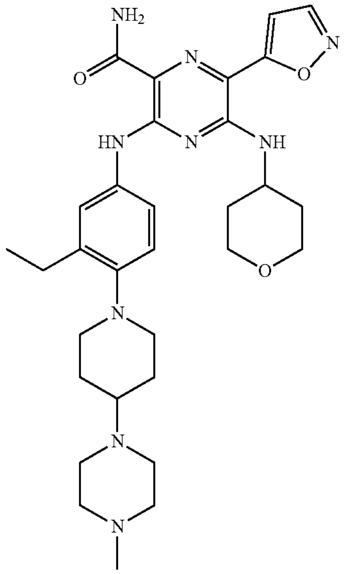

-continued
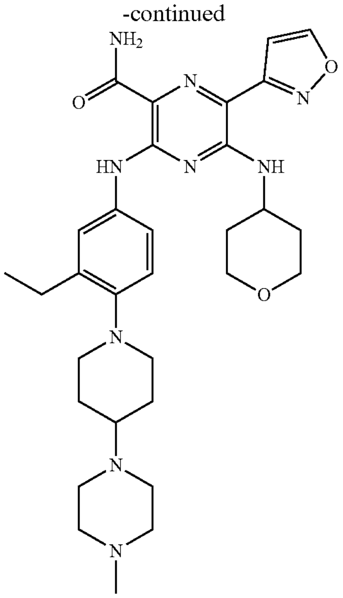
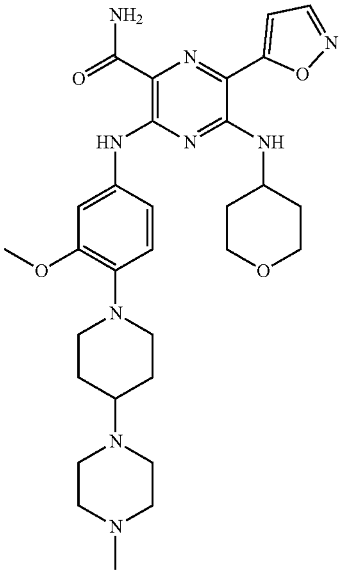
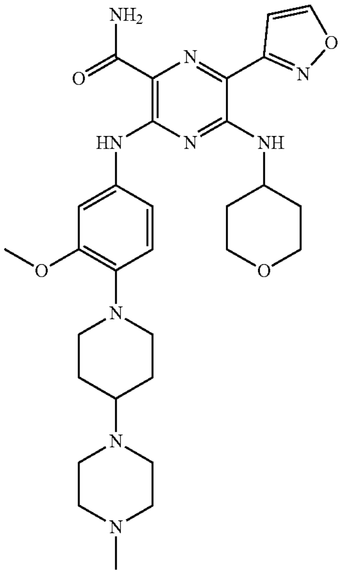
-continued
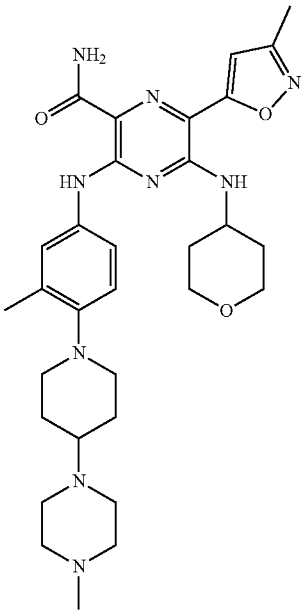
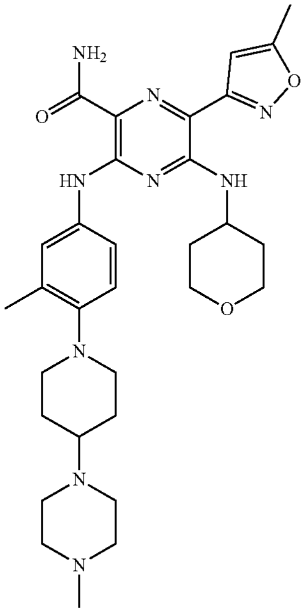

-continued
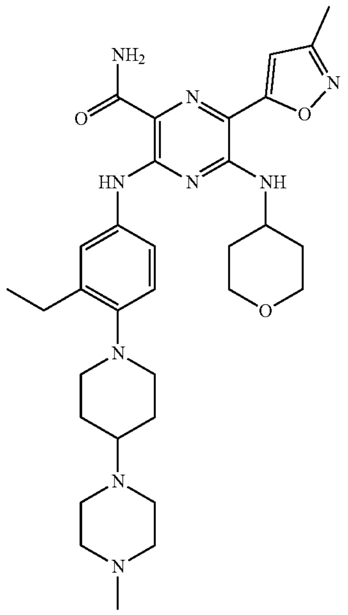
-continued
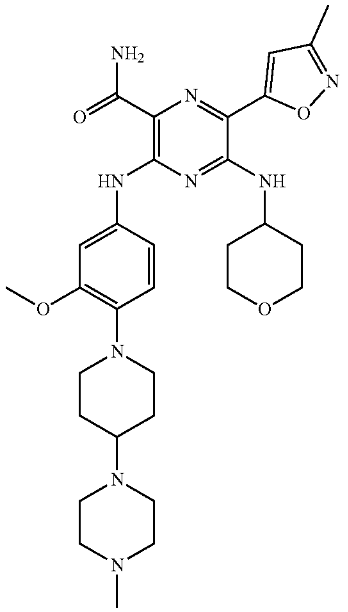
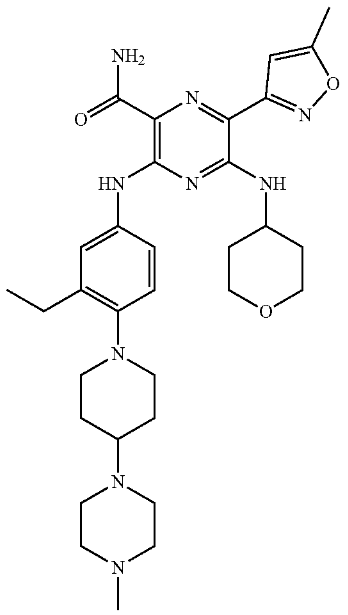
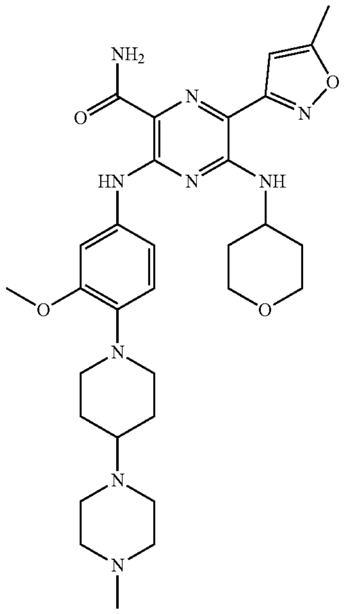

-continued
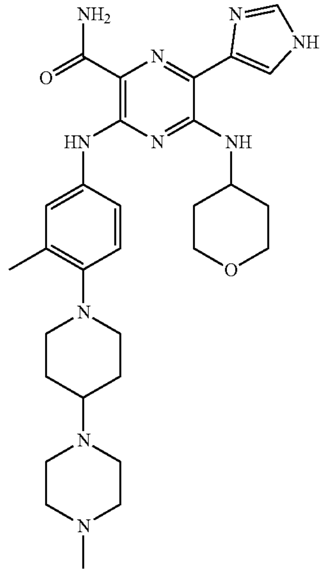
-continued
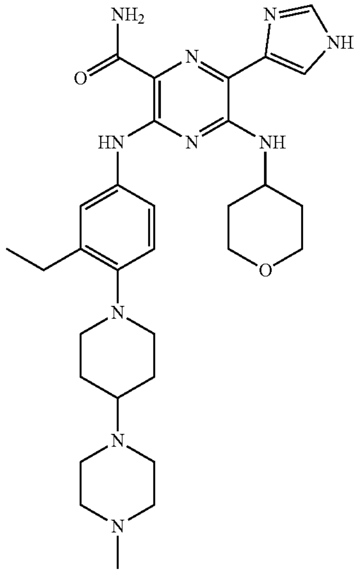
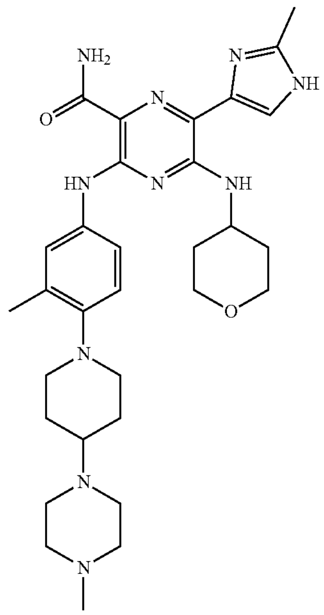
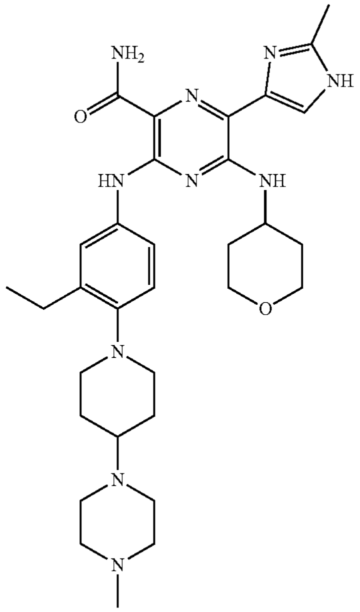

-continued
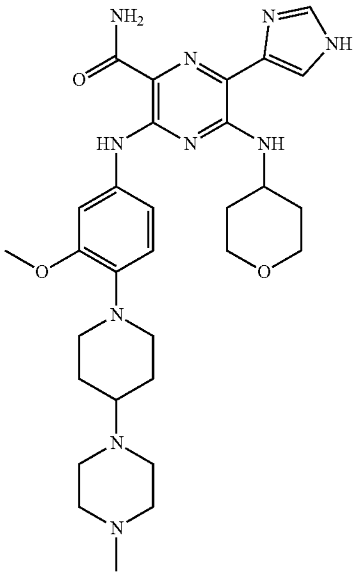
-continued
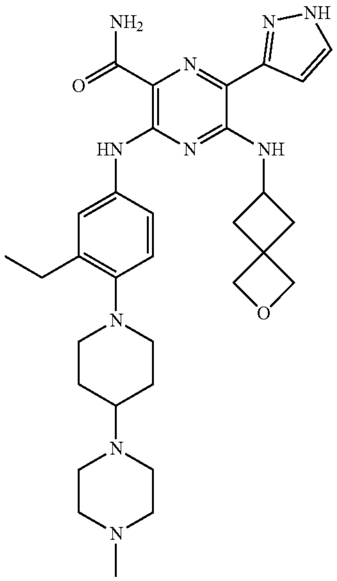
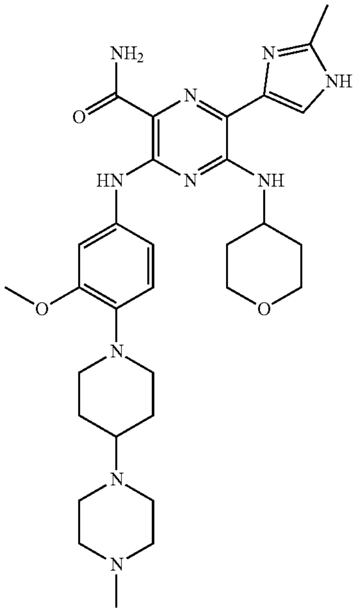
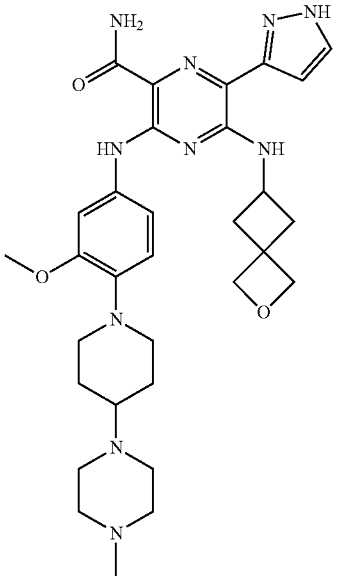 [SMILES: COc1cc(Nc2nc(NC3CC4(COC4)C3)c(-c3cc[nH]n3)nc2C(N)=O)ccc1N1CCC(N2CCN(C)CC2)CC1]

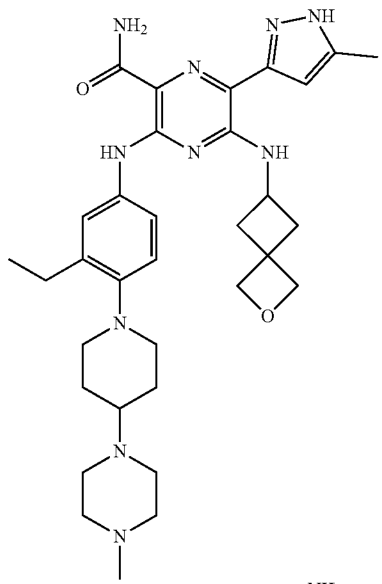
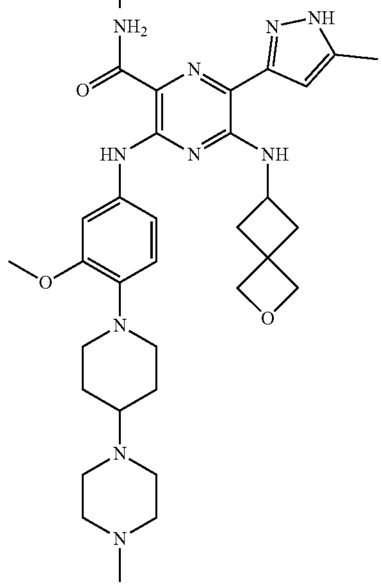
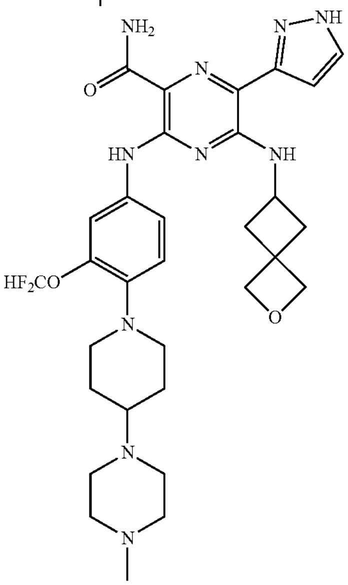
-continued
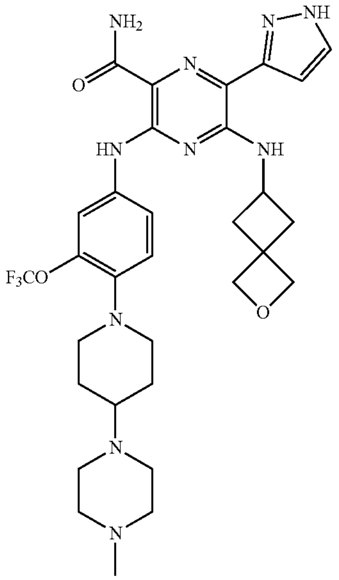
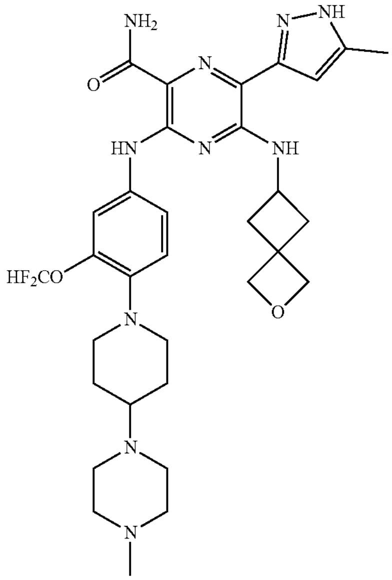

-continued
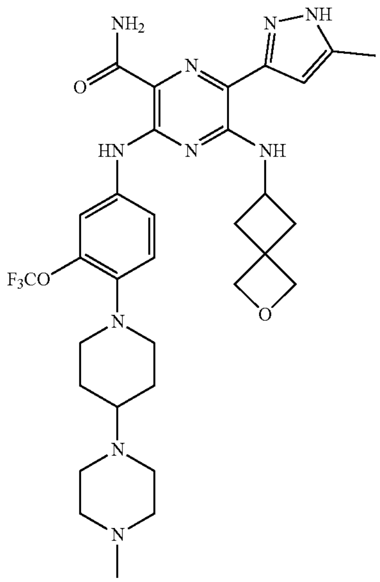
-continued
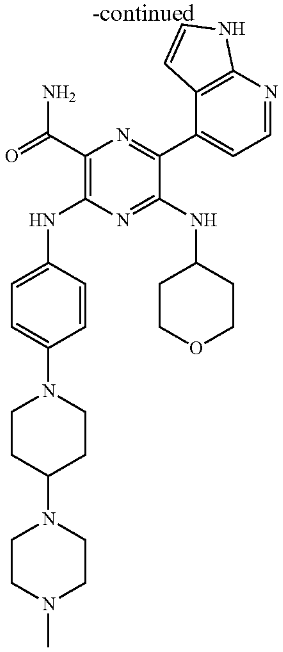
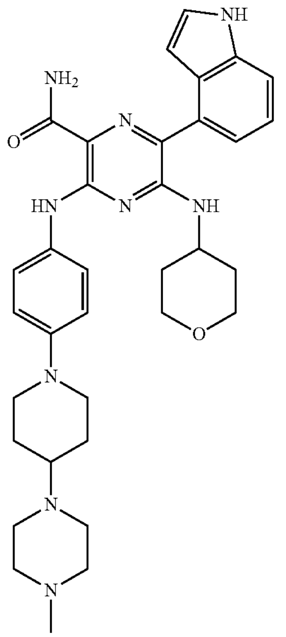
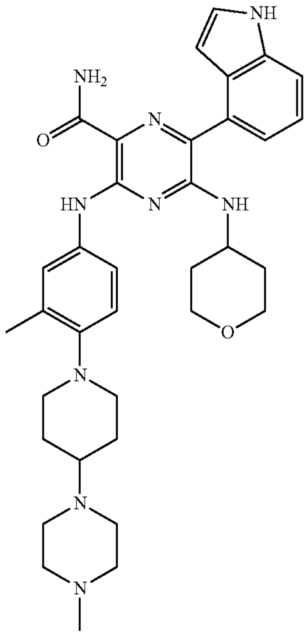

-continued
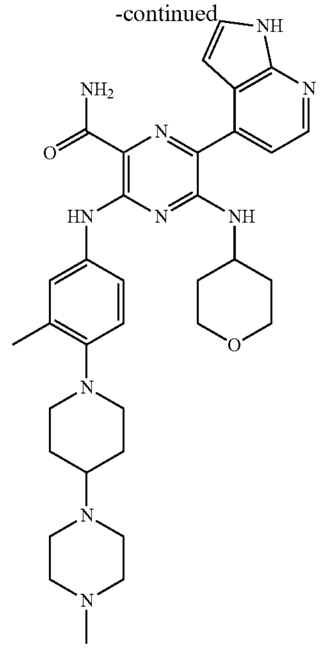
-continued
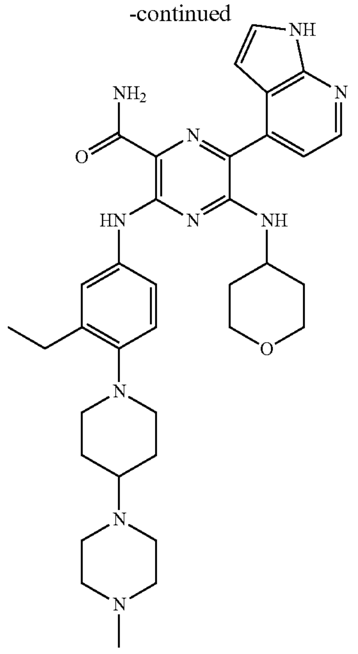
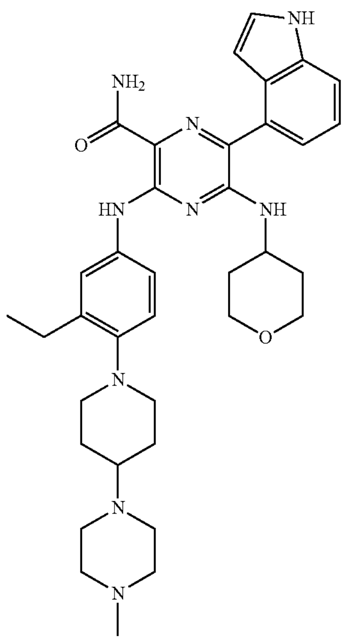
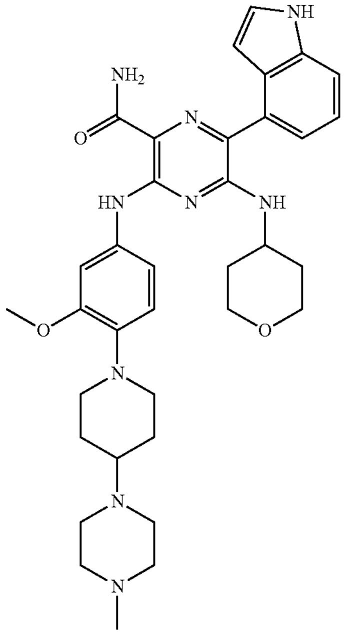

-continued
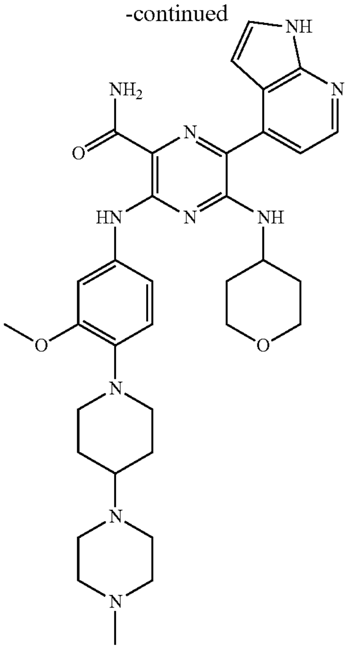
-continued
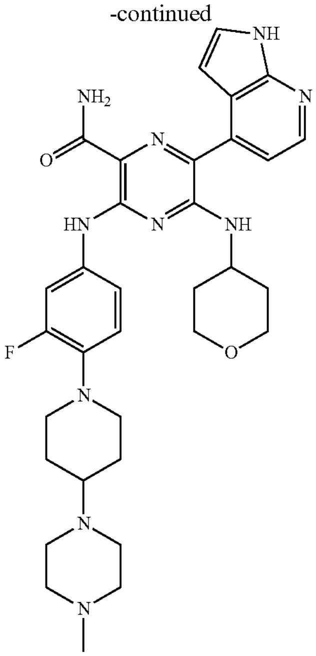
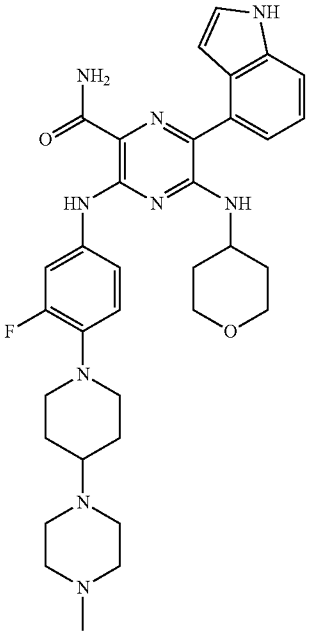
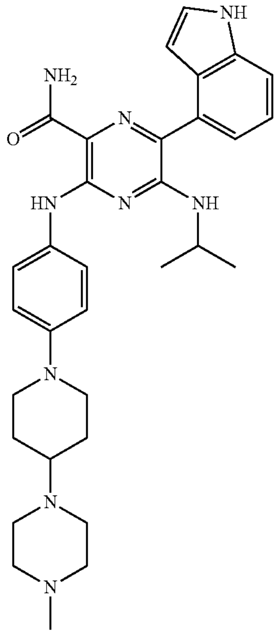

-continued
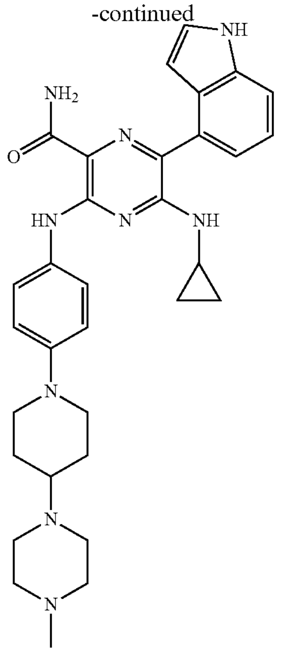
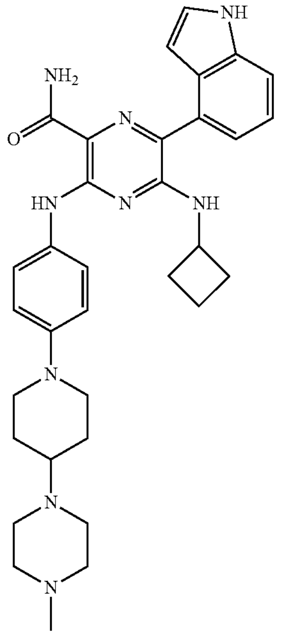
-continued
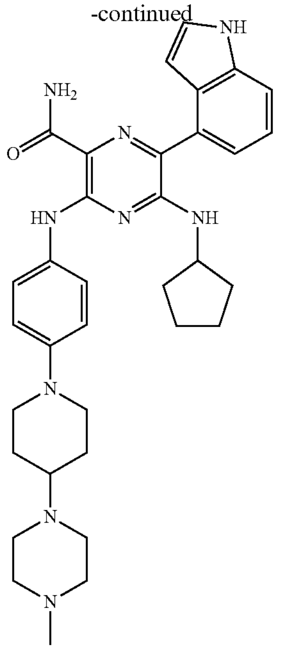
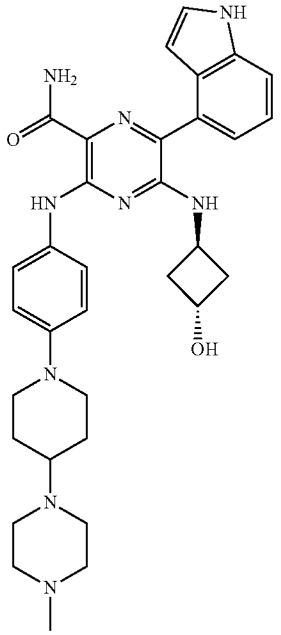

-continued
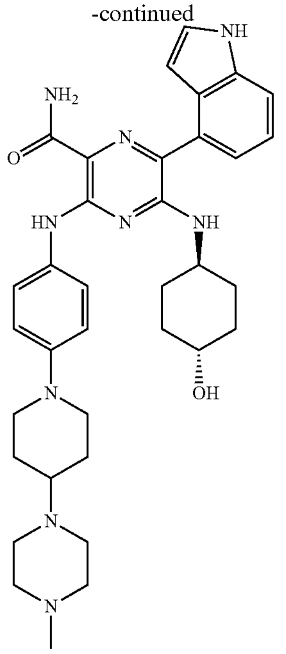
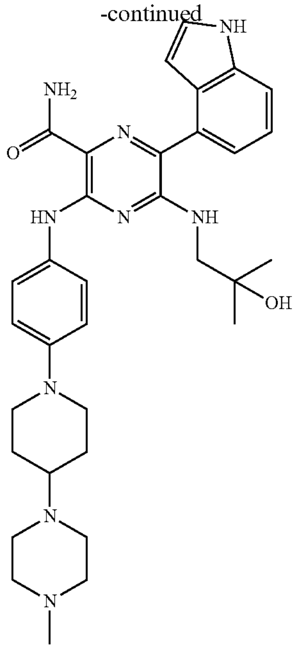
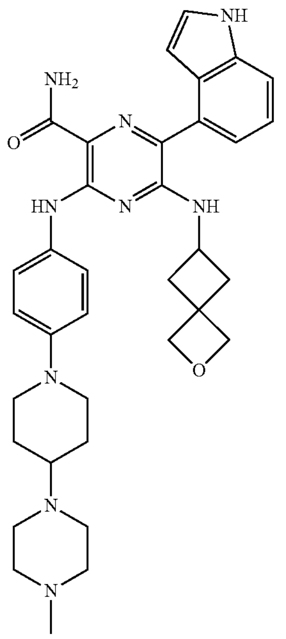
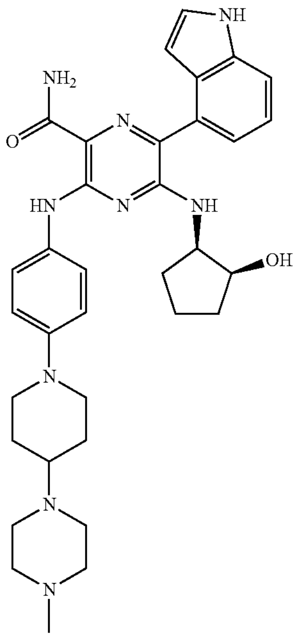
-continued

-continued
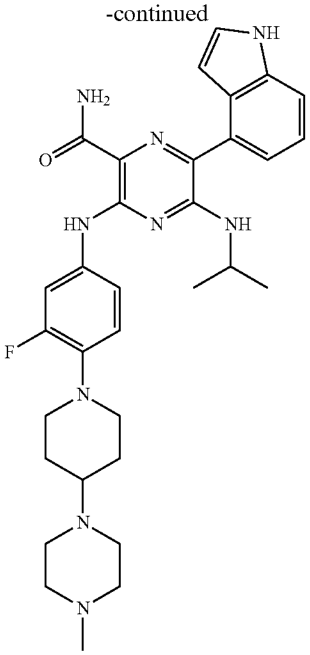
-continued
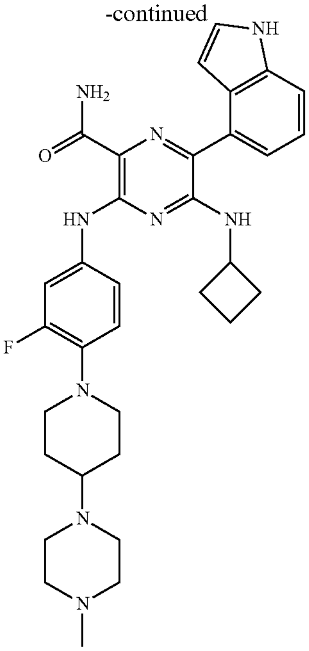
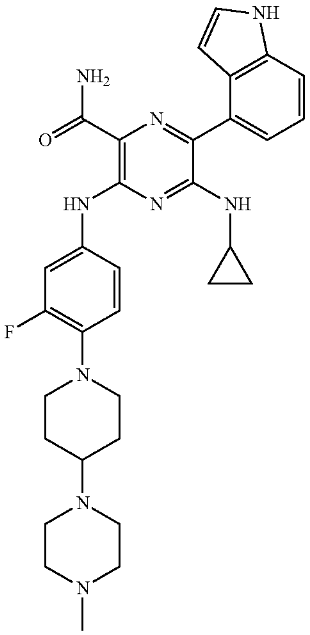
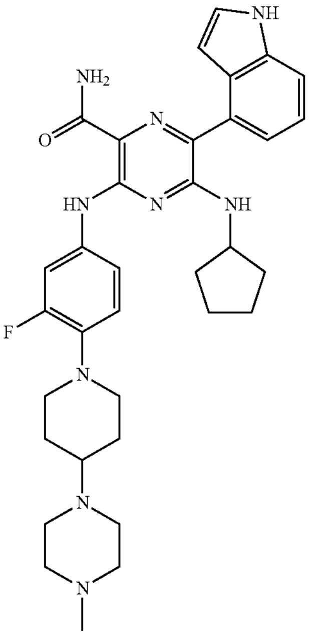

-continued
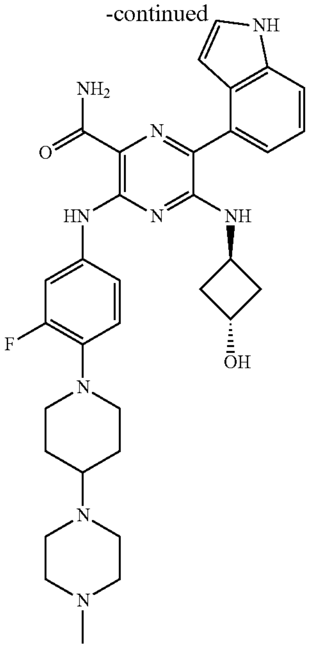
-continued
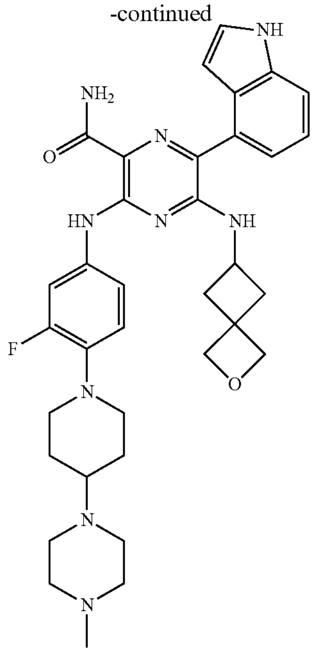
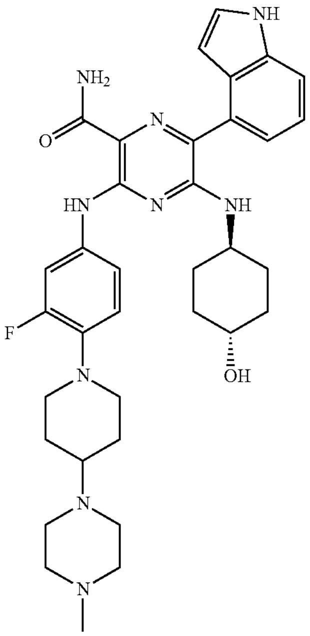
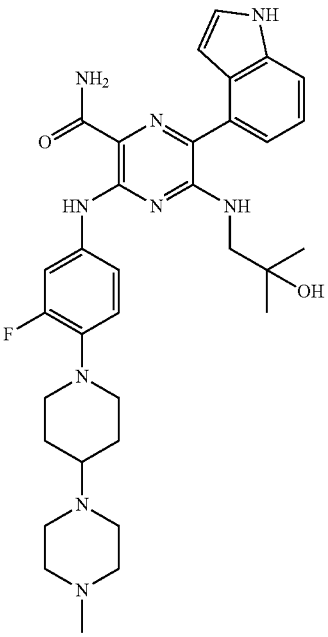

-continued
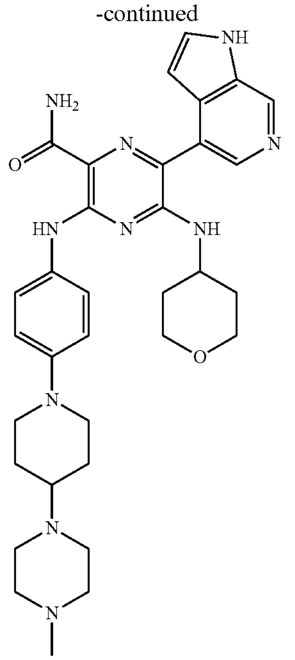
-continued
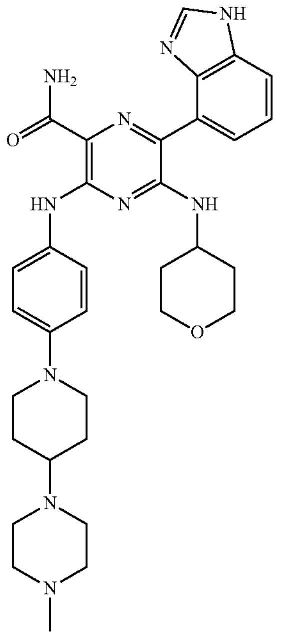
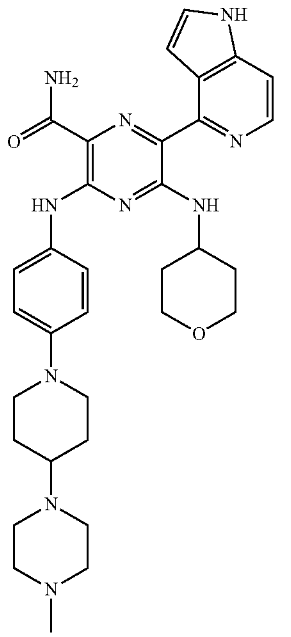
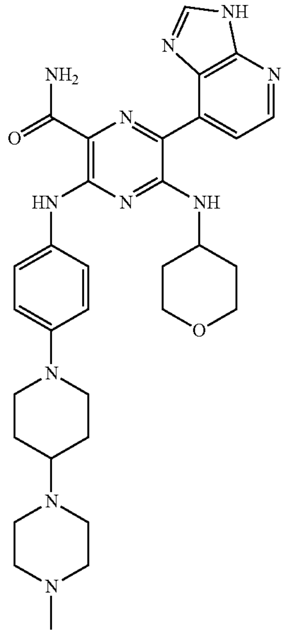

-continued
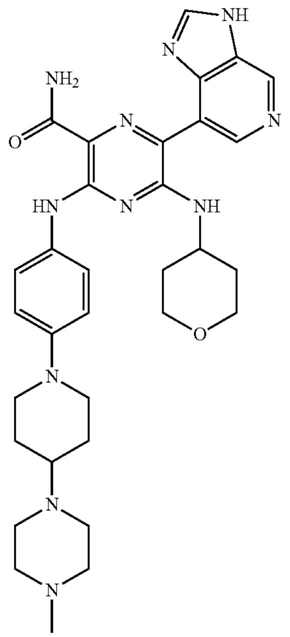
-continued
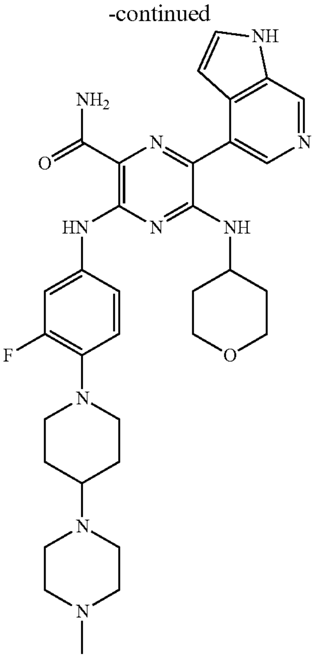
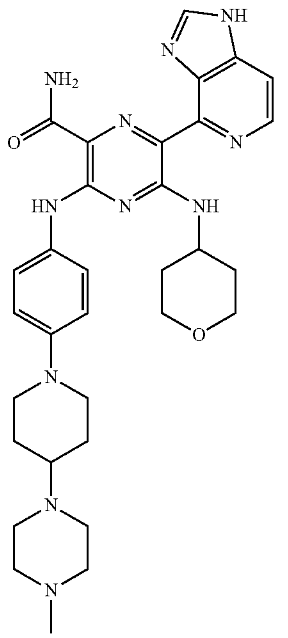
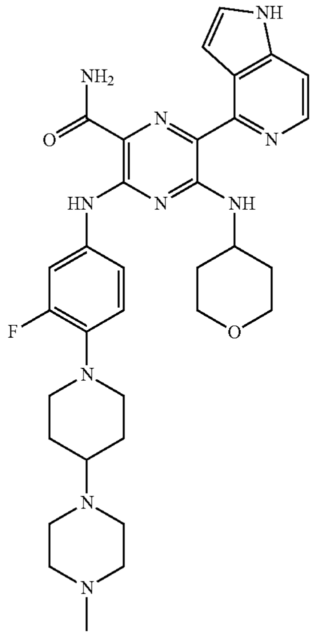

-continued
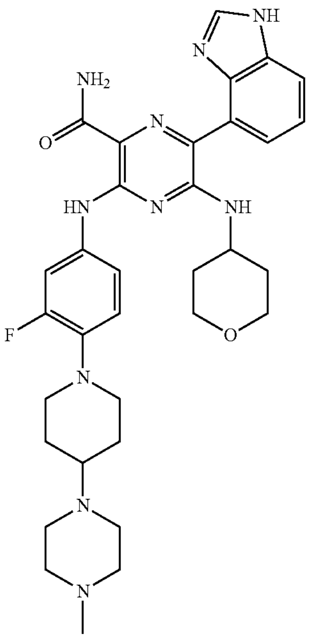
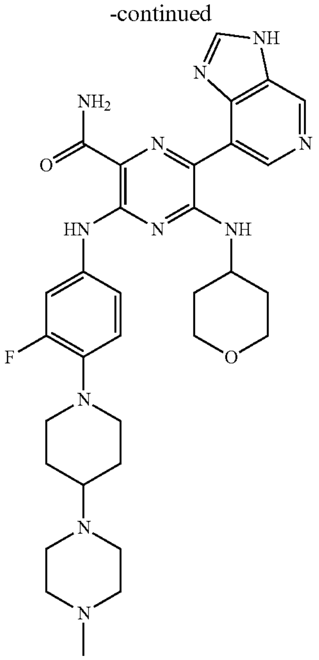
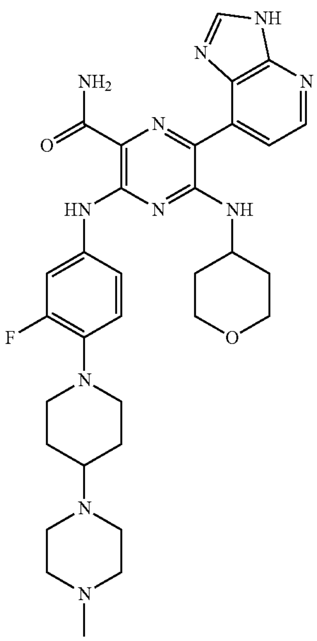
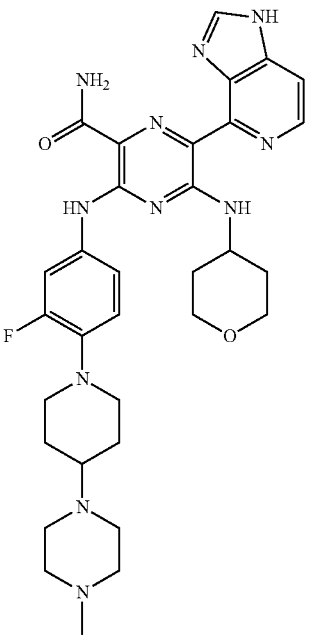
-continued

-continued
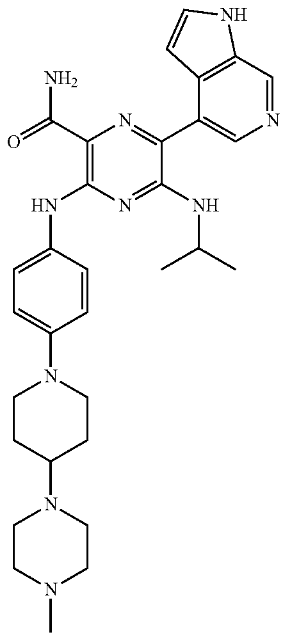
-continued
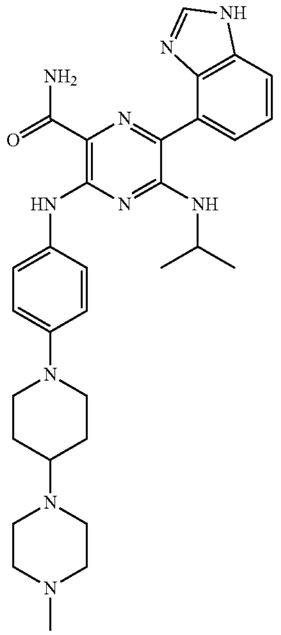
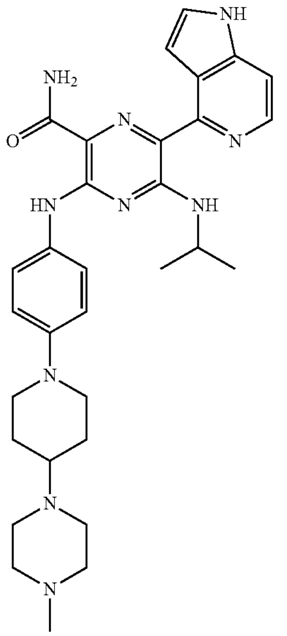
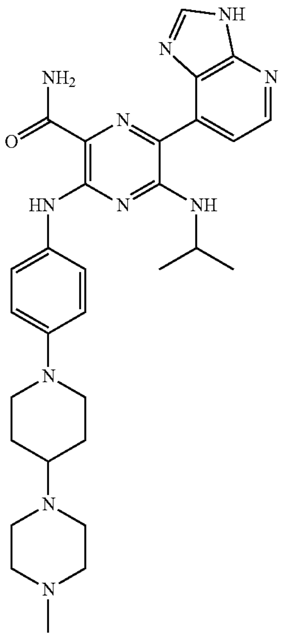

-continued
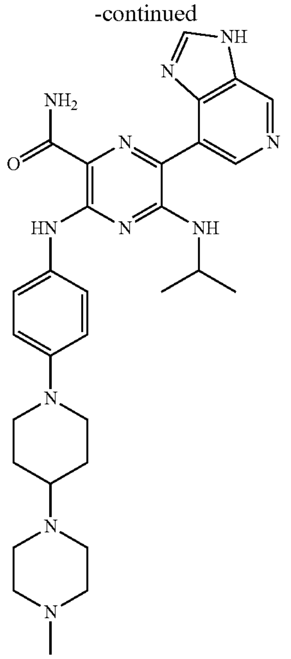
-continued
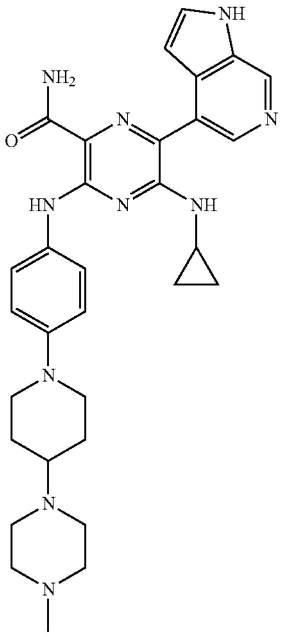
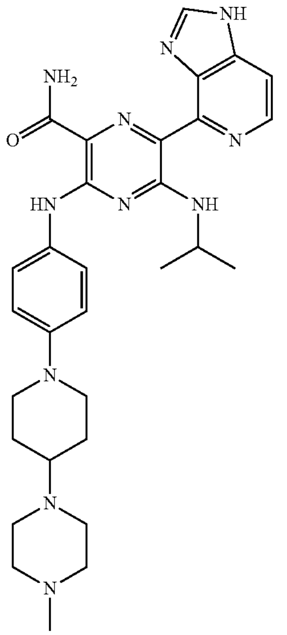
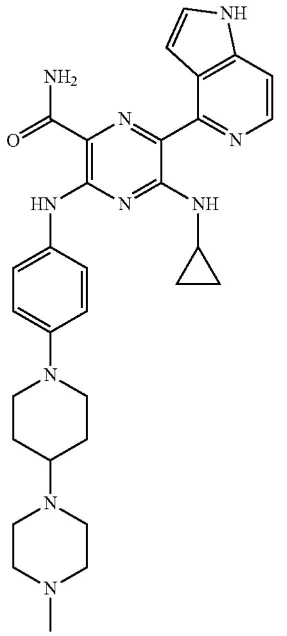

-continued
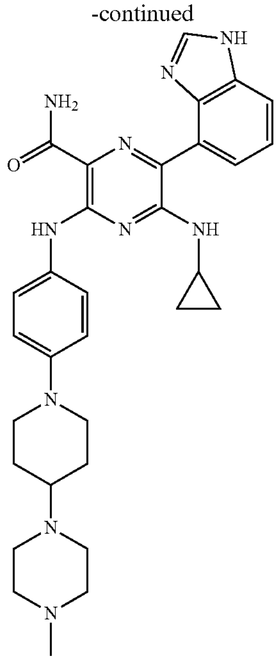
-continued
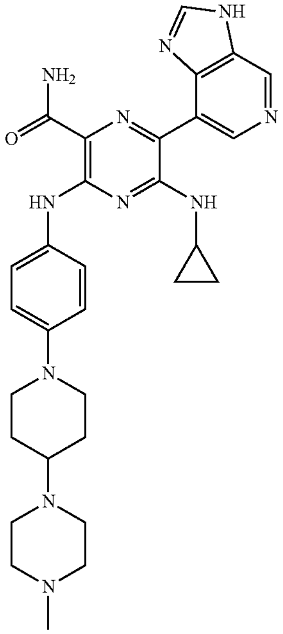
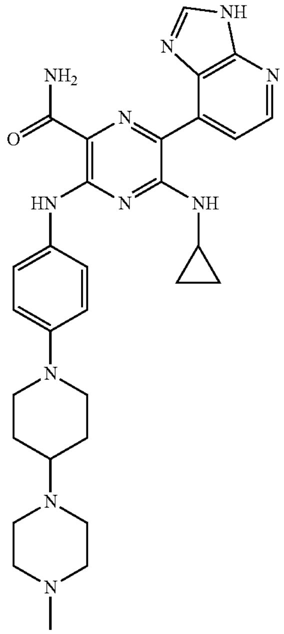
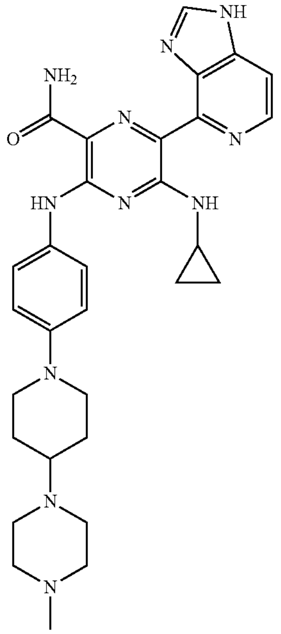

-continued
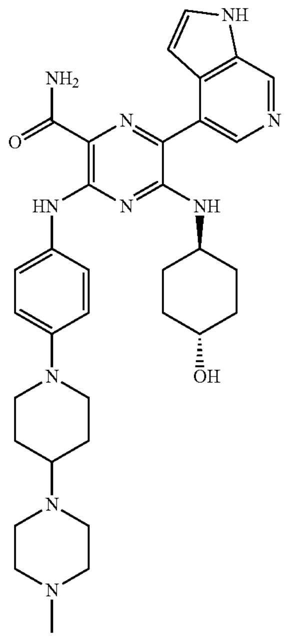
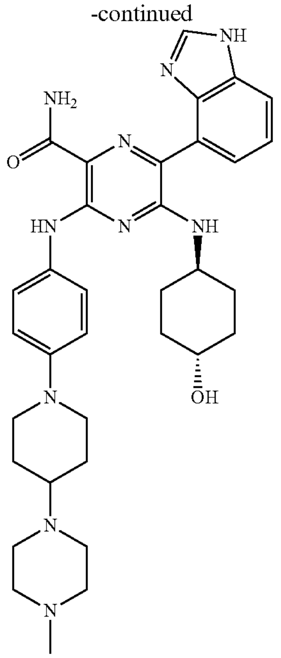
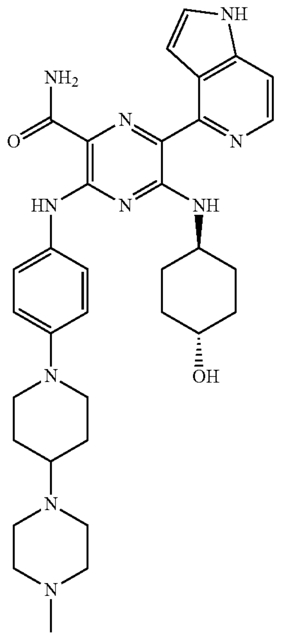
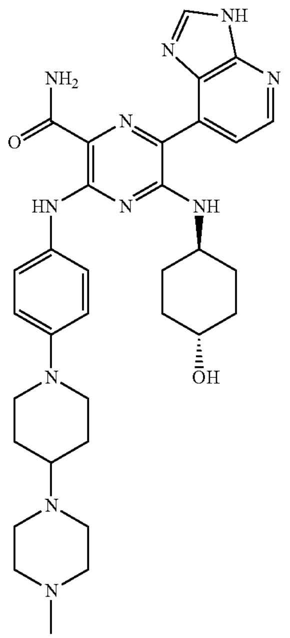

-continued
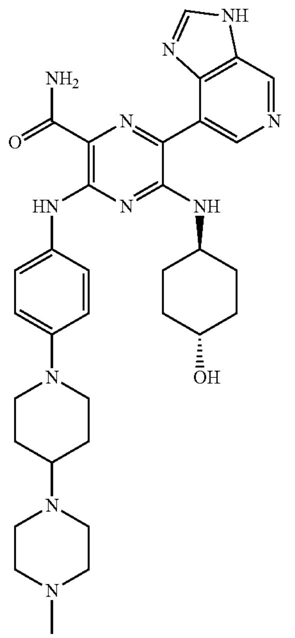
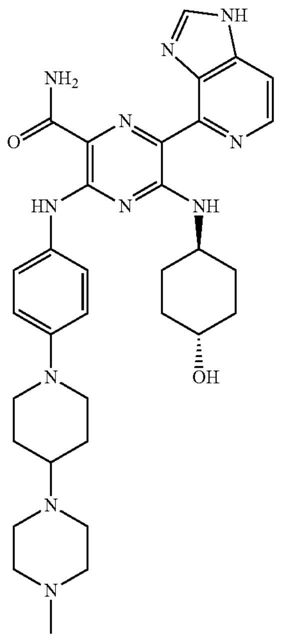
-continued
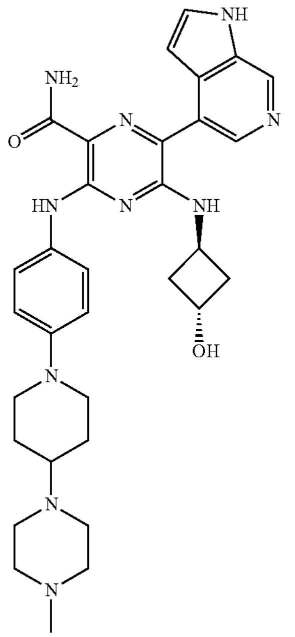
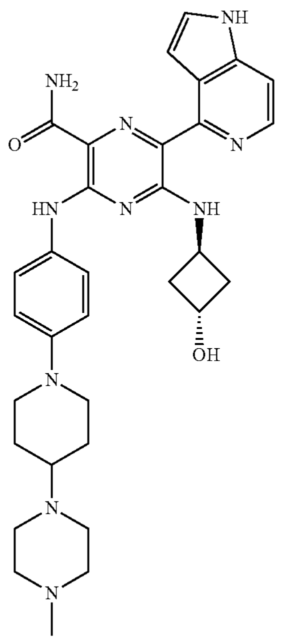

-continued
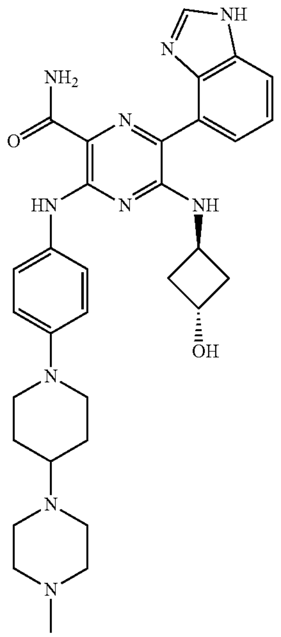
-continued
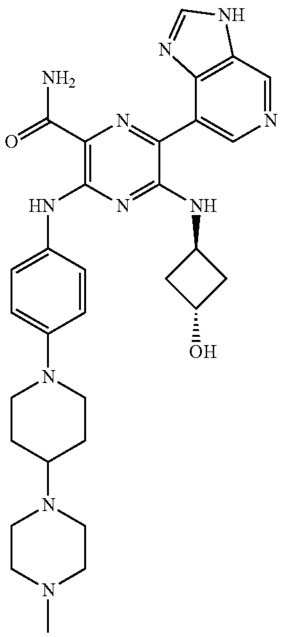
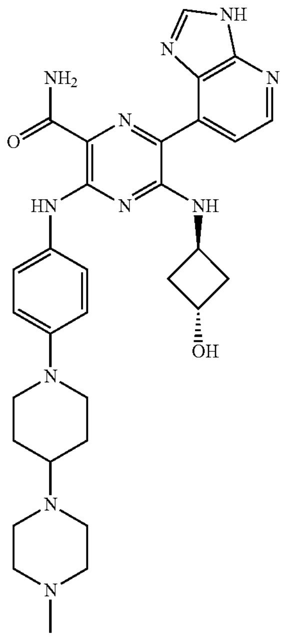
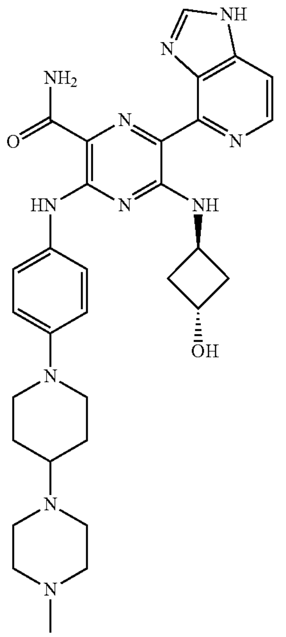

-continued
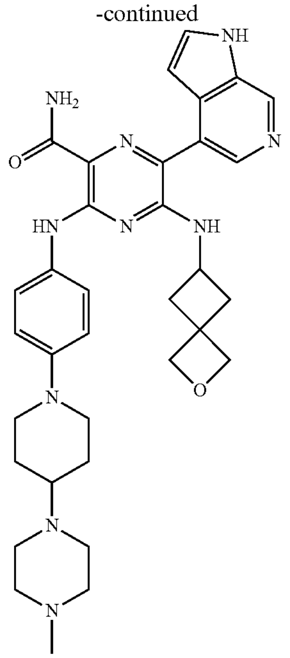
-continued
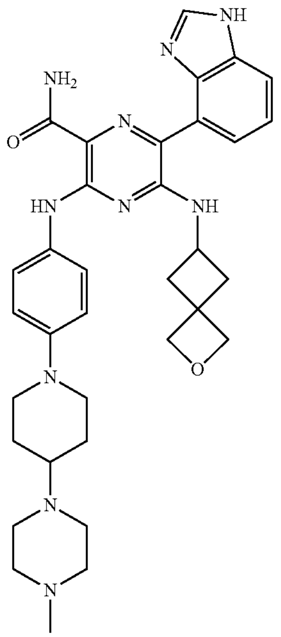
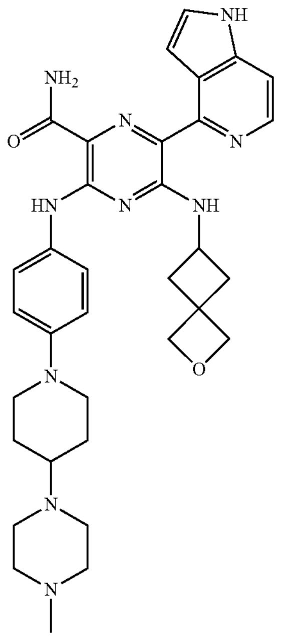
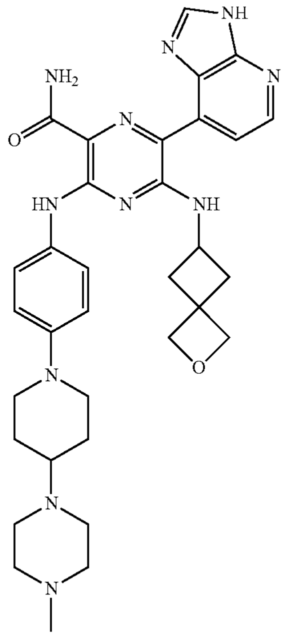

-continued
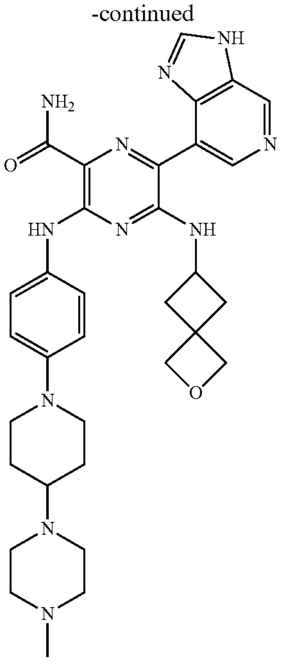
-continued
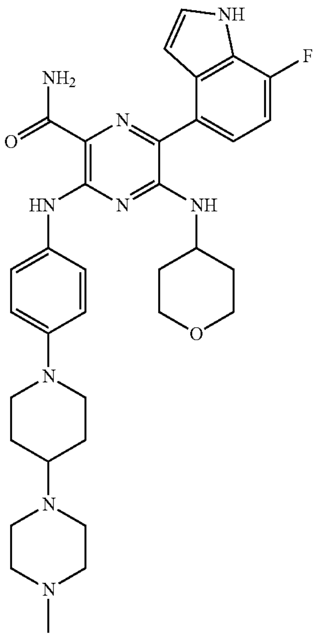
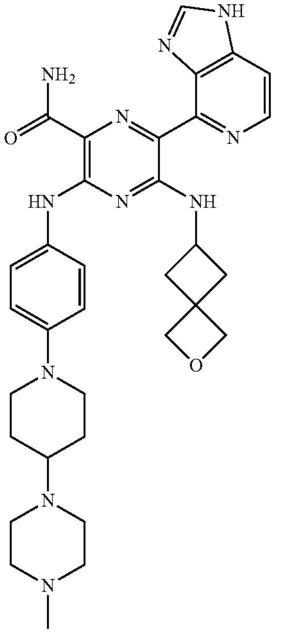
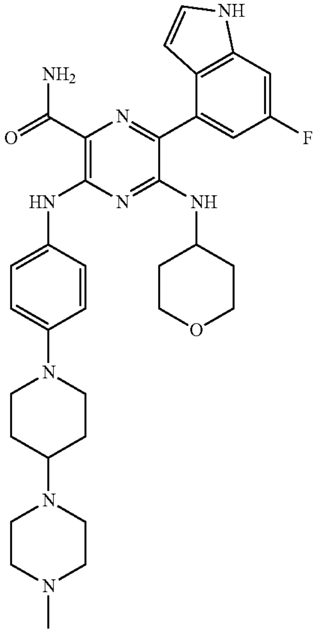

-continued
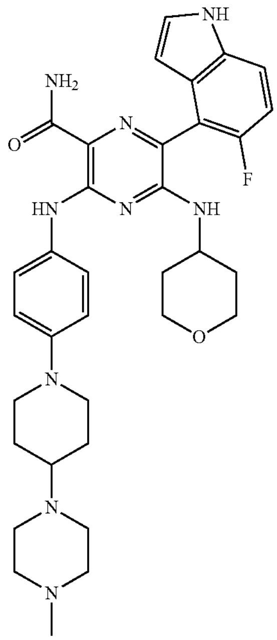
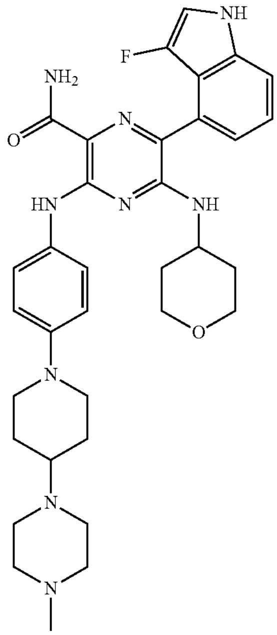
-continued
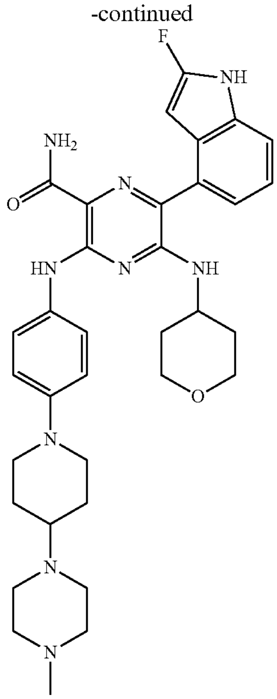
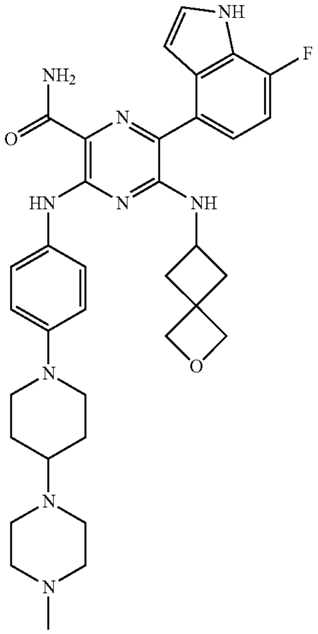

-continued
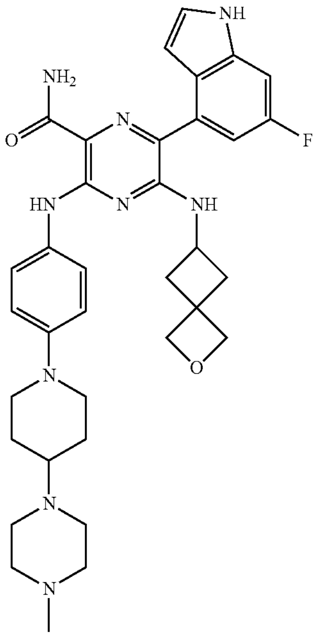
-continued
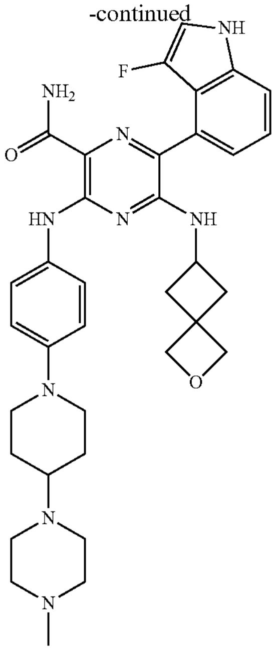
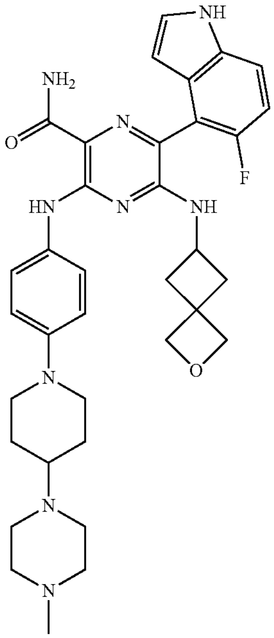
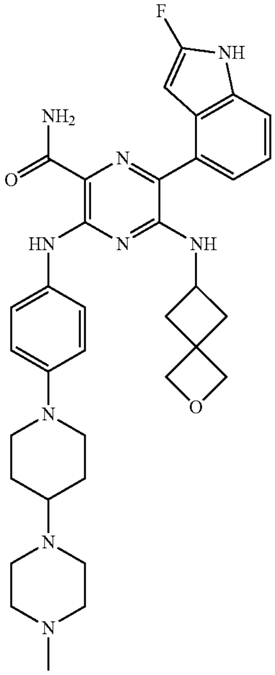

-continued
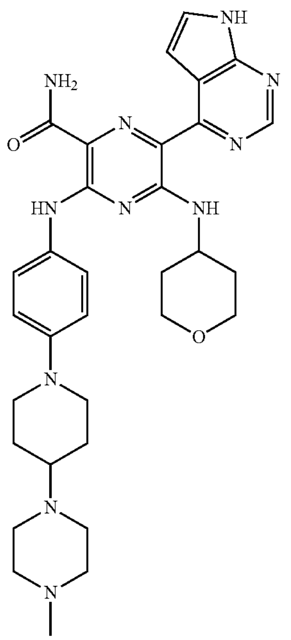
-continued
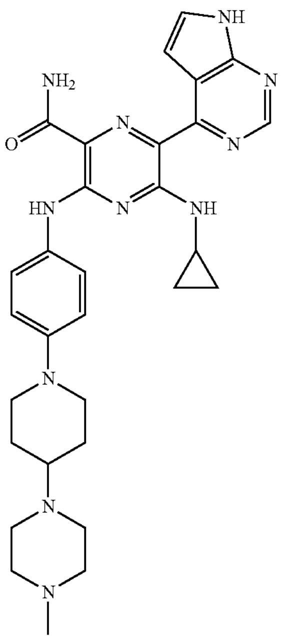
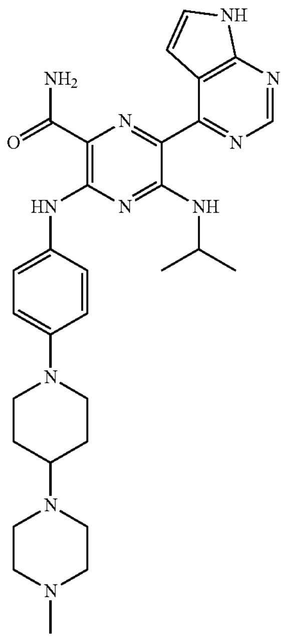
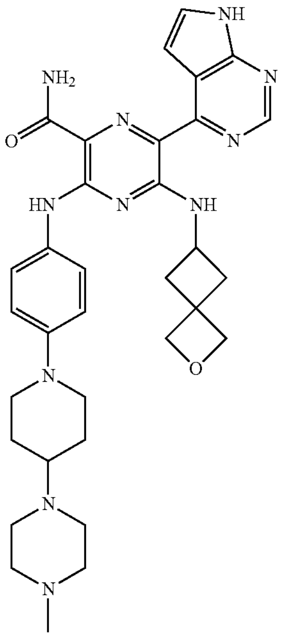

-continued
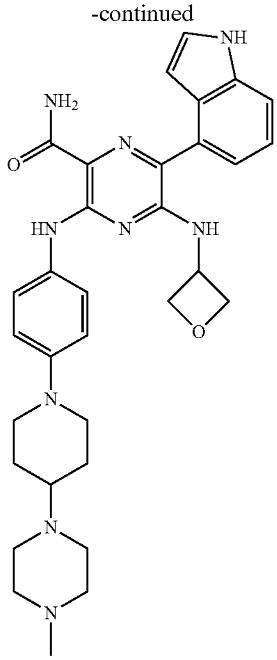
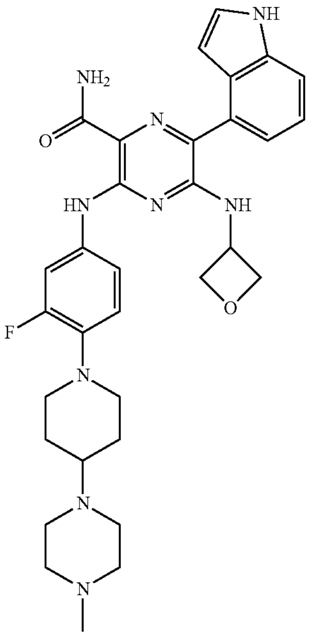
-continued
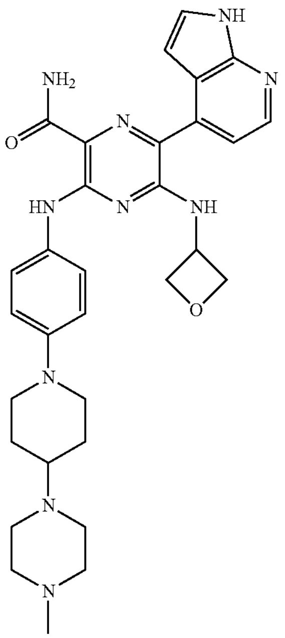
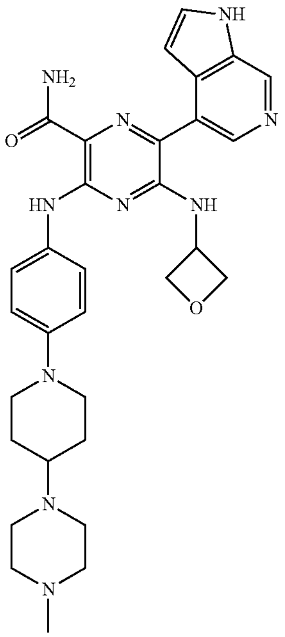

-continued
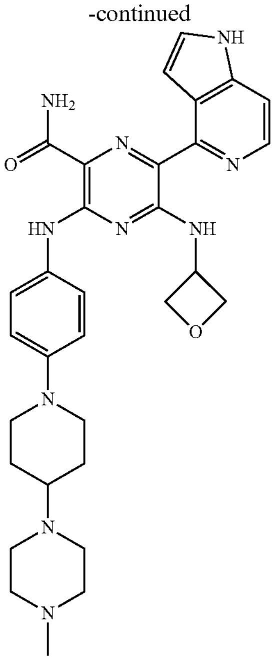
-continued
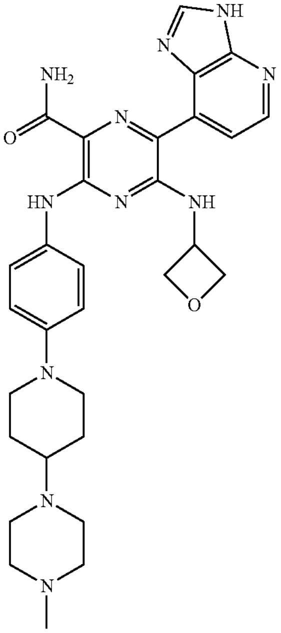
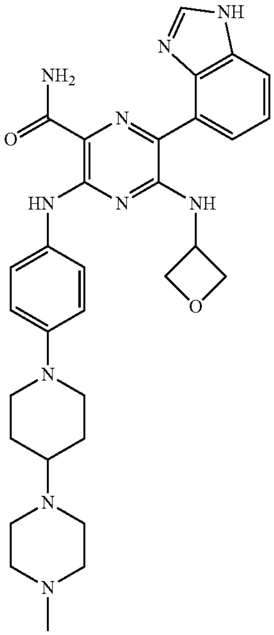
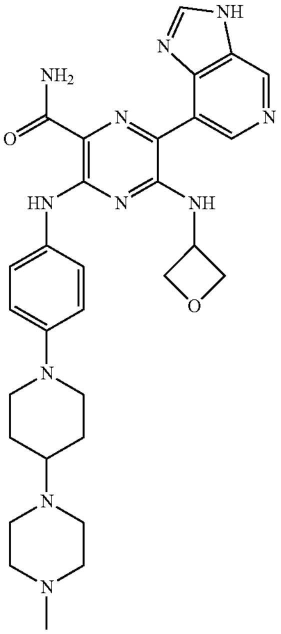

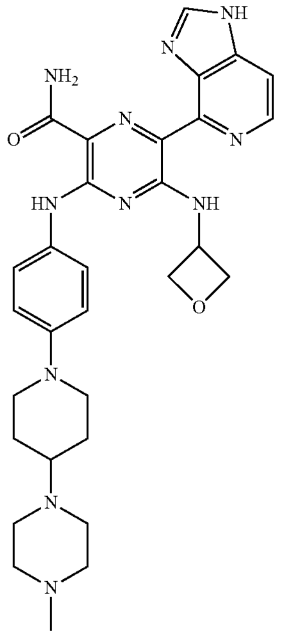
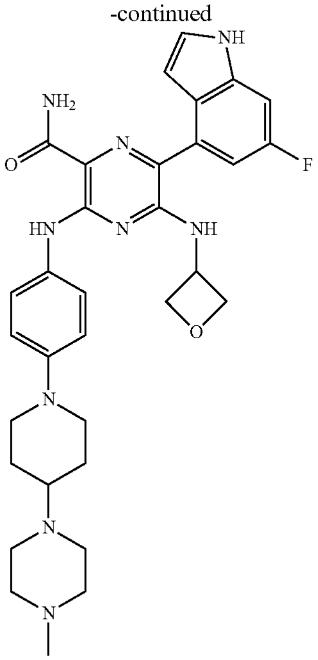
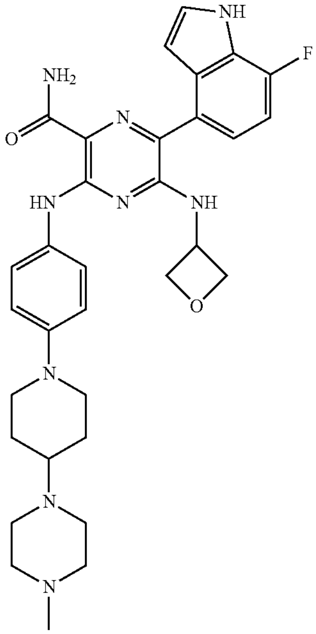
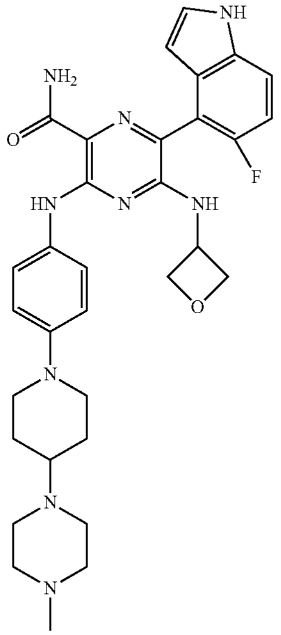

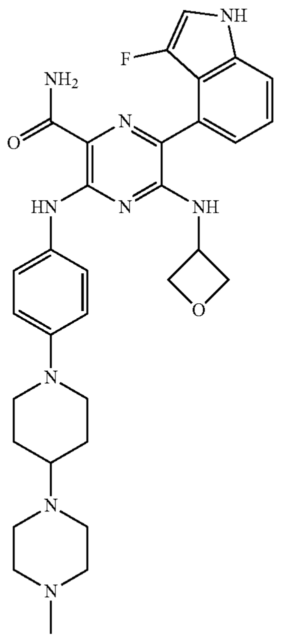
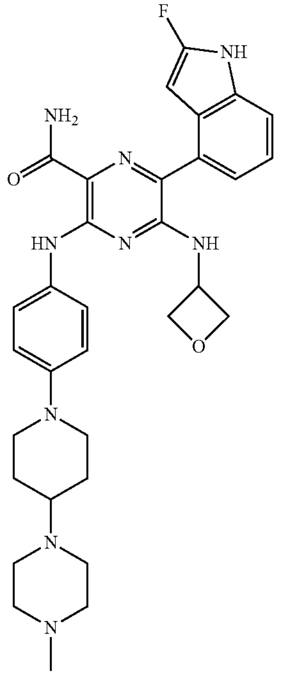
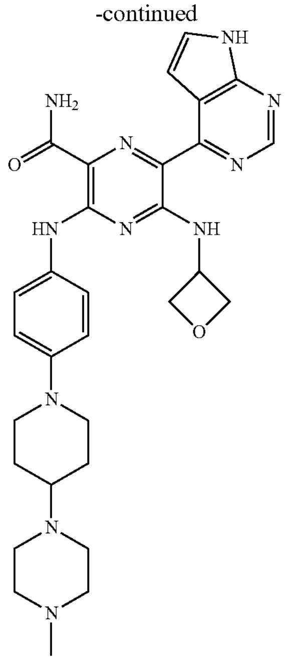
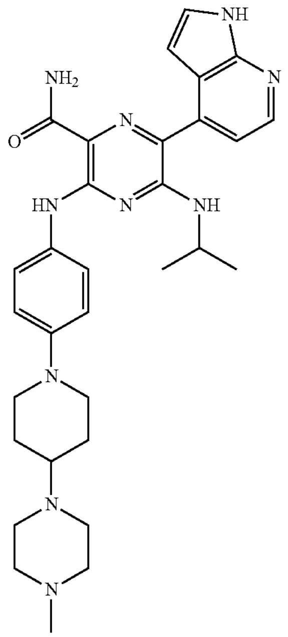

-continued
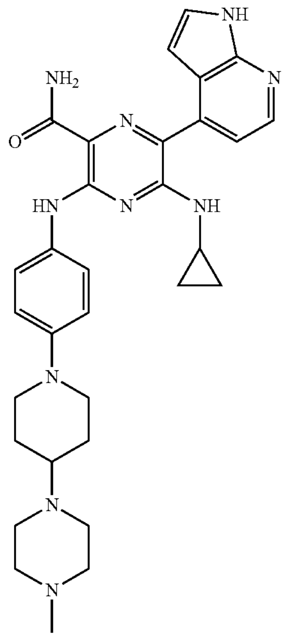
-continued
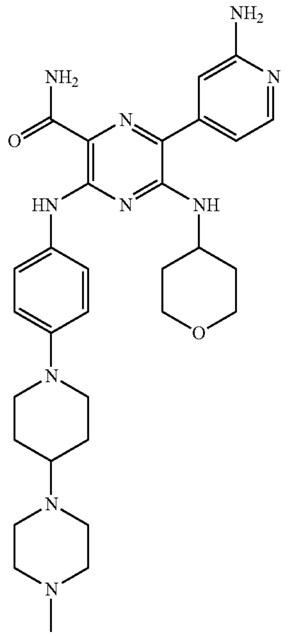
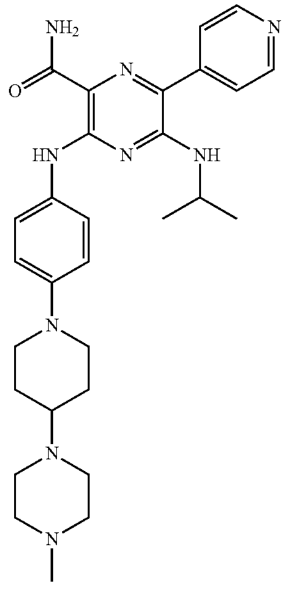
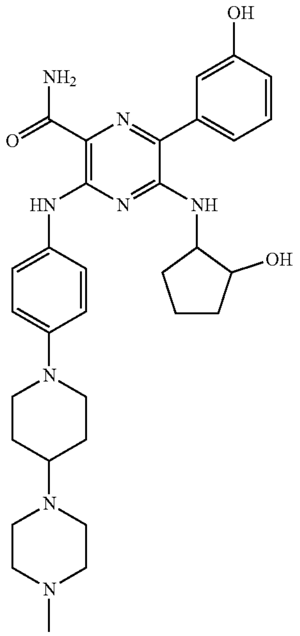

-continued
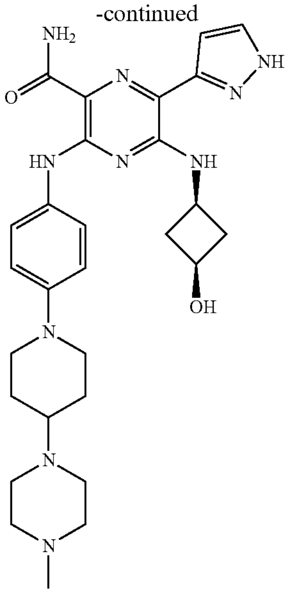
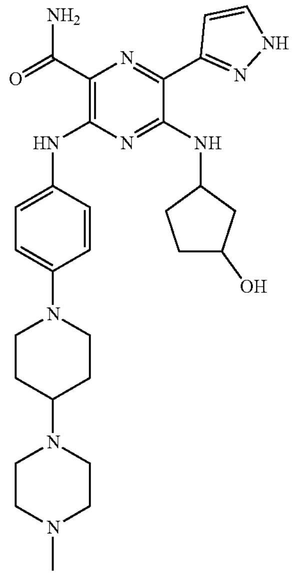
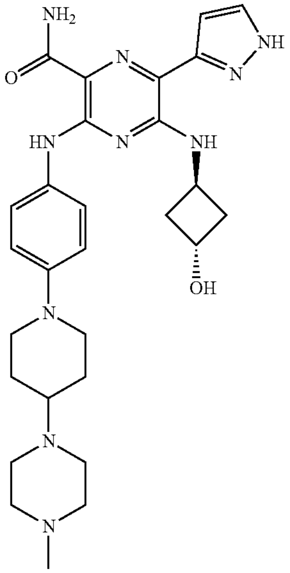
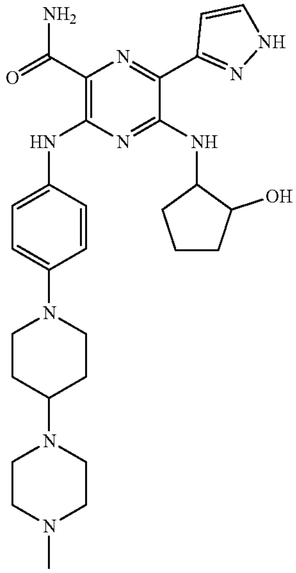
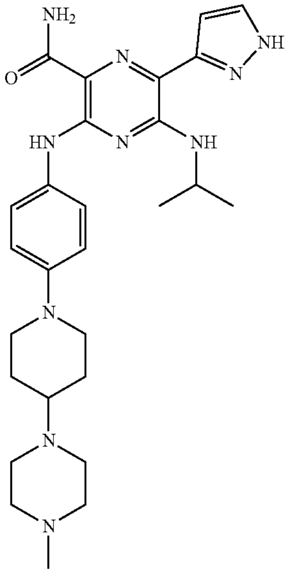
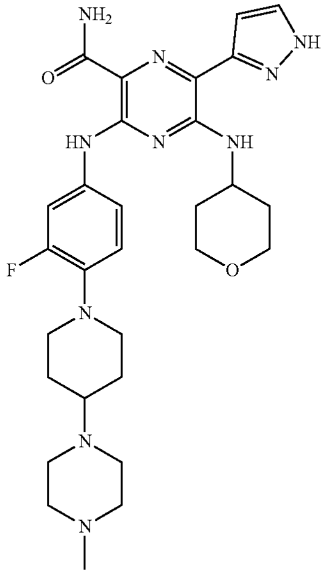
-continued -continued
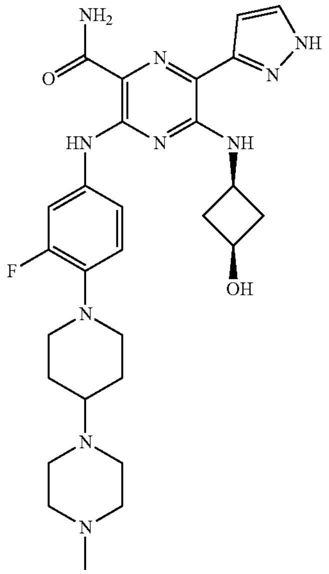
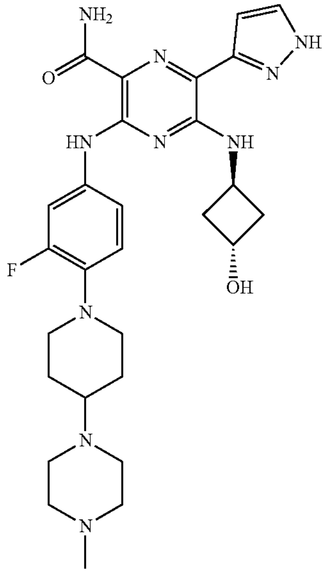
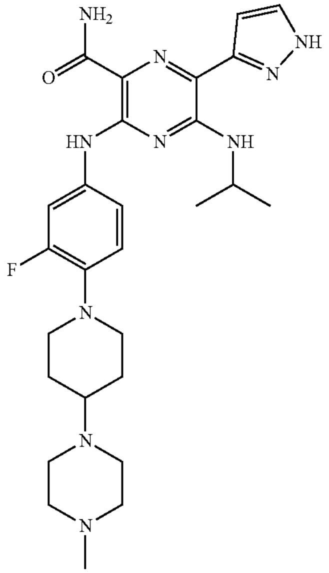
-continued
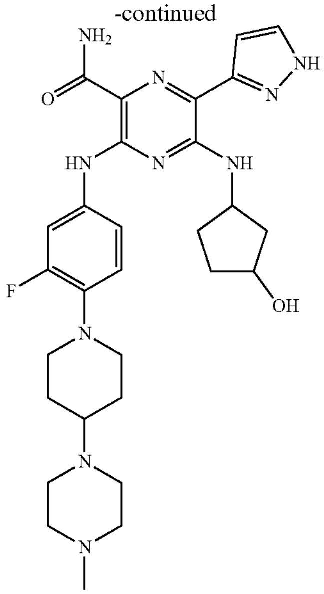
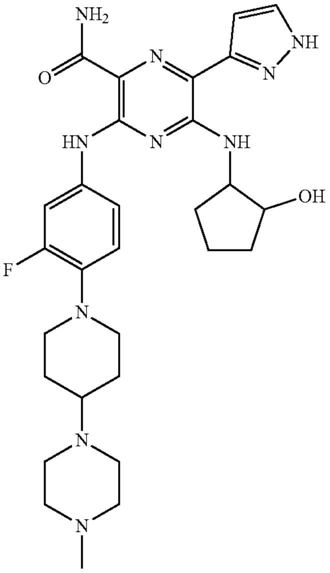
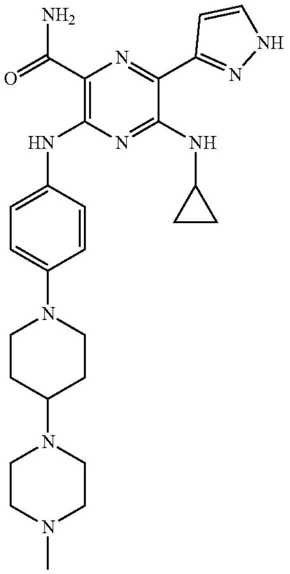

-continued
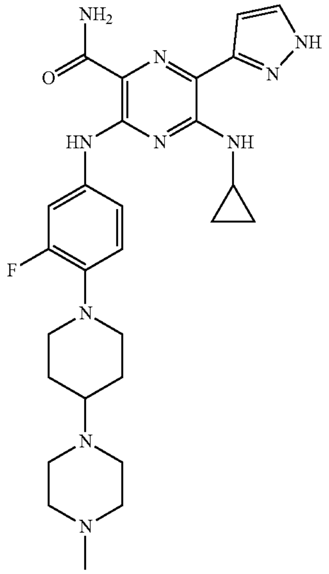
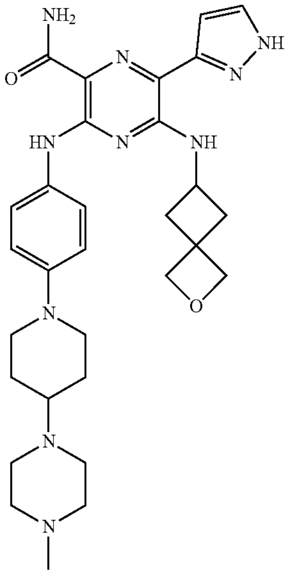
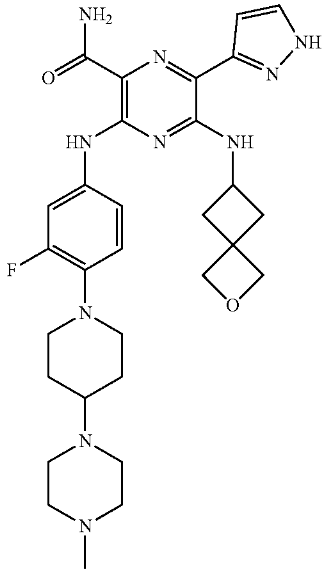
-continued
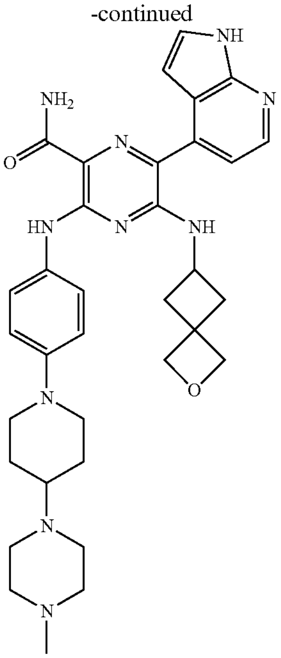
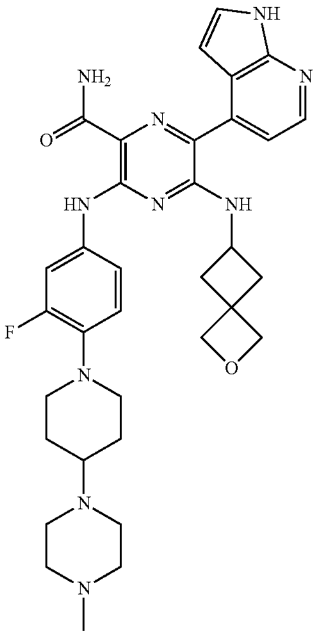

-continued
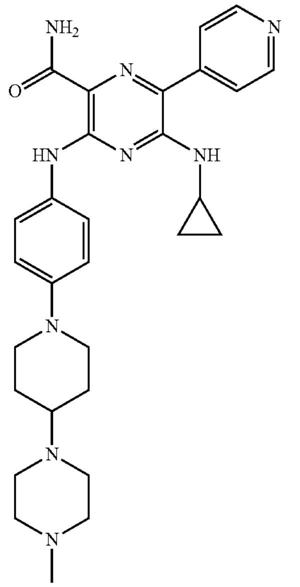
-continued
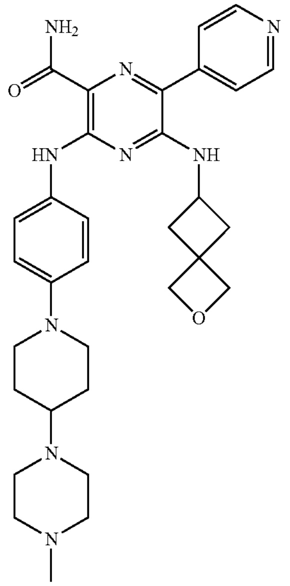
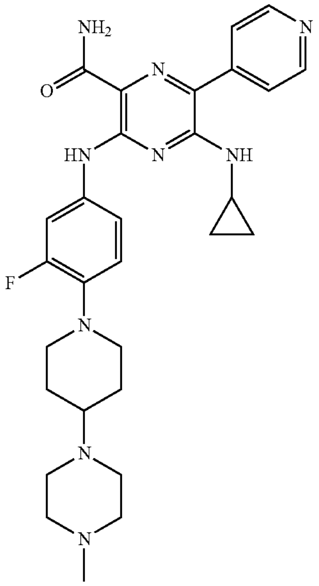
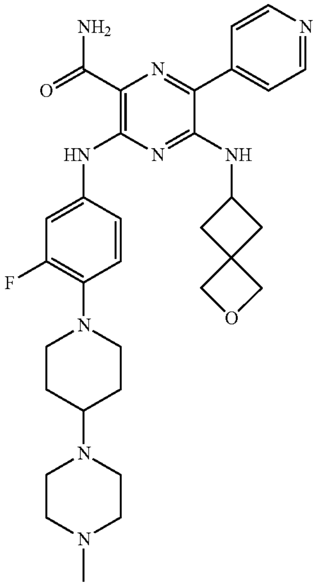

-continued
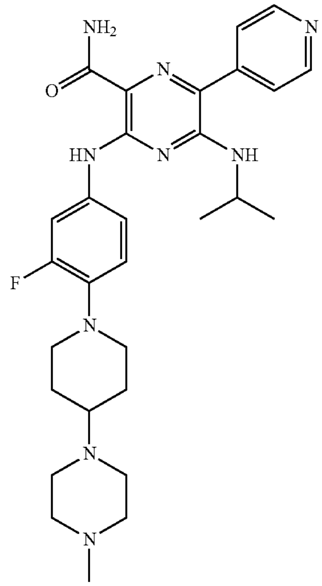
-continued
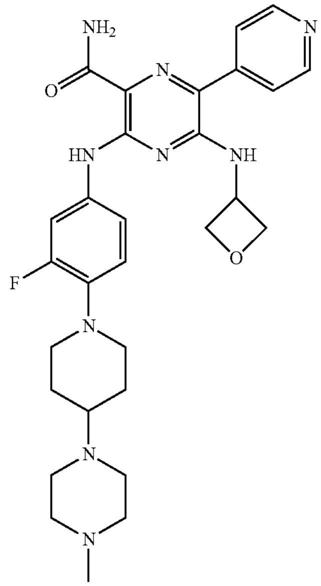
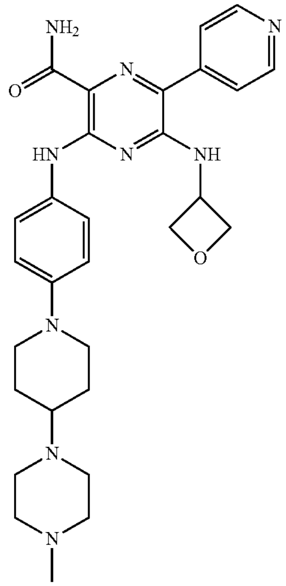
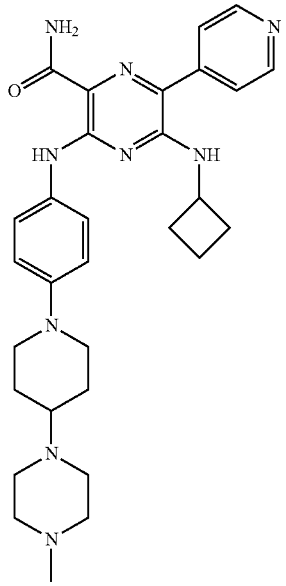

-continued
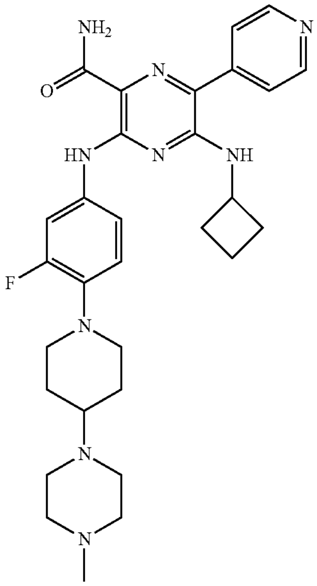
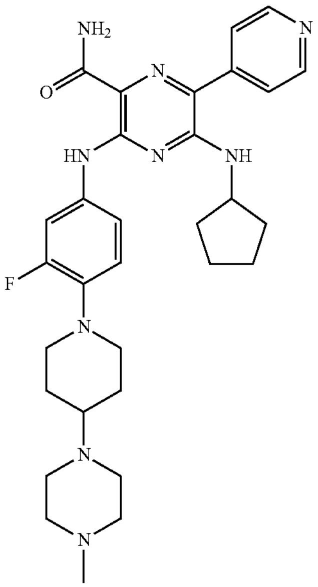
-continued
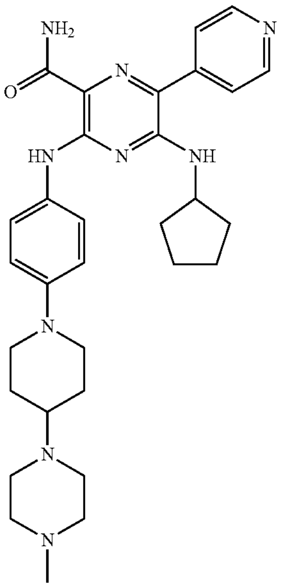
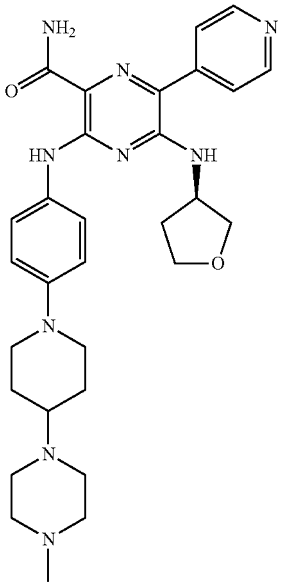

-continued

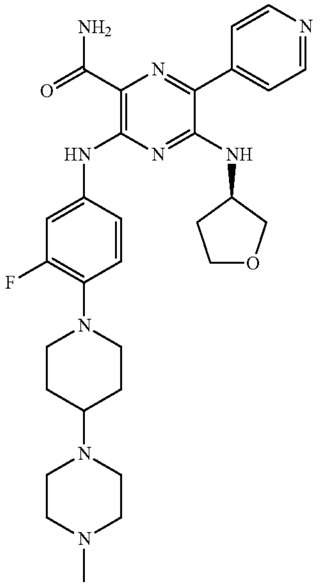

-continued

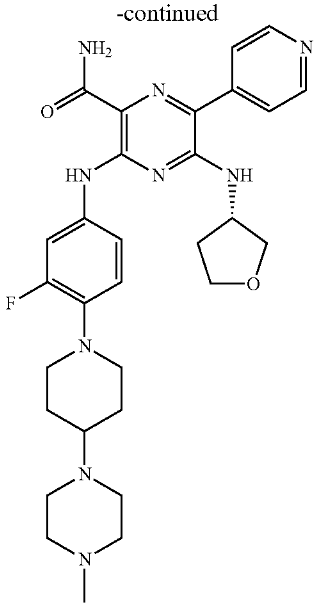

.

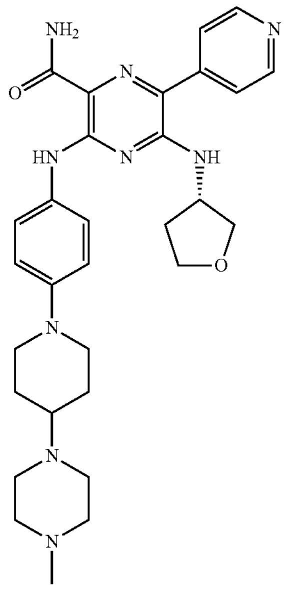

The present invention is further intended to provide a pharmaceutical composition comprising a pharmaceutically acceptable excipient or carrier, and the compound of general formula (1) or the isomer, the crystalline form, the pharmaceutically acceptable salt, the hydrate or the solvate thereof disclosed herein as an active ingredient.

The present invention is still further intended to provide use of the compound, or the isomer, the crystalline form, the pharmaceutically acceptable salt, the hydrate or the solvate thereof, or the pharmaceutical composition disclosed herein in preparing a medicament for treating a disease related to an EGFR mutation.

The present invention is even further intended to provide a method for treating, regulating and/or preventing a disease related to an EGFR mutant protein, comprising administering to a subject a therapeutically effective amount of the compound, or the isomer, the crystalline form, the pharmaceutically acceptable salt, the hydrate or the solvate thereof or the pharmaceutical composition. Through synthesis and careful studies on various novel compounds with EGFR inhibitory effects, the inventors surprisingly found that the compound of general formula (1) has strong inhibitory activity against EGFR$^{del19/T790M/C797S}$ and EGFR$^{L858R/T790M/C797S}$, and has high selectivity for wild-type EGFR WT when Y is a heterocycloalkyl, an aromatic heterocyclic ring or an aryl.

It should be understood that both the above general description and the following detailed description of the present invention are exemplary and explanatory, and are intended to provide further explanation of the present invention claimed.

SYNTHESIS OF THE COMPOUNDS

Figure 1:
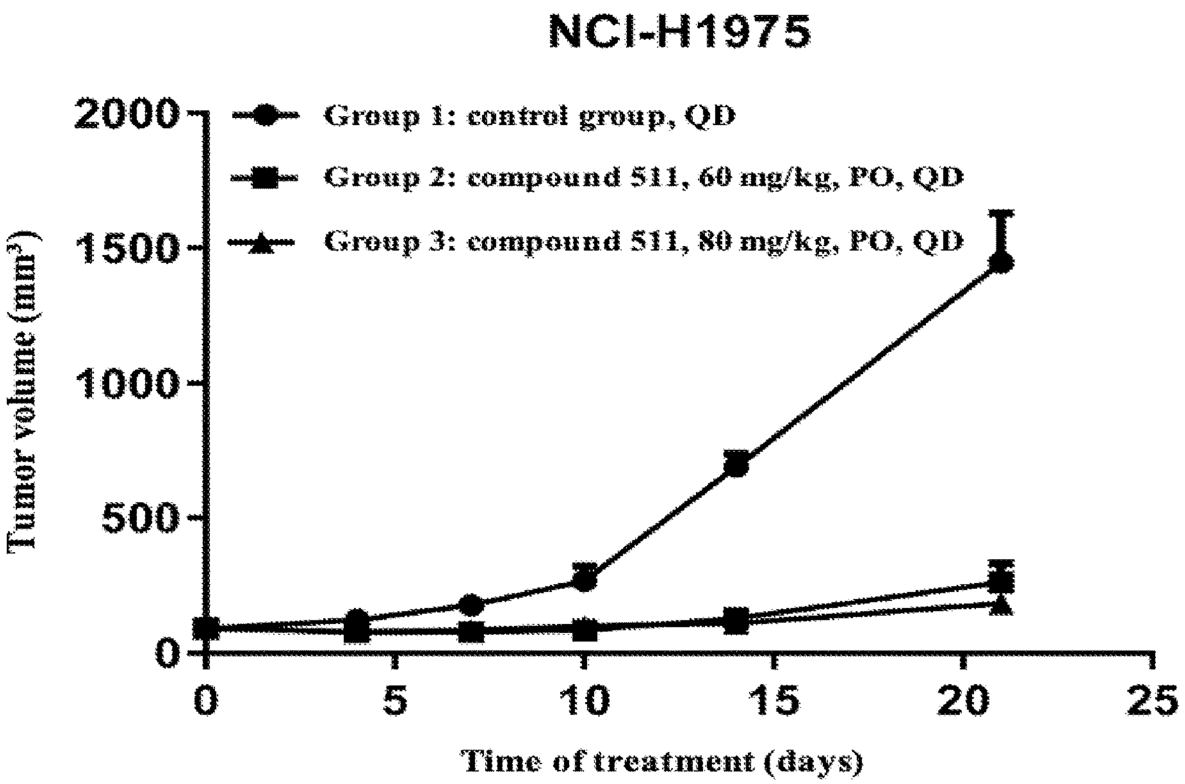
FIG. 1 shows the results of the tumor growth inhibition in an in vivo pharmacodynamic study in mice according to Example 4 of the present invention.

Methods for preparing the compounds of general formulas (1) of the present invention are hereafter described in detail, but these specific methods do not limit the present invention in any way.

The compounds of general formulas (1) described above may be synthesized using standard synthetic techniques or well-known techniques in combination with the methods described herein. In addition, solvents, temperatures and other reaction conditions mentioned herein may vary. Starting materials for the synthesis of the compounds may be obtained synthetically or commercially. The compounds described herein and other related compounds having different substituents may be synthesized using well-known techniques and starting materials, including the methods found in March, ADVANCED ORGANIC CHEMISTRY, $4^{th}$ Ed., (Wiley 1992); Carey and Sundberg, ADVANCED ORGANIC CHEMISTRY, $4^{th}$ Ed., Vols. A and B (Plenum 2000, 2001), and Green and Wuts, PROTECTIVE GROUPS IN ORGANIC SYNTHESIS, $3^{rd}$ Ed., (Wiley 1999). General methods for preparing a compound can be changed by using appropriate reagents and conditions for introducing different groups into the formulas provided herein.

In one aspect, the compounds described herein are prepared according to methods well known in the art. However, the conditions involved in the methods, such as reactants, solvent, base, amount of the compound used, reaction temperature and time required for the reaction are not limited to the following explanation. The compounds of the present invention can also be conveniently prepared by optionally combining various synthetic methods described herein or known in the art, and such combinations can be easily determined by those skilled in the art to which the present invention pertains. In one aspect, the present invention also provides a method for preparing the compounds of general formulas (1), which are prepared using general reaction scheme 1 or general reaction scheme 2 below:

General reaction scheme 1

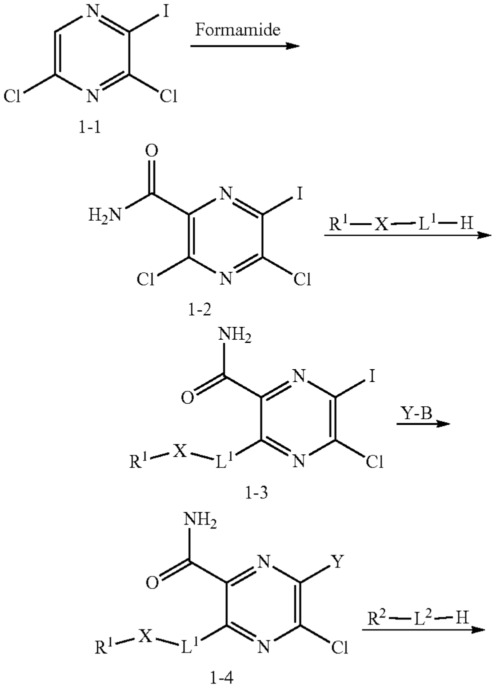

1-1

1-2

1-3

1-4

-continued

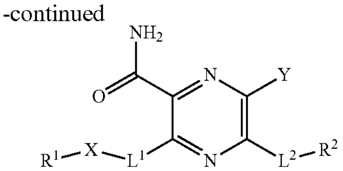

1-5

Embodiments of a compound of general formula (1) may be prepared according to general reaction scheme 1, wherein $R^1$, $R^2$, X, Y, $L^1$ and $L^2$ are as defined above, H represents hydrogen and B represents boric acid, a borate or a trifluoroborate. As shown in general reaction scheme 1, compound 1-1 reacts with formamide to give compound 1-2, compound 1-2 reacts with $R^1$—X-$L^1$-H under a basic condition to give compound 1-3, compound 1-3 and Y—B are subjected to coupling reaction to give compound 1-4, and compound 1-4 reacts with $R^2$-$L^2$-H under a basic condition to give target compound 1-5.

General reaction scheme 2

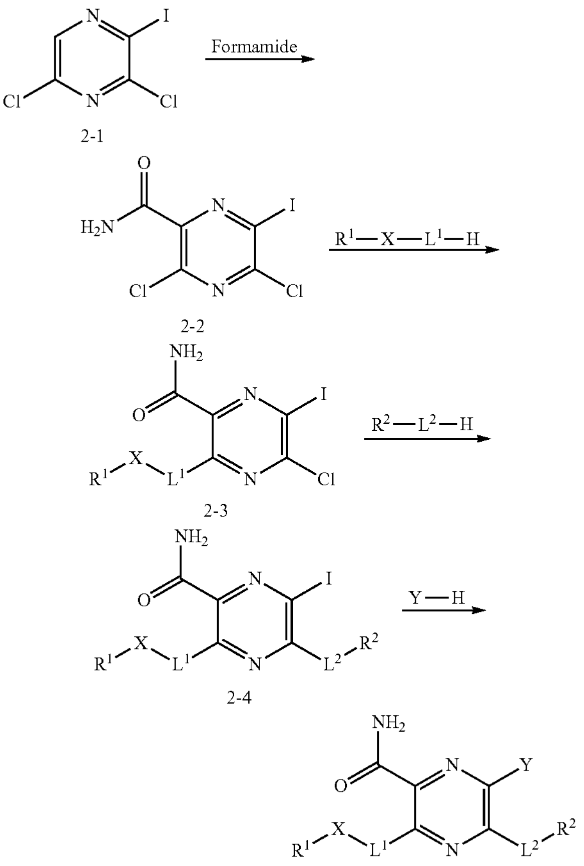

2-1

2-2

2-3

2-4

2-5

Embodiments of a compound of general formula (1) may be prepared according to general reaction scheme 2, wherein $R^1$, $R^2$, X, Y, $L^1$ and $L^2$ are as defined above, and H represents hydrogen. As shown in general reaction scheme 2, compound 2-1 reacts with formamide to give compound 2-2, compound 2-2 reacts with $R^1$—X-$L^1$-H under a basic condition to give compound 2-3, compound 2-3 reacts with $R^2$-$L^2$-H under a basic condition to give compound 2-4, and compound 2-4 reacts with Y—H under a basic condition to give target compound 2-5.

Further Forms of Compounds

"Pharmaceutically acceptable" herein refers to a substance, such as a carrier or diluent, which will not cause a compound to lose its biological activity or properties. It is relatively non-toxic; for example, when an individual is given a substance, it will not cause unwanted biological effects or interact with any component contained therein in a deleterious manner.

The term "pharmaceutically acceptable salt" refers to a form of a compound that does not cause significant irritation to the organism for drug administration or eliminate the biological activity and properties of the compound. In certain specific aspects, pharmaceutically acceptable salts are obtained by reacting the compounds of general formulas (1) with acids, e.g. inorganic acids such as hydrochloric acid, hydrobromic acid, hydrofluoric acid, sulfuric acid, phosphoric acid and nitric acid, organic acids such as formic acid, acetic acid, propionic acid, oxalic acid, trifluoroacetic acid, malonic acid, succinic acid, fumaric acid, maleic acid, lactic acid, malic acid, tartaric acid, citric acid, picric acid, methanesulfonic acid, benzenesulfonic acid and p-toluenesulfonic acid, and acidic amino acids such as aspartic acid and glutamic acid.

It should be understood that references to pharmaceutically acceptable salts include solvent addition forms or crystal forms, especially solvates or polymorphs. A solvate contains either stoichiometric or non-stoichiometric amount of solvent and is selectively formed during crystallization with pharmaceutically acceptable solvents such as water and ethanol. Hydrates are formed when the solvent is water, or alcoholates are formed when the solvent is ethanol. The solvates of the compounds of general formulas (1) are conveniently prepared or formed according to the methods described herein. For example, the hydrates of the compounds of general formulas (1) are conveniently prepared by recrystallization from a mixed solvent of water/organic solvent, wherein the organic solvent used includes, but is not limited to, tetrahydrofuran, acetone, ethanol or methanol. Furthermore, the compounds mentioned herein can exist in both non-solvated and solvated forms. In general, the solvated forms are considered equivalent to the non-solvated forms for purposes of the compounds and methods provided herein.

In other specific examples, the compounds of general formulas (1) are prepared into different forms, including but not limited to amorphous, pulverized and nanoparticle forms. In addition, the compound of general formula (1) includes crystalline forms, and may also be polymorphs. Polymorphs include different lattice arrangements of the same elements of a compound. Polymorphs usually have different X-ray diffraction patterns, infrared spectra, melting points, density, hardness, crystalline forms, optical and electrical properties, stability and solubility. Different factors such as recrystallization solvent, crystallization rate and storage temperature may lead to monocrystalline form being dominant.

In another aspect, the compound of general formula (1) may have a chiral center and/or axial chirality, and thus may be present in the form of a racemate, a racemic mixture, a single enantiomer, a diastereomeric compound, a single diastereomer and a cis-trans isomer. Each chiral center or axial chirality will independently produce two optical isomers, and all possible optical isomers, diastereomeric mixtures and pure or partially pure compounds are included within the scope of the present invention. The present invention is meant to include all such isomeric forms of these compounds.

The compound of the present invention may contain unnatural proportions of atomic isotopes at one or more of the atoms that constitute such the compound. For example, the compound may be labeled with radioactive isotopes, such as tritium (3H), iodine-125 (125I) and C-14 (14C). For another example, deuterium can be used to substitute a hydrogen atom to form a deuterated compound, the bond formed by deuterium and carbon is stronger than that formed by common hydrogen and carbon, and compared with an undeuterated medicament, the deuterated medicament generally has the advantages of reducing toxic and side effects, increasing medicament stability, enhancing curative effect, prolonging in vivo half-life period of the medicament and the like. All isotopic variations of the compound of the present invention, whether radioactive or not, are intended to be encompassed within the scope of the present invention.

Terminology

Unless otherwise stated, the terms used in the present application, including those in the specification and claims, are defined as follows. It must be noted that in the specification and the appended claims, the singular forms "a" and "an" include plural meanings unless clearly indicated otherwise. Unless otherwise stated, conventional methods for mass spectrometry, nuclear magnetic resonance spectroscopy, HPLC, protein chemistry, biochemistry, recombinant DNA technology and pharmacology are used. As used herein, "or" or "and" refers to "and/or" unless otherwise stated.

Unless otherwise specified, "alkyl" refers to a saturated aliphatic hydrocarbon group, including linear and branched groups containing 1 to 14 carbon atoms. Lower alkyls containing 1 to 4 carbon atoms, such as methyl, ethyl, propyl, 2-propyl, n-butyl, isobutyl or tert-butyl, are preferred. As used herein, "alkyl" includes unsubstituted and substituted alkyl, particularly alkyl substituted with one or more halogens. Preferred alkyl is selected from $CH_3$, $CH_3CH_2$, $CF_3$, $CHF_2$, $CF_3CH_2$, $CF_3(CH_3)CH$, $^i$Pr, $^n$Pr, $^i$Bu, $^n$Bu and $^t$Bu.

Unless otherwise specified, "alkenyl" refers to an unsaturated aliphatic hydrocarbon group containing carbon-carbon double bonds, including linear or branched groups containing 1 to 14 carbon atoms. Lower alkenyls containing 1 to 4 carbon atoms, such as vinyl, 1-propenyl, 1-butenyl or 2-methylpropenyl, are preferred.

Unless otherwise specified, "alkynyl" refers to an unsaturated aliphatic hydrocarbon group containing carbon-carbon triple bonds, including linear and branched groups containing 1 to 14 carbon atoms. Lower alkynyls containing 1 to 4 carbon atoms, such as ethynyl, 1-propynyl or 1-butynyl, are preferred.

Unless otherwise specified, "cycloalkyl" refers to a 3- to 14-membered all-carbon monocyclic aliphatic hydrocarbon group, wherein one or more of the rings may contain one or more double bonds, but none of them has a fully conjugated π-electron system. For example, cyclopropyl, cyclobutyl, cyclopentyl, cyclohexane, and cyclohexadiene.

Unless otherwise specified, "alkoxy" refers to an alkyl group that bonds to the rest of the molecule through an ether oxygen atom. Representative alkoxy groups are those having 1-6 carbon atoms, such as methoxy, ethoxy, propoxy, isopropoxy, butoxy, isobutoxy, sec-butoxy and tert-butoxy. As used herein, "alkoxy" includes unsubstituted and substituted alkoxy, particularly alkoxy substituted with one or more halogens. Preferred alkoxy is selected from $OCH_3$, $OCF_3$, $CHF_2O$, $CF_3CH_2O$, $^{i-}$PrO, $^{n-}$PrO, $^{i-}$BuO, $^{n-}$BuO and $^{t-}$BuO.

Unless otherwise specified, "aryl" refers to a monocyclic or polycyclic aromatic hydrocarbon group; for example, a monocyclic aryl ring may be fused with one or more carbocyclic aromatic groups. Examples of aryl include, but are not limited to, phenyl, naphthyl, and phenanthryl.

Unless otherwise specified, "arylene" refers to a divalent aryl defined as above. Examples of arylene include, but are not limited to, phenylene, naphthylene, and phenanthrylene.

Unless otherwise specified, "heteroaryl" refers to a monocyclic or polycyclic aromatic group containing one or more heteroatoms (O, S or N); for example, a monocyclic heteroaryl ring may be fused with one or more carbocyclic aromatic groups or other monocyclic heterocyclyl groups. Examples of heteroaryl include, but are not limited to, pyridinyl, pyridazinyl, imidazolyl, pyrimidinyl, pyrazolyl, triazolyl, pyrazinyl, quinolinyl, isoquinolinyl, furyl, thienyl, isoxazolyl, thiazolyl, oxazolyl, isothiazolyl, pyrrolyl, indolyl, benzimidazolyl, benzofuryl, benzothiazolyl, benzothienyl, benzoxazolyl, benzopyridyl, and pyrrolopyrimidinyl.

Unless otherwise specified, "heteroarylene" refers to a divalent heteroaryl defined as above.

Unless otherwise specified, "heterocycloalkyl" refers to a saturated or partially unsaturated ring system group containing one or more heteroatoms (O, S or N), wherein the nitrogen and sulfur atoms are optionally oxidized, and the nitrogen atom is optionally quaternized as a ring atom. Unless otherwise stated, the "heterocycloalkyl" ring system may be a monocyclic, bicyclic, spiro or polycyclic ring system. "Heterocycloalkyl" may link to the rest of the molecule through one or more ring carbons or heteroatoms. Examples of "heterocycloalkyl" include, but are not limited to, pyrrolidine, piperidine, N-methylpiperidine, tetrahydroimidazole, pyrazolidine, butyrolactam, valerolactam, imidazolidinone, hydantoin, dioxolane, phthalimide, pyrimidine-2,4(1H,3H)-dione, 1,4-dioxane, morpholine, thiomorpholine, thiomorpholine-S-oxide, thiomorpholine-S,S-oxide, piperazine, pyran, pyridone, 3-pyrroline, thiopyran, pyrone, tetrahydrofuran, tetrahydrothiophene, quinuclidine, 2-azaspiro[3.3]heptane, etc.

Unless otherwise specified, "halogen" (or halo) refers to fluorine, chlorine, bromine, or iodine.

The term "halo" (or "halogenated") before a group name indicates that the group is partially or fully halogenated, that is, substituted in any combination by F, Cl, Br or I, preferably by F or Cl.

"Optional" or "optionally" means that the subsequently described event or circumstance may, but does not necessarily, occur, and the description includes instances where the event or circumstance occurs and instances where it does not.

The substituent "$-O-CH_2-O-$" means that two oxygen atoms in the substituent are linked to two adjacent carbon atoms in the heterocycloalkyl, aryl or heteroaryl, for example:

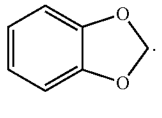

When the number of a linker group is 0, such as $-(CH_2)_0-$, it means that the linker group is a single bond.

When one of the variables is selected from a chemical bond, it means that the two groups linked by this variable are linked directly. For example, when L in X-L-Y represents a chemical bond, it means that the structure is actually X—Y.

Specific Pharmaceutical and Medical Terminology

The term "acceptable", as used herein, means that a formula component or an active ingredient does not unduly adversely affect a general therapeutic target's health.

The terms "treatment," "treatment course," or "therapy", as used herein, include alleviating, inhibiting, or ameliorating a symptom or condition of a disease; inhibiting the development of complications; ameliorating or preventing underlying metabolic syndrome; inhibiting the development of the disease or symptom, e.g., controlling the progression of the disease or condition; alleviating the disease or symptom; causing the disease or symptom to subside; alleviating a complication caused by the disease or symptom, or preventing or treating a sign caused by the disease or symptom. As used herein, a compound or pharmaceutical composition, when administered, can ameliorate a disease, symptom, or condition, particularly meaning ameliorating the severity, delaying the onset, slowing the progression, or reducing the duration of the disease. Fixed or temporary administration, or continuous or intermittent administration, may be attributed to or associated with the administration.

The "active ingredient" refers to compounds of general formulas (1) through (3), and pharmaceutically acceptable inorganic or organic salts of the compounds of general formulas (1) through (3). The compounds of the present invention may contain one or more asymmetric centers (axial chirality) and thus occur in the form of a racemate, racemic mixture, single enantiomer, diastereomeric compound and single diastereomer. Asymmetric centers that may be present depend on the nature of the various substituents on the molecule. Each of these asymmetric centers will independently produce two optical isomers, and all possible optical isomers, diastereomeric mixtures and pure or partially pure compounds are included within the scope of the present invention. The present invention is meant to include all such isomeric forms of these compounds.

The terms such as "compound", "composition", "agent" or "medicine or medicament" are used interchangeably herein and all refer to a compound or composition that, when administered to an individual (human or animal), is capable of inducing a desired pharmacological and/or physiological response by local and/or systemic action.

The term "administered, administering or administration" refers herein to the direct administration of the compound or composition, or the administration of a prodrug, derivative, analog or the like of the active compound.

Although the numerical ranges and parameters defining the broad scope of the present invention are approximations, the related numerical values set forth in the specific examples have been present herein as precisely as possible. Any numerical value, however, inherently contains a standard deviation necessarily resulting from certain methods of testing. Herein, "about" generally means that the actual value is within a particular value or range±10%, 5%, 1%, or 0.5%. Alternatively, the term "about" indicates that the actual value falls within the acceptable standard error of a mean, as considered by those skilled in the art. All ranges, quantities, values and percentages used herein (e.g., to describe an amount of a material, a length of time, a temperature, an operating condition, a quantitative ratio and the like) are to be understood as being modified by the word "about", except in the experimental examples or where otherwise explicitly indicated. Accordingly, unless otherwise contrarily stated, the numerical parameters set forth in the specification and the appended claims are all approximations that may vary as desired. At the very least, these numerical parameters should be construed as the significant digits indicated or the numerical value obtained using conventional rounding rules.

Unless otherwise defined in the specification, the scientific and technical terms used herein have the same meaning as commonly understood by those skilled in the art. Furthermore, the singular nouns used in the specification encompass their plural forms, unless contradicted by context; the plural nouns used also encompass their singular forms.

Therapeutic Use

The present invention provides a method for treating a disease, including but not limited to a condition involving EGFR mutation (e.g., cancer), with the compound or pharmaceutical composition disclosed herein.

In some embodiments, a method for treating cancer is provided, comprising administering to an individual in need an effective amount of any aforementioned pharmaceutical composition comprising the compound of structural formula (1). In some embodiments, the cancer is mediated by EGFR mutation. In other embodiments, the cancer is lung cancer, pancreatic cancer, colon cancer, bladder cancer, brain cancer, breast cancer, urothelial carcinoma, prostate cancer, ovarian cancer, head and neck cancer, gastric cancer, mesothelioma, or all cancer metastases.

Route of Administration

The compound and the pharmaceutically acceptable salt thereof of the present invention can be prepared into various preparations which include the compound or the pharmaceutically acceptable salt thereof disclosed herein in a safe and effective amount range and a pharmaceutically acceptable excipient or carrier, wherein the "safe and effective amount" means that the amount of the compound is sufficient to significantly improve the condition without causing serious side effects. The safe and effective amount of the compound is determined according to the age, condition, course of treatment and other specific conditions of a treated subject.

The "pharmaceutically acceptable excipient or carrier" refers to one or more compatible solid or liquid fillers or gel substances which are suitable for human use and must be of sufficient purity and sufficiently low toxicity. "Compatible" means that the components of the composition are capable of intermixing with the compound of the present invention and with each other, without significantly diminishing the pharmaceutical efficacy of the compound. Examples of pharmaceutically acceptable excipients or carriers are cellulose and its derivatives (e.g., sodium carboxymethylcellulose, sodium ethylcellulose or cellulose acetate), gelatin, talc, solid lubricants (e.g., stearic acid or magnesium stearate), calcium sulfate, vegetable oil (e.g., soybean oil, sesame oil, peanut oil or olive oil), polyols (e.g., propylene glycol, glycerol, mannitol or sorbitol), emulsifiers (e.g., Tween®), wetting agents (e.g., sodium lauryl sulfate), colorants, flavoring agents, stabilizers, antioxidants, preservatives, pyrogen-free water, etc.

When the compound of the present invention is administered, it may be administered orally, rectally, parenterally (intravenously, intramuscularly or subcutaneously) or topically.

Solid dosage forms for oral administration include capsules, tablets, pills, pulvises and granules. In these solid dosage forms, the active compound is mixed with at least one conventional inert excipient (or carrier), such as sodium citrate or dicalcium phosphate, or with the following ingredients: (a) fillers or extenders, such as starch, lactose, sucrose, glucose, mannitol and silicic acid; (b) binders, such as hydroxymethyl cellulose, alginate, gelatin, polyvinylpyrrolidone, sucrose and acacia; (c) humectants, such as glycerol; (d) disintegrants, such as agar, calcium carbonate, potato or tapioca starch, alginic acid, certain complex silicates and sodium carbonate; (e) solution retarders, such as paraffin; (f) absorption accelerators, such as quaternary ammonium compounds; (g) wetting agents, such as cetyl alcohol and glycerol monostearate; (h) adsorbents, such as kaolin; and (i) lubricants, such as talc, calcium stearate, magnesium stearate, solid polyethylene glycol and sodium lauryl sulfate, or mixtures thereof. In the case of capsules, tablets and pills, the dosage forms may also include buffers.

Solid dosage forms such as tablets, dragees, capsules, pills and granules can be prepared using coatings and shells such as enteric coatings and other materials well known in the art. They may include opacifying agents, and the active compound or compound in such a composition may be released in a certain part of the digestive tract in a delayed manner. Examples of embedding components that can be used are polymeric substances and wax-based substances. If necessary, the active compound can also be in microcapsule form with one or more of the above-mentioned excipients.

Liquid dosage forms for oral administration include pharmaceutically acceptable emulsions, solutions, suspensions, syrups and elixirs. In addition to the active compound, the liquid dosage form may include inert diluents commonly used in the art, such as water or other solvents, solubilizers and emulsifiers, for example, ethanol, isopropanol, ethyl carbonate, ethyl acetate, propylene glycol, 1,3-butanediol, dimethylformamide, and oils, especially cottonseed oil, groundnut oil, corn germ oil, olive oil, castor oil and sesame oil, or mixtures of these substances. Besides such inert diluents, the composition may also include adjuvants, such as wetting agents, emulsifiers, suspending agents, sweeteners, flavoring agents, and perfuming agents.

Suspensions, in addition to the active compound, may include suspending agents, such as ethoxylated isostearyl alcohols, polyoxyethylene sorbitol and sorbitan esters, microcrystalline cellulose, aluminum methylate and agar, or mixtures of these substances.

Compositions for parenteral injection may include physiologically acceptable sterile aqueous or anhydrous solutions, dispersions, suspensions or emulsions, and sterile powders for redissolving into sterile injectable solutions or dispersions. Suitable aqueous and non-aqueous carriers, diluents, solvents or excipients include water, ethanol, polyols and suitable mixtures thereof.

Dosage forms for topical administration of the compound of the present invention include ointments, pulvises, patches, sprays and inhalants. The active ingredient is mixed under sterile conditions with a physiologically acceptable carrier and any preservatives, buffers or propellants that may be required if necessary.

The compound of the present invention may be administered alone or in combination with other pharmaceutically acceptable compounds.

When the pharmaceutical composition is used, a safe and effective amount of the compound of the present invention is administered to a mammal (such as a human) to be treated, wherein the administration dose is a pharmaceutically effective administration dose. For a human weighing 60 kg, the daily dose of administration is usually 1-2000 mg, preferably 50-1000 mg. In determining a specific dose, such factors as the route of administration, the health condition of the patient and the like will also be considered, which are well known to skilled physicians.

The above features mentioned in the present invention or those mentioned in the examples may be combined arbitrarily. All the features disclosed in this specification may be used with any composition form and the various features disclosed in this specification may be replaced with any alternative features that provide the same, equivalent or similar purpose. Thus, unless otherwise expressly stated, the features disclosed are merely general examples of equivalent or similar features.

DETAILED DESCRIPTION

Various specific aspects, features and advantages of the compounds, methods and pharmaceutical compositions described above are set forth in detail in the following description, which makes the present invention clear. It should be understood that the detailed description and examples below describe specific embodiments for reference only. After reading the description of the present invention, those skilled in the art can make various changes or modifications to the present invention, and such equivalents also fall within the scope of the present invention defined herein.

In all examples, 1H-NMR spectra were recorded with a Vian Mercury 400 nuclear magnetic resonance spectrometer, and chemical shifts are expressed in δ (ppm); silica gel for separation was 200-300 mesh silica gel if not specified, and the ratio of the eluents was volume ratio.

In the present invention, the following abbreviations are used: $CDCl_3$ for deuterated chloroform; $CD_3OD$ for deuterated methanol; DMSO-d6 for deuterated dimethyl sulfoxide; EtOAc for ethyl acetate; Hexane for n-hexane; MeCN for acetonitrile; DCM for dichloromethane; DIPEA for diisopropylethylamine; NMP for 1-methylpyrrolidin-2-one; Dioxane for 1,4-dioxane; DMF for N,N-dimethylformamide; DMSO for dimethyl sulfoxide; h for hour; $K_3PO_4$ for potassium phosphate; min for minute; MS for mass spectroscopy; NaH for sodium hydride; NMR for nuclear magnetic resonance; $Pd_2(dba)_3$ for tris(dibenzylideneacetone) dipalladium; $Pd(dppf)Cl_2$ for [1,1'-bis(diphenylphosphino) ferrocene]palladium dichloride; TFA ($CF_3COOH$) for trifluoroacetic acid; TLC for thin layer chromatography; THF for tetrahydrofuran; Xantphos for 4,5-bis(diphenylphosphane)-9,9-dimethylxanthene.

Synthesis Method A

Synthesis of Compound 135 (5-((3-hydroxycyclopentyl)amino)-3-((4-(4-(4-methylpiperazin-1-yl)piperidin-1-yl)phenyl)amino)-6-phenylpyrazine-2-carboxamide) and Optical Isomers Thereof (Compounds 136, 137, 138 and 139) Using Synthesis Method A

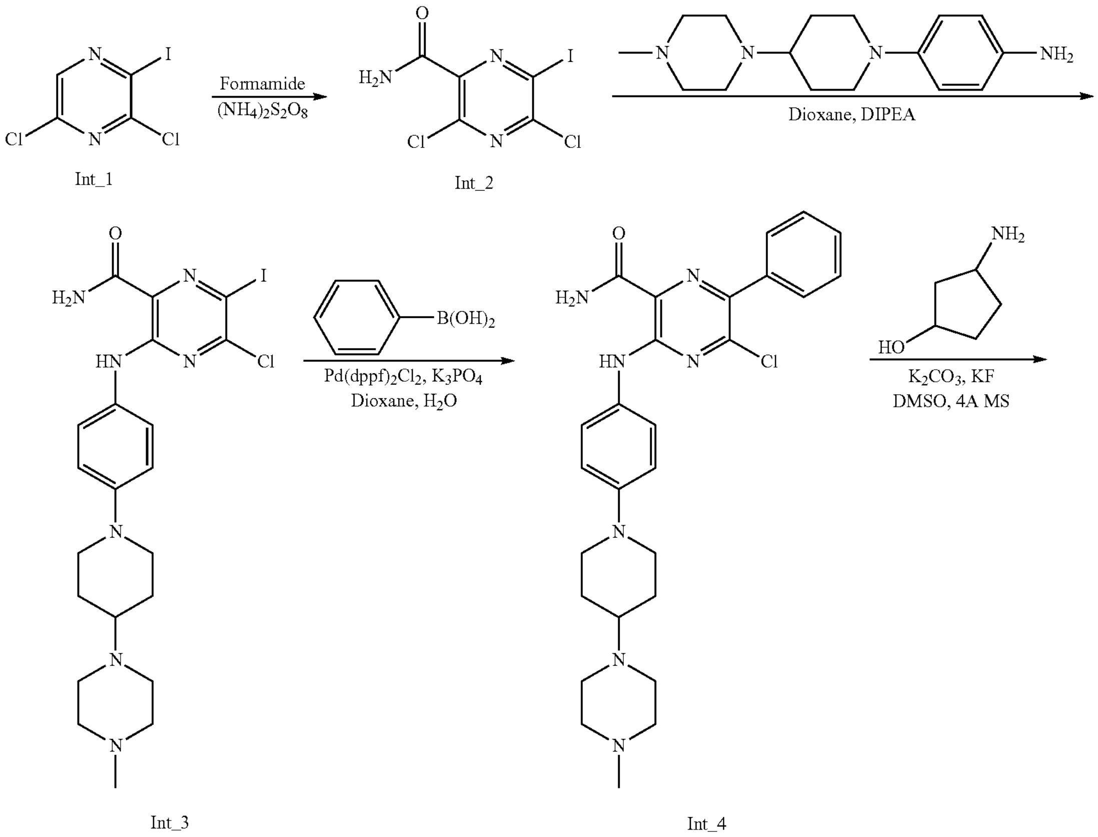

-continued

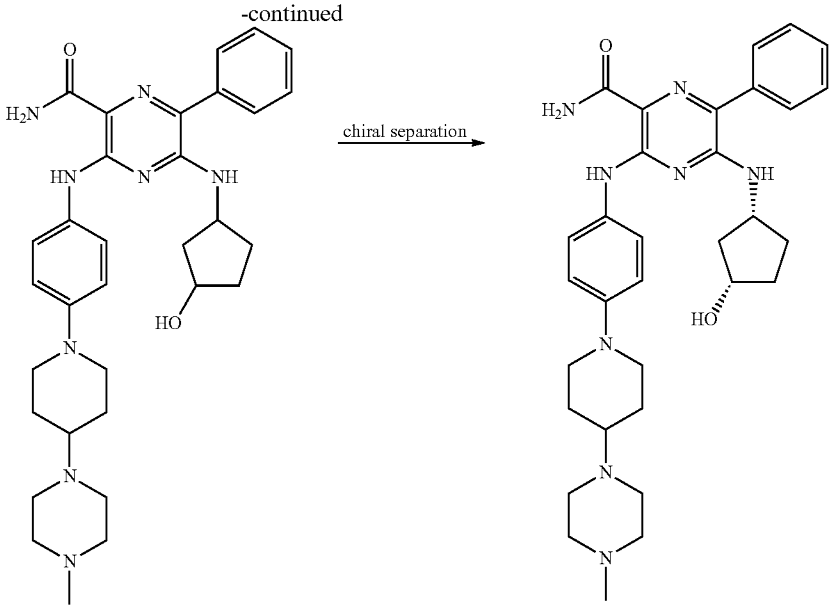

135

136

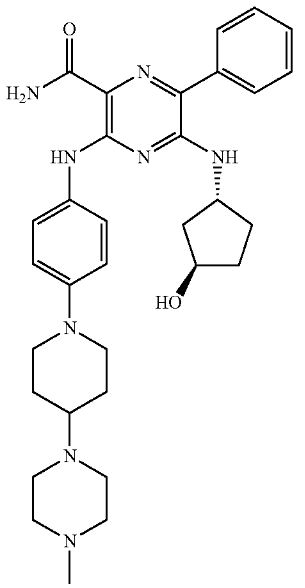

137

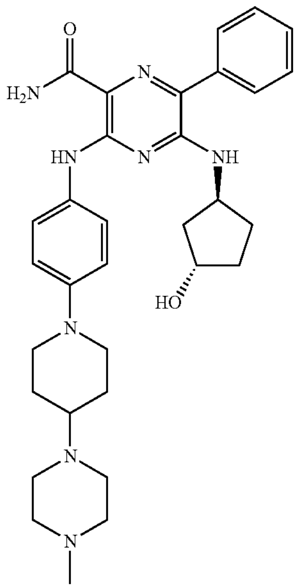

138

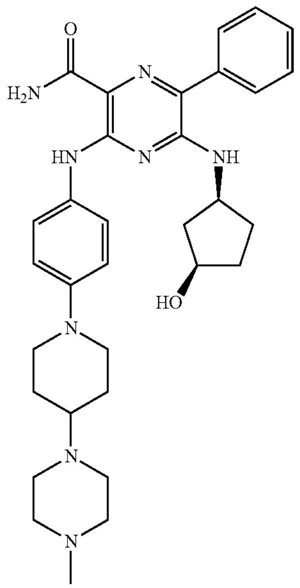

139

Step 1: Synthesis of Compound 3,5-dichloro-6-iodopyrazine-2-carboxamide (Compound int_2)

3,5-Dichloro-2-iodopyrazine (15 g, 54.57 mmol) and formamide (300 mL) were added into a 500-mL single-neck flask, and the mixture was stirred and heated to 90° C. Solid $(NH_4)_2S_2O_8$ (25 g, 109.1 mmol) was added in batches, and the mixture was stirred at 90° C. for 2 h. Solid $K_2S_2O_8$ (30 g, 109.1 mmol) was supplemented in batches, and the mixture was stirred at 90° C. for 20 h. The reaction product was monitored by LC-MS, and there were starting materials left. The mixture was added with EtOAc (150 mL) and water (300 mL), stirred and separated. The aqueous phase was again extracted with EtOAc (150 mL). The organic phases were combined, washed with saturated sodium chloride solution (150 mL) and concentrated, and the residue was purified by column chromatography (EtOAc:Hexane=0:1 to 1:5 to 1:2) to give a product (1.82 g, 10.5% yield). The remaining starting materials were recovered (10.3 g, 68.7% yield).

$^1$H NMR (400 MHz, $CDCl_3$) δ: 7.28 (s, 1H), 5.78 (s, 1H); MS (ESI): 317 $[M+H]^+$.

Step 2: Synthesis of Compound 5-chloro-6-iodo-3-((4-(4-(4-methylpiperazin-1-yl)piperidin-1-yl)phenyl)amino)pyrazine-2-carboxamide (Compound int_3)

3,5-Dichloro-6-iodopyrazine-2-carboxamide (280 mg, 0.883 mmol), 4-(4-(4-methylpiperazin-1-yl)piperidin-1-yl) aniline (267 mg, 0.971 mmol), dioxane (20 mL) and DIPEA (228 mg, 1.766 mmol) were added into a 50-mL single-neck flask. The mixture was purged with argon, stirred and heated at reflux for 2 h. After the completion of the reaction as indicated by LC-MS, the mixture was concentrated, and the residue was purified by column chromatography to give a product (368 mg, 75% yield).

$^1H$ NMR (400 MHz, $CDCl_3$) δ: 10.69 (s, 1H), 7.53 (d, J=3.8 Hz, 1H), 7.51-7.44 (m, 2H), 6.99-6.88 (m, 2H), 5.67 (d, J=3.9 Hz, 1H), 3.80-3.63 (m, 2H), 2.84-2.42 (m, 10H), 2.39 (ddt, J=11.4, 7.3, 3.7 Hz, 1H), 1.96 (dt, J=12.2, 3.0 Hz, 2H), 1.70 (qd, J=12.1, 4.0 Hz, 2H); MS (ESI): 556 $[M+H]^+$.

Step 3: Synthesis of Compound 5-chloro-3-((4-(4-(4-methylpiperazin-1-yl)piperidin-1-yl)phenyl)amino)-6-phenylpyrazine-2-carboxamide (Compound int_4)

5-Chloro-6-iodo-3-((4-(4-(4-methylpiperazin-1-yl)piperidin-1-yl)phenyl)amino)pyrazine-2-carboxamide (167 mg, 0.30 mmol), anhydrous potassium phosphate (160 mg, 0.75 mmol), phenylboronic acid (40.23 mg, 0.33 mmol), dioxane/$H_2O$ (10 mL/2 mL) and $Pd(dppf)_2Cl_2$ (22 mg) were added into a 50-mL single-neck flask. The mixture was purged with argon, rapidly heated to 105° C. and incubated for 30 min. After the completion of the reaction as indicated by LC-MS, the mixture was cooled and purified by column chromatography to give a product (115 mg, 75.6% yield).

$^1H$ NMR (400 MHz, $CDCl_3$) δ: 10.74 (s, 1H), 7.70 (d, J=6.5 Hz, 3H), 7.56 (d, J=8.5 Hz, 2H), 7.44 (p, J=6.8 Hz, 3H), 6.94 (d, J=8.6 Hz, 2H), 5.67 (s, 1H), 3.70 (d, J=11.9 Hz, 2H), 2.83-2.55 (m, 7H), 2.47 (s, 3H), 2.40-2.32 (m, 1H), 2.28 (s, 3H), 1.93 (d, J=12.4 Hz, 2H), 1.67 (tt, J=12.5, 6.8 Hz, 2H); LC-MS: 506 $[M+H]^+$.

Step 4: Synthesis of Compound 5-((3-hydroxycyclopentyl)amino)-3-((4-(4-(4-methylpiperazin-1-yl)piperidin-1-yl)phenyl)amino)-6-phenylpyrazine-2-carboxamide (Compound 135)

5-Chloro-3-((4-(4-(4-methylpiperazin-1-yl)piperidin-1-yl)phenyl)amino)-6-phenylpyrazine carboxamide (133.6 mg, 0.27 mmol), anhydrous potassium carbonate (186 mg, 1.35 mmol), anhydrous potassium fluoride (31 mg, 0.54 mmol), DMSO (5 mL) and a 4 Å molecular sieve (200 mg, powder) were added into a 50-mL single-neck flask. The mixture was purged with argon and stirred at room temperature for 15 min. Then 3-aminocyclopentanol hydrochloride (45 mg, 0.32 mmol) was added, and the mixture was purged with argon, heated to 120° C. and stirred for 2 h. After the completion of the reaction as indicated by LC-MS, the mixture was cooled and purified by column chromatography to give a product (92 mg, 59.7% yield).

MS (ESI): 571 $[M+H]^+$.

By the chiral separation, four pure optically chiral isomers were obtained:

136

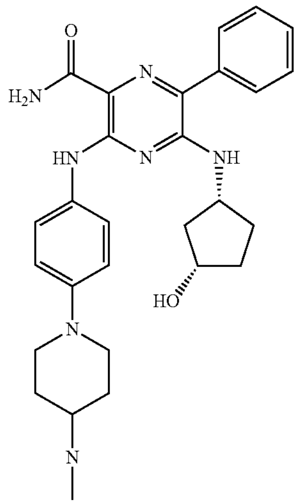

137

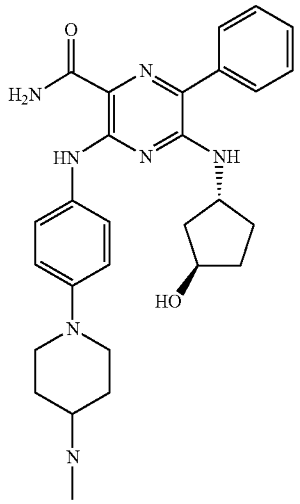

138

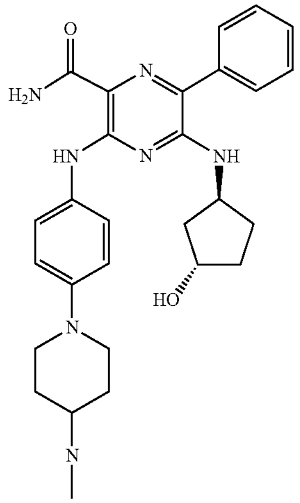

-continued

139

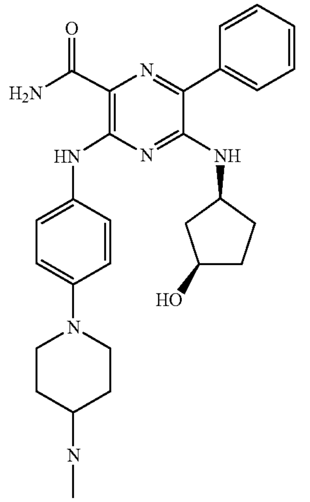

5-(((1R,3S)-3-hydroxycyclopentyl)amino)-3-((4-(4-(4-methylpiperazin-1-yl)piperidin-1-yl)phenyl)amino)-6-phenylpyrazine-2-carboxamide (Compound 136)

$^1$H NMR (400 MHz, $CDCl_3$) δ: 10.71 (s, 1H), 7.65-7.53 (m, 4H), 7.53-7.41 (m, 3H), 7.41-7.31 (m, 1H), 6.98-6.80 (m, 2H), 5.21 (d, J=6.5 Hz, 1H), 5.13 (s, 1H), 4.56 (h, J=7.1 Hz, 1H), 4.39 (tt, J=5.8, 2.9 Hz, 1H), 3.69 (d, J=12.0 Hz, 2H), 2.80-2.58 (m, 5H), 2.50 (s, 3H), 2.35 (d, J=9.8 Hz, 1H), 2.30 (s, 3H), 2.29-2.22 (m, 1H), 2.18 (dd, J=13.8, 7.2 Hz, 1H), 2.06-1.96 (m, 1H), 1.92 (d, J=12.4 Hz, 2H), 1.71-1.54 (m, 6H), 1.43 (ddd, J=13.0, 9.1, 6.6 Hz, 1H); MS (ESI): 571 $[M+H]^+$.

5-(((1R,3R)-3-hydroxycyclopentyl)amino)-3-((4-(4-(4-methylpiperazin-1-yl)piperidin-1-yl)phenyl)amino)-6-phenylpyrazine-2-carboxamide (Compound 137)

$^1$H NMR (400 MHz, $CDCl_3$) δ: 10.78 (s, 1H), 7.60 (dd, J=8.6, 6.7 Hz, 4H), 7.44 (t, J=7.5 Hz, 3H), 7.36 (t, J=7.3 Hz, 1H), 6.91 (d, J=8.9 Hz, 2H), 6.04 (d, J=7.4 Hz, 1H), 5.10 (s, 1H), 4.54 (d, J=7.8 Hz, 1H), 4.44 (s, 1H), 3.68 (d, J=11.9 Hz, 2H), 2.77-2.57 (m, 5H), 2.48 (s, 3H), 2.36 (s, 1H), 2.29 (s, 3H), 2.17-1.99 (m, 3H), 1.99-1.63 (m, 9H); MS (ESI): 571 $[M+H]^+$.

5-(((1S,3S)-3-hydroxycyclopentyl)amino)-3-((4-(4-(4-methylpiperazin-1-yl)piperidin-1-yl)phenyl)amino)-6-phenylpyrazine-2-carboxamide (Compound 138)

$^1$H NMR (400 MHz, $CDCl_3$) δ: 10.71 (s, 1H), 7.65-7.53 (m, 4H), 7.53-7.41 (m, 3H), 7.41-7.31 (m, 1H), 6.98-6.80 (m, 2H), 5.21 (d, J=6.5 Hz, 1H), 5.13 (s, 1H), 4.56 (h, J=7.1 Hz, 1H), 4.39 (tt, J=5.8, 2.9 Hz, 1H), 3.69 (d, J=12.0 Hz, 2H), 2.80-2.58 (m, 5H), 2.50 (s, 3H), 2.35 (d, J=9.8 Hz, 1H), 2.30 (s, 3H), 2.29-2.22 (m, 1H), 2.18 (dd, J=13.8, 7.2 Hz, 1H), 2.06-1.96 (m, 1H), 1.92 (d, J=12.4 Hz, 2H), 1.71-1.54 (m, 6H), 1.43 (ddd, J=13.0, 9.1, 6.6 Hz, 1H); MS (ESI): 571 $[M+H]^+$.

5-(((1S,3R)-3-hydroxycyclopentyl)amino)-3-((4-(4-(4-methylpiperazin-1-yl)piperidin-1-yl)phenyl)amino)-6-phenylpyrazine-2-carboxamide (Compound 139)

$^1$H NMR (400 MHz, $CDCl_3$) δ: 10.78 (s, 1H), 7.60 (dd, J=8.6, 6.7 Hz, 4H), 7.44 (t, J=7.5 Hz, 3H), 7.36 (t, J=7.3 Hz, 1H), 6.91 (d, J=8.9 Hz, 2H), 6.04 (d, J=7.4 Hz, 1H), 5.10 (s, 1H), 4.54 (d, J=7.8 Hz, 1H), 4.44 (s, 1H), 3.68 (d, J=11.9 Hz, 2H), 2.77-2.57 (m, 5H), 2.48 (s, 3H), 2.36 (s, 1H), 2.29 (s, 3H), 2.17-1.99 (m, 3H), 1.99-1.63 (m, 9H); MS (ESI): 571 $[M+H]^+$.

Synthesis of Compound 39 (3-((4-(4-(4-methylpiperazin-1-yl)piperidin-1-yl)phenyl)amino)-6-(pyridin-4-yl)-5-((tetrahydro-2H-pyran-4-yl)amino)pyrazine-2-carboxamide) Using Synthesis Method A

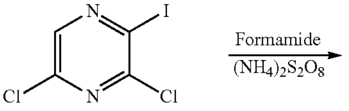

int_1

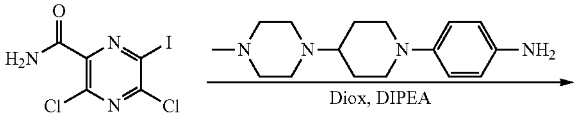

int_2

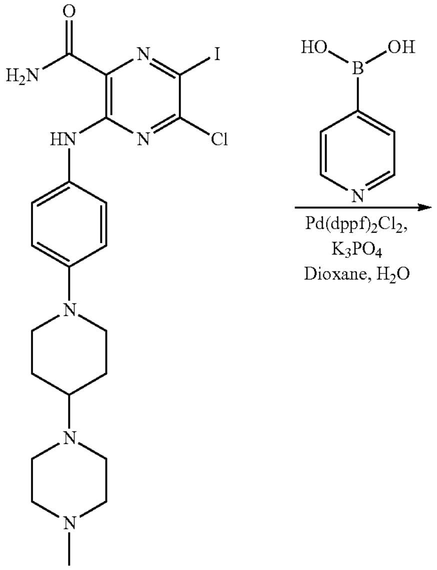

int_3

-continued

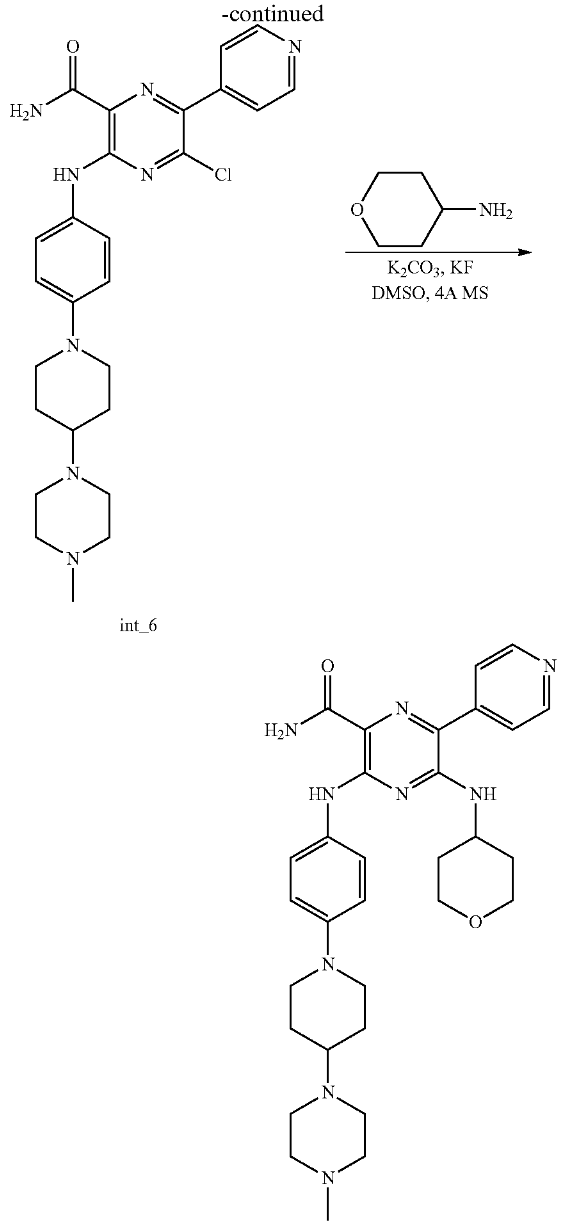

int_6

39

Step 1: Synthesis of Compound 3,5-dichloro-6-iodopyrazine-2-carboxamide (Compound int_2)

3,5-Dichloro-2-iodopyrazine (15 g, 54.57 mmol) and formamide (300 mL) were added into a 500-mL single-neck flask, and the mixture was stirred and heated to 90° C. Solid $(NH_4)_2S_2O_8$ (25 g, 109.1 mmol) was added in batches, and the mixture was stirred at 90° C. for 2 h. Solid $K_2S_2O_8$ (30 g, 109.1 mmol) was supplemented in batches, and the mixture was stirred at 90° C. for 20 h. The reaction product was monitored by LC-MS, and there were starting materials left. The mixture was added with EtOAc (150 mL) and water (300 mL), stirred and separated. The aqueous phase was again extracted with EtOAc (150 mL). The organic phases were combined, washed with saturated sodium chloride solution (150 mL) and concentrated, and the residue was purified by column chromatography (EtOAc:Hexane=0:1 to 1:5 to 1:2) to give a product (1.82 g, 10.5% yield). The remaining starting materials were recovered (10.3 g, 68.7% yield).

$^1$H NMR (400 MHz, $CDCl_3$) δ: 7.28 (s, 1H), 5.78 (s, 1H); MS (ESI): 317 $[M+H]^+$.

Step 2: Synthesis of Compound 5-chloro-6-iodo-3-((4-(4-(4-methylpiperazin-1-yl)piperidin-1-yl)phenyl)amino)pyrazine-2-carboxamide (Compound int_3)

3,5-Dichloro-6-iodopyrazine-2-carboxamide (280 mg, 0.883 mmol), 4-(4-(4-methylpiperazin-1-yl)piperidin-1-yl) aniline (267 mg, 0.971 mmol), dioxane (20 mL) and DIPEA (228 mg, 1.766 mmol) were added into a 50-mL single-neck flask. The mixture was purged with argon, stirred and heated at reflux for 2 h. After the completion of the reaction as indicated by LC-MS, the mixture was concentrated, and the residue was purified by column chromatography to give a product (368 mg, 75% yield).

$^1$H NMR (400 MHz, $CDCl_3$) δ: 10.69 (s, 1H), 7.53 (d, J=3.8 Hz, 1H), 7.51-7.44 (m, 2H), 6.99-6.88 (m, 2H), 5.67 (d, J=3.9 Hz, 1H), 3.80-3.63 (m, 2H), 2.84-2.42 (m, 10H), 2.39 (ddt, J=11.4, 7.3, 3.7 Hz, 1H), 1.96 (dt, J=12.2, 3.0 Hz, 2H), 1.70 (qd, J=12.1, 4.0 Hz, 2H); MS (ESI): 556 $[M+H]^+$.

Step 3: Synthesis of Compound 5-chloro-3-((4-(4-(4-methylpiperazin-1-yl)piperidin-1-yl)phenyl)amino)-6-(pyridin-4-yl)pyrazine-2-carboxamide (Compound int_6)

5-Chloro-6-iodo-3-((4-(4-(4-methylpiperazin-1-yl)piperidin-1-yl)phenyl)amino)pyrazine-2-carboxamide (166.76 mg, 0.30 mmol), anhydrous potassium phosphate (160 mg, 0.75 mmol), (pyridin-4-yl)boronic acid (40.56 mg, 0.33 mmol), dioxane/$H_2O$ (10 mL/2 mL) and $Pd(dppf)_2Cl_2$ (22 mg) were added into a 50-mL single-neck flask. The mixture was purged with argon, rapidly heated to 105° C. and incubated for 60 min. After the completion of the reaction as indicated by LC-MS, the mixture was cooled and purified by column chromatography to give a product (126 mg, 82.8% yield).

MS (ESI): 507 $[M+H]^+$.

Step 4: Synthesis of Compound 3-((4-(4-(4-methylpiperazin-1-yl)piperidin-1-yl)phenyl)amino)-6-(pyridin-4-yl)-5-((tetrahydro-2H-pyran-4-yl)amino) pyrazine-2-carboxamide (Compound 39)

5-Chloro-3-((4-(4-(4-methylpiperazin-1-yl)piperidin-1-yl)phenyl)amino)-6-(pyridin-4-yl)pyrazine-2-carboxamide (152.1 mg, 0.3 mmol), anhydrous potassium carbonate (186 mg, 1.35 mmol), anhydrous potassium fluoride (35 mg, 0.6 mmol), DMSO (5 mL) and a 4 Å molecular sieve (200 mg, powder) were added into a 50-mL single-neck flask. The mixture was purged with argon and stirred at room temperature for 15 min. Then 3-tetrahydro-2H-pyran-4-amine (33.4 mg, 0.33 mmol) was added, and the mixture was purged with argon, heated to 120° C. and stirred for 2 h. After the completion of the reaction as indicated by LC-MS, the mixture was cooled and purified by column chromatography to give a product (130 mg, 75.8% yield).

$^1$H NMR (400 MHz, $CDCl_3$) δ 10.86 (s, 1H), 8.71 (d, J=5.1 Hz, 2H), 7.55 (t, J=6.8 Hz, 4H), 7.42 (s, 1H), 6.91 (d, J=8.8 Hz, 2H), 5.22 (s, 1H), 5.14 (d, J=7.0 Hz, 1H), 4.17 (m, 1H), 4.01 (d, J=11.7 Hz, 2H), 3.69 (d, J=9.2 Hz, 2H), 3.52

(t, J=11.6 Hz, 2H), 2.69 (m, 11H), 2.38 (s, 3H), 2.09-1.96 (m, 4H), 1.76-1.64 (m, 4H); MS (ESI): 572 $[M+H]^+$.

Synthesis of Compound 55 (3-((4-(4-(4-methylpiperazin-1-yl)piperidin-1-yl)phenyl)amino)-6-(1H-pyrazol-3-yl)-5-((tetrahydro-2H-pyran-4-yl)amino)pyrazine-2-carboxamide) Using Synthesis Method A

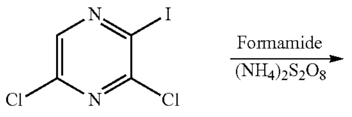

int_1

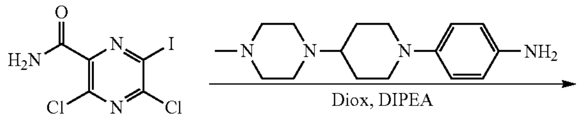

int_2

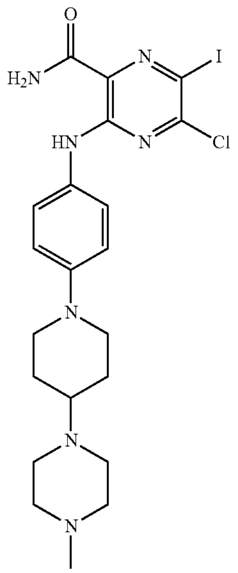

int_3

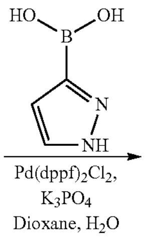

-continued

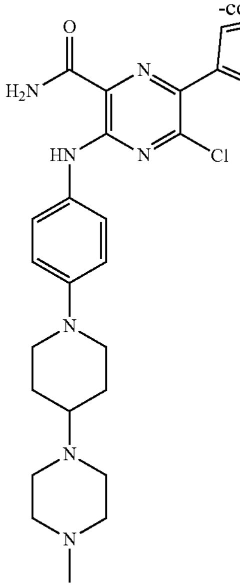

int_7

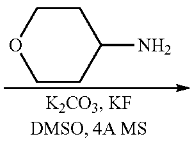

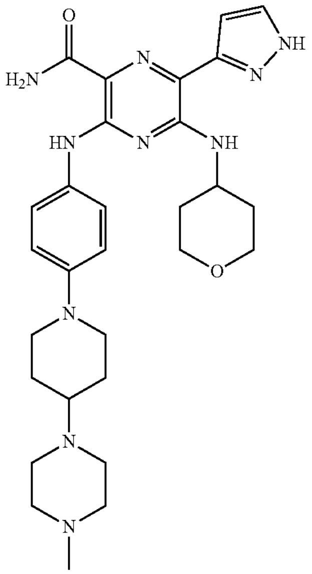

55

Step 1: Synthesis of Compound 3,5-dichloro-6-iodopyrazine-2-carboxamide (Compound int_2)

3,5-Dichloro-2-iodopyrazine (15 g, 54.57 mmol) and formamide (300 mL) were added into a 500-mL single-neck flask, and the mixture was stirred and heated to 90° C. Solid $(NH_4)_2S_2O_8$ (25 g, 109.1 mmol) was added in batches, and the mixture was stirred at 90° C. for 2 h. Solid $K_2S_2O_8$ (30 g, 109.1 mmol) was supplemented in batches, and the mixture was stirred at 90° C. for 20 h. The reaction product was monitored by LC-MS, and there were starting materials left. The mixture was added with EtOAc (150 mL) and water (300 mL), stirred and separated. The aqueous phase was again extracted with EtOAc (150 mL). The organic phases were combined, washed with saturated sodium chloride solution (150 mL) and concentrated, and the residue was purified by column chromatography (EtOAc:Hexane=0:1 to 1:5 to 1:2) to give a product (1.82 g, 10.5% yield). The remaining starting materials were recovered (10.3 g, 68.7% yield).

$^1$H NMR (400 MHz, $CDCl_3$) δ: 7.28 (s, 1H), 5.78 (s, 1H); MS (ESI): 317 $[M+H]^+$.

Step 2: Synthesis of Compound 5-chloro-6-iodo-3-((4-(4-(4-methylpiperazin-1-yl)piperidin-1-yl)phenyl)amino)pyrazine-2-carboxamide (Compound int_3)

3,5-Dichloro-6-iodopyrazine-2-carboxamide (280 mg, 0.883 mmol), 4-(4-(4-methylpiperazin-1-yl)piperidin-1-yl)aniline (267 mg, 0.971 mmol), dioxane (20 mL) and DIPEA (228 mg, 1.766 mmol) were added into a 50-mL single-neck flask. The mixture was purged with argon, stirred and heated at reflux for 2 h. After the completion of the reaction as indicated by LC-MS, the mixture was concentrated, and the residue was purified by column chromatography to give a product (368 mg, 75% yield).

$^1$H NMR (400 MHz, $CDCl_3$) δ: 10.69 (s, 1H), 7.53 (d, J=3.8 Hz, 1H), 7.51-7.44 (m, 2H), 6.99-6.88 (m, 2H), 5.67 (d, J=3.9 Hz, 1H), 3.80-3.63 (m, 2H), 2.84-2.42 (m, 10H), 2.39 (ddt, J=11.4, 7.3, 3.7 Hz, 1H), 1.96 (dt, J=12.2, 3.0 Hz, 2H), 1.70 (qd, J=12.1, 4.0 Hz, 2H); MS (ESI): 556 $[M+H]^+$.

Step 3: Synthesis of Compound 5-chloro-3-((4-(4-(4-methylpiperazin-1-yl)piperidin-1-yl)phenyl)amino)-6-(1H-pyrazol-3-yl)pyrazine-2-carboxamide (Compound int_7)

5-Chloro-6-iodo-3-((4-(4-(4-methylpiperazin-1-yl)piperidin-1-yl)phenyl)amino)pyrazine-2-carboxamide (166.76 mg, 0.30 mmol), anhydrous potassium phosphate (160 mg, 0.75 mmol), (1H-pyrazol-3-yl)boronic acid (37 mg, 0.33 mmol), dioxane/$H_2O$ (10 mL/2 mL) and $Pd(dppf)_2Cl_2$ (22 mg) were added into a 50-mL single-neck flask. The mixture was purged with argon, rapidly heated to 105° C. and incubated for 60 min. After the completion of the reaction as indicated by LC-MS, the mixture was cooled and purified by column chromatography to give a product (119 mg, 80% yield).

MS (ESI): 496 $[M+H]^+$.

Step 4: Synthesis of Compound 3-((4-(4-(4-methylpiperazin-1-yl)piperidin-1-yl)phenyl)amino)-6-(1H-pyrazol-3-yl)-5-((tetrahydro-2H-pyran-4-yl)amino)pyrazine carboxamide (Compound 55)

5-Chloro-3-((4-(4-(4-methylpiperazin-1-yl)piperidin-1-yl)phenyl)amino)-6-(1H-pyrazol-3-yl)pyrazine-2-carboxamide (148.8 mg, 0.3 mmol), anhydrous potassium carbonate (186 mg, 1.35 mmol), anhydrous potassium fluoride (35 mg, 0.6 mmol), DMSO (5 mL) and a 4 Å molecular sieve (200 mg, powder) were added into a 50-mL single-neck flask. The mixture was purged with argon and stirred at room temperature for 15 min. Then 3-tetrahydro-2H-pyran-4-amine (33.4 mg, 0.33 mmol) was added, and the mixture was purged with argon, heated to 120° C. and stirred for 2 h. After the completion of the reaction as indicated by LC-MS, the mixture was cooled and purified by column chromatography to give a product (115 mg, 68.3% yield).

Compound 55 fumarate: $^1$H NMR (400 MHz, DMSO-$d_6$) δ 13.05 (s, 1H), 11.21 (s, 1H), 8.90 (s, 1H), 8.00-7.92 (m, 1H), 7.81 (d, J=2.4 Hz, 1H), 7.55-7.47 (m, 2H), 7.31 (d, J=2.8 Hz, 1H), 7.21 (d, J=2.4 Hz, 1H), 6.89 (d, J=8.9 Hz, 2H), 6.54 (s, 4H), 4.11 (m, J=6.2 Hz, 1H), 3.89 (dt, J=11.5, 3.7 Hz, 2H), 3.62 (d, J=11.8 Hz, 2H), 3.49 (td, J=11.5, 2.4 Hz, 2H), 2.88-2.52 (m, 9H), 2.42 (s, 3H), 2.10-1.99 (m, 2H), 1.84 (d, J=11.1 Hz, 2H), 1.61-1.40 (m, 4H); MS (ESI): 561 $[M+H]^+$.

Synthesis of Compound 511 (6-(1H-indol-4-yl)-3-((4-(4-(4-methylpiperazin-1-yl)piperidin-1-yl)phenyl)amino)-5-((tetrahydro-2H-pyran-4-yl)amino)pyrazine-2-carboxamide) Using Synthesis Method A

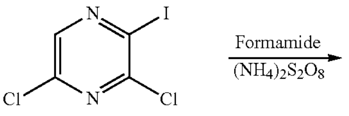

int_1

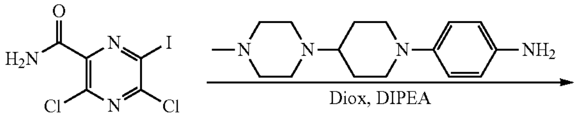

int_2

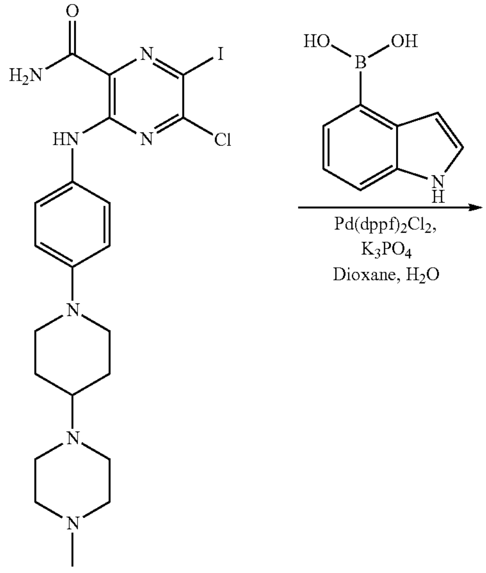

int_3

-continued

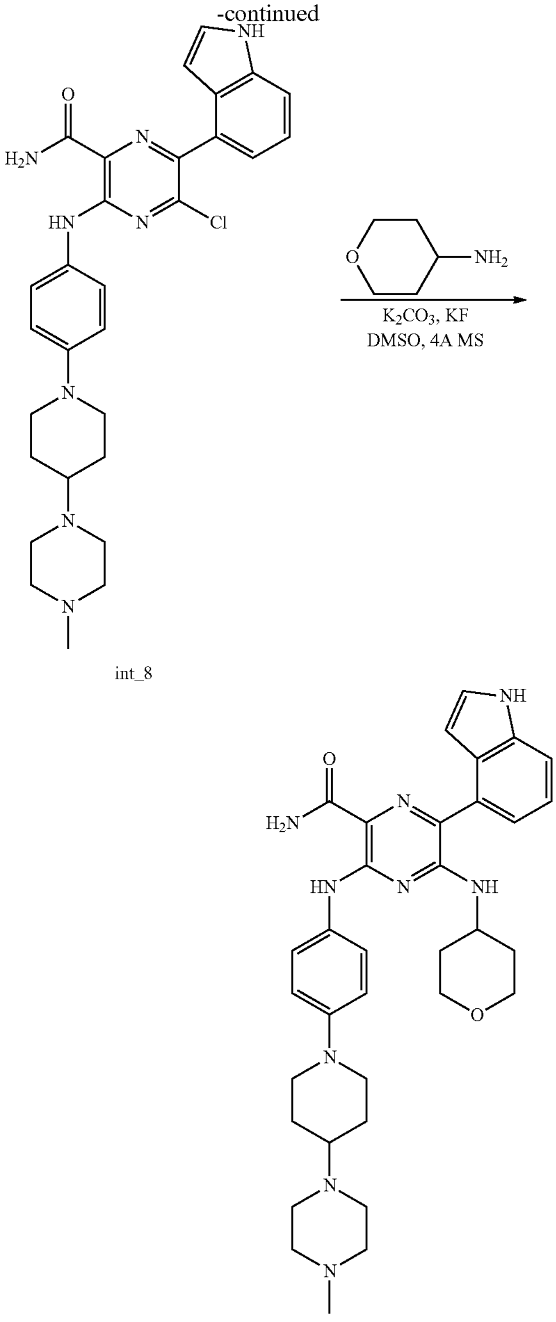

int_8

511

Step 1: Synthesis of Compound 3,5-dichloro-6-iodopyrazine-2-carboxamide (Compound int_2)

3,5-Dichloro-2-iodopyrazine (15 g, 54.57 mmol) and formamide (300 mL) were added into a 500-mL single-neck flask, and the mixture was stirred and heated to 90° C. Solid $(NH_4)_2S_2O_8$ (25 g, 109.1 mmol) was added in batches, and the mixture was stirred at 90° C. for 2 h. Solid $K_2S_2O_8$ (30 g, 109.1 mmol) was supplemented in batches, and the mixture was stirred at 90° C. for 20 h. The reaction product was monitored by LC-MS, and there were starting materials left. The mixture was added with EtOAc (150 mL) and water (300 mL), stirred and separated. The aqueous phase was again extracted with EtOAc (150 mL). The organic phases were combined, washed with saturated sodium chloride solution (150 mL) and concentrated, and the residue was purified by column chromatography (EtOAc:Hexane=0:1 to 1:5 to 1:2) to give a product (1.82 g, 10.5% yield). The remaining starting materials were recovered (10.3 g, 68.7% yield).

$^1$H NMR (400 MHz, $CDCl_3$) δ: 7.28 (s, 1H), 5.78 (s, 1H); MS (ESI): 317 [M+H]$^+$.

Step 2: Synthesis of Compound 5-chloro-6-iodo-3-((4-(4-(4-methylpiperazin-1-yl)piperidin-1-yl)phenyl)amino)pyrazine-2-carboxamide (Compound int_3)

3,5-Dichloro-6-iodopyrazine-2-carboxamide (280 mg, 0.883 mmol), 4-(4-(4-methylpiperazin-1-yl)piperidin-1-yl)aniline (267 mg, 0.971 mmol), dioxane (20 mL) and DIPEA (228 mg, 1.766 mmol) were added into a 50-mL single-neck flask. The mixture was purged with argon, stirred and heated at reflux for 2 h. After the completion of the reaction as indicated by LC-MS, the mixture was concentrated, and the residue was purified by column chromatography to give a product (368 mg, 75% yield).

$^1$H NMR (400 MHz, $CDCl_3$) δ: 10.69 (s, 1H), 7.53 (d, J=3.8 Hz, 1H), 7.51-7.44 (m, 2H), 6.99-6.88 (m, 2H), 5.67 (d, J=3.9 Hz, 1H), 3.80-3.63 (m, 2H), 2.84-2.42 (m, 10H), 2.39 (ddt, J=11.4, 7.3, 3.7 Hz, 1H), 1.96 (dt, J=12.2, 3.0 Hz, 2H), 1.70 (qd, J=12.1, 4.0 Hz, 2H); MS (ESI): 556 [M+H]$^+$.

Step 3: Synthesis of Compound 5-chloro-6-(1H-indol-4-yl)-3-((4-(4-(4-methylpiperazin-1-yl)piperidin-1-yl)phenyl)amino)pyrazine-2-carboxamide (Compound int_8)

5-Chloro-6-iodo-3-((4-(4-(4-methylpiperazin-1-yl)piperidin-1-yl)phenyl)amino)pyrazine-2-carboxamide (166.76 mg, 0.30 mmol), anhydrous potassium phosphate (160 mg, 0.75 mmol), (1H-indol-4-yl)boronic acid (53.12 mg, 0.33 mmol), dioxane/$H_2O$ (10 mL/2 mL) and Pd(dppf)$_2$Cl$_2$ (22 mg) were added into a 50-mL single-neck flask. The mixture was purged with argon, rapidly heated to 105° C. and incubated for 60 min. After the completion of the reaction as indicated by LC-MS, the mixture was cooled and purified by column chromatography to give a product (131 mg, 80% yield).

MS (ESI): 545 [M+H]$^+$.

Step 4: Synthesis of Compound 6-(1H-indol-4-yl)-3-((4-(4-(4-methylpiperazin-1-yl)piperidin-1-yl)phenyl)amino)-5-((tetrahydro-2H-pyran-4-yl)amino)pyrazine-2-carboxamide (Compound 511)

5-Chloro-6-(1H-indol-4-yl)-3-((4-(4-(4-methylpiperazin-1-yl)piperidin-1-yl)phenyl)amino)pyrazine-2-carboxamide (164 mg, 0.3 mmol), anhydrous potassium carbonate (186 mg, 1.35 mmol), anhydrous potassium fluoride (35 mg, 0.6 mmol), DMSO (5 mL) and a 4 Å molecular sieve (200 mg, powder) were added into a 50-mL single-neck flask. The mixture was purged with argon and stirred at room temperature for 15 min. Then 3-tetrahydro-2H-pyran-4-amine (33.4 mg, 0.33 mmol) was added, and the mixture was purged with argon, heated to 120° C. and stirred for 2 h. After the completion of the reaction as indicated by LC-MS, the mixture was cooled and purified by column chromatography to give a product (127 mg, 69.4% yield).

$^1$H NMR (400 MHz, $CDCl_3$) δ 10.81 (s, 1H), 8.39 (s, 1H), 7.62 (d, J=8.9 Hz, 2H), 7.55-7.45 (m, 2H), 7.30 (td, J=6.3, 5.7, 4.0 Hz, 3H), 6.92 (d, J=8.9 Hz, 2H), 6.54 (d, J=2.8 Hz, 1H), 5.25 (d, J=7.2 Hz, 1H), 5.13 (s, 1H), 4.23-4.14 (m, 1H), 3.96 (d, J=11.7 Hz, 2H), 3.69 (d, J=11.9 Hz, 2H), 3.56-3.47 (m, 2H), 2.77-2.37 (m, 11H), 2.32 (s, 3H), 2.00 (dd, J=26.0, 11.4 Hz, 4H), 1.72 (dd, J=11.8, 3.8 Hz, 2H), 1.49-1.42 (m, 2H); MS (ESI): 610 [M+H]$^+$.

Synthesis Method B

Synthesis of Compound 19 (5-methoxy-3-((4-(4-(4-methylpiperazin-1-yl)piperidin-1-yl)phenyl)amino)-6-phenylpyrazine-2-carboxamide) Using Synthesis Method B

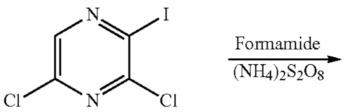

int_1

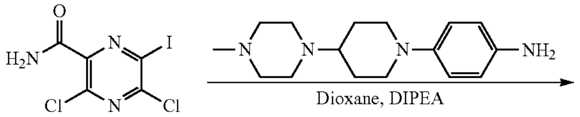

int_2

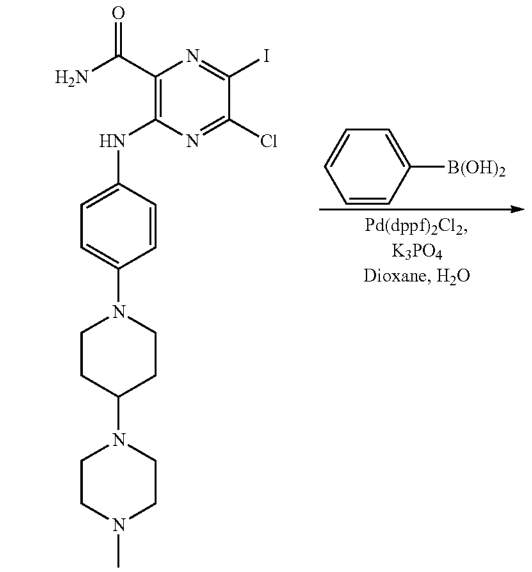

int_3

-continued

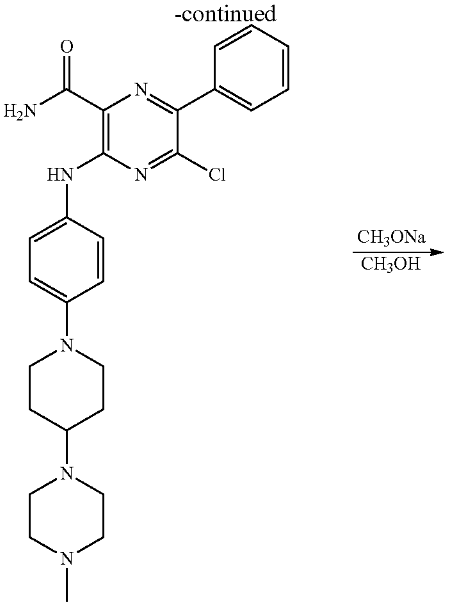

int_4

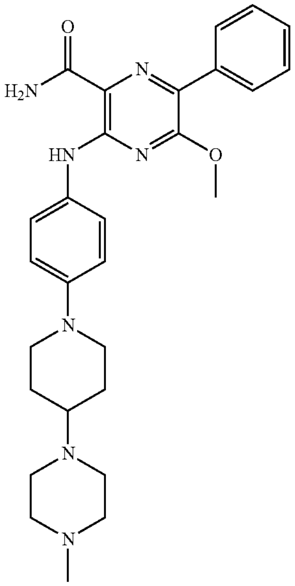

19

Step 1: Synthesis of Compound 3,5-dichloro-6-iodopyrazine-2-carboxamide (Compound int_2)

3,5-Dichloro-2-iodopyrazine (15 g, 54.57 mmol) and formamide (300 mL) were added into a 500-mL single-neck flask, and the mixture was stirred and heated to 90° C. Solid $(NH_4)_2S_2O_8$ (25 g, 109.1 mmol) was added in batches, and the mixture was stirred at 90° C. for 2 h. Solid $K_2S_2O_8$ (30 g, 109.1 mmol) was supplemented in batches, and the mixture was stirred at 90° C. for 20 h. The reaction product was monitored by LC-MS, and there were starting materials left. The mixture was added with EtOAc (150 mL) and water (300 mL), stirred and separated. The aqueous phase was again extracted with EtOAc (150 mL). The organic phases were combined, washed with saturated sodium chloride solution (150 mL) and concentrated, and the residue was purified by column chromatography (EtOAc:Hexane=0:1 to 1:5 to 1:2) to give a product (1.82 g, 10.5% yield). The remaining starting materials were recovered (10.3 g, 68.7% yield).

$^1$H NMR (400 MHz, $CDCl_3$) δ: 7.28 (s, 1H), 5.78 (s, 1H); MS (ESI): 317 $[M+H]^+$.

Step 2: Synthesis of Compound 5-chloro-6-iodo-3-((4-(4-(4-methylpiperazin-1-yl)piperidin-1-yl)phenyl)amino)pyrazine-2-carboxamide (Compound int_3)

3,5-Dichloro-6-iodopyrazine-2-carboxamide (280 mg, 0.883 mmol), 4-(4-(4-methylpiperazin-1-yl)piperidin-1-yl)aniline (267 mg, 0.971 mmol), dioxane (20 mL) and DIPEA (228 mg, 1.766 mmol) were added into a 50-mL single-neck flask. The mixture was purged with argon, stirred and heated at reflux for 2 h. After the completion of the reaction as indicated by LC-MS, the mixture was concentrated, and the residue was purified by column chromatography to give a product (368 mg, 75% yield).

$^1$H NMR (400 MHz, $CDCl_3$) δ: 10.69 (s, 1H), 7.53 (d, J=3.8 Hz, 1H), 7.51-7.44 (m, 2H), 6.99-6.88 (m, 2H), 5.67 (d, J=3.9 Hz, 1H), 3.80-3.63 (m, 2H), 2.84-2.42 (m, 10H), 2.39 (ddt, J=11.4, 7.3, 3.7 Hz, 1H), 1.96 (dt, J=12.2, 3.0 Hz, 2H), 1.70 (qd, J=12.1, 4.0 Hz, 2H); MS (ESI): 556 $[M+H]^+$.

Step 3: Synthesis of Compound 5-chloro-3-((4-(4-(4-methylpiperazin-1-yl)piperidin-1-yl)phenyl)amino)-6-phenylpyrazine-2-carboxamide (Compound int_4)

5-Chloro-6-iodo-3-((4-(4-(4-methylpiperazin-1-yl)piperidin-1-yl)phenyl)amino)pyrazine-2-carboxamide (167 mg, 0.30 mmol), anhydrous potassium phosphate (160 mg, 0.75 mmol), phenylboronic acid (40.23 mg, 0.33 mmol), dioxane/$H_2O$ (10 mL/2 mL) and $Pd(dppf)_2Cl_2$ (22 mg) were added into a 50-mL single-neck flask. The mixture was purged with argon, rapidly heated to 105° C. and incubated for 30 min. After the completion of the reaction as indicated by LC-MS, the mixture was cooled and purified by column chromatography to give a product (115 mg, 75.6% yield).

$^1$H NMR (400 MHz, $CDCl_3$) δ: 10.74 (s, 1H), 7.70 (d, J=6.5 Hz, 3H), 7.56 (d, J=8.5 Hz, 2H), 7.44 (p, J=6.8 Hz, 3H), 6.94 (d, J=8.6 Hz, 2H), 5.67 (s, 1H), 3.70 (d, J=11.9 Hz, 2H), 2.83-2.55 (m, 7H), 2.47 (s, 3H), 2.40-2.32 (m, 1H), 2.28 (s, 3H), 1.93 (d, J=12.4 Hz, 2H), 1.67 (tt, J=12.5, 6.8 Hz, 2H); LC-MS: 506 $[M+H]^+$.

Step 4: Synthesis of Compound 5-methoxy-3-((4-(4-(4-methylpiperazin-1-yl)piperidin-1-yl)phenyl)amino)-6-phenylpyrazine-2-carboxamide (Compound 19)

5-Chloro-3-((4-(4-(4-methylpiperazin-1-yl)piperidin-1-yl)phenyl)amino)-6-phenylpyrazine-2-carboxamide (50 mg, 0.10 mmol), DMF (5 mL) and a 4 Å molecular sieve (200 mg, powder) were added into a 50-mL single-neck flask. The mixture was purged with argon and stirred at room temperature for 15 min. Then sodium methoxide (16 mg, 0.3 mmol) was added, and the mixture was purged with argon, heated to 80° C. and stirred for 2 h. After the completion of the reaction as indicated by LC-MS, the mixture was cooled and purified by column chromatography to give a product (21 mg, 42% yield).

$^1$H NMR (400 MHz, $CDCl_3$) δ: 10.81 (s, 1H), 7.99-7.87 (m, 2H), 7.65 (d, J=4.4 Hz, 1H), 7.61-7.55 (m, 2H), 7.41 (d, J=7.8 Hz, 2H), 6.94 (dd, J=9.0, 3.6 Hz, 2H), 5.42-5.33 (m, 1H), 4.05 (s, 3H), 3.70 (d, J=12.0 Hz, 2H), 2.78-2.41 (m, 11H), 2.41-2.32 (m, 1H), 2.30 (s, 3H), 1.94 (d, J=12.4 Hz, 2H), 1.69 (qd, J=11.8, 3.7 Hz, 2H); MS (ESI): 502 $[M+H]^+$.

Synthesis Method C

Synthesis of Compound 116 (3-((4-(4-(4-methylpiperazin-1-yl)piperidin-1-yl)phenyl)amino)-6-phenyl-5-((tetrahydro-2H-pyran-4-yl)oxo)pyrazine-2-formamide) Using Synthesis Method C

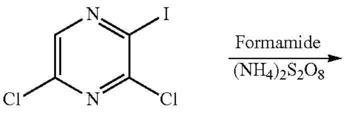

int_1

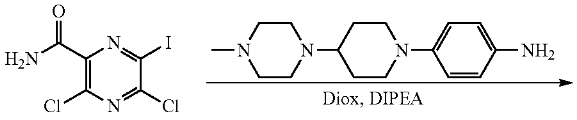

int_2

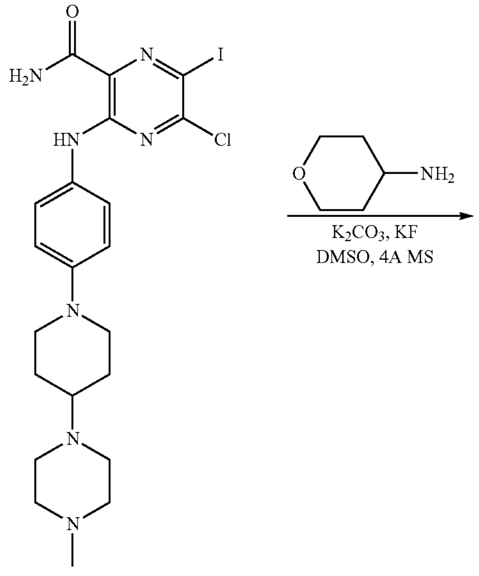

int_3

-continued

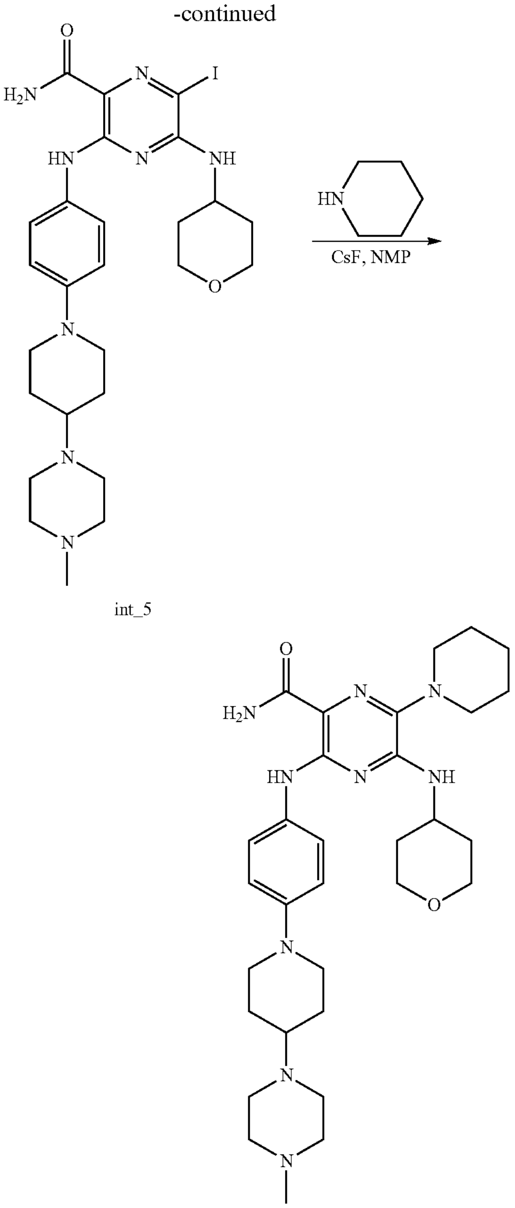

int_5

116

Step 1: Synthesis of Compound 3,5-dichloro-6-iodopyrazine-2-carboxamide (Compound int_2)

3,5-Dichloro-2-iodopyrazine (15 g, 54.57 mmol) and formamide (300 mL) were added into a 500-mL single-neck flask, and the mixture was stirred and heated to 90° C. Solid $(NH_4)_2S_2O_8$ (25 g, 109.1 mmol) was added in batches, and the mixture was stirred at 90° C. for 2 h. Solid $K_2S_2O_8$ (30 g, 109.1 mmol) was supplemented in batches, and the mixture was stirred at 90° C. for 20 h. The reaction product was monitored by LC-MS, and there were starting materials left. The mixture was added with EtOAc (150 mL) and water (300 mL), stirred and separated. The aqueous phase was again extracted with EtOAc (150 mL). The organic phases were combined, washed with saturated sodium chloride solution (150 mL) and concentrated, and the residue was purified by column chromatography (EtOAc:Hexane=0:1 to 1:5 to 1:2) to give a product (1.82 g, 10.5% yield). The remaining starting materials were recovered (10.3 g, 68.7% yield).

$^1H$ NMR (400 MHz, $CDCl_3$) δ: 7.28 (s, 1H), 5.78 (s, 1H); MS (ESI): 317 $[M+H]^+$.

Step 2: Synthesis of Compound 5-chloro-6-iodo-3-((4-(4-(4-methylpiperazin-1-yl)piperidin-1-yl)phenyl)amino)pyrazine-2-carboxamide (Compound int_3)

3,5-Dichloro-6-iodopyrazine-2-carboxamide (280 mg, 0.883 mmol), 4-(4-(4-methylpiperazin-1-yl)piperidin-1-yl)aniline (267 mg, 0.971 mmol), dioxane (20 mL) and DIPEA (228 mg, 1.766 mmol) were added into a 50-mL single-neck flask. The mixture was purged with argon, stirred and heated at reflux for 2 h. After the completion of the reaction as indicated by LC-MS, the mixture was concentrated, and the residue was purified by column chromatography to give a product (368 mg, 75% yield).

$^1H$ NMR (400 MHz, $CDCl_3$) δ: 10.69 (s, 1H), 7.53 (d, J=3.8 Hz, 1H), 7.51-7.44 (m, 2H), 6.99-6.88 (m, 2H), 5.67 (d, J=3.9 Hz, 1H), 3.80-3.63 (m, 2H), 2.84-2.42 (m, 10H), 2.39 (ddt, J=11.4, 7.3, 3.7 Hz, 1H), 1.96 (dt, J=12.2, 3.0 Hz, 2H), 1.70 (qd, J=12.1, 4.0 Hz, 2H); MS (ESI): 556 $[M+H]^+$.

Step 3: Synthesis of Compound 6-iodo-3-((4-(4-(4-methylpiperazin-1-yl)piperidin-1-yl)phenyl)amino)-5-((tetrahydro-2H-pyran-4-yl)amino)pyrazine-2-carboxamide (Compound int_5)

5-Chloro-6-iodo-3-((4-(4-(4-methylpiperazin-1-yl)piperidin-1-yl)phenyl)amino)pyrazine-2-carboxamide (150 mg, 0.27 mmol), anhydrous potassium carbonate (186 mg, 1.35 mmol), anhydrous potassium fluoride (31 mg, 0.54 mmol), DMSO (5 mL) and a 4 Å molecular sieve (200 mg, powder) were added into a 50-mL single-neck flask. The mixture was purged with argon and stirred at room temperature for 15 min. Then 3-tetrahydro-2H-pyran-4-amine (32 mg, 0.32 mmol) was added, and the mixture was purged with argon, and heated to 120° C. and stirred for 2 h. After the completion of the reaction as indicated by LC-MS, the mixture was cooled and purified by column chromatography to give a product (110 mg, 65.7% yield).

$^1H$ NMR (400 MHz, $CDCl_3$) δ: 10.64 (s, 1H), 7.62-7.39 (m, 2H), 7.21 (s, 1H), 6.96-6.76 (m, 2H), 5.41-5.12 (m, 2H), 4.03 (dq, J=11.4, 3.7 Hz, 3H), 3.67 (d, J=12.0 Hz, 2H), 3.51 (td, J=11.6, 2.2 Hz, 2H), 2.84-2.50 (m, 10H), 2.44 (d, J=11.4 Hz, 1H), 2.37 (s, 3H), 2.11-1.89 (m, 4H), 1.78-1.51 (m, 4H); MS (ESI): 621 $[M+H]^+$.

Step 4: Synthesis of Compound 3-((4-(4-(4-methylpiperazin-1-yl)piperidin-1-yl)phenyl)amino)-6-(piperidin-1-yl)-5-((tetrahydro-2H-pyran-4-yl)amino)pyrazine-2-carboxamide (compound 116)

6-Iodo-3-((4-(4-(4-methylpiperazin-1-yl)piperidin-1-yl)phenyl)amino)-5-((tetrahydro-2H-pyran-4-yl)amino)pyrazine-2-carboxamide (57 mg, 0.10 mmol), piperidine (34 mg, 0.40 mmol), anhydrous cesium fluoride (45 mg, 0.30 mmol) and NMP (5 mL) were added into a 10-mL microwave reactor. The mixture was heated to 180° C. and stirred for 8 h. After the completion of the reaction as indicated by LC-MS, the mixture was cooled and purified by column chromatography to give a product (32 mg, 57.4% yield).

$^1H$ NMR (400 MHz, $CDCl_3$) δ: 10.57 (s, 1H), 7.55-7.48 (m, 2H), 6.90-6.82 (m, 2H), 5.51 (d, J=7.3 Hz, 1H), 5.06 (s, 1H), 4.13-4.04 (m, 1H), 4.02-3.96 (m, 2H), 3.64 (d, J=11.7 Hz, 2H), 3.55 (td, J=11.5, 2.3 Hz, 2H), 2.87 (t, J=5.3 Hz, 4H), 2.71-2.58 (m, 5H), 2.48 (s, 3H), 2.36 (t, J=11.4 Hz, 1H), 2.29 (s, 3H), 2.06 (d, J=13.1 Hz, 2H), 1.93 (d, J=12.3 Hz, 2H), 1.73-1.52 (m, 12H); MS (ESI): 578 $[M+H]^+$.

Examples 1

Synthesis of Compounds 1-645

The target compounds 1-18, compounds 20-115, compounds 117-135 and compounds 140-645 in Table 2 were obtained by using the synthesis method A, the synthesis method B or the synthesis method C with different starting materials.

The LC-MS analysis process is as follows:

Instrument: Agilent 6125B

Chromatographic column: Core-shell 2.7 μm 4.3×50 mm

Column temperature: 30° C.

Wavelength: 254 nm/214 nm

Mobile phase A: $H_2O$ (0.1% formic acid)

Mobile phase B: acetonitrile (0.1% formic acid)

Gradient:

TABLE 1

| Time (min) | Flow rate (mL/min) | Mobile phase B % | Mobile phase A % |
|---|---|---|---|
| 0 | 2 | 5 | 95 |
| 0.1 | 2 | 5 | 95 |
| 2.2 | 2 | 95 | 5 |
| 2.7 | 2 | 95 | 5 |
| 2.71 | 2 | 5 | 95 |
| 3.2 | 2 | 5 | 95 |

TABLE 2

| Compound | Structure of compound | Synthesis method | MS $(M + H)^+$ | Retention time in LC-MS (min) |
|---|---|---|---|---|
| 1 | 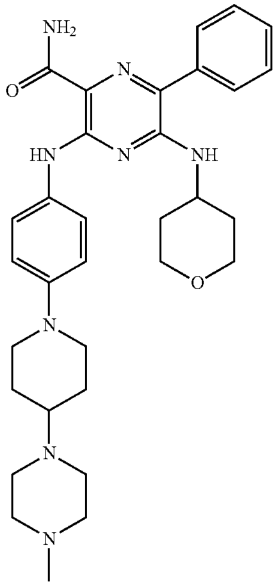 [SMILES: CN1CCN(C2CCN(c3ccc(Nc4nc(NC5CCOCC5)c(-c5ccccc5)nc4C(N)=O)cc3)CC2)CC1] | A | 571 | 1.409 |

TABLE 2-continued
| | | | | |
|---|---|---|---|---|
| 2 | 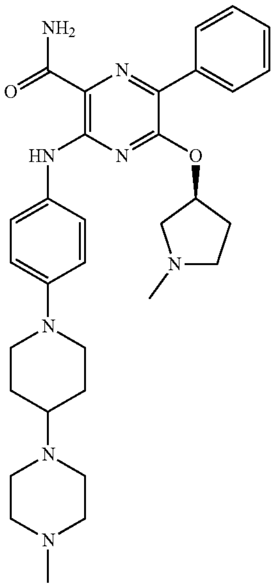 [SMILES: CN1CCN(C2CCN(c3ccc(Nc4nc(O[C@H]5CCN(C)C5)c(-c5ccccc5)nc4C(N)=O)cc3)CC2)CC1] | B | 571 | 1.278 |
| 3 | 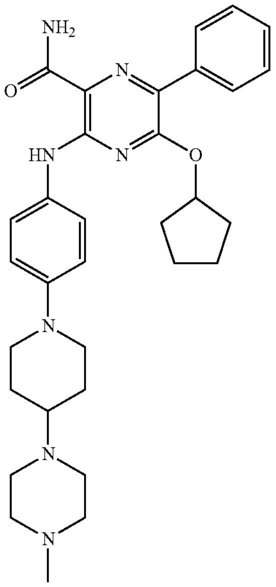 [SMILES: CN1CCN(C2CCN(c3ccc(Nc4nc(OC5CCCC5)c(-c5ccccc5)nc4C(N)=O)cc3)CC2)CC1] | B | 556 | 1.597 |

TABLE 2-continued
| | | | | |
|---|---|---|---|---|
| 4 | 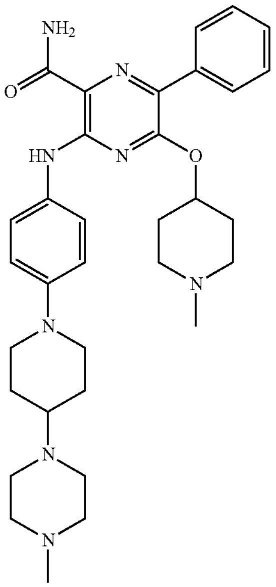 [SMILES: CN1CCC(Oc2nc(Nc3ccc(N4CCC(N5CCN(C)CC5)CC4)cc3)c(C(N)=O)nc2-c2ccccc2)CC1] | B | 585 | 1.198 |
| 5 | 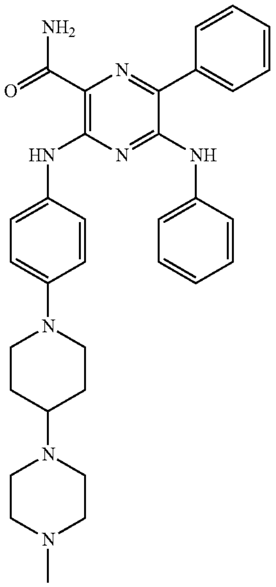 [SMILES: CN1CCN(C2CCN(c3ccc(Nc4nc(Nc5ccccc5)c(-c5ccccc5)nc4C(N)=O)cc3)CC2)CC1] | A | 563 | 1.507 |

TABLE 2-continued
| | | | | |
|---|---|---|---|---|
| 6 | 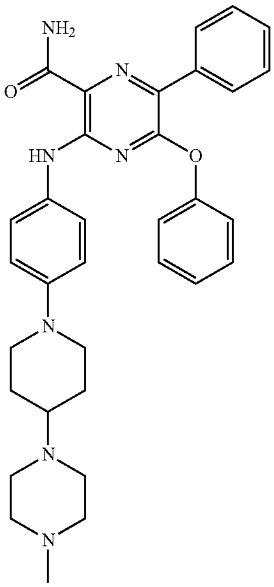 [SMILES: CN1CCN(C2CCN(c3ccc(Nc4nc(Oc5ccccc5)c(-c5ccccc5)nc4C(N)=O)cc3)CC2)CC1] | B | 564 | 1.649 |
| 7 | 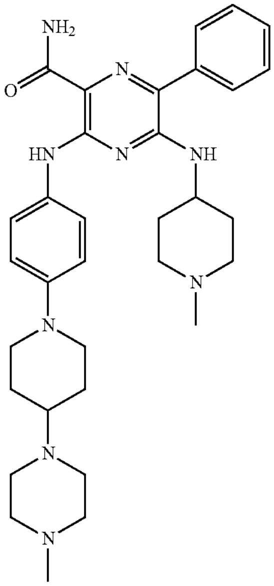 [SMILES: CN1CCC(Nc2nc(Nc3ccc(N4CCC(N5CCN(C)CC5)CC4)cc3)c(C(N)=O)nc2-c2ccccc2)CC1] | A | 584 | 1.186 |

TABLE 2-continued
| | | | | |
|---|---|---|---|---|
| 8 | 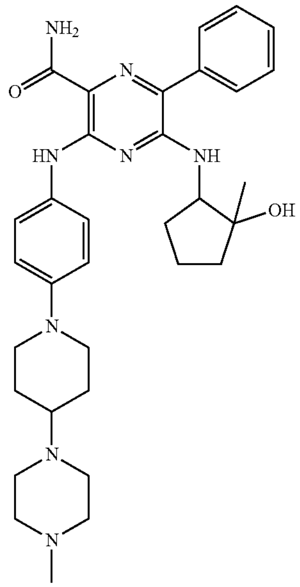 [SMILES: CN1CCN(C2CCN(c3ccc(Nc4nc(NC5CCCC5(C)O)c(-c5ccccc5)nc4C(N)=O)cc3)CC2)CC1] | A | 585 | 1.434 |
| 9 | 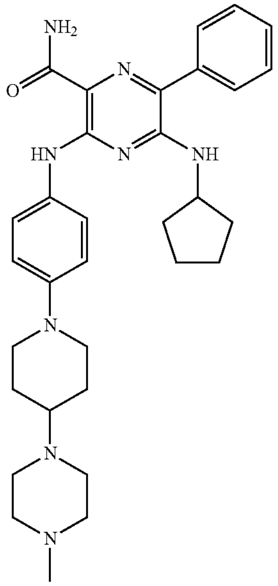 [SMILES: CN1CCN(C2CCN(c3ccc(Nc4nc(NC5CCCC5)c(-c5ccccc5)nc4C(N)=O)cc3)CC2)CC1] | A | 555 | 1.464 |

TABLE 2-continued
| | | | | |
|---|---|---|---|---|
| 10 | 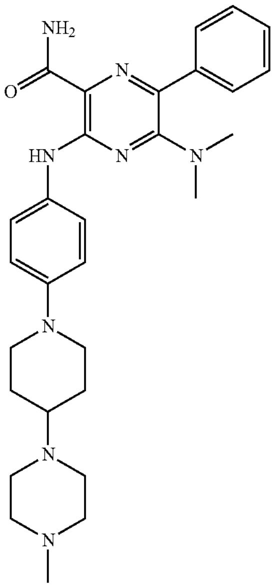 [SMILES: CN1CCN(C2CCN(c3ccc(Nc4nc(N(C)C)c(-c5ccccc5)nc4C(N)=O)cc3)CC2)CC1] | A | 515 | 1.463 |
| 11 | 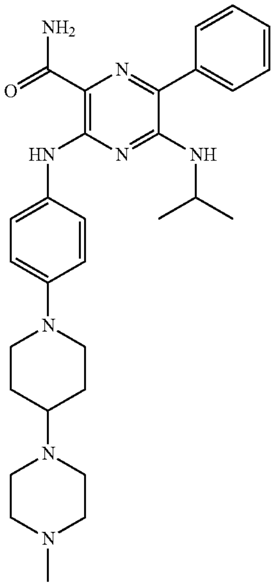 [SMILES: CC(C)Nc1nc(Nc2ccc(N3CCC(N4CCN(C)CC4)CC3)cc2)c(C(N)=O)nc1-c1ccccc1] | A | 529 | 1.489 |

TABLE 2-continued
| | | | | |
|---|---|---|---|---|
| 12 | 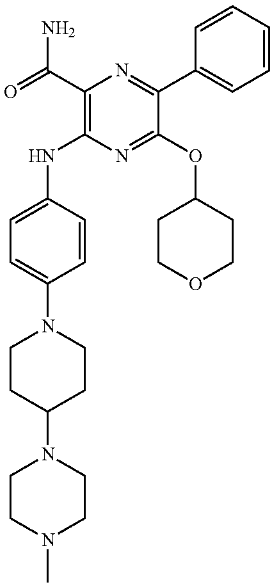 [SMILES: CN1CCN(C2CCN(c3ccc(Nc4nc(OC5CCOCC5)c(-c5ccccc5)nc4C(N)=O)cc3)CC2)CC1] | B | 572 | 1.461 |
| 13 | 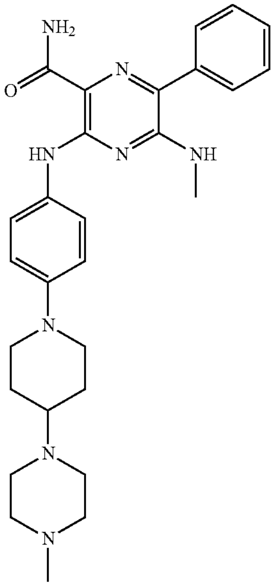 [SMILES: CNc1nc(Nc2ccc(N3CCC(N4CCN(C)CC4)CC3)cc2)c(C(N)=O)nc1-c1ccccc1] | A | 501 | 1.350 |

TABLE 2-continued
| | | | | |
|---|---|---|---|---|
| 14 | 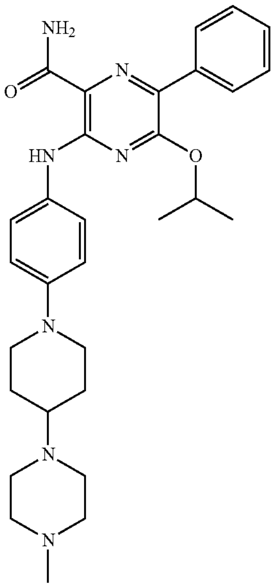 [SMILES: CC(C)Oc1nc(Nc2ccc(N3CCC(N4CCN(C)CC4)CC3)cc2)c(C(N)=O)nc1-c1ccccc1] | B | 530 | 1.521 |
| 15 | 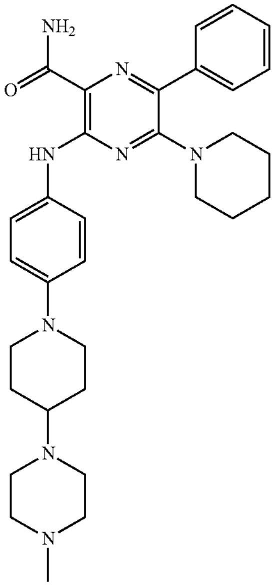 [SMILES: CN1CCN(C2CCN(c3ccc(Nc4nc(N5CCCCC5)c(-c5ccccc5)nc4C(N)=O)cc3)CC2)CC1] | A | 555 | 1.560 |

TABLE 2-continued
| | | | | |
|---|---|---|---|---|
| 16 | 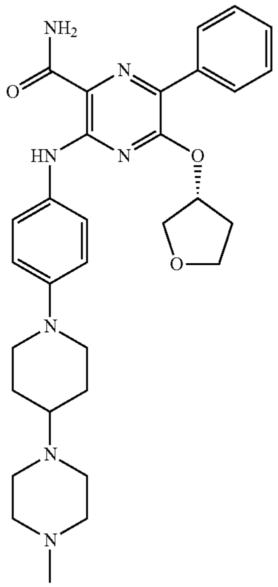 [SMILES: CN1CCN(C2CCN(c3ccc(Nc4nc(O[C@@H]5CCOC5)c(-c5ccccc5)nc4C(N)=O)cc3)CC2)CC1] | B | 558 | 1.430 |
| 17 | 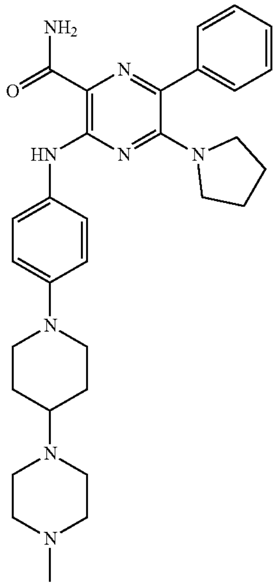 [SMILES: CN1CCN(C2CCN(c3ccc(Nc4nc(N5CCCC5)c(-c5ccccc5)nc4C(N)=O)cc3)CC2)CC1] | A | 541 | 1.542 |

TABLE 2-continued
| | | | | |
|---|---|---|---|---|
| 18 | 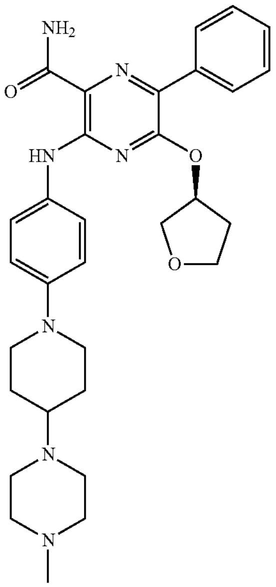 [SMILES: CN1CCN(C2CCN(c3ccc(Nc4nc(O[C@H]5CCOC5)c(-c5ccccc5)nc4C(N)=O)cc3)CC2)CC1] | B | 558 | 1.450 |
| 20 | 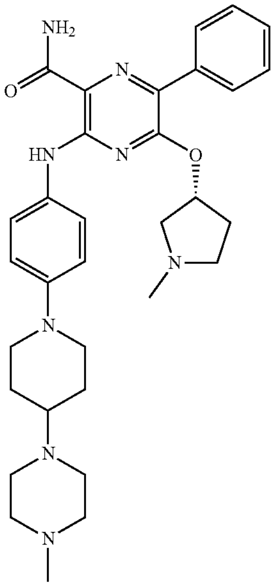 [SMILES: CN1CCN(C2CCN(c3ccc(Nc4nc(O[C@@H]5CCN(C)C5)c(-c5ccccc5)nc4C(N)=O)cc3)CC2)CC1] | B | 571 | 1.310 |

TABLE 2-continued
| | | | | |
|---|---|---|---|---|
| 21 | 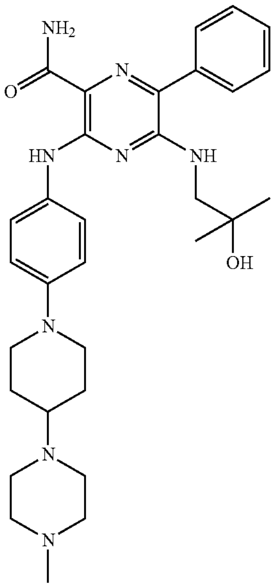 [SMILES: CN1CCN(C2CCN(c3ccc(Nc4nc(NCC(C)(C)O)c(-c5ccccc5)nc4C(N)=O)cc3)CC2)CC1] | A | 559 | 1.350 |
| 22 | 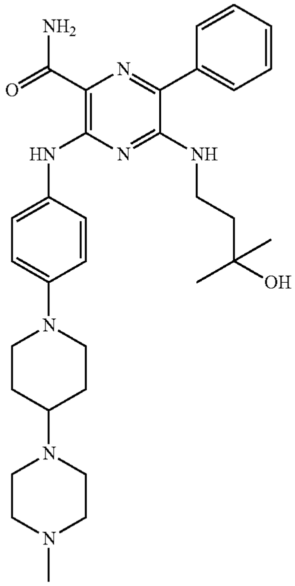 [SMILES: CN1CCN(C2CCN(c3ccc(Nc4nc(NCCC(C)(C)O)c(-c5ccccc5)nc4C(N)=O)cc3)CC2)CC1] | A | 573 | 1.337 |

TABLE 2-continued
| | | | | |
|---|---|---|---|---|
| 23 | 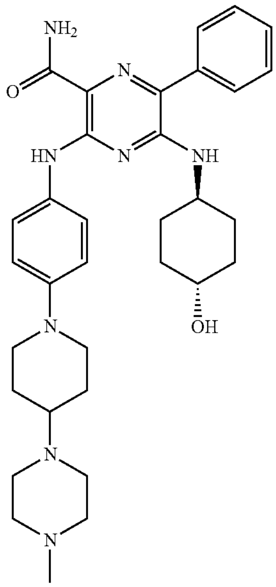 [SMILES: CN1CCN(C2CCN(c3ccc(Nc4nc(N[C@H]5CC[C@H](O)CC5)c(-c5ccccc5)nc4C(N)=O)cc3)CC2)CC1] | A | 585 | 1.356 |
| 24 | 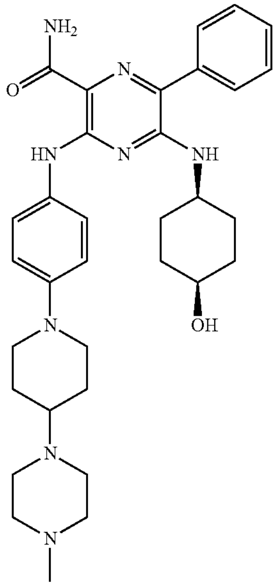 [SMILES: CN1CCN(C2CCN(c3ccc(Nc4nc(N[C@H]5CC[C@@H](O)CC5)c(-c5ccccc5)nc4C(N)=O)cc3)CC2)CC1] | A | 585 | 1.338 |

TABLE 2-continued
| | | | | |
|---|---|---|---|---|
| 25 | 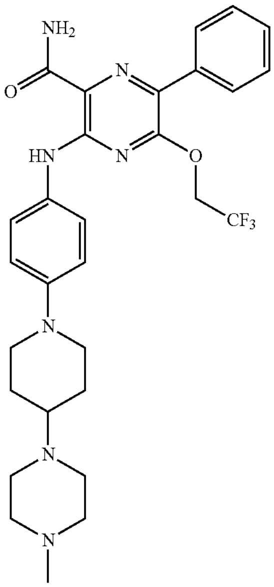 [SMILES: CN1CCN(C2CCN(c3ccc(Nc4nc(OCC(F)(F)F)c(-c5ccccc5)nc4C(N)=O)cc3)CC2)CC1] | B | 570 | 1.551 |
| 26 | 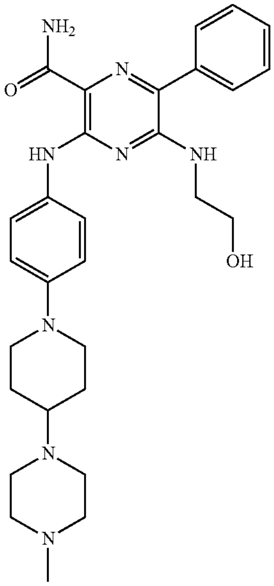 [SMILES: CN1CCN(C2CCN(c3ccc(Nc4nc(NCCO)c(-c5ccccc5)nc4C(N)=O)cc3)CC2)CC1] | A | 531 | — |

TABLE 2-continued
| | | | | |
|---|---|---|---|---|
| 27 | 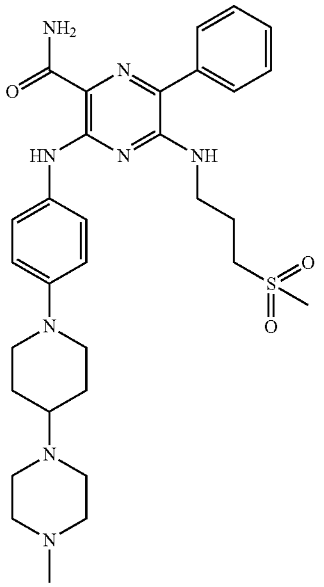 [SMILES: CN1CCN(C2CCN(c3ccc(Nc4nc(NCCCS(C)(=O)=O)c(-c5ccccc5)nc4C(N)=O)cc3)CC2)CC1] | A | 607 | 1.325 |
| 28 | 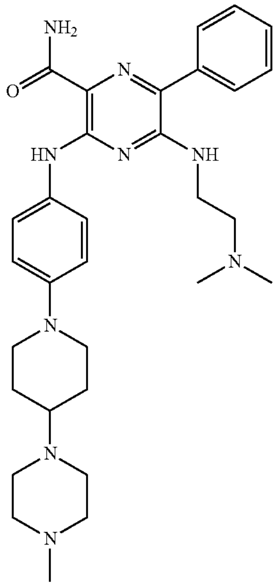 [SMILES: CN(C)CCNc1nc(Nc2ccc(N3CCC(N4CCN(C)CC4)CC3)cc2)c(C(N)=O)nc1-c1ccccc1] | A | 558 | 1.147 |

TABLE 2-continued
| | | | | |
|---|---|---|---|---|
| 29 | 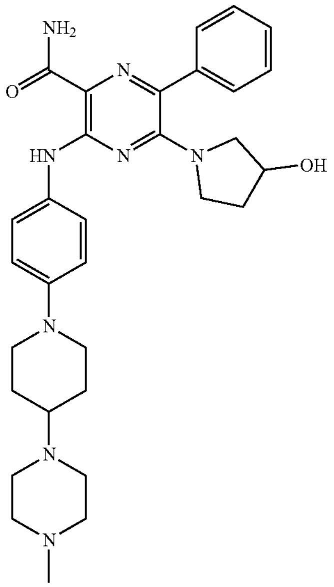 [SMILES: CN1CCN(C2CCN(c3ccc(Nc4nc(N5CCC(O)C5)c(-c5ccccc5)nc4C(N)=O)cc3)CC2)CC1] | A | 557 | 1.289 |
| 30 | 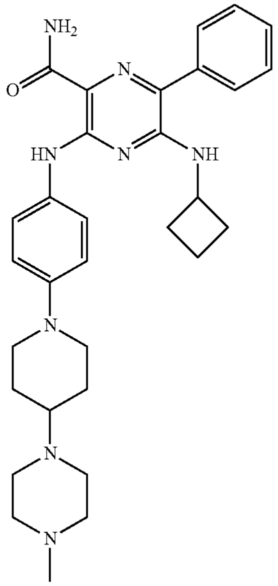 [SMILES: CN1CCN(C2CCN(c3ccc(Nc4nc(NC5CCC5)c(-c5ccccc5)nc4C(N)=O)cc3)CC2)CC1] | A | 541 | 1.491 |

TABLE 2-continued
| | | | | |
|---|---|---|---|---|
| 31 | 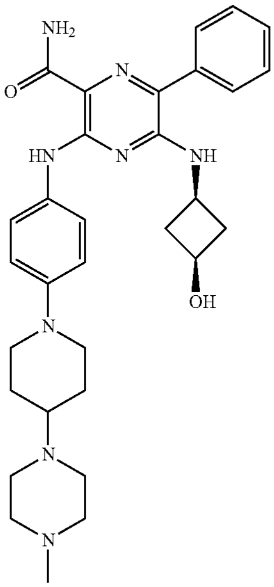 [SMILES: CN1CCN(C2CCN(c3ccc(Nc4nc(N[C@H]5C[C@@H](O)C5)c(-c5ccccc5)nc4C(N)=O)cc3)CC2)CC1] | A | 557 | 1.325 |
| 32 | 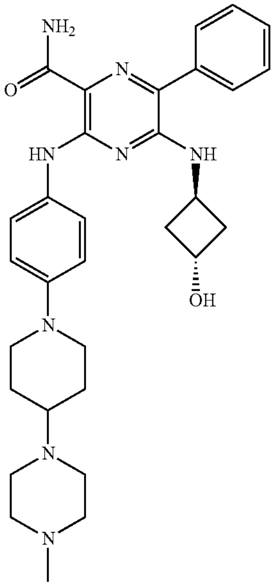 [SMILES: CN1CCN(C2CCN(c3ccc(Nc4nc(N[C@H]5C[C@H](O)C5)c(-c5ccccc5)nc4C(N)=O)cc3)CC2)CC1] | A | 557 | 1.310 |

TABLE 2-continued
| | | | | |
|---|---|---|---|---|
| 33 | 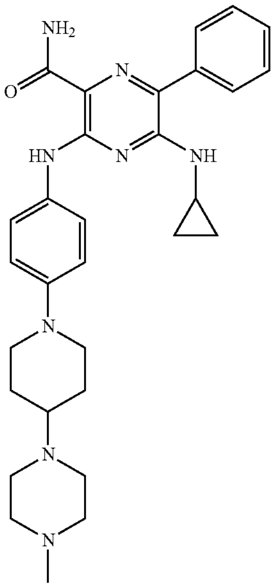 [SMILES: CN1CCN(C2CCN(c3ccc(Nc4nc(NC5CC5)c(-c5ccccc5)nc4C(N)=O)cc3)CC2)CC1] | A | 557 | 1.389 |
| 34 | 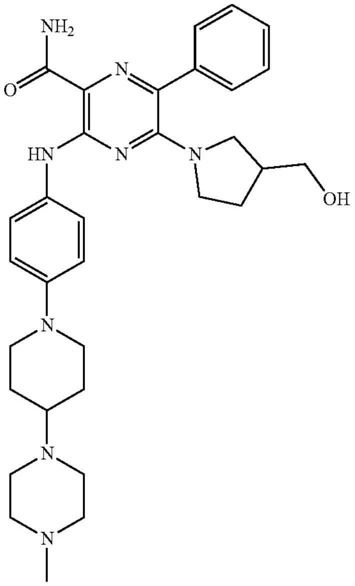 [SMILES: CN1CCN(C2CCN(c3ccc(Nc4nc(N5CCC(CO)C5)c(-c5ccccc5)nc4C(N)=O)cc3)CC2)CC1] | A | 571 | 1.358 |

TABLE 2-continued
| | | | | |
|---|---|---|---|---|
| 35 | 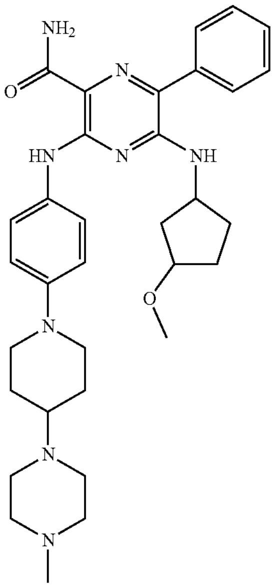 [SMILES: COC1CCC(Nc2nc(Nc3ccc(N4CCC(N5CCN(C)CC5)CC4)cc3)c(C(N)=O)nc2-c2ccccc2)C1] | A | 585 | 1.425 |
| 36 | 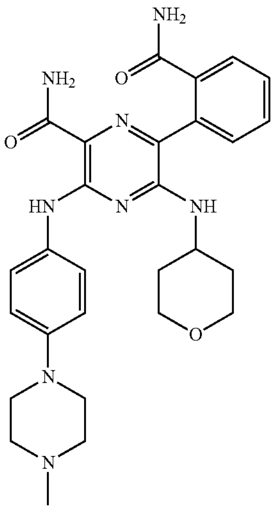 [SMILES: CN1CCN(c2ccc(Nc3nc(NC4CCOCC4)c(-c4ccccc4C(N)=O)nc3C(N)=O)cc2)CC1] | A | 531 | 1.332 |

TABLE 2-continued
| | | | | |
|---|---|---|---|---|
| 37 | 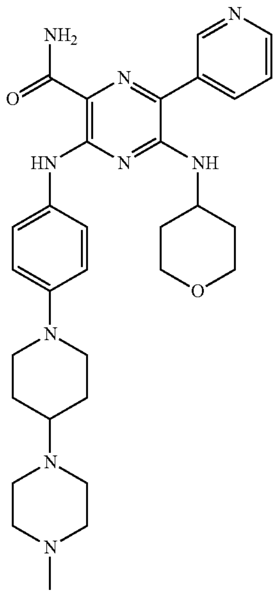 [SMILES: CN1CCN(C2CCN(c3ccc(Nc4nc(NC5CCOCC5)c(-c5cccnc5)nc4C(N)=O)cc3)CC2)CC1] | A | 572 | 1.122 |
| 38 | 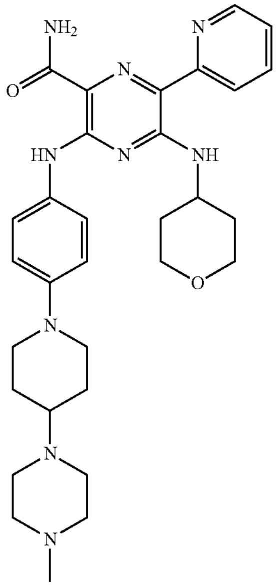 | A | 571 | 1.475 |

TABLE 2-continued
| | | | | |
|---|---|---|---|---|
| 39 | 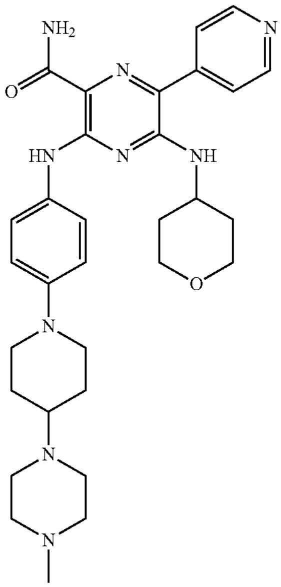 | A | 572 | 1.104 |
| 40 | 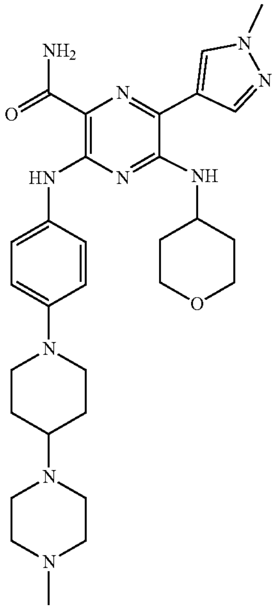 [SMILES: CN1CCN(C2CCN(c3ccc(Nc4nc(NC5CCOCC5)c(-c5cnn(C)c5)nc4C(N)=O)cc3)CC2)CC1] | A | 575 | 1.244 |

TABLE 2-continued
| | | | | |
|---|---|---|---|---|
| 41 | 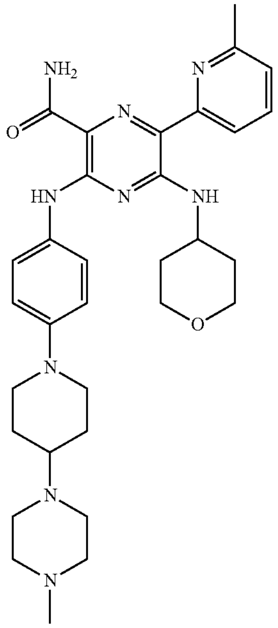 [SMILES: Cc1cccc(-c2nc(C(N)=O)c(Nc3ccc(N4CCC(N5CCN(C)CC5)CC4)cc3)nc2NC2CCOCC2)n1] | A | 586 | — |
| 42 | 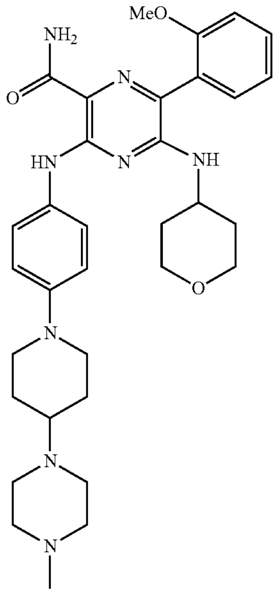 [SMILES: COc1ccccc1-c1nc(C(N)=O)c(Nc2ccc(N3CCC(N4CCN(C)CC4)CC3)cc2)nc1NC1CCOCC1] | A | 601 | 1.457 |

TABLE 2-continued
| | | | | |
|---|---|---|---|---|
| 43 | 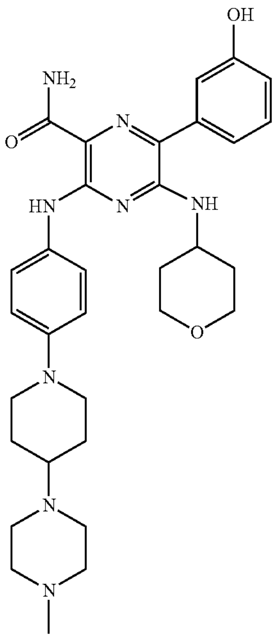 | A | 587 | 1.378 |
| 44 | 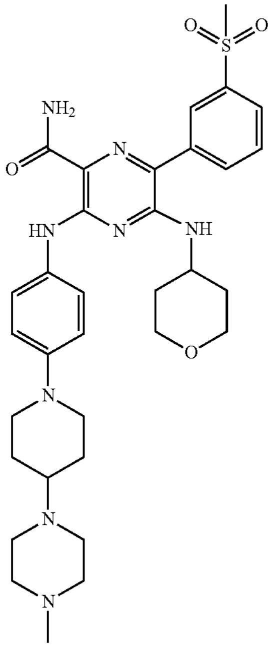 [SMILES: CN1CCN(C2CCN(c3ccc(Nc4nc(NC5CCOCC5)c(-c5cccc(S(C)(=O)=O)c5)nc4C(N)=O)cc3)CC2)CC1] | A | 649 | 1.396 |

TABLE 2-continued
| | | | | |
|---|---|---|---|---|
| 45 | 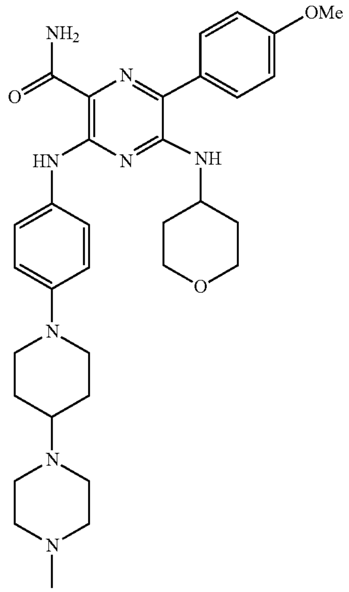 [SMILES: COc1ccc(-c2nc(C(N)=O)c(Nc3ccc(N4CCC(N5CCN(C)CC5)CC4)cc3)nc2NC2CCOCC2)cc1] | A | 601 | 1.479 |
| 46 | 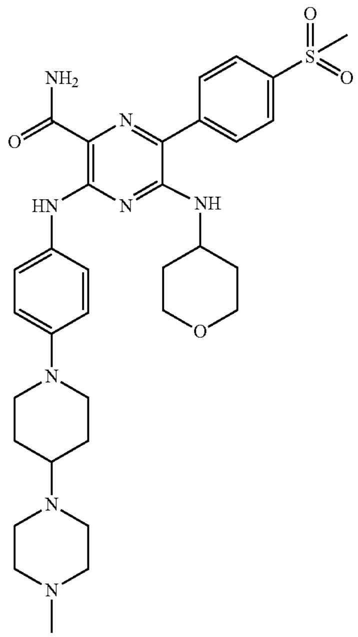 [SMILES: CN1CCN(C2CCN(c3ccc(Nc4nc(NC5CCOCC5)c(-c5ccc(S(C)(=O)=O)cc5)nc4C(N)=O)cc3)CC2)CC1] | A | 649 | 1.402 |

TABLE 2-continued
| | | | | |
|---|---|---|---|---|
| 47 | 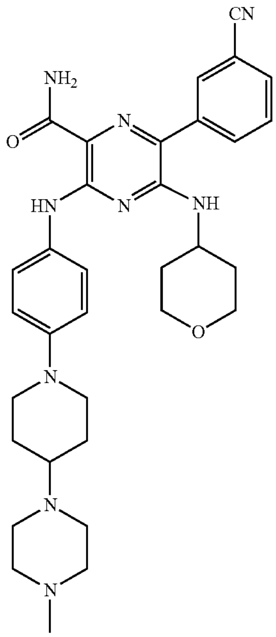 [SMILES: CN1CCN(C2CCN(c3ccc(Nc4nc(NC5CCOCC5)c(-c5cccc(C#N)c5)nc4C(N)=O)cc3)CC2)CC1] | A | 596 | 1.401 |
| 48 | 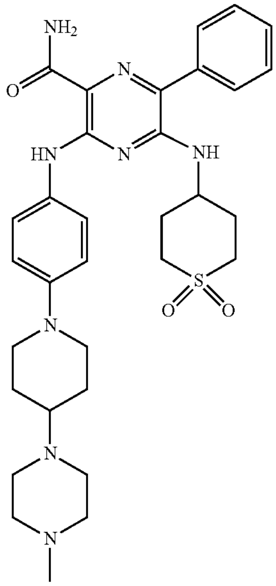 [SMILES: CN1CCN(C2CCN(c3ccc(Nc4nc(NC5CCS(=O)(=O)CC5)c(-c5ccccc5)nc4C(N)=O)cc3)CC2)CC1] | A | 619 | 1.342 |

TABLE 2-continued
| | | | | |
|---|---|---|---|---|
| 49 | 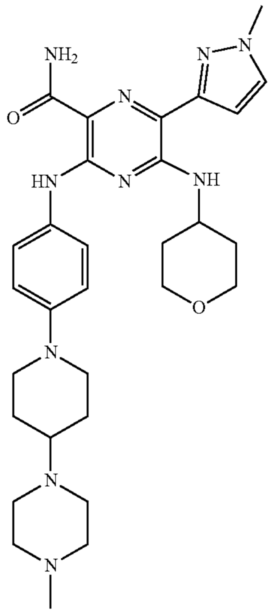 [SMILES: CN1CCN(C2CCN(c3ccc(Nc4nc(NC5CCOCC5)c(-c5ccn(C)n5)nc4C(N)=O)cc3)CC2)CC1] | A | 575 | 1.294 |
| 50 | 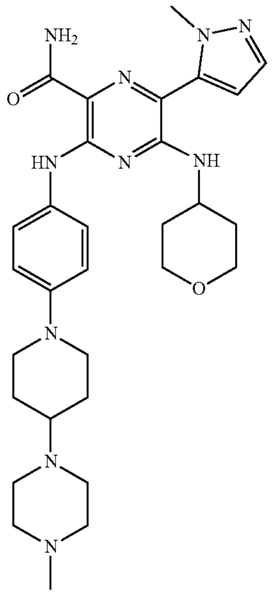 [SMILES: CN1CCN(C2CCN(c3ccc(Nc4nc(NC5CCOCC5)c(-c5ccnn5C)nc4C(N)=O)cc3)CC2)CC1] | A | 575 | 1.268 |

TABLE 2-continued
| | | | | |
|---|---|---|---|---|
| 51 | 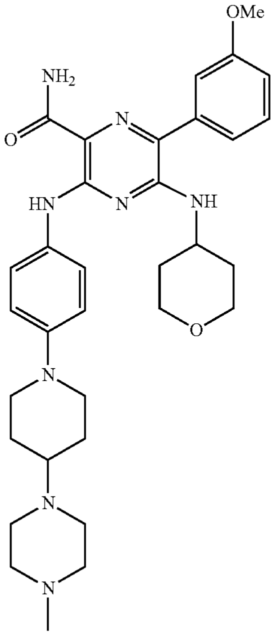 [SMILES: COc1cccc(-c2nc(C(N)=O)c(Nc3ccc(N4CCC(N5CCN(C)CC5)CC4)cc3)nc2NC2CCOCC2)c1] | A | 601 | 1.407 |
| 52 | 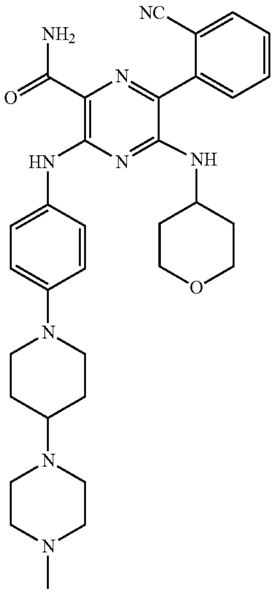 [SMILES: CN1CCN(C2CCN(c3ccc(Nc4nc(NC5CCOCC5)c(-c5ccccc5C#N)nc4C(N)=O)cc3)CC2)CC1] | A | 596 | — |

TABLE 2-continued
| | | | | |
|---|---|---|---|---|
| 53 | 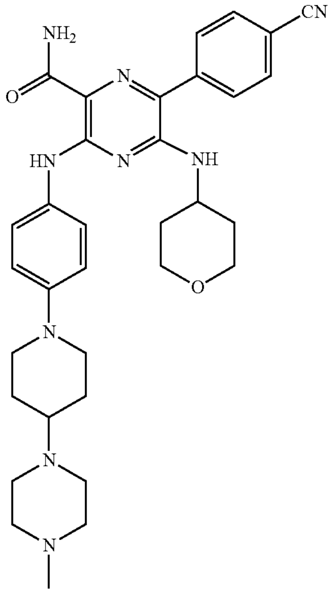 [SMILES: CN1CCN(C2CCN(c3ccc(Nc4nc(NC5CCOCC5)c(-c5ccc(C#N)cc5)nc4C(N)=O)cc3)CC2)CC1] | A | 596 | 1.368 |
| 54 | 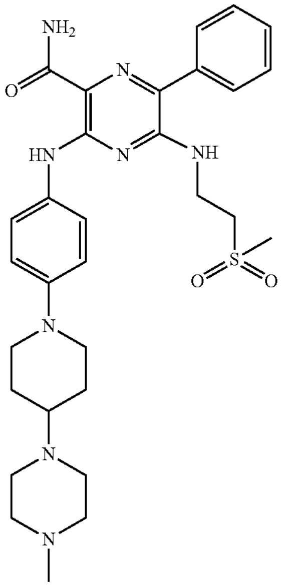 [SMILES: CN1CCN(C2CCN(c3ccc(Nc4nc(NCCS(C)(=O)=O)c(-c5ccccc5)nc4C(N)=O)cc3)CC2)CC1] | A | 593 | 1.272 |

TABLE 2-continued
| | | | | |
|---|---|---|---|---|
| 55 | 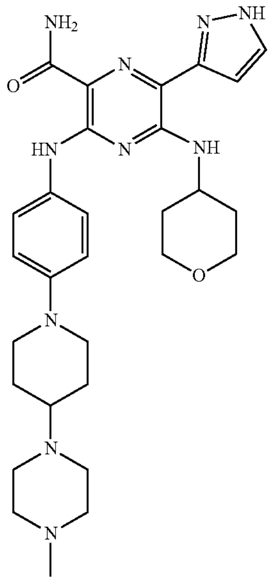 [SMILES: CN1CCN(C2CCN(c3ccc(Nc4nc(NC5CCOCC5)c(-c5cc[nH]n5)nc4C(N)=O)cc3)CC2)CC1] | A | 561 | 1.254 |
| 56 | 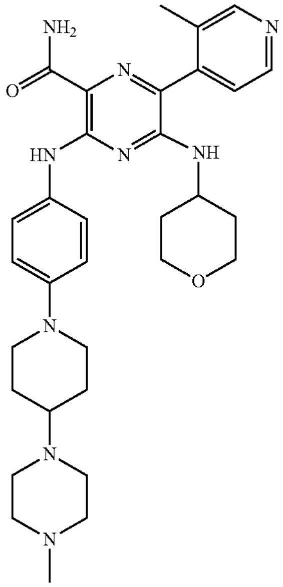 [SMILES: Cc1cnccc1-c1nc(C(N)=O)c(Nc2ccc(N3CCC(N4CCN(C)CC4)CC3)cc2)nc1NC1CCOCC1] | A | 586 | 1.094 |

TABLE 2-continued
| | | | | |
|---|---|---|---|---|
| 57 | 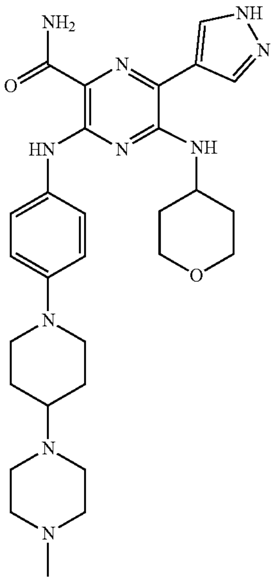 [SMILES: CN1CCN(C2CCN(c3ccc(Nc4nc(NC5CCOCC5)c(-c5cn[nH]c5)nc4C(N)=O)cc3)CC2)CC1] | A | 561 | 1.199 |
| 58 | 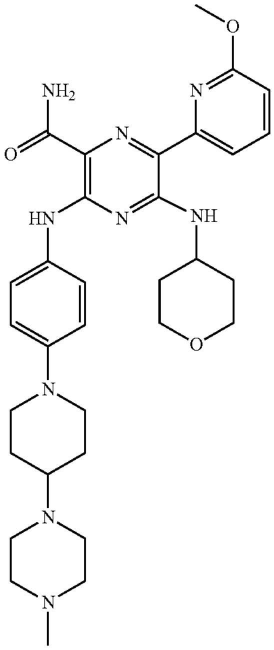 [SMILES: COc1cccc(-c2nc(C(N)=O)c(Nc3ccc(N4CCC(N5CCN(C)CC5)CC4)cc3)nc2NC2CCOCC2)n1] | A | 602 | — |

TABLE 2-continued
| | | | | |
|---|---|---|---|---|
| 59 | 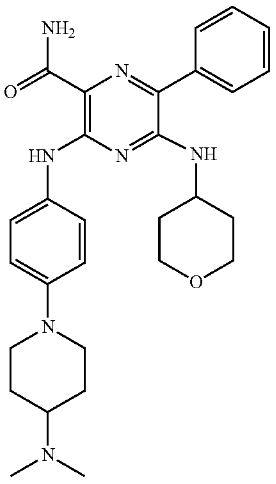 [SMILES: CN(C)C1CCN(c2ccc(Nc3nc(NC4CCOCC4)c(-c4ccccc4)nc3C(N)=O)cc2)CC1] | A | 516 | 1.523 |
| 60 | 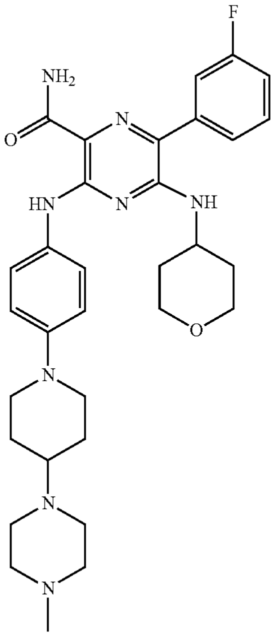 [SMILES: CN1CCN(C2CCN(c3ccc(Nc4nc(NC5CCOCC5)c(-c5cccc(F)c5)nc4C(N)=O)cc3)CC2)CC1] | A | 589 | — |

TABLE 2-continued
| | | | | |
|---|---|---|---|---|
| 61 | 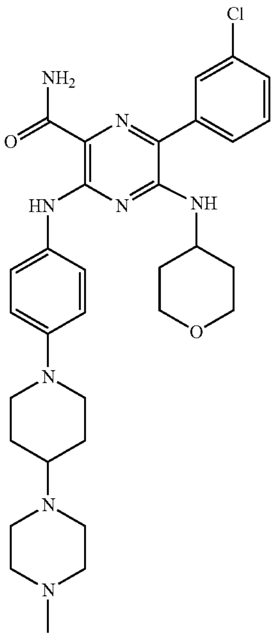 [SMILES: CN1CCN(C2CCN(c3ccc(Nc4nc(NC5CCOCC5)c(-c5cccc(Cl)c5)nc4C(N)=O)cc3)CC2)CC1] | A | 605 | — |
| 62 | 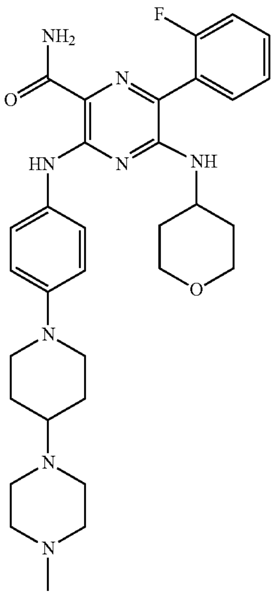 | A | 589 | 1.400 |

TABLE 2-continued
| | | | | |
|---|---|---|---|---|
| 63 | 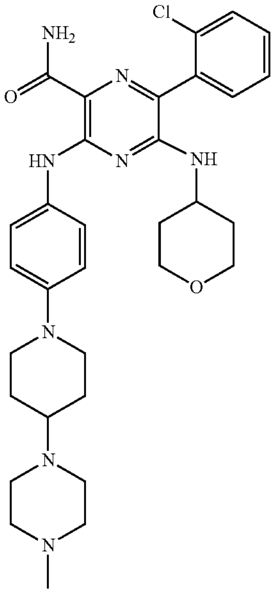 [SMILES: CN1CCN(C2CCN(c3ccc(Nc4nc(NC5CCOCC5)c(-c5ccccc5F)nc4C(N)=O)cc3)CC2)CC1] | A | 605 | 1.423 |
| 64 | 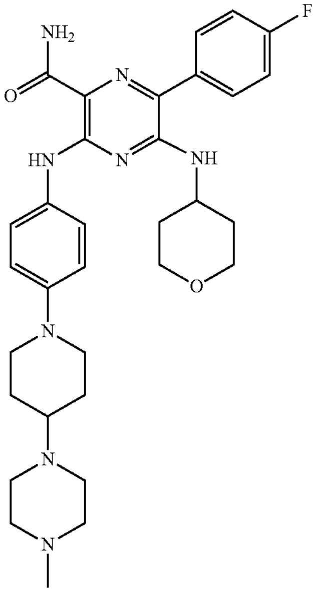 [SMILES: CN1CCN(C2CCN(c3ccc(Nc4nc(NC5CCOCC5)c(-c5ccc(F)cc5)nc4C(N)=O)cc3)CC2)CC1] | A | 589 | 1.438 |

TABLE 2-continued
| | | | | |
|---|---|---|---|---|
| 65 | 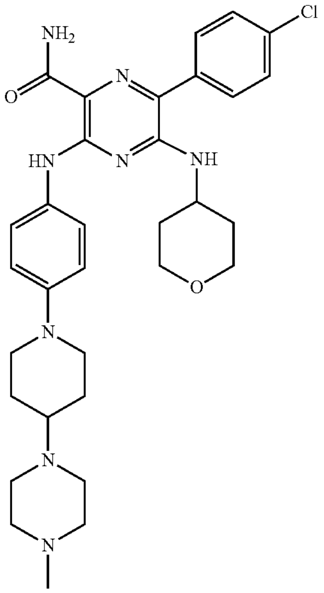 [SMILES: CN1CCN(C2CCN(c3ccc(Nc4nc(NC5CCOCC5)c(-c5ccc(Cl)cc5)nc4C(N)=O)cc3)CC2)CC1] | A | 605 | 1.532 |
| 66 | 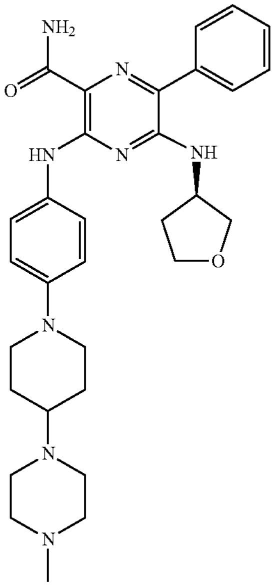 [SMILES: CN1CCN(C2CCN(c3ccc(Nc4nc(N[C@@H]5CCOC5)c(-c5ccccc5)nc4C(N)=O)cc3)CC2)CC1] | A | 557 | — |

TABLE 2-continued
| | | | | |
|---|---|---|---|---|
| 67 | 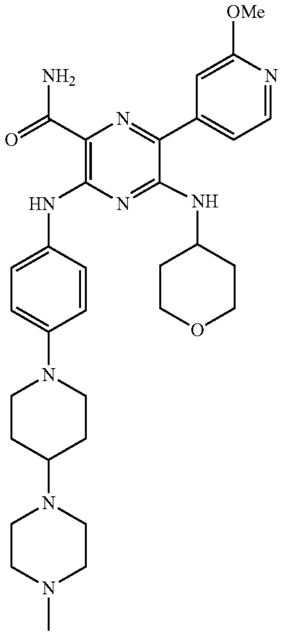 [SMILES: COc1cc(-c2nc(C(N)=O)c(Nc3ccc(N4CCC(N5CCN(C)CC5)CC4)cc3)nc2NC2CCOCC2)ccn1] | A | 602 | — |
| 68 | 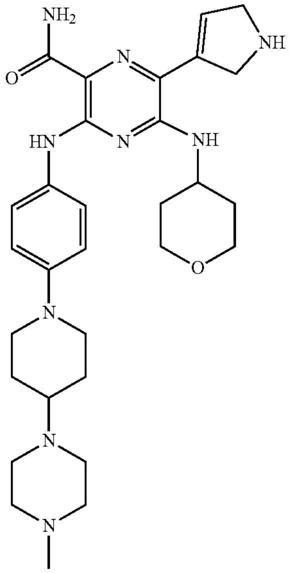 [SMILES: CN1CCN(C2CCN(c3ccc(Nc4nc(NC5CCOCC5)c(C5=CCNC5)nc4C(N)=O)cc3)CC2)CC1] | A | 562 | 1.047 |

TABLE 2-continued
| | | | | |
|---|---|---|---|---|
| 69 | 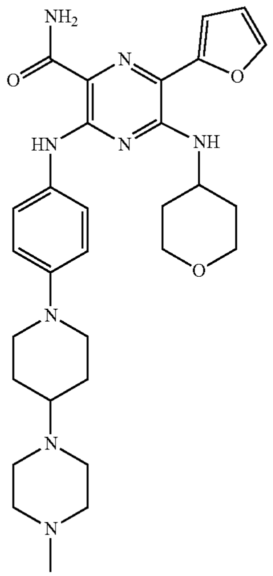 [SMILES: CN1CCN(C2CCN(c3ccc(Nc4nc(NC5CCOCC5)c(-c5ccco5)nc4C(N)=O)cc3)CC2)CC1] | A | 561 | 1.331 |
| 70 | 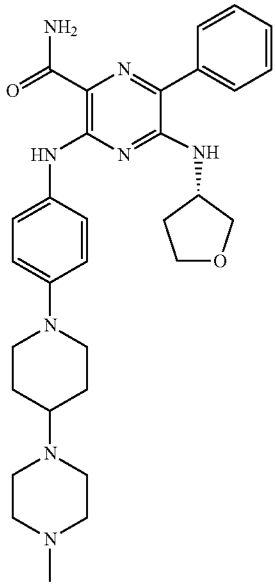 [SMILES: CN1CCN(C2CCN(c3ccc(Nc4nc(N[C@H]5CCOC5)c(-c5ccccc5)nc4C(N)=O)cc3)CC2)CC1] | A | 557 | 1.350 |

TABLE 2-continued
| | | | | |
|---|---|---|---|---|
| 71 | 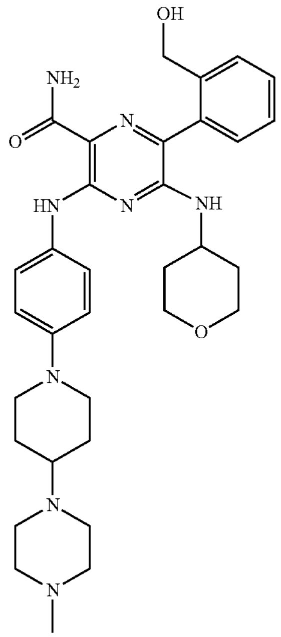 [SMILES: CN1CCN(C2CCN(c3ccc(Nc4nc(NC5CCOCC5)c(-c5ccccc5CO)nc4C(N)=O)cc3)CC2)CC1] | A | 601 | 1.260 |
| 72 | 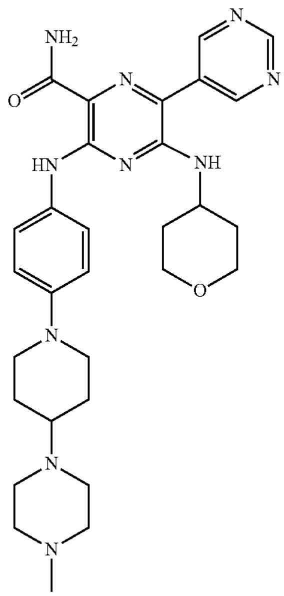 [SMILES: CN1CCN(C2CCN(c3ccc(Nc4nc(NC5CCOCC5)c(-c5cncnc5)nc4C(N)=O)cc3)CC2)CC1] | A | 573 | 1.236 |

TABLE 2-continued
| | | | | |
|---|---|---|---|---|
| 73 | 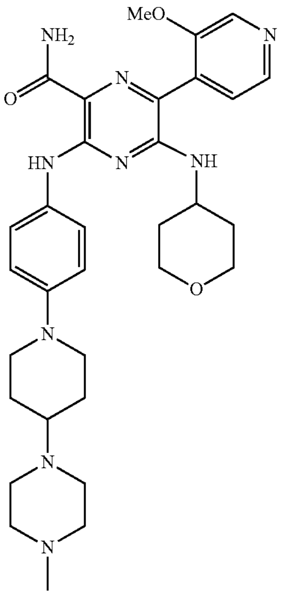 [SMILES: COc1cnccc1-c1nc(C(N)=O)c(Nc2ccc(N3CCC(N4CCN(C)CC4)CC3)cc2)nc1NC1CCOCC1] | A | 602 | 1.137 |
| 74 | 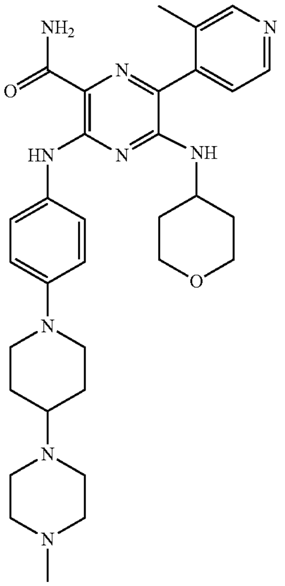 [SMILES: Cc1cnccc1-c1nc(C(N)=O)c(Nc2ccc(N3CCC(N4CCN(C)CC4)CC3)cc2)nc1NC1CCOCC1] | A | 586 | — |

TABLE 2-continued
| | | | | |
|---|---|---|---|---|
| 75 | 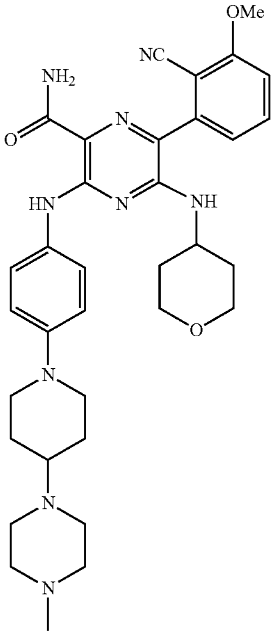 [SMILES: COc1cccc(-c2nc(C(N)=O)c(Nc3ccc(N4CCC(N5CCN(C)CC5)CC4)cc3)nc2NC2CCOCC2)c1C#N] | A | 626 | — |
| 76 | 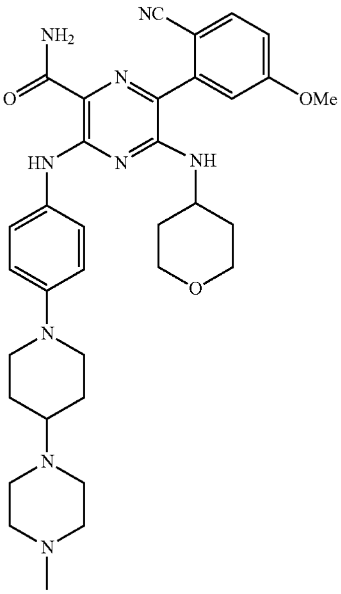 [SMILES: COc1ccc(C#N)c(-c2nc(C(N)=O)c(Nc3ccc(N4CCC(N5CCN(C)CC5)CC4)cc3)nc2NC2CCOCC2)c1] | A | 626 | — |

TABLE 2-continued
| | | | | |
|---|---|---|---|---|
| 77 | 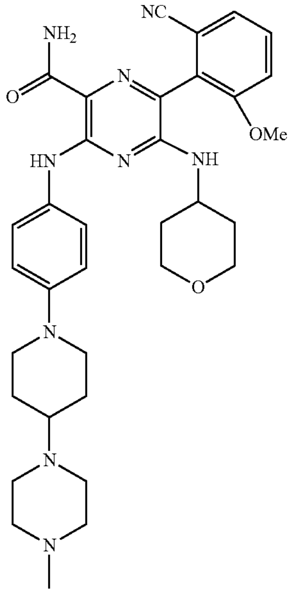 [SMILES: COc1cccc(C#N)c1-c1nc(C(N)=O)c(Nc2ccc(N3CCC(N4CCN(C)CC4)CC3)cc2)nc1NC1CCOCC1] | A | 626 | — |
| 78 | 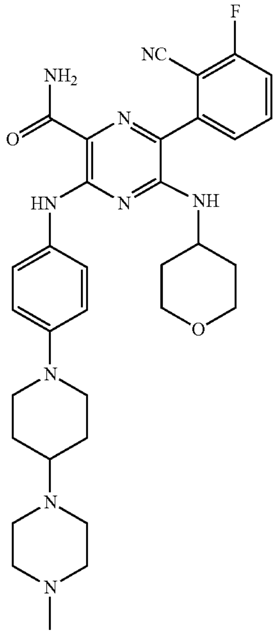 [SMILES: CN1CCN(C2CCN(c3ccc(Nc4nc(NC5CCOCC5)c(-c5cccc(F)c5C#N)nc4C(N)=O)cc3)CC2)CC1] | A | 614 | — |

TABLE 2-continued
| | | | | |
|---|---|---|---|---|
| 79 | 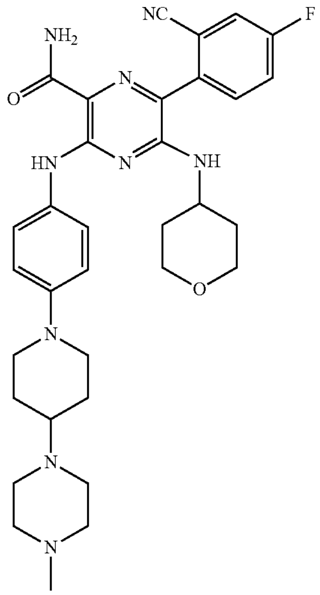 [SMILES: CN1CCN(C2CCN(c3ccc(Nc4nc(NC5CCOCC5)c(-c5ccc(F)cc5C#N)nc4C(N)=O)cc3)CC2)CC1] | A | 614 | — |
| 80 | 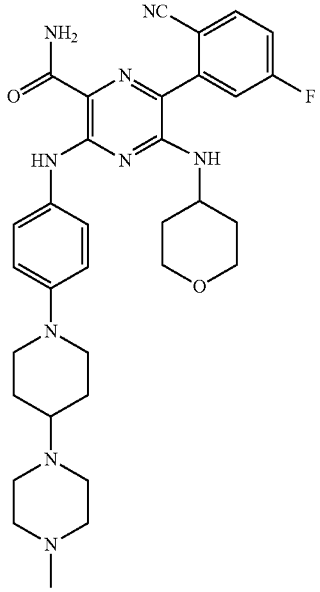 [SMILES: CN1CCN(C2CCN(c3ccc(Nc4nc(NC5CCOCC5)c(-c5cc(F)ccc5C#N)nc4C(N)=O)cc3)CC2)CC1] | A | 614 | — |

TABLE 2-continued
| | | | | |
|---|---|---|---|---|
| 81 | 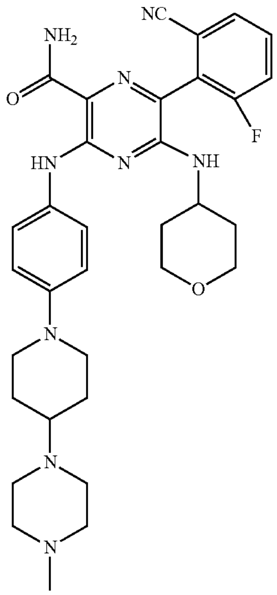 [SMILES: CN1CCN(C2CCN(c3ccc(Nc4nc(NC5CCOCC5)c(-c5c(F)cccc5C#N)nc4C(N)=O)cc3)CC2)CC1] | A | 614 | — |
| 82 | 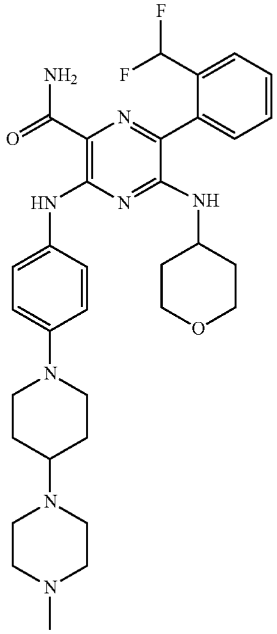 [SMILES: CN1CCN(C2CCN(c3ccc(Nc4nc(NC5CCOCC5)c(-c5ccccc5C(F)F)nc4C(N)=O)cc3)CC2)CC1] | A | 621 | 1.370 |

TABLE 2-continued
| | | | | |
|---|---|---|---|---|
| 83 | 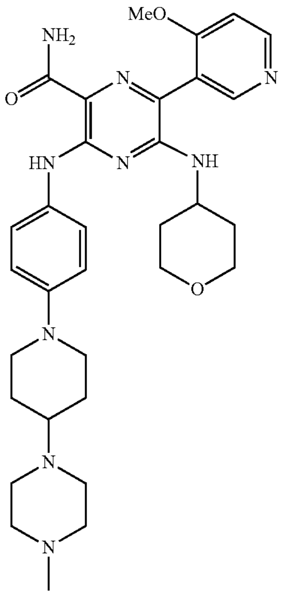 [SMILES: COc1ccncc1-c1nc(C(N)=O)c(Nc2ccc(N3CCC(N4CCN(C)CC4)CC3)cc2)nc1NC1CCOCC1] | A | 602 | 1.058 |
| 84 | 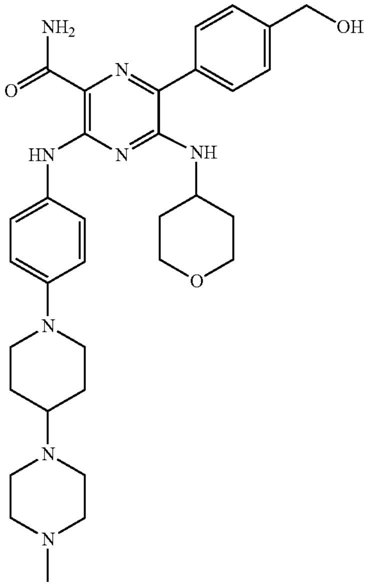 [SMILES: CN1CCN(C2CCN(c3ccc(Nc4nc(NC5CCOCC5)c(-c5ccc(CO)cc5)nc4C(N)=O)cc3)CC2)CC1] | A | 601 | 1.241 |

TABLE 2-continued
| | | | | |
|---|---|---|---|---|
| 85 | 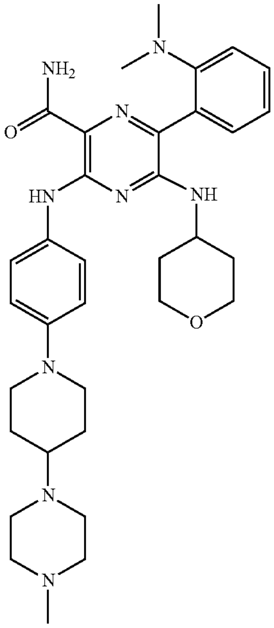 [SMILES: CN1CCN(C2CCN(c3ccc(Nc4nc(NC5CCOCC5)c(-c5ccccc5N(C)C)nc4C(N)=O)cc3)CC2)CC1] | A | 614 | 1.235 |
| 86 | 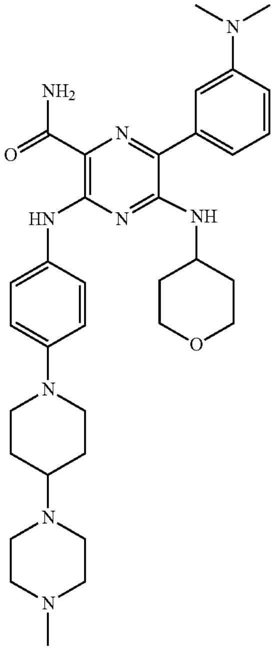 [SMILES: CN1CCN(C2CCN(c3ccc(Nc4nc(NC5CCOCC5)c(-c5cccc(N(C)C)c5)nc4C(N)=O)cc3)CC2)CC1] | A | 614 | 1.268 |

TABLE 2-continued
| | | | | |
|---|---|---|---|---|
| 87 | 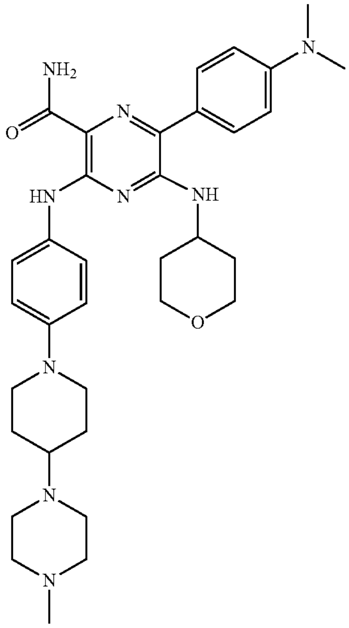 [SMILES: CN1CCN(C2CCN(c3ccc(Nc4nc(NC5CCOCC5)c(-c5ccc(N(C)C)cc5)nc4C(N)=O)cc3)CC2)CC1] | A | 614 | 1.292 |
| 88 | 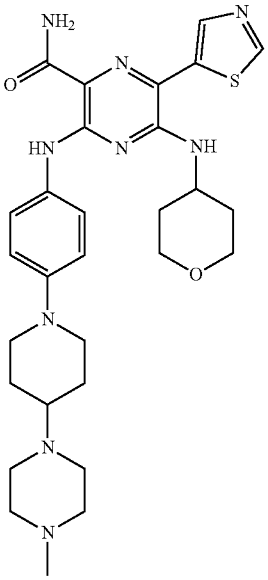 [SMILES: CN1CCN(C2CCN(c3ccc(Nc4nc(NC5CCOCC5)c(-c5cncs5)nc4C(N)=O)cc3)CC2)CC1] | A | 578 | 1.272 |

TABLE 2-continued
| | | | | |
|---|---|---|---|---|
| 89 | 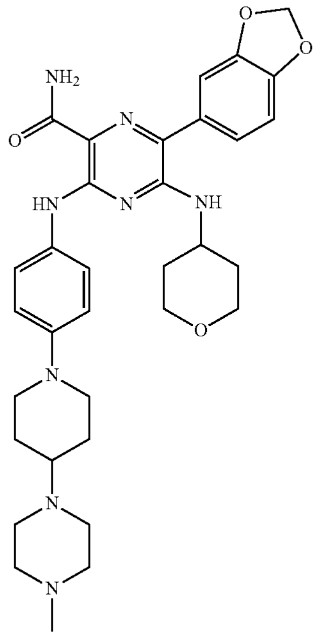 [SMILES: CN1CCN(C2CCN(c3ccc(Nc4nc(NC5CCOCC5)c(-c5ccc6c(c5)OCO6)nc4C(N)=O)cc3)CC2)CC1] | A | 615 | 1.396 |
| 90 | 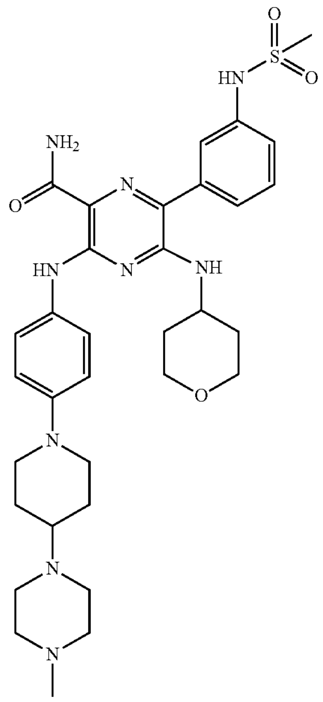 [SMILES: CN1CCN(C2CCN(c3ccc(Nc4nc(NC5CCOCC5)c(-c5cccc(NS(C)(=O)=O)c5)nc4C(N)=O)cc3)CC2)CC1] | A | 664 | 1.312 |

TABLE 2-continued
| | | | | |
|---|---|---|---|---|
| 91 | 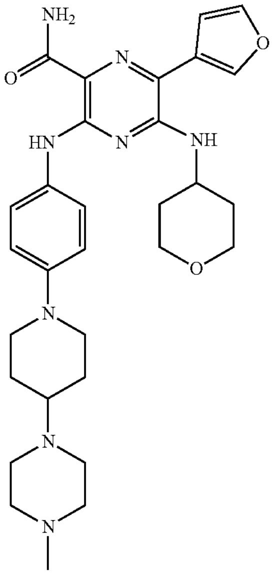 [SMILES: CN1CCN(C2CCN(c3ccc(Nc4nc(NC5CCOCC5)c(-c5ccoc5)nc4C(N)=O)cc3)CC2)CC1] | A | 561 | 1.332 |
| 92 | 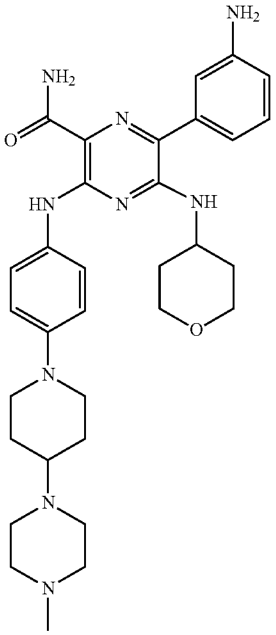 [SMILES: CN1CCN(C2CCN(c3ccc(Nc4nc(NC5CCOCC5)c(-c5cccc(N)c5)nc4C(N)=O)cc3)CC2)CC1] | A | 586 | 1.204 |

TABLE 2-continued
| | | | | |
|---|---|---|---|---|
| 93 | 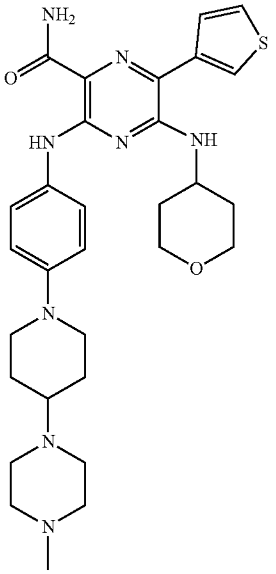 [SMILES: CN1CCN(C2CCN(c3ccc(Nc4nc(NC5CCOCC5)c(-c5ccsc5)nc4C(N)=O)cc3)CC2)CC1] | A | 577 | 1.350 |
| 94 | 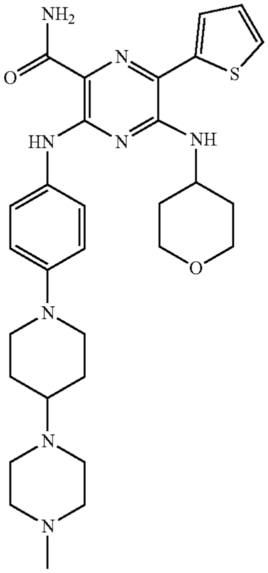 [SMILES: CN1CCN(C2CCN(c3ccc(Nc4nc(NC5CCOCC5)c(-c5cccs5)nc4C(N)=O)cc3)CC2)CC1] | A | 577 | 1.399 |

TABLE 2-continued
| | | | | |
|---|---|---|---|---|
| 95 | 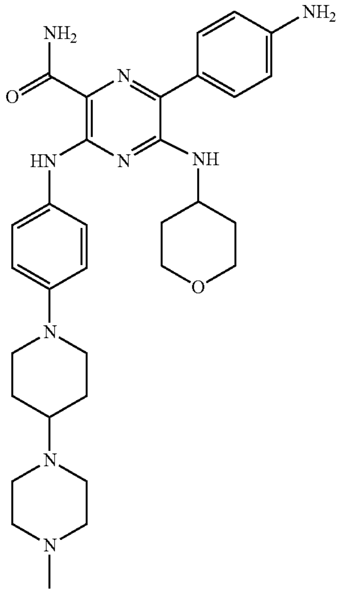 [SMILES: CN1CCN(C2CCN(c3ccc(Nc4nc(NC5CCOCC5)c(-c5ccc(N)cc5)nc4C(N)=O)cc3)CC2)CC1] | A | 586 | 1.220 |
| 96 | 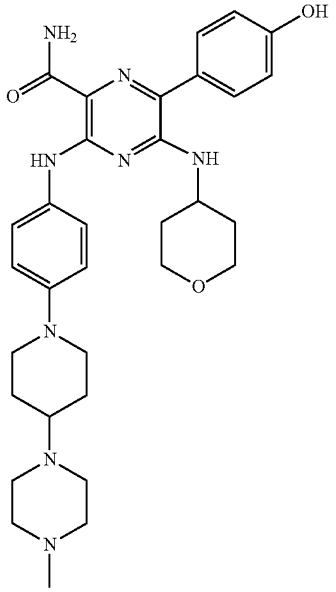 | A | 587 | 1.225 |

TABLE 2-continued
| | | | | |
|---|---|---|---|---|
| 97 | 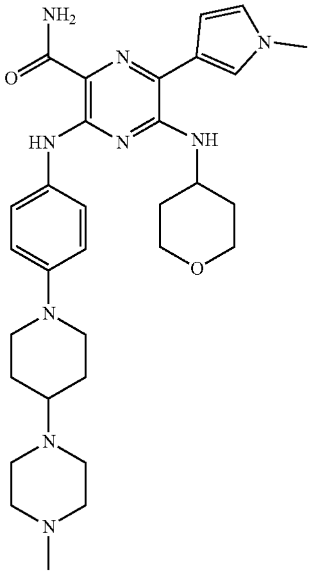 [SMILES: CN1CCN(C2CCN(c3ccc(Nc4nc(NC5CCOCC5)c(-c5ccn(C)c5)nc4C(N)=O)cc3)CC2)CC1] | A | 574 | 1.313 |
| 98 | 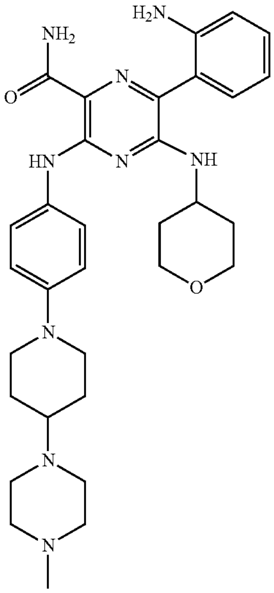 [SMILES: CN1CCN(C2CCN(c3ccc(Nc4nc(NC5CCOCC5)c(-c5ccccc5N)nc4C(N)=O)cc3)CC2)CC1] | A | 586 | 1.295 |

TABLE 2-continued
| | | | | |
|---|---|---|---|---|
| 99 | 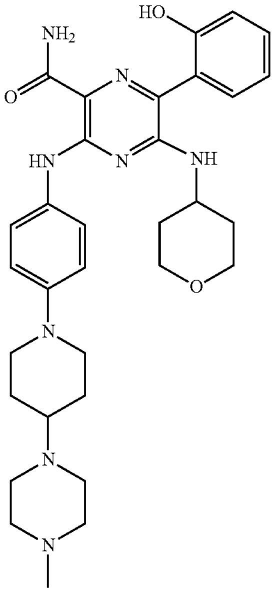 [SMILES: CN1CCN(C2CCN(c3ccc(Nc4nc(NC5CCOCC5)c(-c5ccccc5O)nc4C(N)=O)cc3)CC2)CC1] | A | 587 | 1.336 |
| 100 | 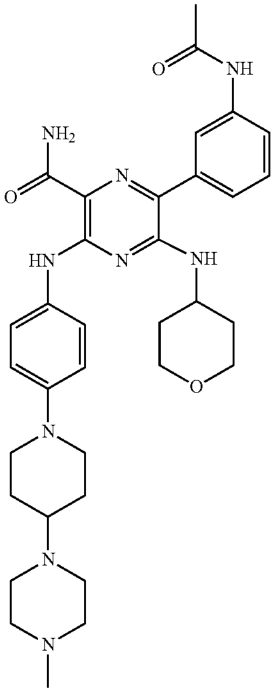 [SMILES: CC(=O)Nc1cccc(-c2nc(C(N)=O)c(Nc3ccc(N4CCC(N5CCN(C)CC5)CC4)cc3)nc2NC2CCOCC2)c1] | A | 628 | 1.314 |

TABLE 2-continued
| | | | | |
|---|---|---|---|---|
| 101 | 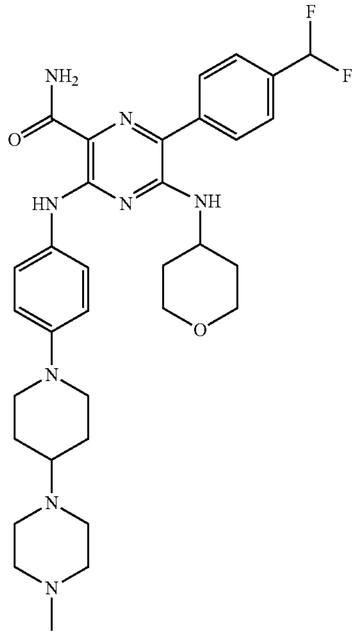 [SMILES: CN1CCN(C2CCN(c3ccc(Nc4nc(NC5CCOCC5)c(-c5ccc(C(F)F)cc5)nc4C(N)=O)cc3)CC2)CC1] | A | 621 | 1.446 |
| 102 | 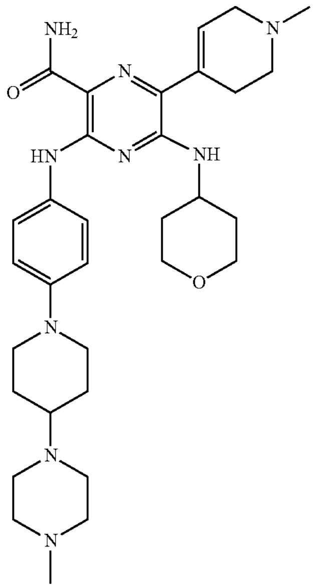 [SMILES: CN1CC=C(c2nc(C(N)=O)c(Nc3ccc(N4CCC(N5CCN(C)CC5)CC4)cc3)nc2NC2CCOCC2)CC1] | A | 590 | 1.058 |

TABLE 2-continued
| | | | | |
|---|---|---|---|---|
| 103 | 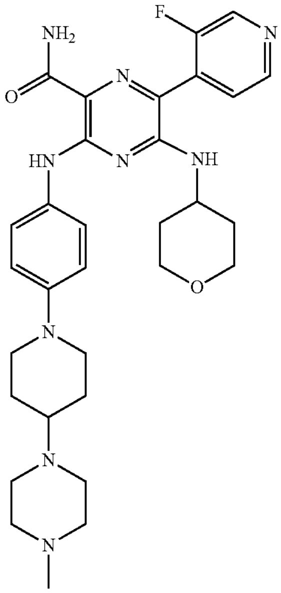 [SMILES: CN1CCN(C2CCN(c3ccc(Nc4nc(NC5CCOCC5)c(-c5ccncc5F)nc4C(N)=O)cc3)CC2)CC1] | A | 590 | 1.270 |
| 104 | 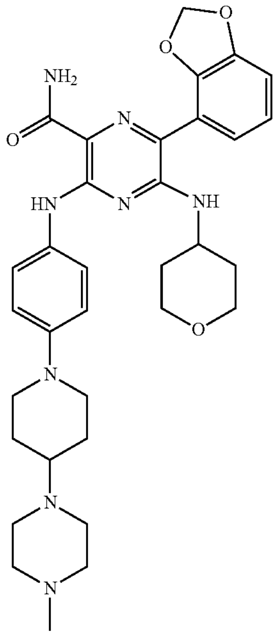 [SMILES: CN1CCN(C2CCN(c3ccc(Nc4nc(NC5CCOCC5)c(-c5cccc6c5OCO6)nc4C(N)=O)cc3)CC2)CC1] | A | 615 | 1.398 |

TABLE 2-continued
| | | | | |
|---|---|---|---|---|
| 105 | 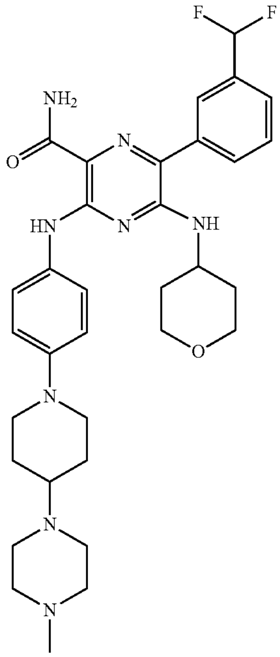 [SMILES: CN1CCN(C2CCN(c3ccc(Nc4nc(NC5CCOCC5)c(-c5cccc(C(F)F)c5)nc4C(N)=O)cc3)CC2)CC1] | A | 621 | 1.393 |
| 106 | 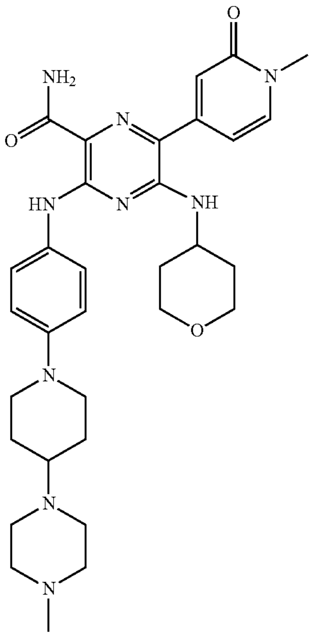 [SMILES: CN1CCN(C2CCN(c3ccc(Nc4nc(NC5CCOCC5)c(-c5ccn(C)c(=O)c5)nc4C(N)=O)cc3)CC2)CC1] | A | 602 | 1.194 |

TABLE 2-continued
| | | | | |
|---|---|---|---|---|
| 107 | 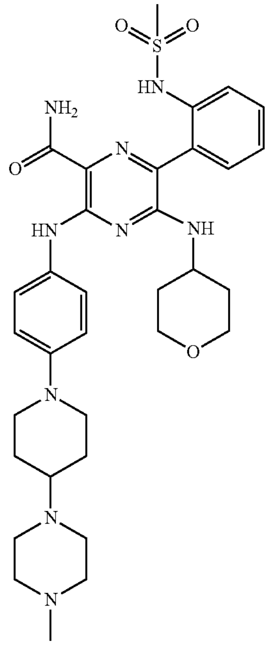 [SMILES: CN1CCN(C2CCN(c3ccc(Nc4nc(NC5CCOCC5)c(-c5ccccc5NS(C)(=O)=O)nc4C(N)=O)cc3)CC2)CC1] | A | 664 | 1.296 |
| 108 | 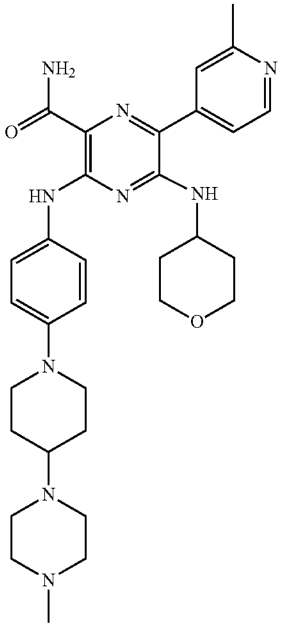 [SMILES: Cc1cc(-c2nc(C(N)=O)c(Nc3ccc(N4CCC(N5CCN(C)CC5)CC4)cc3)nc2NC2CCOCC2)ccn1] | A | 586 | 1.109 |

TABLE 2-continued
| | | | | |
|---|---|---|---|---|
| 109 | 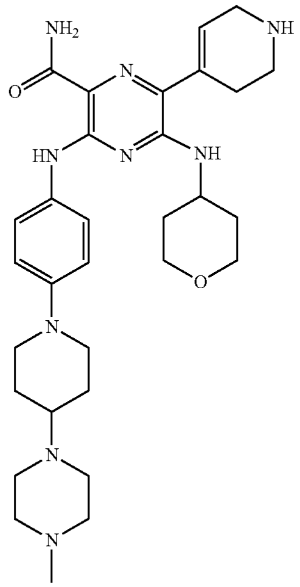 [SMILES: CN1CCN(C2CCN(c3ccc(Nc4nc(NC5CCOCC5)c(C5=CCNCC5)nc4C(N)=O)cc3)CC2)CC1] | A | 576 | 1.084 |
| 110 | 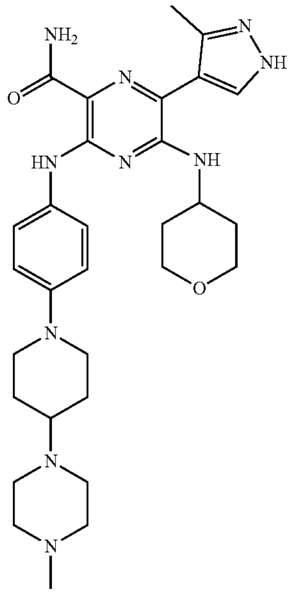 [SMILES: Cc1n[nH]cc1-c1nc(C(N)=O)c(Nc2ccc(N3CCC(N4CCN(C)CC4)CC3)cc2)nc1NC1CCOCC1] | A | 575 | 1.159 |

TABLE 2-continued
| | | | | |
|---|---|---|---|---|
| 111 | 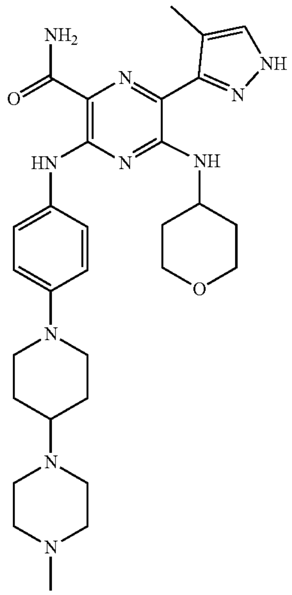 [SMILES: Cc1c[nH]nc1-c1nc(C(N)=O)c(Nc2ccc(N3CCC(N4CCN(C)CC4)CC3)cc2)nc1NC1CCOCC1] | A | 575 | 1.308 |
| 112 | 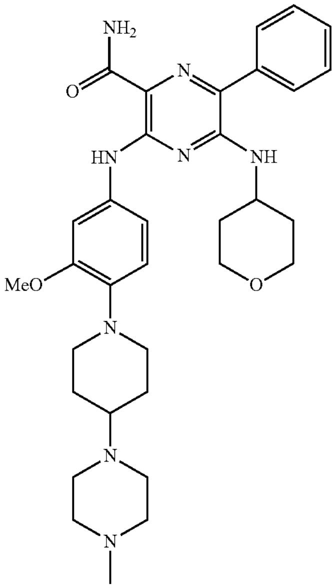 [SMILES: COc1cc(Nc2nc(NC3CCOCC3)c(-c3ccccc3)nc2C(N)=O)ccc1N1CCC(N2CCN(C)CC2)CC1] | A | 601 | 1.363 |

TABLE 2-continued
| | | | | |
|---|---|---|---|---|
| 113 | 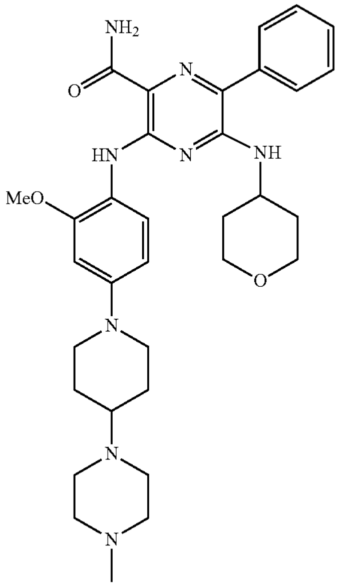 [SMILES: COc1cc(N2CCC(N3CCN(C)CC3)CC2)ccc1Nc1nc(NC2CCOCC2)c(-c2ccccc2)nc1C(N)=O] | A | 601 | 1.456 |
| 114 | 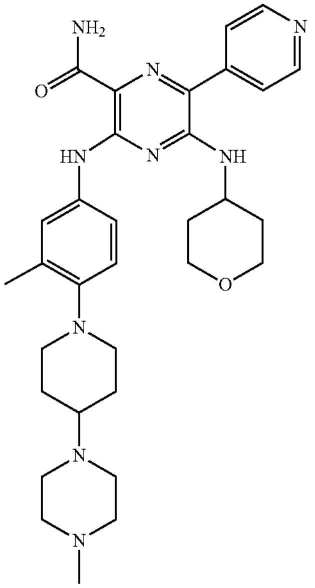 [SMILES: Cc1cc(Nc2nc(NC3CCOCC3)c(-c3ccncc3)nc2C(N)=O)ccc1N1CCC(N2CCN(C)CC2)CC1] | A | 586 | 1.226 |

TABLE 2-continued
| | | | | |
|---|---|---|---|---|
| 115 | 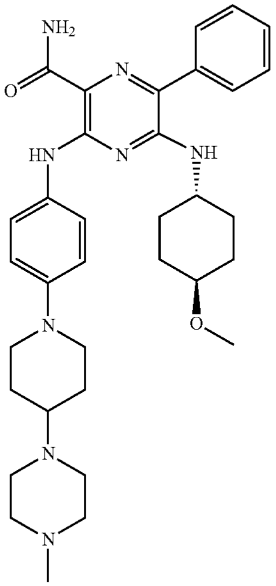 [SMILES: CO[C@H]1CC[C@H](Nc2nc(Nc3ccc(N4CCC(N5CCN(C)CC5)CC4)cc3)c(C(N)=O)nc2-c2ccccc2)CC1] | A | 599 | 1.491 |
| 117 | 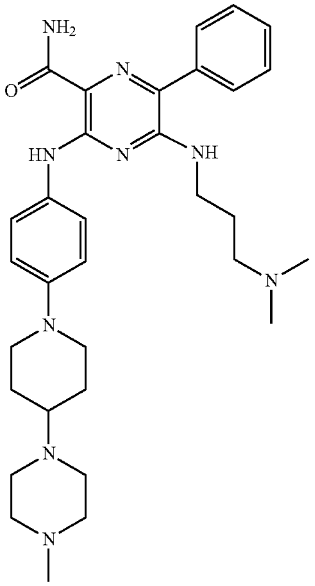 [SMILES: CN(C)CCCNc1nc(Nc2ccc(N3CCC(N4CCN(C)CC4)CC3)cc2)c(C(N)=O)nc1-c1ccccc1] | A | 572 | 1.107 |
| 118 | 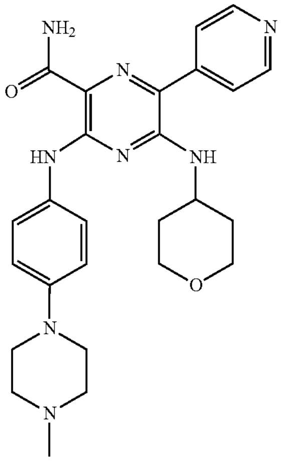 [SMILES: CN1CCN(c2ccc(Nc3nc(NC4CCOCC4)c(-c4ccncc4)nc3C(N)=O)cc2)CC1] | A | 489 | 1.201 |

TABLE 2-continued
| | | | | |
|---|---|---|---|---|
| 119 | 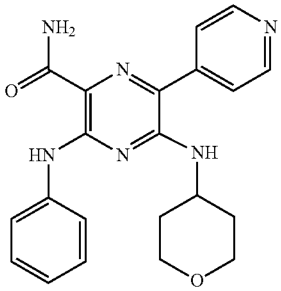 [SMILES: NC(=O)c1nc(-c2ccncc2)c(NC2CCOCC2)nc1Nc1ccccc1] | A | 391 | 1.499 |
| 120 | 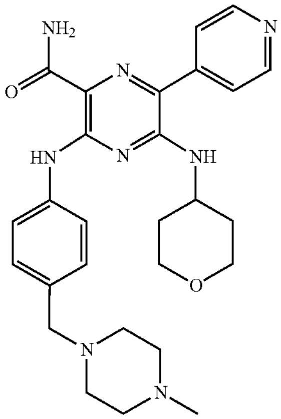 [SMILES: CN1CCN(Cc2ccc(Nc3nc(NC4CCOCC4)c(-c4ccncc4)nc3C(N)=O)cc2)CC1] | A | 503 | 1.156 |
| 121 | 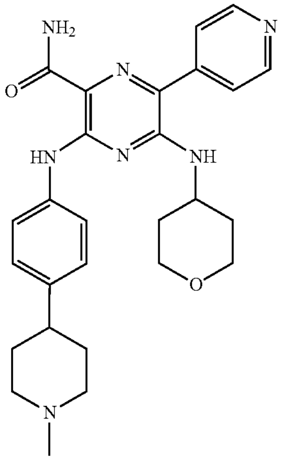 [SMILES: CN1CCC(c2ccc(Nc3nc(NC4CCOCC4)c(-c4ccncc4)nc3C(N)=O)cc2)CC1] | A | 488 | 1.219 |

TABLE 2-continued
| | | | | |
|---|---|---|---|---|
| 122 | 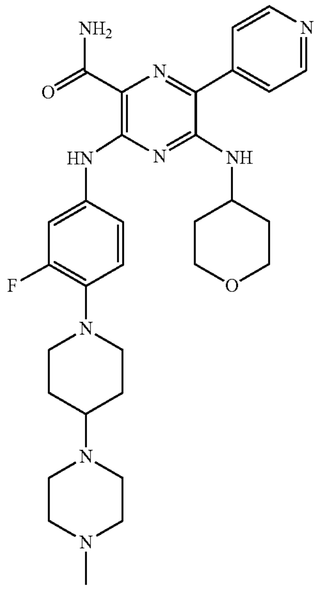 [SMILES: CN1CCN(C2CCN(c3ccc(Nc4nc(NC5CCOCC5)c(-c5ccncc5)nc4C(N)=O)cc3F)CC2)CC1] | A | 590 | 1.222 |
| 123 | 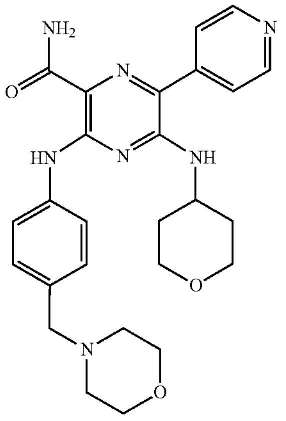 [SMILES: NC(=O)c1nc(-c2ccncc2)c(NC2CCOCC2)nc1Nc1ccc(CN2CCOCC2)cc1] | A | 490 | 1.114 |
| 124 | 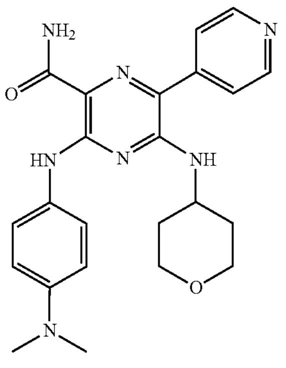 [SMILES: CN(C)c1ccc(Nc2nc(NC3CCOCC3)c(-c3ccncc3)nc2C(N)=O)cc1] | A | 434 | 1.232 |

TABLE 2-continued
| | | | | |
|---|---|---|---|---|
| 125 | 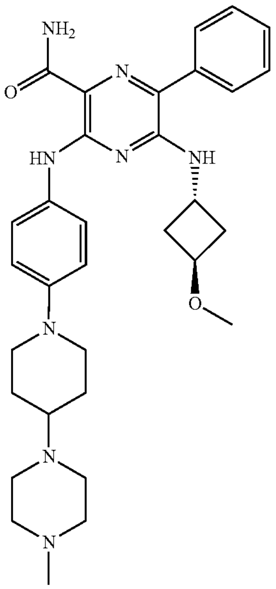 [SMILES: CO[C@H]1C[C@H](Nc2nc(Nc3ccc(N4CCC(N5CCN(C)CC5)CC4)cc3)c(C(N)=O)nc2-c2ccccc2)C1] | A | 571 | 1.387 |
| 126 | 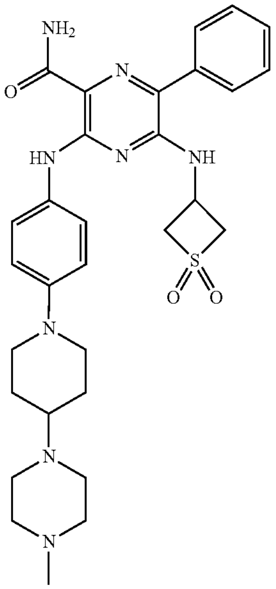 [SMILES: CN1CCN(C2CCN(c3ccc(Nc4nc(NC5CS(=O)(=O)C5)c(-c5ccccc5)nc4C(N)=O)cc3)CC2)CC1] | A | 591 | 1.344 |

TABLE 2-continued
| | | | | |
|---|---|---|---|---|
| 127 | 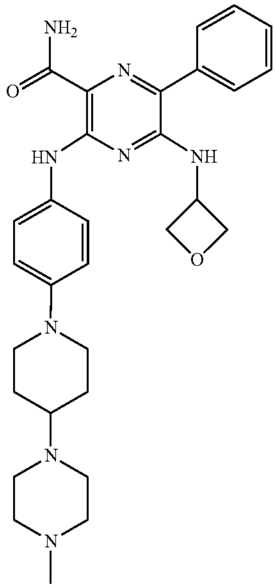 [SMILES: CN1CCN(C2CCN(c3ccc(Nc4nc(NC5COC5)c(-c5ccccc5)nc4C(N)=O)cc3)CC2)CC1] | A | 543 | 0.982 |
| 128 | 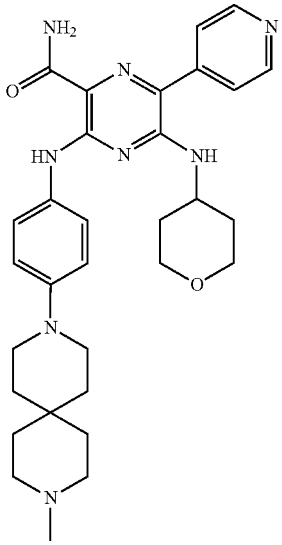 [SMILES: CN1CCC2(CC1)CCN(c1ccc(Nc3nc(NC4CCOCC4)c(-c4ccncc4)nc3C(N)=O)cc1)CC2] | A | 557 | 1.192 |
| 129 | 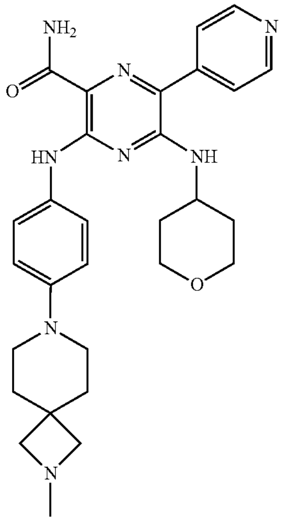 [SMILES: CN1CC2(CCN(c3ccc(Nc4nc(NC5CCOCC5)c(-c5ccncc5)nc4C(N)=O)cc3)CC2)C1] | A | 529 | — |

TABLE 2-continued
| | | | | |
|---|---|---|---|---|
| 130 | 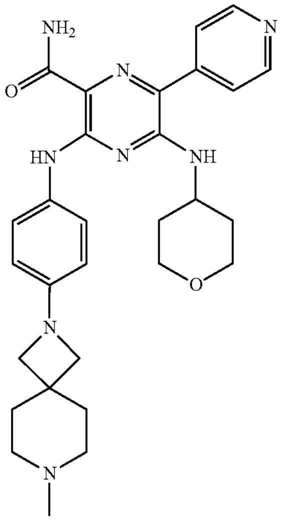 [SMILES: CN1CCC2(CC1)CN(c1ccc(Nc3nc(NC4CCOCC4)c(-c4ccncc4)nc3C(N)=O)cc1)C2] | A | 529 | — |
| 131 | 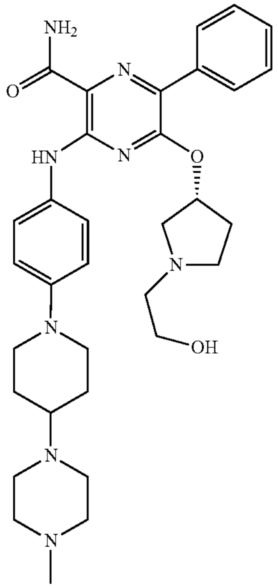 [SMILES: CN1CCN(C2CCN(c3ccc(Nc4nc(O[C@@H]5CCN(CCO)C5)c(-c5ccccc5)nc4C(N)=O)cc3)CC2)CC1] | B | 601 | 1.138 |

TABLE 2-continued
| | | | | |
|---|---|---|---|---|
| 132 | 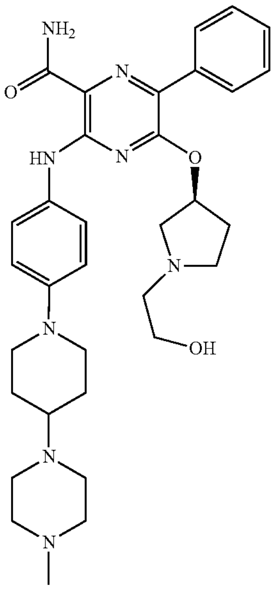 [SMILES: CN1CCN(C2CCN(c3ccc(Nc4nc(O[C@H]5CCN(CCO)C5)c(-c5ccccc5)nc4C(N)=O)cc3)CC2)CC1] | B | 601 | 1.140 |
| 133 | 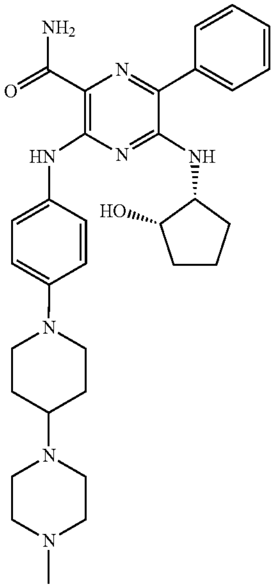 [SMILES: CN1CCN(C2CCN(c3ccc(Nc4nc(N[C@@H]5CCC[C@@H]5O)c(-c5ccccc5)nc4C(N)=O)cc3)CC2)CC1] | A | 571 | 1.371 |

TABLE 2-continued
| | | | | |
|---|---|---|---|---|
| 134 | 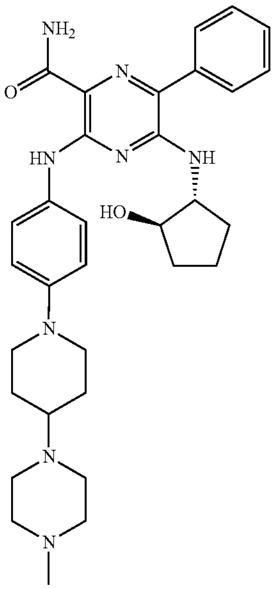 [SMILES: CN1CCN(C2CCN(c3ccc(Nc4nc(N[C@@H]5CCC[C@H]5O)c(-c5ccccc5)nc4C(N)=O)cc3)CC2)CC1] | A | 571 | — |
| 135 | 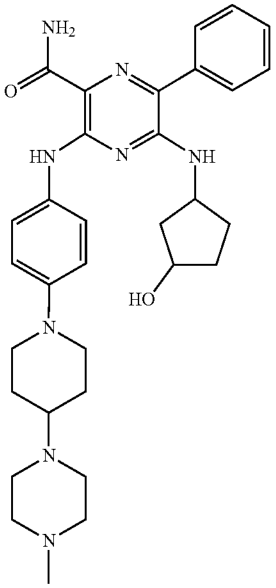 [SMILES: CN1CCN(C2CCN(c3ccc(Nc4nc(NC5CCC(O)C5)c(-c5ccccc5)nc4C(N)=O)cc3)CC2)CC1] | A | 571 | 1.397 |

TABLE 2-continued
| | | | | |
|---|---|---|---|---|
| 140 | 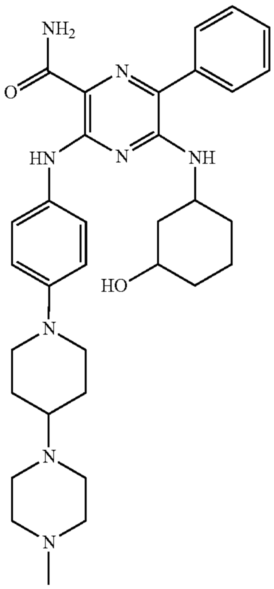 [SMILES: CN1CCN(C2CCN(c3ccc(Nc4nc(NC5CCCC(O)C5)c(-c5ccccc5)nc4C(N)=O)cc3)CC2)CC1] | A | 585 | 1.443 |
| 141 | 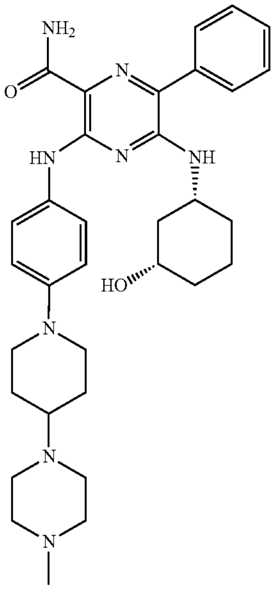 [SMILES: CN1CCN(C2CCN(c3ccc(Nc4nc(N[C@@H]5CCC[C@H](O)C5)c(-c5ccccc5)nc4C(N)=O)cc3)CC2)CC1] | A | 585 | 1.401 |

TABLE 2-continued
| | | | | |
|---|---|---|---|---|
| 142 | 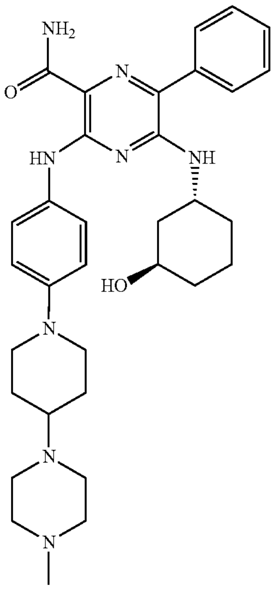 [SMILES: CN1CCN(C2CCN(c3ccc(Nc4nc(N[C@@H]5CCC[C@@H](O)C5)c(-c5ccccc5)nc4C(N)=O)cc3)CC2)CC1] | A | 585 | 1.443 |
| 143 | 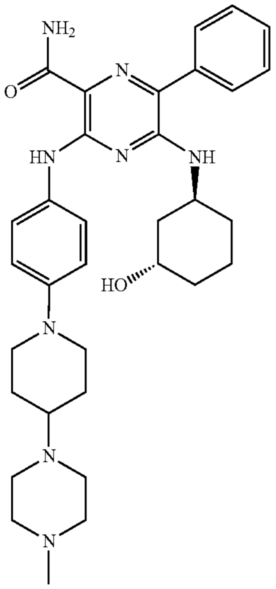 [SMILES: CN1CCN(C2CCN(c3ccc(Nc4nc(N[C@H]5CCC[C@H](O)C5)c(-c5ccccc5)nc4C(N)=O)cc3)CC2)CC1] | A | 585 | 1.436 |

TABLE 2-continued
| | | | | |
|---|---|---|---|---|
| 144 | 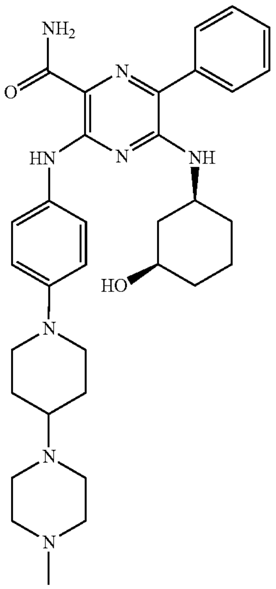 [SMILES: CN1CCN(C2CCN(c3ccc(Nc4nc(N[C@H]5CCC[C@@H](O)C5)c(-c5ccccc5)nc4C(N)=O)cc3)CC2)CC1] | A | 585 | 1.389 |
| 145 | 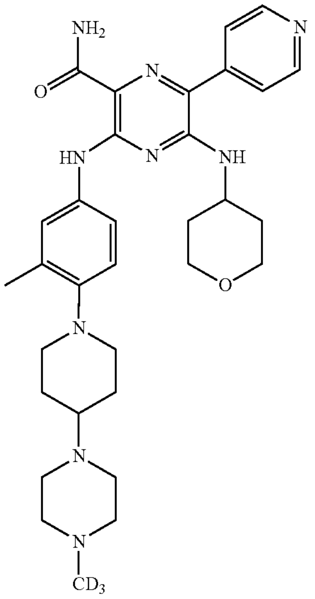 [SMILES: [2H]C([2H])([2H])N1CCN(C2CCN(c3ccc(Nc4nc(NC5CCOCC5)c(-c5ccncc5)nc4C(N)=O)cc3C)CC2)CC1] | A | 589 | — |

TABLE 2-continued
| | | | | |
|---|---|---|---|---|
| 146 | 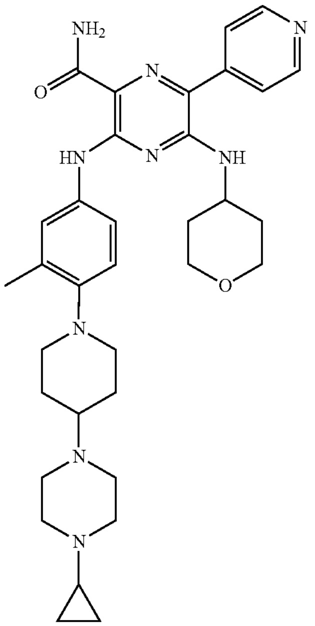 [SMILES: Cc1cc(Nc2nc(NC3CCOCC3)c(-c3ccncc3)nc2C(N)=O)ccc1N1CCC(N2CCN(C3CC3)CC2)CC1] | A | 612 | — |
| 147 | 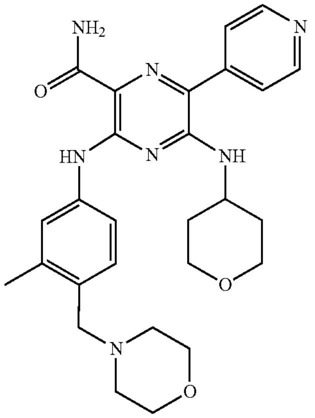 [SMILES: Cc1cc(Nc2nc(NC3CCOCC3)c(-c3ccncc3)nc2C(N)=O)ccc1CN1CCOCC1] | A | 504 | — |
| 148 | 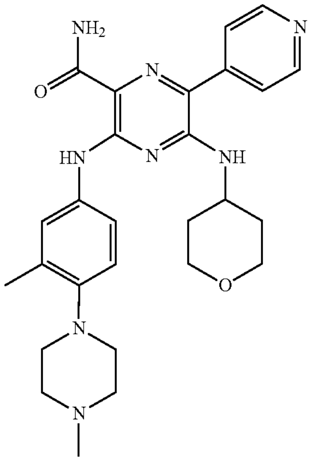 [SMILES: Cc1cc(Nc2nc(NC3CCOCC3)c(-c3ccncc3)nc2C(N)=O)ccc1N1CCN(C)CC1] | A | 503 | 1.204 |

TABLE 2-continued
| | | | | |
|---|---|---|---|---|
| 149 | 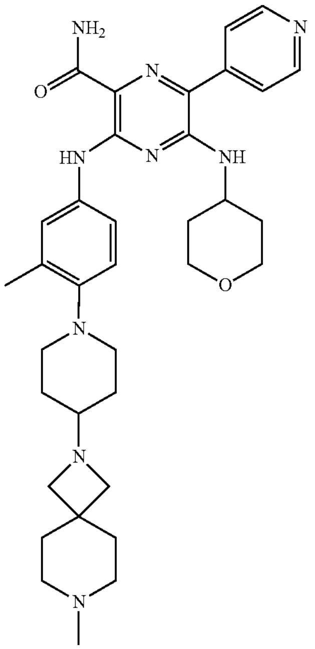 [SMILES: Cc1cc(Nc2nc(NC3CCOCC3)c(-c3ccncc3)nc2C(N)=O)ccc1N1CCC(N2CC3(CCN(C)CC3)C2)CC1] | A | 626 | — |
| 150 | 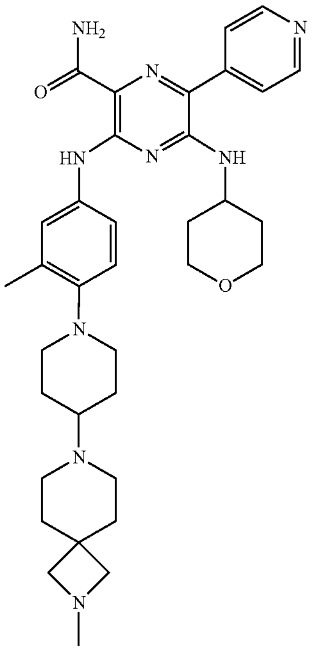 [SMILES: Cc1cc(Nc2nc(NC3CCOCC3)c(-c3ccncc3)nc2C(N)=O)ccc1N1CCC(N2CCC3(CC2)CN(C)C3)CC1] | A | 626 | — |

TABLE 2-continued
| | | | | |
|---|---|---|---|---|
| 151 | 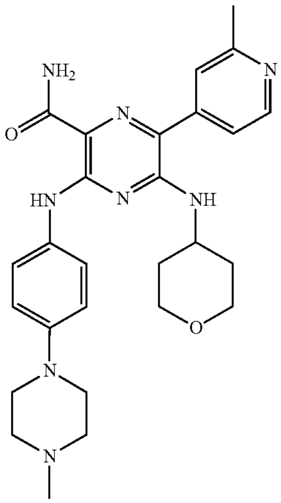 [SMILES: Cc1cc(-c2nc(C(N)=O)c(Nc3ccc(N4CCN(C)CC4)cc3)nc2NC2CCOCC2)ccn1] | A | 503 | — |
| 152 | 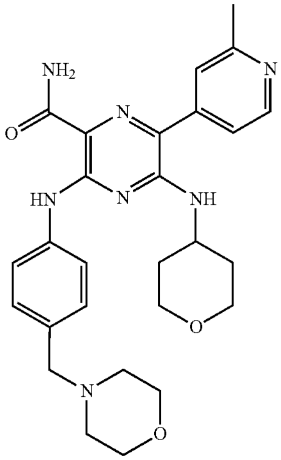 [SMILES: Cc1cc(-c2nc(C(N)=O)c(Nc3ccc(CN4CCOCC4)cc3)nc2NC2CCOCC2)ccn1] | A | 504 | — |
| 153 | 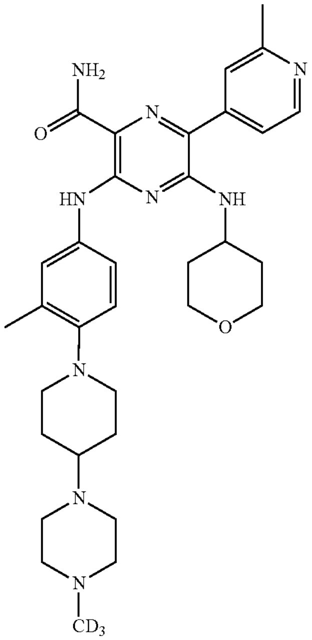 [SMILES: [2H]C([2H])([2H])N1CCN(C2CCN(c3ccc(Nc4nc(NC5CCOCC5)c(-c5ccnc(C)c5)nc4C(N)=O)cc3C)CC2)CC1] | A | 603 | — |

TABLE 2-continued
| | | | | |
|---|---|---|---|---|
| 154 | 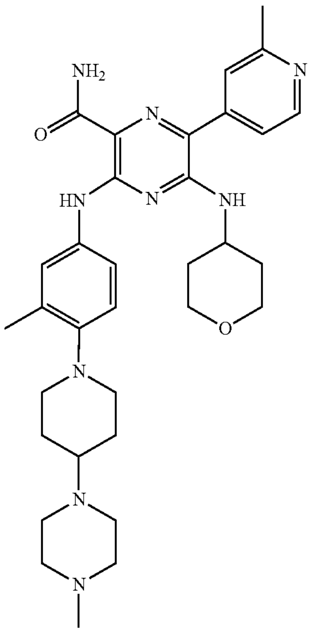 [SMILES: Cc1cc(-c2nc(C(N)=O)c(Nc3ccc(N4CCC(N5CCN(C)CC5)CC4)c(C)c3)nc2NC2CCOCC2)ccn1] | A | 600 | — |
| 155 | 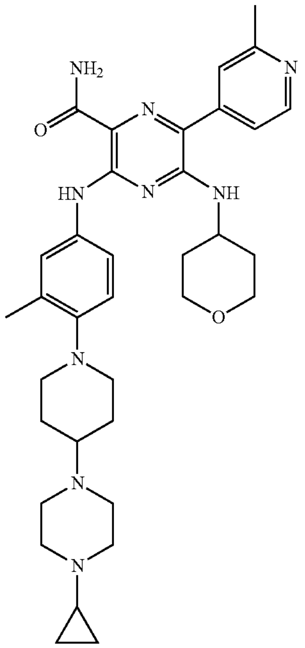 [SMILES: Cc1cc(-c2nc(C(N)=O)c(Nc3ccc(N4CCC(N5CCN(C6CC6)CC5)CC4)c(C)c3)nc2NC2CCOCC2)ccn1] | A | 626 | — |

TABLE 2-continued
| | | | | |
|---|---|---|---|---|
| 156 | 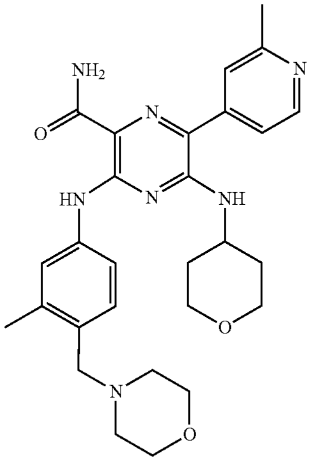 [SMILES: Cc1cc(-c2nc(C(N)=O)c(Nc3ccc(CN4CCOCC4)c(C)c3)nc2NC2CCOCC2)ccn1] | A | 518 | — |
| 157 | 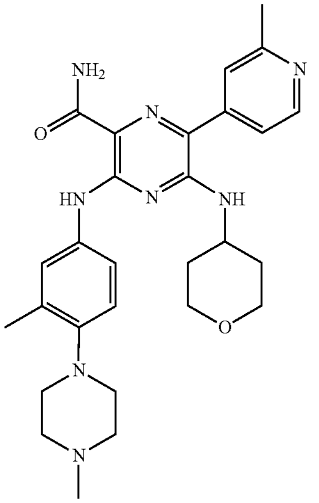 [SMILES: Cc1cc(-c2nc(C(N)=O)c(Nc3ccc(N4CCN(C)CC4)c(C)c3)nc2NC2CCOCC2)ccn1] | A | 517 | — |
| 158 | 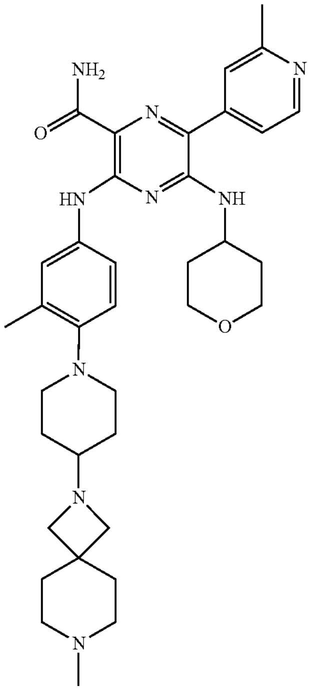 [SMILES: Cc1cc(-c2nc(C(N)=O)c(Nc3ccc(N4CCC(N5CC6(CCN(C)CC6)C5)CC4)c(C)c3)nc2NC2CCOCC2)ccn1] | A | 640 | — |

TABLE 2-continued
| | | | | |
|---|---|---|---|---|
| 159 | 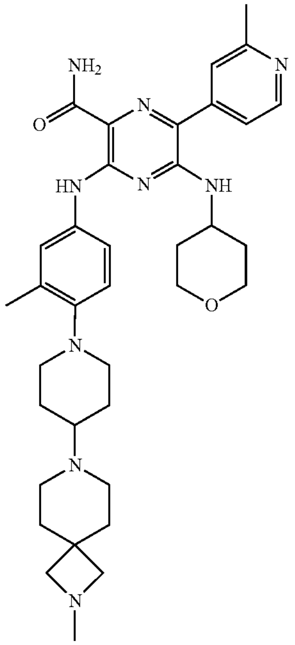 [SMILES: Cc1cc(-c2nc(C(N)=O)c(Nc3ccc(N4CCC(N5CCC6(CC5)CN(C)C6)CC4)c(C)c3)nc2NC2CCOCC2)ccn1] | A | 640 | — |
| 160 | 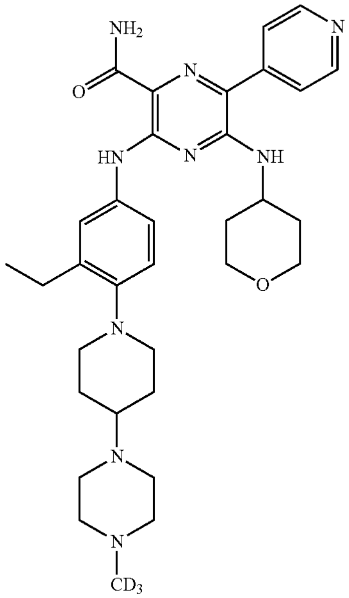 [SMILES: [2H]C([2H])([2H])N1CCN(C2CCN(c3ccc(Nc4nc(NC5CCOCC5)c(-c5ccncc5)nc4C(N)=O)cc3CC)CC2)CC1] | A | 603 | — |

TABLE 2-continued
| | | | | |
|---|---|---|---|---|
| 161 | 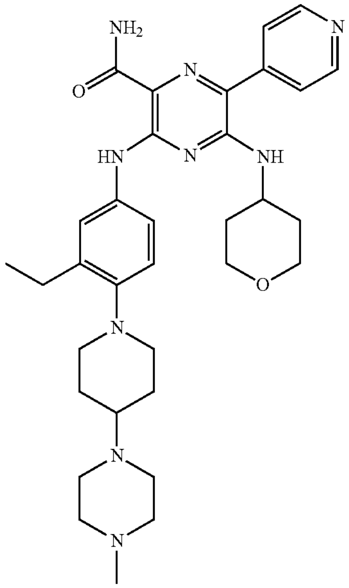 [SMILES: CCc1cc(Nc2nc(NC3CCOCC3)c(-c3ccncc3)nc2C(N)=O)ccc1N1CCC(N2CCN(C)CC2)CC1] | A | 600 | 1.181 |
| 162 | 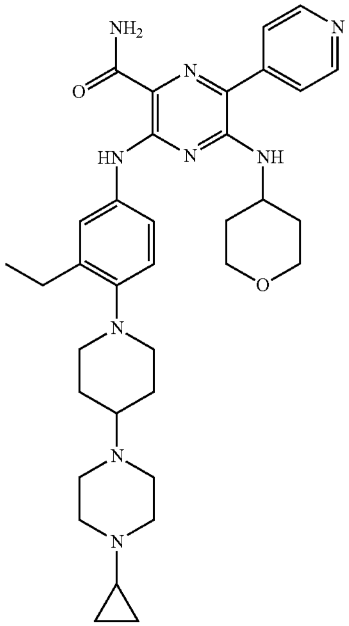 [SMILES: CCc1cc(Nc2nc(NC3CCOCC3)c(-c3ccncc3)nc2C(N)=O)ccc1N1CCC(N2CCN(C3CC3)CC2)CC1] | A | 626 | — |
| 163 | 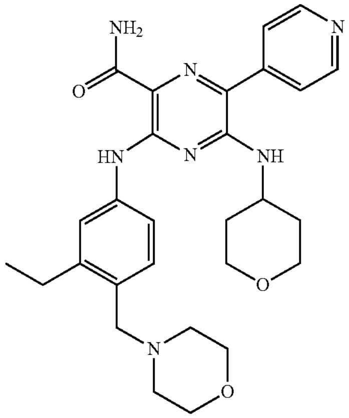 [SMILES: CCc1cc(Nc2nc(NC3CCOCC3)c(-c3ccncc3)nc2C(N)=O)ccc1CN1CCOCC1] | A | 518 | — |

TABLE 2-continued
| | | | | |
|---|---|---|---|---|
| 164 | 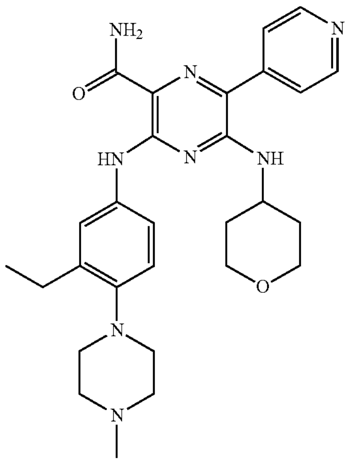 [SMILES: CCc1cc(Nc2nc(NC3CCOCC3)c(-c3ccncc3)nc2C(N)=O)ccc1N1CCN(C)CC1] | A | 517 | — |
| 165 | 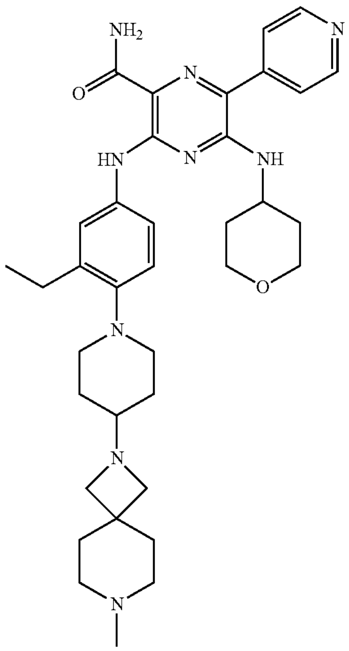 [SMILES: CCc1cc(Nc2nc(NC3CCOCC3)c(-c3ccncc3)nc2C(N)=O)ccc1N1CCC(N2CC3(CCN(C)CC3)C2)CC1] | A | 640 | — |

TABLE 2-continued
| | | | | |
|---|---|---|---|---|
| 166 | 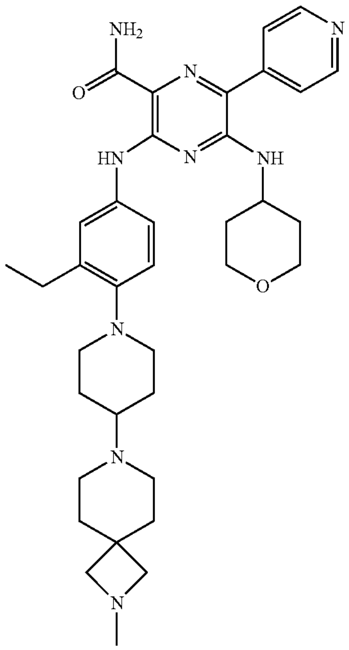 [SMILES: CCc1cc(Nc2nc(NC3CCOCC3)c(-c3ccncc3)nc2C(N)=O)ccc1N1CCC(N2CCC3(CC2)CN(C)C3)CC1] | A | 640 | — |
| 167 | 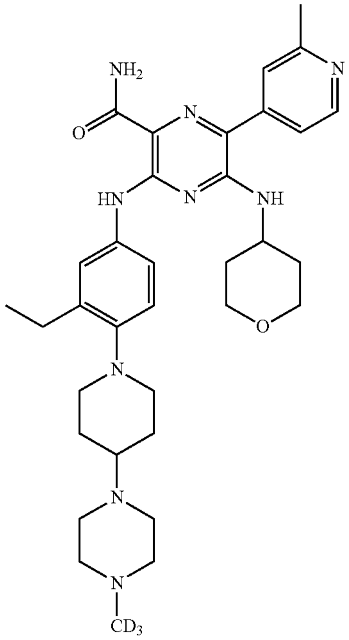 [SMILES: [2H]C([2H])([2H])N1CCN(C2CCN(c3ccc(Nc4nc(NC5CCOCC5)c(-c5ccnc(C)c5)nc4C(N)=O)cc3CC)CC2)CC1] | A | 617 | — |

TABLE 2-continued
| | | | | |
|---|---|---|---|---|
| 168 | 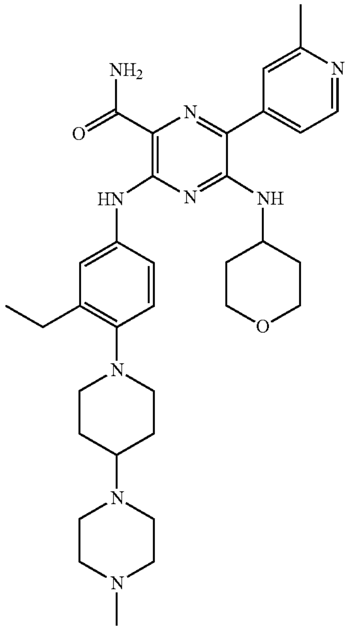 [SMILES: CCc1cc(Nc2nc(NC3CCOCC3)c(-c3ccnc(C)c3)nc2C(N)=O)ccc1N1CCC(N2CCN(C)CC2)CC1] | A | 614 | — |
| 169 | 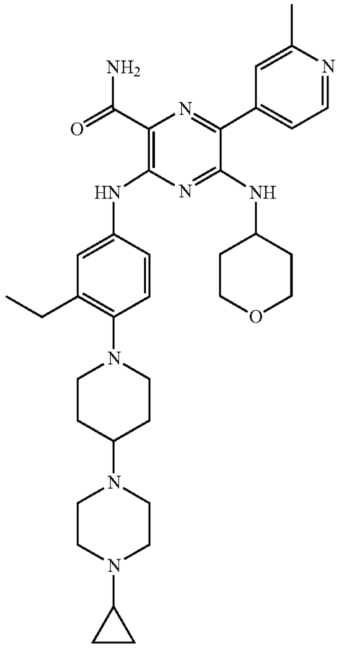 [SMILES: CCc1cc(Nc2nc(NC3CCOCC3)c(-c3ccnc(C)c3)nc2C(N)=O)ccc1N1CCC(N2CCN(C3CC3)CC2)CC1] | A | 640 | — |

TABLE 2-continued
| | | | | |
|---|---|---|---|---|
| 170 | 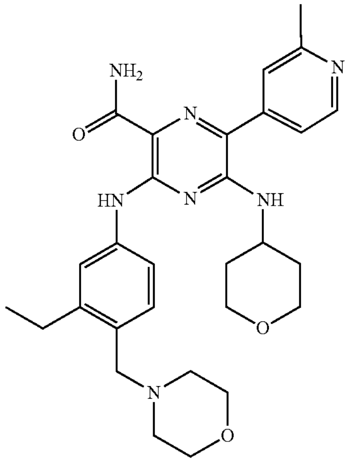 [SMILES: CCc1cc(Nc2nc(NC3CCOCC3)c(-c3ccnc(C)c3)nc2C(N)=O)ccc1CN1CCOCC1] | A | 532 | — |
| 171 | 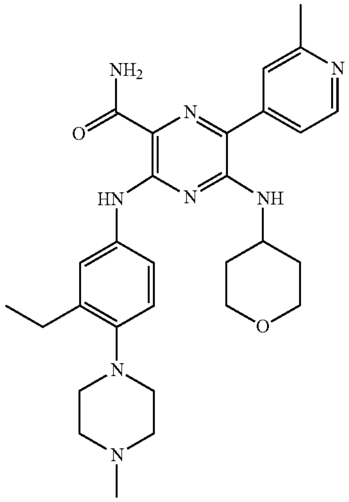 [SMILES: CCc1cc(Nc2nc(NC3CCOCC3)c(-c3ccnc(C)c3)nc2C(N)=O)ccc1N1CCN(C)CC1] | A | 531 | — |
| 172 | 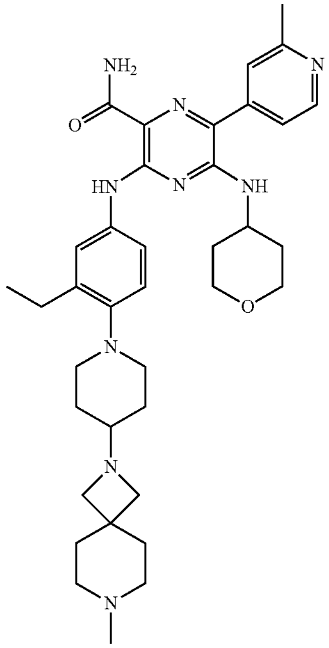 [SMILES: CCc1cc(Nc2nc(NC3CCOCC3)c(-c3ccnc(C)c3)nc2C(N)=O)ccc1N1CCC(N2CC3(CCN(C)CC3)C2)CC1] | A | 654 | — |

TABLE 2-continued
| | | | | |
|---|---|---|---|---|
| 173 | 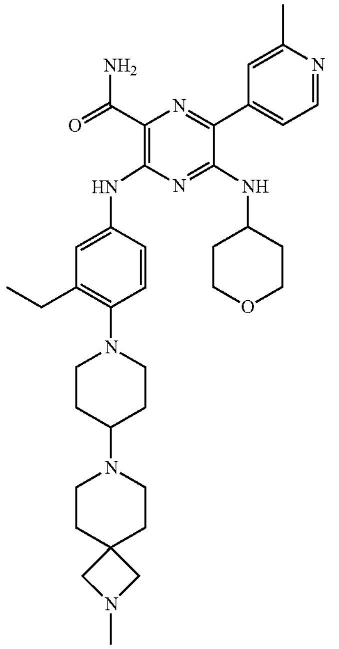 [SMILES: CCc1cc(Nc2nc(NC3CCOCC3)c(-c3ccnc(C)c3)nc2C(N)=O)ccc1N1CCC(N2CCC3(CC2)CN(C)C3)CC1] | A | 654 | — |
| 174 | 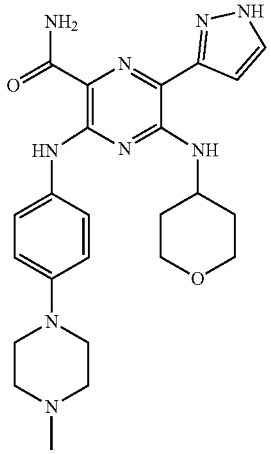 [SMILES: CN1CCN(c2ccc(Nc3nc(NC4CCOCC4)c(-c4cc[nH]n4)nc3C(N)=O)cc2)CC1] | A | 478 | 1.436 |
| 175 | 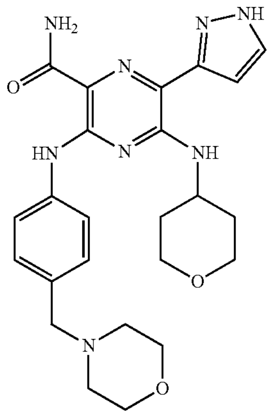 [SMILES: NC(=O)c1nc(-c2cc[nH]n2)c(NC2CCOCC2)nc1Nc1ccc(CN2CCOCC2)cc1] | A | 479 | — |

TABLE 2-continued
| | | | | |
|---|---|---|---|---|
| 176 | 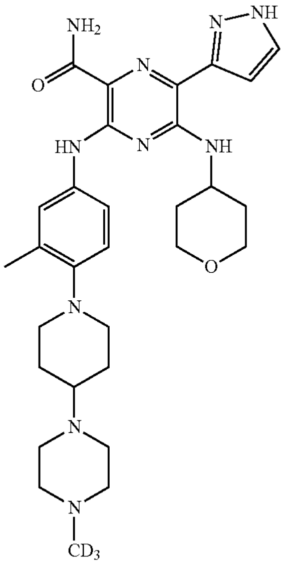 [SMILES: [2H]C([2H])([2H])N1CCN(C2CCN(c3ccc(Nc4nc(NC5CCOCC5)c(-c5cc[nH]n5)nc4C(N)=O)cc3C)CC2)CC1] | A | 578 | — |
| 177 | 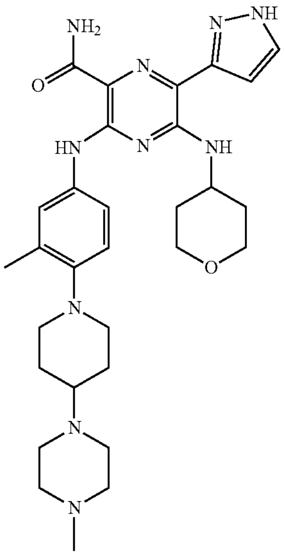 [SMILES: Cc1cc(Nc2nc(NC3CCOCC3)c(-c3cc[nH]n3)nc2C(N)=O)ccc1N1CCC(N2CCN(C)CC2)CC1] | A | 575 | 1.439 |

TABLE 2-continued
| | | | | |
|---|---|---|---|---|
| 178 | 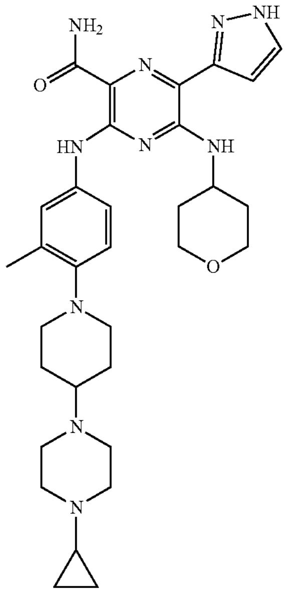 [SMILES: Cc1cc(Nc2nc(NC3CCOCC3)c(-c3cc[nH]n3)nc2C(N)=O)ccc1N1CCC(N2CCN(C3CC3)CC2)CC1] | A | 601 | — |
| 179 | 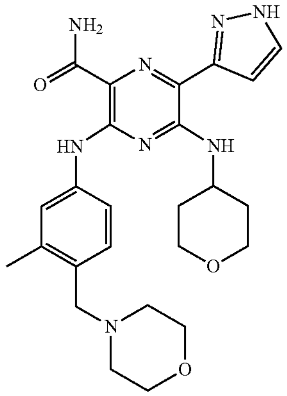 [SMILES: Cc1cc(Nc2nc(NC3CCOCC3)c(-c3cc[nH]n3)nc2C(N)=O)ccc1CN1CCOCC1] | A | 493 | — |
| 180 | 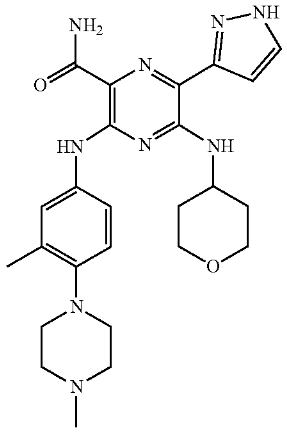 [SMILES: Cc1cc(Nc2nc(NC3CCOCC3)c(-c3cc[nH]n3)nc2C(N)=O)ccc1N1CCN(C)CC1] | A | 492 | — |

TABLE 2-continued
| | | | | |
|---|---|---|---|---|
| 181 | 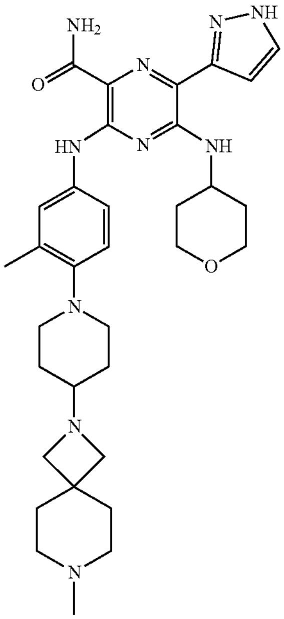 [SMILES: Cc1cc(Nc2nc(NC3CCOCC3)c(-c3cc[nH]n3)nc2C(N)=O)ccc1N1CCC(N2CC3(CCN(C)CC3)C2)CC1] | A | 615 | — |
| 182 | 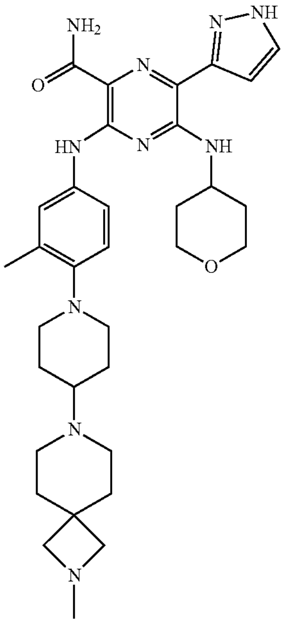 [SMILES: Cc1cc(Nc2nc(NC3CCOCC3)c(-c3cc[nH]n3)nc2C(N)=O)ccc1N1CCC(N2CCC3(CC2)CN(C)C3)CC1] | A | 615 | — |

TABLE 2-continued
| | | | | |
|---|---|---|---|---|
| 183 | 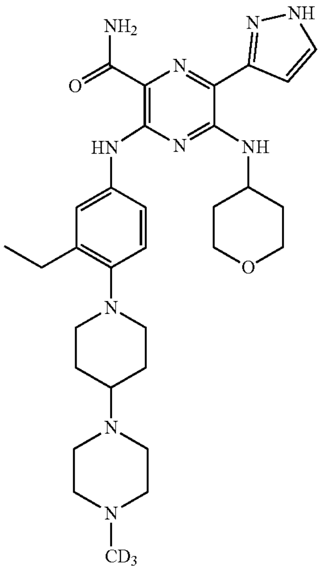 [SMILES: [2H]C([2H])([2H])N1CCN(C2CCN(c3ccc(Nc4nc(NC5CCOCC5)c(-c5cc[nH]n5)nc4C(N)=O)cc3CC)CC2)CC1] | A | 592 | — |
| 184 | 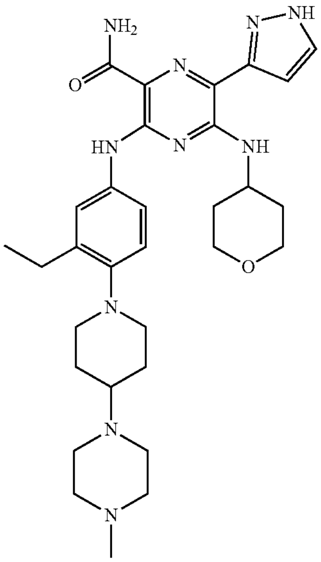 [SMILES: CCc1cc(Nc2nc(NC3CCOCC3)c(-c3cc[nH]n3)nc2C(N)=O)ccc1N1CCC(N2CCN(C)CC2)CC1] | A | 589 | 1.398 |

TABLE 2-continued
| | | | | |
|---|---|---|---|---|
| 185 | 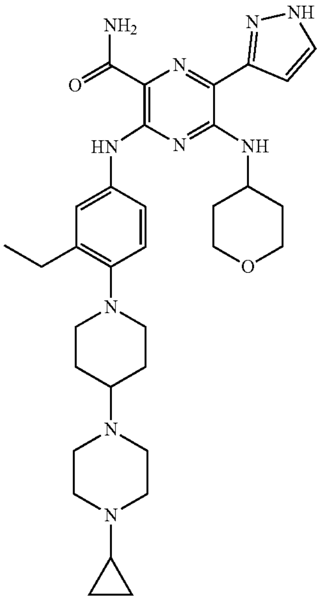 [SMILES: CCc1cc(Nc2nc(NC3CCOCC3)c(-c3cc[nH]n3)nc2C(N)=O)ccc1N1CCC(N2CCN(C3CC3)CC2)CC1] | A | 615 | — |
| 186 | 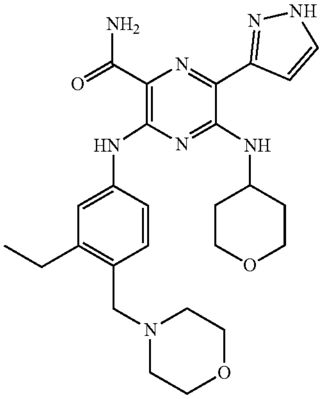 [SMILES: CCc1cc(Nc2nc(NC3CCOCC3)c(-c3cc[nH]n3)nc2C(N)=O)ccc1CN1CCOCC1] | A | 507 | — |
| 187 | 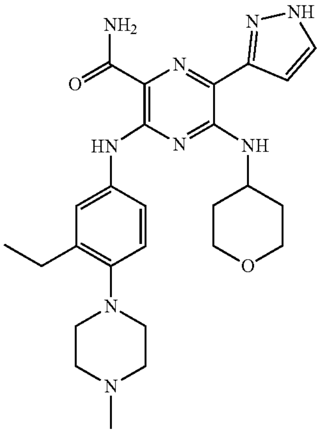 [SMILES: CCc1cc(Nc2nc(NC3CCOCC3)c(-c3cc[nH]n3)nc2C(N)=O)ccc1N1CCN(C)CC1] | A | 506 | — |

TABLE 2-continued
| | | | | |
|---|---|---|---|---|
| 188 | 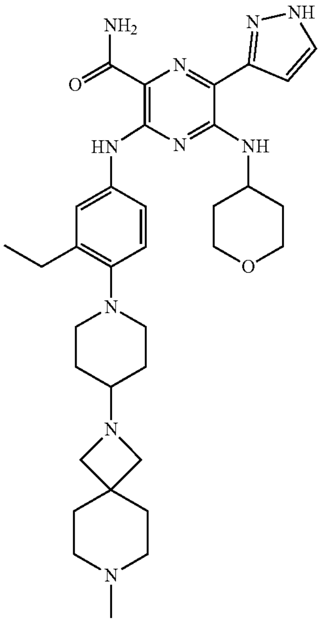 [SMILES: CCc1cc(Nc2nc(NC3CCOCC3)c(-c3cc[nH]n3)nc2C(N)=O)ccc1N1CCC(N2CC3(CCN(C)CC3)C2)CC1] | A | 629 | — |
| 189 | 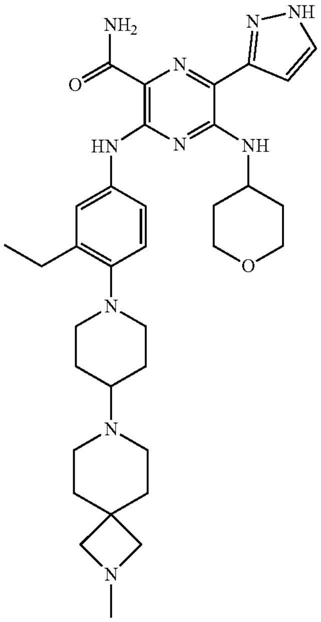 [SMILES: CCc1cc(Nc2nc(NC3CCOCC3)c(-c3cc[nH]n3)nc2C(N)=O)ccc1N1CCC(N2CCC3(CC2)CN(C)C3)CC1] | A | 629 | — |

TABLE 2-continued
| | | | | |
|---|---|---|---|---|
| 190 | 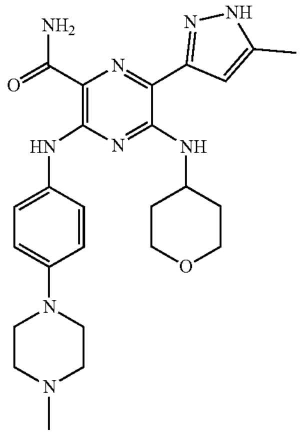 [SMILES: Cc1cc(-c2nc(C(N)=O)c(Nc3ccc(N4CCN(C)CC4)cc3)nc2NC2CCOCC2)n[nH]1] | A | 492 | — |
| 191 | 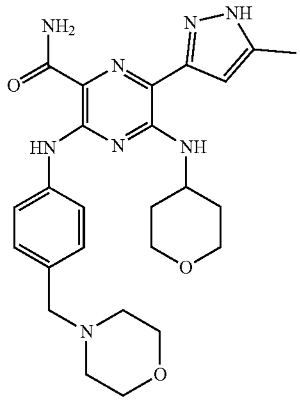 [SMILES: Cc1cc(-c2nc(C(N)=O)c(Nc3ccc(CN4CCOCC4)cc3)nc2NC2CCOCC2)n[nH]1] | A | 493 | — |
| 192 | 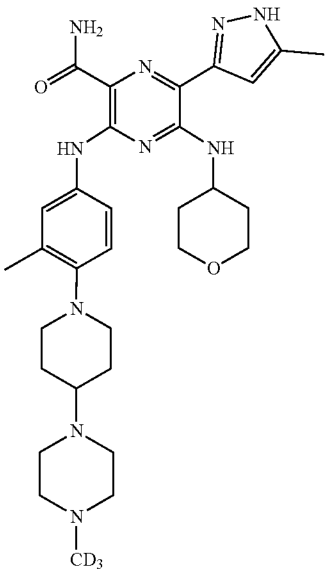 | A | 592 | — |

TABLE 2-continued
| | | | | |
|---|---|---|---|---|
| 193 | 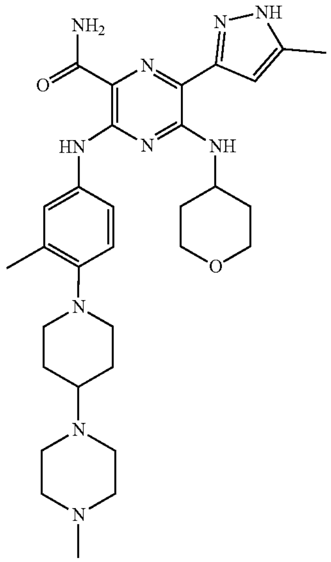 | A | 589 | — |
| 194 | 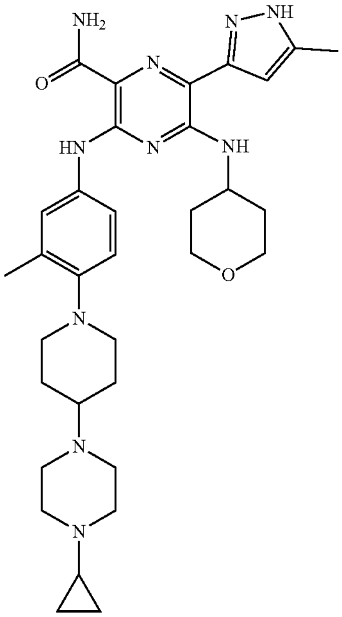 | A | 615 | — |
| 195 | 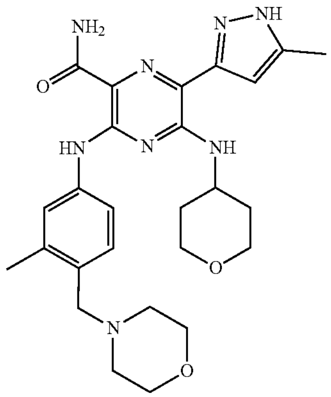 | A | 507 | — |

TABLE 2-continued
| | | | | |
|---|---|---|---|---|
| 196 | 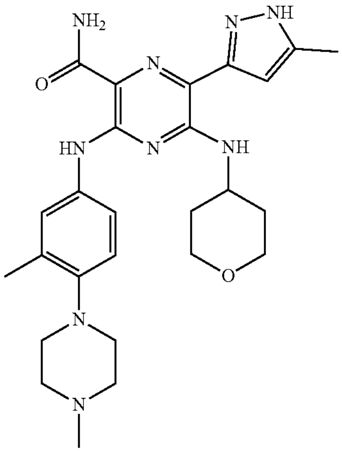 | A | 506 | — |
| 197 | 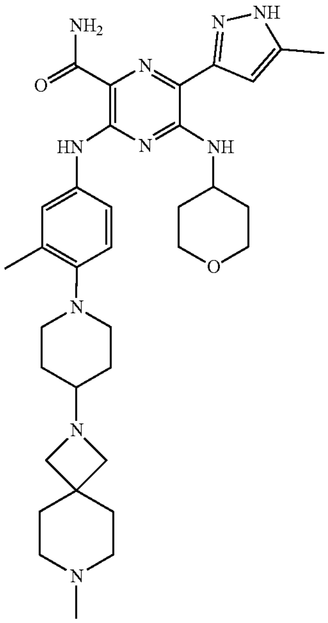 | A | 629 | — |

TABLE 2-continued
| | | | | |
|---|---|---|---|---|
| 198 | 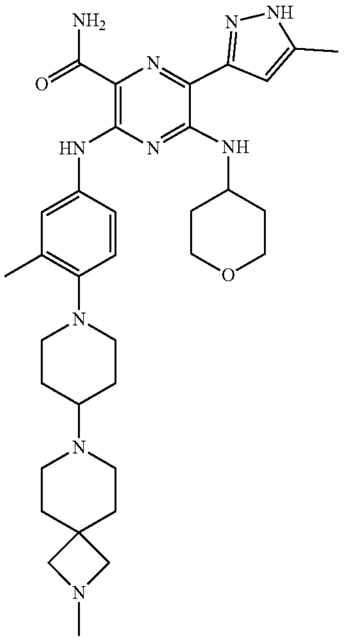 | A | 629 | — |
| 199 | 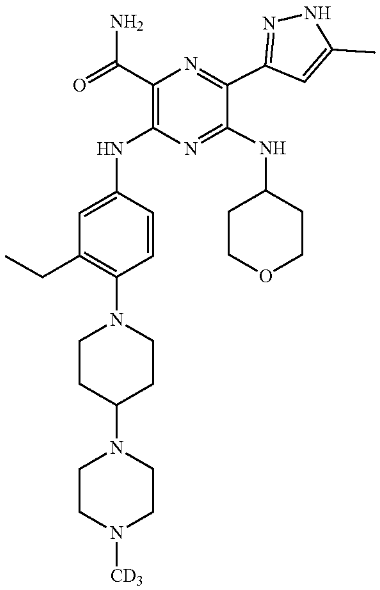 [SMILES: [2H]C([2H])([2H])N1CCN(C2CCN(c3ccc(Nc4nc(NC5CCOCC5)c(-c5cc(C)[nH]n5)nc4C(N)=O)cc3CC)CC2)CC1] | A | 606 | — |

TABLE 2-continued
| | | | | |
|---|---|---|---|---|
| 200 | 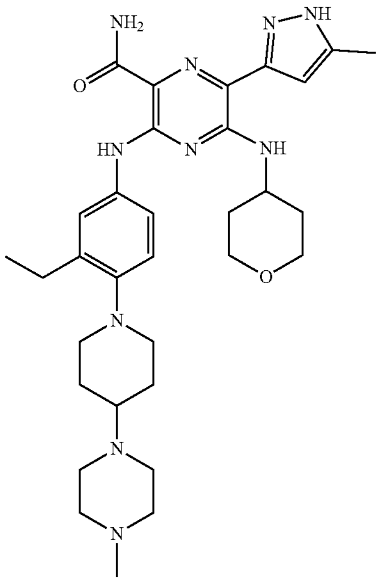 [SMILES: CCc1cc(Nc2nc(NC3CCOCC3)c(-c3cc(C)[nH]n3)nc2C(N)=O)ccc1N1CCC(N2CCN(C)CC2)CC1] | A | 603 | — |
| 201 | 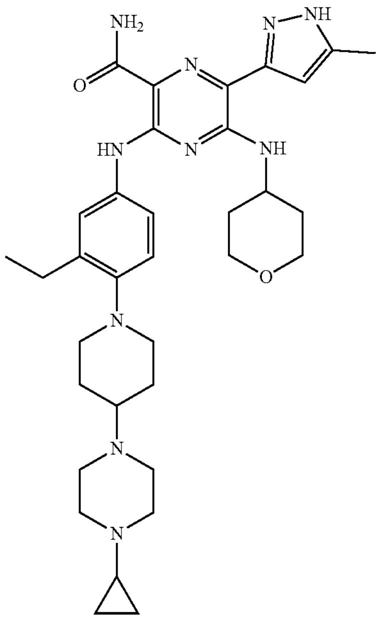 [SMILES: CCc1cc(Nc2nc(NC3CCOCC3)c(-c3cc(C)[nH]n3)nc2C(N)=O)ccc1N1CCC(N2CCN(C3CC3)CC2)CC1] | A | 629 | — |
| 202 | 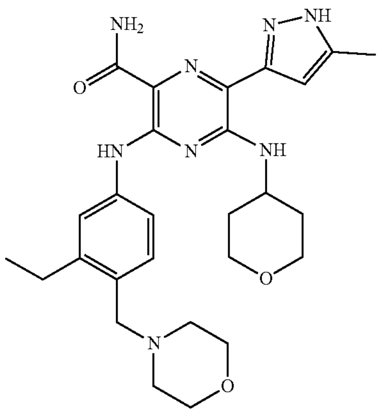 [SMILES: CCc1cc(Nc2nc(NC3CCOCC3)c(-c3cc(C)[nH]n3)nc2C(N)=O)ccc1CN1CCOCC1] | A | 521 | — |

TABLE 2-continued
| | | | | |
|---|---|---|---|---|
| 203 | 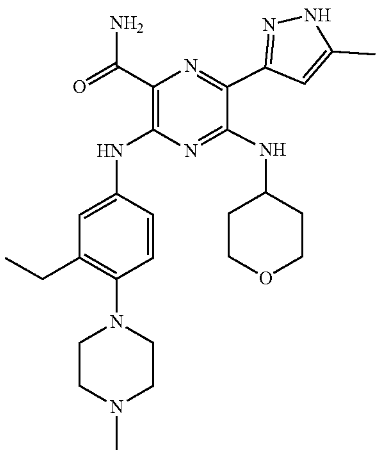 [SMILES: CCc1cc(Nc2nc(NC3CCOCC3)c(-c3cc(C)[nH]n3)nc2C(N)=O)ccc1N1CCN(C)CC1] | A | 520 | — |
| 204 | 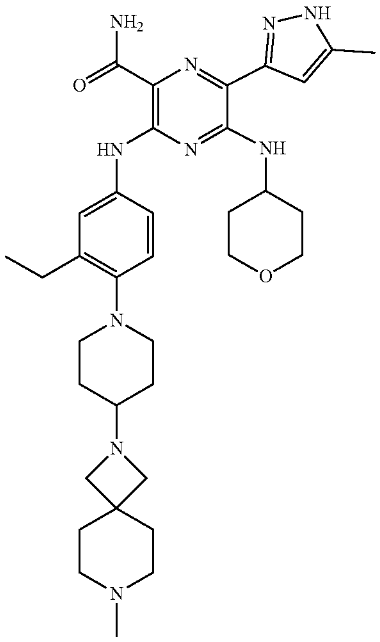 [SMILES: CCc1cc(Nc2nc(NC3CCOCC3)c(-c3cc(C)[nH]n3)nc2C(N)=O)ccc1N1CCC(N2CC3(CCN(C)CC3)C2)CC1] | A | 643 | — |

TABLE 2-continued
| | | | | |
|---|---|---|---|---|
| 205 | 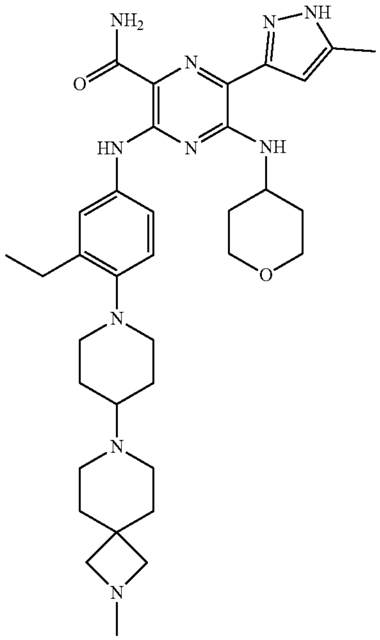 [SMILES: CCc1cc(Nc2nc(NC3CCOCC3)c(-c3cc(C)[nH]n3)nc2C(N)=O)ccc1N1CCC(N2CCC3(CC2)CN(C)C3)CC1] | A | 643 | — |
| 206 | 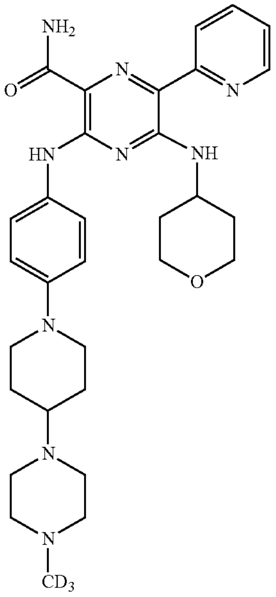 [SMILES: [2H]C([2H])([2H])N1CCN(C2CCN(c3ccc(Nc4nc(NC5CCOCC5)c(-c5ccccn5)nc4C(N)=O)cc3)CC2)CC1] | A | 575 | — |

TABLE 2-continued
| | | | | |
|---|---|---|---|---|
| 207 | 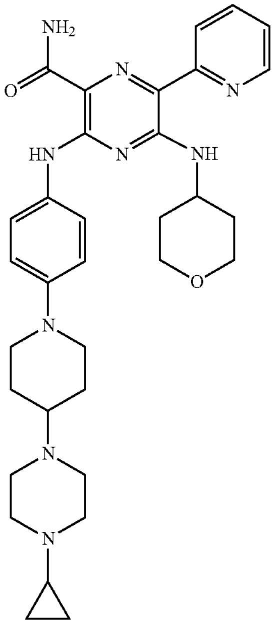 [SMILES: NC(=O)c1nc(-c2ccccn2)c(NC2CCOCC2)nc1Nc1ccc(N2CCC(N3CCN(C4CC4)CC3)CC2)cc1] | A | 598 | — |
| 208 | 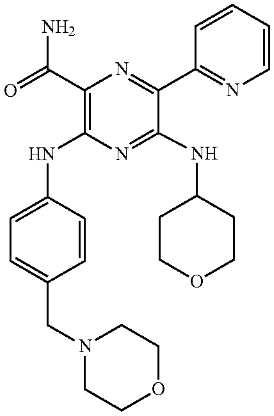 [SMILES: NC(=O)c1nc(-c2ccccn2)c(NC2CCOCC2)nc1Nc1ccc(CN2CCOCC2)cc1] | A | 490 | — |
| 209 | 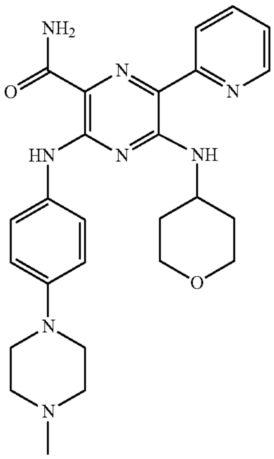 [SMILES: CN1CCN(c2ccc(Nc3nc(NC4CCOCC4)c(-c4ccccn4)nc3C(N)=O)cc2)CC1] | A | 489 | — |

TABLE 2-continued
| | | | | |
|---|---|---|---|---|
| 210 | 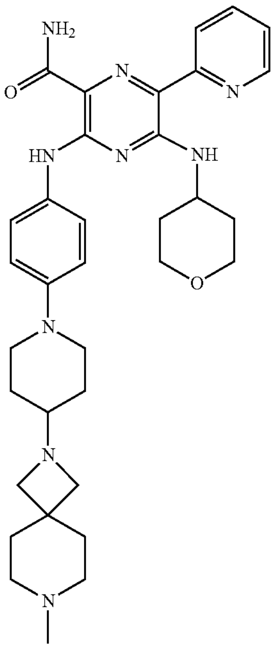 [SMILES: CN1CCC2(CC1)CN(C1CCN(c3ccc(Nc4nc(NC5CCOCC5)c(-c5ccccn5)nc4C(N)=O)cc3)CC1)C2] | A | 612 | — |
| 211 | 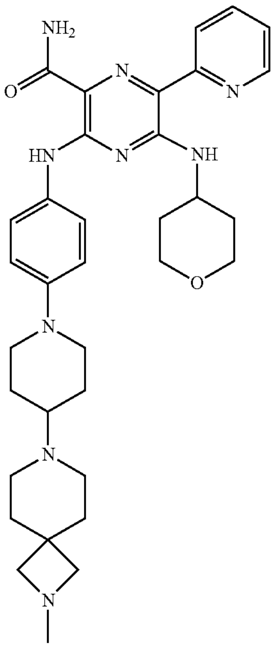 [SMILES: CN1CC2(CCN(C3CCN(c4ccc(Nc5nc(NC6CCOCC6)c(-c6ccccn6)nc5C(N)=O)cc4)CC3)CC2)C1] | A | 612 | — |

TABLE 2-continued
| | | | | |
|---|---|---|---|---|
| 212 | 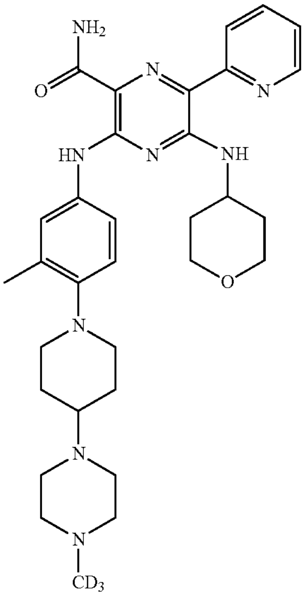 [SMILES: [2H]C([2H])([2H])N1CCN(C2CCN(c3ccc(Nc4nc(NC5CCOCC5)c(-c5ccccn5)nc4C(N)=O)cc3C)CC2)CC1] | A | 589 | — |
| 213 | 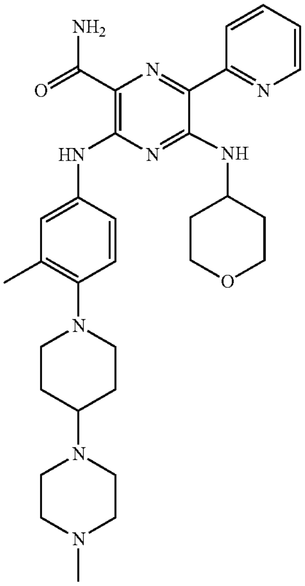 [SMILES: Cc1cc(Nc2nc(NC3CCOCC3)c(-c3ccccn3)nc2C(N)=O)ccc1N1CCC(N2CCN(C)CC2)CC1] | A | 586 | 1.580 |

TABLE 2-continued
| | | | | |
|---|---|---|---|---|
| 214 | 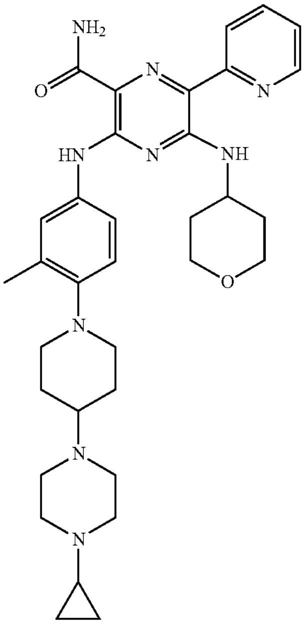 [SMILES: Cc1cc(Nc2nc(NC3CCOCC3)c(-c3ccccn3)nc2C(N)=O)ccc1N1CCC(N2CCN(C3CC3)CC2)CC1] | A | 612 | — |
| 215 | 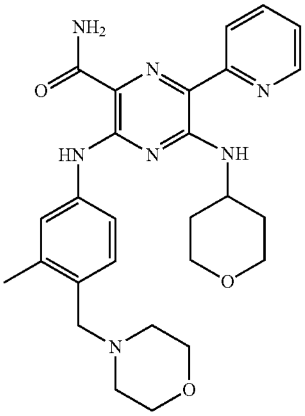 [SMILES: Cc1cc(Nc2nc(NC3CCOCC3)c(-c3ccccn3)nc2C(N)=O)ccc1CN1CCOCC1] | A | 504 | — |
| 216 | 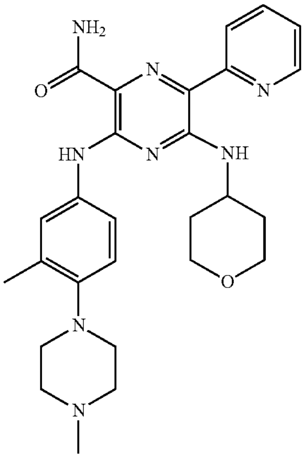 [SMILES: Cc1cc(Nc2nc(NC3CCOCC3)c(-c3ccccn3)nc2C(N)=O)ccc1N1CCN(C)CC1] | A | 503 | — |

TABLE 2-continued
| | | | | |
|---|---|---|---|---|
| 217 | 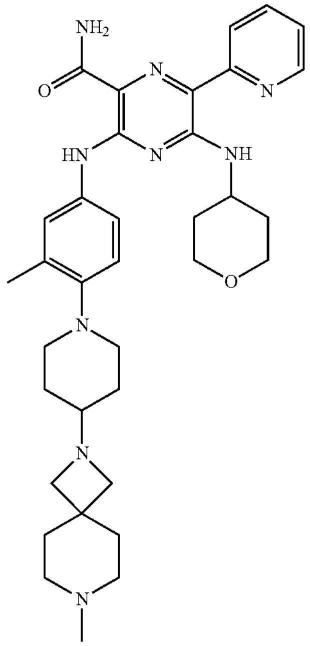 [SMILES: Cc1cc(Nc2nc(NC3CCOCC3)c(-c3ccccn3)nc2C(N)=O)ccc1N1CCC(N2CC3(CCN(C)CC3)C2)CC1] | A | 626 | — |
| 218 | 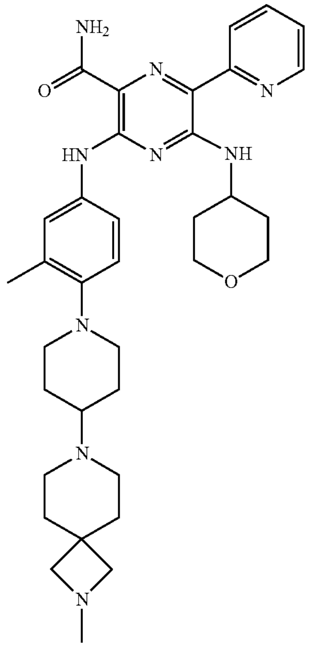 [SMILES: Cc1cc(Nc2nc(NC3CCOCC3)c(-c3ccccn3)nc2C(N)=O)ccc1N1CCC(N2CCC3(CC2)CN(C)C3)CC1] | A | 626 | — |

TABLE 2-continued
| | | | | |
|---|---|---|---|---|
| 219 | 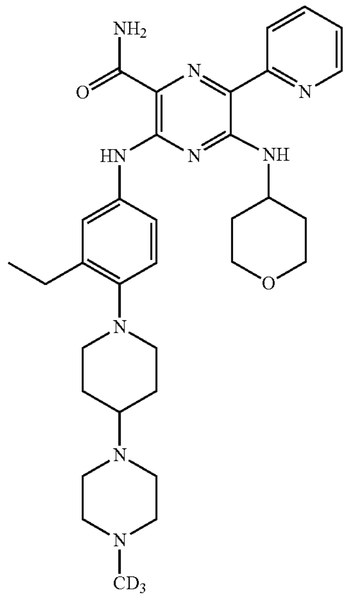 [SMILES: [2H]C([2H])([2H])N1CCN(C2CCN(c3ccc(Nc4nc(NC5CCOCC5)c(-c5ccccn5)nc4C(N)=O)cc3CC)CC2)CC1] | A | 603 | — |
| 220 | 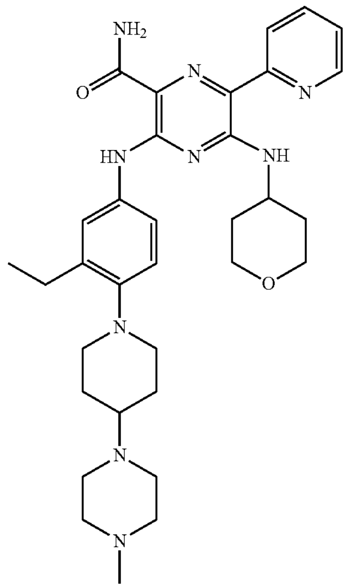 [SMILES: CCc1cc(Nc2nc(NC3CCOCC3)c(-c3ccccn3)nc2C(N)=O)ccc1N1CCC(N2CCN(C)CC2)CC1] | A | 600 | — |

TABLE 2-continued
| | | | | |
|---|---|---|---|---|
| 221 | 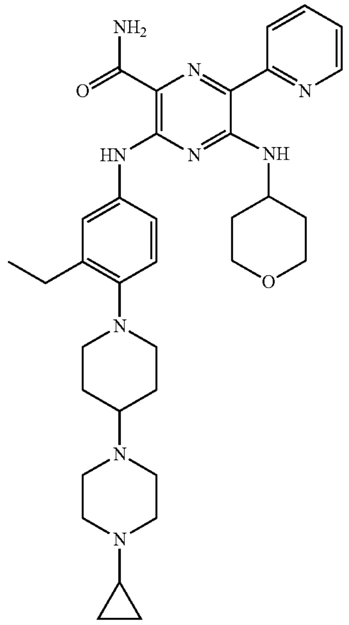 [SMILES: CCc1cc(Nc2nc(NC3CCOCC3)c(-c3ccccn3)nc2C(N)=O)ccc1N1CCC(N2CCN(C3CC3)CC2)CC1] | | | |
| 222 | 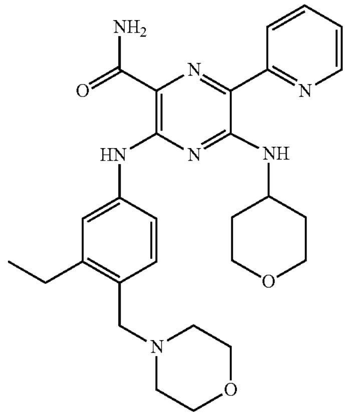 [SMILES: CCc1cc(Nc2nc(NC3CCOCC3)c(-c3ccccn3)nc2C(N)=O)ccc1CN1CCOCC1] | A | 518 | — |
| 223 | 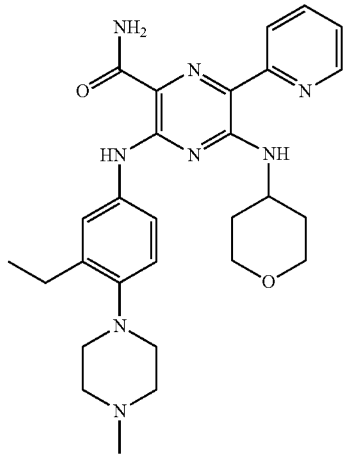 [SMILES: CCc1cc(Nc2nc(NC3CCOCC3)c(-c3ccccn3)nc2C(N)=O)ccc1N1CCN(C)CC1] | A | 517 | — |

TABLE 2-continued
| | | | | |
|---|---|---|---|---|
| 224 | 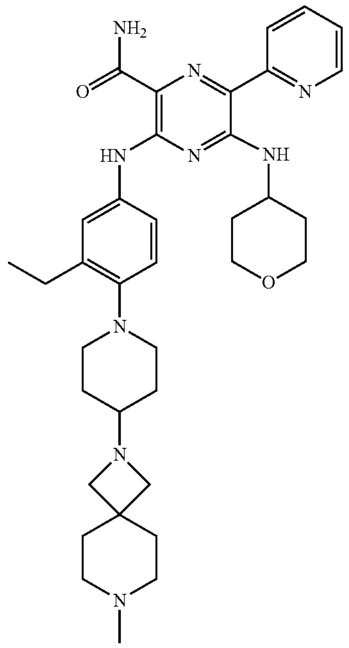 [SMILES: CCc1cc(Nc2nc(NC3CCOCC3)c(-c3ccccn3)nc2C(N)=O)ccc1N1CCC(N2CC3(CCN(C)CC3)C2)CC1] | A | 640 | — |
| 225 | 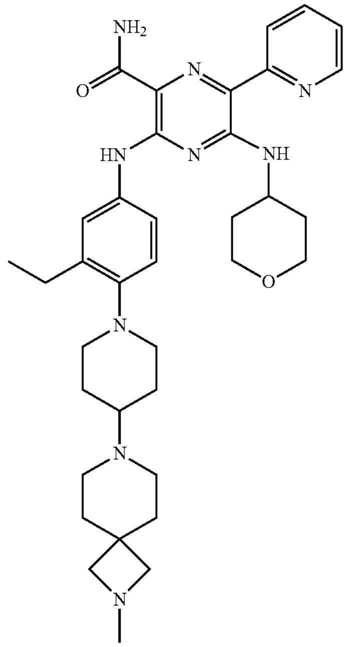 [SMILES: CCc1cc(Nc2nc(NC3CCOCC3)c(-c3ccccn3)nc2C(N)=O)ccc1N1CCC(N2CCC3(CC2)CN(C)C3)CC1] | A | 640 | — |

TABLE 2-continued
| | | | | |
|---|---|---|---|---|
| 226 | 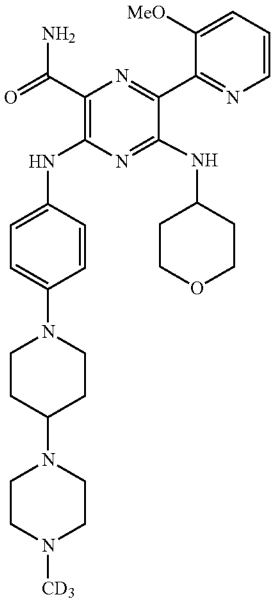 [SMILES: [2H]C([2H])([2H])N1CCN(C2CCN(c3ccc(Nc4nc(NC5CCOCC5)c(-c5ncccc5OC)nc4C(N)=O)cc3)CC2)CC1] | A | 605 | — |
| 227 | 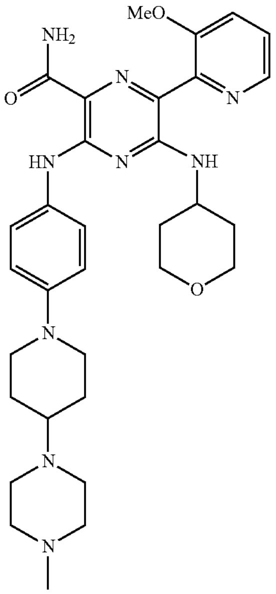 [SMILES: COc1cccnc1-c1nc(C(N)=O)c(Nc2ccc(N3CCC(N4CCN(C)CC4)CC3)cc2)nc1NC1CCOCC1] | A | 602 | — |

TABLE 2-continued
| | | | | |
|---|---|---|---|---|
| 228 | 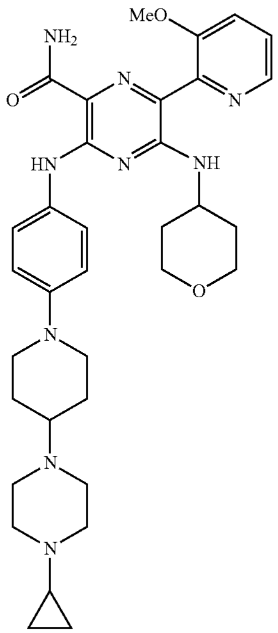 [SMILES: COc1cccnc1-c1nc(C(N)=O)c(Nc2ccc(N3CCC(N4CCN(C5CC5)CC4)CC3)cc2)nc1NC1CCOCC1] | A | 628 | — |
| 229 | 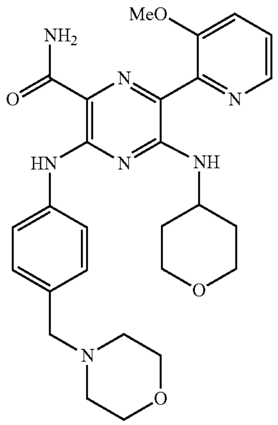 [SMILES: COc1cccnc1-c1nc(C(N)=O)c(Nc2ccc(CN3CCOCC3)cc2)nc1NC1CCOCC1] | A | 520 | — |
| 230 | 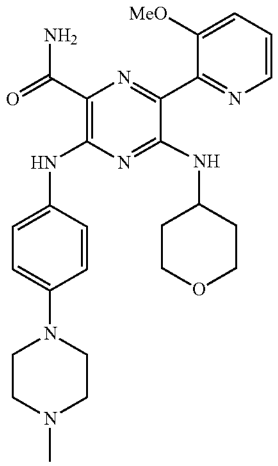 [SMILES: COc1cccnc1-c1nc(C(N)=O)c(Nc2ccc(N3CCN(C)CC3)cc2)nc1NC1CCOCC1] | A | 519 | — |

TABLE 2-continued
| | | | | |
|---|---|---|---|---|
| 231 | 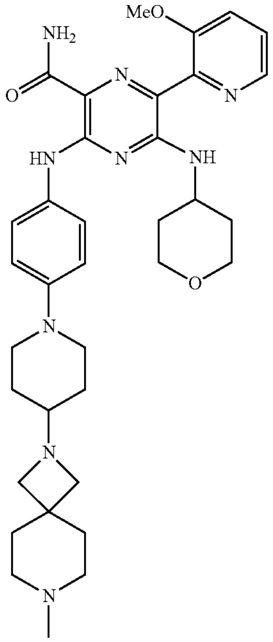 [SMILES: COc1cccnc1-c1nc(C(N)=O)c(Nc2ccc(N3CCC(N4CC5(CCN(C)CC5)C4)CC3)cc2)nc1NC1CCOCC1] | A | 642 | — |
| 232 | 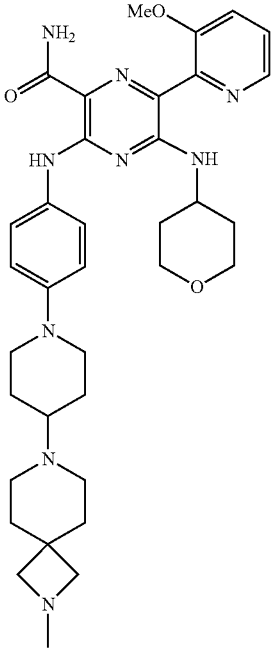 [SMILES: COc1cccnc1-c1nc(C(N)=O)c(Nc2ccc(N3CCC(N4CCC5(CC4)CN(C)C5)CC3)cc2)nc1NC1CCOCC1] | A | 642 | — |

TABLE 2-continued
| | | | | |
|---|---|---|---|---|
| 233 | 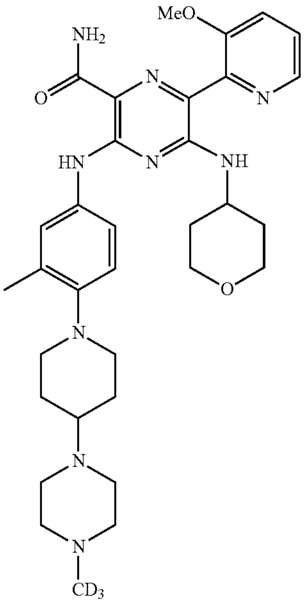 [SMILES: [2H]C([2H])([2H])N1CCN(C2CCN(c3ccc(Nc4nc(NC5CCOCC5)c(-c5ncccc5OC)nc4C(N)=O)cc3C)CC2)CC1] | A | 619 | — |
| 234 | 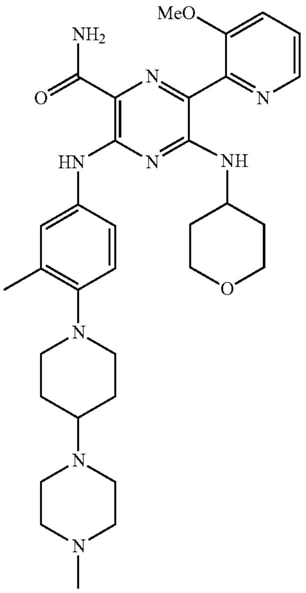 [SMILES: COc1cccnc1-c1nc(C(N)=O)c(Nc2ccc(N3CCC(N4CCN(C)CC4)CC3)c(C)c2)nc1NC1CCOCC1] | A | 616 | — |

TABLE 2-continued
| | | | | |
|---|---|---|---|---|
| 235 | 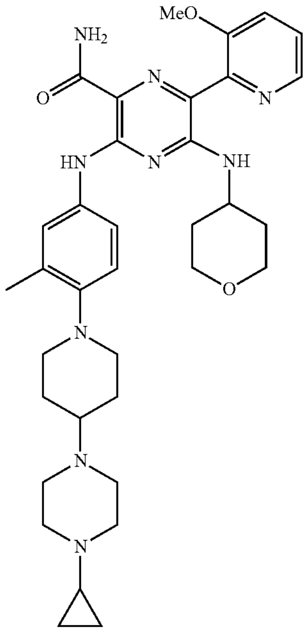 [SMILES: COc1cccnc1-c1nc(C(N)=O)c(Nc2ccc(N3CCC(N4CCN(C5CC5)CC4)CC3)c(C)c2)nc1NC1CCOCC1] | A | 642 | — |
| 236 | 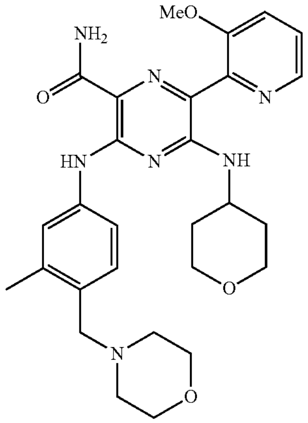 [SMILES: COc1cccnc1-c1nc(C(N)=O)c(Nc2ccc(CN3CCOCC3)c(C)c2)nc1NC1CCOCC1] | A | 534 | — |
| 237 | 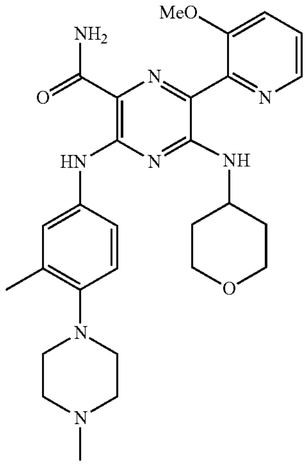 [SMILES: COc1cccnc1-c1nc(C(N)=O)c(Nc2ccc(N3CCN(C)CC3)c(C)c2)nc1NC1CCOCC1] | A | 533 | — |

TABLE 2-continued
| | | | | |
|---|---|---|---|---|
| 238 | 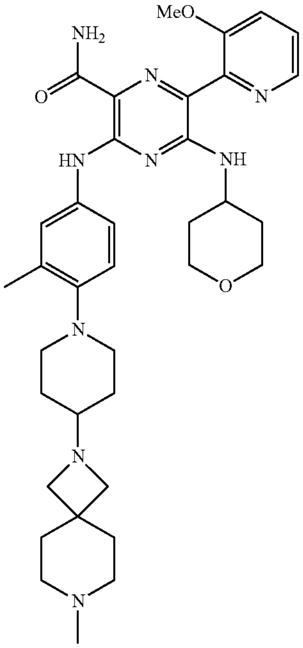 [SMILES: COc1cccnc1-c1nc(C(N)=O)c(Nc2ccc(N3CCC(N4CC5(CCN(C)CC5)C4)CC3)c(C)c2)nc1NC1CCOCC1] | A | 656 | — |
| 239 | 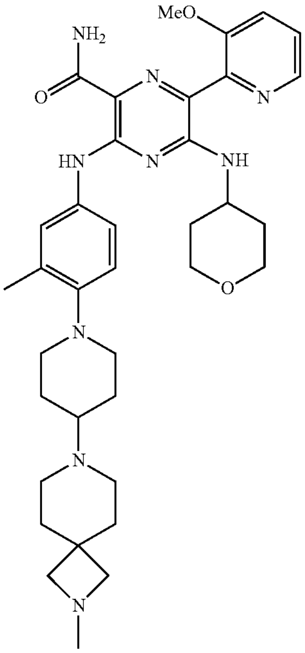 [SMILES: COc1cccnc1-c1nc(C(N)=O)c(Nc2ccc(N3CCC(N4CCC5(CC4)CN(C)C5)CC3)c(C)c2)nc1NC1CCOCC1] | A | 656 | — |

TABLE 2-continued
| | | | | |
|---|---|---|---|---|
| 240 | 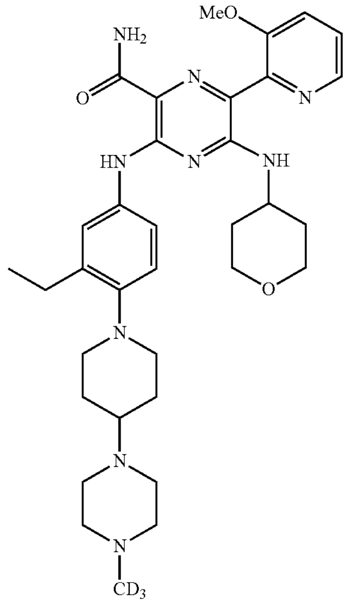 [SMILES: [2H]C([2H])([2H])N1CCN(C2CCN(c3ccc(Nc4nc(NC5CCOCC5)c(-c5ncccc5OC)nc4C(N)=O)cc3CC)CC2)CC1] | A | 633 | — |
| 241 | 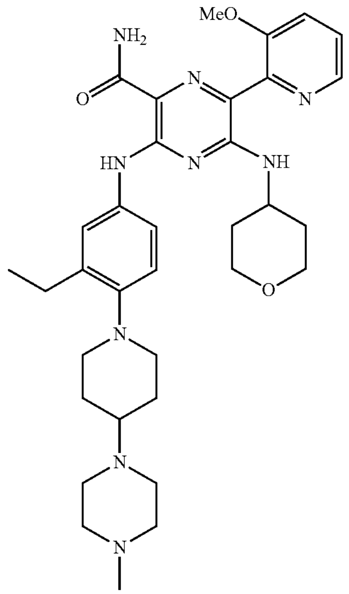 [SMILES: CCc1cc(Nc2nc(NC3CCOCC3)c(-c3ncccc3OC)nc2C(N)=O)ccc1N1CCC(N2CCN(C)CC2)CC1] | A | 630 | — |

TABLE 2-continued
| | | | | |
|---|---|---|---|---|
| 242 | 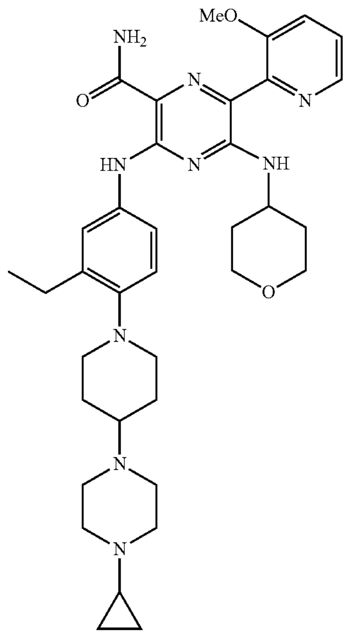 [SMILES: CCc1cc(Nc2nc(NC3CCOCC3)c(-c3ncccc3OC)nc2C(N)=O)ccc1N1CCC(N2CCN(C3CC3)CC2)CC1] | A | 656 | — |
| 243 | 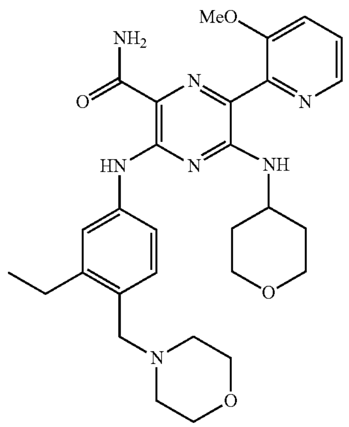 [SMILES: CCc1cc(Nc2nc(NC3CCOCC3)c(-c3ncccc3OC)nc2C(N)=O)ccc1CN1CCOCC1] | A | 548 | — |
| 244 | 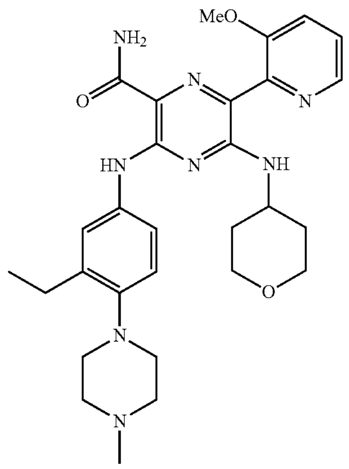 [SMILES: CCc1cc(Nc2nc(NC3CCOCC3)c(-c3ncccc3OC)nc2C(N)=O)ccc1N1CCN(C)CC1] | A | 547 | — |

TABLE 2-continued
| | | | | |
|---|---|---|---|---|
| 245 | 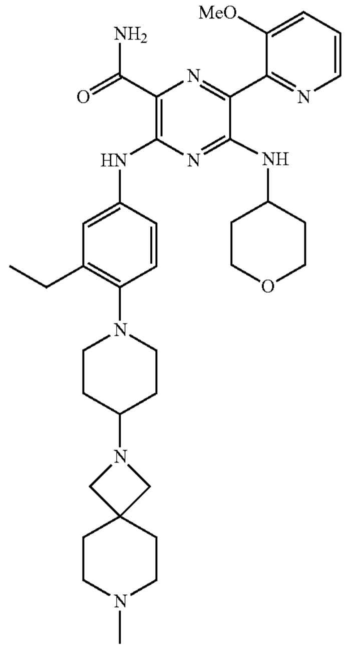 [SMILES: CCc1cc(Nc2nc(NC3CCOCC3)c(-c3ncccc3OC)nc2C(N)=O)ccc1N1CCC(N2CC3(CCN(C)CC3)C2)CC1] | A | 670 | — |
| 246 | 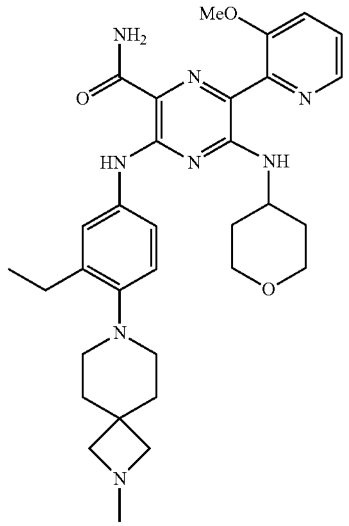 [SMILES: CCc1cc(Nc2nc(NC3CCOCC3)c(-c3ncccc3OC)nc2C(N)=O)ccc1N1CCC2(CC1)CN(C)C2] | A | 670 | — |

TABLE 2-continued
| | | | | |
|---|---|---|---|---|
| 247 | 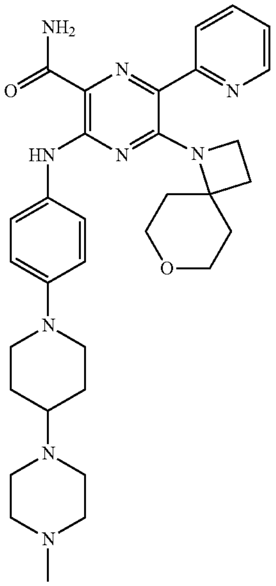 [SMILES: CN1CCN(C2CCN(c3ccc(Nc4nc(N5CCC56CCOCC6)c(-c5ccccn5)nc4C(N)=O)cc3)CC2)CC1] | A | 598 | — |
| 248 | 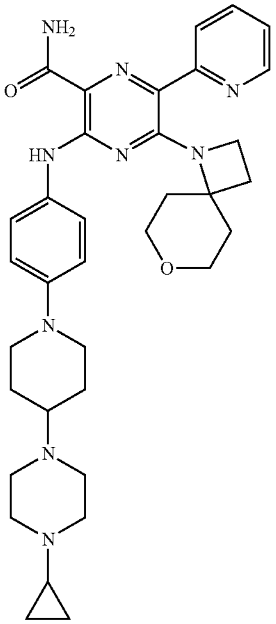 [SMILES: NC(=O)c1nc(-c2ccccn2)c(N2CCC23CCOCC3)nc1Nc1ccc(N2CCC(N3CCN(C4CC4)CC3)CC2)cc1] | A | 624 | — |

TABLE 2-continued
| | | | | |
|---|---|---|---|---|
| 249 | 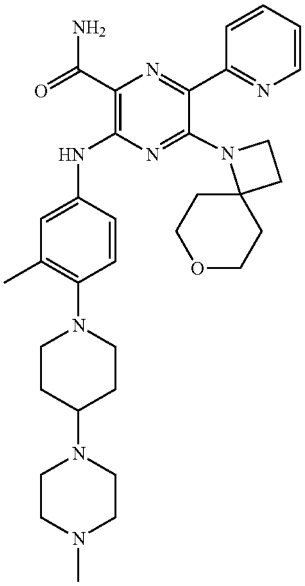 [SMILES: Cc1cc(Nc2nc(N3CCC34CCOCC4)c(-c3ccccn3)nc2C(N)=O)ccc1N1CCC(N2CCN(C)CC2)CC1] | A | 612 | — |
| 250 | 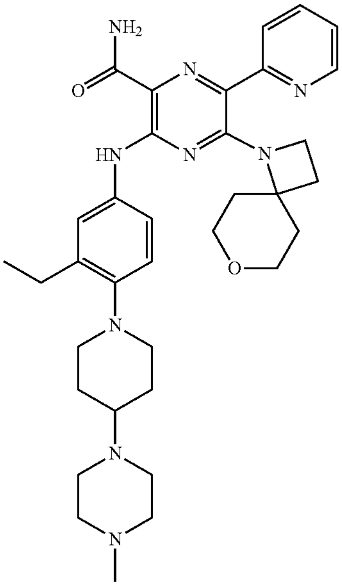 [SMILES: CCc1cc(Nc2nc(N3CCC34CCOCC4)c(-c3ccccn3)nc2C(N)=O)ccc1N1CCC(N2CCN(C)CC2)CC1] | A | 626 | — |
| 251 | 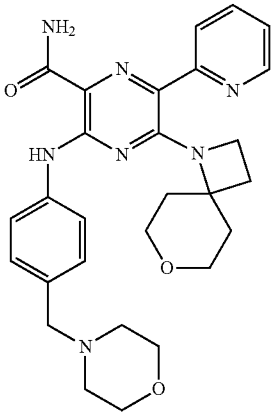 [SMILES: NC(=O)c1nc(-c2ccccn2)c(N2CCC23CCOCC3)nc1Nc1ccc(CN2CCOCC2)cc1] | A | 516 | — |

TABLE 2-continued
| | | | | |
|---|---|---|---|---|
| 252 | 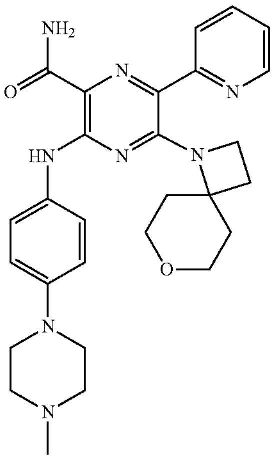 [SMILES: CN1CCN(c2ccc(Nc3nc(N4CCC45CCOCC5)c(-c4ccccn4)nc3C(N)=O)cc2)CC1] | A | 515 | — |
| 253 | 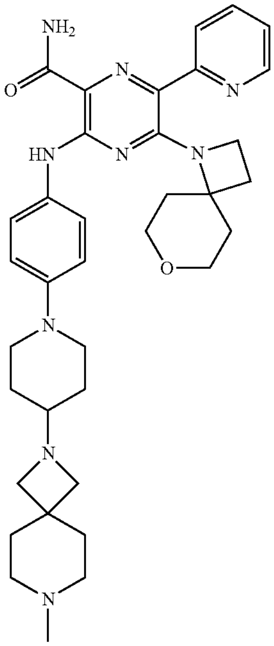 [SMILES: CN1CCC2(CC1)CN(C1CCN(c3ccc(Nc4nc(N5CCC56CCOCC6)c(-c5ccccn5)nc4C(N)=O)cc3)CC1)C2] | A | 638 | — |

TABLE 2-continued
| | | | | |
|---|---|---|---|---|
| 254 | 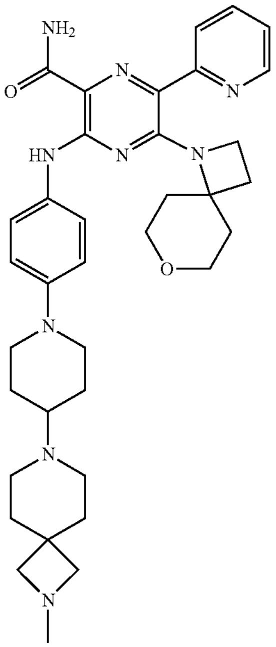 [SMILES: CN1CC2(CCN(C3CCN(c4ccc(Nc5nc(N6CCC67CCOCC7)c(-c6ccccn6)nc5C(N)=O)cc4)CC3)CC2)C1] | A | 638 | — |
| 255 | 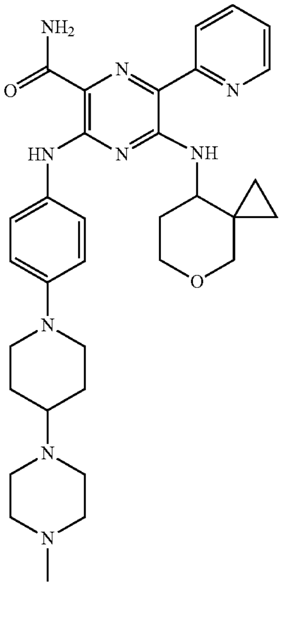 [SMILES: CN1CCN(C2CCN(c3ccc(Nc4nc(NC5CCOCC56CC6)c(-c5ccccn5)nc4C(N)=O)cc3)CC2)CC1] | A | 598 | — |

TABLE 2-continued
| | | | | |
|---|---|---|---|---|
| 256 | 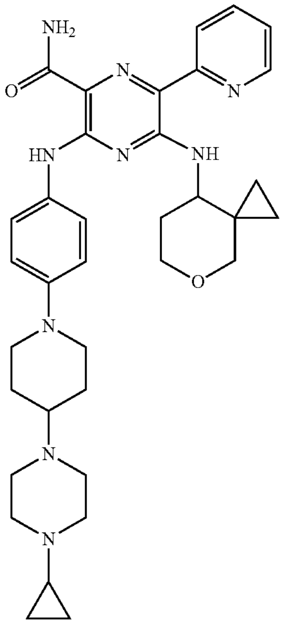 [SMILES: NC(=O)c1nc(-c2ccccn2)c(NC2CCOCC23CC3)nc1Nc1ccc(N2CCC(N3CCN(C4CC4)CC3)CC2)cc1] | A | 624 | — |
| 257 | 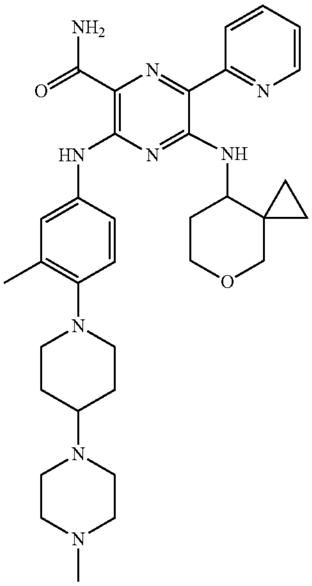 [SMILES: Cc1cc(Nc2nc(NC3CCOCC34CC4)c(-c3ccccn3)nc2C(N)=O)ccc1N1CCC(N2CCN(C)CC2)CC1] | A | 612 | — |

TABLE 2-continued
| | | | | |
|---|---|---|---|---|
| 258 | 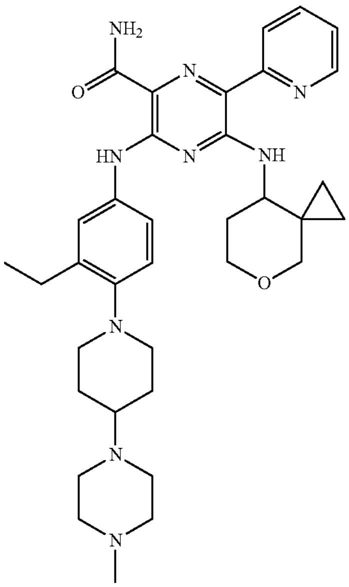 [SMILES: CCc1cc(Nc2nc(NC3CCOCC34CC4)c(-c3ccccn3)nc2C(N)=O)ccc1N1CCC(N2CCN(C)CC2)CC1] | A | 626 | — |
| 259 | 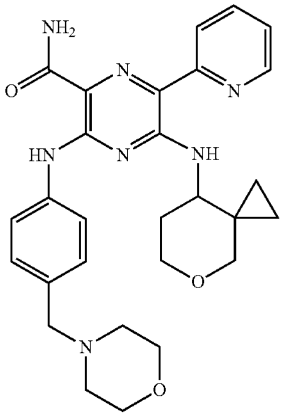 [SMILES: NC(=O)c1nc(-c2ccccn2)c(NC2CCOCC23CC3)nc1Nc1ccc(CN2CCOCC2)cc1] | A | 516 | — |
| 260 | 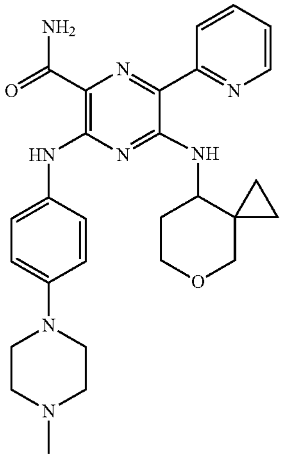 [SMILES: CN1CCN(c2ccc(Nc3nc(NC4CCOCC45CC5)c(-c4ccccn4)nc3C(N)=O)cc2)CC1] | A | 515 | — |

TABLE 2-continued
| | | | | |
|---|---|---|---|---|
| 261 | 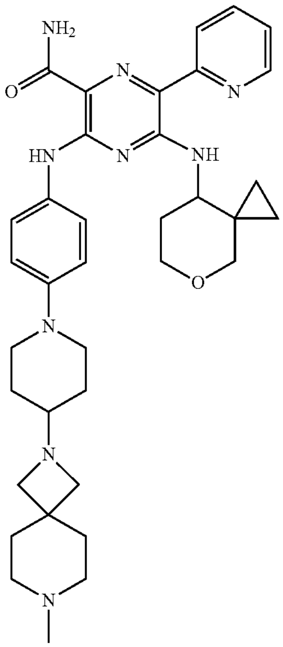 [SMILES: CN1CCC2(CC1)CN(C1CCN(c3ccc(Nc4nc(NC5CCOCC56CC6)c(-c5ccccn5)nc4C(N)=O)cc3)CC1)C2] | A | 638 | — |
| 262 | 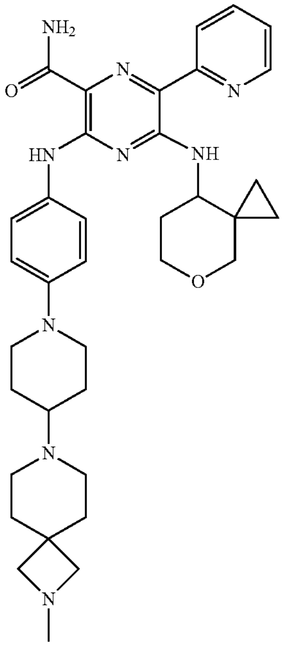 [SMILES: CN1CC2(CCN(C3CCN(c4ccc(Nc5nc(NC6CCOCC67CC7)c(-c6ccccn6)nc5C(N)=O)cc4)CC3)CC2)C1] | A | 638 | — |

TABLE 2-continued
| | | | | |
|---|---|---|---|---|
| 263 | 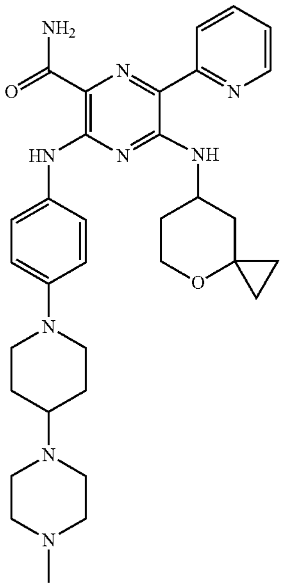 [SMILES: CN1CCN(C2CCN(c3ccc(Nc4nc(NC5CCOC6(CC6)C5)c(-c5ccccn5)nc4C(N)=O)cc3)CC2)CC1] | A | 598 | — |
| 264 | 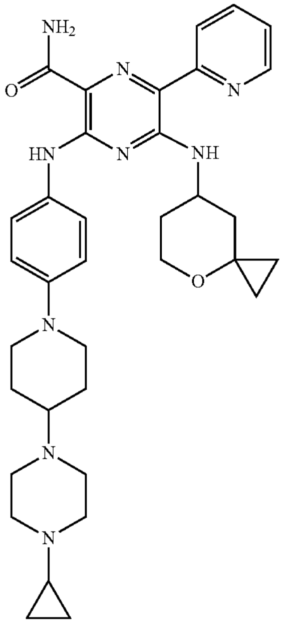 [SMILES: NC(=O)c1nc(-c2ccccn2)c(NC2CCOC3(CC3)C2)nc1Nc1ccc(N2CCC(N3CCN(C4CC4)CC3)CC2)cc1] | A | 624 | — |

TABLE 2-continued
| | | | | |
|---|---|---|---|---|
| 265 | 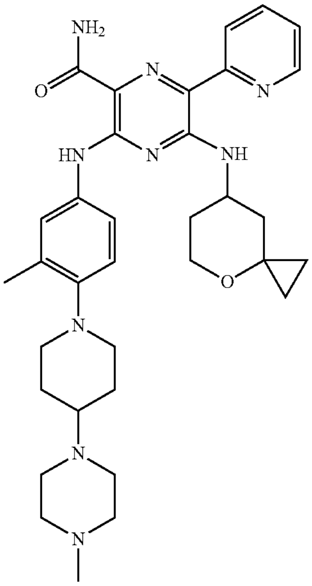 [SMILES: Cc1cc(Nc2nc(NC3CCOC4(CC4)C3)c(-c3ccccn3)nc2C(N)=O)ccc1N1CCC(N2CCN(C)CC2)CC1] | A | 612 | — |
| 266 | 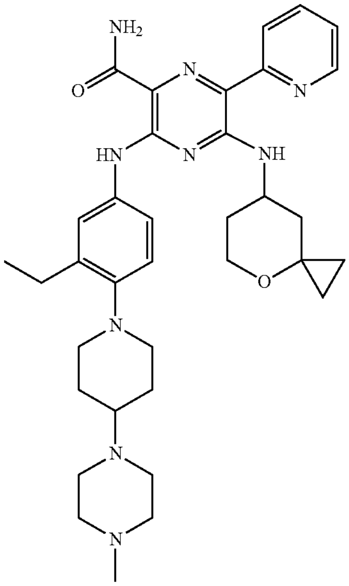 [SMILES: CCc1cc(Nc2nc(NC3CCOC4(CC4)C3)c(-c3ccccn3)nc2C(N)=O)ccc1N1CCC(N2CCN(C)CC2)CC1] | A | 626 | — |
| 267 | 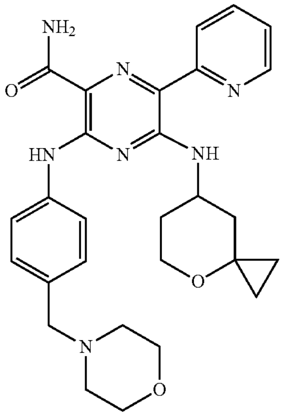 [SMILES: NC(=O)c1nc(-c2ccccn2)c(NC2CCOC3(CC3)C2)nc1Nc1ccc(CN2CCOCC2)cc1] | A | 516 | — |

TABLE 2-continued
| | | | | |
|---|---|---|---|---|
| 268 | 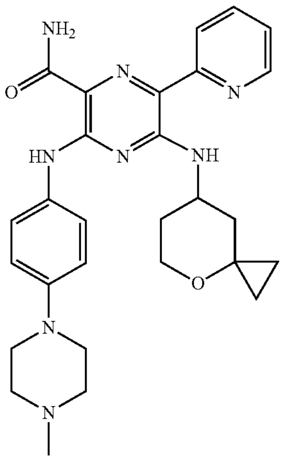 [SMILES: CN1CCN(c2ccc(Nc3nc(NC4CCOC5(CC5)C4)c(-c4ccccn4)nc3C(N)=O)cc2)CC1] | A | 515 | — |
| 269 | 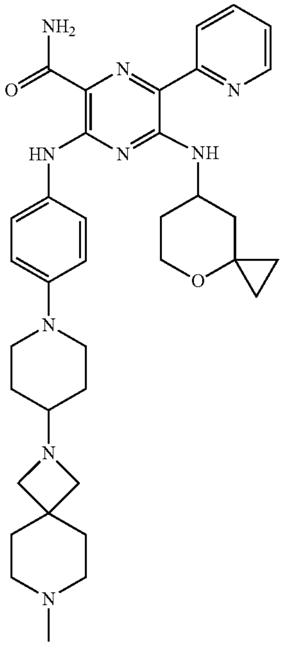 [SMILES: CN1CCC2(CC1)CN(C1CCN(c3ccc(Nc4nc(NC5CCOC6(CC6)C5)c(-c5ccccn5)nc4C(N)=O)cc3)CC1)C2] | A | 638 | — |

TABLE 2-continued
| | | | | |
|---|---|---|---|---|
| 270 | 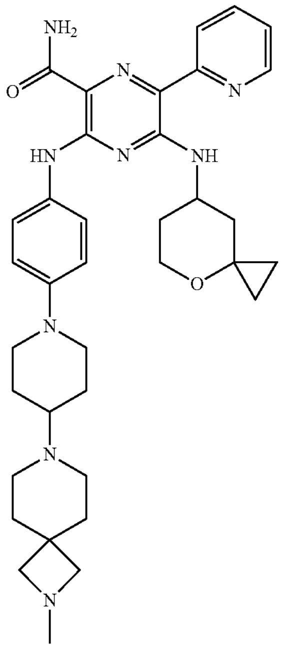 [SMILES: CN1CC2(CCN(C3CCN(c4ccc(Nc5nc(NC6CCOC7(CC7)C6)c(-c6ccccn6)nc5C(N)=O)cc4)CC3)CC2)C1] | A | 638 | — |
| 271 | 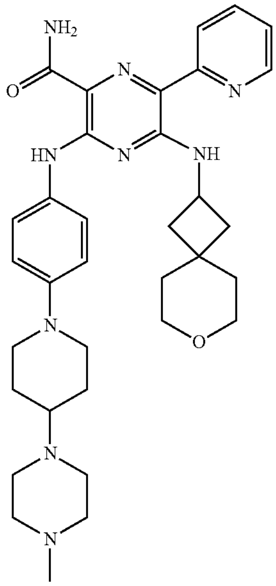 [SMILES: CN1CCN(C2CCN(c3ccc(Nc4nc(NC5CC6(CCOCC6)C5)c(-c5ccccn5)nc4C(N)=O)cc3)CC2)CC1] | A | 612 | — |

TABLE 2-continued
| | | | | |
|---|---|---|---|---|
| 272 | 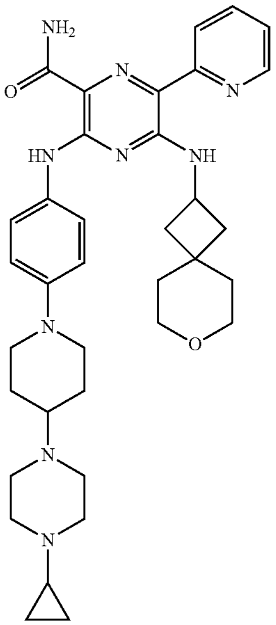 [SMILES: NC(=O)c1nc(-c2ccccn2)c(NC2CC3(CCOCC3)C2)nc1Nc1ccc(N2CCC(N3CCN(C4CC4)CC3)CC2)cc1] | A | 638 | — |
| 273 | 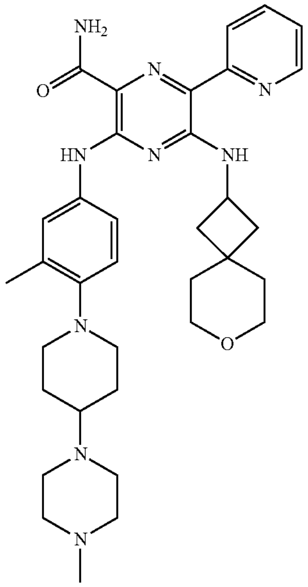 [SMILES: Cc1cc(Nc2nc(NC3CC4(CCOCC4)C3)c(-c3ccccn3)nc2C(N)=O)ccc1N1CCC(N2CCN(C)CC2)CC1] | A | 626 | — |

TABLE 2-continued
| | | | | |
|---|---|---|---|---|
| 274 | 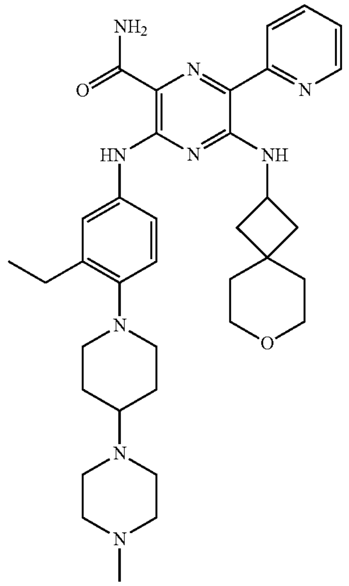 [SMILES: CCc1cc(Nc2nc(NC3CC4(CCOCC4)C3)c(-c3ccccn3)nc2C(N)=O)ccc1N1CCC(N2CCN(C)CC2)CC1] | A | 640 | — |
| 275 | 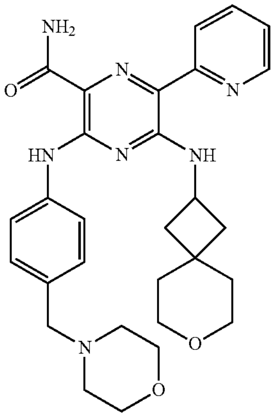 [SMILES: NC(=O)c1nc(-c2ccccn2)c(NC2CC3(CCOCC3)C2)nc1Nc1ccc(CN2CCOCC2)cc1] | A | 530 | — |
| 276 | 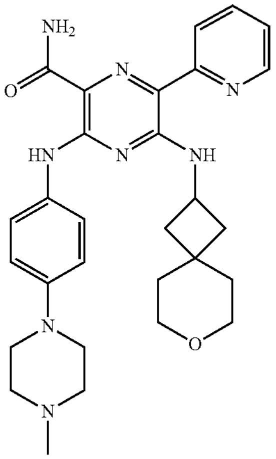 [SMILES: CN1CCN(c2ccc(Nc3nc(NC4CC5(CCOCC5)C4)c(-c4ccccn4)nc3C(N)=O)cc2)CC1] | A | 529 | — |

TABLE 2-continued
| | | | | |
|---|---|---|---|---|
| 277 | 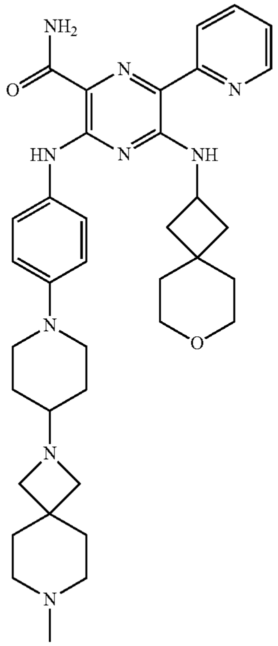 [SMILES: CN1CCC2(CC1)CN(C1CCN(c3ccc(Nc4nc(NC5CC6(CCOCC6)C5)c(-c5ccccn5)nc4C(N)=O)cc3)CC1)C2] | A | 652 | — |
| 278 | 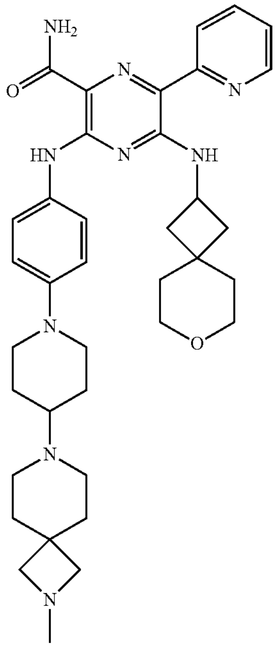 [SMILES: CN1CC2(CCN(C3CCN(c4ccc(Nc5nc(NC6CC7(CCOCC7)C6)c(-c6ccccn6)nc5C(N)=O)cc4)CC3)CC2)C1] | A | 652 | — |

TABLE 2-continued
| | | | | |
|---|---|---|---|---|
| 279 | 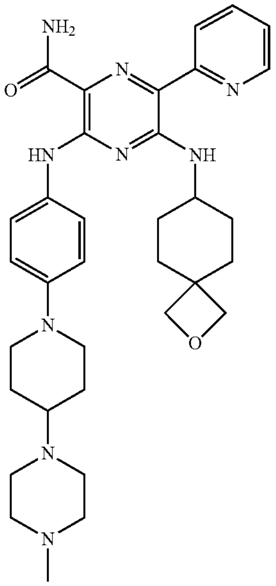 [SMILES: CN1CCN(C2CCN(c3ccc(Nc4nc(NC5CCC6(CC5)COC6)c(-c5ccccn5)nc4C(N)=O)cc3)CC2)CC1] | A | 612 | — |
| 280 | 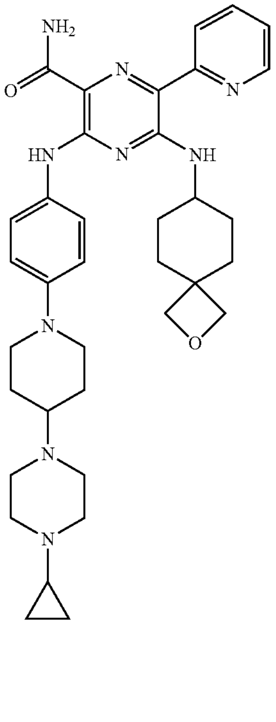 [SMILES: NC(=O)c1nc(-c2ccccn2)c(NC2CCC3(CC2)COC3)nc1Nc1ccc(N2CCC(N3CCN(C4CC4)CC3)CC2)cc1] | A | 638 | — |

TABLE 2-continued
| | | | | |
|---|---|---|---|---|
| 281 | 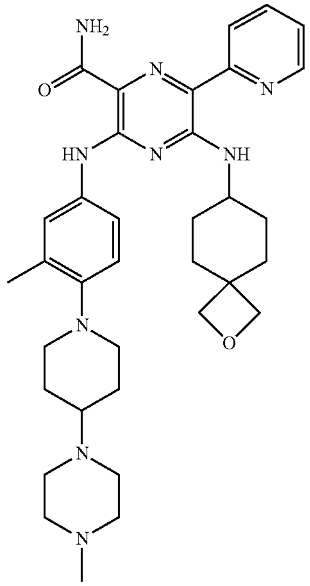 [SMILES: Cc1cc(Nc2nc(NC3CCC4(CC3)COC4)c(-c3ccccn3)nc2C(N)=O)ccc1N1CCC(N2CCN(C)CC2)CC1] | A | 626 | — |
| 282 | 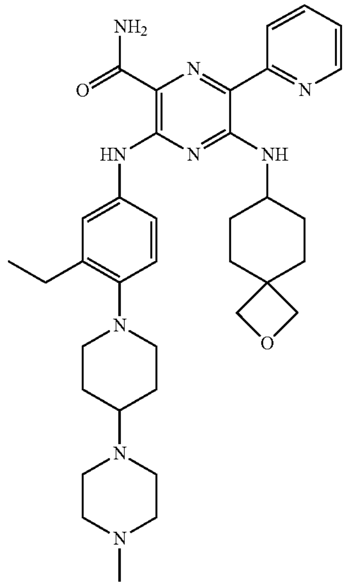 [SMILES: CCc1cc(Nc2nc(NC3CCC4(CC3)COC4)c(-c3ccccn3)nc2C(N)=O)ccc1N1CCC(N2CCN(C)CC2)CC1] | A | 640 | — |
| 283 | 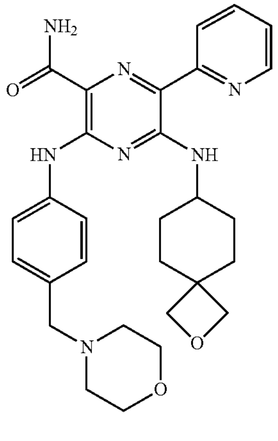 [SMILES: NC(=O)c1nc(-c2ccccn2)c(NC2CCC3(CC2)COC3)nc1Nc1ccc(CN2CCOCC2)cc1] | A | 530 | — |

TABLE 2-continued
| | | | | |
|---|---|---|---|---|
| 284 | 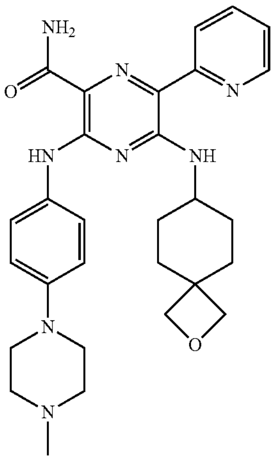 [SMILES: CN1CCN(c2ccc(Nc3nc(NC4CCC5(CC4)COC5)c(-c4ccccn4)nc3C(N)=O)cc2)CC1] | A | 529 | — |
| 285 | 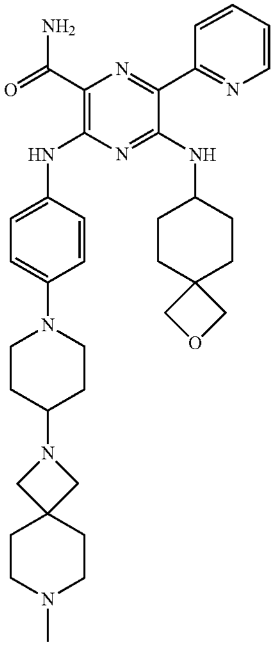 [SMILES: CN1CCC2(CC1)CN(C1CCN(c3ccc(Nc4nc(NC5CCC6(CC5)COC6)c(-c5ccccn5)nc4C(N)=O)cc3)CC1)C2] | A | 652 | — |

TABLE 2-continued
| | | | | |
|---|---|---|---|---|
| 286 | 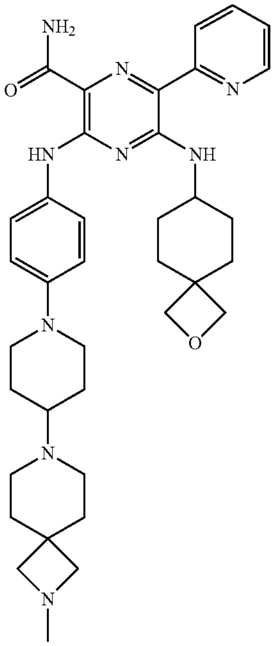 [SMILES: CN1CC2(CCN(C3CCN(c4ccc(Nc5nc(NC6CCC7(CC6)COC7)c(-c6ccccn6)nc5C(N)=O)cc4)CC3)CC2)C1] | A | 652 | — |
| 287 | 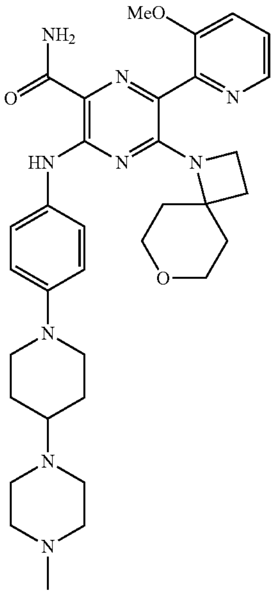 [SMILES: COc1cccnc1-c1nc(C(N)=O)c(Nc2ccc(N3CCC(N4CCN(C)CC4)CC3)cc2)nc1N1CCC12CCOCC2] | A | 628 | — |

TABLE 2-continued
| | | | | |
|---|---|---|---|---|
| 288 | 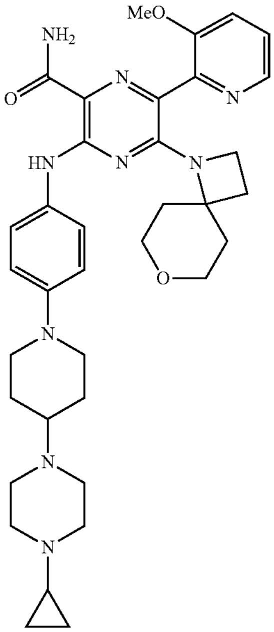 [SMILES: COc1cccnc1-c1nc(C(N)=O)c(Nc2ccc(N3CCC(N4CCN(C5CC5)CC4)CC3)cc2)nc1N1CCC12CCOCC2] | A | 654 | — |
| 289 | 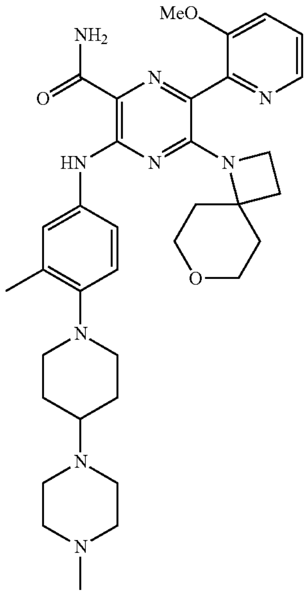 [SMILES: COc1cccnc1-c1nc(C(N)=O)c(Nc2ccc(N3CCC(N4CCN(C)CC4)CC3)c(C)c2)nc1N1CCC12CCOCC2] | A | 642 | — |

TABLE 2-continued
| | | | | |
|---|---|---|---|---|
| 290 | 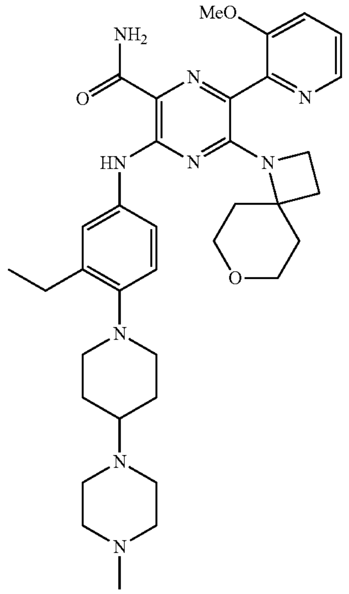 [SMILES: CCc1cc(Nc2nc(N3CCC34CCOCC4)c(-c3ncccc3OC)nc2C(N)=O)ccc1N1CCC(N2CCN(C)CC2)CC1] | A | 656 | — |
| 291 | 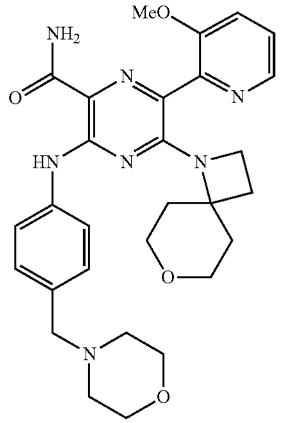 [SMILES: COc1cccnc1-c1nc(C(N)=O)c(Nc2ccc(CN3CCOCC3)cc2)nc1N1CCC12CCOCC2] | A | 546 | — |
| 292 | 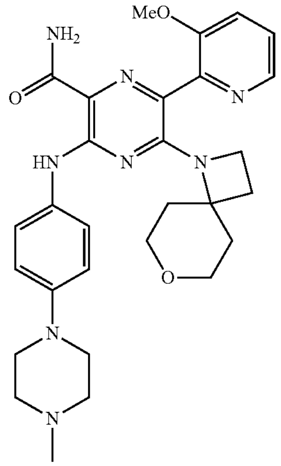 [SMILES: COc1cccnc1-c1nc(C(N)=O)c(Nc2ccc(N3CCN(C)CC3)cc2)nc1N1CCC12CCOCC2] | A | 545 | — |

TABLE 2-continued
| | | | | |
|---|---|---|---|---|
| 293 | 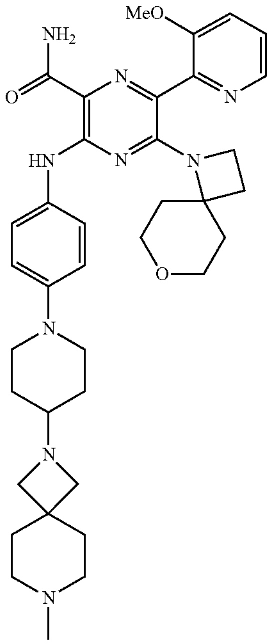 [SMILES: COc1cccnc1-c1nc(C(N)=O)c(Nc2ccc(N3CCC(N4CC5(CCN(C)CC5)C4)CC3)cc2)nc1N1CCC12CCOCC2] | A | 668 | — |
| 294 | 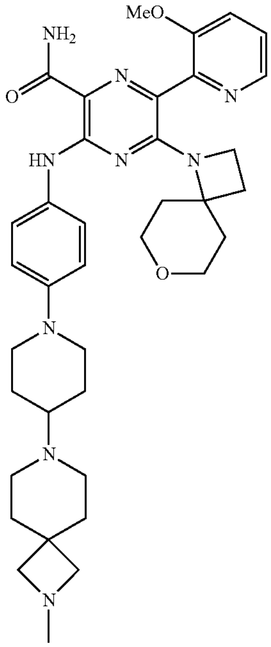 [SMILES: COc1cccnc1-c1nc(C(N)=O)c(Nc2ccc(N3CCC(N4CCC5(CC4)CN(C)C5)CC3)cc2)nc1N1CCC12CCOCC2] | A | 668 | — |

TABLE 2-continued
| | | | | |
|---|---|---|---|---|
| 295 | 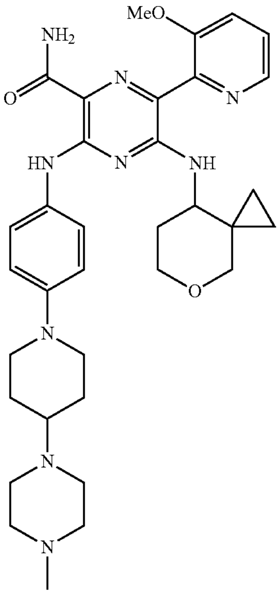 [SMILES: COc1cccnc1-c1nc(C(N)=O)c(Nc2ccc(N3CCC(N4CCN(C)CC4)CC3)cc2)nc1NC1CCOCC12CC2] | A | 628 | — |
| 296 | 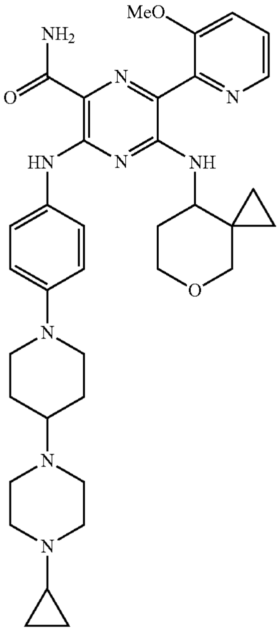 [SMILES: COc1cccnc1-c1nc(C(N)=O)c(Nc2ccc(N3CCC(N4CCN(C5CC5)CC4)CC3)cc2)nc1NC1CCOCC12CC2] | A | 654 | — |

TABLE 2-continued
| | | | | |
|---|---|---|---|---|
| 297 | 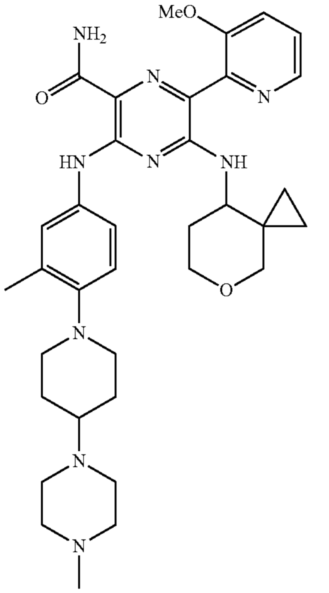 [SMILES: COc1cccnc1-c1nc(C(N)=O)c(Nc2ccc(N3CCC(N4CCN(C)CC4)CC3)c(C)c2)nc1NC1CCOCC12CC2] | A | 642 | — |
| 298 | 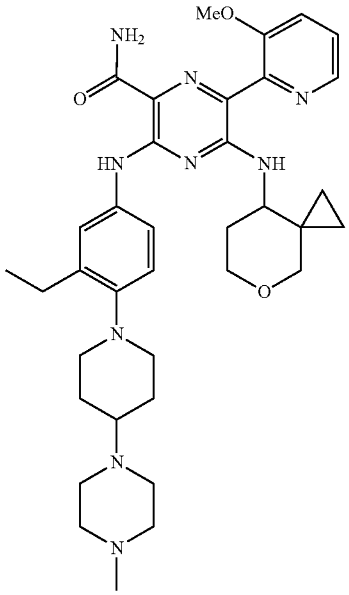 [SMILES: CCc1cc(Nc2nc(NC3CCOCC34CC4)c(-c3ncccc3OC)nc2C(N)=O)ccc1N1CCC(N2CCN(C)CC2)CC1] | A | 656 | — |
| 299 | 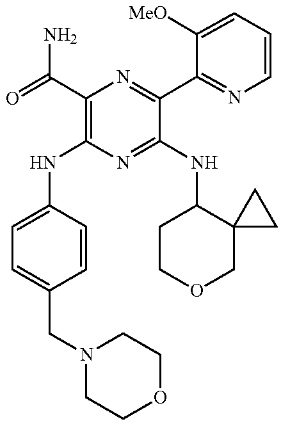 [SMILES: COc1cccnc1-c1nc(C(N)=O)c(Nc2ccc(CN3CCOCC3)cc2)nc1NC1CCOCC12CC2] | A | 546 | — |

TABLE 2-continued
| | | | | |
|---|---|---|---|---|
| 300 | 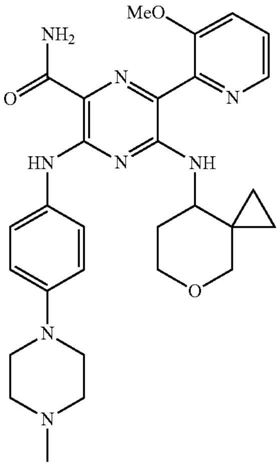 [SMILES: COc1cccnc1-c1nc(C(N)=O)c(Nc2ccc(N3CCN(C)CC3)cc2)nc1NC1CCOCC12CC2] | A | 545 | — |
| 301 | 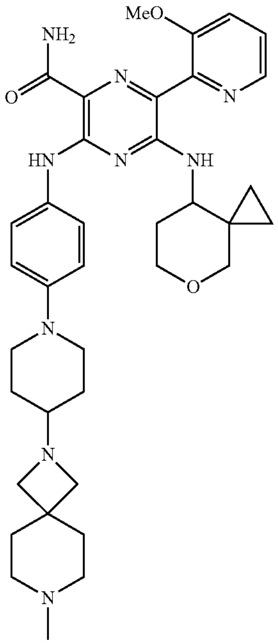 [SMILES: COc1cccnc1-c1nc(C(N)=O)c(Nc2ccc(N3CCC(N4CC5(CCN(C)CC5)C4)CC3)cc2)nc1NC1CCOCC12CC2] | A | 668 | — |

TABLE 2-continued
| | | | | |
|---|---|---|---|---|
| 302 | 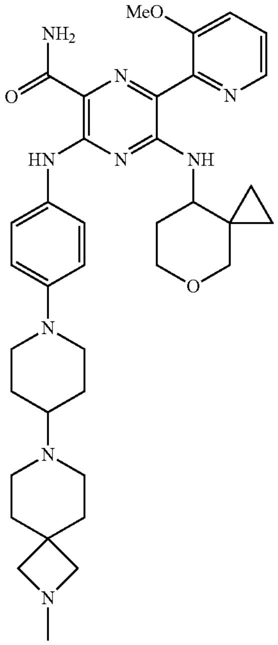 [SMILES: COc1cccnc1-c1nc(C(N)=O)c(Nc2ccc(N3CCC(N4CCC5(CC4)CN(C)C5)CC3)cc2)nc1NC1CCOCC12CC2] | A | 668 | — |
| 303 | 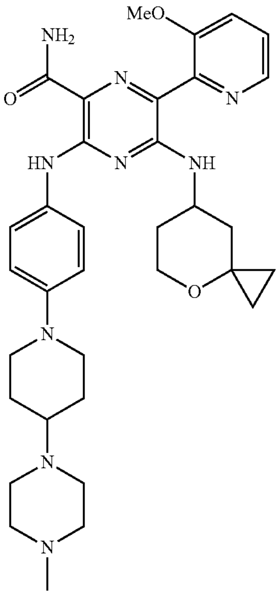 [SMILES: COc1cccnc1-c1nc(C(N)=O)c(Nc2ccc(N3CCC(N4CCN(C)CC4)CC3)cc2)nc1NC1CCOC2(CC2)C1] | A | 628 | — |

TABLE 2-continued
| | | | | |
|---|---|---|---|---|
| 304 | 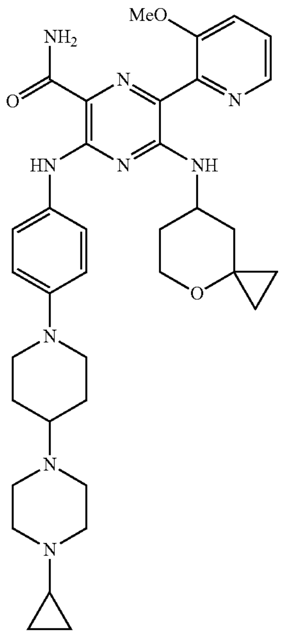 [SMILES: COc1cccnc1-c1nc(C(N)=O)c(Nc2ccc(N3CCC(N4CCN(C5CC5)CC4)CC3)cc2)nc1NC1CCOC2(CC2)C1] | A | 654 | — |
| 305 | 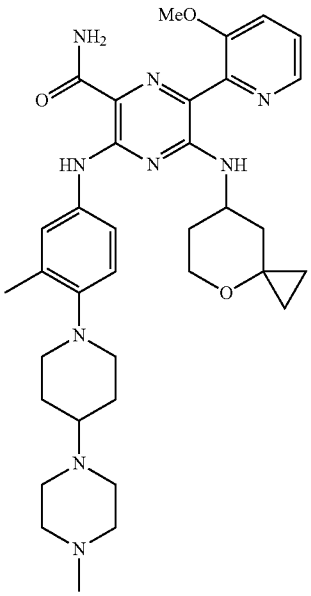 [SMILES: COc1cccnc1-c1nc(C(N)=O)c(Nc2ccc(N3CCC(N4CCN(C)CC4)CC3)c(C)c2)nc1NC1CCOC2(CC2)C1] | A | 642 | — |

TABLE 2-continued
| | | | | |
|---|---|---|---|---|
| 306 | 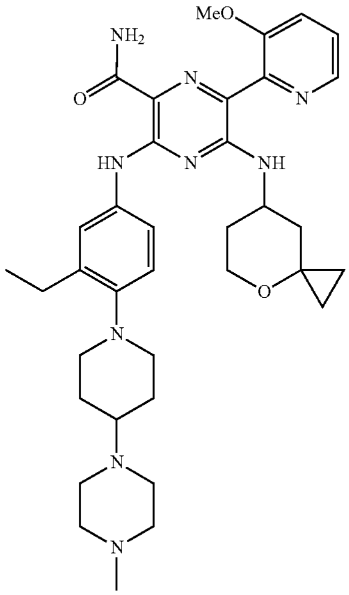 [SMILES: CCc1cc(Nc2nc(NC3CCOC4(CC4)C3)c(-c3ncccc3OC)nc2C(N)=O)ccc1N1CCC(N2CCN(C)CC2)CC1] | A | 656 | — |
| 307 | 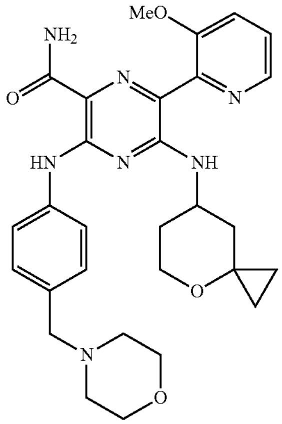 [SMILES: COc1cccnc1-c1nc(C(N)=O)c(Nc2ccc(CN3CCOCC3)cc2)nc1NC1CCOC2(CC2)C1] | A | 546 | — |
| 308 | 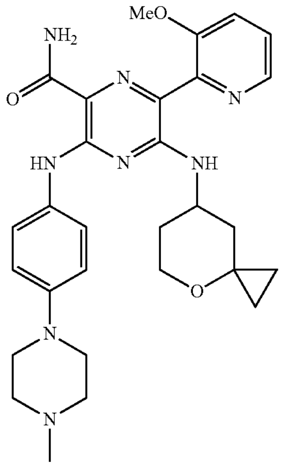 [SMILES: COc1cccnc1-c1nc(C(N)=O)c(Nc2ccc(N3CCN(C)CC3)cc2)nc1NC1CCOC2(CC2)C1] | A | 545 | — |

TABLE 2-continued
| | | | | |
|---|---|---|---|---|
| 309 | 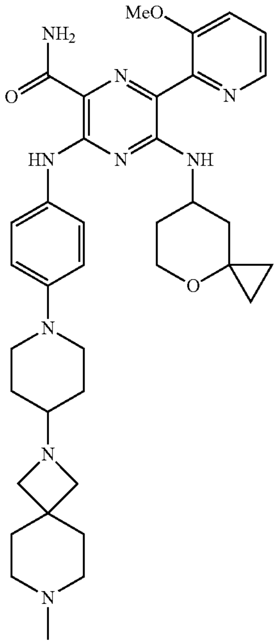 [SMILES: COc1cccnc1-c1nc(C(N)=O)c(Nc2ccc(N3CCC(N4CC5(CCN(C)CC5)C4)CC3)cc2)nc1NC1CCOC2(CC2)C1] | A | 668 | — |
| 310 | 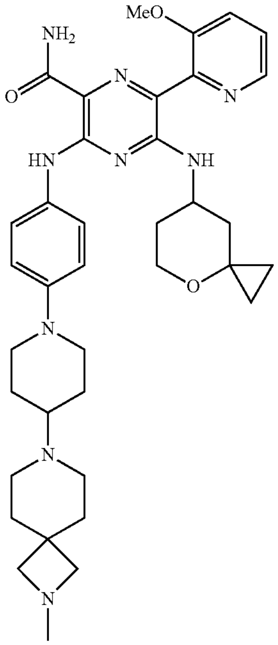 [SMILES: COc1cccnc1-c1nc(C(N)=O)c(Nc2ccc(N3CCC(N4CCC5(CC4)CN(C)C5)CC3)cc2)nc1NC1CCOC2(CC2)C1] | A | 668 | — |

TABLE 2-continued
| | | | | |
|---|---|---|---|---|
| 311 | 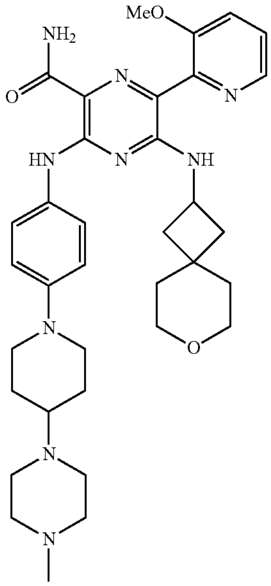 [SMILES: COc1cccnc1-c1nc(C(N)=O)c(Nc2ccc(N3CCC(N4CCN(C)CC4)CC3)cc2)nc1NC1CC2(CCOCC2)C1] | A | 642 | — |
| 312 | 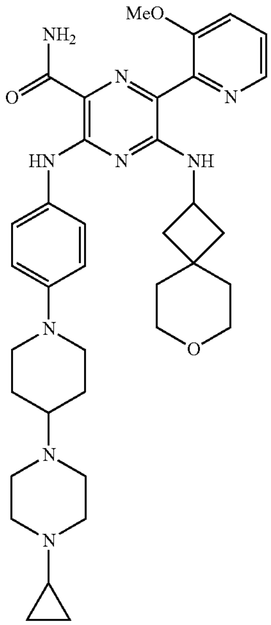 [SMILES: COc1cccnc1-c1nc(C(N)=O)c(Nc2ccc(N3CCC(N4CCN(C5CC5)CC4)CC3)cc2)nc1NC1CC2(CCOCC2)C1] | A | 668 | — |

TABLE 2-continued
| | | | | |
|---|---|---|---|---|
| 313 | 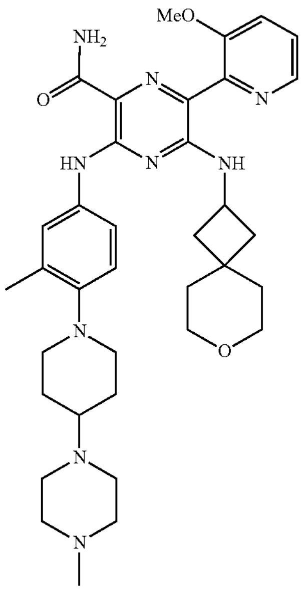 [SMILES: COc1cccnc1-c1nc(C(N)=O)c(Nc2ccc(N3CCC(N4CCN(C)CC4)CC3)c(C)c2)nc1NC1CC2(CCOCC2)C1] | A | 656 | — |
| 314 | 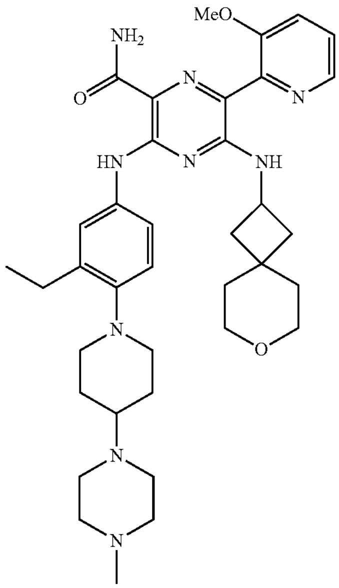 [SMILES: CCc1cc(Nc2nc(NC3CC4(CCOCC4)C3)c(-c3ncccc3OC)nc2C(N)=O)ccc1N1CCC(N2CCN(C)CC2)CC1] | A | 670 | — |
| 315 | 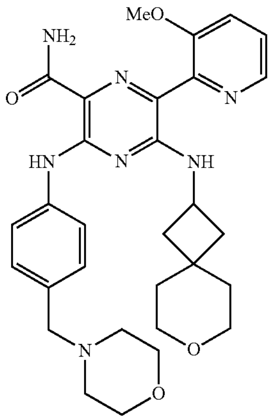 [SMILES: COc1cccnc1-c1nc(C(N)=O)c(Nc2ccc(CN3CCOCC3)cc2)nc1NC1CC2(CCOCC2)C1] | A | 560 | — |

TABLE 2-continued
| | | | | |
|---|---|---|---|---|
| 316 | 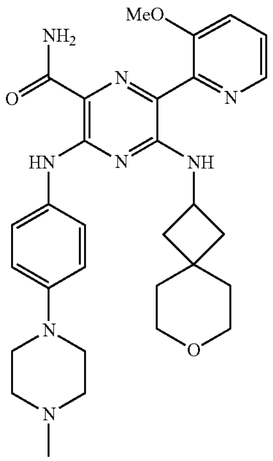 [SMILES: COc1cccnc1-c1nc(C(N)=O)c(Nc2ccc(N3CCN(C)CC3)cc2)nc1NC1CC2(CCOCC2)C1] | A | 559 | — |
| 317 | 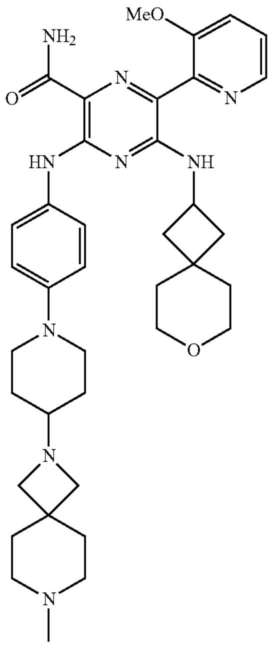 [SMILES: COc1cccnc1-c1nc(C(N)=O)c(Nc2ccc(N3CCC(N4CC5(CCN(C)CC5)C4)CC3)cc2)nc1NC1CC2(CCOCC2)C1] | A | 682 | — |

TABLE 2-continued
| | | | | |
|---|---|---|---|---|
| 318 | 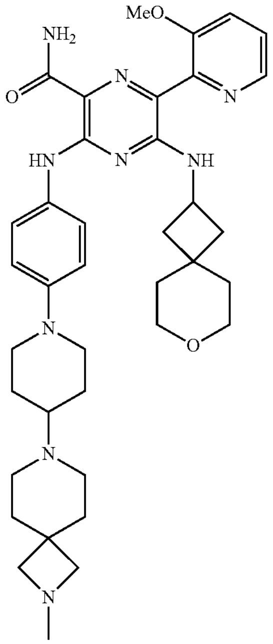 [SMILES: COc1cccnc1-c1nc(C(N)=O)c(Nc2ccc(N3CCC(N4CCC5(CC4)CN(C)C5)CC3)cc2)nc1NC1CC2(CCOCC2)C1] | A | 682 | — |
| 319 | 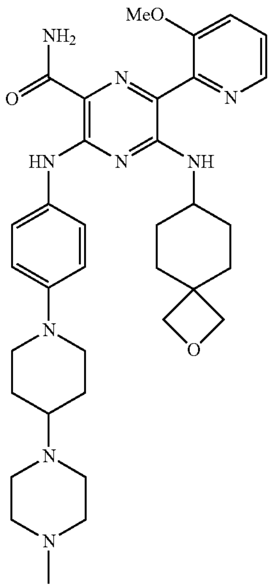 [SMILES: COc1cccnc1-c1nc(C(N)=O)c(Nc2ccc(N3CCC(N4CCN(C)CC4)CC3)cc2)nc1NC1CCC2(CC1)COC2] | A | 642 | — |

TABLE 2-continued
| | | | | |
|---|---|---|---|---|
| 320 | 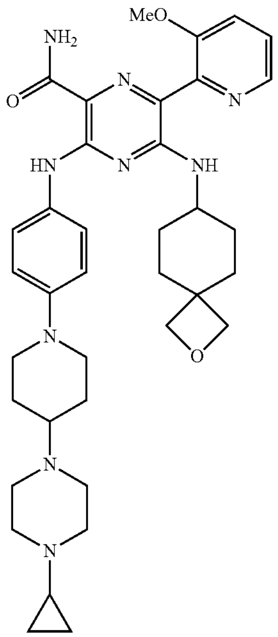 [SMILES: COc1cccnc1-c1nc(C(N)=O)c(Nc2ccc(N3CCC(N4CCN(C5CC5)CC4)CC3)cc2)nc1NC1CCC2(CC1)COC2] | A | 668 | — |
| 321 | 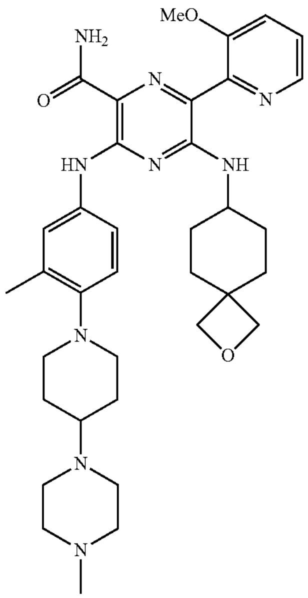 [SMILES: COc1cccnc1-c1nc(C(N)=O)c(Nc2ccc(N3CCC(N4CCN(C)CC4)CC3)c(C)c2)nc1NC1CCC2(CC1)COC2] | A | 656 | — |

TABLE 2-continued
| | | | | |
|---|---|---|---|---|
| 322 | 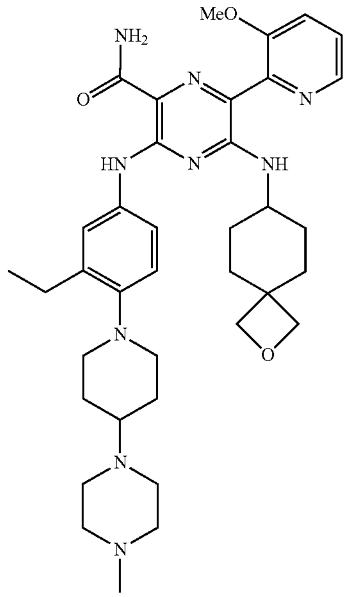 [SMILES: CCc1cc(Nc2nc(NC3CCC4(CC3)COC4)c(-c3ncccc3OC)nc2C(N)=O)ccc1N1CCC(N2CCN(C)CC2)CC1] | A | 670 | — |
| 323 | 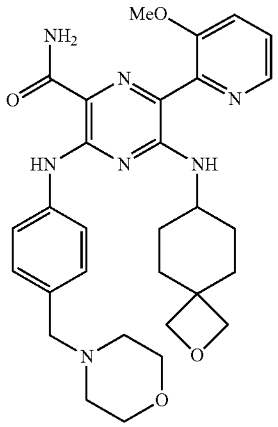 [SMILES: COc1cccnc1-c1nc(C(N)=O)c(Nc2ccc(CN3CCOCC3)cc2)nc1NC1CCC2(CC1)COC2] | A | 560 | — |
| 324 | 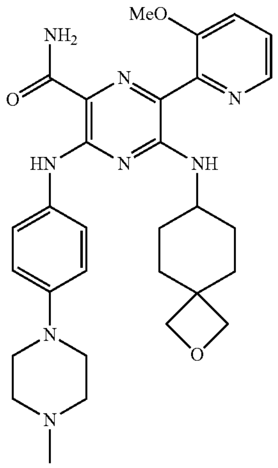 [SMILES: COc1cccnc1-c1nc(C(N)=O)c(Nc2ccc(N3CCN(C)CC3)cc2)nc1NC1CCC2(CC1)COC2] | A | 559 | — |

TABLE 2-continued
| | | | | |
|---|---|---|---|---|
| 325 | 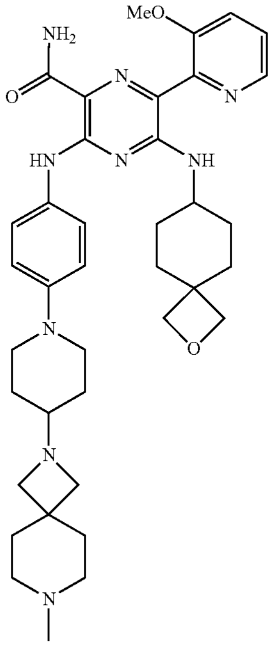 [SMILES: COc1cccnc1-c1nc(C(N)=O)c(Nc2ccc(N3CCC(N4CC5(CCN(C)CC5)C4)CC3)cc2)nc1NC1CCC2(CC1)COC2] | A | 682 | — |
| 326 | 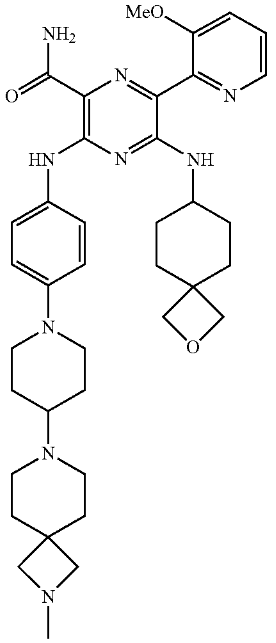 [SMILES: COc1cccnc1-c1nc(C(N)=O)c(Nc2ccc(N3CCC(N4CCC5(CC4)CN(C)C5)CC3)cc2)nc1NC1CCC2(CC1)COC2] | A | 682 | — |

TABLE 2-continued
| | | | | |
|---|---|---|---|---|
| 327 | 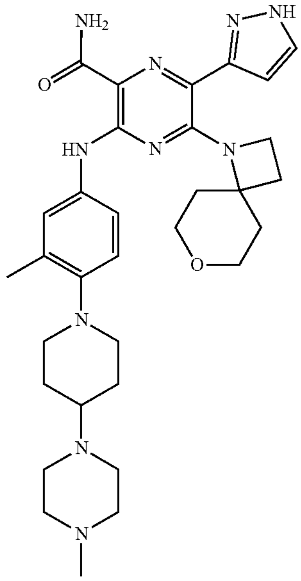 [SMILES: Cc1cc(Nc2nc(N3CCC34CCOCC4)c(-c3cc[nH]n3)nc2C(N)=O)ccc1N1CCC(N2CCN(C)CC2)CC1] | A | 601 | — |
| 328 | 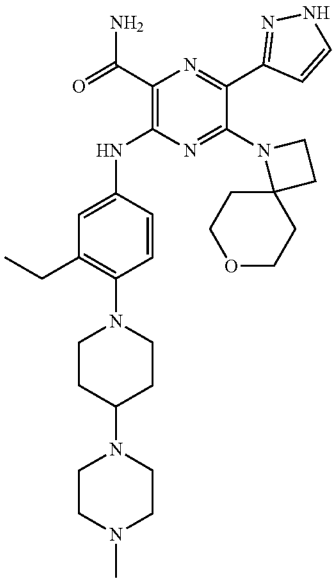 [SMILES: CCc1cc(Nc2nc(N3CCC34CCOCC4)c(-c3cc[nH]n3)nc2C(N)=O)ccc1N1CCC(N2CCN(C)CC2)CC1] | A | 615 | — |
| 329 | 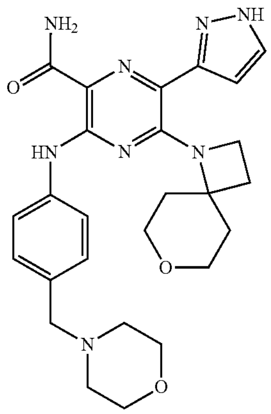 [SMILES: NC(=O)c1nc(-c2cc[nH]n2)c(N2CCC23CCOCC3)nc1Nc1ccc(CN2CCOCC2)cc1] | A | 505 | — |

TABLE 2-continued
| | | | | |
|---|---|---|---|---|
| 330 | 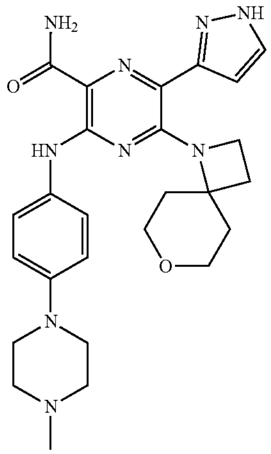 [SMILES: CN1CCN(c2ccc(Nc3nc(N4CCC45CCOCC5)c(-c4cc[nH]n4)nc3C(N)=O)cc2)CC1] | A | 504 | — |
| 331 | 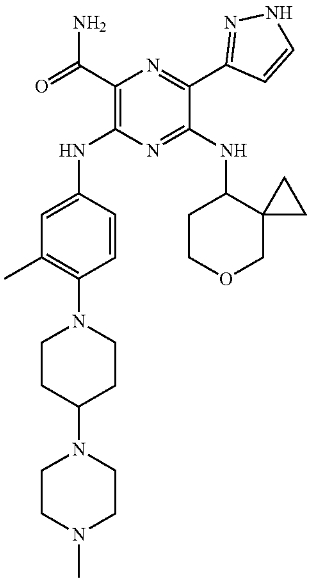 [SMILES: Cc1cc(Nc2nc(NC3CCOCC34CC4)c(-c3cc[nH]n3)nc2C(N)=O)ccc1N1CCC(N2CCN(C)CC2)CC1] | A | 601 | — |
| 332 | 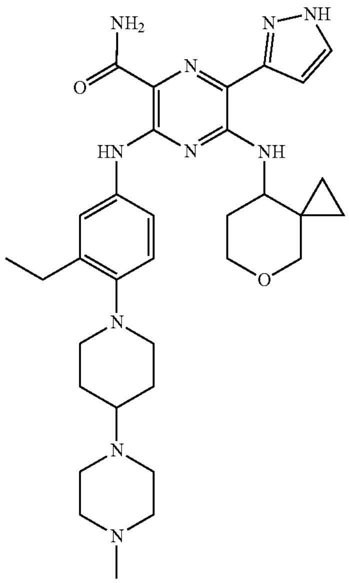 [SMILES: CCc1cc(Nc2nc(NC3CCOCC34CC4)c(-c3cc[nH]n3)nc2C(N)=O)ccc1N1CCC(N2CCN(C)CC2)CC1] | A | 615 | — |

TABLE 2-continued
| | | | | |
|---|---|---|---|---|
| 333 | 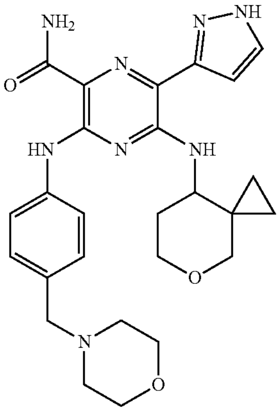 [SMILES: NC(=O)c1nc(-c2cc[nH]n2)c(NC2CCOCC23CC3)nc1Nc1ccc(CN2CCOCC2)cc1] | A | 505 | — |
| 334 | 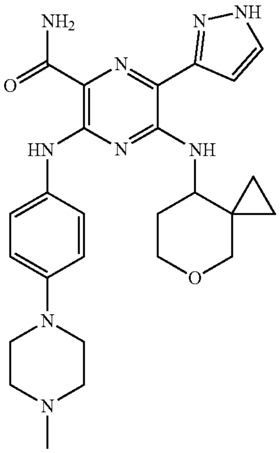 [SMILES: CN1CCN(c2ccc(Nc3nc(NC4CCOCC45CC5)c(-c4cc[nH]n4)nc3C(N)=O)cc2)CC1] | A | 504 | — |
| 335 | 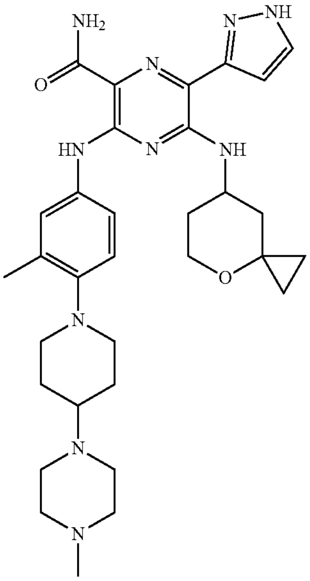 [SMILES: Cc1cc(Nc2nc(NC3CCOC4(CC4)C3)c(-c3cc[nH]n3)nc2C(N)=O)ccc1N1CCC(N2CCN(C)CC2)CC1] | A | 601 | — |

TABLE 2-continued
| | | | | |
|---|---|---|---|---|
| 336 | 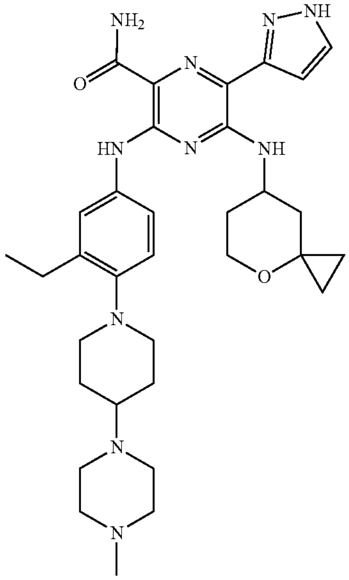 [SMILES: CCc1cc(Nc2nc(NC3CCOC4(CC4)C3)c(-c3cc[nH]n3)nc2C(N)=O)ccc1N1CCC(N2CCN(C)CC2)CC1] | A | 615 | — |
| 337 | 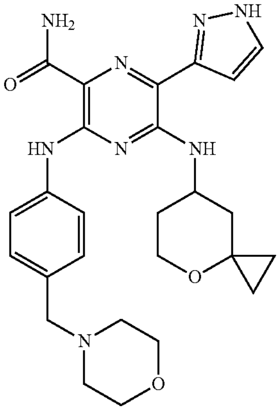 [SMILES: NC(=O)c1nc(-c2cc[nH]n2)c(NC2CCOC3(CC3)C2)nc1Nc1ccc(CN2CCOCC2)cc1] | A | 505 | — |
| 338 | 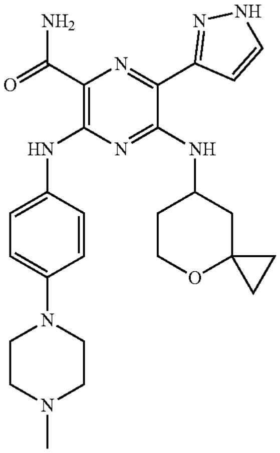 [SMILES: CN1CCN(c2ccc(Nc3nc(NC4CCOC5(CC5)C4)c(-c4cc[nH]n4)nc3C(N)=O)cc2)CC1] | A | 504 | — |

TABLE 2-continued
| | | | | |
|---|---|---|---|---|
| 339 | 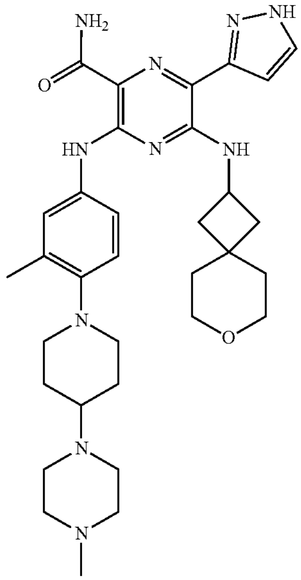 [SMILES: Cc1cc(Nc2nc(NC3CC4(CCOCC4)C3)c(-c3cc[nH]n3)nc2C(N)=O)ccc1N1CCC(N2CCN(C)CC2)CC1] | A | 615 | — |
| 340 | 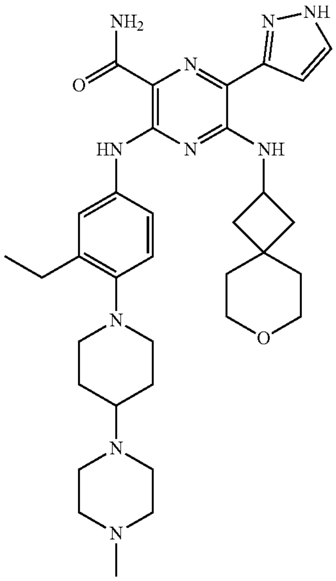 [SMILES: CCc1cc(Nc2nc(NC3CC4(CCOCC4)C3)c(-c3cc[nH]n3)nc2C(N)=O)ccc1N1CCC(N2CCN(C)CC2)CC1] | A | 629 | — |
| 341 | 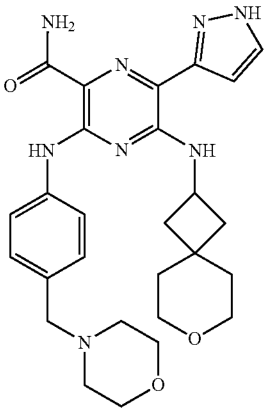 [SMILES: NC(=O)c1nc(-c2cc[nH]n2)c(NC2CC3(CCOCC3)C2)nc1Nc1ccc(CN2CCOCC2)cc1] | A | 519 | — |

TABLE 2-continued
| | | | | |
|---|---|---|---|---|
| 342 | 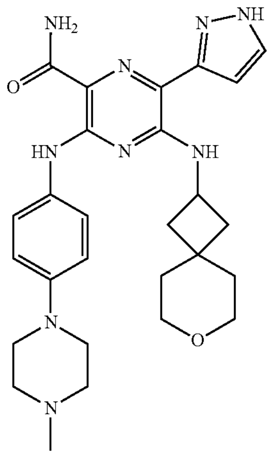 [SMILES: CN1CCN(c2ccc(Nc3nc(NC4CC5(CCOCC5)C4)c(-c4cc[nH]n4)nc3C(N)=O)cc2)CC1] | A | 518 | — |
| 343 | 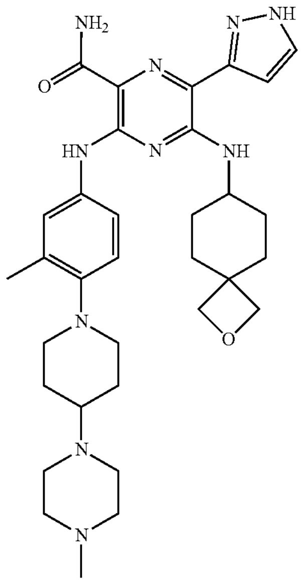 [SMILES: Cc1cc(Nc2nc(NC3CCC4(CC3)COC4)c(-c3cc[nH]n3)nc2C(N)=O)ccc1N1CCC(N2CCN(C)CC2)CC1] | A | 615 | — |
| 344 | 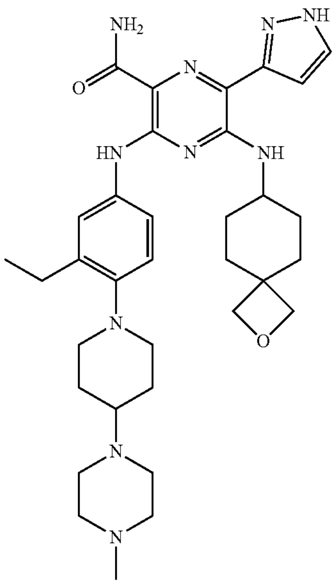 [SMILES: CCc1cc(Nc2nc(NC3CCC4(CC3)COC4)c(-c3cc[nH]n3)nc2C(N)=O)ccc1N1CCC(N2CCN(C)CC2)CC1] | A | 629 | — |

TABLE 2-continued
| | | | | |
|---|---|---|---|---|
| 345 | 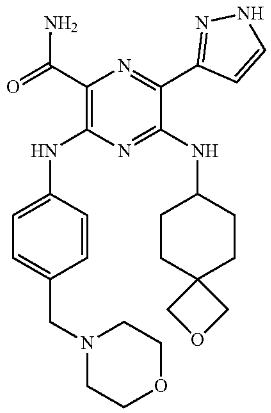 [SMILES: NC(=O)c1nc(-c2cc[nH]n2)c(NC2CCC3(CC2)COC3)nc1Nc1ccc(CN2CCOCC2)cc1] | A | 519 | — |
| 346 | 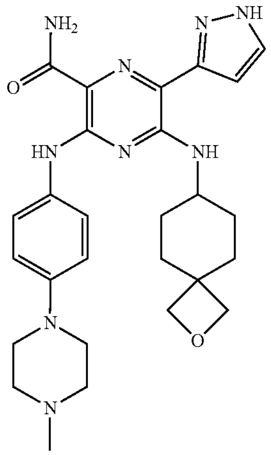 [SMILES: CN1CCN(c2ccc(Nc3nc(NC4CCC5(CC4)COC5)c(-c4cc[nH]n4)nc3C(N)=O)cc2)CC1] | A | 518 | — |
| 347 | 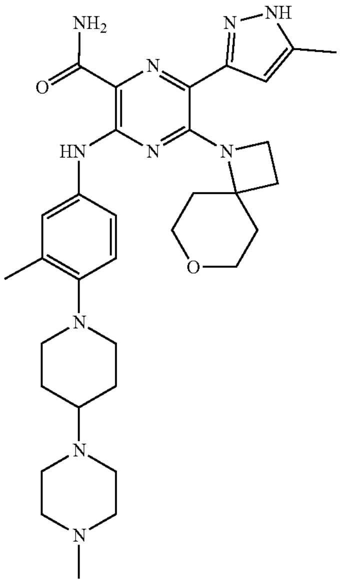 | A | 615 | — |

TABLE 2-continued
| | | | | |
|---|---|---|---|---|
| 348 | 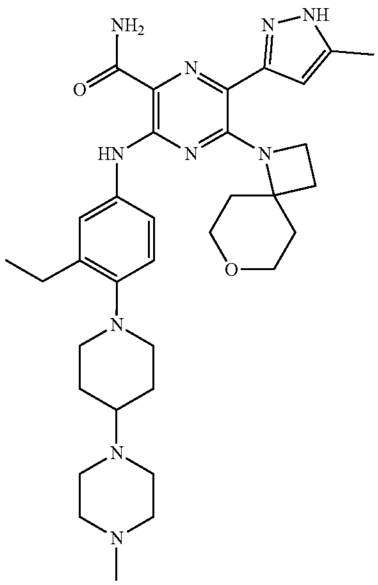 [SMILES: CCc1cc(Nc2nc(N3CCC34CCOCC4)c(-c3cc(C)[nH]n3)nc2C(N)=O)ccc1N1CCC(N2CCN(C)CC2)CC1] | A | 629 | — |
| 349 | 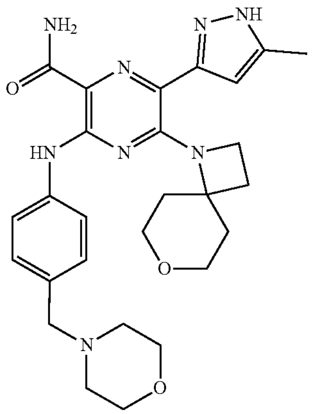 [SMILES: Cc1cc(-c2nc(C(N)=O)c(Nc3ccc(CN4CCOCC4)cc3)nc2N2CCC23CCOCC3)n[nH]1] | A | 519 | — |
| 350 | 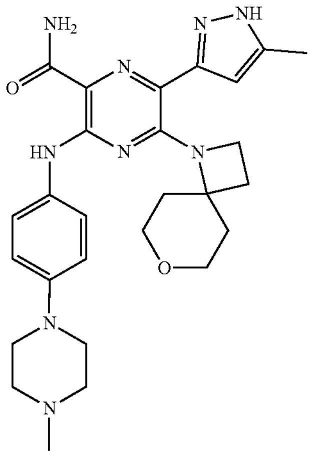 [SMILES: Cc1cc(-c2nc(C(N)=O)c(Nc3ccc(N4CCN(C)CC4)cc3)nc2N2CCC23CCOCC3)n[nH]1] | A | 518 | — |

TABLE 2-continued
| | | | | |
|---|---|---|---|---|
| 351 | 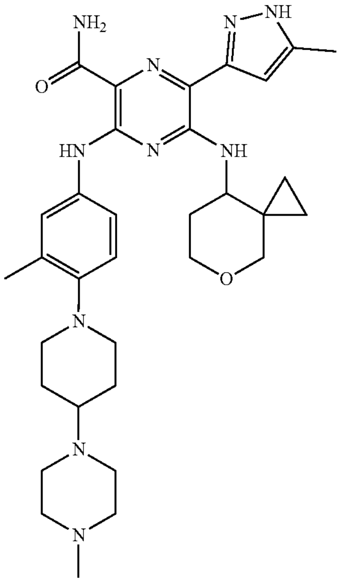 | A | 615 | — |
| 352 | 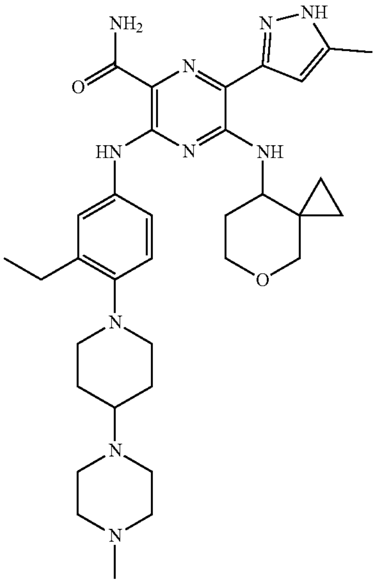 [SMILES: CCc1cc(Nc2nc(NC3CCOCC34CC4)c(-c3cc(C)[nH]n3)nc2C(N)=O)ccc1N1CCC(N2CCN(C)CC2)CC1] | A | 629 | — |
| 353 | 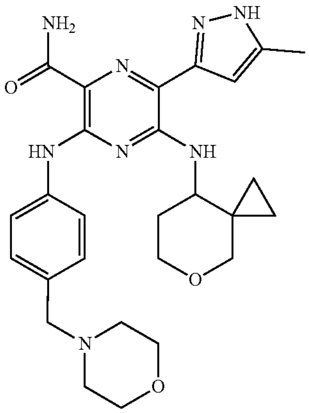 [SMILES: Cc1cc(-c2nc(C(N)=O)c(Nc3ccc(CN4CCOCC4)cc3)nc2NC2CCOCC23CC3)n[nH]1] | A | 519 | — |

TABLE 2-continued
| | | | | |
|---|---|---|---|---|
| 354 | 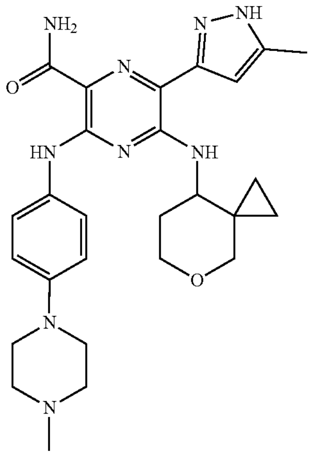 [SMILES: Cc1cc(-c2nc(C(N)=O)c(Nc3ccc(N4CCN(C)CC4)cc3)nc2NC2CCOCC23CC3)n[nH]1] | A | 518 | — |
| 355 | 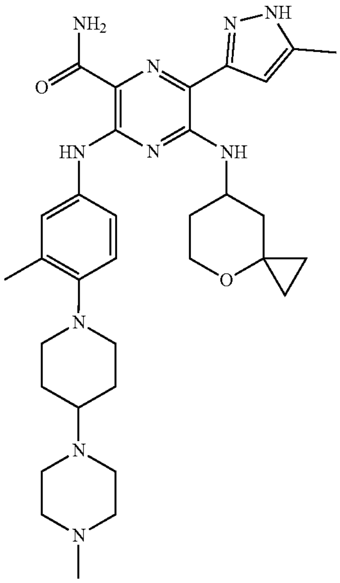 | A | 615 | — |
| 356 | 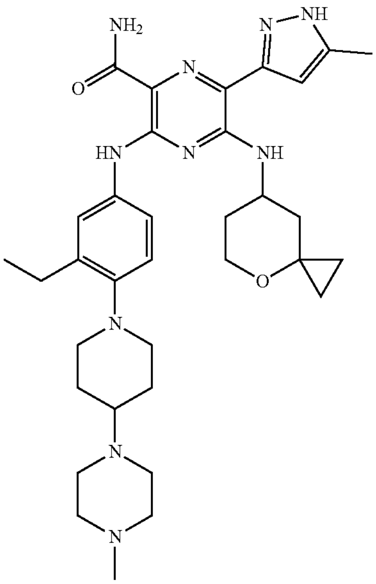 [SMILES: CCc1cc(Nc2nc(NC3CCOC4(CC4)C3)c(-c3cc(C)[nH]n3)nc2C(N)=O)ccc1N1CCC(N2CCN(C)CC2)CC1] | A | 629 | — |

TABLE 2-continued
| | | | | |
|---|---|---|---|---|
| 357 | 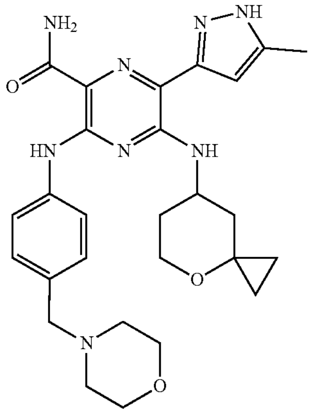 [SMILES: Cc1cc(-c2nc(C(N)=O)c(Nc3ccc(CN4CCOCC4)cc3)nc2NC2CCOC3(CC3)C2)n[nH]1] | A | 519 | — |
| 358 | 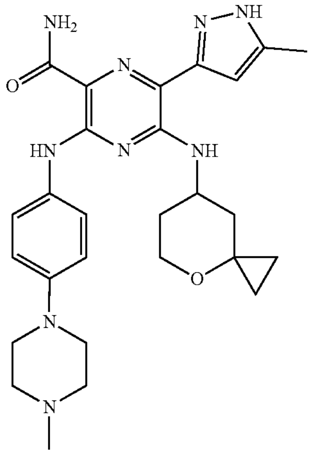 [SMILES: Cc1cc(-c2nc(C(N)=O)c(Nc3ccc(N4CCN(C)CC4)cc3)nc2NC2CCOC3(CC3)C2)n[nH]1] | A | 518 | — |
| 359 | 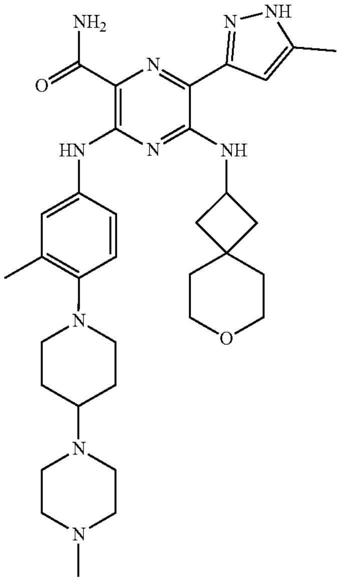 | A | 629 | — |

TABLE 2-continued
| | | | | |
|---|---|---|---|---|
| 360 | 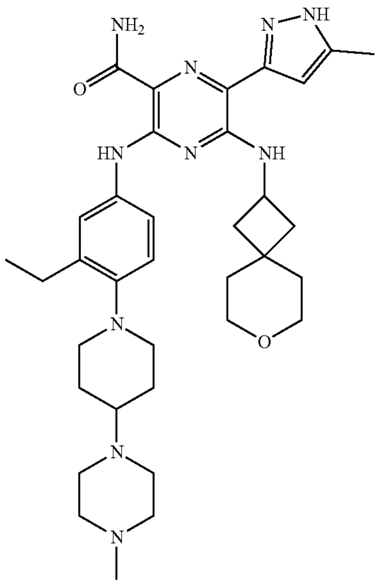 [SMILES: CCc1cc(Nc2nc(NC3CC4(CCOCC4)C3)c(-c3cc(C)[nH]n3)nc2C(N)=O)ccc1N1CCC(N2CCN(C)CC2)CC1] | A | 643 | — |
| 361 | 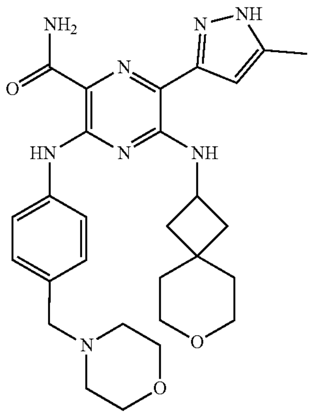 [SMILES: Cc1cc(-c2nc(C(N)=O)c(Nc3ccc(CN4CCOCC4)cc3)nc2NC2CC3(CCOCC3)C2)n[nH]1] | A | 533 | — |
| 362 | 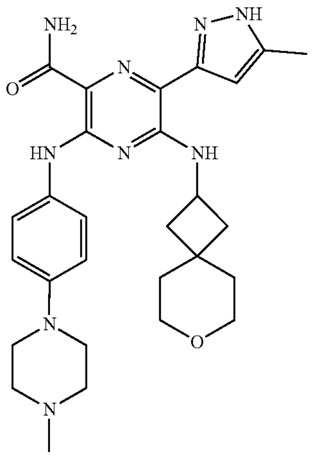 [SMILES: Cc1cc(-c2nc(C(N)=O)c(Nc3ccc(N4CCN(C)CC4)cc3)nc2NC2CC3(CCOCC3)C2)n[nH]1] | A | 532 | — |

TABLE 2-continued
| | | | | |
|---|---|---|---|---|
| 363 | 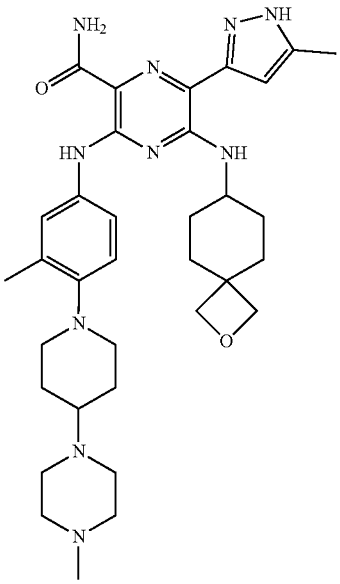 | A | 629 | — |
| 364 | 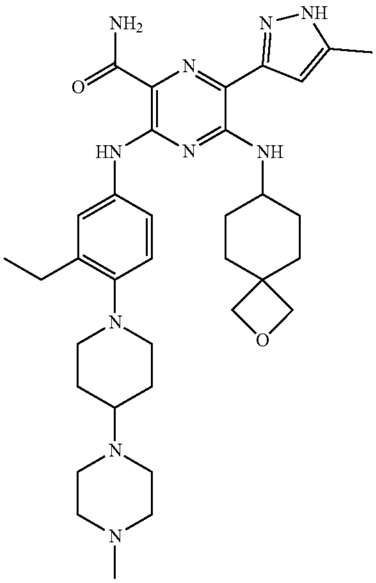 [SMILES: CCc1cc(Nc2nc(NC3CCC4(CC3)COC4)c(-c3cc(C)[nH]n3)nc2C(N)=O)ccc1N1CCC(N2CCN(C)CC2)CC1] | A | 643 | — |
| 365 | 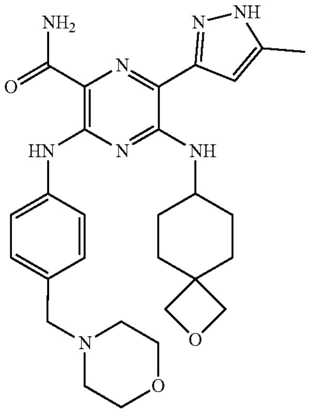 [SMILES: Cc1cc(-c2nc(C(N)=O)c(Nc3ccc(CN4CCOCC4)cc3)nc2NC2CCC3(CC2)COC3)n[nH]1] | A | 533 | — |

TABLE 2-continued
| | | | | |
|---|---|---|---|---|
| 366 | 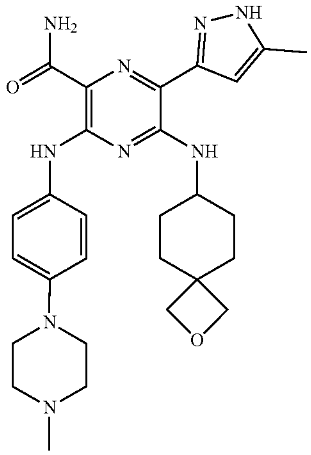 [SMILES: Cc1cc(-c2nc(C(N)=O)c(Nc3ccc(N4CCN(C)CC4)cc3)nc2NC2CCC3(CC2)COC3)n[nH]1] | A | 532 | — |
| 367 | 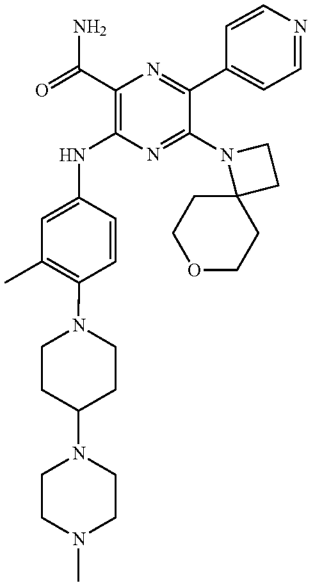 [SMILES: Cc1cc(Nc2nc(N3CCC34CCOCC4)c(-c3ccncc3)nc2C(N)=O)ccc1N1CCC(N2CCN(C)CC2)CC1] | A | 612 | — |
| 368 | 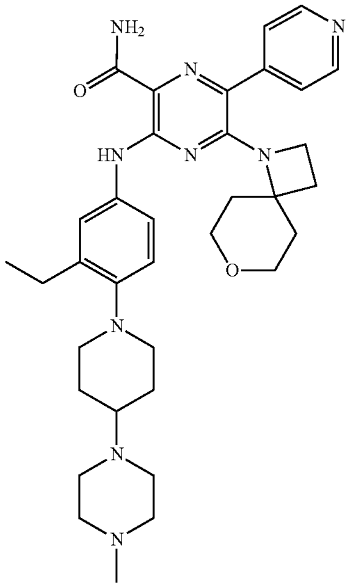 [SMILES: CCc1cc(Nc2nc(N3CCC34CCOCC4)c(-c3ccncc3)nc2C(N)=O)ccc1N1CCC(N2CCN(C)CC2)CC1] | A | 626 | — |

TABLE 2-continued
| | | | | |
|---|---|---|---|---|
| 369 | 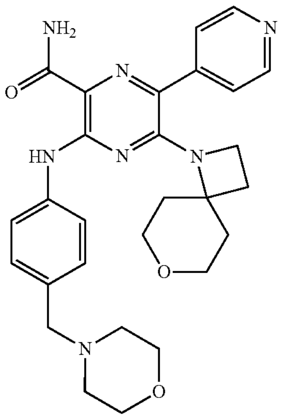 [SMILES: NC(=O)c1nc(-c2ccncc2)c(N2CCC23CCOCC3)nc1Nc1ccc(CN2CCOCC2)cc1] | A | 516 | — |
| 370 | 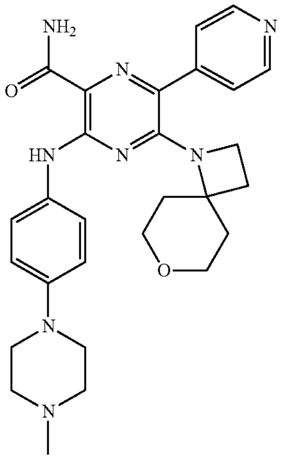 [SMILES: CN1CCN(c2ccc(Nc3nc(N4CCC45CCOCC5)c(-c4ccncc4)nc3C(N)=O)cc2)CC1] | A | 515 | — |
| 371 | 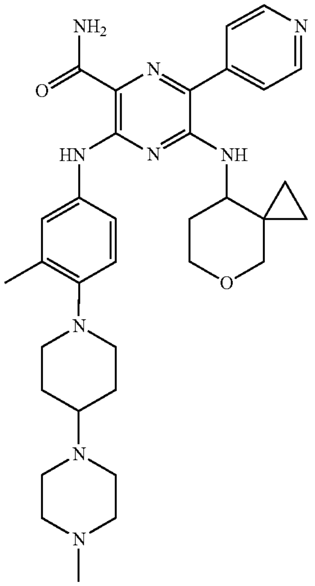 [SMILES: Cc1cc(Nc2nc(NC3CCOCC34CC4)c(-c3ccncc3)nc2C(N)=O)ccc1N1CCC(N2CCN(C)CC2)CC1] | A | 612 | — |

TABLE 2-continued
| | | | | |
|---|---|---|---|---|
| 372 | 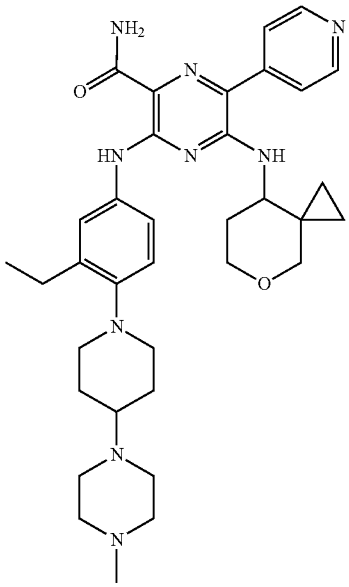 [SMILES: CCc1cc(Nc2nc(NC3CCOCC34CC4)c(-c3ccncc3)nc2C(N)=O)ccc1N1CCC(N2CCN(C)CC2)CC1] | A | 626 | — |
| 373 | 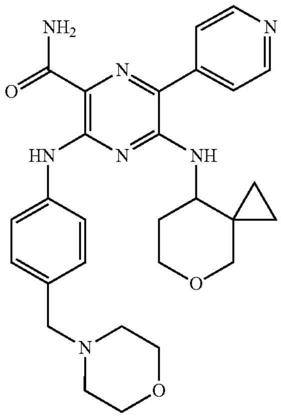 [SMILES: NC(=O)c1nc(-c2ccncc2)c(NC2CCOCC23CC3)nc1Nc1ccc(CN2CCOCC2)cc1] | A | 516 | — |
| 374 | 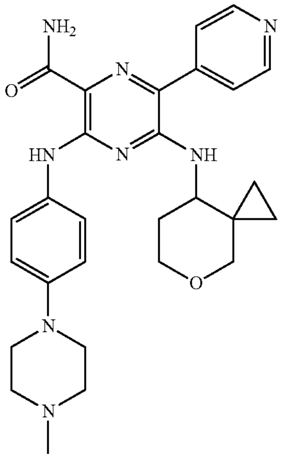 [SMILES: CN1CCN(c2ccc(Nc3nc(NC4CCOCC45CC5)c(-c4ccncc4)nc3C(N)=O)cc2)CC1] | A | 515 | — |

TABLE 2-continued
| | | | | |
|---|---|---|---|---|
| 375 | 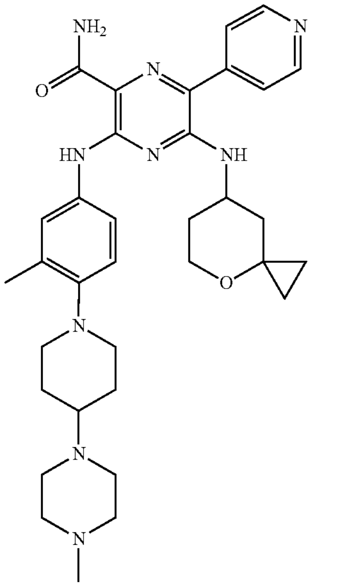 [SMILES: Cc1cc(Nc2nc(NC3CCOC4(CC4)C3)c(-c3ccncc3)nc2C(N)=O)ccc1N1CCC(N2CCN(C)CC2)CC1] | A | 612 | — |
| 376 | 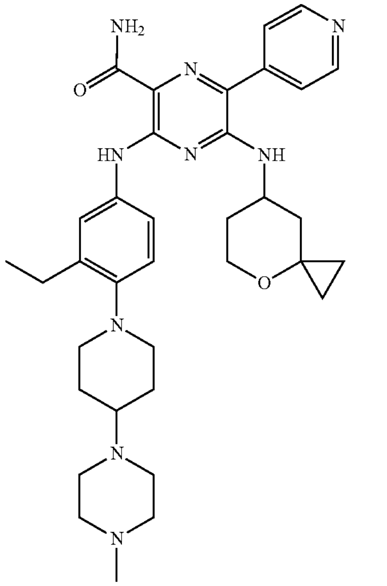 [SMILES: CCc1cc(Nc2nc(NC3CCOC4(CC4)C3)c(-c3ccncc3)nc2C(N)=O)ccc1N1CCC(N2CCN(C)CC2)CC1] | A | 626 | — |
| 377 | 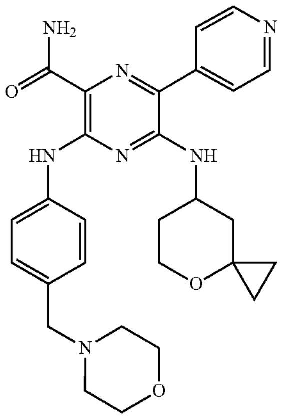 [SMILES: NC(=O)c1nc(-c2ccncc2)c(NC2CCOC3(CC3)C2)nc1Nc1ccc(CN2CCOCC2)cc1] | A | 516 | — |

TABLE 2-continued
| | | | | |
|---|---|---|---|---|
| 378 | 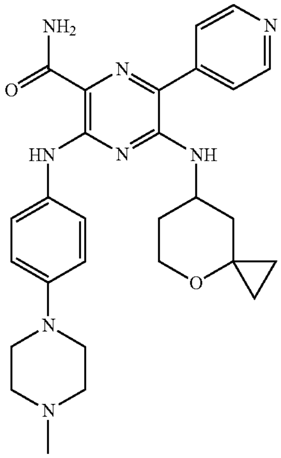 [SMILES: CN1CCN(c2ccc(Nc3nc(NC4CCOC5(CC5)C4)c(-c4ccncc4)nc3C(N)=O)cc2)CC1] | A | 515 | — |
| 379 | 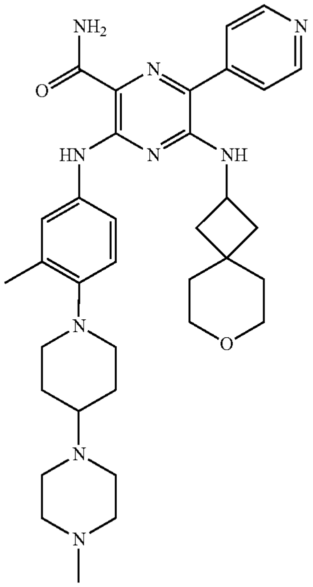 [SMILES: Cc1cc(Nc2nc(NC3CC4(CCOCC4)C3)c(-c3ccncc3)nc2C(N)=O)ccc1N1CCC(N2CCN(C)CC2)CC1] | A | 626 | — |
| 380 | 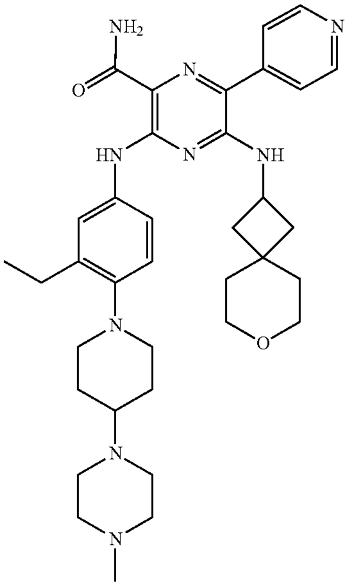 [SMILES: CCc1cc(Nc2nc(NC3CC4(CCOCC4)C3)c(-c3ccncc3)nc2C(N)=O)ccc1N1CCC(N2CCN(C)CC2)CC1] | A | 640 | — |

TABLE 2-continued
| | | | | |
|---|---|---|---|---|
| 381 | 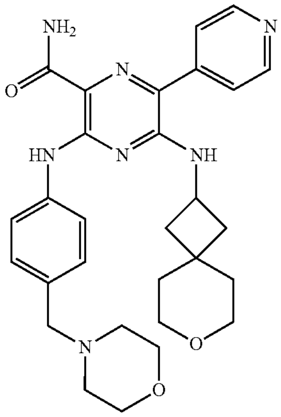 [SMILES: NC(=O)c1nc(-c2ccncc2)c(NC2CC3(CCOCC3)C2)nc1Nc1ccc(CN2CCOCC2)cc1] | A | 530 | — |
| 382 | 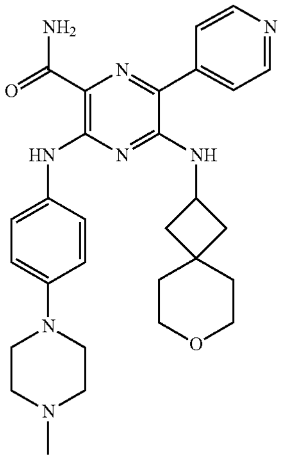 [SMILES: CN1CCN(c2ccc(Nc3nc(NC4CC5(CCOCC5)C4)c(-c4ccncc4)nc3C(N)=O)cc2)CC1] | A | 529 | — |
| 383 | 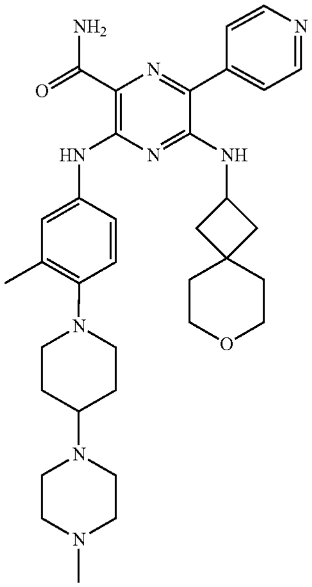 [SMILES: Cc1cc(Nc2nc(NC3CC4(CCOCC4)C3)c(-c3ccncc3)nc2C(N)=O)ccc1N1CCC(N2CCN(C)CC2)CC1] | A | 626 | — |

TABLE 2-continued
| | | | | |
|---|---|---|---|---|
| 384 | 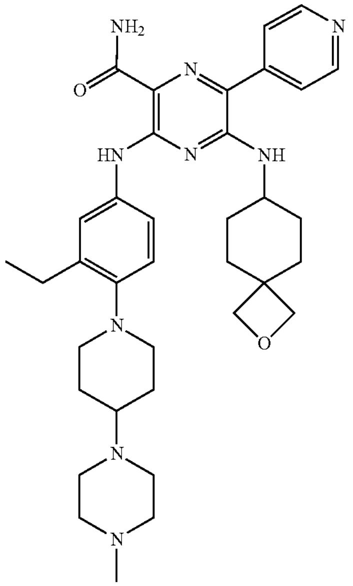 [SMILES: CCc1cc(Nc2nc(NC3CCC4(CC3)COC4)c(-c3ccncc3)nc2C(N)=O)ccc1N1CCC(N2CCN(C)CC2)CC1] | A | 640 | — |
| 385 | 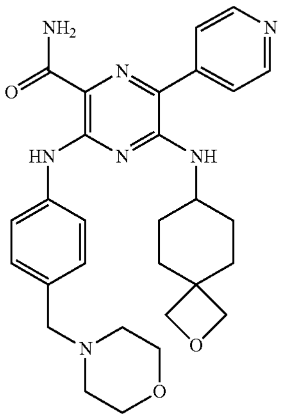 [SMILES: NC(=O)c1nc(-c2ccncc2)c(NC2CCC3(CC2)COC3)nc1Nc1ccc(CN2CCOCC2)cc1] | A | 530 | — |
| 386 | 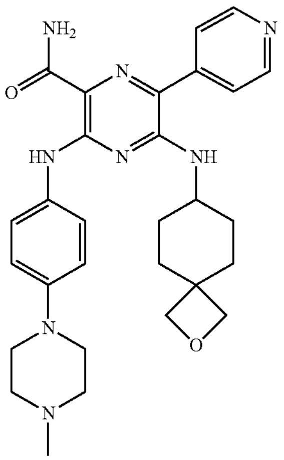 [SMILES: CN1CCN(c2ccc(Nc3nc(NC4CCC5(CC4)COC5)c(-c4ccncc4)nc3C(N)=O)cc2)CC1] | A | 529 | — |

TABLE 2-continued
| | | | | |
|---|---|---|---|---|
| 387 | 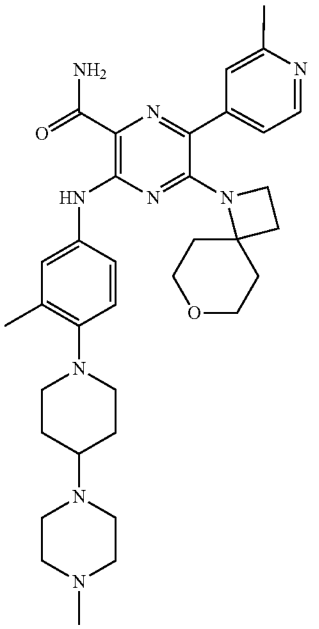 [SMILES: Cc1cc(-c2nc(C(N)=O)c(Nc3ccc(N4CCC(N5CCN(C)CC5)CC4)c(C)c3)nc2N2CCC23CCOCC3)ccn1] | A | 626 | — |
| 388 | 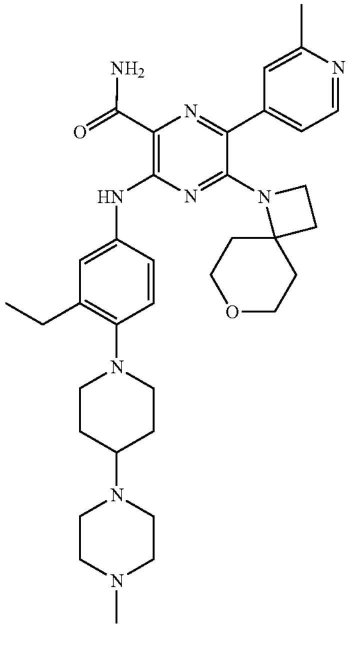 [SMILES: CCc1cc(Nc2nc(N3CCC34CCOCC4)c(-c3ccnc(C)c3)nc2C(N)=O)ccc1N1CCC(N2CCN(C)CC2)CC1] | A | 640 | — |

TABLE 2-continued
| | | | | |
|---|---|---|---|---|
| 389 | 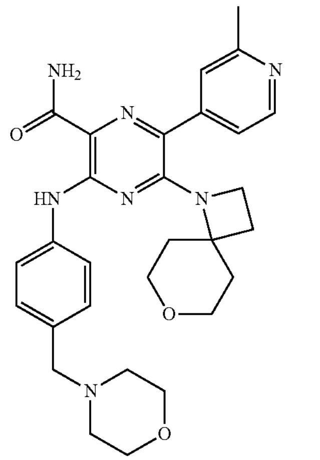 [SMILES: Cc1cc(-c2nc(C(N)=O)c(Nc3ccc(CN4CCOCC4)cc3)nc2N2CCC23CCOCC3)ccn1] | A | 530 | — |
| 390 | 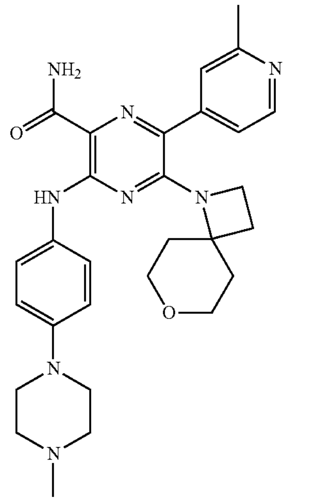 [SMILES: Cc1cc(-c2nc(C(N)=O)c(Nc3ccc(N4CCN(C)CC4)cc3)nc2N2CCC23CCOCC3)ccn1] | A | 529 | — |
| 391 | 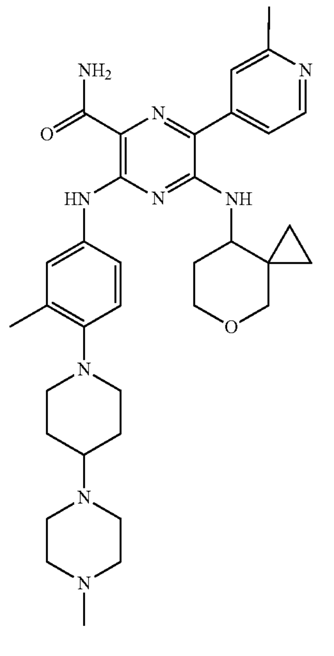 [SMILES: Cc1cc(-c2nc(C(N)=O)c(Nc3ccc(N4CCC(N5CCN(C)CC5)CC4)c(C)c3)nc2NC2CCOCC23CC3)ccn1] | A | 626 | — |

TABLE 2-continued
| | | | | |
|---|---|---|---|---|
| 392 | 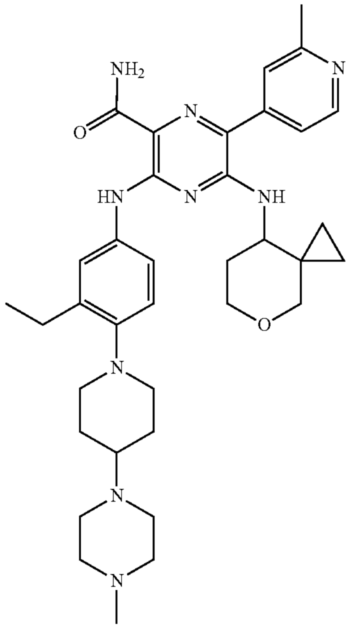 [SMILES: CCc1cc(Nc2nc(NC3CCOCC34CC4)c(-c3ccnc(C)c3)nc2C(N)=O)ccc1N1CCC(N2CCN(C)CC2)CC1] | A | 640 | — |
| 393 | 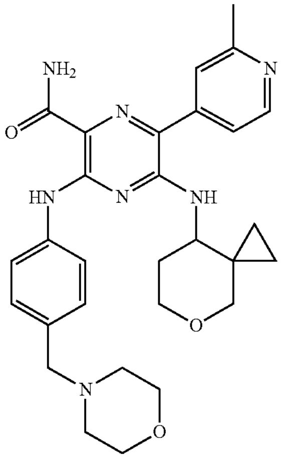 [SMILES: Cc1cc(-c2nc(C(N)=O)c(Nc3ccc(CN4CCOCC4)cc3)nc2NC2CCOCC23CC3)ccn1] | A | 530 | — |
| 394 | 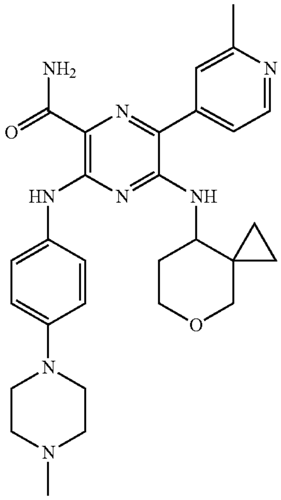 [SMILES: Cc1cc(-c2nc(C(N)=O)c(Nc3ccc(N4CCN(C)CC4)cc3)nc2NC2CCOCC23CC3)ccn1] | A | 529 | — |

TABLE 2-continued
| | | | | |
|---|---|---|---|---|
| 395 | 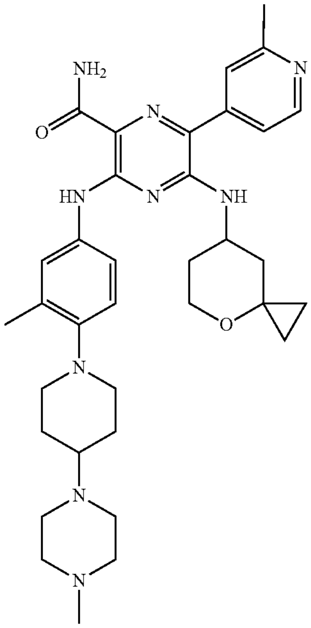 [SMILES: Cc1cc(-c2nc(C(N)=O)c(Nc3ccc(N4CCC(N5CCN(C)CC5)CC4)c(C)c3)nc2NC2CCOC3(CC3)C2)ccn1] | A | 626 | — |
| 396 | 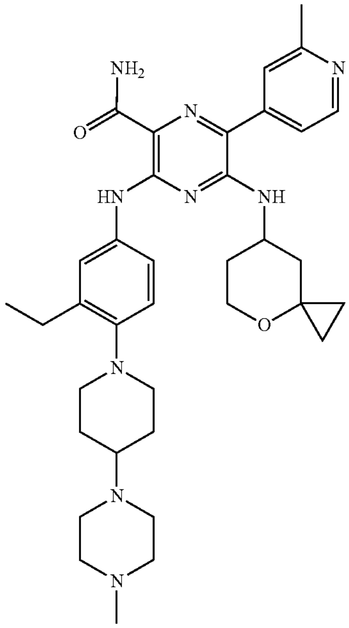 [SMILES: CCc1cc(Nc2nc(NC3CCOC4(CC4)C3)c(-c3ccnc(C)c3)nc2C(N)=O)ccc1N1CCC(N2CCN(C)CC2)CC1] | A | 640 | — |

TABLE 2-continued
| | | | | |
|---|---|---|---|---|
| 397 | 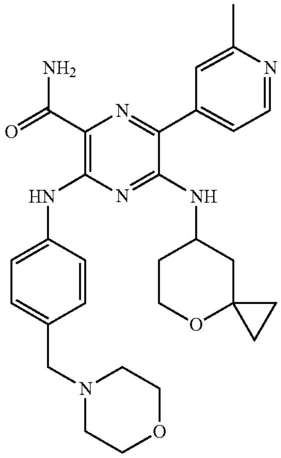 [SMILES: Cc1cc(-c2nc(C(N)=O)c(Nc3ccc(CN4CCOCC4)cc3)nc2NC2CCOC3(CC3)C2)ccn1] | A | 530 | — |
| 398 | 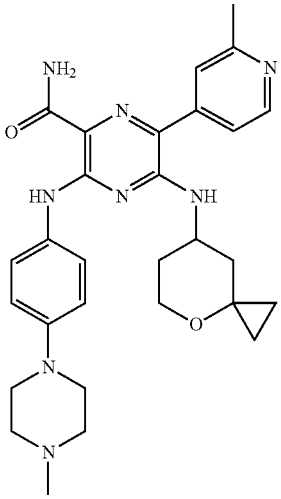 [SMILES: Cc1cc(-c2nc(C(N)=O)c(Nc3ccc(N4CCN(C)CC4)cc3)nc2NC2CCOC3(CC3)C2)ccn1] | A | 529 | — |
| 399 | 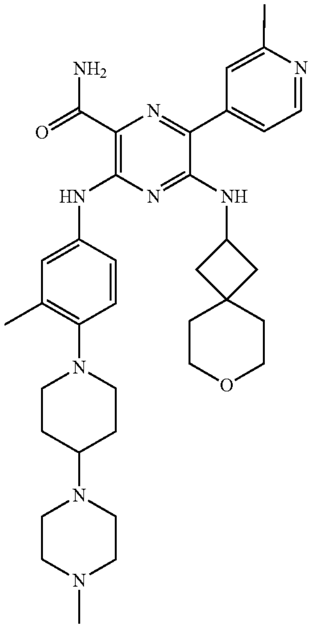 [SMILES: Cc1cc(-c2nc(C(N)=O)c(Nc3ccc(N4CCC(N5CCN(C)CC5)CC4)c(C)c3)nc2NC2CC3(CCOCC3)C2)ccn1] | A | 640 | — |

TABLE 2-continued
| | | | | |
|---|---|---|---|---|
| 400 | 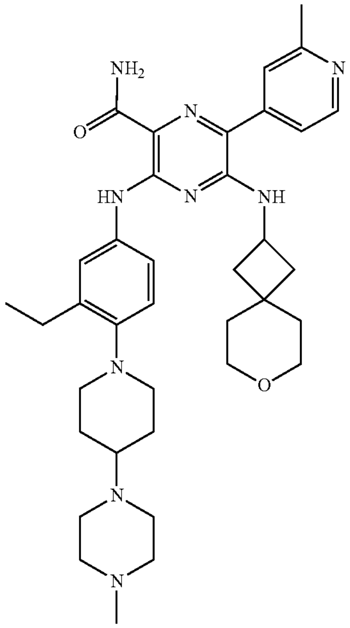 [SMILES: CCc1cc(Nc2nc(NC3CC4(CCOCC4)C3)c(-c3ccnc(C)c3)nc2C(N)=O)ccc1N1CCC(N2CCN(C)CC2)CC1] | A | 654 | — |
| 401 | 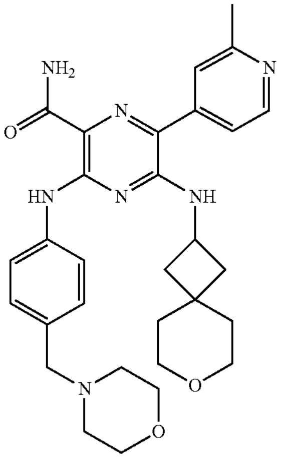 [SMILES: Cc1cc(-c2nc(C(N)=O)c(Nc3ccc(CN4CCOCC4)cc3)nc2NC2CC3(CCOCC3)C2)ccn1] | A | 544 | — |
| 402 | 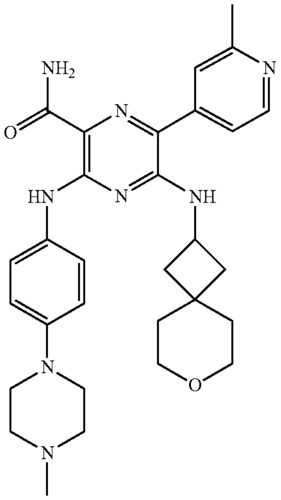 [SMILES: Cc1cc(-c2nc(C(N)=O)c(Nc3ccc(N4CCN(C)CC4)cc3)nc2NC2CC3(CCOCC3)C2)ccn1] | A | 543 | — |

TABLE 2-continued
| | | | | |
|---|---|---|---|---|
| 403 | 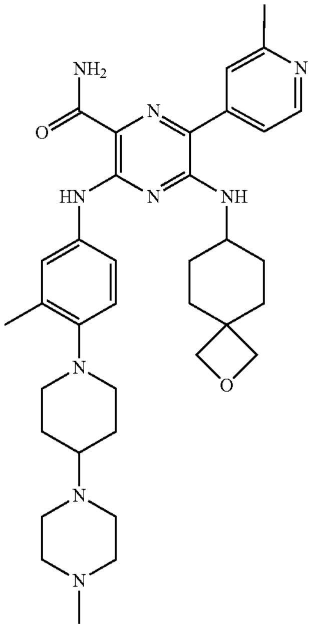 [SMILES: Cc1cc(-c2nc(C(N)=O)c(Nc3ccc(N4CCC(N5CCN(C)CC5)CC4)c(C)c3)nc2NC2CCC3(CC2)COC3)ccn1] | A | 640 | — |
| 404 | 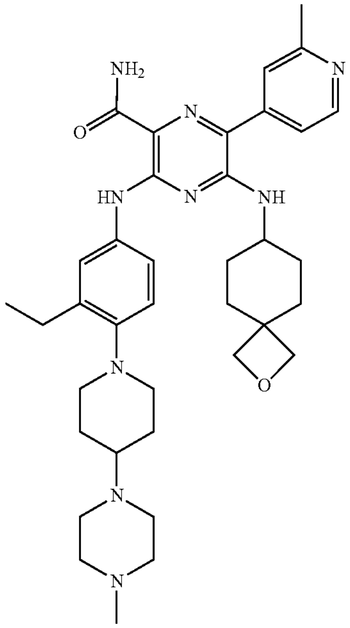 [SMILES: CCc1cc(Nc2nc(NC3CCC4(CC3)COC4)c(-c3ccnc(C)c3)nc2C(N)=O)ccc1N1CCC(N2CCN(C)CC2)CC1] | A | 654 | — |

TABLE 2-continued
| | | | | |
|---|---|---|---|---|
| 405 | 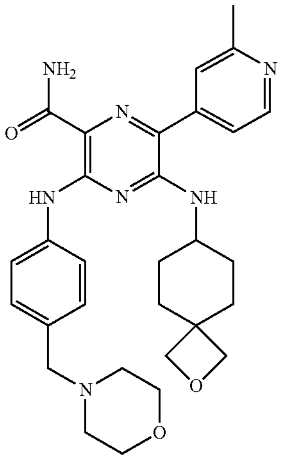 [SMILES: Cc1cc(-c2nc(C(N)=O)c(Nc3ccc(CN4CCOCC4)cc3)nc2NC2CCC3(CC2)COC3)ccn1] | A | 544 | — |
| 406 | 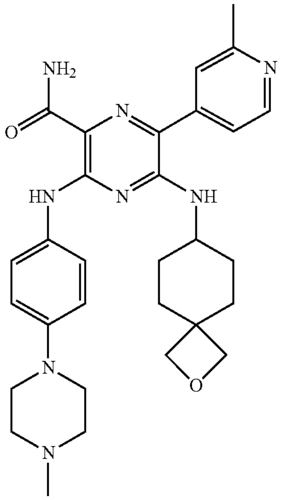 [SMILES: Cc1cc(-c2nc(C(N)=O)c(Nc3ccc(N4CCN(C)CC4)cc3)nc2NC2CCC3(CC2)COC3)ccn1] | A | 543 | — |
| 407 | 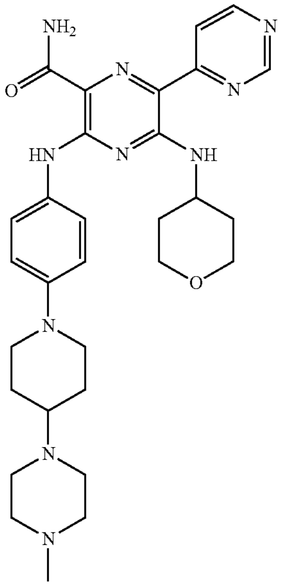 [SMILES: CN1CCN(C2CCN(c3ccc(Nc4nc(NC5CCOCC5)c(-c5ccncn5)nc4C(N)=O)cc3)CC2)CC1] | A | 573 | — |

TABLE 2-continued
| | | | | |
|---|---|---|---|---|
| 408 | 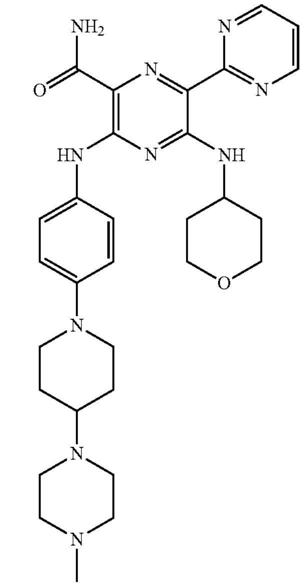 [SMILES: CN1CCN(C2CCN(c3ccc(Nc4nc(NC5CCOCC5)c(-c5ncccn5)nc4C(N)=O)cc3)CC2)CC1] | A | 573 | — |
| 409 | 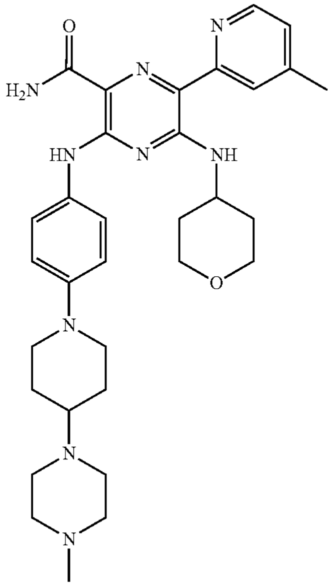 [SMILES: Cc1ccnc(-c2nc(C(N)=O)c(Nc3ccc(N4CCC(N5CCN(C)CC5)CC4)cc3)nc2NC2CCOCC2)c1] | A | 586 | — |

TABLE 2-continued
| | | | | |
|---|---|---|---|---|
| 410 | 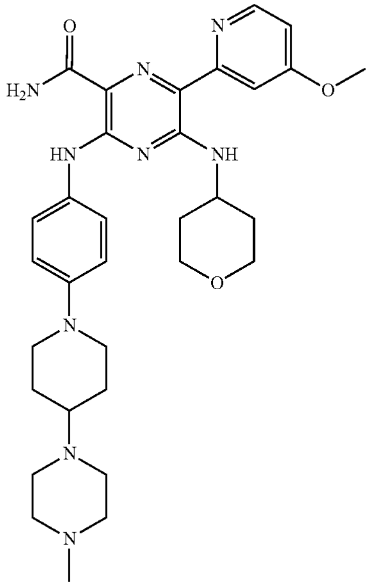 [SMILES: COc1ccnc(-c2nc(C(N)=O)c(Nc3ccc(N4CCC(N5CCN(C)CC5)CC4)cc3)nc2NC2CCOCC2)c1] | A | 602 | 1.534 |
| 411 | 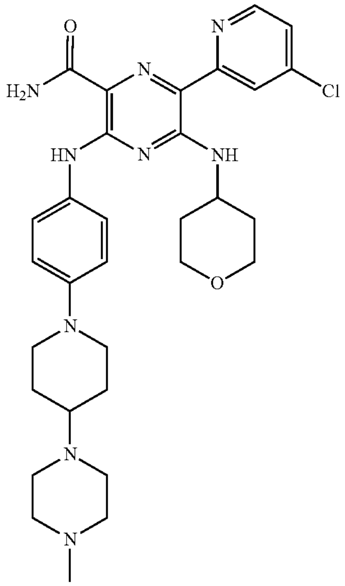 [SMILES: CN1CCN(C2CCN(c3ccc(Nc4nc(NC5CCOCC5)c(-c5cc(Cl)ccn5)nc4C(N)=O)cc3)CC2)CC1] | A | 606 | — |

TABLE 2-continued
| | | | | |
|---|---|---|---|---|
| 412 | 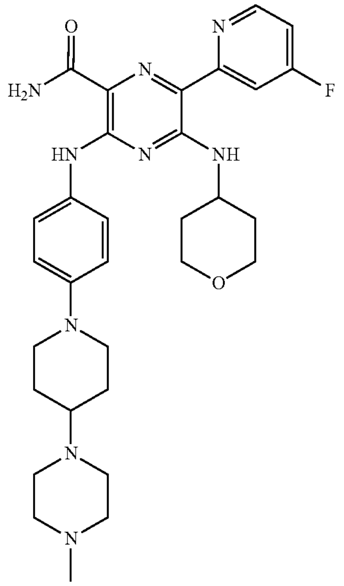 [SMILES: CN1CCN(C2CCN(c3ccc(Nc4nc(NC5CCOCC5)c(-c5cc(F)ccn5)nc4C(N)=O)cc3)CC2)CC1] | A | 590 | — |
| 413 | 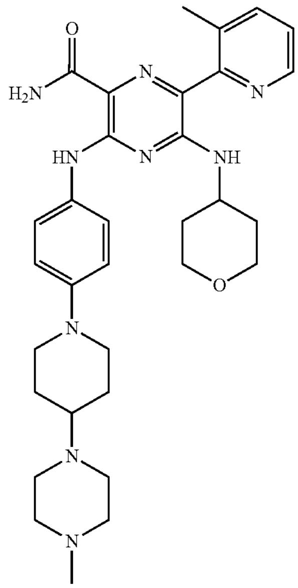 [SMILES: Cc1cccnc1-c1nc(C(N)=O)c(Nc2ccc(N3CCC(N4CCN(C)CC4)CC3)cc2)nc1NC1CCOCC1] | A | 586 | — |

TABLE 2-continued
| | | | | |
|---|---|---|---|---|
| 414 | 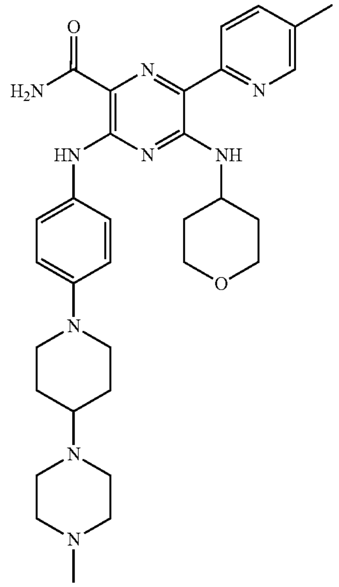 [SMILES: Cc1ccc(-c2nc(C(N)=O)c(Nc3ccc(N4CCC(N5CCN(C)CC5)CC4)cc3)nc2NC2CCOCC2)nc1] | A | 586 | — |
| 415 | 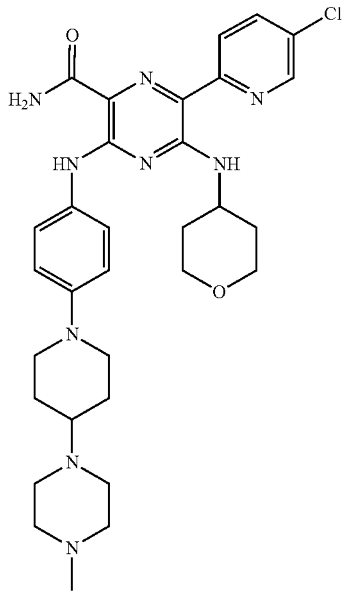 [SMILES: CN1CCN(C2CCN(c3ccc(Nc4nc(NC5CCOCC5)c(-c5ccc(Cl)cn5)nc4C(N)=O)cc3)CC2)CC1] | A | 606 | — |

TABLE 2-continued
| | | | | |
|---|---|---|---|---|
| 416 | 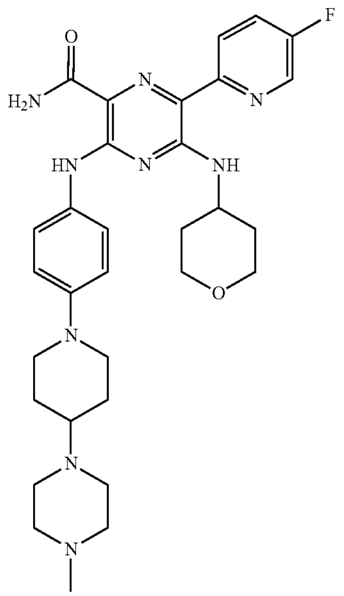 [SMILES: CN1CCN(C2CCN(c3ccc(Nc4nc(NC5CCOCC5)c(-c5ccc(F)cn5)nc4C(N)=O)cc3)CC2)CC1] | A | 590 | — |
| 417 | 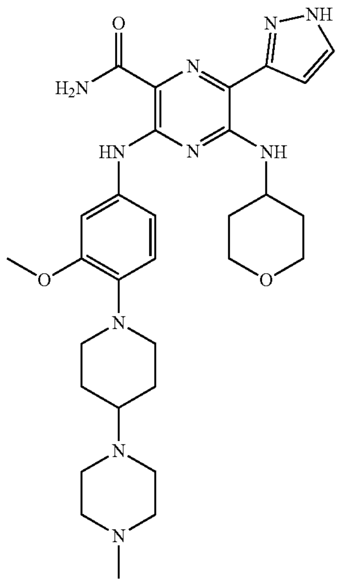 [SMILES: COc1cc(Nc2nc(NC3CCOCC3)c(-c3cc[nH]n3)nc2C(N)=O)ccc1N1CCC(N2CCN(C)CC2)CC1] | A | 591 | 1.347 |

TABLE 2-continued
| | | | | |
|---|---|---|---|---|
| 418 | 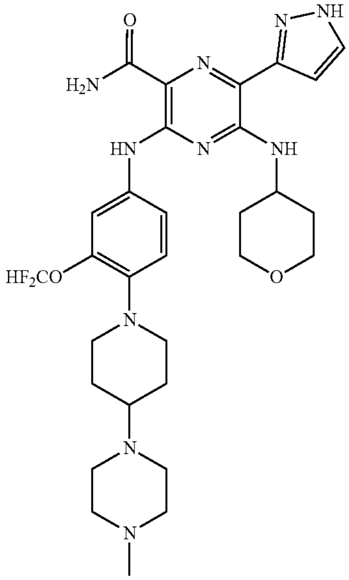 | A | 627 | — |
| 419 | 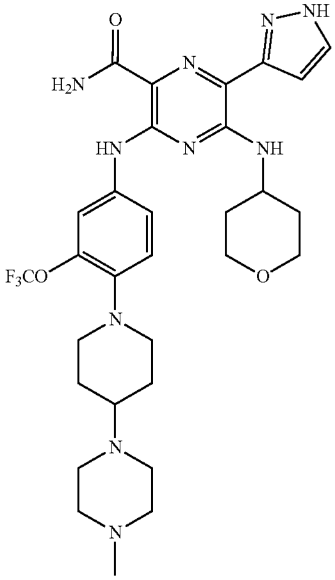 [SMILES: CN1CCN(C2CCN(c3ccc(Nc4nc(NC5CCOCC5)c(-c5cc[nH]n5)nc4C(N)=O)cc3OC(F)(F)F)CC2)CC1] | A | 645 | 1.608 |

TABLE 2-continued
| | | | | |
|---|---|---|---|---|
| 420 | 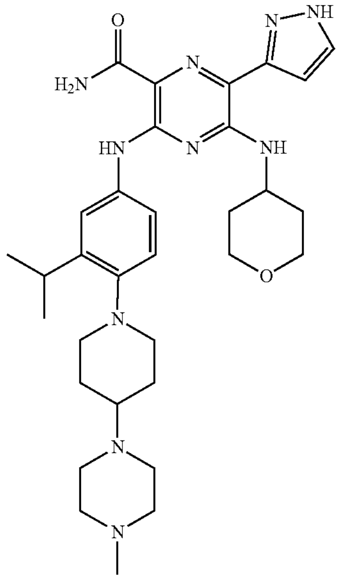 [SMILES: CC(C)c1cc(Nc2nc(NC3CCOCC3)c(-c3cc[nH]n3)nc2C(N)=O)ccc1N1CCC(N2CCN(C)CC2)CC1] | A | 603 | 1.516 |
| 421 | 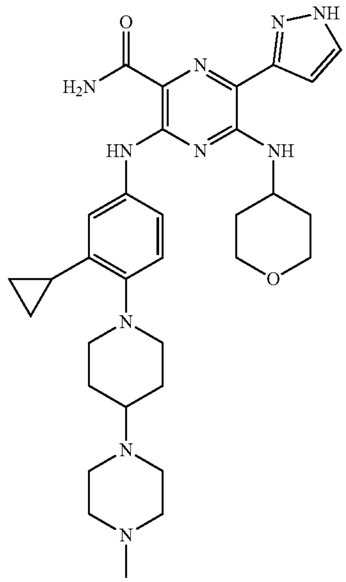 [SMILES: CN1CCN(C2CCN(c3ccc(Nc4nc(NC5CCOCC5)c(-c5cc[nH]n5)nc4C(N)=O)cc3C3CC3)CC2)CC1] | A | 601 | 1.491 |

TABLE 2-continued
| | | | | |
|---|---|---|---|---|
| 422 | 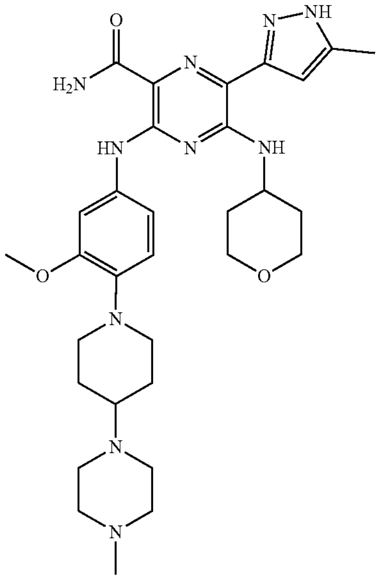 | A | 605 | — |
| 423 | 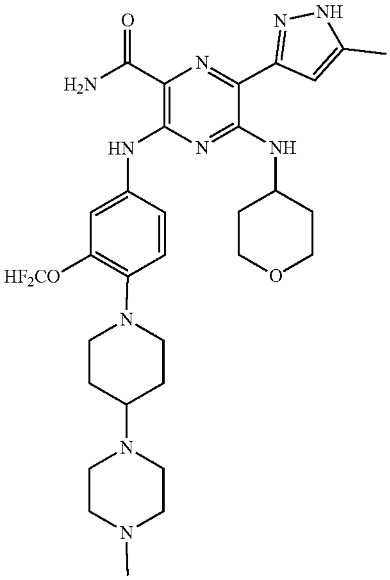 | A | 641 | — |

TABLE 2-continued
| | | | | |
|---|---|---|---|---|
| 424 | 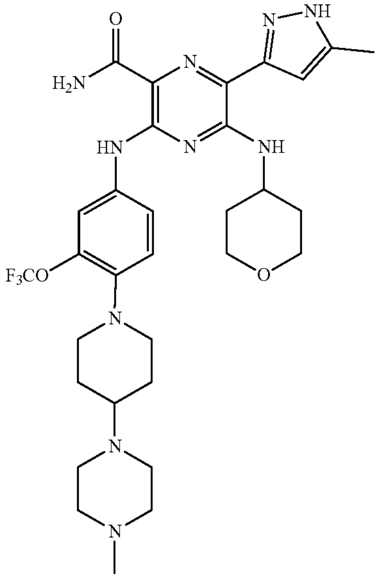 [SMILES: Cc1cc(-c2nc(C(N)=O)c(Nc3ccc(N4CCC(N5CCN(C)CC5)CC4)c(OC(F)(F)F)c3)nc2NC2CCOCC2)n[nH]1] | A | 659 | — |
| 425 | 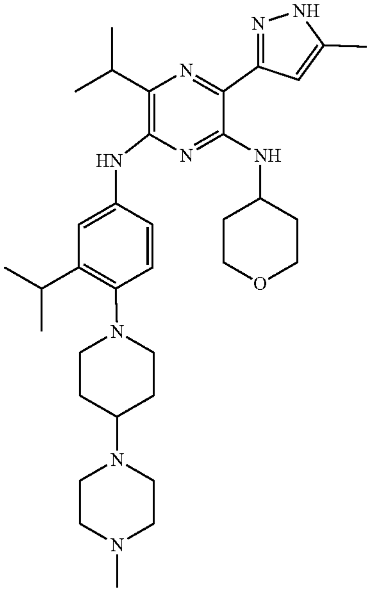 [SMILES: Cc1cc(-c2nc(C(C)C)c(Nc3ccc(N4CCC(N5CCN(C)CC5)CC4)c(C(C)C)c3)nc2NC2CCOCC2)n[nH]1] | A | 617 | — |

TABLE 2-continued
| | | | | |
|---|---|---|---|---|
| 426 | 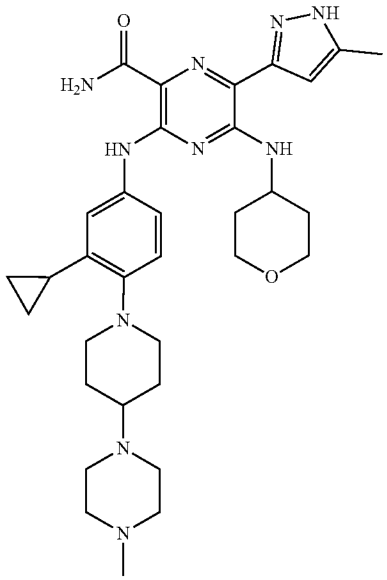 [SMILES: Cc1cc(-c2nc(C(N)=O)c(Nc3ccc(N4CCC(N5CCN(C)CC5)CC4)c(C4CC4)c3)nc2NC2CCOCC2)n[nH]1] | A | 615 | — |
| 427 | 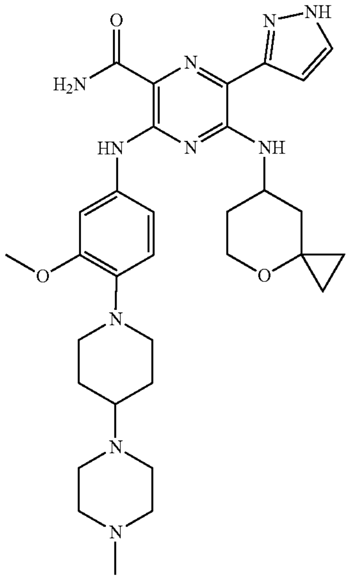 | A | 617 | — |

TABLE 2-continued
| | | | | |
|---|---|---|---|---|
| 428 | 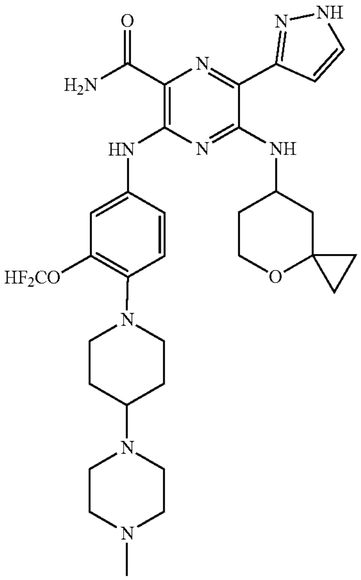 | A | 653 | — |
| 429 | 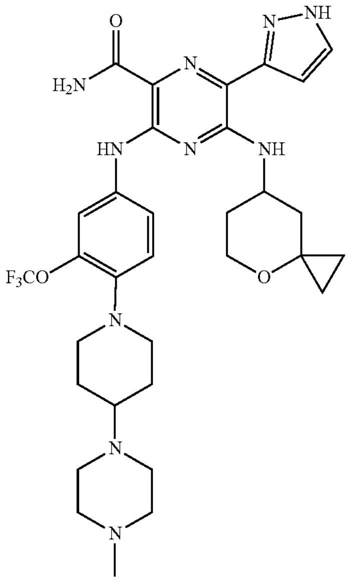 [SMILES: CN1CCN(C2CCN(c3ccc(Nc4nc(NC5CCOC6(CC6)C5)c(-c5cc[nH]n5)nc4C(N)=O)cc3OC(F)(F)F)CC2)CC1] | A | 671 | — |

TABLE 2-continued
| | | | | |
|---|---|---|---|---|
| 430 | 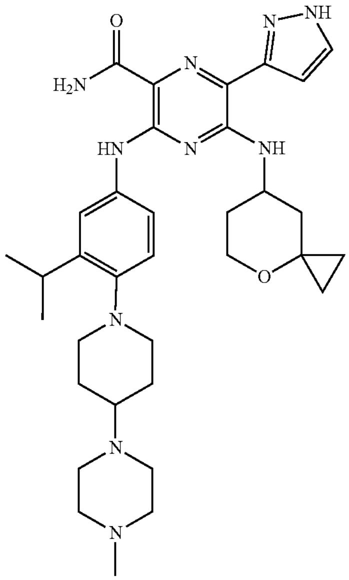 [SMILES: CC(C)c1cc(Nc2nc(NC3CCOC4(CC4)C3)c(-c3cc[nH]n3)nc2C(N)=O)ccc1N1CCC(N2CCN(C)CC2)CC1] | A | 629 | — |
| 431 | 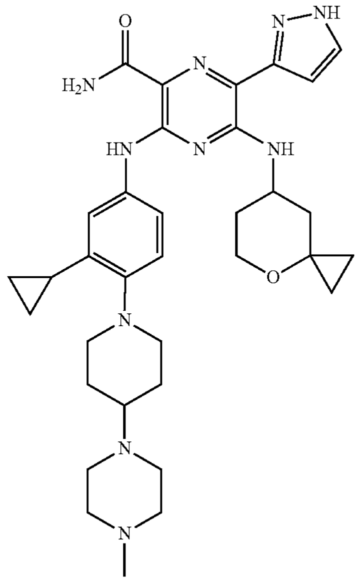 [SMILES: CN1CCN(C2CCN(c3ccc(Nc4nc(NC5CCOC6(CC6)C5)c(-c5cc[nH]n5)nc4C(N)=O)cc3C3CC3)CC2)CC1] | A | 627 | — |

TABLE 2-continued
| | | | | |
|---|---|---|---|---|
| 432 | 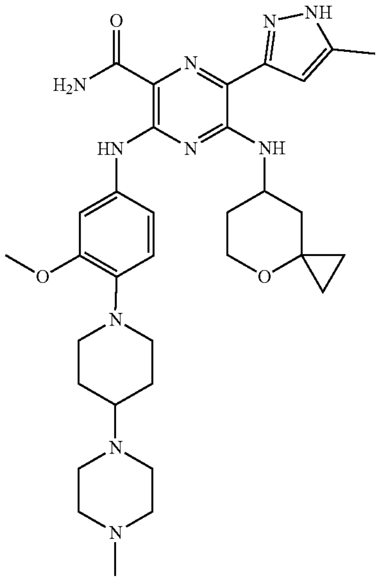 | A | 631 | — |
| 433 | 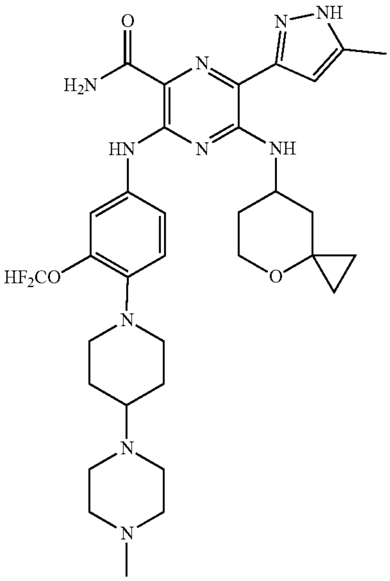 | A | 667 | — |

TABLE 2-continued
| | | | | |
|---|---|---|---|---|
| 434 | 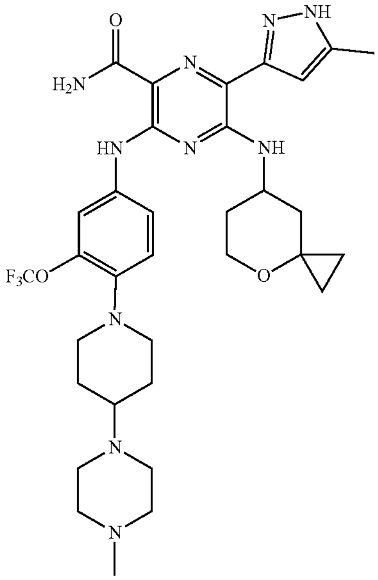 [SMILES: Cc1cc(-c2nc(C(N)=O)c(Nc3ccc(N4CCC(N5CCN(C)CC5)CC4)c(OC(F)(F)F)c3)nc2NC2CCOC3(CC3)C2)n[nH]1] | A | 685 | — |
| 435 | 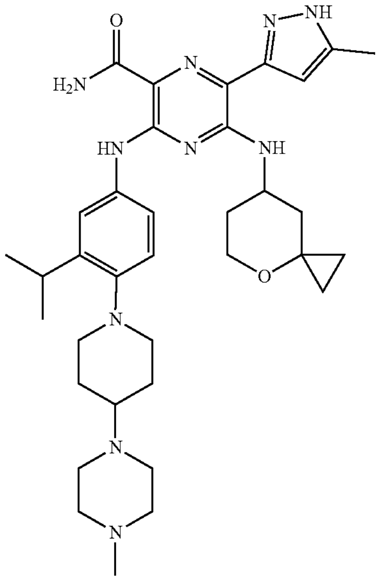 [SMILES: Cc1cc(-c2nc(C(N)=O)c(Nc3ccc(N4CCC(N5CCN(C)CC5)CC4)c(C(C)C)c3)nc2NC2CCOC3(CC3)C2)n[nH]1] | A | 643 | — |

TABLE 2-continued
| | | | | |
|---|---|---|---|---|
| 436 | 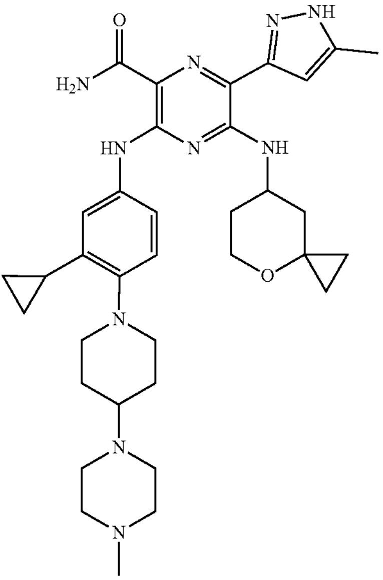 [SMILES: Cc1cc(-c2nc(C(N)=O)c(Nc3ccc(N4CCC(N5CCN(C)CC5)CC4)c(C4CC4)c3)nc2NC2CCOC3(CC3)C2)n[nH]1] | A | 641 | — |
| 437 | 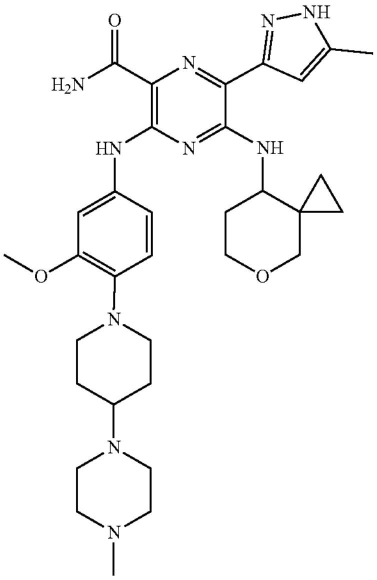 | A | 617 | — |

TABLE 2-continued
| | | | | |
|---|---|---|---|---|
| 438 | 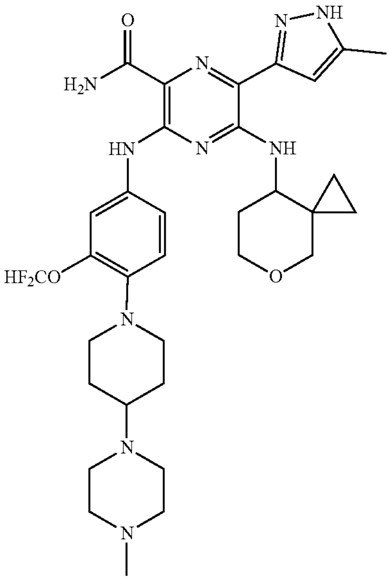 | A | 653 | — |
| 439 | 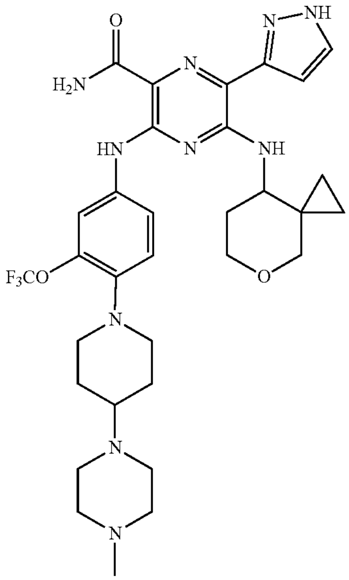 [SMILES: CN1CCN(C2CCN(c3ccc(Nc4nc(NC5CCOCC56CC6)c(-c5cc[nH]n5)nc4C(N)=O)cc3OC(F)(F)F)CC2)CC1] | A | 671 | — |

TABLE 2-continued
| | | | | |
|---|---|---|---|---|
| 440 | 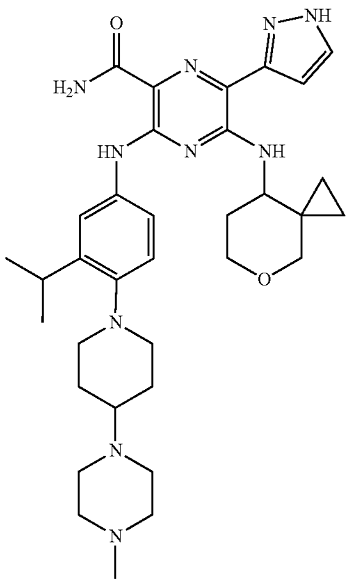 [SMILES: CC(C)c1cc(Nc2nc(NC3CCOCC34CC4)c(-c3cc[nH]n3)nc2C(N)=O)ccc1N1CCC(N2CCN(C)CC2)CC1] | A | 629 | — |
| 441 | 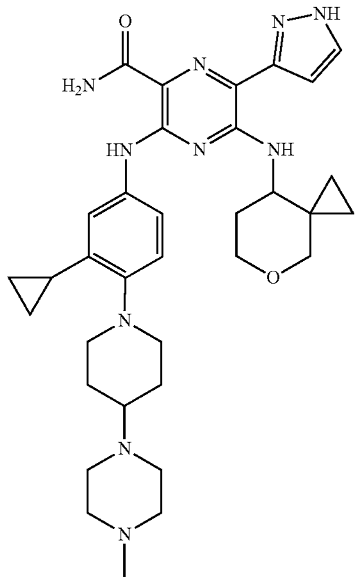 [SMILES: CN1CCN(C2CCN(c3ccc(Nc4nc(NC5CCOCC56CC6)c(-c5cc[nH]n5)nc4C(N)=O)cc3C3CC3)CC2)CC1] | A | 627 | — |

TABLE 2-continued
| | | | | |
|---|---|---|---|---|
| 442 | 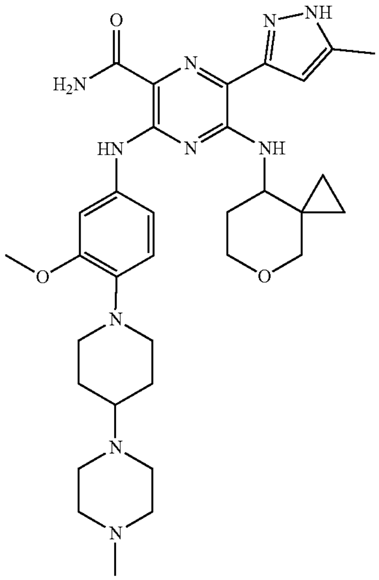 | A | 631 | — |
| 443 | 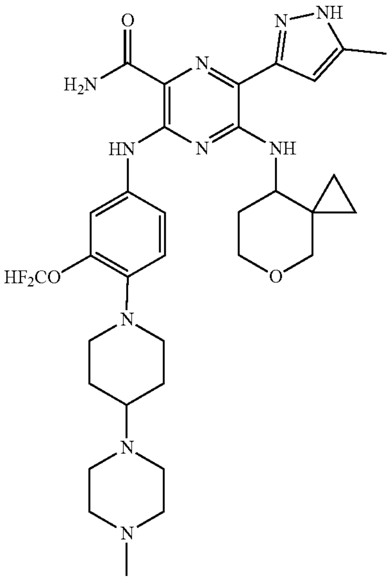 | A | 667 | — |

TABLE 2-continued
| | | | | |
|---|---|---|---|---|
| 444 | 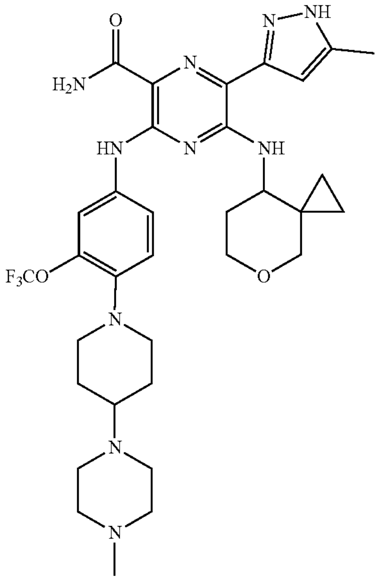 [SMILES: Cc1cc(-c2nc(C(N)=O)c(Nc3ccc(N4CCC(N5CCN(C)CC5)CC4)c(OC(F)(F)F)c3)nc2NC2CCOCC23CC3)n[nH]1] | A | 685 | — |
| 445 | 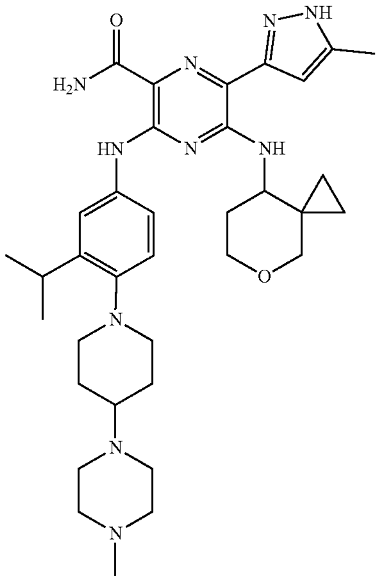 [SMILES: Cc1cc(-c2nc(C(N)=O)c(Nc3ccc(N4CCC(N5CCN(C)CC5)CC4)c(C(C)C)c3)nc2NC2CCOCC23CC3)n[nH]1] | A | 643 | — |

TABLE 2-continued
| | | | | |
|---|---|---|---|---|
| 446 | 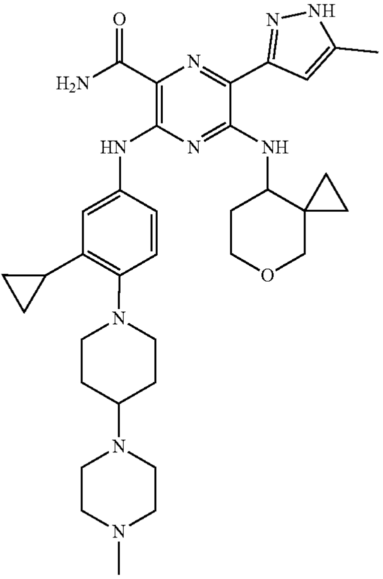 [SMILES: Cc1cc(-c2nc(C(N)=O)c(Nc3ccc(N4CCC(N5CCN(C)CC5)CC4)c(C4CC4)c3)nc2NC2CCOCC23CC3)n[nH]1] | A | 641 | — |
| 447 | 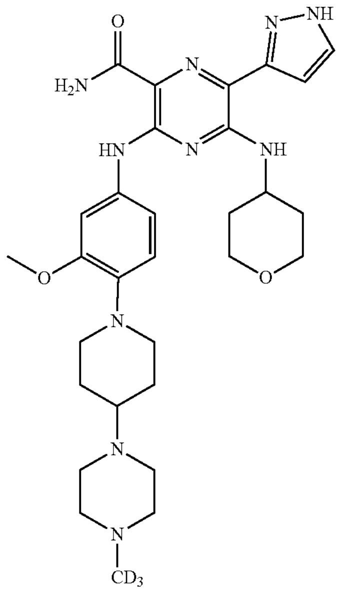 [SMILES: [2H]C([2H])([2H])N1CCN(C2CCN(c3ccc(Nc4nc(NC5CCOCC5)c(-c5cc[nH]n5)nc4C(N)=O)cc3OC)CC2)CC1] | A | 594 | — |

TABLE 2-continued
| | | | | |
|---|---|---|---|---|
| 448 | 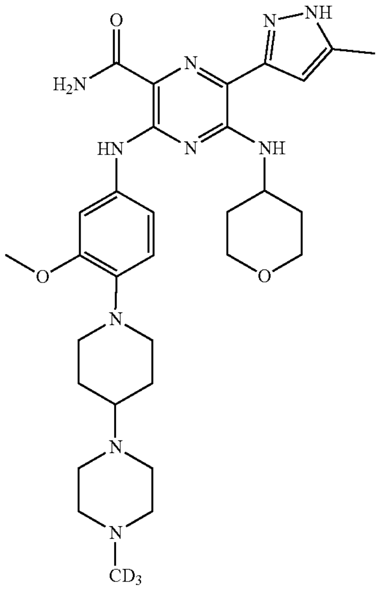 | A | 608 | — |
| 449 | 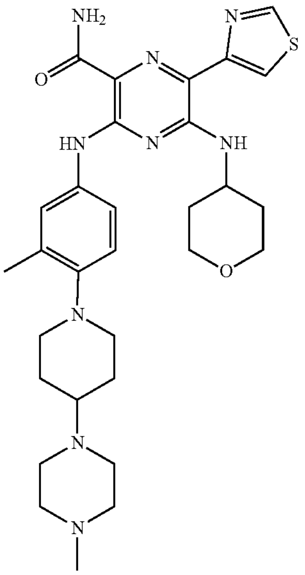 [SMILES: Cc1cc(Nc2nc(NC3CCOCC3)c(-c3cscn3)nc2C(N)=O)ccc1N1CCC(N2CCN(C)CC2)CC1] | A | 592 | — |

TABLE 2-continued
| | | | | |
|---|---|---|---|---|
| 450 | 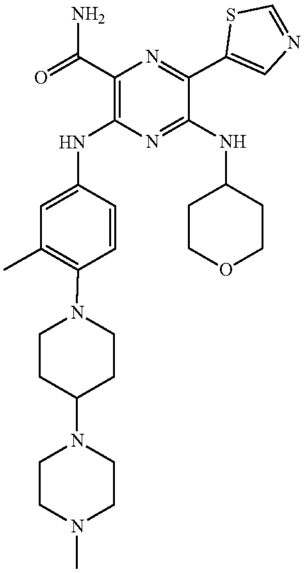 [SMILES: Cc1cc(Nc2nc(NC3CCOCC3)c(-c3cncs3)nc2C(N)=O)ccc1N1CCC(N2CCN(C)CC2)CC1] | A | 592 | — |
| 451 | 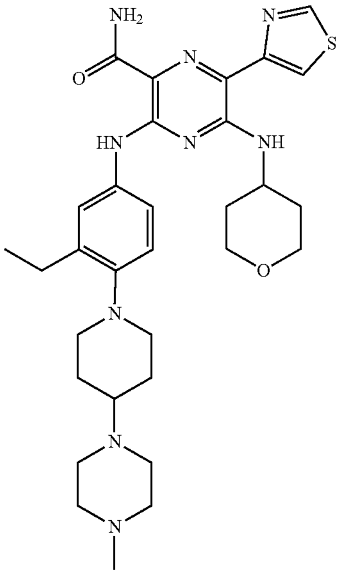 [SMILES: CCc1cc(Nc2nc(NC3CCOCC3)c(-c3cscn3)nc2C(N)=O)ccc1N1CCC(N2CCN(C)CC2)CC1] | A | 606 | — |

TABLE 2-continued
| | | | | |
|---|---|---|---|---|
| 452 | 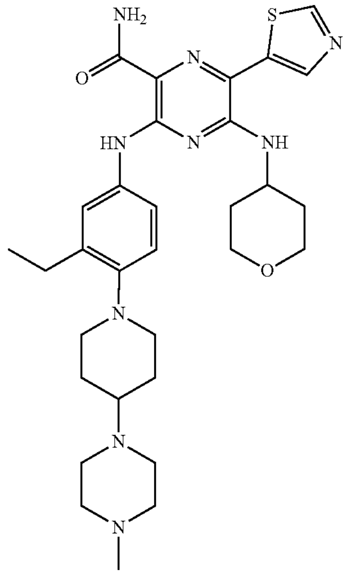 [SMILES: CCc1cc(Nc2nc(NC3CCOCC3)c(-c3cncs3)nc2C(N)=O)ccc1N1CCC(N2CCN(C)CC2)CC1] | A | 606 | — |
| 453 | 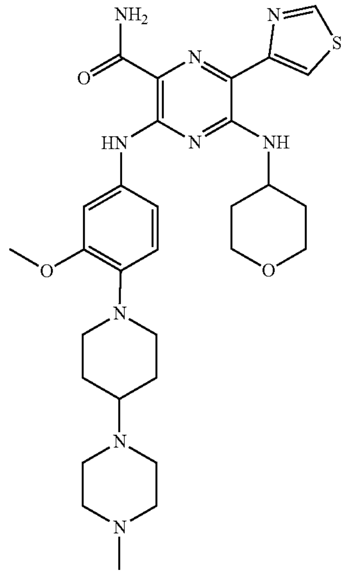 [SMILES: COc1cc(Nc2nc(NC3CCOCC3)c(-c3cscn3)nc2C(N)=O)ccc1N1CCC(N2CCN(C)CC2)CC1] | A | 608 | — |

TABLE 2-continued
| | | | | |
|---|---|---|---|---|
| 454 | 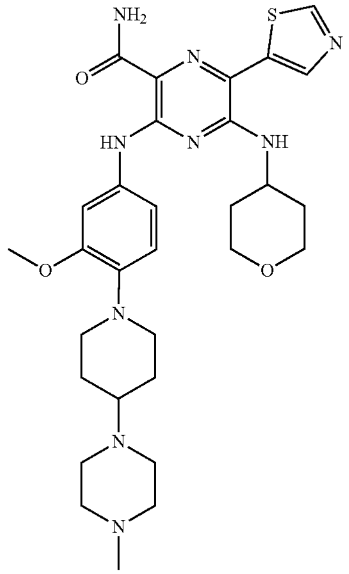 [SMILES: COc1cc(Nc2nc(NC3CCOCC3)c(-c3cncs3)nc2C(N)=O)ccc1N1CCC(N2CCN(C)CC2)CC1] | A | 608 | — |
| 455 | 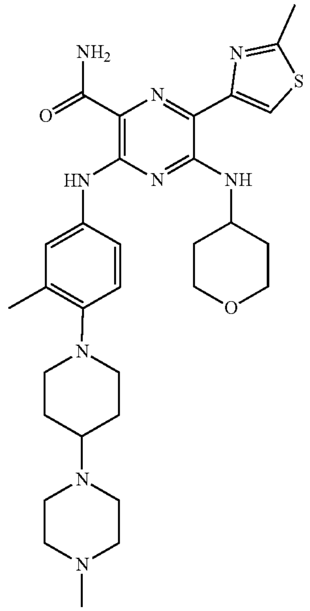 [SMILES: Cc1nc(-c2nc(C(N)=O)c(Nc3ccc(N4CCC(N5CCN(C)CC5)CC4)c(C)c3)nc2NC2CCOCC2)cs1] | A | 606 | — |

TABLE 2-continued
| | | | | |
|---|---|---|---|---|
| 456 | 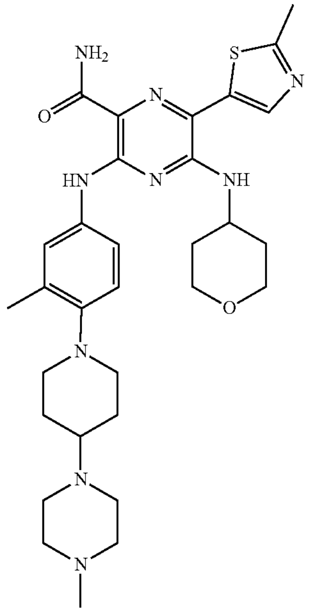 [SMILES: Cc1ncc(-c2nc(C(N)=O)c(Nc3ccc(N4CCC(N5CCN(C)CC5)CC4)c(C)c3)nc2NC2CCOCC2)s1] | A | 606 | — |
| 457 | 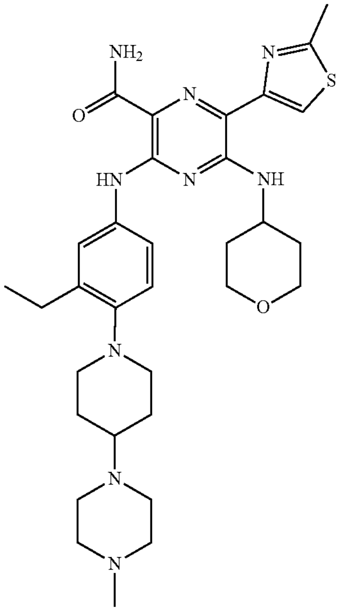 | A | 620 | — |

TABLE 2-continued
| | | | | |
|---|---|---|---|---|
| 458 | 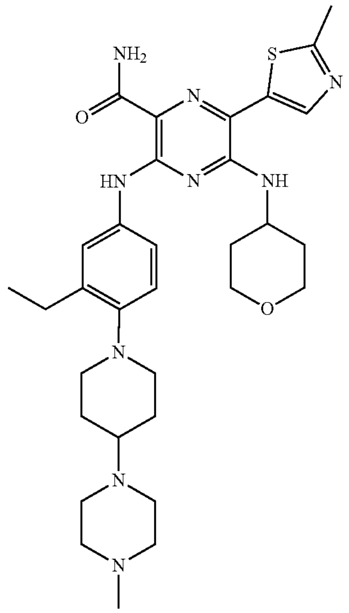 [SMILES: CCc1cc(Nc2nc(NC3CCOCC3)c(-c3cnc(C)s3)nc2C(N)=O)ccc1N1CCC(N2CCN(C)CC2)CC1] | A | 620 | — |
| 459 | 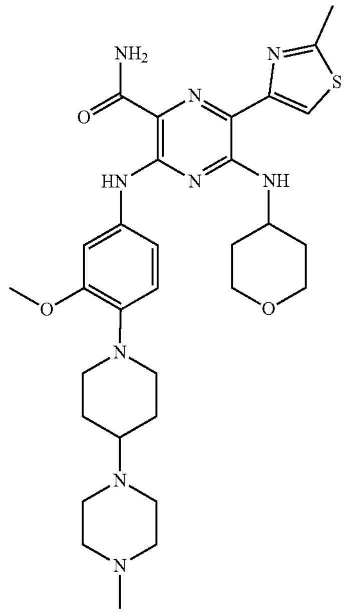 | A | 622 | — |

TABLE 2-continued
| | | | | |
|---|---|---|---|---|
| 460 | 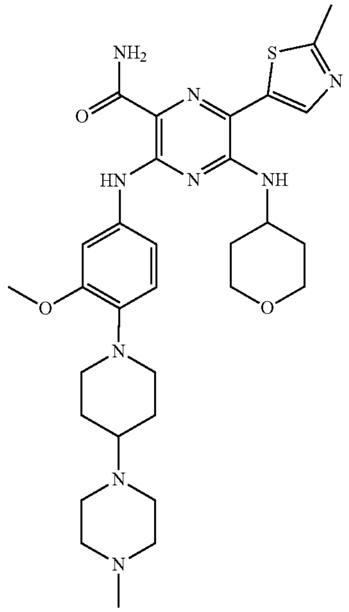 [SMILES: COc1cc(Nc2nc(NC3CCOCC3)c(-c3cnc(C)s3)nc2C(N)=O)ccc1N1CCC(N2CCN(C)CC2)CC1] | A | 622 | — |
| 461 | 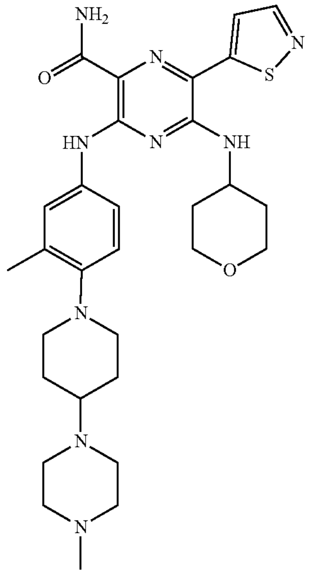 | A | 592 | — |

TABLE 2-continued
| | | | | |
|---|---|---|---|---|
| 462 | 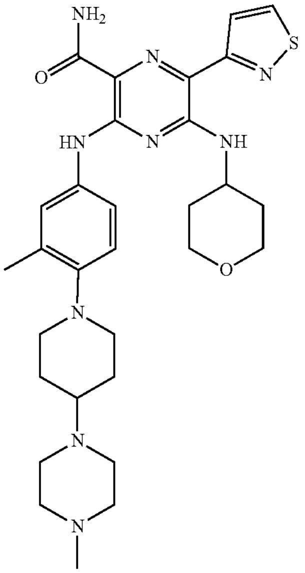 [SMILES: Cc1cc(Nc2nc(NC3CCOCC3)c(-c3ccsn3)nc2C(N)=O)ccc1N1CCC(N2CCN(C)CC2)CC1] | A | 592 | — |
| 463 | 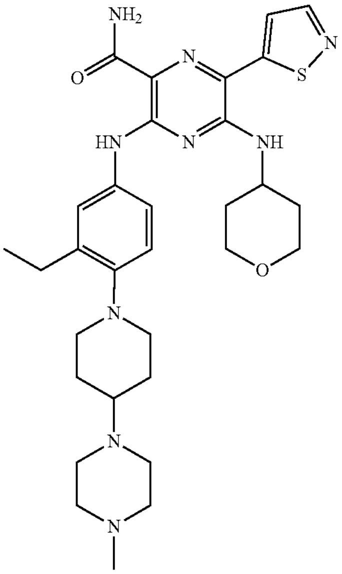 | A | 606 | — |

TABLE 2-continued
| | | | | |
|---|---|---|---|---|
| 464 | 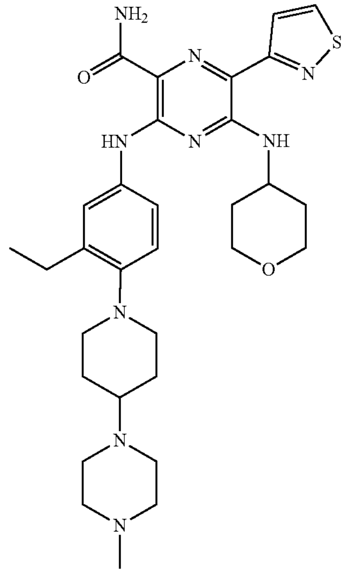 | A | 606 | — |
| 465 | 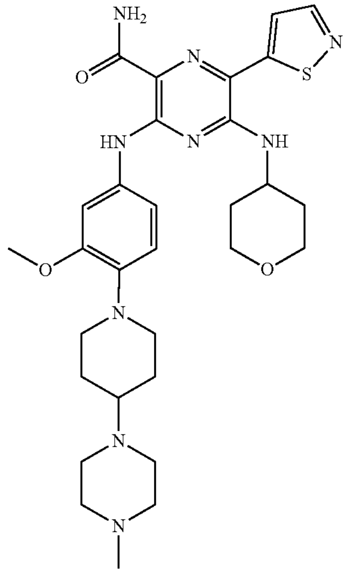 | A | 608 | — |

TABLE 2-continued
| | | | | |
|---|---|---|---|---|
| 466 | 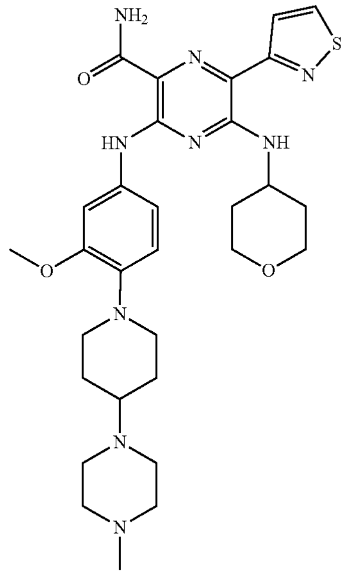 | A | 608 | — |
| 467 | 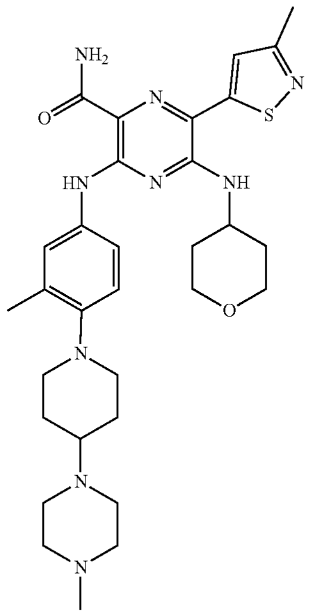 | A | 606 | — |

TABLE 2-continued
| | | | | |
|---|---|---|---|---|
| 468 | 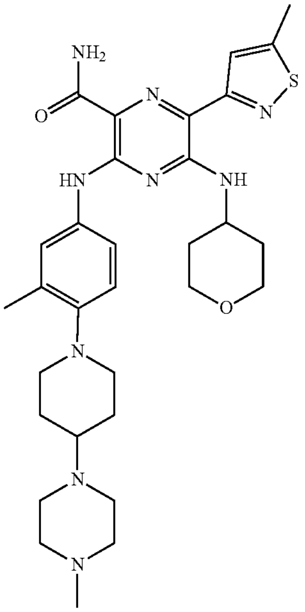 | A | 606 | — |
| 469 | 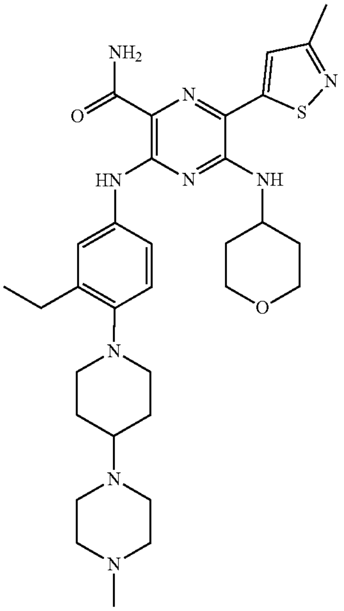 [SMILES: CCc1cc(Nc2nc(NC3CCOCC3)c(-c3cc(C)ns3)nc2C(N)=O)ccc1N1CCC(N2CCN(C)CC2)CC1] | A | 620 | — |

TABLE 2-continued
| | | | | |
|---|---|---|---|---|
| 470 | 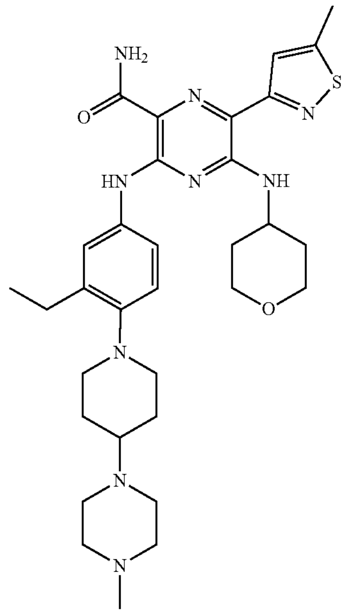 [SMILES: CCc1cc(Nc2nc(NC3CCOCC3)c(-c3cc(C)sn3)nc2C(N)=O)ccc1N1CCC(N2CCN(C)CC2)CC1] | A | 620 | — |
| 471 | 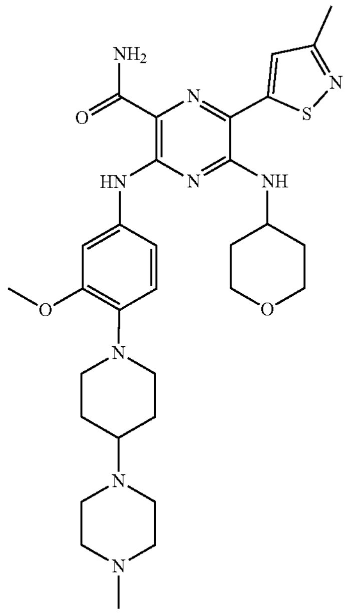 [SMILES: COc1cc(Nc2nc(NC3CCOCC3)c(-c3cc(C)ns3)nc2C(N)=O)ccc1N1CCC(N2CCN(C)CC2)CC1] | A | 622 | — |

TABLE 2-continued
| | | | | |
|---|---|---|---|---|
| 472 | 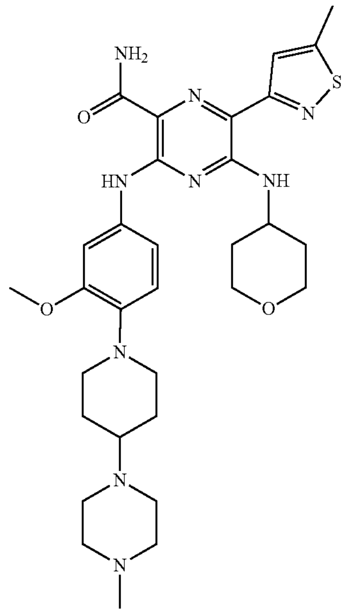 [SMILES: COc1cc(Nc2nc(NC3CCOCC3)c(-c3cc(C)sn3)nc2C(N)=O)ccc1N1CCC(N2CCN(C)CC2)CC1] | A | 622 | — |
| 473 | 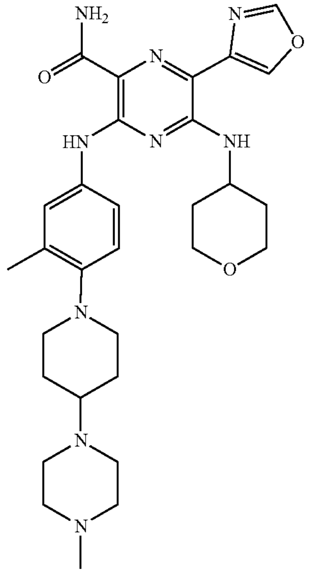 [SMILES: Cc1cc(Nc2nc(NC3CCOCC3)c(-c3cocn3)nc2C(N)=O)ccc1N1CCC(N2CCN(C)CC2)CC1] | A | 576 | — |

TABLE 2-continued
| | | | | |
|---|---|---|---|---|
| 474 | 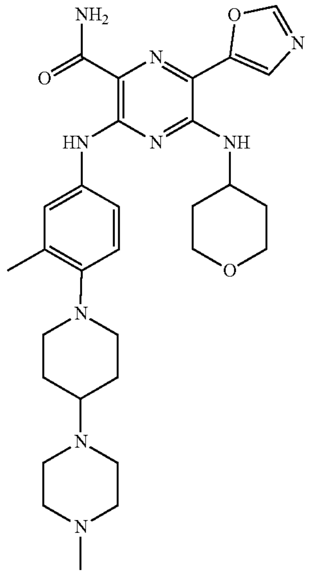 [SMILES: Cc1cc(Nc2nc(NC3CCOCC3)c(-c3cnco3)nc2C(N)=O)ccc1N1CCC(N2CCN(C)CC2)CC1] | A | 576 | — |
| 475 | 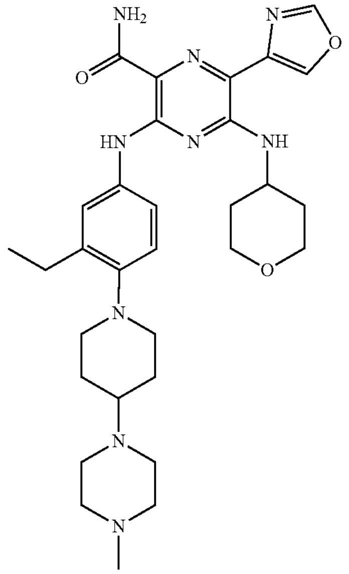 [SMILES: CCc1cc(Nc2nc(NC3CCOCC3)c(-c3cocn3)nc2C(N)=O)ccc1N1CCC(N2CCN(C)CC2)CC1] | A | 590 | — |

TABLE 2-continued
| | | | | |
|---|---|---|---|---|
| 476 | 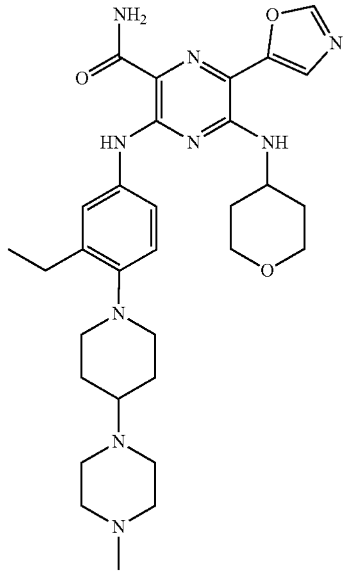 | A | 590 | — |
| 477 | 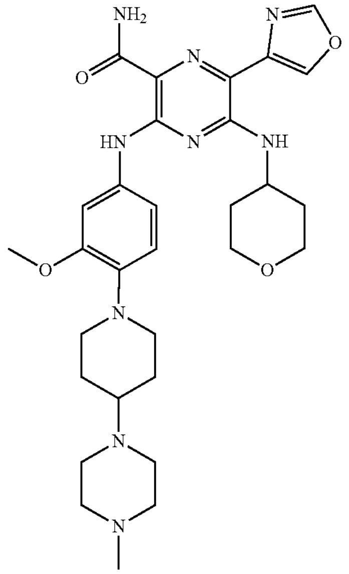 [SMILES: COc1cc(Nc2nc(NC3CCOCC3)c(-c3cocn3)nc2C(N)=O)ccc1N1CCC(N2CCN(C)CC2)CC1] | A | 592 | — |

TABLE 2-continued
| | | | | |
|---|---|---|---|---|
| 478 | 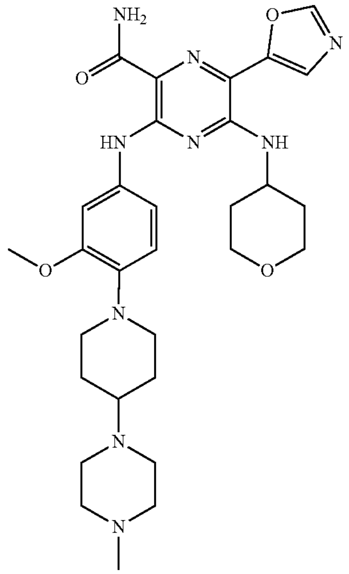 | A | 592 | — |
| 479 | 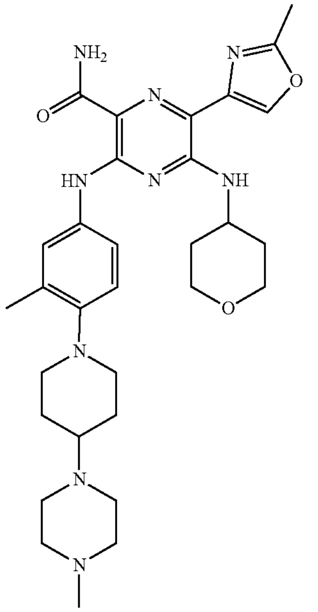 [SMILES: Cc1nc(-c2nc(C(N)=O)c(Nc3ccc(N4CCC(N5CCN(C)CC5)CC4)c(C)c3)nc2NC2CCOCC2)co1] | A | 590 | — |

TABLE 2-continued
| | | | | |
|---|---|---|---|---|
| 480 | 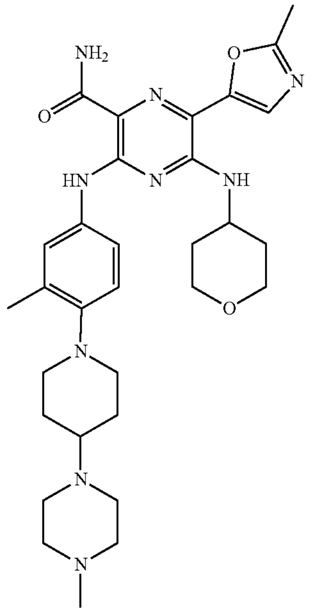 [SMILES: Cc1ncc(-c2nc(C(N)=O)c(Nc3ccc(N4CCC(N5CCN(C)CC5)CC4)c(C)c3)nc2NC2CCOCC2)o1] | A | 590 | — |
| 481 | 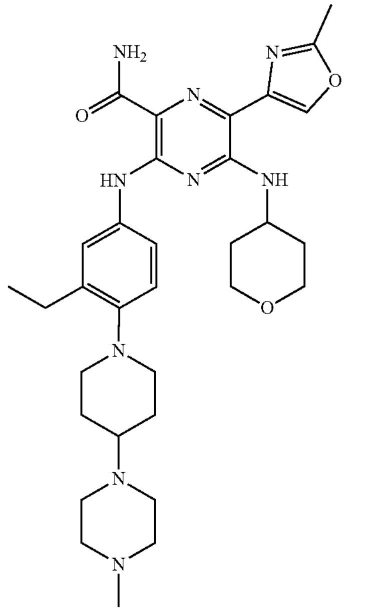 | A | 604 | — |

TABLE 2-continued
| | | | | |
|---|---|---|---|---|
| 482 | 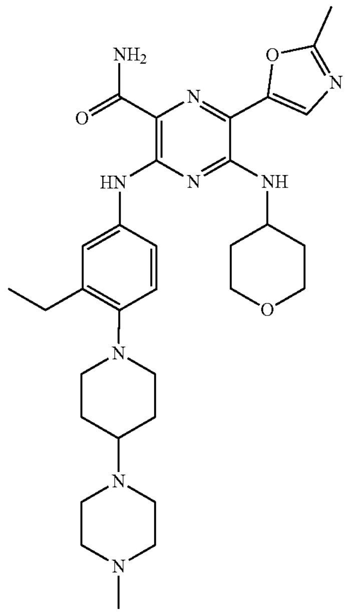 | A | 604 | — |
| 483 | 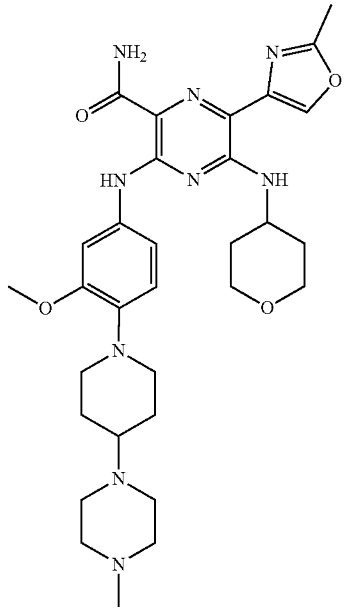 | A | 606 | — |

TABLE 2-continued
| | | | | |
|---|---|---|---|---|
| 484 | 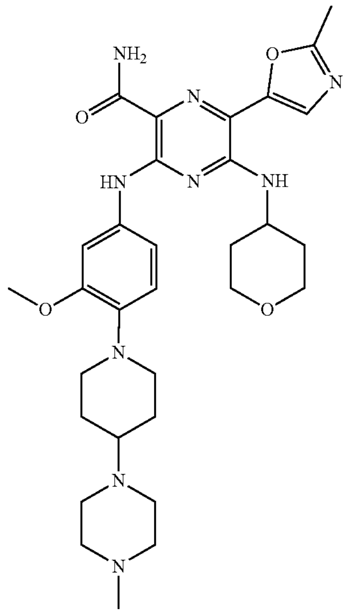 | A | 606 | — |
| 485 | 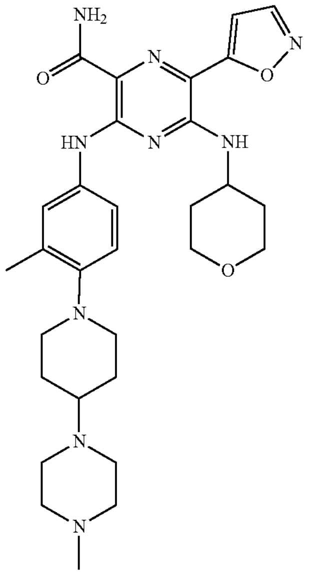 | A | 576 | — |

TABLE 2-continued
| | | | | |
|---|---|---|---|---|
| 486 | 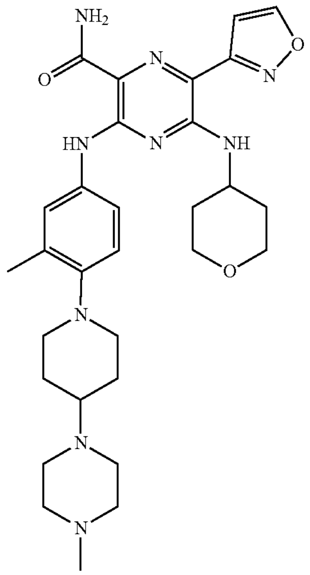 [SMILES: Cc1cc(Nc2nc(NC3CCOCC3)c(-c3ccon3)nc2C(N)=O)ccc1N1CCC(N2CCN(C)CC2)CC1] | A | 576 | — |
| 487 | 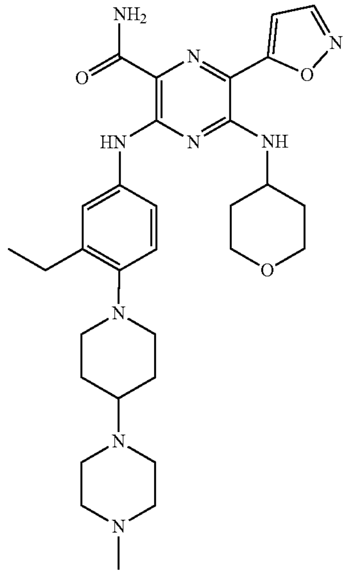 [SMILES: COc1cc(Nc2nc(NC3CCOCC3)c(-c3ccno3)nc2C(N)=O)ccc1N1CCC(N2CCN(C)CC2)CC1] | A | 590 | — |

TABLE 2-continued
| | | | | |
|---|---|---|---|---|
| 488 | 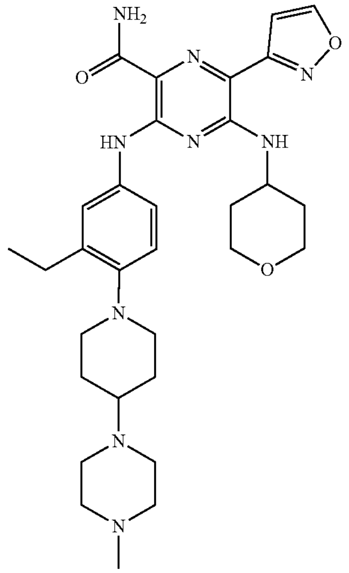 [SMILES: COc1cc(Nc2nc(NC3CCOCC3)c(-c3ccon3)nc2C(N)=O)ccc1N1CCC(N2CCN(C)CC2)CC1] | A | 590 | — |
| 489 | 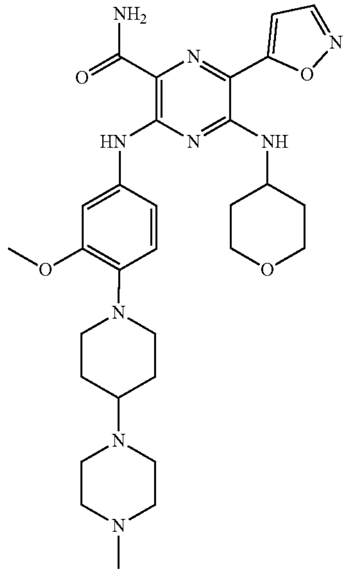 | A | 592 | — |

TABLE 2-continued
| | | | | |
|---|---|---|---|---|
| 490 | 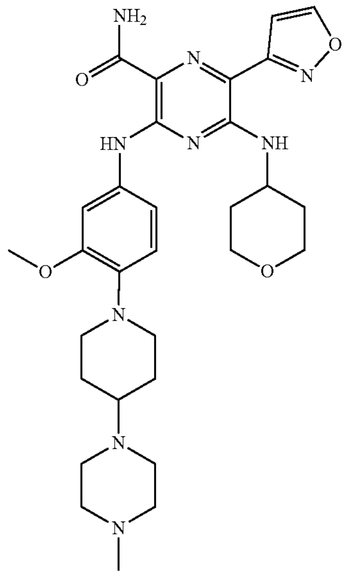 | A | 592 | — |
| 491 | 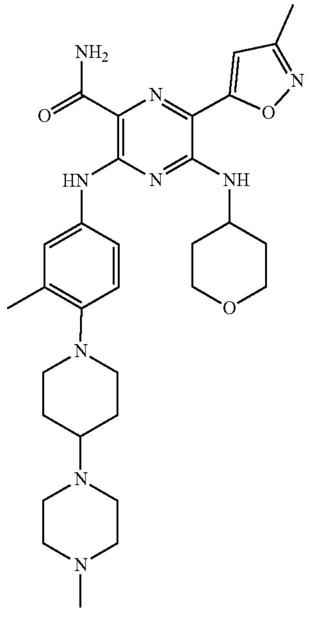 | A | 590 | — |

TABLE 2-continued
| | | | | |
|---|---|---|---|---|
| 492 | 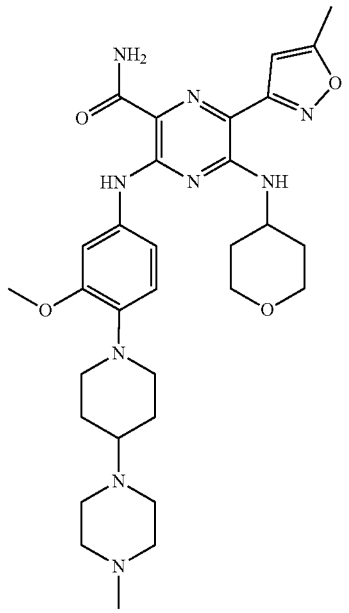 [SMILES: COc1cc(Nc2nc(NC3CCOCC3)c(-c3cc(C)on3)nc2C(N)=O)ccc1N1CCC(N2CCN(C)CC2)CC1] | A | 590 | — |
| 493 | 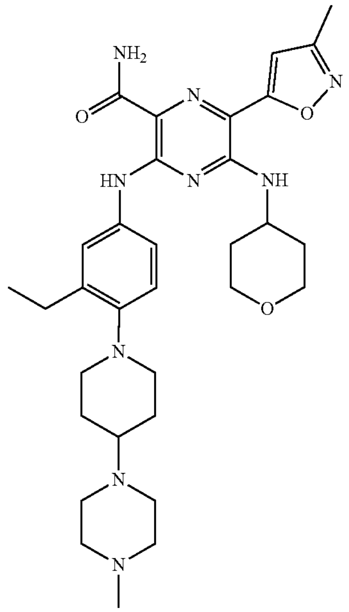 | A | 604 | — |

TABLE 2-continued
| | | | | |
|---|---|---|---|---|
| 494 | 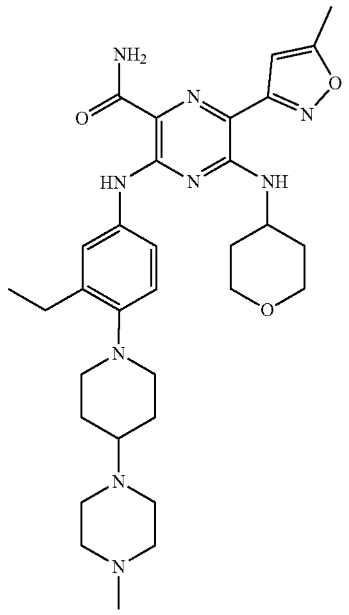 [SMILES: CCc1cc(Nc2nc(NC3CCOCC3)c(-c3cc(C)on3)nc2C(N)=O)ccc1N1CCC(N2CCN(C)CC2)CC1] | A | 604 | — |
| 495 | 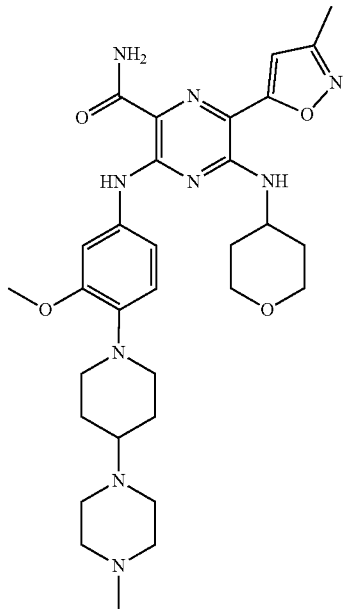 | A | 606 | — |

TABLE 2-continued
| | | | | |
|---|---|---|---|---|
| 496 | 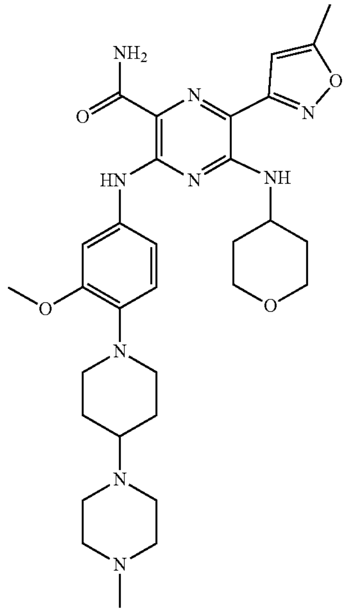 [SMILES: COc1cc(Nc2nc(NC3CCOCC3)c(-c3cc(C)on3)nc2C(N)=O)ccc1N1CCC(N2CCN(C)CC2)CC1] | A | 606 | — |
| 497 | 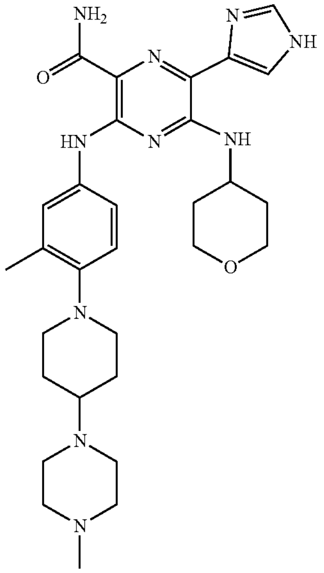 [SMILES: Cc1cc(Nc2nc(NC3CCOCC3)c(-c3c[nH]cn3)nc2C(N)=O)ccc1N1CCC(N2CCN(C)CC2)CC1] | A | 575 | — |

TABLE 2-continued
| | | | | |
|---|---|---|---|---|
| 498 | 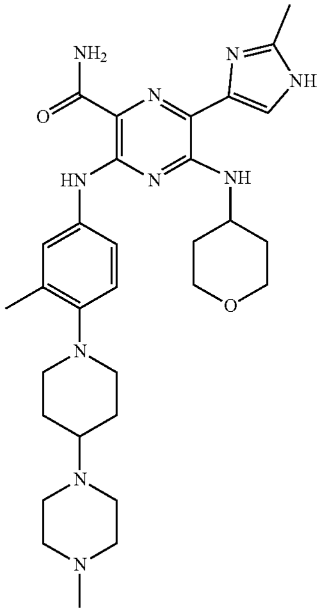 [SMILES: Cc1nc(-c2nc(C(N)=O)c(Nc3ccc(N4CCC(N5CCN(C)CC5)CC4)c(C)c3)nc2NC2CCOCC2)c[nH]1] | A | 589 | — |
| 499 | 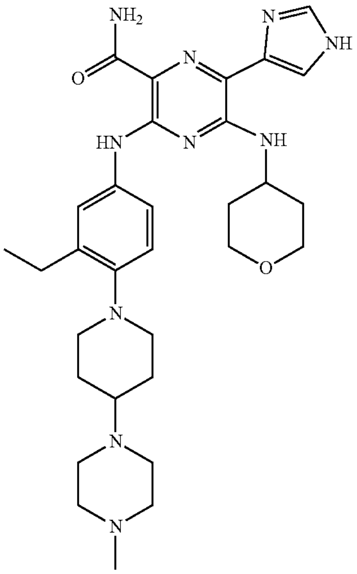 [SMILES: CCc1cc(Nc2nc(NC3CCOCC3)c(-c3c[nH]cn3)nc2C(N)=O)ccc1N1CCC(N2CCN(C)CC2)CC1] | A | 589 | — |

TABLE 2-continued
| | | | | |
|---|---|---|---|---|
| 500 | 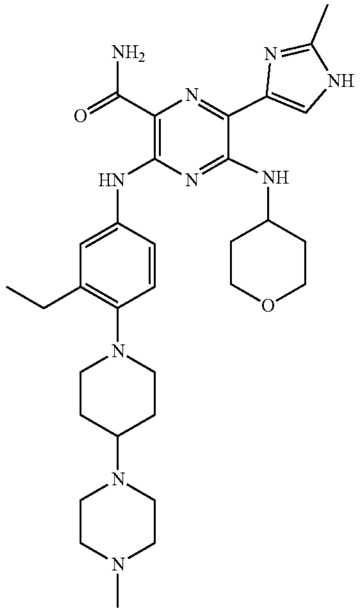 [SMILES: CCc1cc(Nc2nc(NC3CCOCC3)c(-c3c[nH]c(C)n3)nc2C(N)=O)ccc1N1CCC(N2CCN(C)CC2)CC1] | A | 603 | — |
| 501 | 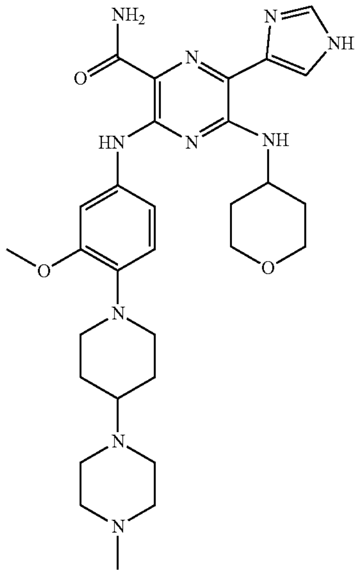 [SMILES: COc1cc(Nc2nc(NC3CCOCC3)c(-c3c[nH]cn3)nc2C(N)=O)ccc1N1CCC(N2CCN(C)CC2)CC1] | A | 591 | — |

TABLE 2-continued
| | | | | |
|---|---|---|---|---|
| 502 | 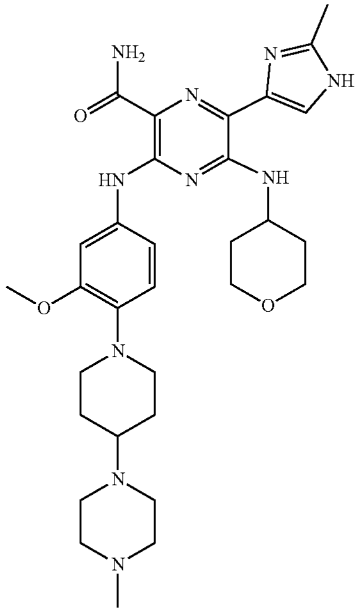 [SMILES: COc1cc(Nc2nc(NC3CCOCC3)c(-c3c[nH]c(C)n3)nc2C(N)=O)ccc1N1CCC(N2CCN(C)CC2)CC1] | A | 605 | — |
| 503 | 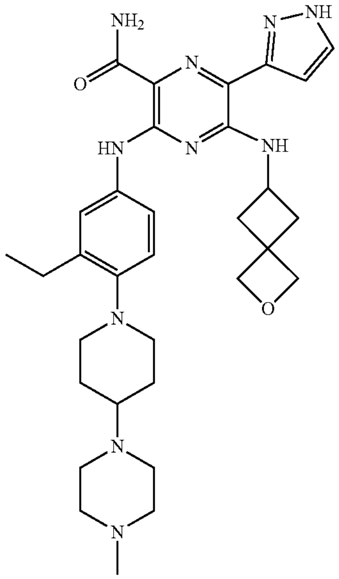 [SMILES: CCc1cc(Nc2nc(NC3CC4(COC4)C3)c(-c3cc[nH]n3)nc2C(N)=O)ccc1N1CCC(N2CCN(C)CC2)CC1] | A | 601 | 1.384 |

TABLE 2-continued
| | | | | |
|---|---|---|---|---|
| 504 | 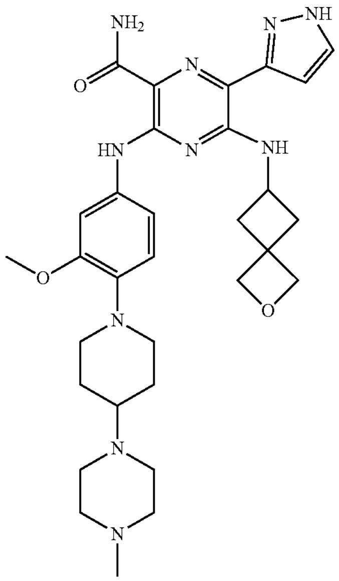 [SMILES: COc1cc(Nc2nc(NC3CC4(COC4)C3)c(-c3cc[nH]n3)nc2C(N)=O)ccc1N1CCC(N2CCN(C)CC2)CC1] | A | 603 | 1.320 |
| 505 | 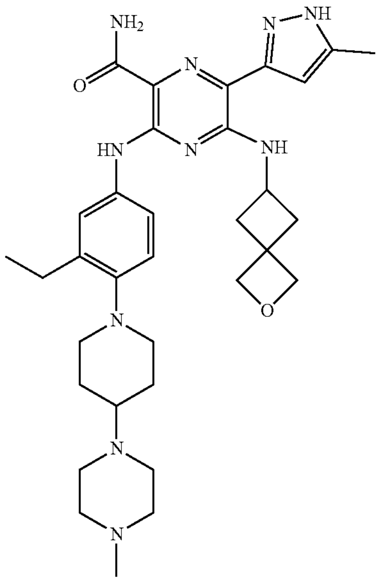 [SMILES: CCc1cc(Nc2nc(NC3CC4(COC4)C3)c(-c3cc(C)[nH]n3)nc2C(N)=O)ccc1N1CCC(N2CCN(C)CC2)CC1] | A | 615 | — |

TABLE 2-continued
| | | | | |
|---|---|---|---|---|
| 506 | 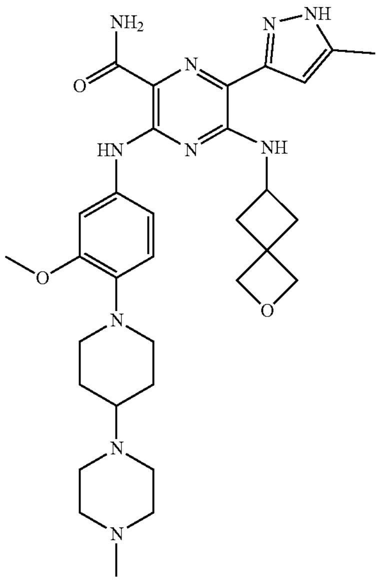 | A | 617 | — |
| 507 | 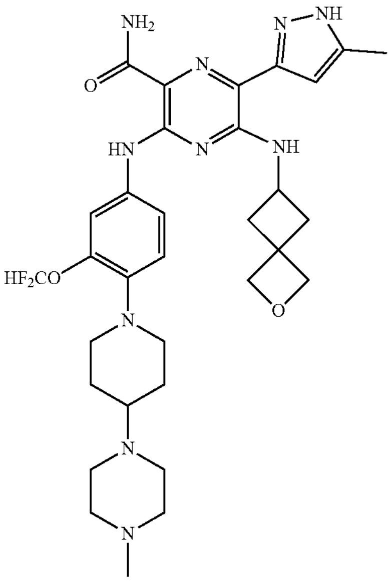 | A | 639 | — |

TABLE 2-continued
| | | | | |
|---|---|---|---|---|
| 508 | 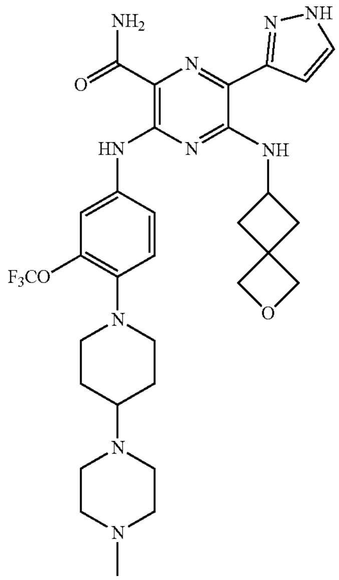 [SMILES: CN1CCN(C2CCN(c3ccc(Nc4nc(NC5CC6(COC6)C5)c(-c5cc[nH]n5)nc4C(N)=O)cc3OC(F)(F)F)CC2)CC1] | A | 657 | — |
| 509 | 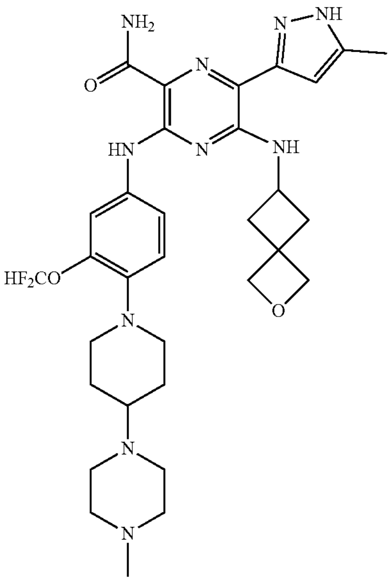 | A | 653 | — |

TABLE 2-continued
| | | | | |
|---|---|---|---|---|
| 510 | 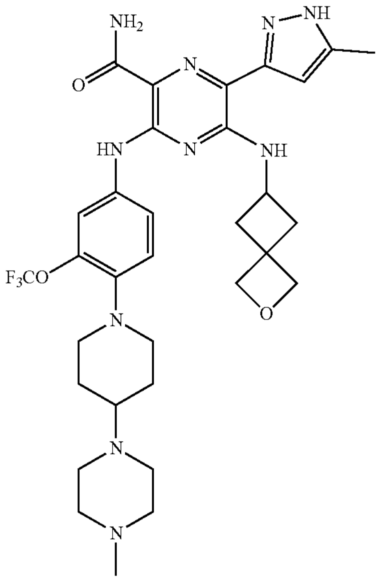 [SMILES: Cc1cc(-c2nc(C(N)=O)c(Nc3ccc(N4CCC(N5CCN(C)CC5)CC4)c(OC(F)(F)F)c3)nc2NC2CC3(COC3)C2)n[nH]1] | A | 671 | — |
| 511 | 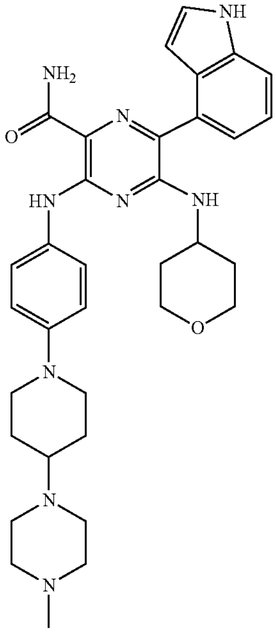 [SMILES: CN1CCN(C2CCN(c3ccc(Nc4nc(NC5CCOCC5)c(-c5cccc6[nH]ccc56)nc4C(N)=O)cc3)CC2)CC1] | A | 610 | 1.357 |

TABLE 2-continued
| | | | | |
|---|---|---|---|---|
| 512 | 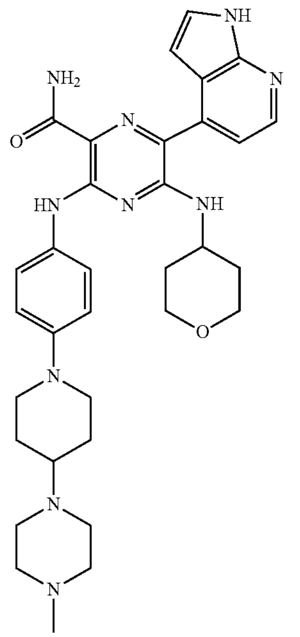 [SMILES: CN1CCN(C2CCN(c3ccc(Nc4nc(NC5CCOCC5)c(-c5ccnc6[nH]ccc56)nc4C(N)=O)cc3)CC2)CC1] | A | 611 | 1.235 |
| 513 | 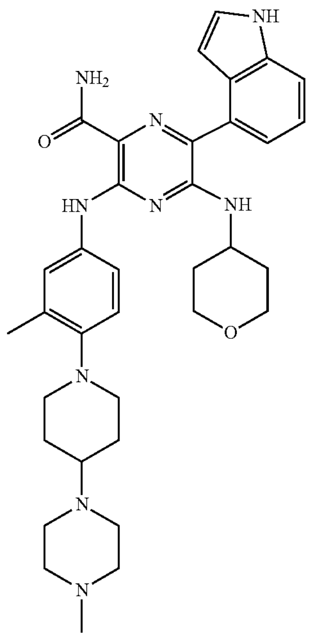 [SMILES: Cc1cc(Nc2nc(NC3CCOCC3)c(-c3cccc4[nH]ccc34)nc2C(N)=O)ccc1N1CCC(N2CCN(C)CC2)CC1] | A | 624 | 1.459 |

TABLE 2-continued
| | | | | |
|---|---|---|---|---|
| 514 | 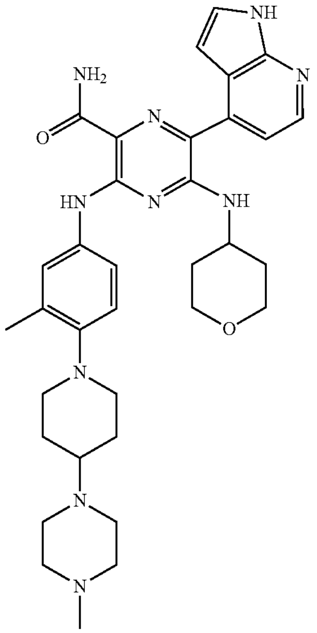 [SMILES: Cc1cc(Nc2nc(NC3CCOCC3)c(-c3ccnc4[nH]ccc34)nc2C(N)=O)ccc1N1CCC(N2CCN(C)CC2)CC1] | A | 625 | 1.337 |
| 515 | 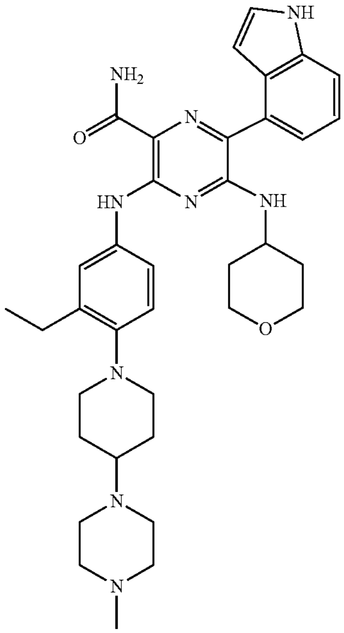 | A | 638 | 1.465 |

TABLE 2-continued
| | | | | |
|---|---|---|---|---|
| 516 | 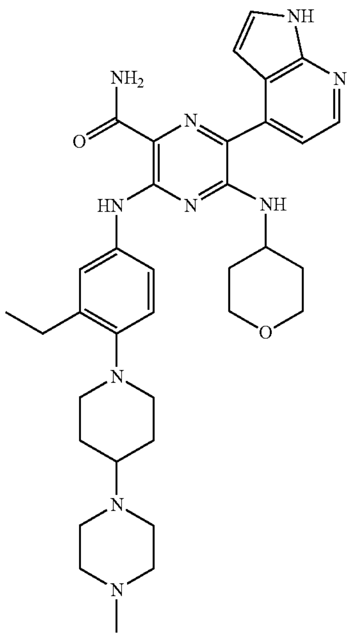 [SMILES: CCc1cc(Nc2nc(NC3CCOCC3)c(-c3ccnc4[nH]ccc34)nc2C(N)=O)ccc1N1CCC(N2CCN(C)CC2)CC1] | A | 639 | 1.325 |
| 517 | 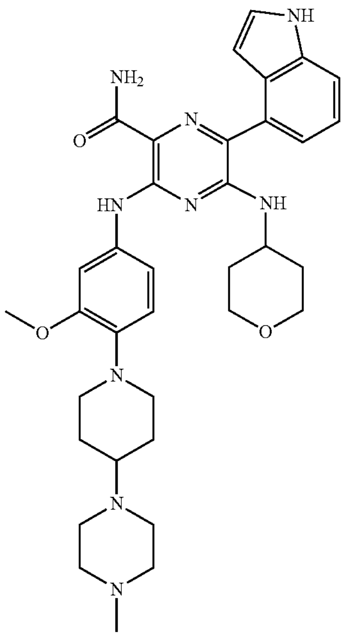 [SMILES: COc1cc(Nc2nc(NC3CCOCC3)c(-c3cccc4[nH]ccc34)nc2C(N)=O)ccc1N1CCC(N2CCN(C)CC2)CC1] | A | 640 | — |

TABLE 2-continued
| | | | | |
|---|---|---|---|---|
| 518 | 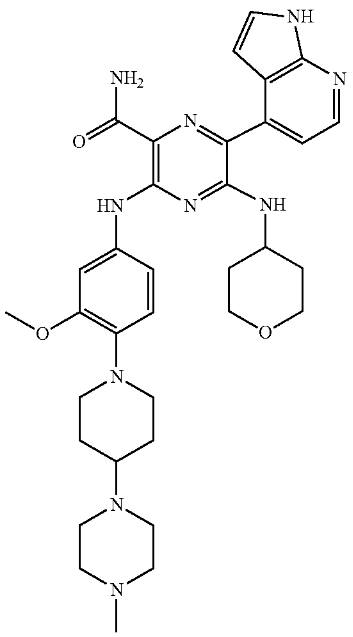 [SMILES: COc1cc(Nc2nc(NC3CCOCC3)c(-c3ccnc4[nH]ccc34)nc2C(N)=O)ccc1N1CCC(N2CCN(C)CC2)CC1] | A | 641 | — |
| 519 | 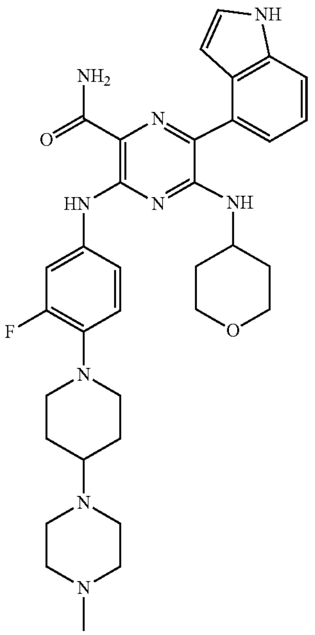 [SMILES: CN1CCN(C2CCN(c3ccc(Nc4nc(NC5CCOCC5)c(-c5cccc6[nH]ccc56)nc4C(N)=O)cc3F)CC2)CC1] | A | 628 | 1.505 |

TABLE 2-continued
| | | | | |
|---|---|---|---|---|
| 520 | 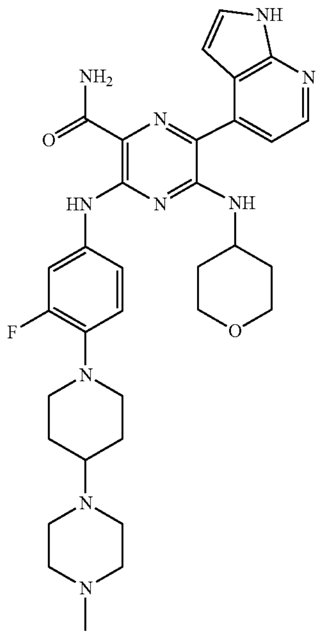 [SMILES: CN1CCN(C2CCN(c3ccc(Nc4nc(NC5CCOCC5)c(-c5ccnc6[nH]ccc56)nc4C(N)=O)cc3F)CC2)CC1] | A | 629 | — |
| 521 | 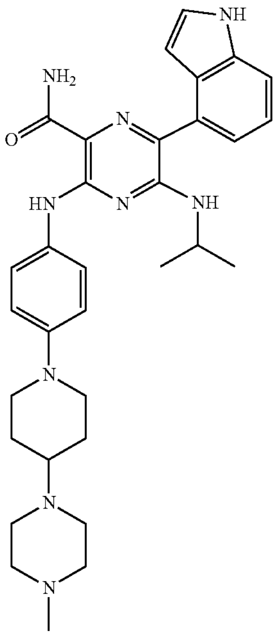 [SMILES: CC(C)Nc1nc(Nc2ccc(N3CCC(N4CCN(C)CC4)CC3)cc2)c(C(N)=O)nc1-c1cccc2[nH]ccc12] | A | 568 | 1.439 |

TABLE 2-continued
| | | | | |
|---|---|---|---|---|
| 522 | 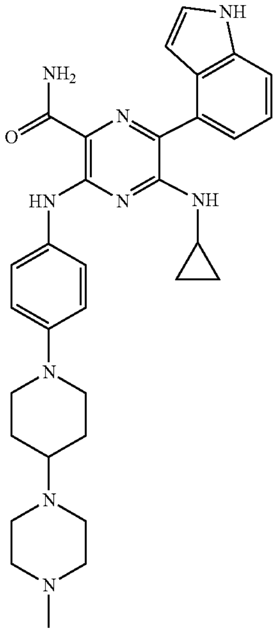 [SMILES: CN1CCN(C2CCN(c3ccc(Nc4nc(NC5CC5)c(-c5cccc6[nH]ccc56)nc4C(N)=O)cc3)CC2)CC1] | A | 566 | 1.473 |
| 523 | 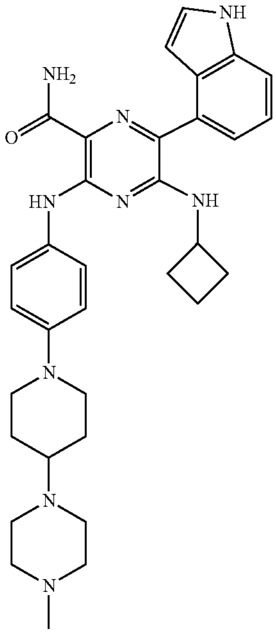 [SMILES: CN1CCN(C2CCN(c3ccc(Nc4nc(NC5CCC5)c(-c5cccc6[nH]ccc56)nc4C(N)=O)cc3)CC2)CC1] | A | 580 | — |

TABLE 2-continued
| | | | | |
|---|---|---|---|---|
| 524 | 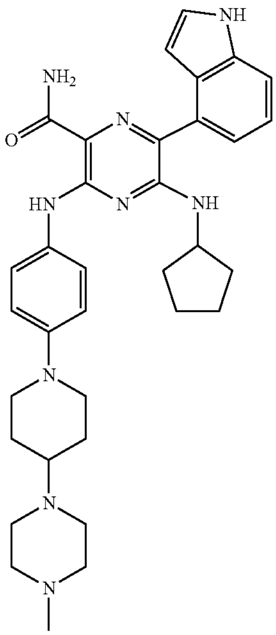 [SMILES: CN1CCN(C2CCN(c3ccc(Nc4nc(NC5CCCC5)c(-c5cccc6[nH]ccc56)nc4C(N)=O)cc3)CC2)CC1] | A | 594 | — |
| 525 | 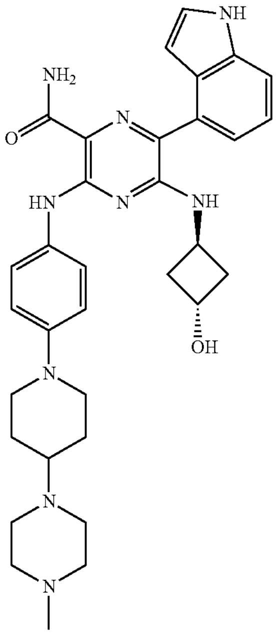 [SMILES: CN1CCN(C2CCN(c3ccc(Nc4nc(N[C@H]5C[C@H](O)C5)c(-c5cccc6[nH]ccc56)nc4C(N)=O)cc3)CC2)CC1] | A | 596 | 1.288 |

TABLE 2-continued
| | | | | |
|---|---|---|---|---|
| 526 | 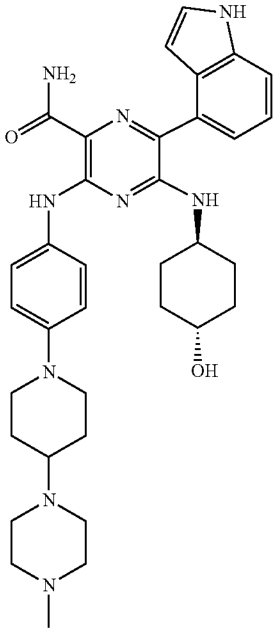 [SMILES: CN1CCN(C2CCN(c3ccc(Nc4nc(N[C@H]5CC[C@H](O)CC5)c(-c5cccc6[nH]ccc56)nc4C(N)=O)cc3)CC2)CC1] | A | 624 | 1.356 |
| 527 | 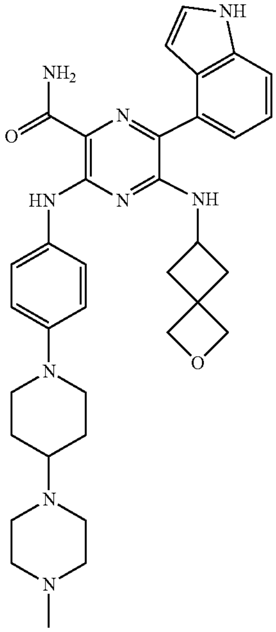 [SMILES: CN1CCN(C2CCN(c3ccc(Nc4nc(NC5CC6(COC6)C5)c(-c5cccc6[nH]ccc56)nc4C(N)=O)cc3)CC2)CC1] | A | 622 | 1.437 |

TABLE 2-continued
| | | | | |
|---|---|---|---|---|
| 528 | 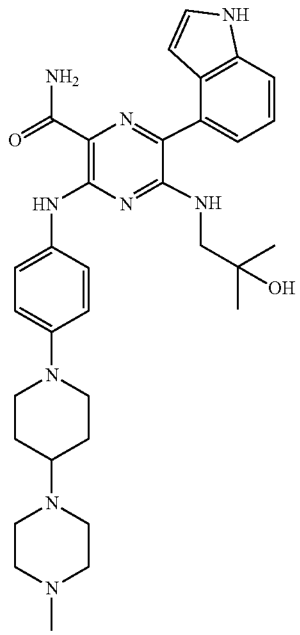 [SMILES: CN1CCN(C2CCN(c3ccc(Nc4nc(NCC(C)(C)O)c(-c5cccc6[nH]ccc56)nc4C(N)=O)cc3)CC2)CC1] | A | 598 | 1.372 |
| 529 | 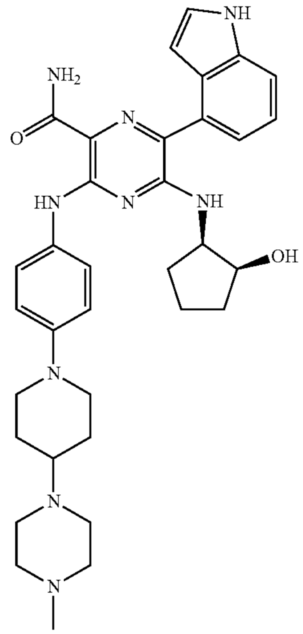 [SMILES: CN1CCN(C2CCN(c3ccc(Nc4nc(N[C@@H]5CCC[C@@H]5O)c(-c5cccc6[nH]ccc56)nc4C(N)=O)cc3)CC2)CC1] | A | 610 | 1.469 |

TABLE 2-continued
| | | | | |
|---|---|---|---|---|
| 530 | 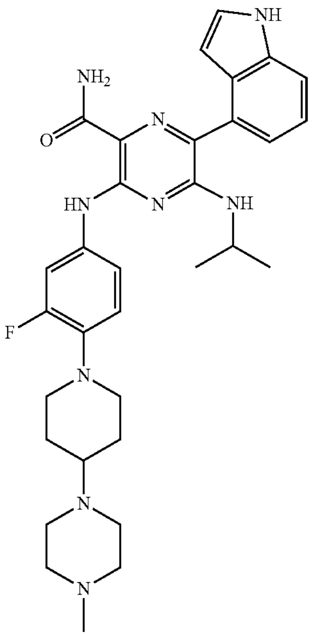 [SMILES: CC(C)Nc1nc(Nc2ccc(N3CCC(N4CCN(C)CC4)CC3)c(F)c2)c(C(N)=O)nc1-c1cccc2[nH]ccc12] | A | 586 | — |
| 531 | 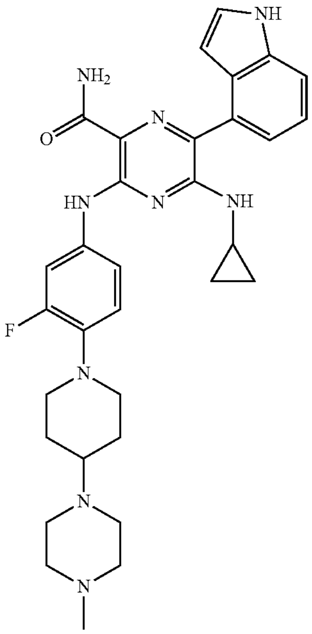 [SMILES: CN1CCN(C2CCN(c3ccc(Nc4nc(NC5CC5)c(-c5cccc6[nH]ccc56)nc4C(N)=O)cc3F)CC2)CC1] | A | 584 | — |

TABLE 2-continued
| | | | | |
|---|---|---|---|---|
| 532 | 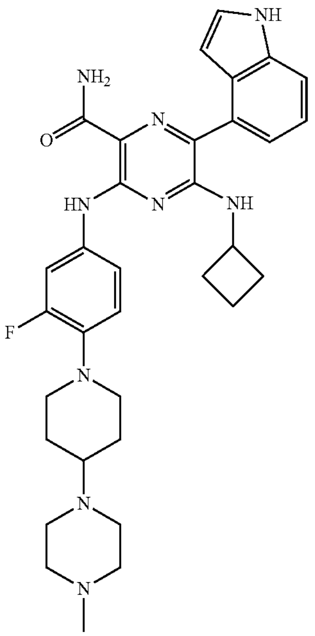 [SMILES: CN1CCN(C2CCN(c3ccc(Nc4nc(NC5CCC5)c(-c5cccc6[nH]ccc56)nc4C(N)=O)cc3F)CC2)CC1] | A | 598 | — |
| 533 | 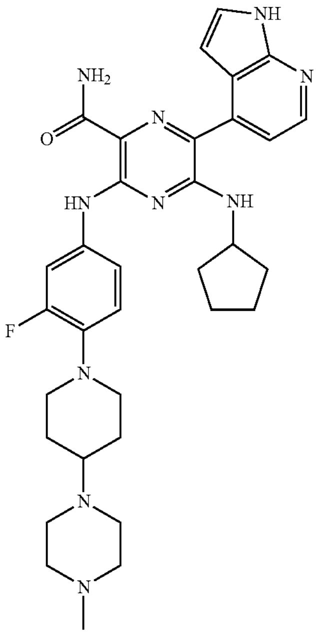 [SMILES: CN1CCN(C2CCN(c3ccc(Nc4nc(NC5CCCC5)c(-c5ccnc6[nH]ccc56)nc4C(N)=O)cc3F)CC2)CC1] | A | 612 | — |

TABLE 2-continued
| | | | | |
|---|---|---|---|---|
| 534 | 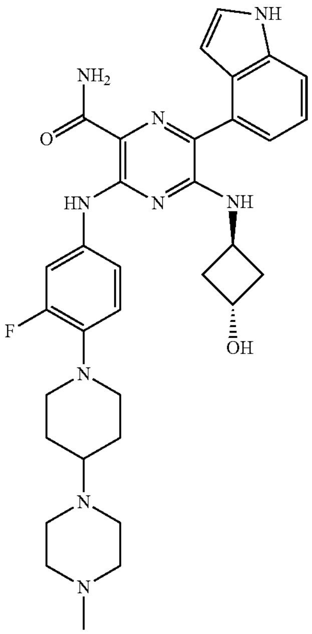 [SMILES: CN1CCN(C2CCN(c3ccc(Nc4nc(N[C@H]5C[C@H](O)C5)c(-c5cccc6[nH]ccc56)nc4C(N)=O)cc3F)CC2)CC1] | A | 614 | — |
| 535 | 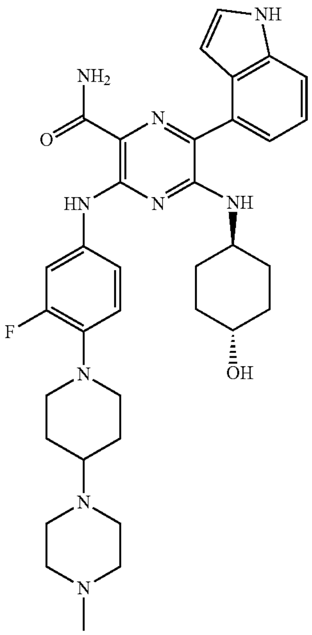 [SMILES: CN1CCN(C2CCN(c3ccc(Nc4nc(N[C@H]5CC[C@H](O)CC5)c(-c5cccc6[nH]ccc56)nc4C(N)=O)cc3F)CC2)CC1] | A | 642 | — |

TABLE 2-continued
| | | | | |
|---|---|---|---|---|
| 536 | 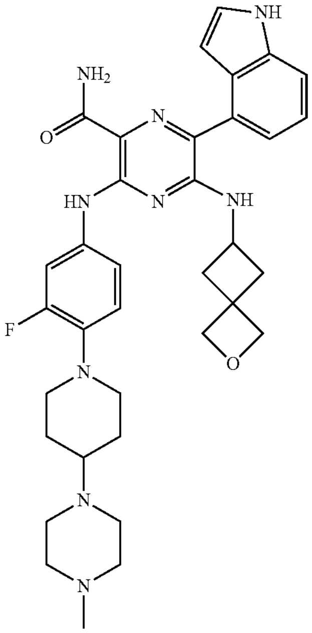 [SMILES: CN1CCN(C2CCN(c3ccc(Nc4nc(NC5CC6(COC6)C5)c(-c5cccc6[nH]ccc56)nc4C(N)=O)cc3F)CC2)CC1] | A | 640 | — |
| 537 | 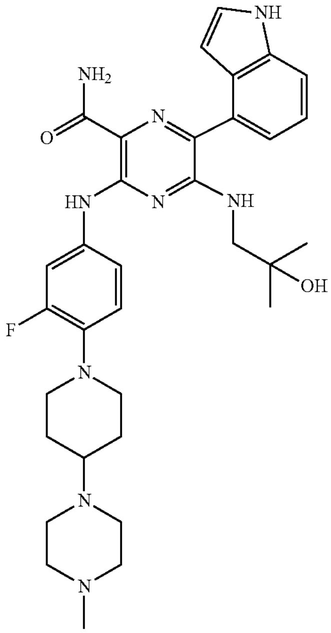 [SMILES: CN1CCN(C2CCN(c3ccc(Nc4nc(NCC(C)(C)O)c(-c5cccc6[nH]ccc56)nc4C(N)=O)cc3F)CC2)CC1] | A | 616 | — |

TABLE 2-continued
| | | | | |
|---|---|---|---|---|
| 538 | 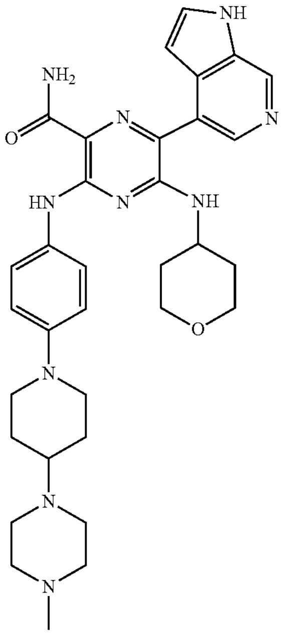 [SMILES: CN1CCN(C2CCN(c3ccc(Nc4nc(NC5CCOCC5)c(-c5cncc6[nH]ccc56)nc4C(N)=O)cc3)CC2)CC1] | A | 611 | 1.168 |
| 539 | 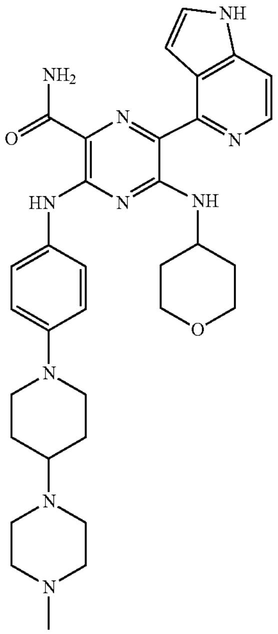 [SMILES: CN1CCN(C2CCN(c3ccc(Nc4nc(NC5CCOCC5)c(-c5nccc6[nH]ccc56)nc4C(N)=O)cc3)CC2)CC1] | A | 611 | — |

TABLE 2-continued
| | | | | |
|---|---|---|---|---|
| 540 | 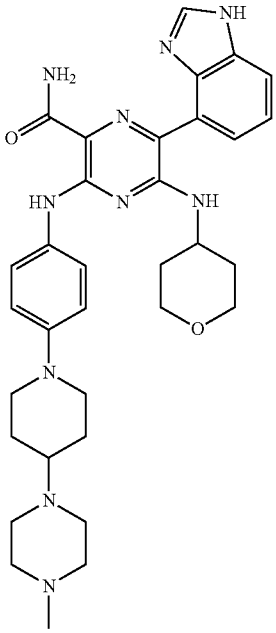 [SMILES: CN1CCN(C2CCN(c3ccc(Nc4nc(NC5CCOCC5)c(-c5cccc6[nH]cnc56)nc4C(N)=O)cc3)CC2)CC1] | A | 611 | 1.232 |
| 541 | 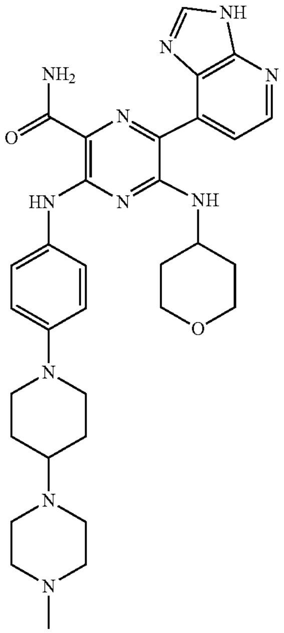 [SMILES: CN1CCN(C2CCN(c3ccc(Nc4nc(NC5CCOCC5)c(-c5ccnc6[nH]cnc56)nc4C(N)=O)cc3)CC2)CC1] | A | 612 | — |

TABLE 2-continued
| | | | | |
|---|---|---|---|---|
| 542 | 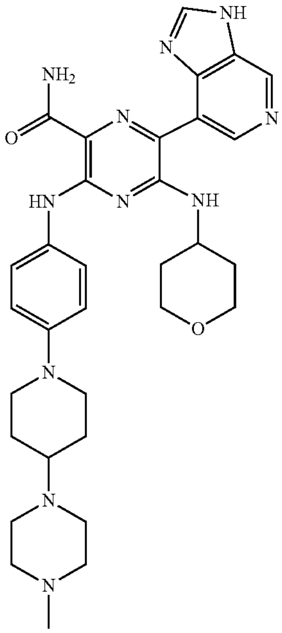 [SMILES: CN1CCN(C2CCN(c3ccc(Nc4nc(NC5CCOCC5)c(-c5cncc6[nH]cnc56)nc4C(N)=O)cc3)CC2)CC1] | A | 612 | — |
| 543 | 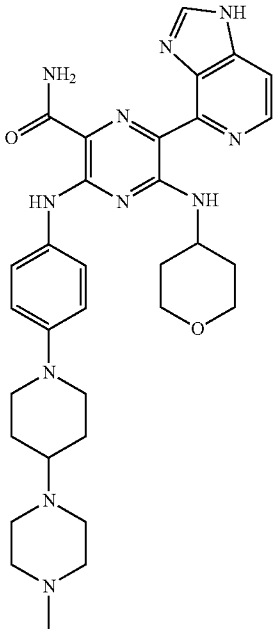 [SMILES: CN1CCN(C2CCN(c3ccc(Nc4nc(NC5CCOCC5)c(-c5nccc6[nH]cnc56)nc4C(N)=O)cc3)CC2)CC1] | A | 612 | — |

TABLE 2-continued
| | | | | |
|---|---|---|---|---|
| 544 | 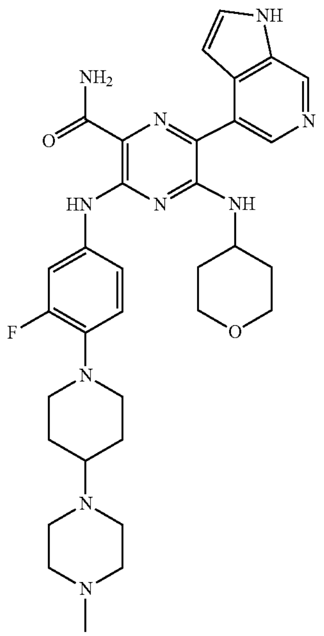 [SMILES: CN1CCN(C2CCN(c3ccc(Nc4nc(NC5CCOCC5)c(-c5cncc6[nH]ccc56)nc4C(N)=O)cc3F)CC2)CC1] | A | 629 | — |
| 545 | 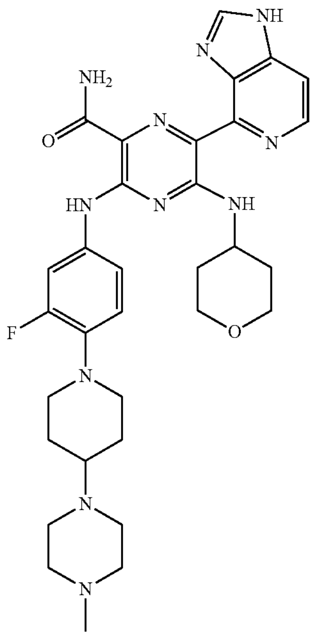 [SMILES: CN1CCN(C2CCN(c3ccc(Nc4nc(NC5CCOCC5)c(-c5nccc6[nH]cnc56)nc4C(N)=O)cc3F)CC2)CC1] | A | 629 | — |

TABLE 2-continued
| | | | | |
|---|---|---|---|---|
| 546 | 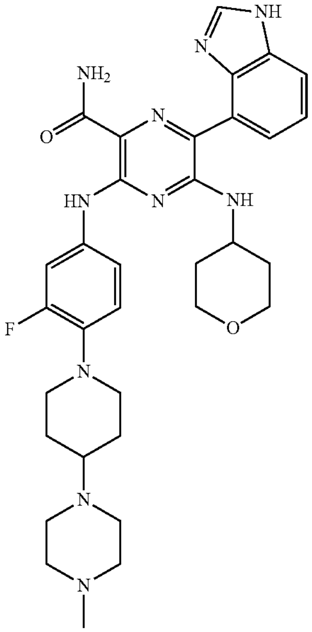 [SMILES: CN1CCN(C2CCN(c3ccc(Nc4nc(NC5CCOCC5)c(-c5cccc6[nH]cnc56)nc4C(N)=O)cc3F)CC2)CC1] | A | 629 | — |
| 547 | 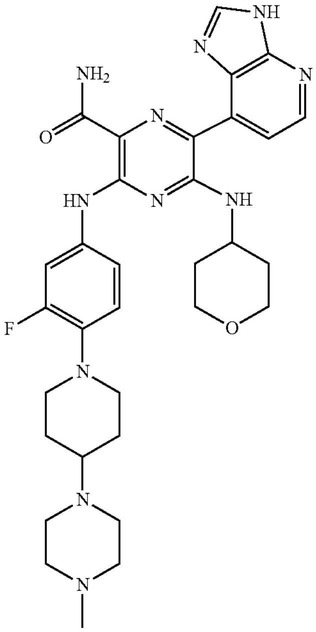 [SMILES: CN1CCN(C2CCN(c3ccc(Nc4nc(NC5CCOCC5)c(-c5ccnc6[nH]cnc56)nc4C(N)=O)cc3F)CC2)CC1] | A | 630 | — |

TABLE 2-continued
| | | | | |
|---|---|---|---|---|
| 548 | 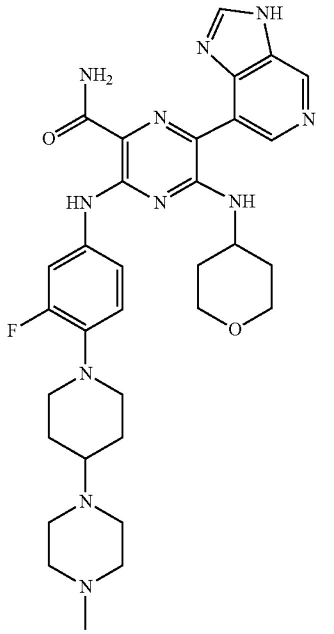 [SMILES: CN1CCN(C2CCN(c3ccc(Nc4nc(NC5CCOCC5)c(-c5cncc6[nH]cnc56)nc4C(N)=O)cc3F)CC2)CC1] | A | 630 | — |
| 549 | 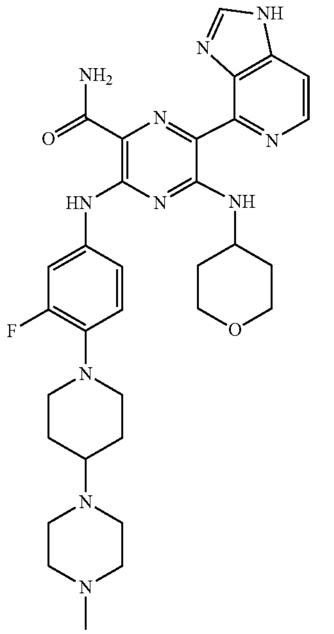 [SMILES: CN1CCN(C2CCN(c3ccc(Nc4nc(NC5CCOCC5)c(-c5nccc6[nH]cnc56)nc4C(N)=O)cc3F)CC2)CC1] | A | 630 | — |

TABLE 2-continued
| | | | | |
|---|---|---|---|---|
| 550 | 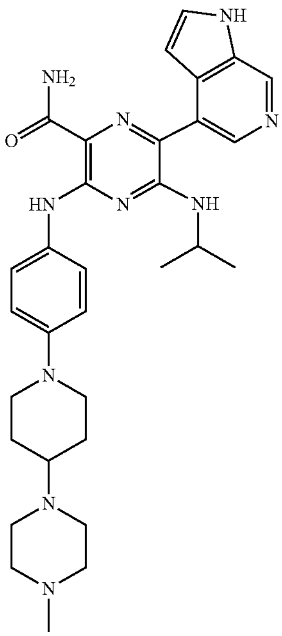 [SMILES: CC(C)Nc1nc(Nc2ccc(N3CCC(N4CCN(C)CC4)CC3)cc2)c(C(N)=O)nc1-c1cncc2[nH]ccc12] | A | 569 | — |
| 551 | 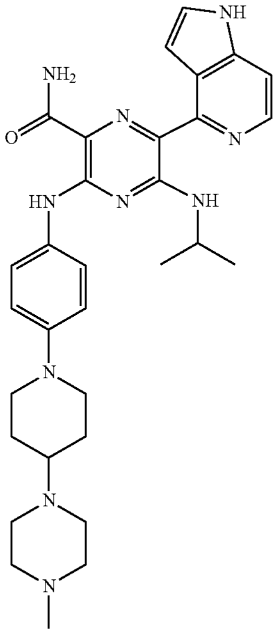 [SMILES: CC(C)Nc1nc(Nc2ccc(N3CCC(N4CCN(C)CC4)CC3)cc2)c(C(N)=O)nc1-c1nccc2[nH]ccc12] | A | 569 | — |

TABLE 2-continued
| | | | | |
|---|---|---|---|---|
| 552 | 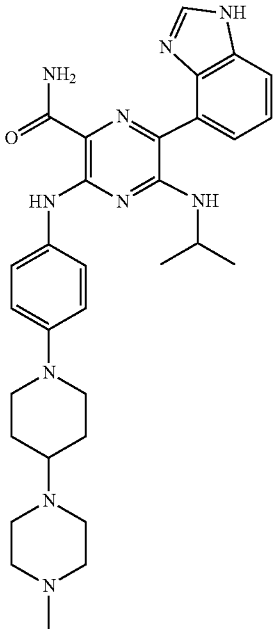 [SMILES: CC(C)Nc1nc(Nc2ccc(N3CCC(N4CCN(C)CC4)CC3)cc2)c(C(N)=O)nc1-c1cccc2[nH]cnc12] | A | 569 | — |
| 553 | 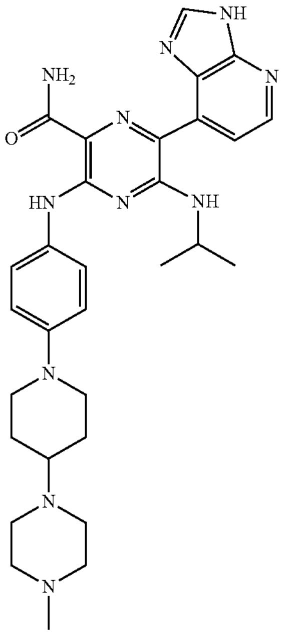 [SMILES: CC(C)Nc1nc(Nc2ccc(N3CCC(N4CCN(C)CC4)CC3)cc2)c(C(N)=O)nc1-c1ccnc2[nH]cnc12] | A | 570 | — |

TABLE 2-continued
| | | | | |
|---|---|---|---|---|
| 554 | 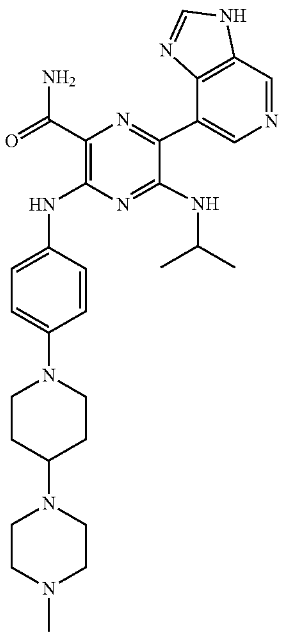 [SMILES: CC(C)Nc1nc(Nc2ccc(N3CCC(N4CCN(C)CC4)CC3)cc2)c(C(N)=O)nc1-c1cncc2[nH]cnc12] | A | 570 | — |
| 555 | 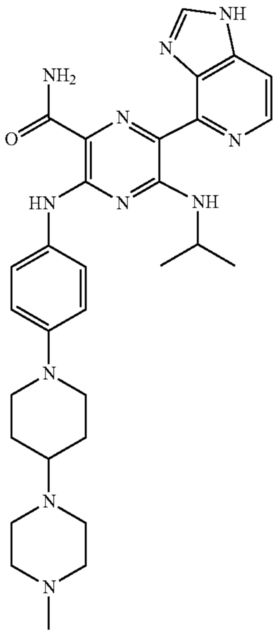 [SMILES: CC(C)Nc1nc(Nc2ccc(N3CCC(N4CCN(C)CC4)CC3)cc2)c(C(N)=O)nc1-c1nccc2[nH]cnc12] | A | 570 | — |

TABLE 2-continued
| | | | | |
|---|---|---|---|---|
| 556 | 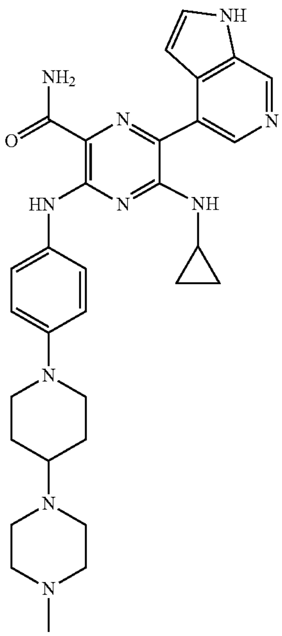 [SMILES: CN1CCN(C2CCN(c3ccc(Nc4nc(NC5CC5)c(-c5cncc6[nH]ccc56)nc4C(N)=O)cc3)CC2)CC1] | A | 567 | — |
| 557 | 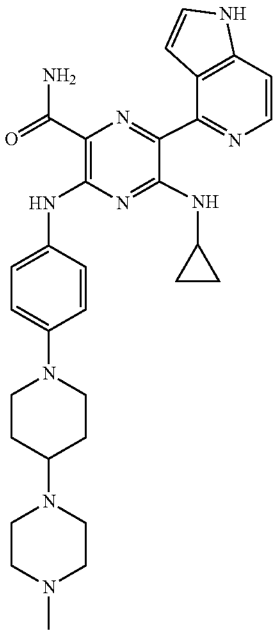 [SMILES: CN1CCN(C2CCN(c3ccc(Nc4nc(NC5CC5)c(-c5nccc6[nH]ccc56)nc4C(N)=O)cc3)CC2)CC1] | A | 567 | — |

TABLE 2-continued
| | | | | |
|---|---|---|---|---|
| 558 | 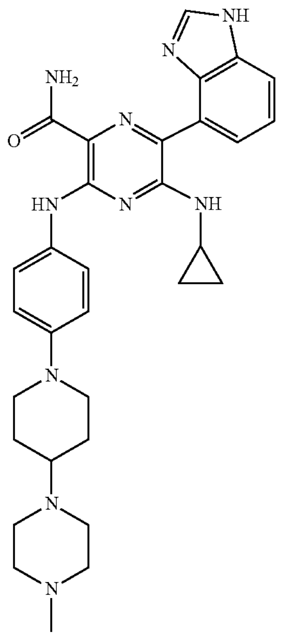 [SMILES: CN1CCN(C2CCN(c3ccc(Nc4nc(NC5CC5)c(-c5cccc6[nH]cnc56)nc4C(N)=O)cc3)CC2)CC1] | A | 567 | — |
| 559 | 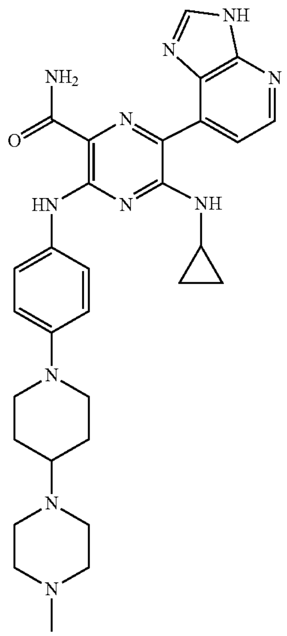 [SMILES: CN1CCN(C2CCN(c3ccc(Nc4nc(NC5CC5)c(-c5ccnc6[nH]cnc56)nc4C(N)=O)cc3)CC2)CC1] | A | 568 | — |

TABLE 2-continued
| | | | | |
|---|---|---|---|---|
| 560 | 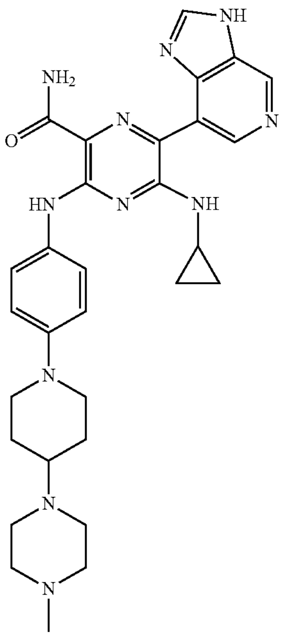 [SMILES: CN1CCN(C2CCN(c3ccc(Nc4nc(NC5CC5)c(-c5cncc6[nH]cnc56)nc4C(N)=O)cc3)CC2)CC1] | A | 568 | — |
| 561 | 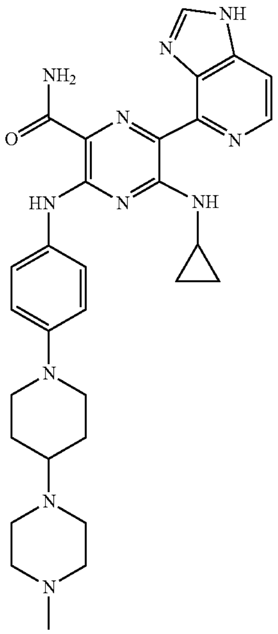 [SMILES: CN1CCN(C2CCN(c3ccc(Nc4nc(NC5CC5)c(-c5nccc6[nH]cnc56)nc4C(N)=O)cc3)CC2)CC1] | A | 568 | — |

TABLE 2-continued
| | | | | |
|---|---|---|---|---|
| 562 | 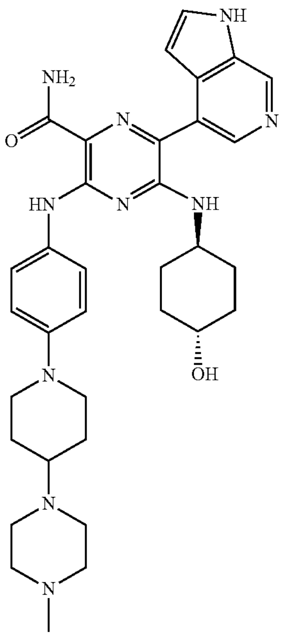 [SMILES: CN1CCN(C2CCN(c3ccc(Nc4nc(N[C@H]5CC[C@H](O)CC5)c(-c5cncc6[nH]ccc56)nc4C(N)=O)cc3)CC2)CC1] | A | 625 | — |
| 563 | 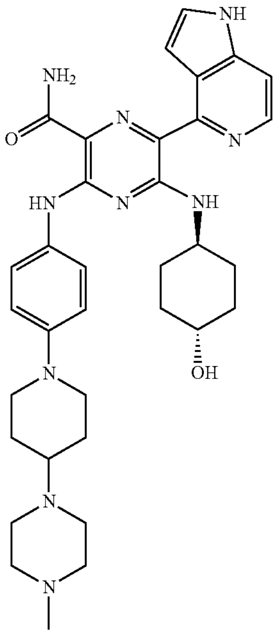 [SMILES: CN1CCN(C2CCN(c3ccc(Nc4nc(N[C@H]5CC[C@H](O)CC5)c(-c5nccc6[nH]ccc56)nc4C(N)=O)cc3)CC2)CC1] | A | 625 | — |

TABLE 2-continued
| | | | | |
|---|---|---|---|---|
| 564 | 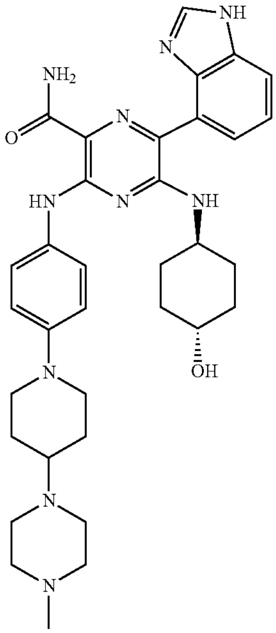 [SMILES: CN1CCN(C2CCN(c3ccc(Nc4nc(N[C@H]5CC[C@H](O)CC5)c(-c5cccc6[nH]cnc56)nc4C(N)=O)cc3)CC2)CC1] | A | 625 | — |
| 565 | 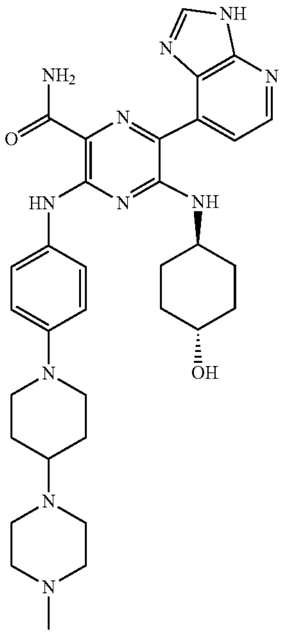 [SMILES: CN1CCN(C2CCN(c3ccc(Nc4nc(N[C@H]5CC[C@H](O)CC5)c(-c5ccnc6[nH]cnc56)nc4C(N)=O)cc3)CC2)CC1] | A | 626 | — |

TABLE 2-continued
| | | | | |
|---|---|---|---|---|
| 566 | 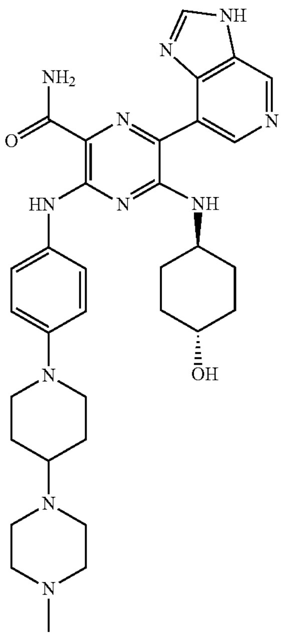 [SMILES: CN1CCN(C2CCN(c3ccc(Nc4nc(N[C@H]5CC[C@H](O)CC5)c(-c5cncc6[nH]cnc56)nc4C(N)=O)cc3)CC2)CC1] | A | 626 | — |
| 567 | 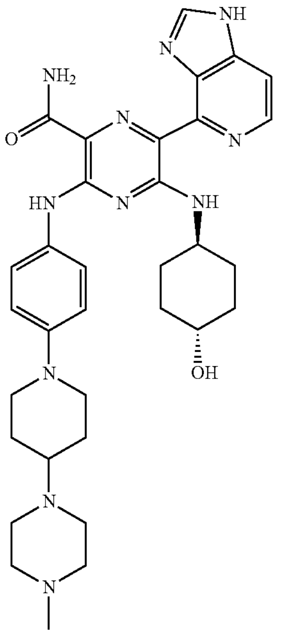 [SMILES: CN1CCN(C2CCN(c3ccc(Nc4nc(N[C@H]5CC[C@H](O)CC5)c(-c5nccc6[nH]cnc56)nc4C(N)=O)cc3)CC2)CC1] | A | 626 | — |

TABLE 2-continued
| | | | | |
|---|---|---|---|---|
| 568 | 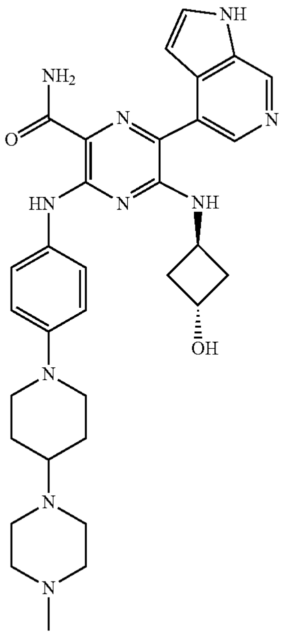 [SMILES: CN1CCN(C2CCN(c3ccc(Nc4nc(N[C@H]5C[C@H](O)C5)c(-c5cncc6[nH]ccc56)nc4C(N)=O)cc3)CC2)CC1] | A | 597 | — |
| 569 | 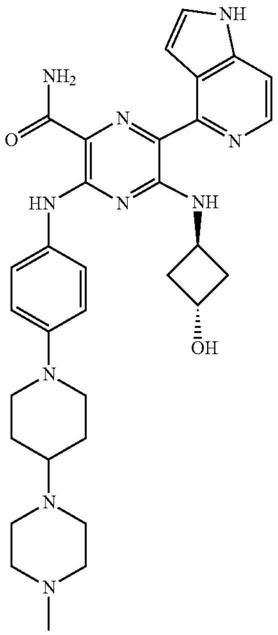 [SMILES: CN1CCN(C2CCN(c3ccc(Nc4nc(N[C@H]5C[C@H](O)C5)c(-c5nccc6[nH]ccc56)nc4C(N)=O)cc3)CC2)CC1] | A | 597 | — |

TABLE 2-continued
| | | | | |
|---|---|---|---|---|
| 570 | 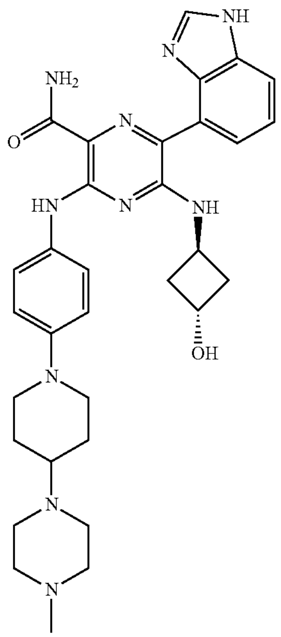 [SMILES: CN1CCN(C2CCN(c3ccc(Nc4nc(N[C@H]5C[C@H](O)C5)c(-c5cccc6[nH]cnc56)nc4C(N)=O)cc3)CC2)CC1] | A | 597 | — |
| 571 | 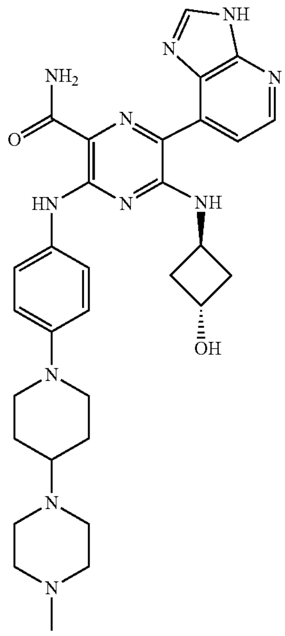 [SMILES: CN1CCN(C2CCN(c3ccc(Nc4nc(N[C@H]5C[C@H](O)C5)c(-c5ccnc6[nH]cnc56)nc4C(N)=O)cc3)CC2)CC1] | A | 598 | — |

TABLE 2-continued
| | | | | |
|---|---|---|---|---|
| 572 | 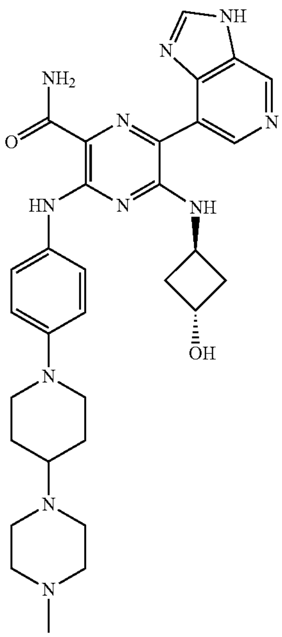 [SMILES: CN1CCN(C2CCN(c3ccc(Nc4nc(N[C@H]5C[C@H](O)C5)c(-c5cncc6[nH]cnc56)nc4C(N)=O)cc3)CC2)CC1] | A | 598 | — |
| 573 | 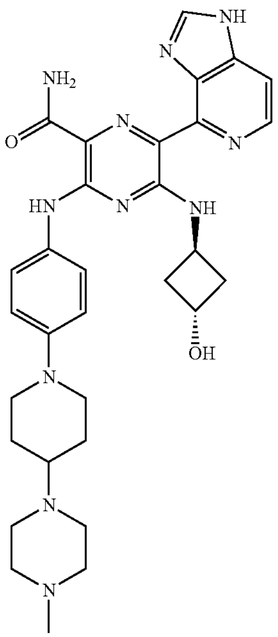 [SMILES: CN1CCN(C2CCN(c3ccc(Nc4nc(N[C@H]5C[C@H](O)C5)c(-c5nccc6[nH]cnc56)nc4C(N)=O)cc3)CC2)CC1] | A | 598 | — |

TABLE 2-continued
| | | | | |
|---|---|---|---|---|
| 574 | 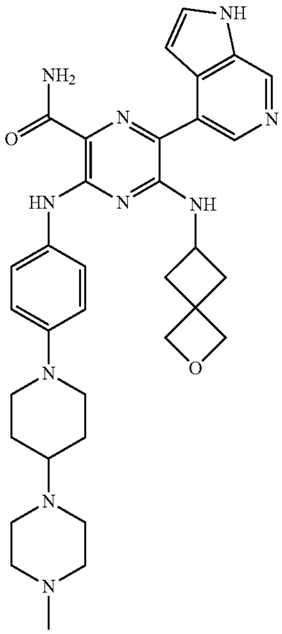 [SMILES: CN1CCN(C2CCN(c3ccc(Nc4nc(NC5CC6(COC6)C5)c(-c5cncc6[nH]ccc56)nc4C(N)=O)cc3)CC2)CC1] | A | 623 | — |
| 575 | 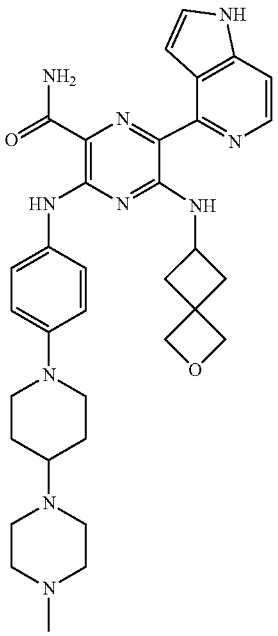 [SMILES: CN1CCN(C2CCN(c3ccc(Nc4nc(NC5CC6(COC6)C5)c(-c5nccc6[nH]ccc56)nc4C(N)=O)cc3)CC2)CC1] | A | 623 | — |

TABLE 2-continued
| | | | | |
|---|---|---|---|---|
| 576 | 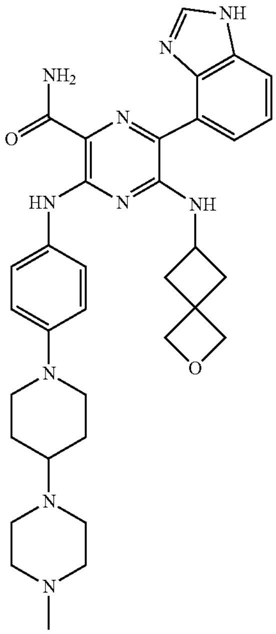 [SMILES: CN1CCN(C2CCN(c3ccc(Nc4nc(NC5CC6(COC6)C5)c(-c5cccc6[nH]cnc56)nc4C(N)=O)cc3)CC2)CC1] | A | 623 | — |
| 577 | 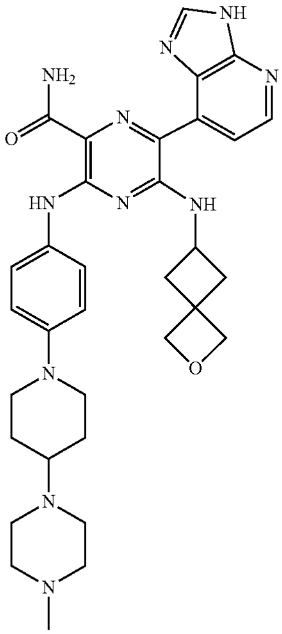 [SMILES: CN1CCN(C2CCN(c3ccc(Nc4nc(NC5CC6(COC6)C5)c(-c5ccnc6[nH]cnc56)nc4C(N)=O)cc3)CC2)CC1] | A | 624 | — |

TABLE 2-continued
| | | | | |
|---|---|---|---|---|
| 578 | 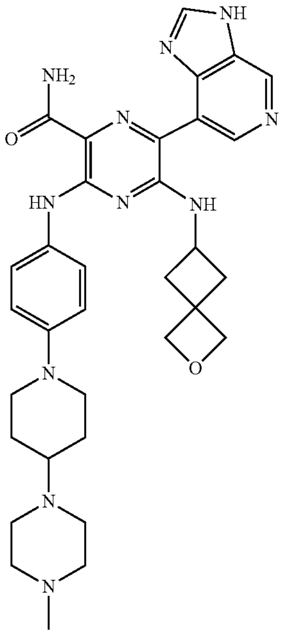 [SMILES: CN1CCN(C2CCN(c3ccc(Nc4nc(NC5CC6(COC6)C5)c(-c5cncc6[nH]cnc56)nc4C(N)=O)cc3)CC2)CC1] | A | 624 | — |
| 579 | 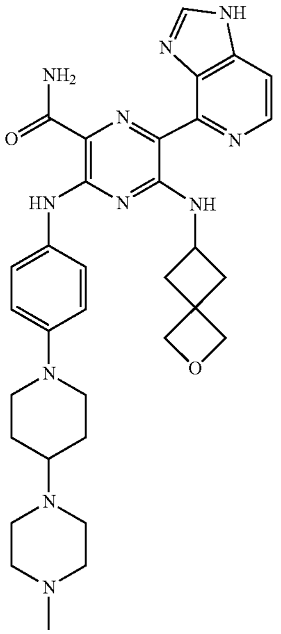 [SMILES: CN1CCN(C2CCN(c3ccc(Nc4nc(NC5CC6(COC6)C5)c(-c5nccc6[nH]cnc56)nc4C(N)=O)cc3)CC2)CC1] | A | 624 | — |

TABLE 2-continued
| | | | | |
|---|---|---|---|---|
| 580 | 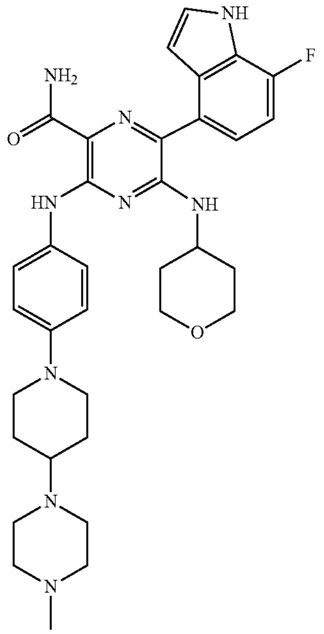 [SMILES: CN1CCN(C2CCN(c3ccc(Nc4nc(NC5CCOCC5)c(-c5ccc(F)c6[nH]ccc56)nc4C(N)=O)cc3)CC2)CC1] | A | 628 | — |
| 581 | 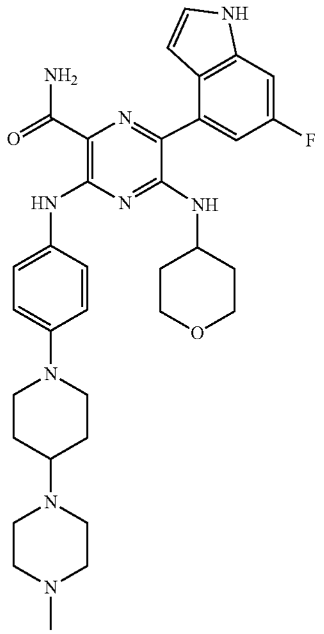 [SMILES: CN1CCN(C2CCN(c3ccc(Nc4nc(NC5CCOCC5)c(-c5cc(F)cc6[nH]ccc56)nc4C(N)=O)cc3)CC2)CC1] | A | 628 | — |

TABLE 2-continued
| | | | | |
|---|---|---|---|---|
| 582 | 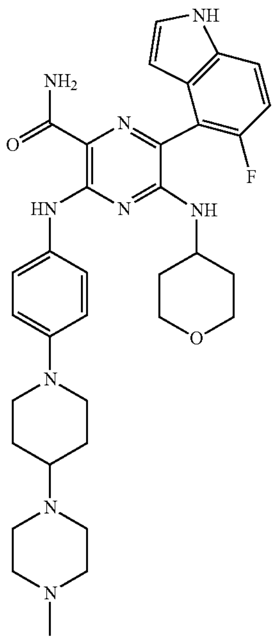 [SMILES: CN1CCN(C2CCN(c3ccc(Nc4nc(NC5CCOCC5)c(-c5c(F)ccc6[nH]ccc56)nc4C(N)=O)cc3)CC2)CC1] | A | 628 | — |
| 583 | 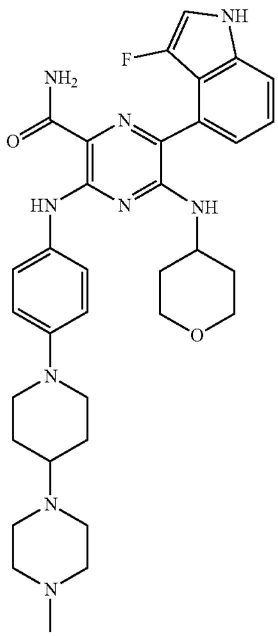 [SMILES: CN1CCN(C2CCN(c3ccc(Nc4nc(NC5CCOCC5)c(-c5cccc6[nH]cc(F)c56)nc4C(N)=O)cc3)CC2)CC1] | A | 628 | — |

TABLE 2-continued
| | | | | |
|---|---|---|---|---|
| 584 | 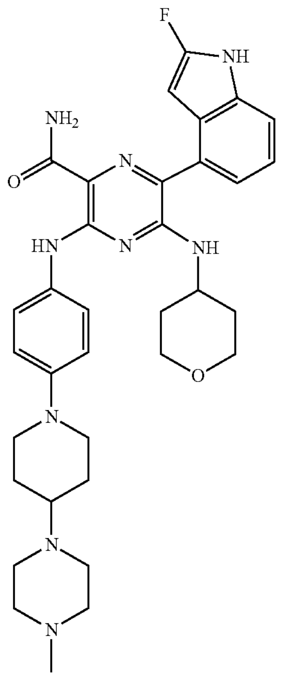 [SMILES: CN1CCN(C2CCN(c3ccc(Nc4nc(NC5CCOCC5)c(-c5cccc6[nH]c(F)cc56)nc4C(N)=O)cc3)CC2)CC1] | A | 628 | — |
| 585 | 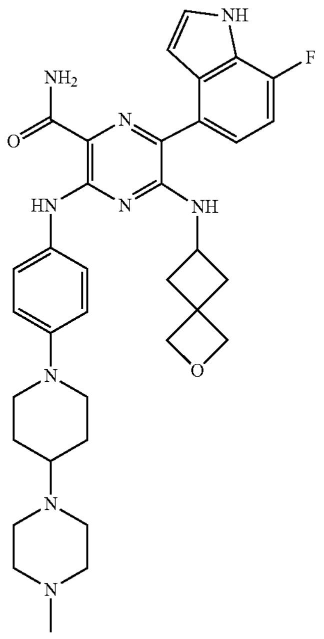 [SMILES: CN1CCN(C2CCN(c3ccc(Nc4nc(NC5CC6(COC6)C5)c(-c5ccc(F)c6[nH]ccc56)nc4C(N)=O)cc3)CC2)CC1] | A | 640 | — |

TABLE 2-continued
| | | | | |
|---|---|---|---|---|
| 586 | 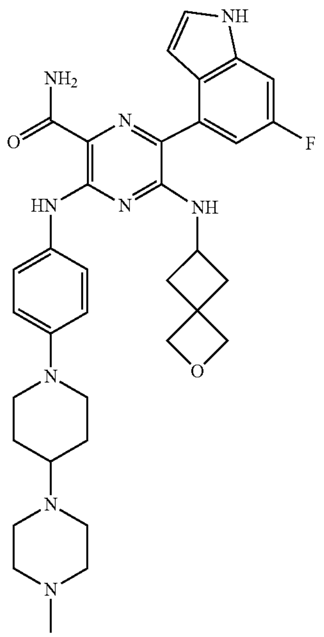 [SMILES: CN1CCN(C2CCN(c3ccc(Nc4nc(NC5CC6(COC6)C5)c(-c5cc(F)cc6[nH]ccc56)nc4C(N)=O)cc3)CC2)CC1] | A | 640 | — |
| 587 | 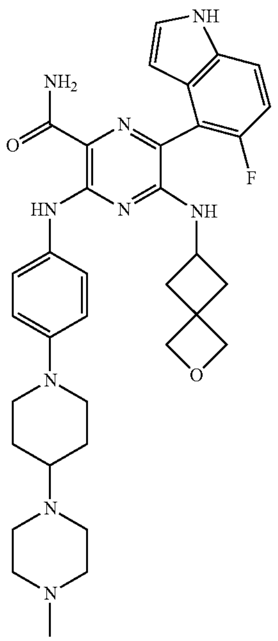 [SMILES: CN1CCN(C2CCN(c3ccc(Nc4nc(NC5CC6(COC6)C5)c(-c5c(F)ccc6[nH]ccc56)nc4C(N)=O)cc3)CC2)CC1] | A | 640 | — |

TABLE 2-continued
| | | | | |
|---|---|---|---|---|
| 588 | 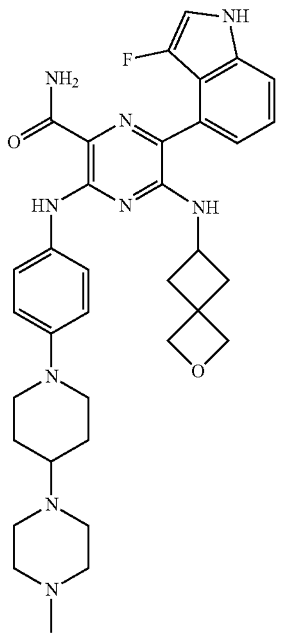 [SMILES: CN1CCN(C2CCN(c3ccc(Nc4nc(NC5CC6(COC6)C5)c(-c5cccc6[nH]cc(F)c56)nc4C(N)=O)cc3)CC2)CC1] | A | 640 | — |
| 589 | 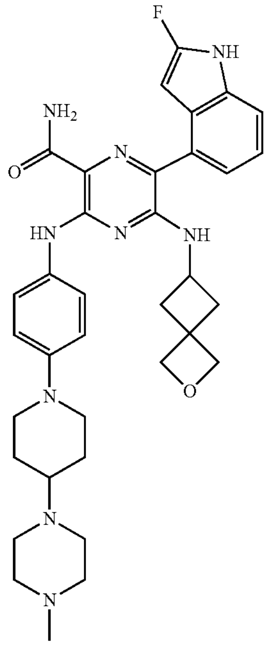 [SMILES: CN1CCN(C2CCN(c3ccc(Nc4nc(NC5CC6(COC6)C5)c(-c5cccc6[nH]c(F)cc56)nc4C(N)=O)cc3)CC2)CC1] | A | 640 | — |

TABLE 2-continued
| | | | | |
|---|---|---|---|---|
| 590 | 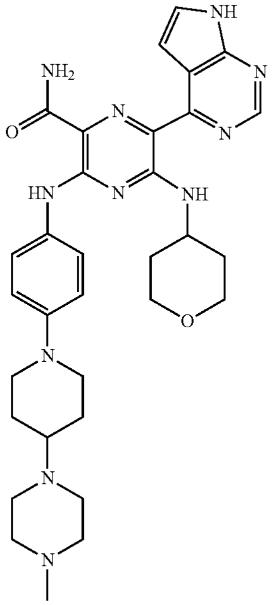 [SMILES: CN1CCN(C2CCN(c3ccc(Nc4nc(NC5CCOCC5)c(-c5ncnc6[nH]ccc56)nc4C(N)=O)cc3)CC2)CC1] | A | 612 | — |
| 591 | 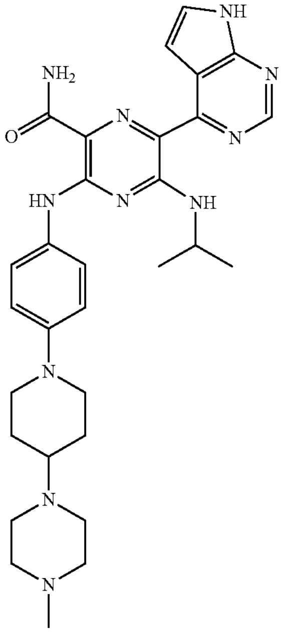 [SMILES: CC(C)Nc1nc(Nc2ccc(N3CCC(N4CCN(C)CC4)CC3)cc2)c(C(N)=O)nc1-c1ncnc2[nH]ccc12] | A | 570 | — |

TABLE 2-continued
| | | | | |
|---|---|---|---|---|
| 592 | 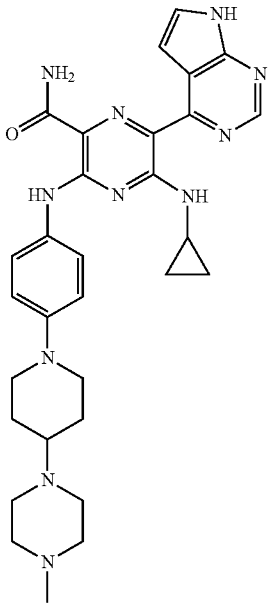 [SMILES: CN1CCN(C2CCN(c3ccc(Nc4nc(NC5CC5)c(-c5ncnc6[nH]ccc56)nc4C(N)=O)cc3)CC2)CC1] | A | 568 | — |
| 593 | 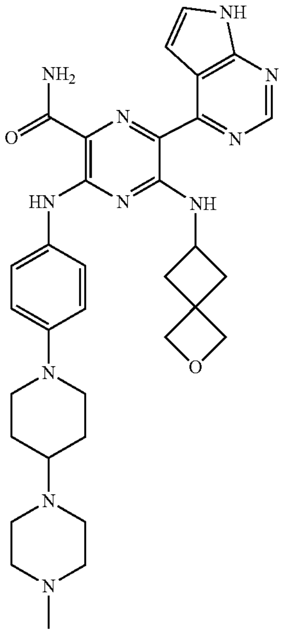 [SMILES: CN1CCN(C2CCN(c3ccc(Nc4nc(NC5CC6(COC6)C5)c(-c5ncnc6[nH]ccc56)nc4C(N)=O)cc3)CC2)CC1] | A | 624 | — |

TABLE 2-continued
| | | | | |
|---|---|---|---|---|
| 594 | 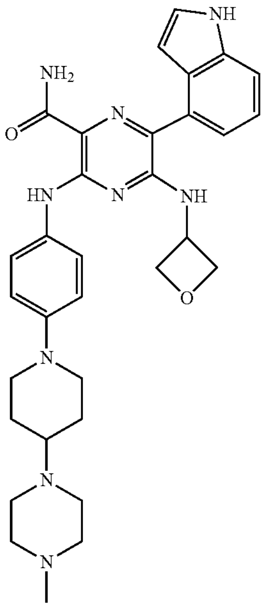 [SMILES: CN1CCN(C2CCN(c3ccc(Nc4nc(NC5COC5)c(-c5cccc6[nH]ccc56)nc4C(N)=O)cc3)CC2)CC1] | A | 582 | 1.325 |
| 595 | 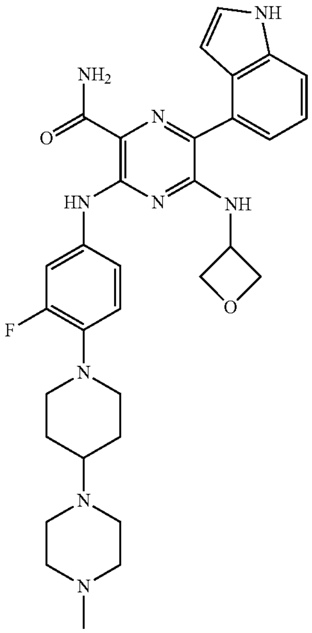 [SMILES: CN1CCN(C2CCN(c3ccc(Nc4nc(NC5COC5)c(-c5cccc6[nH]ccc56)nc4C(N)=O)cc3F)CC2)CC1] | A | 600 | — |

TABLE 2-continued
| | | | | |
|---|---|---|---|---|
| 596 | 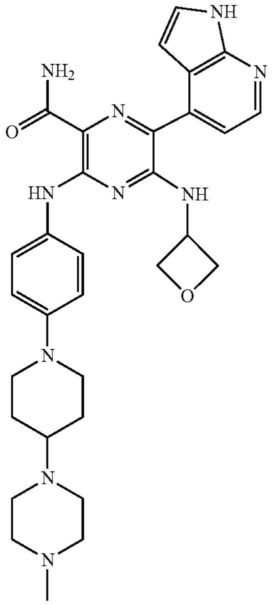 [SMILES: CN1CCN(C2CCN(c3ccc(Nc4nc(NC5COC5)c(-c5ccnc6[nH]ccc56)nc4C(N)=O)cc3)CC2)CC1] | A | 583 | — |
| 597 | 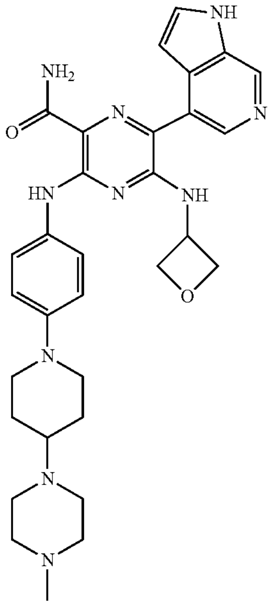 [SMILES: CN1CCN(C2CCN(c3ccc(Nc4nc(NC5COC5)c(-c5cncc6[nH]ccc56)nc4C(N)=O)cc3)CC2)CC1] | A | 583 | — |

TABLE 2-continued
| | | | | |
|---|---|---|---|---|
| 598 | 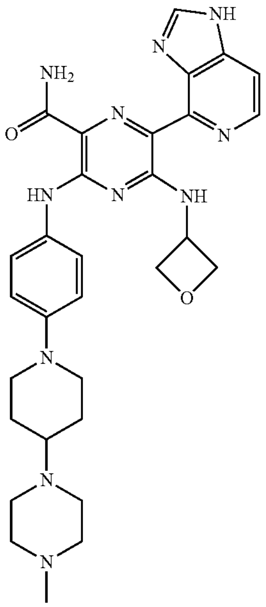 [SMILES: CN1CCN(C2CCN(c3ccc(Nc4nc(NC5COC5)c(-c5nccc6[nH]cnc56)nc4C(N)=O)cc3)CC2)CC1] | A | 583 | — |
| 599 | 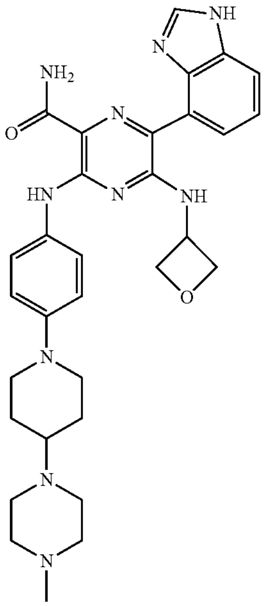 [SMILES: CN1CCN(C2CCN(c3ccc(Nc4nc(NC5COC5)c(-c5cccc6[nH]cnc56)nc4C(N)=O)cc3)CC2)CC1] | A | 583 | — |

TABLE 2-continued
| | | | | |
|---|---|---|---|---|
| 600 | 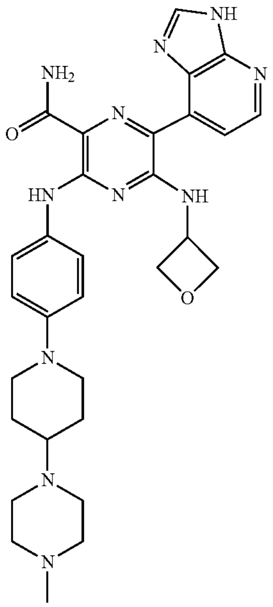 [SMILES: CN1CCN(C2CCN(c3ccc(Nc4nc(NC5COC5)c(-c5ccnc6[nH]cnc56)nc4C(N)=O)cc3)CC2)CC1] | A | 584 | — |
| 601 | 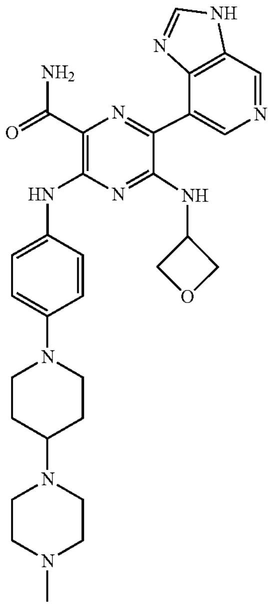 [SMILES: CN1CCN(C2CCN(c3ccc(Nc4nc(NC5COC5)c(-c5cncc6[nH]cnc56)nc4C(N)=O)cc3)CC2)CC1] | A | 584 | — |

TABLE 2-continued
| | | | | |
|---|---|---|---|---|
| 602 | 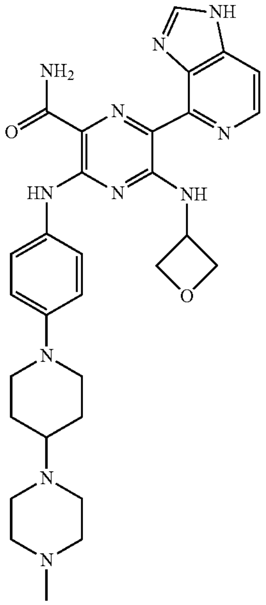 [SMILES: CN1CCN(C2CCN(c3ccc(Nc4nc(NC5COC5)c(-c5nccc6[nH]cnc56)nc4C(N)=O)cc3)CC2)CC1] | A | 584 | — |
| 603 | 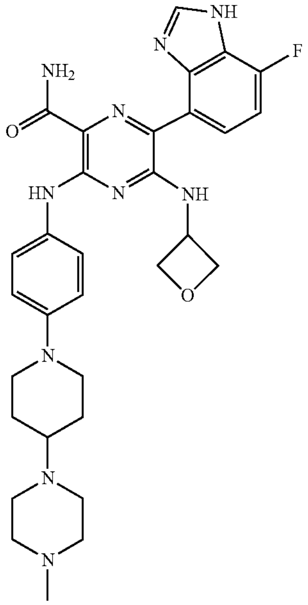 [SMILES: CN1CCN(C2CCN(c3ccc(Nc4nc(NC5COC5)c(-c5ccc(F)c6[nH]cnc56)nc4C(N)=O)cc3)CC2)CC1] | A | 600 | — |

TABLE 2-continued
| | | | | |
|---|---|---|---|---|
| 604 | 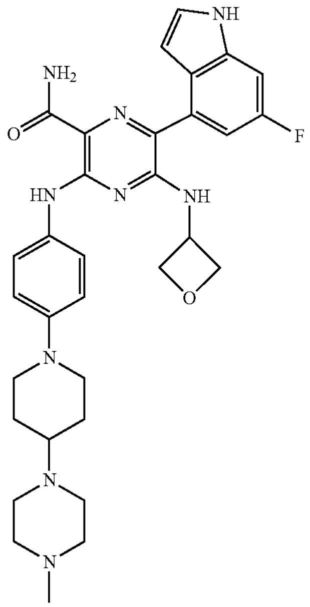 [SMILES: CN1CCN(C2CCN(c3ccc(Nc4nc(NC5COC5)c(-c5cc(F)cc6[nH]ccc56)nc4C(N)=O)cc3)CC2)CC1] | A | 600 | — |
| 605 | 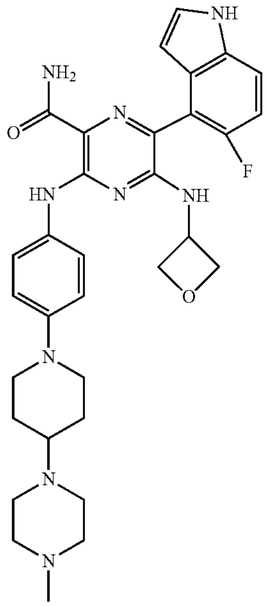 [SMILES: CN1CCN(C2CCN(c3ccc(Nc4nc(NC5COC5)c(-c5c(F)ccc6[nH]ccc56)nc4C(N)=O)cc3)CC2)CC1] | A | 600 | — |

TABLE 2-continued
| | | | | |
|---|---|---|---|---|
| 606 | 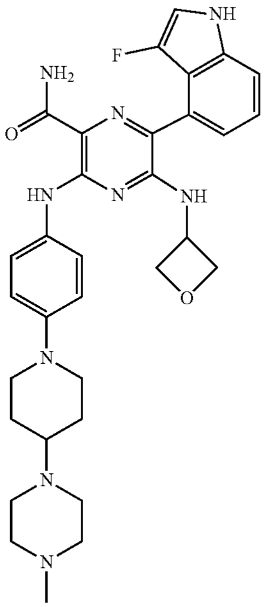 [SMILES: CN1CCN(C2CCN(c3ccc(Nc4nc(NC5COC5)c(-c5cccc6[nH]cc(F)c56)nc4C(N)=O)cc3)CC2)CC1] | A | 600 | — |
| 607 | 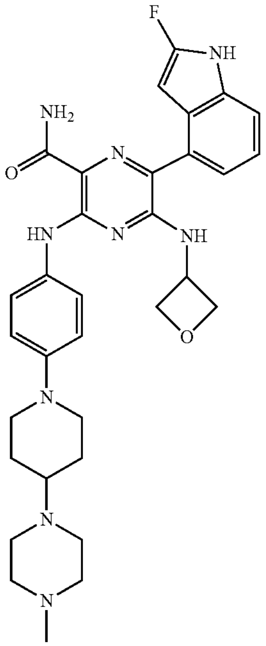 [SMILES: CN1CCN(C2CCN(c3ccc(Nc4nc(NC5COC5)c(-c5cccc6[nH]c(F)cc56)nc4C(N)=O)cc3)CC2)CC1] | A | 600 | — |

TABLE 2-continued
| | | | | |
|---|---|---|---|---|
| 608 | 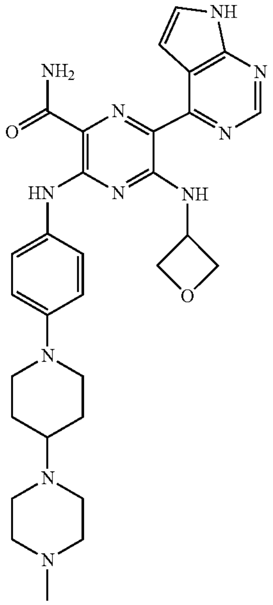 [SMILES: CN1CCN(C2CCN(c3ccc(Nc4nc(NC5COC5)c(-c5ncnc6[nH]ccc56)nc4C(N)=O)cc3)CC2)CC1] | A | 584 | — |
| 609 | 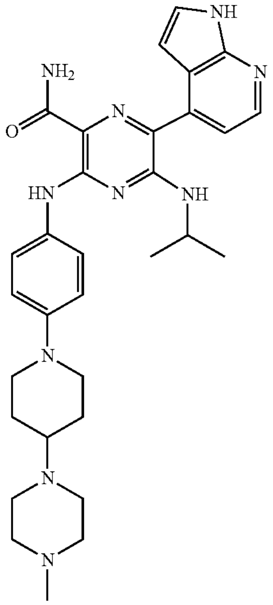 [SMILES: CC(C)Nc1nc(Nc2ccc(N3CCC(N4CCN(C)CC4)CC3)cc2)c(C(N)=O)nc1-c1ccnc2[nH]ccc12] | A | 569 | — |

TABLE 2-continued
| | | | | |
|---|---|---|---|---|
| 610 | 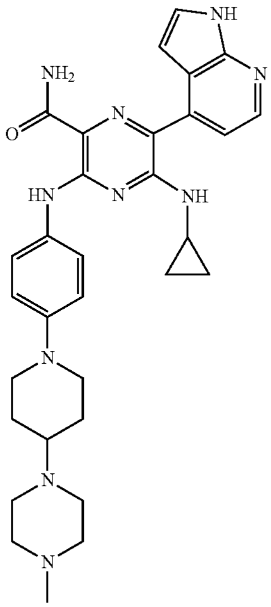 [SMILES: CN1CCN(C2CCN(c3ccc(Nc4nc(NC5CC5)c(-c5ccnc6[nH]ccc56)nc4C(N)=O)cc3)CC2)CC1] | A | 567 | — |
| 611 | 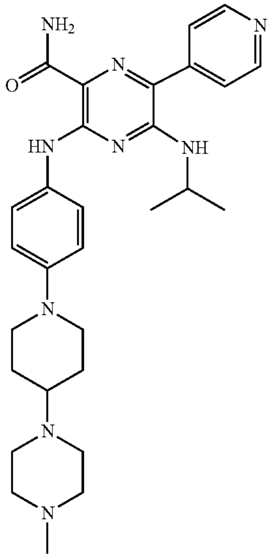 [SMILES: CC(C)Nc1nc(Nc2ccc(N3CCC(N4CCN(C)CC4)CC3)cc2)c(C(N)=O)nc1-c1ccncc1] | A | 530 | 1.105 |

TABLE 2-continued
| | | | | |
|---|---|---|---|---|
| 612 | 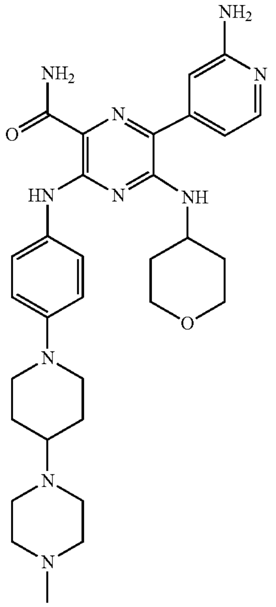 [SMILES: CN1CCN(C2CCN(c3ccc(Nc4nc(NC5CCOCC5)c(-c5ccnc(N)c5)nc4C(N)=O)cc3)CC2)CC1] | A | 587 | 1.181 |
| 613 | 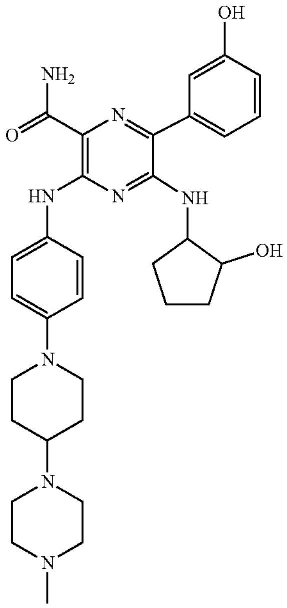 [SMILES: CN1CCN(C2CCN(c3ccc(Nc4nc(NC5CCCC5O)c(-c5cccc(O)c5)nc4C(N)=O)cc3)CC2)CC1] | A | 587 | 1.347 |

TABLE 2-continued
| | | | | |
|---|---|---|---|---|
| 614 | 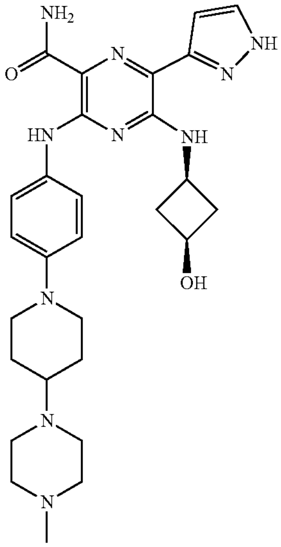 [SMILES: CN1CCN(C2CCN(c3ccc(Nc4nc(N[C@H]5C[C@@H](O)C5)c(-c5cc[nH]n5)nc4C(N)=O)cc3)CC2)CC1] | A | 547 | 1.294 |
| 615 | 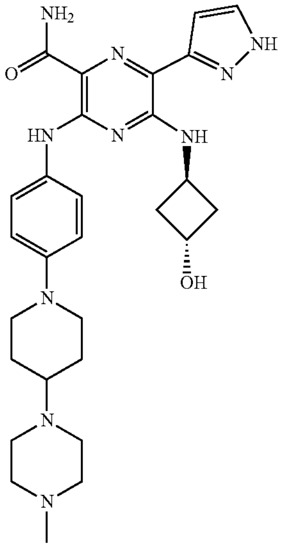 [SMILES: CN1CCN(C2CCN(c3ccc(Nc4nc(N[C@H]5C[C@H](O)C5)c(-c5cc[nH]n5)nc4C(N)=O)cc3)CC2)CC1] | A | 547 | 1.292 |
| 616 | 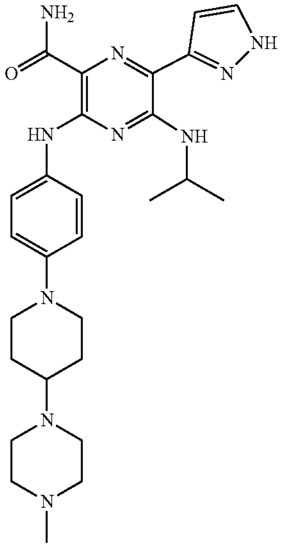 [SMILES: CC(C)Nc1nc(Nc2ccc(N3CCC(N4CCN(C)CC4)CC3)cc2)c(C(N)=O)nc1-c1cc[nH]n1] | A | 519 | 1.340 |

TABLE 2-continued
| | | | | |
|---|---|---|---|---|
| 617 | 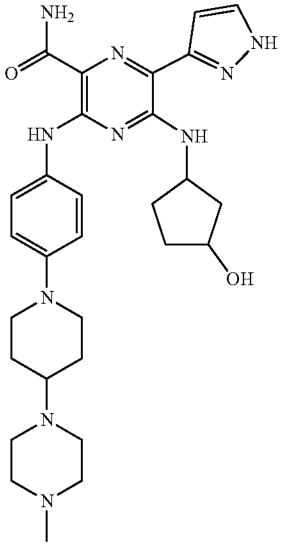 [SMILES: CN1CCN(C2CCN(c3ccc(Nc4nc(NC5CCC(O)C5)c(-c5cc[nH]n5)nc4C(N)=O)cc3)CC2)CC1] | A | 561 | 1.337 |
| 618 | 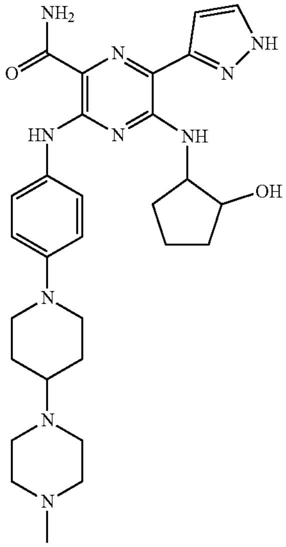 [SMILES: CN1CCN(C2CCN(c3ccc(Nc4nc(NC5CCCC5O)c(-c5cc[nH]n5)nc4C(N)=O)cc3)CC2)CC1] | A | 561 | 1.297 |
| 619 | 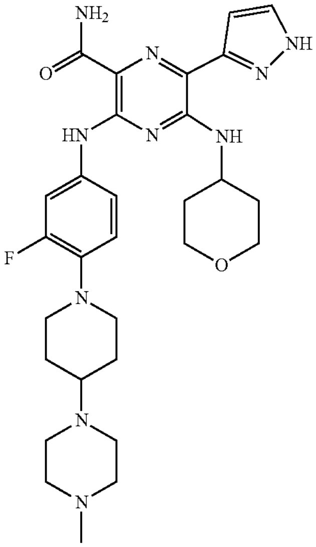 [SMILES: CN1CCN(C2CCN(c3ccc(Nc4nc(NC5CCOCC5)c(-c5cc[nH]n5)nc4C(N)=O)cc3F)CC2)CC1] | A | 579 | — |

TABLE 2-continued
| | | | | |
|---|---|---|---|---|
| 620 | 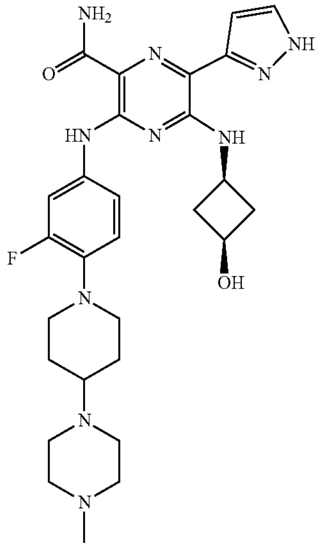 [SMILES: CN1CCN(C2CCN(c3ccc(Nc4nc(N[C@H]5C[C@@H](O)C5)c(-c5cc[nH]n5)nc4C(N)=O)cc3F)CC2)CC1] | A | 565 | — |
| 621 | 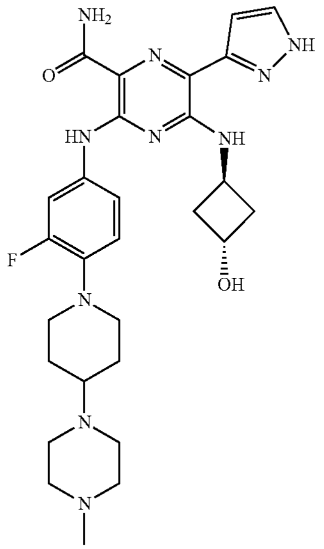 [SMILES: CN1CCN(C2CCN(c3ccc(Nc4nc(N[C@H]5C[C@H](O)C5)c(-c5cc[nH]n5)nc4C(N)=O)cc3F)CC2)CC1] | A | 565 | — |
| 622 | 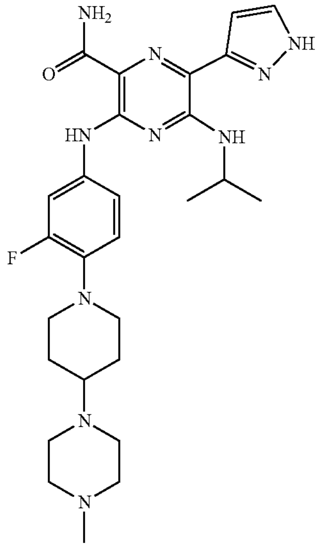 [SMILES: CC(C)Nc1nc(Nc2ccc(N3CCC(N4CCN(C)CC4)CC3)c(F)c2)c(C(N)=O)nc1-c1cc[nH]n1] | A | 537 | — |

TABLE 2-continued
| | | | | |
|---|---|---|---|---|
| 623 | 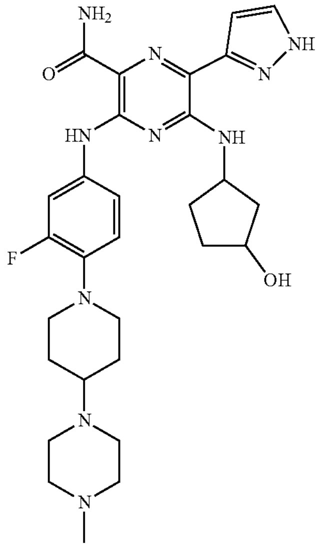 [SMILES: CN1CCN(C2CCN(c3ccc(Nc4nc(NC5CCC(O)C5)c(-c5cc[nH]n5)nc4C(N)=O)cc3F)CC2)CC1] | A | 579 | — |
| 624 | 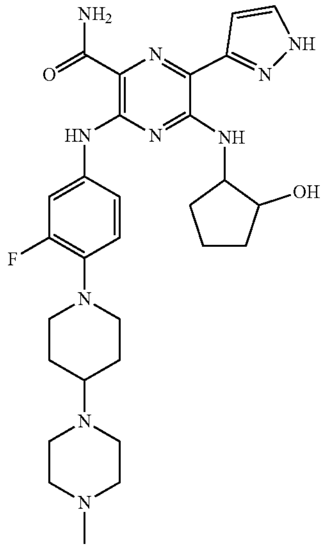 [SMILES: CN1CCN(C2CCN(c3ccc(Nc4nc(NC5CCCC5O)c(-c5cc[nH]n5)nc4C(N)=O)cc3F)CC2)CC1] | A | 579 | — |
| 625 | 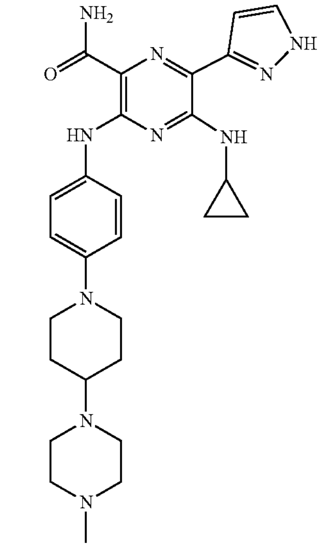 [SMILES: CN1CCN(C2CCN(c3ccc(Nc4nc(NC5CC5)c(-c5cc[nH]n5)nc4C(N)=O)cc3)CC2)CC1] | A | 517 | — |

TABLE 2-continued
| | | | | |
|---|---|---|---|---|
| 626 | 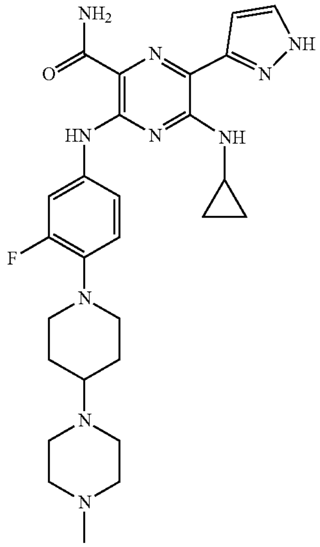 [SMILES: CN1CCN(C2CCN(c3ccc(Nc4nc(NC5CC5)c(-c5cc[nH]n5)nc4C(N)=O)cc3F)CC2)CC1] | A | 535 | — |
| 627 | 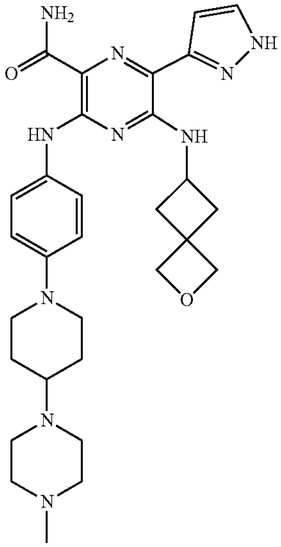 [SMILES: CN1CCN(C2CCN(c3ccc(Nc4nc(NC5CC6(COC6)C5)c(-c5cc[nH]n5)nc4C(N)=O)cc3)CC2)CC1] | A | 573 | 1.455 |
| 628 | 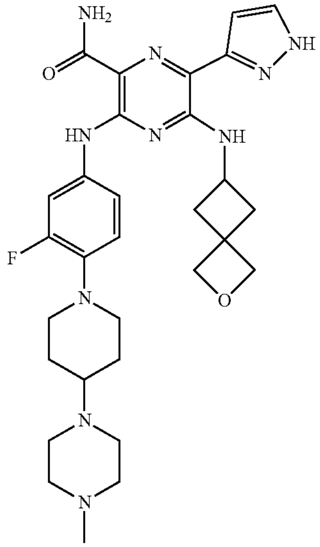 [SMILES: CN1CCN(C2CCN(c3ccc(Nc4nc(NC5CC6(COC6)C5)c(-c5cc[nH]n5)nc4C(N)=O)cc3F)CC2)CC1] | A | 591 | — |

TABLE 2-continued
| | | | | |
|---|---|---|---|---|
| 629 | 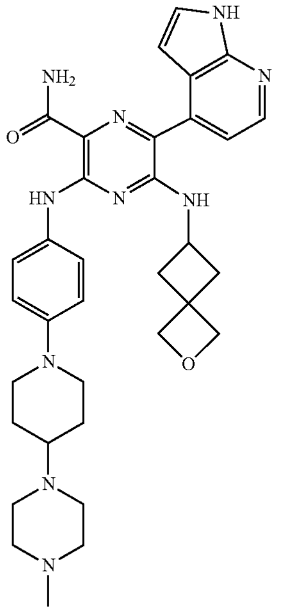 [SMILES: CN1CCN(C2CCN(c3ccc(Nc4nc(NC5CC6(COC6)C5)c(-c5ccnc6[nH]ccc56)nc4C(N)=O)cc3)CC2)CC1] | A | 623 | — |
| 630 | 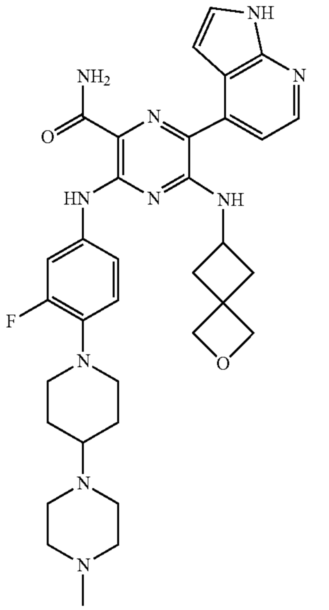 [SMILES: CN1CCN(C2CCN(c3ccc(Nc4nc(NC5CC6(COC6)C5)c(-c5ccnc6[nH]ccc56)nc4C(N)=O)cc3F)CC2)CC1] | A | 641 | — |

TABLE 2-continued
| | | | | |
|---|---|---|---|---|
| 631 | 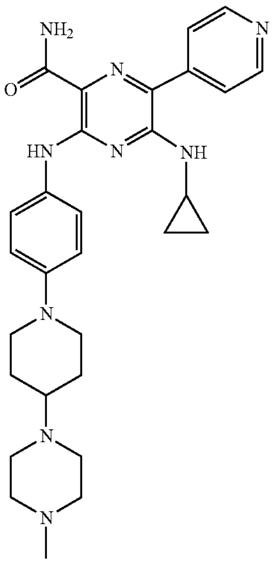 [SMILES: CN1CCN(C2CCN(c3ccc(Nc4nc(NC5CC5)c(-c5ccncc5)nc4C(N)=O)cc3)CC2)CC1] | A | 528 | — |
| 632 | 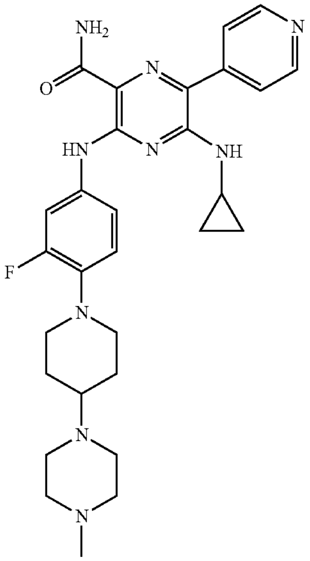 [SMILES: CN1CCN(C2CCN(c3ccc(Nc4nc(NC5CC5)c(-c5ccncc5)nc4C(N)=O)cc3F)CC2)CC1] | A | 546 | — |

TABLE 2-continued
| | | | | |
|---|---|---|---|---|
| 633 | 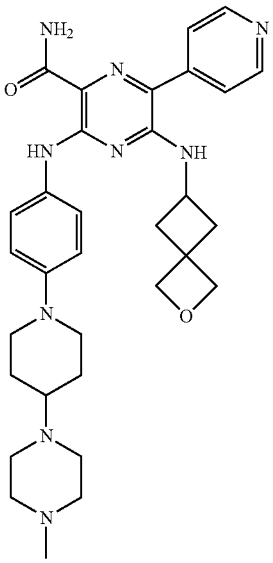 [SMILES: CN1CCN(C2CCN(c3ccc(Nc4nc(NC5CC6(COC6)C5)c(-c5ccncc5)nc4C(N)=O)cc3)CC2)CC1] | A | 584 | — |
| 634 | 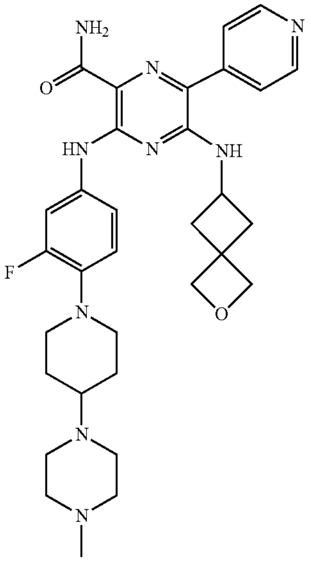 [SMILES: CN1CCN(C2CCN(c3ccc(Nc4nc(NC5CC6(COC6)C5)c(-c5ccncc5)nc4C(N)=O)cc3F)CC2)CC1] | A | 602 | — |

TABLE 2-continued
| | | | | |
|---|---|---|---|---|
| 635 | 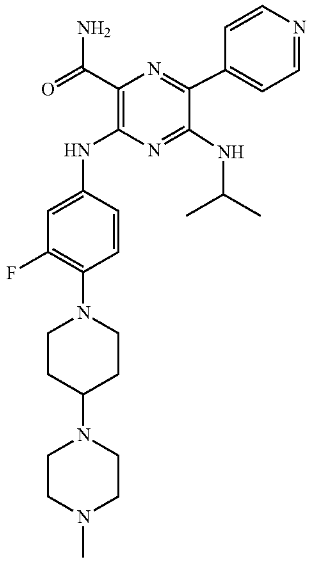 [SMILES: CC(C)Nc1nc(Nc2ccc(N3CCC(N4CCN(C)CC4)CC3)c(F)c2)c(C(N)=O)nc1-c1ccncc1] | A | 548 | — |
| 636 | 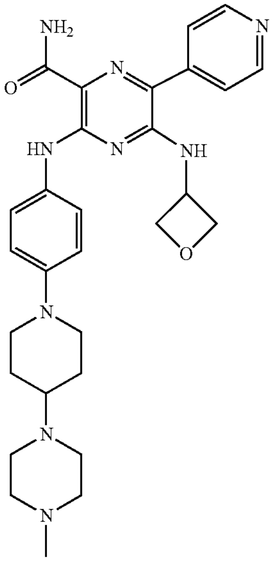 [SMILES: CN1CCN(C2CCN(c3ccc(Nc4nc(NC5COC5)c(-c5ccncc5)nc4C(N)=O)cc3)CC2)CC1] | A | 544 | — |

TABLE 2-continued
| | | | | |
|---|---|---|---|---|
| 637 | 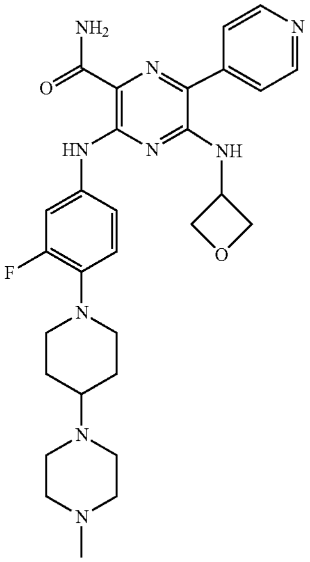 [SMILES: CN1CCN(C2CCN(c3ccc(Nc4nc(NC5COC5)c(-c5ccncc5)nc4C(N)=O)cc3F)CC2)CC1] | A | 562 | — |
| 638 | 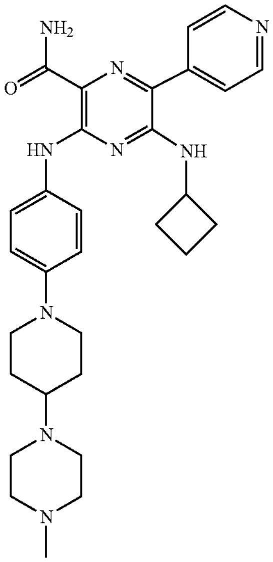 [SMILES: CN1CCN(C2CCN(c3ccc(Nc4nc(NC5CCC5)c(-c5ccncc5)nc4C(N)=O)cc3)CC2)CC1] | A | 542 | — |

TABLE 2-continued
| | | | | |
|---|---|---|---|---|
| 639 | 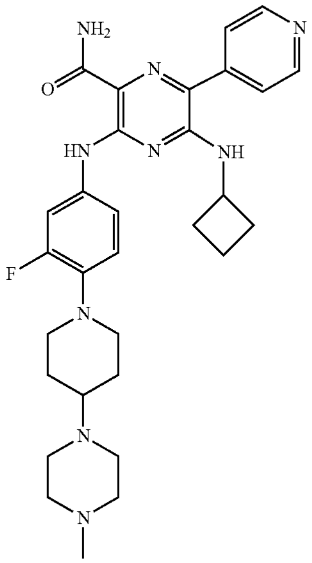 [SMILES: CN1CCN(C2CCN(c3ccc(Nc4nc(NC5CCC5)c(-c5ccncc5)nc4C(N)=O)cc3F)CC2)CC1] | A | 560 | — |
| 640 | 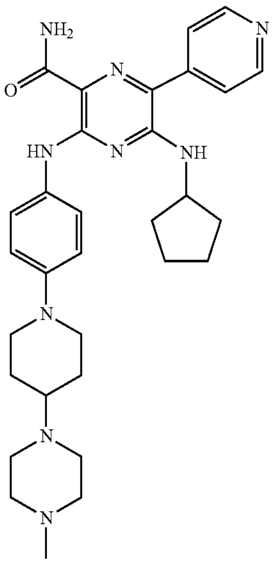 [SMILES: CN1CCN(C2CCN(c3ccc(Nc4nc(NC5CCCC5)c(-c5ccncc5)nc4C(N)=O)cc3)CC2)CC1] | A | 556 | — |

TABLE 2-continued
| | | | | |
|---|---|---|---|---|
| 641 | 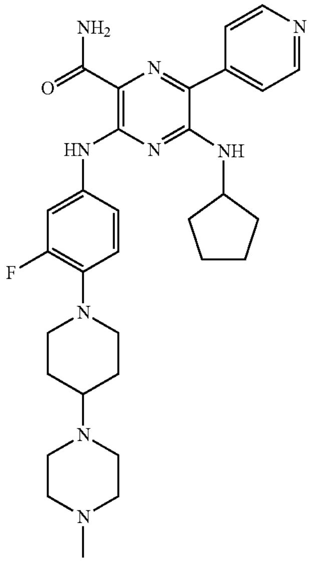 [SMILES: CN1CCN(C2CCN(c3ccc(Nc4nc(NC5CCCC5)c(-c5ccncc5)nc4C(N)=O)cc3F)CC2)CC1] | A | 574 | — |
| 642 | 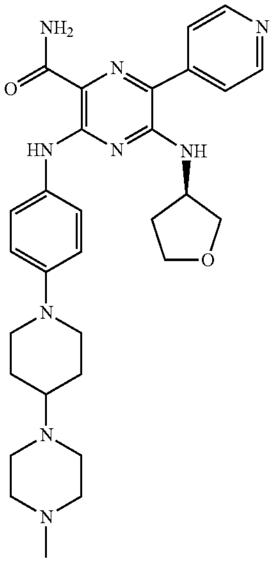 [SMILES: CN1CCN(C2CCN(c3ccc(Nc4nc(N[C@@H]5CCOC5)c(-c5ccncc5)nc4C(N)=O)cc3)CC2)CC1] | A | 558 | — |

TABLE 2-continued
| | | | | |
|---|---|---|---|---|
| 643 | 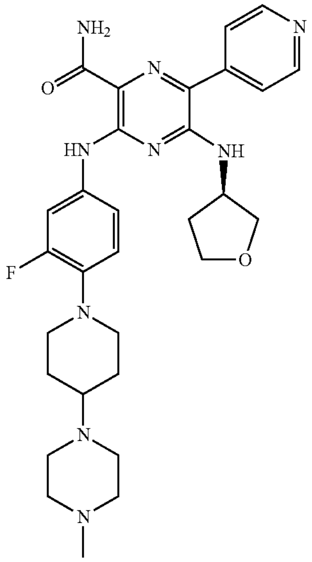 [SMILES: CN1CCN(C2CCN(c3ccc(Nc4nc(N[C@@H]5CCOC5)c(-c5ccncc5)nc4C(N)=O)cc3F)CC2)CC1] | A | 576 | — |
| 644 | 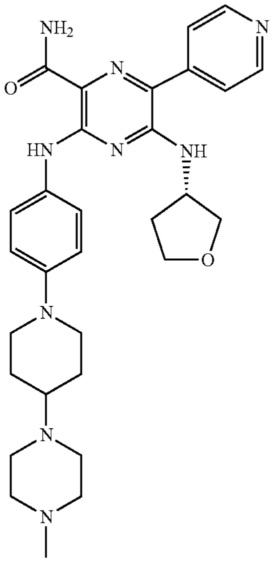 [SMILES: CN1CCN(C2CCN(c3ccc(Nc4nc(N[C@H]5CCOC5)c(-c5ccncc5)nc4C(N)=O)cc3)CC2)CC1] | A | 558 | — |

TABLE 2-continued

| | | | | |
|---|---|---|---|---|
| 645 | 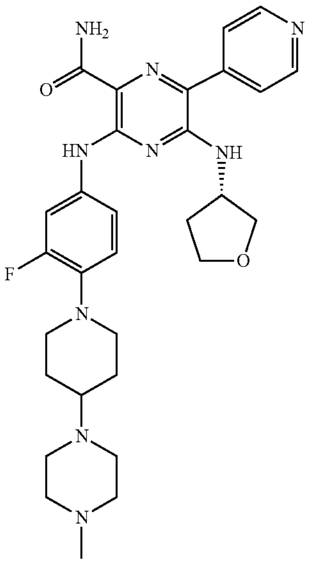 [SMILES: CN1CCN(C2CCN(c3ccc(Nc4nc(N[C@H]5CCOC5)c(-c5ccncc5)nc4C(N)=O)cc3F)CC2)CC1] | A | 576 | — |

TABLE 3

| NMR data of some of the compounds in Table 2 | |
|---|---|
| Compound | NMR |
| 1 | $^1$H NMR (400 MHz, DMSO-$d_6$) δ 11.06 (s, 1H), 7.73-7.67 (m, 2H), 7.60 (s, 1H), 7.51-7.46 (m, 2H), 7.46-7.40 (m, 2H), 7.37-7.31 (m, 1H), 7.27 (d, J = 2.9 Hz, 1H), 6.92-6.85 (m, 2H), 6.62 (d, J = 7.4 Hz, 1H), 4.11-4.01 (m, 1H), 3.90-3.82 (m, 2H), 3.61 (d, J = 11.9 Hz, 2H), 3.43-3.34 (m, 2H), 2.62-2.55 (m, 2H), 2.48 (m, 4H), 2.38-2.19 (m, 5H), 2.12 (s, 3H), 1.82 (t, J = 11.7 Hz, 4H), 1.61-1.44 (m, 4H). |
| 6 | $^1$H NMR (400 MHz, $CDCl_3$) δ 10.81 (s, 1H), 8.10 (d, J = 7.6 Hz, 2H), 7.70 (s, 1H), 7.48 (t, J = 7.6 Hz, 3H), 7.42-7.32 (m, 2H), 7.22 (d, J = 7.9 Hz, 2H), 7.11 (d, J = 8.8 Hz, 2H), 6.83 (d, J = 8.0 Hz, 1H), 6.60 (d, J = 8.7 Hz, 2H), 5.41 (s, 1H), 3.58 (d, J = 12.0 Hz, 2H), 2.77-2.36 (m, 11H), 2.33 (s, 3H), 1.94 (m, 2H), 1.69 (m, 2H). |
| 8 | $^1$H NMR (400 MHz, $CDCl_3$) δ 10.59 (s, 1H), 7.60-7.55 (m, 2H), 7.49 (t, J = 7.5 Hz, 2H), 7.42 (d, J = 7.5 Hz, 1H), 7.39 (d, J = 8.8 Hz, 2H), 6.94 (d, J = 8.8 Hz, 2H), 5.19 (d, J = 6.7 Hz, 1H), 5.15 (s, 1H), 4.26-4.18 (m, 1H), 3.71 (d, J = 12.0 Hz, 2H), 3.15 (s, 1H), 2.78-2.59 (m, 6H), 2.52 (s, 3H), 2.40 (s, 2H), 2.32 (s, 3H), 2.24-2.13 (m, 1H), 1.93 (d, J = 12.4 Hz, 2H), 1.82-1.65 (m, 7H), 1.08 (s, 3H). |
| 10 | $^1$H NMR (400 MHz, $CDCl_3$) δ 10.66 (s, 1H), 7.64-7.56 (m, 4H), 7.50 (s, 1H), 7.43-7.38 (m, 2H), 7.34-7.28 (m, 1H), 6.96-6.91 (m, 2H), 5.19 (s, 1H), 3.69 (d, J = 11.9 Hz, 2H), 2.88 (s, 6H), 2.74-2.36 (m, 11H), 2.32 (s, 3H), 1.95 (d, J = 12.4 Hz, 2H), 1.74 (m, 2H). |
| 11 | $^1$H NMR (400 MHz, $CDCl_3$) δ 10.82 (s, 1H), 7.65-7.55 (m, 4H), 7.51-7.36 (m, 4H), 6.96-6.89 (m, 2H), 5.13 (d, J = 7.1 Hz, 2H), 4.26 (dt, J = 13.2, 6.6 Hz, 1H), 3.69 (d, J = 11.9 Hz, 2H), 2.75-2.33 (m, 11H), 2.31 (s, 3H), 1.95 (d, J = 11.8 Hz, 2H), 1.74 (m, 2H). |
| 16 | $^1$H NMR (400 MHz, $CDCl_3$) δ 10.79 (s, 1H), 7.60-7.53 (m, 4H), 7.51-7.44 (m, 3H), 7.43-7.37 (m, 1H), 6.95-6.90 (m, 2H), 5.37 (d, J = 6.4 Hz, 1H), 5.19 (s, 1H), 4.63 (d, J = 9.9 Hz, 1H), 3.97-3.87 (m, 2H), 3.81 (td, J = 8.5, 5.8 Hz, 1H), 3.75-3.66 (m, 3H), 2.76-2.32 (m, 11H), 2.30 (s, 3H), 1.95 (d, J = 12.3 Hz, 2H), 1.83 m, 1H), 1.71 (m, 3H). |
| 24 | $^1$H NMR (400 MHz, $CDCl_3$) δ 10.81 (s, 1H), 7.60 (dd, J = 8.8, 6.7 Hz, 4H), 7.48 (t, J = 7.6 Hz, 3H), 7.40 (t, J = 7.3 Hz, 1H), 6.90 (d, J = 8.9 Hz, 2H), 5.30 (d, J = 7.1 Hz, 1H), 5.14 (s, 1H), 4.00 (d, J = 17.1 Hz, 2H), 3.67 (d, J = 12.0 Hz, 2H), 2.69 (t, J = 11.5 Hz, 6H), 2.53 (s, 4H), 2.44-2.36 (m, 1H), 2.32 (s, 3H), 1.95 (d, J = 12.4 Hz, 2H), 1.84 (d, J = 10.1 Hz, 2H), 1.77-1.68 (m, 8H). |
| 28 | $^1$H NMR (400 MHz, $CDCl_3$) δ 10.81 (s, 1H), 7.64-7.57 (m, 4H), 7.47 (t, J = 7.5 Hz, 3H), 7.41-7.35 (m, 1H), 6.98-6.89 (m, 2H), 6.02 (t, J = 4.6 Hz, 1H), 5.15 (s, 1H), 3.68 (d, J = 11.9 Hz, 2H), 3.53 (q, J = 5.8 Hz, 2H), 2.75-2.60 (m, 6H), 2.51 (t, J = 6.1 Hz, 6H), 2.42-2.33 (m, 1H), 2.31 (s, 3H), 2.21 (s, 6H), 1.94 (d, J = 11.8 Hz, 2H), 1.67 (d, J = 9.1 Hz, 2H). |
| 30 | $^1$H NMR (400 MHz, $CDCl_3$) δ 10.80 (s, 1H), 7.65-7.57 (m, 4H), 7.52-7.44 (m, 3H), 7.43-7.38 (m, 1H), 6.97-6.91 (m, 2H), 5.42 (d, J = 6.8 Hz, 1H), 5.14 (s, 1H), 4.49 (p, J = 7.6 Hz, 1H), 3.70 (d, J = 11.8 Hz, 2H), 2.77-2.63 (m, 6H), 2.52 (s, 4H), 2.47-2.36 (m, 3H), 2.32 (s, 3H), 1.96 (d, J = 12.5 Hz, 2H), 1.90-1.74 (m, 6H). |
| 32 | $^1$H NMR (400 MHz, $CDCl_3$) δ 10.70 (s, 1H), 7.62-7.54 (m, 4H), 7.49 (dd, J = 8.4, 6.8 Hz, 3H), 7.41 (t, J = 7.4 Hz, 1H), 6.93 (d, J = 8.9 Hz, 2H), 5.38 (d, J = 5.1 Hz, 1H), 5.17 (s, 1H), 4.50 (q, J = 6.2, 5.2 Hz, 2H), 3.72 (d, J = 12.4 Hz, 2H), 2.72 (dd, J = 24.4, 12.2 Hz, 6H), 2.57 (d, J = 33.4 Hz, 4H), 2.45-2.33 (m, 4H), 2.32 (s, 3H), 2.25 (dt, J = 13.3, 6.6 Hz, 3H), 1.94 (d, J = 12.2 Hz, 2H). |

TABLE 3-continued

| NMR data of some of the compounds in Table 2 | |
|---|---|
| Compound | NMR |
| 37 | $^1$H NMR (400 MHz, $CDCl_3$) δ 10.81 (s, 1H), 8.85 (d, J = 2.2 Hz, 1H), 8.62 (dd, J = 4.9, 1.7 Hz, 1H), 7.89 (dt, J = 8.0, 2.0 Hz, 1H), 7.54 (d, J = 8.9 Hz, 2H), 7.40 (dd, J = 7.9, 4.7 Hz, 2H), 6.89 (d, J = 8.9 Hz, 2H), 5.23 (s, 1H), 5.00 (d, J = 7.1 Hz, 1H), 4.14 (q, J = 8.1, 6.2 Hz, 1H), 4.03-3.92 (m, 2H), 3.67 (d, J = 11.8 Hz, 2H), 3.50 (td, J = 11.6, 2.1 Hz, 2H), 2.78-2.42 (m, 10H), 2.41-2.33 (m, 1H), 2.30 (s, 3H), 2.03 (d, J = 12.7 Hz, 2H), 1.94 (d, J = 12.4 Hz, 2H), 1.70 (tt, J = 13.2, 6.6 Hz, 2H), 1.49 (qd, J = 12.1, 4.3 Hz, 2H). |
| 39 | $^1$H NMR (400 MHz, $CDCl_3$) δ 10.86 (s, 1H), 8.71 (d, J = 5.1 Hz, 2H), 7.55 (t, J = 6.8 Hz, 4H), 7.42 (s, 1H), 6.91 (d, J = 8.8 Hz, 2H), 5.22 (s, 1H), 5.14 (d, J = 7.0 Hz, 1H), 4.17 (m, 1H), 4.01 (d, J = 11.7 Hz, 2H), 3.69 (d, J = 9.2 Hz, 2H), 3.52 (t, J = 11.6 Hz, 2H), 2.69 (m, 11H), 2.38 (s, 3H), 2.09-1.96 (m, 4H), 1.76 - 1.64 (m, 4H). |
| 40 | $^1$H NMR (400 MHz, $CDCl_3$) δ 10.74 (s, 1H), 7.75 (s, 1H), 7.65 (s, 1H), 7.55 (d, J = 8.8 Hz, 2H), 7.42 (s, 1H), 6.90 (d, J = 8.9 Hz, 2H), 5.17 (s, 1H), 5.11 (d, J = 7.0 Hz, 1H), 4.19-4.08 (m, 1H), 3.99 (m, 5H), 3.67 (d, J = 11.9 Hz, 2H), 3.54 (dd, J = 12.4, 10.3 Hz, 2H), 2.78-2.35 (m, 11H), 2.33 (s, 3H), 2.06 (t, J = 11.3 Hz, 2H), 1.96 (d, J = 12.3 Hz, 2H), 1.72 (m, 2H), 1.53 (m, 2H). |
| 43 | $^1$H NMR (400 MHz, $CDCl_3$) δ 10.75 (s, 1H), 7.55 (d, J = 8.7 Hz, 2H), 7.47 (s, 1H), 7.34 (t, J = 7.9 Hz, 1H), 7.14-7.10 (m, 1H), 7.05 (s, 1H), 6.88 (t, J = 9.0 Hz, 3H), 5.27 (d, J = 7.1 Hz, 1H), 5.18 (s, 1H), 4.13 (dd, J = 10.2, 3.8 Hz, 1H), 3.98 (d, J = 11.8 Hz, 2H), 3.67 (d, J = 11.9 Hz, 2H), 3.51 (t, J = 11.4 Hz, 2H), 2.73-2.35 (m, 11H), 2.31 (s, 3H), 2.04 (d, J = 8.3 Hz, 2H), 1.95 (d, J = 12.4 Hz, 2H), 1.72 (m, 2H), 1.52-1.48 (m, 2H). |
| 44 | $^1$H NMR (400 MHz, $CDCl_3$) δ 10.85 (s, 1H), 8.21 (d, J = 2.1 Hz, 1H), 7.96 (d, J = 7.8 Hz, 1H), 7.90 (d, J = 7.7 Hz, 1H), 7.69 (t, J = 7.8 Hz, 1H), 7.56 (d, J = 8.8 Hz, 2H), 7.40 (s, 1H), 6.91 (d, J = 8.8 Hz, 2H), 5.22 (s, 1H), 5.03 (d, J = 6.9 Hz, 1H), 4.19-4.12 (m, 1H), 3.99 (d, J = 11.7 Hz, 2H), 3.69 (d, J = 11.8 Hz, 2H), 3.52 (t, J = 11.4 Hz, 2H), 3.11 (s, 3H), 2.76-2.38 (m, 11H), 2.35 (s, 3H), 2.01 (m, 4H), 1.74 (m, 2H), 1.50 (m, 2H). |
| 49 | $^1$H NMR (400 MHz, $CDCl_3$) δ 10.82 (s, 1H), 8.76 (d, J = 7.1 Hz, 1H), 7.65-7.57 (m, 2H), 7.54-7.44 (m, 1H), 7.37 (d, J = 2.3 Hz, 1H), 6.94-6.86 (m, 2H), 6.81 (d, J = 2.3 Hz, 1H), 5.24 (s, 1H), 4.27 (ddt, J = 14.3, 10.1, 5.2 Hz, 1H), 4.04 (dt, J = 11.9, 4.0 Hz, 2H), 3.94 (s, 3H), 3.71-3.56 (m, 4H), 2.76-2.34 (m, 11H), 2.32 (s, 3H), 2.14 (dd, J = 13.1, 3.2 Hz, 2H), 1.95 (m, 2H), 1.71 (m, 4H). |
| 53 | $^1$H NMR (400 MHz, $CDCl_3$) δ 10.87 (s, 1H), 7.79-7.69 (m, 4H), 7.59-7.53 (m, 2H), 7.40 (s, 1H), 6.90 (d, J = 8.8 Hz, 2H), 5.23 (s, 1H), 5.08-5.01 (m, 1H), 4.23-4.09 (m, 1H), 4.00 (d, J = 11.6 Hz, 2H), 3.69 (d, J = 12.1 Hz, 2H), 3.58-3.46 (m, 3H), 2.95 (s, 8H), 2.72 (t, J = 12.0 Hz, 3H), 2.56 (s, 3H), 2.05 (d, J = 14.1 Hz, 4H), 1.52 (td, J = 11.5, 7.3 Hz, 4H). |
| 55 Fumarate | $^1$H NMR (400 MHz, DMSO-$d_6$) δ 13.05 (s, 1H), 11.21 (s, 1H), 8.90 (s, 1H), 8.00-7.92 (m, 1H), 7.81 (d, J = 2.4 Hz, 1H), 7.55-7.47 (m, 2H), 7.31 (d, J = 2.8 Hz, 1H), 7.21 (d, J = 2.4 Hz, 1H), 6.89 (d, J = 8.9 Hz, 2H), 6.54 (s, 4H), 4.11 (m, J = 6.2 Hz, 1H), 3.89 (dt, J = 11.5, 3.7 Hz, 2H), 3.62 (d, J = 11.8 Hz, 2H), 3.49 (td, J = 11.5, 2.4 Hz, 2H), 2.88-2.52 (m, 9H), 2.42 (s, 3H), 2.10-1.99 (m, 2H), 1.84 (d, J = 11.1 Hz, 2H), 1.61-1.40 (m, 4H). |
| 59 | $^1$H NMR (400 MHz, $CDCl_3$) δ 10.79 (s, 1H), 7.61-7.55 (m, 4H), 7.49 (t, J = 7.6 Hz, 3H), 7.41 (t, J = 7.3 Hz, 1H), 6.91 (d, J = 8.9 Hz, 2H), 5.22-5.12 (m, 2H), 4.19-4.11 (m, 1H), 3.99 (d, J = 11.8 Hz, 2H), 3.68 (d, J = 11.9 Hz, 2H), 3.58-3.47 (m, 2H), 2.71 (t, J = 12.0 Hz, 2H), 2.39 (s, 7H), 2.08-1.97 (m, 4H), 1.76-1.70 (m, 2H), 1.51 (m, 2H). |
| 64 | $^1$H NMR (400 MHz, $CDCl_3$) δ 10.77 (s, 1H), 7.55 (dd, J = 8.7, 5.4 Hz, 4H), 7.42 (s, 1H), 7.18 (t, J = 8.6 Hz, 2H), 6.94-6.87 (m, 2H), 5.16 (s, 1H), 5.04 (d, J = 7.1 Hz, 1H), 4.21-4.09 (m, 1H), 3.99 (d, J = 11.5 Hz, 2H), 3.68 (d, J = 12.0 Hz, 2H), 3.57-3.48 (m, 2H), 2.77-2.63 (m, 6H), 2.52 (s, 4H), 2.38 (d, J = 11.7 Hz, 1H), 2.32 (s, 3H), 2.05 (d, J = 12.5 Hz, 3H), 1.96 (d, J = 12.4 Hz, 2H), 1.78-1.70 (m, 2H), 1.52-1.44 (m, 2H). |
| 65 | $^1$H NMR (400 MHz, $CDCl_3$) δ 10.78 (s, 1H), 7.59-7.50 (m, 4H), 7.48-7.43 (m, 2H), 7.42 (s, 1H), 6.90 (d, J = 8.9 Hz, 2H), 5.19 (s, 1H), 5.05 (d, J = 7.1 Hz, 1H), 4.19-4.07 (m, 1H), 4.04-3.95 (m, 2H), 3.68 (d, J = 11.8 Hz, 2H), 3.52 (td, J = 11.6, 2.2 Hz, 2H), 2.76-2.59 (m, 6H), 2.50 (s, 4H), 2.38 (t, J = 11.5 Hz, 1H), 2.30 (s, 3H), 2.08-2.01 (m, 2H), 1.96 (d, J = 12.4 Hz, 2H), 1.77-1.69 (m, 2H), 1.56-1.45 (m, 2H). |
| 67 | $^1$H NMR (400 MHz, $CDCl_3$) δ 10.82 (s, 1H), 8.42 (s, 1H), 8.39 (d, J = 4.8 Hz, 1H), 7.61-7.53 (m, 2H), 7.38 (d, J = 4.8 Hz, 2H), 6.94-6.87 (m, 2H), 5.20 (s, 1H), 4.92 (d, J = 7.3 Hz, 1H), 4.23-4.12 (m, 1H), 4.04-3.97 (m, 2H), 3.96 (s, 3H), 3.69 (d, J = 11.9 Hz, 2H), 3.53 (td, J = 11.6, 2.2 Hz, 2H), 2.75-2.36 (m, 11H), 2.32 (s, 3H), 2.04 (d, J = 12.8 Hz, 2H), 1.96 (d, J = 12.5 Hz, 2H), 1.72-1.67 (m, 2H), 1.49 (qd, J = 11.7,4.3 Hz, 2H). |
| 69 Hydrochloride | $^1$H NMR (400 MHz, DMSO-$d_6$) δ 11.51 (s, 1H), 7.96 (s, 1H), 7.78 (d, J = 1.8 Hz, 1H), 7.73 (d, J = 8.8 Hz, 2H), 7.48 (s, 3H), 7.26 (d, J = 3.5 Hz, 1H), 7.00 (d, J = 7.2 Hz, 1H), 6.66 (dd, J = 3.5, 1.8 Hz, 1H), 4.17-4.09 (m, 1H), 3.98-3.89 (m, 2H), 3.74 -3.70 (m, 2H) 3.57-3.43 (m, 11H), 3.28 (m, 2H), 2.83 (s, 3H), 2.27 (d, J = 36.8 Hz, 4H), 1.98 (d, J = 12.6 Hz, 2H), 1.67 (qd, J = 12.2, 4.5 Hz, 2H). |
| 87 | $^1$H NMR (400 MHz, $CDCl_3$) δ 10.72 (s, 1H), 7.60-7.54 (m, 2H), 7.49 (s, 1H), 7.45 (d, J = 8.5 Hz, 2H), 6.92-6.86 (m, 2H), 6.80 (d, J = 8.5 Hz, 2H), 5.26 (d, J = 7.2 Hz, 1H), 5.19 (s, 1H), 4.20-4.08 (m, 1H), 3.98 (dt, J = 11.7, 3.6 Hz, 2H), 3.67 (d, J = 11.9 Hz, 2H), 3.53 (td, J = 11.5, 2.2 Hz, 2H), 3.02 (s, 6H), 2.79-2.61 (m, 6H), 2.51 (s, 4H), 2.39 (td, J = 11.6, 11.2, 5.6 Hz, 1H), 2.31 (s, 3H), 2.05 (d, J = 13.0 Hz, 2H), 1.95 (d, J = 12.6 Hz, 2H), 1.71 (qd, J = 12.0, 3.7 Hz, 2H), 1.57-1.43 (m, 2H). |
| 91 | $^1$H NMR (400 MHz, $CDCl_3$) δ 10.76 (s, 1H), 7.74 (t, J = 1.2 Hz, 1H), 7.58-7.52 (m, 3H), 7.44 (s, 1H), 6.93-6.87 (m, 2H), 6.74 (dd, J = 1.8, 0.9 Hz, 1H), 5.20 (s, 1H), 5.12 (d, J = 7.0 Hz, 1H), 4.18-4.10 (m, 1H), 4.05-3.97 (m, 2H), 3.68 (d, J = 12.0 Hz, 2H), 3.54 (td, J = 11.5, 2.1 Hz, 2H), 2.78-2.37 (m, 11H), 2.34 (s, 3H), 2.08 (d, J = 12.9 Hz, 2H), 1.96 (d, J = 12.4 Hz, 2H), 1.70 (m, 2H), 1.57-1.51 (m, 2H). |
| 93 | $^1$H NMR (400 MHz, $CDCl_3$) δ 10.79 (s, 1H), 7.59-7.53 (m, 2H), 7.51 (dd, J = 2.9, 1.3 Hz, 1H), 7.48-7.42 (m, 2H), 7.38 (dd, J = 5.0, 1.4 Hz, 1H), 6.92-6.87 (m, 2H), 5.30 (d, J = 7.1 Hz, 1H), 5.20 (s, 1H), 4.15 (ddd, J = 10.9, 8.8, 5.1 Hz, 1H), 4.00 (dt, J = 11.7, 3.5 Hz, 2H), 3.68 (d, J = 12.1 Hz, 2H), 3.54 (td, J = 11.6, 2.2 Hz, 2H), 2.86-2.46 (m, 11H), 2.42 (s, 3H), 2.07 (d, J = 12.9 Hz, 2H), 1.98 (d, J = 11.7 Hz, 2H), 1.78-1.67 (m, 2H), 1.60-1.49 (m, 2H). |

TABLE 3-continued

| NMR data of some of the compounds in Table 2 | |
|---|---|
| Compound | NMR |
| 94 | $^1$H NMR (400 MHz, $CDCl_3$) δ 10.79 (s, 1H), 7.58-7.53 (m, 2H), 7.44 (s, 1H), 7.37 (dd, J = 5.1, 1.1 Hz, 1H), 7.27 (dd, J = 3.5, 1.0 Hz, 1H), 7.12 (dd, J = 5.1, 3.6 Hz, 1H), 6.93-6.87 (m, 2H), 5.51 (d, J = 7.0 Hz, 1H), 5.24 (s, 1H), 4.22-4.14 (m, 1H), 4.06-3.98 (m, 2H), 3.68 (d, J = 11.9 Hz, 2H), 3.55 (td, J = 11.5, 2.2 Hz, 2H), 2.78-2.36 (m, 11H), 2.34 (s, 3H), 2.09 (d, J = 12.8 Hz, 2H), 1.96 (d, J = 12.4 Hz, 2H), 1.72 (m, 2H), 1.61-1.54 (m, 2H). |
| 101 | $^1$H NMR (400 MHz, $CDCl_3$) δ 10.81 (s, 1H), 7.69 (d, J = 8.1 Hz, 2H), 7.63 (d, J = 8.1 Hz, 2H), 7.59-7.53 (m, 2H), 7.43 (s, 1H), 6.94-6.88 (m, 2H), 6.71 (t, J = 56.4 Hz, 1H), 5.22 (s, 1H), 5.10(d, J = 7.1 Hz, 1H), 4.15 (dd, J = 11.0, 4.0 Hz, 1H), 4.01 (dd, J = 11.8, 4.2 Hz, 2H), 3.99 (dt, J = 12.4, 3.7 Hz, 2H), 3.69 (d, J = 11.9 Hz, 2H), 3.52 (td, J = 11.6, 2.1 Hz, 2H), 2.92-2.57 (m, 11H), 2.45 (d, J = 12.1 Hz, 1H), 2.40 (s, 3H), 2.08-2.00 (m, 4H), 1.73 (dd, J = 12.1, 3.9 Hz, 2H), 1.55-1.46 (m, 2H). |
| 108 | $^1$H NMR (400 MHz, $CDCl_3$) δ 10.85 (s, 1H), 8.59 (d, J = 5.1 Hz, 1H), 7.58-7.51 (m, 2H), 7.43 (s, 1H), 7.38 (s, 1H), 7.32 (dd, J = 5.2, 1.7 Hz, 1H), 6.94-6.88 (m, 2H), 5.25 (s, 1H), 5.13 (d, J = 7.0 Hz, 1H), 4.21-4.10 (m, 1H), 4.01 (dd, J = 11.8, 4.2 Hz, 2H), 3.69 (d, J = 11.9 Hz, 2H), 3.52 (td, J = 11.6, 2.1 Hz, 2H), 2.75-2.64 (m, 6H), 2.63 (s, 3H), 2.51 (s, 4H), 2.39 (t, J = 11.4 Hz, 1H), 2.31 (s, 3H), 2.10-2.02 (m, 2H), 1.96 (d, J = 12.1 Hz, 2H), 1.75-1.65 (m, 2H), 1.52 (tt, J = 11.5, 5.7 Hz, 2H). |
| 112 | $^1$H NMR (400 MHz, $CDCl_3$) δ 10.90 (s, 1H), 7.61-7.56 (m, 2H), 7.53-7.45 (m, 4H), 7.45-7.40 (m, 1H), 6.96 (d, J = 2.3 Hz, 1H), 6.86 (d, J = 8.6 Hz, 1H), 5.22 (d, J = 7.3 Hz, 1H), 5.18 (s, 1H), 4.19 (dd, J = 10.9, 4.0 Hz, 1H), 3.96 (d, J = 11.7 Hz, 2H), 3.89 (s, 3H), 3.51 (t, J = 11.4 Hz, 4H), 2.94-2.49 (m, 11H), 2.43 (s, 3H), 2.08-1.95 (m, 4H), 1.84 (m, 2H), 1.53-1.47 (m, 2H). |
| 113 | $^1$H NMR (400 MHz, DMSO-$d_6$) δ 11.18 (s, 1H), 8.25 (d, J = 8.9 Hz, 1H), 7.75-7.68 (m, 2H), 7.55 (s, 1H), 7.44 (t, J = 7.7 Hz, 2H), 7.38-7.32 (m, 1H), 7.14 (s, 1H), 6.64-6.56 (m, 2H), 6.47 (dd, J = 8.9, 2.5 Hz, 1H), 4.14-3.99 (m, 2H), 3.93-3.79 (m, 5H), 3.65 (d, J = 12.1 Hz, 2H), 3.44-3.35 (m, 4H), 2.60 (t, J = 11.6 Hz, 2H), 2.27 (q, J = 11.0, 10.3 Hz, 5H), 2.12 (s, 3H), 1.84 (t, J = 12.8 Hz, 4H), 1.56 (dtd, J = 36.4, 12.0, 4.1 Hz, 5H). |
| 114 | $^1$H NMR (400 MHz, $CDCl_3$) δ 10.94 (s, 1H), 8.73-8.70 (m, 2H), 7.54 (d, J = 5.3 Hz, 2H), 7.51-7.41 (m, 3H), 6.96 (d, J = 8.5 Hz, 1H), 5.23 (s, 1H), 5.14 (d, J = 7.1 Hz, 1H), 4.20 (s, 1H), 4.00 (d, J = 11.6 Hz, 2H), 3.53 (t, J = 11.5 Hz, 2H), 3.16 (d, J = 11.7 Hz, 2H), 2.85-2.57 (m, 11H), 2.39 (s, 3H), 2.31 (s, 3H), 2.07 (d, J = 13.1 Hz, 2H), 1.98 (d, J = 14.9 Hz, 2H), 1.73 (m, 2H), 1.46 (m, 2H). |
| 118 Hydrochloride | $^1$H NMR (400 MHz, DMSO-$d_6$) δ 11.54 (s, 1H), 8.76 (d, J = 6.8 Hz, 2H), 8.45 (d, J = 6.2 Hz, 2H), 8.13 (s, 1H), 7.60 (t, J = 9.0 Hz, 4H), 7.02 (d, J = 9.0 Hz, 2H),4.10 (m, 1H) 3.92 (d, J = 11.3 Hz, 2H), 3.79 (d, J = 13.0 Hz, 2H), 3.15 (d, J = 11.2 Hz, 3H), 3.01 (t, J = 12.4 Hz, 3H), 2.82 (d, J = 4.3 Hz, 3H), 1.92 (d, J = 12.6 Hz, 2H), 1.64-1.56 (m, 2H). |
| 124 | $^1$H NMR (400 MHz, $CDCl_3$) δ 10.76 (s, 1H), 8.71 (s, 2H), 7.59-7.48 (m, 4H), 7.42 (s, 1H), 6.77-6.69 (m, 2H), 5.28 (s, 1H), 5.13 (d, J = 7.0 Hz, 1H), 4.20-4.11 (m, 1H), 4.00 (dt, J = 11.7, 3.8 Hz, 2H), 3.52 (td, J = 11.6, 2.1 Hz, 2H), 2.95 (s, 6H), 2.10-2.01 (m, 2H), 1.52 (qd, J = 11.4, 4.4 Hz, 2H). |
| 125 | $^1$H NMR (400 MHz, $CDCl_3$) δ 10.83 (s, 1H), 7.65-7.57 (m, 4H), 7.50 (t, J = 7.6 Hz, 3H), 7.41 (t, J = 7.2 Hz, 1H), 6.96-6.89 (m, 2H), 5.41 (d, J = 5.3 Hz, 1H), 5.17 (s, 1H), 4.52-4.45 (m, 1H), 4.05 (p, J = 6.1 Hz, 1H), 3.69 (d, J = 11.8 Hz, 2H), 3.26 (s, 3H), 2.96-2.61 (m, 12H), 2.46 (d, J = 9.2 Hz, 4H), 2.18 (dt, J = 12.5, 6.0 Hz, 2H), 2.01 (d, J = 16.2 Hz, 4H). |
| 126 Hydrochloride | $^1$H NMR (400 MHz, DMSO-$d_6$) δ 11.24 (s, 1H), 7.76 (d, J = 7.1 Hz, 3H), 7.54 (dd, J = 16.3, 6.7 Hz, 3H), 7.50-7.37 (m, 4H), 7.26 (s, 2H), 4.64-4.56 (m, 1H), 4.38 (qd, J = 13.3, 7.3 Hz, 4H), 3.81-3.44 (m, 10H), 2.99 (s, 2H), 2.83 (s, 3H), 2.22 (s, 2H), 1.99 (t, J = 7.6 Hz, 3H). |
| 131 | $^1$H NMR (400 MHz, $CDCl_3$) δ 10.74 (s, 1H), 7.96-7.91 (m, 2H), 7.64 (s, 1H), 7.49 (d, J = 8.9 Hz, 2H), 7.42 (t, J = 7.5 Hz, 2H), 7.34 (t, J = 7.3 Hz, 1H), 6.94 (d, J = 9.0 Hz, 2H), 5.47 (t, J = 6.9 Hz, 1H), 5.37 (s, 1H), 3.71 (d, J = 12.1 Hz, 2H), 3.62 (t, J = 5.4 Hz, 2H), 3.10 (dd, J = 11.0, 6.1 Hz, 1H), 2.87-2.78 (m, 2H), 2.76-2.65 (m, 10H), 2.58 (s, 4H), 2.47-2.30 (m, 6H), 2.06 (d, J = 14.1 Hz, 2H), 1.96 (d, J = 12.7 Hz, 2H), 1.42-1.33 (m, 2H). |
| 132 Hydrochloride | $^1$H NMR (400 MHz, $CDCl_3$) δ 10.74 (s, 1H), 7.96-7.91 (m, 2H), 7.64 (s, 1H), 7.49 (d, J = 8.9 Hz, 2H), 7.42 (t, J = 7.5 Hz, 2H), 7.34 (t, J = 7.3 Hz, 1H), 6.94 (d, J = 9.0 Hz, 2H), 5.47 (t, J = 6.9 Hz, 1H), 5.37 (s, 1H), 3.71 (d, J = 12.1 Hz, 2H), 3.62 (t, J = 5.4 Hz, 2H), 3.10 (dd, J = 11.0, 6.1 Hz, 1H), 2.87-2.78 (m, 2H), 2.76-2.65 (m, 10H), 2.58 (s, 4H), 2.47-2.30 (m, 6H), 2.06 (d, J = 14.1 Hz, 2H), 1.96 (d, J = 12.7 Hz, 2H), 1.42-1.33 (m, 2H). |
| 133 Fumarate | $^1$H NMR (400 MHz, DMSO-$d_6$) δ 11.26 (s, 1H), 11.11 (s, 1H), 7.58-7.52 (m, 2H), 7.45 (dt, J = 7.6, 1.2 Hz, 1H), 7.39 (t, J = 2.8 Hz, 2H), 7.25 (d, J = 3.2 Hz, 1H), 7.23-7.16 (m, 2H), 6.93-6.87 (m, 2H), 6.54 (s, 2H), 6.39 (ddd, J = 3.0, 2.0, 1.0 Hz, 1H), 6.20 (d, J = 6.4 Hz, 1H), 4.07-3.99 (m, 3H), 3.62 (d, J = 12.0 Hz, 3H), 2.65-2.49 (m, 8H), 2.33 (t, J = 11.3 Hz, 1H), 2.25 (s, 3H), 2.07 (dd, J = 12.2, 5.6 Hz, 1H), 1.84 (d, J = 12.9 Hz, 3H), 1.74-1.67 (m, 1H), 1.58-1.42 (m, 5H). |
| 148 Hydrochloride | $^1$H NMR (400 MHz, DMSO-$d_6$) δ 11.63 (s, 1H), 10.88 (s, 1H), 8.81-8.75 (m, 2H), 8.53-8.46 (m, 2H), 8.16 (s, 1H), 7.64 (d, J = 7.2 Hz, 1H), 7.58 (d, J = 2.5 Hz, 1H), 7.49 (dd, J = 8.5, 2.6 Hz, 1H), 7.05 (d, J = 8.7 Hz, 1H), 4.17 (dd, J = 11.2, 6.7 Hz, 1H), 3.95-3.88 (m, 2H), 3.43 (td, J = 12.2, 11.7, 8.1 Hz, 4H), 3.13 (tt, J = 24.3, 11.8 Hz, 6H), 2.81 (d, J = 4.5 Hz, 3H), 2.30 (s, 3H), 1.92 (d, J = 12.7 Hz, 2H), 1.62 (qd, J = 11.7, 4.3 Hz, 2H). |
| 174 Hydrochloride | $^1$H NMR (400 MHz, DMSO-$d_6$) δ 11.31 (s, 1H), 10.63 (s, 1H), 8.93 (d, J = 6.6 Hz, 1H), 7.83 (d, J = 2.4 Hz, 1H), 7.64-7.56 (m, 2H), 7.23 (d, J = 2.4 Hz, 1H), 7.03-6.94 (m, 2H), 4.14 (s, 1H), 3.92 (dt, J = 11.7, 3.7 Hz, 2H), 3.75 (m, 2H), 3.55-3.45 (m, 4H), 3.20-3.08 (m, 2H), 3.08-2.98 (m, 2H), 2.81 (d, J = 4.3 Hz, 3H), 2.10-2.01 (m, 2H), 1.60-1.48 (m, 2H). |
| 177 Fumarate | $^1$H NMR (400 MHz, DMSO-$d_6$) δ 13.04 (s, 1H), 11.32 (s, 1H), 8.97 (s, 1H), 7.97 (s, 1H), 7.82 (d, J = 2.5 Hz, 1H), 7.52 (d, J = 2.6 Hz, 1H), 7.38 (dd, J = 8.6, 2.6 Hz, 1H), 7.33 (d, J = 2.8 Hz, 1H), 7.22 (d, J = 2.2 Hz, 1H), 6.95 (d, J = 8.7 Hz, 1H), 6.53 (s, 2H), 4.16 (q, J = 4.5 Hz, 1H), 3.94-3.87 (m, 2H), 3.48-3.46 (m, 4H), 3.02 (d, J = 11.2 Hz, 2H), 2.63-2.48 (m, 8H), 2.32 (d, J = 11.4 Hz, 1H), 2.25 (s, 3H), 2.23 (s, 3H), 2.05 (d, J = 12.7 Hz, 2H), 1.83 (d, J = 12.0 Hz, 2H), 1.54 (q, J = 11.3 Hz, 4H). |

TABLE 3-continued

NMR data of some of the compounds in Table 2

| Compound | NMR |
| --- | --- |
| 213 Hydrochloride | $^1$H NMR (400 MHz, DMSO-$d_6$) δ 11.62 (s, 1H), 10.59 (s, 1H), 8.72 (d, J = 8.3 Hz, 1H), 8.62-8.54 (m, 1H), 8.14 (d, J = 12.3 Hz, 1H), 7.95-7.86 (m, 1H), 7.60 (d, J = 2.5 Hz, 1H), 7.54 (d, J = 8.9 Hz, 2H), 7.35 (dd, J = 7.3, 5.2 Hz, 1H), 7.17 (s, 1H), 4.20 (m, 1H), 3.92 (dt, J = 11.6, 4.0 Hz, 4H), 3.81-3.67 (m, 4H), 3.60-3.47 (m, 6H), 3.31 (m, 2H), 2.90 (m, 1H) 2.84 (s, 3H), 2.36 (s, 3H), 2.25 (d, J = 11.2 Hz, 2H), 2.05 (d, J = 12.0 Hz, 4H), 1.62 (ddd, J = 13.9, 10.1, 5.1 Hz, 2H). |
| 417 Fumarate | $^1$H NMR (400 MHz, DMSO-$d_6$) δ 13.06 (s, 1H), 11.33 (s, 1H), 9.03 (s, 1H), 7.98 (s, 1H), 7.82 (d, J = 2.5 Hz, 1H), 7.34 (d, J = 9.1 Hz, 1H), 7.28 (d, J = 8.4 Hz, 1H), 7.23 (s, 1H), 7.12 (s, 1H), 6.83 (d, J = 8.6 Hz, 1H), 6.57 (s, 2H), 4.19 (m, 1H), 3.91-3.83 (m, 2H),3.80 (s, 3H), 3.48-3.36 (m, 6H), 2.66 (d, J = 115.6 Hz, 8H), 2.46 (s, 3H), 2.02 (d, J = 12.7 Hz, 2H), 1.85 (d, J = 11.6 Hz, 2H), 1.63-1.43 (m, 4H). |
| 419 Trifluoroacetate | $^1$H NMR (400 MHz, DMSO-$d_6$) δ 13.09 (s, 1H), 11.56 (s, 1H), 9.10 (s, 1H), 8.05 (s, 1H), 7.85 (d, J = 2.4 Hz, 1H), 7.59 (dd, J = 8.9, 2.5 Hz, 1H), 7.41 (s, 1H), 7.28 (d, J = 2.4 Hz, 1H), 7.23 (dd, J = 8.9, 1.4 Hz, 1H), 7.13 (d, J = 2.5 Hz, 1H), 4.21 (d, J = 7.9 Hz, 1H), 3.88 (m, 2H), 3.56-3.42 (m, 6H), 3.36-3.28 (m, 1H), 3.05 (m, 2H), 2.80 (s, 3H), 2.72 (t, J = 11.7 Hz, 2H), 2.06 (m, 4H), 1.75-1.45 (m, 6H), 1.23 (m, 2H). |
| 421 | $^1$H NMR (400 MHz, $CDCl_3$) δ 10.84 (s, 1H), 10.31 (s, 1H), 8.74 (d, J = 7.3 Hz, 1H), 7.65 (dd, J = 8.6, 2.5 Hz, 1H), 7.60 (d, J = 2.5 Hz, 1H), 7.50 (s, 1H), 6.93 (d, J = 8.7 Hz, 1H), 6.90 (d, J = 2.5 Hz, 1H), 6.83 (d, J = 2.5 Hz, 1H), 520 (s, 1H), 4.30 (ddt, J = 14.1, 9.8, 5.2 Hz, 1H), 4.00 (dt, J = 11.8, 3.9 Hz, 2H), 3.76-3.69 (m, 1H), 3.60 (ddd, J = 12.0, 10.4, 2.5 Hz, 2H), 3.33 (d, J = 11.5 Hz, 2H), 2.77-2.40 (m, 9H), 2.34 (dt, J = 10.7, 3.2 Hz, 1H), 2.29 (s, 3H), 2.10 (d, J = 13.0 Hz, 2H), 1.94 (d, J = 12.1 Hz, 2H), 1.86-1.81 (m, 1H), 1.77-1.65 (m, 4H), 1.00-0.94 (m, 2H), 0.73-0.68 (m, 2H). |
| 503 Fumarate | $^1$H NMR (400 MHz, DMSO-$d_6$) δ 13.04 (s, 1H), 11.33 (s, 1H), 9.04 (s, 1H), 7.98 (s, 1H), 7.80 (d, J = 2.4 Hz, 1H), 7.62 (d, J = 2.6 Hz, 1H), 7.33 (dd, J = 8.6, 2.7 Hz, 1H), 7.31 (s, 1H), 7.18 (d, J = 2.4 Hz, 1H), 7.02 (d, J = 8.7 Hz, 1H), 6.48 (s, 2H), 4.65 (s, 2H), 4.51 (s, 2H), 4.27 (m, 1H), 2.95 (d, J = 11.1 Hz, 2H), 2.74 (ddd, J = 10.2, 7.5, 2.9 Hz, 2H), 2.61 (dt, J = 21.1, 9.7 Hz, 11H), 2.33 (d, J = 2.6 Hz, 3H), 2.15 (td, J = 8.7, 3.0 Hz, 2H), 1.84 (d, J = 11.6 Hz, 2H), 1.54 (td, J = 12.7, 11.9, 8.9 Hz, 2H), 1.18 (t, J = 7.5 Hz, 3H). |
| 504 Fumarate | $^1$H NMR (400 MHz, DMSO-$d_6$) δ 13.03 (s, 1H), 11.39 (s, 1H), 9.08 (s, 1H), 7.99 (s, 1H), 7.83 (d, J = 2.4 Hz, 1H), 7.34 (d, J = 2.3 Hz, 2H), 7.22 (s, 1H), 7.13 (dd, J = 8.5, 2.3 Hz, 1H), 6.85 (d, J = 8.6 Hz, 1H), 6.55 (s, 2H), 4.65 (s, 2H), 4.52 (s, 2H), 4.38 (q, J = 7.5 Hz, 1H), 3.81 (s, 3H), 3.34 (m, 2H), 2.79-2.72 (m, 2H), 2.56 (d, J = 20.6 Hz, 8H), 2.33 (m, 1H), 2.24 (s, 3H), 2.15 (dd, J = 14.5, 6.2 Hz, 2H), 1.82 (m, 2H), 1.55 (m, 2H). |
| 511 | $^1$H NMR (400 MHz, $CDCl_3$) δ 10.81 (s, 1H), 8.39 (s, 1H), 7.62 (d, J = 8.9 Hz, 2H), 7.55-7.45 (m, 2H), 7.30 (td, J = 6.3, 5.7, 4.0 Hz, 3H), 6.92 (d, J = 8.9 Hz, 2H), 6.54 (d, J = 2.8 Hz, 1H), 5.25 (d, J = 7.2 Hz, 1H), 5.13 (s, 1H), 4.23-4.14 (m, 1H), 3.96 (d, J = 11.7 Hz, 2H), 3.69 (d, J = 11.9 Hz, 2H), 3.56-3.47 (m, 2H), 2.77-2.37 (m, 11H), 2.32 (s, 3H), 2.00 (dd, J = 26.0, 11.4 Hz, 4H), 1.72 (dd, J = 11.8, 3.8 Hz, 2H), 1.49-1.42 (m, 2H). |
| 512 | 1H NMR (400 MHz, DMSO-$d_6$) δ 11.69 (s, 1H), 11.10 (s, 1H), 8.25 (d, J = 4.9 Hz, 1H), 7.57-7.40 (m, 4H), 7.39-7.24 (m, 2H), 6.90 (d, J = 9.1 Hz, 2H), 6.49 (d, J = 7.3 Hz, 1H), 6.40 (dd, J = 3.5, 1.9 Hz, 1H), 4.16-4.02 (m, 1H), 3.84 (d, J = 10.8 Hz, 2H), 3.62 (d, J = 11.8 Hz, 2H), 3.37 (dd, J = 12.7, 10.7 Hz, 2H), 2.58 (t, J = 11.8 Hz, 2H), 2.38-2.16 (m, 4H), 2.10 (s, 3H), 1.82 (t, J = 12.6 Hz, 4H), 1.47 (qd, J = 11.9, 4.1 Hz, 4H). |
| 513 Hydrochloride | $^1$H NMR (400 MHz, DMSO-$d_6$) δ 11.28 (s, 1H), 11.24 (s, 1H), 7.58 (d, J = 2.5 Hz, 1H), 7.50-7.44 (m, 2H), 7.41 (t, J = 2.8 Hz, 1H), 7.25-7.17 (m, 3H), 7.04 (s, 1H), 6.37-6.34 (m, 1H), 6.06 (d, J = 7.4 Hz, 1H), 4.14-4.08 (m, 1H), 3.85 (d, J = 11.3 Hz, 2H), 3.70 (m, 4H), 3.37 (m, 6H), 3.19 (s, 2H), 2.84 (s, 3H), 2.71 (m, 3H), 2.30 (s, 3H), 2.18 (m, 2H), 1.88 (d, J = 12.8 Hz, 4H), 1.47 (d, J = 13.7 Hz, 2H). |
| 515 Hydrochloride | $^1$H NMR (400 MHz, DMSO-$d_6$) δ 11.28 (s, 1H), 7.56 (d, J = 8.8 Hz, 1H), 7.50 (d, J = 2.6 Hz, 1H), 7.49-7.44 (m, 1H), 7.41 (t, J = 2.8 Hz, 1H), 7.25-7.17 (m, 2H), 7.11 (s, 1H), 6.38-6.33 (m, 1H), 6.07 (d, J = 7.5 Hz, 1H), 4.17 (s, 1H), 3.89-3.64 (m, 7H), 3.42-3.29 (m, 5H), 3.11 (s, 2H), 2.84 (s, 3H), 2.71 (m, 5H), 2.18 (m, 2H), 1.87 (m, 4H), 1.54-1.42 (m, 2H), 1.27-1.20 (m,3H). |
| 519 Fumarate | $^1$H NMR (400 MHz, DMSO-$d_6$) δ 11.31 (s, 1H), 11.26 (s, 1H), 7.92 (d, J = 15.6 Hz, 1H), 7.45 (d, J = 7.1 Hz, 2H), 7.38 (d, J = 2.9 Hz, 1H), 7.34 (s, 1H), 7.24-7.15 (m, 2H), 7.06 (d, J = 9.7 Hz, 1H), 6.97 (t, J = 9.3 Hz, 1H), 6.53 (s, 2H), 6.33 (s, 1H), 6.13 (d, J = 7.4 Hz, 1H), 4.11-4.08 (m, 1H), 3.84 (d, J = 11.6 Hz, 2H), 3.38 (t, J = 11.5 Hz, 2H), 3.30 (d, J = 11.3 Hz, 2H), 2.60 (t, J = 10.7 Hz, 10H), 2.37 (d, J = 11.2 Hz, 1H), 2.30 (s, 3H), 1.85 (t, J = 12.8 Hz, 4H), 1.58-1.40 (m, 4H). |
| 521 Fumarate | $^1$H NMR (400 MHz, DMSO-$d_6$) δ 11.26 (s, 1H), 11.11 (s, 1H), 7.53 (d, J = 8.6 Hz, 2H), 7.43 (dd, J = 6.1, 3.0 Hz, 1H), 7.38 (d, J = 2.9 Hz, 2H), 7.24 (s, 1H), 7.17 (d, J = 6.1 Hz, 2H), 6.89 (d, J = 8.6 Hz, 2H), 6.52 (s, 2H), 6.32 (d, J = 2.8 Hz, 1H), 5.79 (d, J = 7.6 Hz, 1H), 4.20 (q, J = 6.7 Hz, 1H), 3.61 (d, J = 11.9 Hz, 2H), 2.63-2.46 (m, 10H), 2.35-2.28 (m, 1H), 2.24 (s, 3H), 1.82 (d, J = 12.2 Hz, 2H), 1.49 (p, J = 10.5, 9.9 Hz, 2H), 1.13 (d, J = 6.4 Hz, 6H). |
| 522 Fumarate | $^1$H NMR (400 MHz, DMSO-$d_6$) δ 11.21 (s, 1H), 11.13 (s, 1H), 7.73 (d, J = 8.6 Hz, 2H), 7.41 (dt, J = 6.3, 3.3 Hz, 2H), 7.36 (d, J = 3.0 Hz, 1H), 7.27 (s, 1H), 7.15 (d, J = 3.6 Hz, 2H), 6.89 (d, J = 8.6 Hz, 2H), 6.52 (s, 2H), 6.42 (d, J = 2.6 Hz, 1H), 6.27 (d, J = 3.1 Hz, 1H), 3.61 (d, J = 12.1 Hz, 2H), 2.74 (dq, J = 6.8, 3.5 Hz, 1H), 2.65-2.47 (m, 10H), 2.36-2.28 (m, 1H), 2.24 (s, 3H), 1.82 (d, J = 12.1 Hz, 2H), 1.55-1.41 (m, 2H), 0.79-0.70 (m, 2H), 0.51 (p, J = 4.6 Hz, 2H). |
| 525 Fumarate | $^1$H NMR (400 MHz, DMSO-$d_6$) δ 11.24 (s, 1H), 11.05 (s, 1H), 7.55 (d, J = 8.6 Hz, 2H), 7.46-7.36 (m, 3H), 7.24-7.14 (m, 3H), 6.90 (d, J = 8.7 Hz, 2H), 6.49 (s, 3H), 6.30 (d, J = 2.6 Hz, 1H), 6.26 (d, J = 5.6 Hz, 1H), 4.35 (q, J = 6.3 Hz, 1H), 4.21 (p, J = 6.0 Hz, 1H), 3.64 (d, J = 9.2 Hz, 2H), 2.73-2.53 (m, 10H), 2.44-2.36 (m, 1H), 2.33 (s, 3H), 2.23-2.11 (m, 4H), 1.84 (d, J = 12.0 Hz, 2H), 1.51 (dt, J = 12.0, 6.6 Hz, 2H). |
| 526 Fumarate | $^1$H NMR (400 MHz, DMSO-$d_6$) δ 11.24 (s, 1H), 11.05 (s, 1H), 7.54 (d, J = 8.6 Hz, 2H), 7.45-7.41 (m, 1H), 7.38 (dt, J = 5.8, 2.9 Hz, 2H), 7.21 (d, J = 3.1 Hz, 1H), 7.16 (d, J = 4.5 Hz, 2H), 6.88 (d, J = 8.7 Hz, 2H), 6.49 (s, 2H), 6.29 (d, J = 3.1 Hz, 1H), 5.76 (d, J = 7.3 Hz, 1H), 5.69 (s, 1H), 3.86-3.74 (m, 2H), 3.63-3.56 (m, 2H), 2.56 (q, J = 18.3, 15.2 Hz, 10H), 2.34 (t, J = 11.3 Hz, 1H), 2.26 (s, 3H), 1.91 (d, J = 10.8 Hz, 2H), 1.81 (t, J = 14.7 Hz, 4H), 1.50 (qd, J = 12.4, 3.9 Hz, 2H), 1.21 (q, J = 13.1, 12.5 Hz, 4H). |

TABLE 3-continued

| NMR data of some of the compounds in Table 2 | |
|---|---|
| Compound | NMR |
| 527 Fumarate | $^1$H NMR (400 MHz, DMSO-$d_6$) δ 11.21 (d, J = 2.4 Hz, 1H), 10.99 (s, 1H), 7.53-7.48 (m, 2H), 7.42 (dd, J = 6.1, 3.0 Hz, 1H), 7.36 (t, J = 2.8 Hz, 2H), 7.23 (d, J = 3.3 Hz, 1H), 7.15 (q, J = 3.7, 3.2 Hz, 2H), 6.93-6.87 (m, 2H), 6.53 (s, 3H), 6.38 (d, J = 6.4 Hz, 1H), 6.28 (t, J = 2.5 Hz, 1H), 4.59 (s, 2H), 4.39 (s, 2H), 4.18 (h, J = 7.8 Hz, 1H), 2.68-2.49 (m, 12H), 2.38 (dd, J = 12.9, 9.1 Hz, 1H), 2.32 (s, 3H), 2.12-2.03 (m, 2H), 1.83 (d, J = 12.1 Hz, 2H), 1.74-1.68 (m, 1H), 1.50 (qd, J = 12.1, 3.8 Hz, 2H), 1.31 (s, 1H) |
| 528 Fumarate | $^1$H NMR (400 MHz, DMSO-$d_6$) δ 11.27 (s, 1H), 11.09 (s, 1H), 7.55-7.49 (m, 2H), 7.44 (dd, J = 6.7, 2.4 Hz, 1H), 7.38 (q, J = 2.9, 2.3 Hz, 2H), 7.24 (d, J = 3.1 Hz, 1H), 7.21-7.15 (m, 2H), 6.89 (d, J = 8.5 Hz, 2H), 6.50 (s, 1H), 6.35 (t, J = 2.5 Hz, 1H), 5.99 (t, J = 5.6 Hz, 1H), 3.61 (d, J = 11.9 Hz, 2H), 3.35 (d, J = 5.6 Hz, 2H), 2.62-2.43 (m, 10H), 2.29 (t, J = 11.2 Hz, 1H), 2.21 (d, J = 2.4 Hz, 3H), 1.81 (d, J = 12.2 Hz, 2H), 1.54-1.42 (m, 2H), 1.06 (d, J = 1.4 Hz, 6H). |
| 538 Trifluoroacetate | $^1$H NMR (400 MHz, DMSO-$d_6$) δ 13.03 (d, J = 2.8 Hz, 1H), 11.33 (s, 1H), 9.19 (s, 1H), 8.52 (s, 1H), 8.30 (t, J = 2.9 Hz, 1H), 7.64 (d, J = 8.5 Hz, 3H), 7.41 (s, 1H), 7.11 (d, J = 8.5 Hz, 2H), 6.85 (d, J = 7.2 Hz, 1H), 6.80 (dt, J = 2.6, 1.5 Hz, 1H), 4.12 (dt, J = 11.1, 5.5 Hz, 1H), 3.91-3.83 (m, 2H), 3.77 (d, J = 12.2 Hz, 2H), 3.64-3.00 (m, 11H), 2.82 (m+s, 5H), 2.09 (d, J = 12.0 Hz, 2H), 1.92-1.83 (m, 2H), 1.74 (q, J = 11.4, 10.5 Hz, 2H), 1.44 (qd, J = 12.5, 4.3 Hz, 2H). |
| 540 | $^1$H NMR (400 MHz, $CDCl_3$) δ 10.75 (s, 1H), 8.45 (s, 1H), 7.55-7.49 (m, 3H), 7.49-7.45 (m, 1H), 7.32-7.28 (m, 3H), 6.97-6.92 (m, 2H), 6.54 (ddd, J = 3.1, 2.0, 0.9 Hz, 1H), 5.67 (d, J = 5.8 Hz, 1H), 5.17 (s, 1H), 5.09 (q, J = 6.6 Hz, 1H), 4.91 (t, J = 6.9 Hz, 2H), 4.44 (t, J = 6.4 Hz, 2H), 3.70 (d, J = 11.8 Hz, 2H), 2.75-2.41 (m, 10H), 2.37 (ddt, J = 11.3, 7.7, 3.8 Hz, 1H), 2.28 (s, 3H), 1.95 (d, J = 13.0 Hz, 2H), 1.71 (td, J = 12.0, 3.8 Hz, 2H). |
| 611 | $^1$H NMR (400 MHz, $CDCl_3$) δ 10.90 (s, 1H), 8.74-8.68 (m, 2H), 7.63-7.56 (m, 2H), 7.56-7.51 (m, 2H), 7.41 (s, 1H), 6.93 (d, J =8.9 Hz, 2H), 5.20 (s, 1H), 5.09 (d, J = 7.4 Hz, 1H), 4.29 (h, J = 6.6 Hz, 1H), 3.70 (d, J = 12.0 Hz, 2H), 2.77-2.62 (m, 6H), 2.53 (s, 4H), 2.38 (d, J = 12.3 Hz, 1H), 2.32 (s, 3H), 1.96 (d, J = 12.5 Hz, 2H), 1.77-1.71 (m, 2H), 1.25 (d, J = 1.8 Hz, 6H). |
| 612 Fumarate | $^1$H NMR (400 MHz, DMSO-$d_6$) δ 11.09 (s, 1H), 7.91 (d, J = 5.3 Hz, 1H), 7.57 (s, 1H), 7.47 (d, J = 8.5 Hz, 2H), 7.34 (s, 1H), 6.89 (d, J = 8.6 Hz, 2H), 6.83 (d, J = 5.1 Hz, 1H), 6.76 (s, 1H), 6.67 (d, J = 7.2 Hz, 1H), 6.54 (s, 4H), 6.03 (s, 2H), 4.03 (s, 1H), 3.88 (s, 2H), 3.63 (d, J = 11.7 Hz, 2H), 3.36 (d, J = 11.4 Hz, 2H), 2.60 (d, J = 14.1 Hz, 10H), 2.40 (d, J = 11.5 Hz, 1H), 2.32 (s, 3H), 1.83 (d, J = 12.1 Hz, 4H), 1.54 (ddd, J = 31.1, 12.9, 7.9 Hz, 4H). |
| 615 Hydrochloride | $^1$H NMR (400 MHz, DMSO-$d_6$) δ 12.14 (s, 1H), 11.70 (s, 1H), 9.15 (s, 1H), 8.06 (s, 1H), 7.94-7.81 (m, 3H), 7.67 (d, J = 8.6 Hz, 2H), 7.41 (d, J = 30.4 Hz, 1H), 7.27 (d, J = 2.4 Hz, 1H), 4.42 (q, J = 6.6 Hz, 2H), 3.75 (s, 8H), 3.55 (d, J = 2.3 Hz, 6H), 2.84 (s, 3H), 2.45-2.34 (m, 4H), 2.28 (ddd, J = 12.6, 6.8, 3.8 Hz, 2H). |
| 616 Hydrochloride | $^1$H NMR (400 MHz, DMSO-$d_6$) δ 12.38 (s, 1H), 11.68 (s, 1H), 8.93 (d, J = 7.2 Hz, 1H), 8.04 (s, 1H), 7.82 (q, J = 3.2 Hz, 3H), 7.67 (s, 2H), 7.40 (d, J = 11.6 Hz, 1H), 7.25 (d, J =2.4 Hz, 1H), 4.24 (q, J = 6.5 Hz, 1H), 3.75-3.59 (m, 12H), 2.82 (s, 3H), 2.37 (s, 4H), 1.32 (d, J = 6.4 Hz, 6H). |
| 627 Fumarate | $^1$H NMR (400 MHz, DMSO-$d_6$) δ 13.02 (s, 1H), 11.20 (s, 1H), 8.96 (s, 1H), 7.95 (s, 1H), 7.82 (d, J = 2.4 Hz, 1H), 7.57-7.50 (m, 2H), 7.31 (s, 1H), 7.20 (d, J = 2.4 Hz, 1H), 6.95-6.88 (m, 2H), 6.55 (s, 2H), 4.68 (s, 2H), 4.52 (s, 2H), 4.27-4.23 (m, 1H), 3.65 (d, J = 11.8 Hz, 2H), 2.75 (ddd, J = 10.1, 7.4, 2.8 Hz, 2H), 2.68-2.51 (m, 10H), 2.40-2.33 (m, 1H), 2.29 (s, 3H), 2.20-2.09 (m, 2H), 1.85 (d, J = 12.2 Hz, 2H), 1.58-1.45 (m, 2H). |

Example 2

Inhibitory Activity Assay of the Compounds Disclosed Herein Against EGFR (del19/T790M/C797S), EGFR (L858R/T790M/C797S) or EGFR (WT) Enzymes The inhibitory effects of the compounds against EGFR (del19/T790M/C797S), EGFR (L858R/T790M/C797S) or EGFR (WT) enzyme activity was determined by using HTRF. The procedures are as follows:

The WT or mutant EGFR proteins were incubated with a serially diluted compounds at 28° C. for 10 min followed by addition of biotin-labeled general tyrosine kinase (TK) substrate and ATP. The mixture was incubated at room temperature for 40 min for reaction. After the termination of the reaction, an Eu3+-Cryptate-labeled antibody against TK and streptavidin-XL665 were added and the mixture was incubated at room temperature for 60 min. The luminescences at 615 nm and 665 nm were detected and the ratio of 665/615 was calculated to quantify the level of TK substrate phosphorylation. Inhibition % and $IC_{50}$ of the compounds were calculated relative to the control group. The results are shown in Table 4 below.

TABLE 4

Inhibitory activity of the compounds disclosed herein against EGFR (del19/T790M/C797S), EGFR (L858R/T790M/C797S) or EGFR (WT)

| Compound | EGFR (del19/T790M/C797S) inhibition (%) (0.3 nM compound) | EGFR (WT) $IC_{50}$ (nM) | EGFR (L858R/T790M/C797S) inhibition (%) (0.3 nM compound) |
|---|---|---|---|
| 1 | + | >300 | + |
| 2 | + | >100 | N.D |
| 4 | + | >100 | + |
| 5 | + | >100 | + |
| 6 | + | N.D | N.D |
| 7 | + | N.D | N.D |
| 8 | + | N.D | N.D |
| 9 | + | N.D | N.D |
| 10 | ++ | >300 | N.D |
| 11 | ++ | >300 | N.D |
| 12 | + | N.D | N.D |
| 13 | + | >300 | N.D |
| 14 | + | >300 | N.D |
| 15 | + | N.D | N.D |
| 16 | + | N.D | N.D |
| 17 | + | N.D | N.D |
| 18 | + | N.D | N.D |
| 19 | + | N.D | N.D |
| 21 | ++ | >300 | N.D |

TABLE 4-continued

Inhibitory activity of the compounds disclosed herein against EGFR (del19/T790M/C797S), EGFR (L858R/T790M/C797S) or EGFR (WT)

| Compound | EGFR (del19/T790M/C797S) inhibition (%) (0.3 nM compound) | EGFR (WT) $IC_{50}$ (nM) | EGFR (L858R/T790M/C797S) inhibition (%) (0.3 nM compound) |
|---|---|---|---|
| 22 | + | N.D | N.D |
| 23 | ++ | N.D | + |
| 24 | ++ | N.D | N.D |
| 25 | + | N.D | N.D |
| 27 | + | N.D | N.D |
| 28 | + | N.D | N.D |
| 29 | ++ | N.D | N.D |
| 30 | ++ | N.D | N.D |
| 31 | +++ | N.D | N.D |
| 32 | +++ | N.D | N.D |
| 33 | +++ | N.D | N.D |
| 35 | ++ | N.D | + |
| 36 | + | N.D | N.D |
| 37 | + | N.D | N.D |
| 38 | ++ | N.D | ++ |
| 39 | +++ | >300 | +++ |
| 40 | + | N.D | N.D |
| 42 | + | N.D | N.D |
| 43 | + | N.D | N.D |
| 44 | + | N.D | N.D |
| 45 | + | N.D | N.D |
| 46 | + | N.D | N.D |
| 47 | + | N.D | N.D |
| 49 | + | N.D | N.D |
| 50 | + | N.D | N.D |
| 51 | + | N.D | N.D |
| 52 | +++ | >300 | N.D |
| 53 | + | N.D | N.D |
| 54 | + | N.D | N.D |
| 55 | +++ | >300 | + |
| 56 | + | N.D | N.D |
| 57 | ++ | >300 | ++ |
| 59 | + | >300 | N.D |
| 60 | ++ | N.D | + |
| 61 | ++ | N.D | N.D |
| 62 | + | N.D | N.D |
| 63 | + | N.D | N.D |
| 64 | + | N.D | N.D |
| 65 | ++ | N.D | N.D |
| 66 | + | N.D | N.D |
| 67 | + | N.D | N.D |
| 68 | + | N.D | N.D |
| 69 | + | N.D | + |
| 70 | + | N.D | N.D |
| 71 | + | N.D | N.D |
| 72 | + | N.D | N.D |
| 82 | + | N.D | N.D |
| 83 | ++ | N.D | ++ |
| 88 | | N.D | N.D |
| 90 | + | N.D | N.D |
| 91 | ++ | N.D | N.D |
| 92 | ++ | N.D | N.D |
| 93 | ++ | N.D | N.D |
| 94 | ++ | N.D | + |
| 95 | ++ | N.D | N.D |
| 96 | ++ | N.D | N.D |
| 98 | + | N.D | N.D |
| 99 | + | N.D | N.D |
| 100 | + | N.D | N.D |
| 101 | + | N.D | N.D |
| 102 | + | N.D | N.D |
| 103 | ++ | N.D | N.D |
| 105 | + | N.D | N.D |
| 106 | + | N.D | N.D |
| 107 | + | N.D | N.D |
| 108 | +++ | N.D | N.D |
| 109 | + | N.D | N.D |
| 110 | + | N.D | N.D |
| 111 | + | N.D | N.D |
| 112 | + | N.D | N.D |
| 113 | + | N.D | N.D |
| 114 | ++ | N.D | +++ |
| 116 | + | N.D | N.D |
| 117 | + | N.D | N.D |
| 118 | ++ | N.D | N.D |
| 119 | + | N.D | N.D |
| 120 | + | N.D | N.D |
| 121 | +++ | N.D | +++ |
| 122 | +++ | N.D | N.D |
| 123 | ++ | N.D | N.D |
| 124 | + | N.D | N.D |
| 125 | ++ | N.D | ++ |
| 126 | + | N.D | + |
| 133 | ++ | N.D | N.D |
| 134 | ++ | N.D | N.D |
| 136 | ++ | N.D | N.D |
| 137 | ++ | N.D | ++ |
| 138 | ++ | N.D | N.D |
| 139 | ++ | N.D | N.D |
| 146 | ++ | N.D | N.D |
| 154 | ++ | N.D | N.D |
| 177 | ++ | N.D | N.D |
| 206 | ++ | N.D | N.D |
| 207 | ++ | N.D | N.D |
| 255 | ++ | N.D | N.D |
| 263 | ++ | N.D | N.D |
| 264 | ++ | N.D | N.D |
| 271 | ++ | N.D | N.D |
| 379 | ++ | N.D | N.D |
| 383 | ++ | N.D | N.D |
| 503 | +++ | 10.16 | + |
| 511 | +++ | 2.82 | +++ |
| 512 | +++ | N.D | N.D |
| 519 | +++ | N.D | +++ |
| 520 | +++ | N.D | N.D |
| 521 | +++ | 0.27 | +++ |
| 522 | +++ | 0.22 | +++ |
| 523 | +++ | N.D | +++ |
| 524 | +++ | N.D | +++ |
| 525 | +++ | N.D | N.D |
| 526 | +++ | 0.33 | +++ |
| 527 | +++ | 1.7 | +++ |
| 528 | +++ | N.D | N.D |
| 529 | +++ | N.D | N.D |
| 530 | +++ | N.D | N.D |
| 531 | +++ | N.D | N.D |
| 532 | +++ | N.D | +++ |
| 533 | +++ | N.D | N.D |
| 534 | +++ | N.D | N.D |
| 535 | +++ | N.D | +++ |
| 536 | +++ | N.D | +++ |
| 537 | +++ | N.D | N.D |
| 594 | +++ | N.D | +++ |
| 595 | +++ | N.D | N.D |
| 596 | +++ | N.D | N.D |
| 609 | +++ | N.D | N.D |
| 610 | +++ | N.D | N.D |
| 611 | +++ | N.D | N.D |
| 614 | +++ | N.D | N.D |
| 615 | +++ | N.D | N.D |
| 616 | +++ | N.D | N.D |
| 617 | ++ | N.D | N.D |
| 618 | ++ | N.D | N.D |
| 619 | ++ | N.D | N.D |
| 620 | ++ | N.D | N.D |
| 621 | +++ | N.D | N.D |
| 622 | +++ | N.D | N.D |
| 623 | +++ | N.D | N.D |
| 624 | ++ | N.D | N.D |
| 625 | +++ | N.D | N.D |
| 626 | +++ | N.D | N.D |
| 627 | ++ | N.D | N.D |

TABLE 4-continued

Inhibitory activity of the compounds disclosed herein against EGFR (del19/T790M/C797S), EGFR (L858R/T790M/C797S) or EGFR (WT)

| Compound | EGFR (del19/ T790M/C797S) inhibition (%) (0.3 nM compound) | EGFR (WT) $IC_{50}$ (nM) | EGFR (L858R/ T790M/C797S) inhibition (%) (0.3 nM compound) |
|---|---|---|---|
| 628 | ++ | N.D | N.D |
| 629 | +++ | N.D | N.D |
| 630 | +++ | N.D | N.D |
| 631 | +++ | N.D | N.D |
| 632 | +++ | N.D | N.D |
| 633 | +++ | N.D | N.D |
| 634 | +++ | N.D | N.D |
| 635 | +++ | N.D | N.D |
| 638 | +++ | N.D | N.D |
| 639 | +++ | N.D | N.D |
| 640 | +++ | N.D | N.D |
| 641 | +++ | N.D | N.D |
| 642 | +++ | N.D | N.D |
| 643 | +++ | N.D | N.D |
| 644 | +++ | N.D | N.D |
| 645 | +++ | N.D | N.D |
| Gilteritinib | + | N.D | + |

+ indicates an inhibition less than or equal to 20%
++ indicates an inhibition from 20% to 50%
+++ indicates an inhibition greater than 50%.
N.D represents not detected As can be seen from the data in Table 4, the compounds disclosed herein have better inhibitory activities against EGFR (del19/T790M/C797S) and EGFR (L858R/T790M/C797S) enzyme activities, and have better selectivity for EGFR (WT).

Example 3

Antiproliferative Activity of the Compounds Disclosed Herein Against Ba/F3 ($EGFR^{del19/T790M/C797S}$) Triple-Mutant Cells and A431 (EGFR WT) Cells 3000 Ba/F3 cells carrying EGFR (del19/T790M/C797S) or 2000 A431 cells were seeded in a 384-well plate. After one day, serially diluted compounds were added (up to 500 nM for Ba/F3 cells and up to 10 μM for A431 cells). Three days after the addition of the compounds, Cell Titer Glow was added to evaluate cell growth and the percentage cell growth inhibition by the compounds and the $IC_{50}$ values were calculated. The results are shown in Table 5 below.

TABLE 5

Antiproliferative activity of the compounds disclosed herein against Ba/F3 ($EGFR^{del19/T790M/C797S}$) triple-mutant cells and A431 wild-type (EGFR WT) cells

| Compound | Antiproliferative activity BaF3($EGFR^{del19/T790M/C797S}$) $IC_{50}$ (nM) | Antiproliferative activity A431 wild-type (WT) $IC_{50}$ (M) |
|---|---|---|
| 1 | 236 | 2.5 |
| 4 | 295 | 1.7 |
| 11 | 107 | 0.54 |
| 13 | 197 | 1.3 |
| 14 | 113 | 0.95 |
| 21 | 48 | 0.52 |
| 23 | 36 | 0.95 |
| 31 | 65 | 0.54 |
| 32 | 26 | 0.19 |

TABLE 5-continued

Antiproliferative activity of the compounds disclosed herein against Ba/F3 ($EGFR^{del19/T790M/C797S}$) triple-mutant cells and A431 wild-type (EGFR WT) cells

| Compound | Antiproliferative activity BaF3($EGFR^{del19/T790M/C797S}$) $IC_{50}$ (nM) | Antiproliferative activity A431 wild-type (WT) $IC_{50}$ (M) |
|---|---|---|
| 33 | 63 | 0.22 |
| 35 | 54 | 0.48 |
| 37 | 48 | >2 |
| 38 | 48 | 1.8 |
| 39 | 29 | 0.34 |
| 54 | >100 | 3.5 |
| 55 | 16 | 0.07 |
| 57 | 79 | 0.32 |
| 59 | 72 | 1.4 |
| 74 | >100 | 2.1 |
| 83 | 233 | 0.75 |
| 85 | 357 | 1.5 |
| 86 | 21 | 1.7 |
| 88 | 52 | 0.28 |
| 96 | >100 | 1.6 |
| 108 | 23 | 0.19 |
| 110 | >100 | 0.46 |
| 111 | 105 | 0.12 |
| 114 | 27 | 0.97 |
| 115 | 214 | 2.0 |
| 118 | 82 | 4.1 |
| 119 | >100 | >10 |
| 120 | 119 | 0.68 |
| 121 | 70 | 0.59 |
| 122 | 40 | 0.38 |
| 123 | 140 | >10 |
| 124 | >100 | >10 |
| 125 | 99 | 0.65 |
| 126 | 248 | 2.6 |
| 131 | >100 | >10 |
| 135 | 40 | 0.34 |
| 141 | 27 | 0.23 |
| 148 | 68 | 1.7 |
| 161 | 54 | 1.2 |
| 174 | 51 | 1.0 |
| 177 | 19 | 0.69 |
| 184 | 18 | 0.98 |
| 213 | 226 | >10 |
| 417 | 57 | 0.19 |
| 420 | 32 | 3.7 |
| 421 | 36 | 0.53 |
| 503 | 61 | 0.66 |
| 504 | 98 | 0.33 |
| 511 | 9 | 0.06 |
| 512 | 6 | 0.02 |
| 513 | 57 | 0.56 |
| 514 | 48 | 0.25 |
| 515 | 42 | 0.52 |
| 516 | 42 | 0.35 |
| 521 | 4 | 0.05 |
| 522 | 2 | 0.03 |
| 525 | 25 | 0.06 |
| 526 | 5 | 0.1 |
| 527 | 4 | 0.1 |
| 528 | 13 | 0.07 |
| 529 | 18 | 0.05 |
| 538 | 35 | 0.29 |
| 540 | 48 | 1.2 |
| 594 | 13 | 0.07 |
| 611 | 21 | 0.36 |
| 616 | 32 | 0.36 |
| Gilteritinib | >500 | |

As can be seen from the data in Table 5, the antiproliferative activities of most compounds disclosed herein against Ba/F3 ($EGFR^{del19/T790M/C797S}$) triple-mutant cells were less than 100 nM, while the antiproliferative activity of gilteritinib against Ba/F3 ($EGFR^{del19/T790M/C797S}$) triple-mutant cells was greater than 500 nM, indicating that when Y is an aryl, a heteroaryl or a heterocycloalkyl, the compounds have strong antiproliferative activity against Ba/F3 ($EGFR^{del19/T790M/C797S}$) triple-mutant cells.

Example 4

In Vivo Pharmacodynamic Study—Mouse H1975 Subcutaneous Xenograft Tumor Model BALB/c nude mice were grafted subcutaneously on the left dorsum with $5\times10^6$ H1975 cells carrying EGFR T790M mutation. After the tumor grew to 100-150 $mm^3$, the mice were randomly divided into the following groups for intragastric administration once daily: group 1: vehicle control; group 2: compound 511 (60 mg/kg); and group 3: compound 511 (80 mg/kg). The tumor volume was measured twice weekly and at the end of treatment. Tumor growth inhibition of the compound was calculated according to the following equation: tumor growth inhibition (TGI)=1−(tumor volume on day 28 in treatment group−tumor volume on day 1 in treatment group)/(tumor volume on day 28 in vehicle control group−tumor volume on day 1 in treatment group). The results are shown in FIG. 1 and Table 6.

TABLE 6

Growth inhibition of H1975 subcutaneous xenograft tumor in mice

| Compound | Dose | TGI |
|---|---|---|
| Control | Not applicable | Not applicable |
| Compound 511 | 60 mg/kg | 99% |
| Compound 511 | 80 mg/kg | 104% |

As can be seen in FIG. 1 and Table 6, compound 511 was able to inhibit tumor growth at doses of 60 mg/kg and 80 mg/kg in the H1975 mouse subcutaneous xenograft tumor model carrying the EGFR T790M mutation.

Example 5

Figure 2:
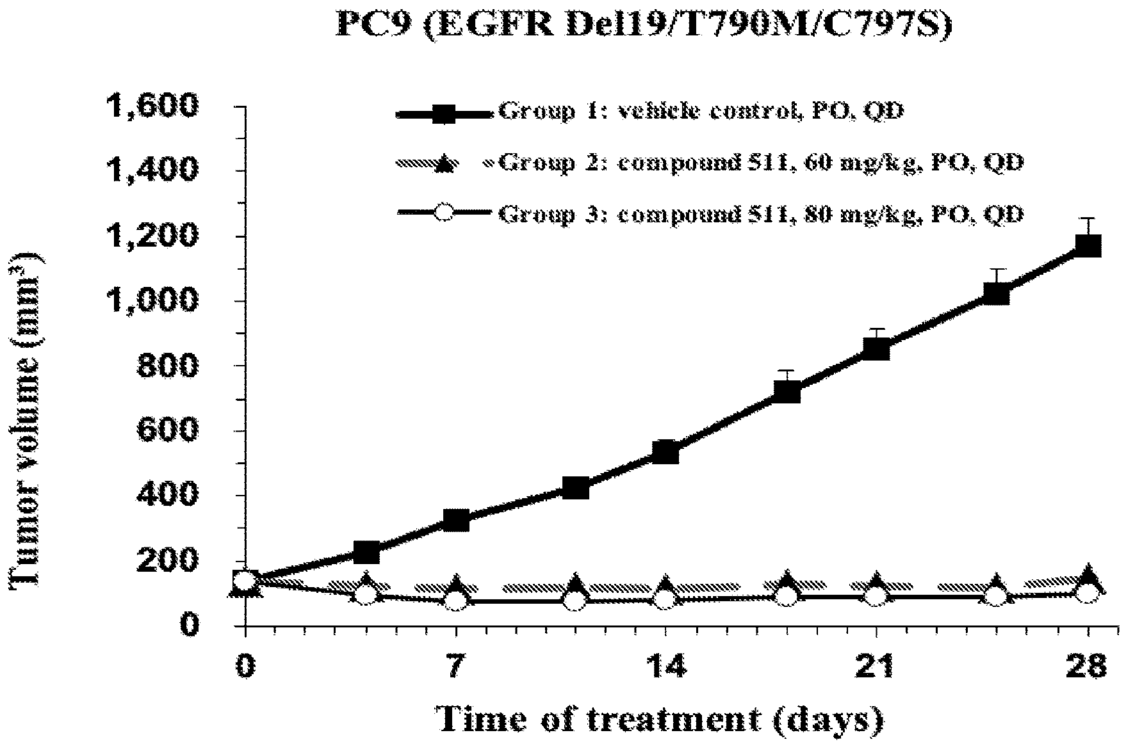
FIG. 2 shows the results of the tumor growth inhibition in an in vivo pharmacodynamic study in mice according to Example 5 of the present invention.

In Vivo Pharmacodynamic Study—Mouse PC9(EGFR Del19/T790M/C797S) Subcutaneous Xenograft Tumor Model BALB/c nude mice were grafted subcutaneously on the left dorsum with $5\times10^6$ PC9 cells with EGFR Del19/T790M/C797S overexpression. After the tumor grew to 100-150 $mm^3$, the mice were randomly divided into the following groups for intragastric administration once daily: group 1: vehicle control; group 2: compound 511 (60 mg/kg); and group 3: compound 511 (80 mg/kg). The tumor volume was measured twice weekly and at the end of treatment. Tumor growth inhibition of the compound was calculated according to the following equation: tumor growth inhibition (TGI) =1−(tumor volume on day 28 in treatment group−tumor volume on day 1 in treatment group)/(tumor volume on day 28 in vehicle control group−tumor volume on day 1 in treatment group). The results are shown in FIG. 2.

TABLE 7

Growth inhibition of PC9(EGFR De119/T790M/C797S) subcutaneous xenograft tumor in mice

| Compound | Dose | TGI |
|---|---|---|
| Control | Not applicable | Not applicable |
| Compound 511 | 60 mg/kg | 87.41% |
| Compound 511 | 80 mg/kg | 93.17% |

As can be seen in FIG. 2 and Table 7, compound 511 was able to inhibit tumor growth at doses of 60 mg/kg and 80 mg/kg in the PC9 mouse subcutaneous xenograft tumor model with EGFR Del19/T790M/C797S overexpression.

The invention claimed is:

1. A compound having a structure of general formula (1), or an isomer, a crystalline form, a pharmaceutically acceptable salt, a hydrate or a solvate thereof:

(1)

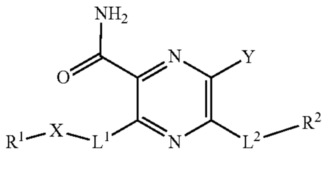

wherein, in general formula (1):

Y is

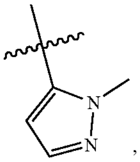, 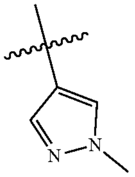, 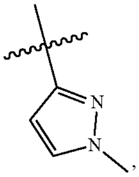,

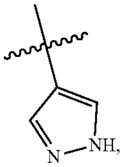, 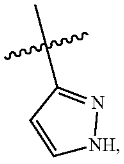, 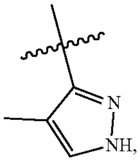, 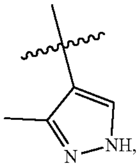,

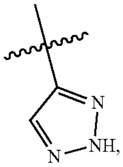, 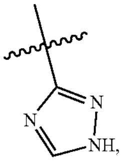, 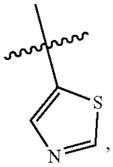, 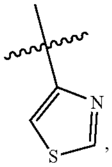,

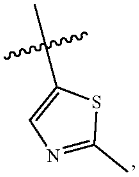, 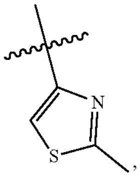, 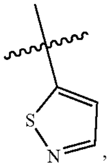, 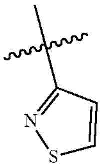,

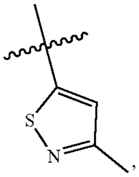, 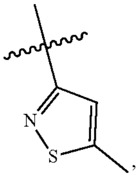, 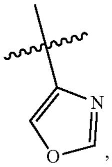, 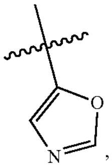,

-continued

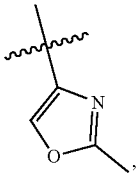,
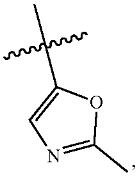,
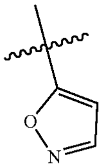,
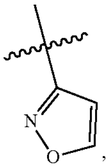,
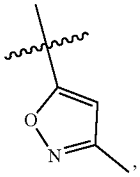,
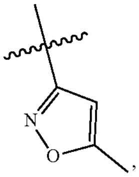,
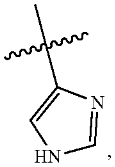,
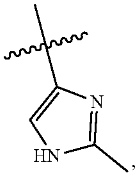,
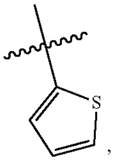,
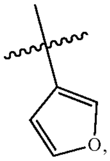,
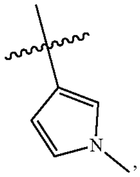,
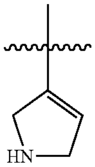,
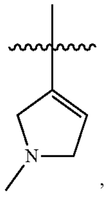,
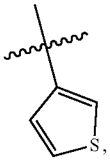,
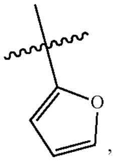,
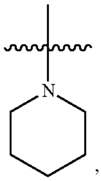,
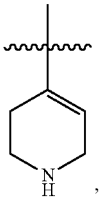,
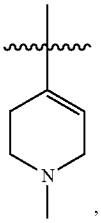,
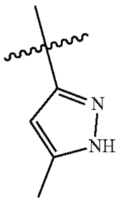,
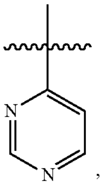,
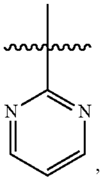,
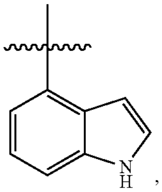,
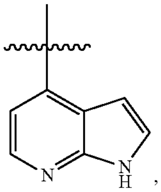,
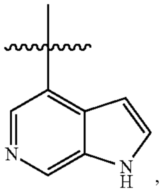,
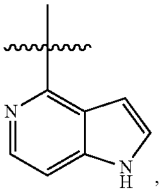,
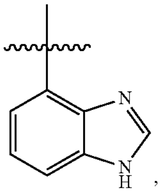,
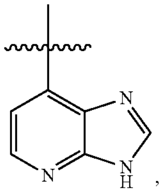,
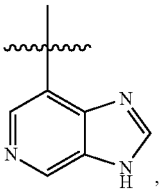,
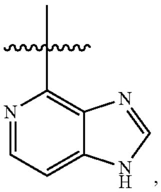,
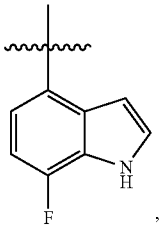, -continued

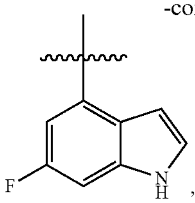,
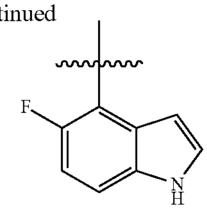,
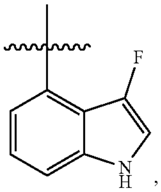,
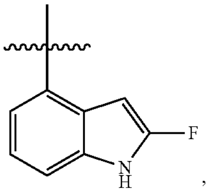, or
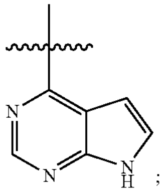;

$L^1$ is —O— or —NH—;

X is a C6-C14 arylene or a 5-11 membered heteroarylene, wherein the arylene and the heteroarylene may be optionally substituted with one or more of the following groups: —H, a halogen, a C1-C6 alkyl, a C3-C6 cycloalkyl, a C1-C6 alkoxy and a C1-C6 haloalkoxy;

$R^1$ is —H, a halogen, $—(CH_2)_nNR^6R^7$, $—NR^6R^7$, $—O(CH_2)_mNR^6R^7$, $—N(R^5)(CH_2)_mNR^6R^7$, a C1-C6 alkoxy, a $—CH_2$-3-15 membered heterocycloalkyl or a 3-15 membered heterocycloalkyl, wherein the alkoxy and the heterocycloalkyl may be optionally substituted with one or more of the following groups: —H, $—R^4$, $—(CH_2)_nNR^6R^7$, $—NR^6R^7$, $—O(CH_2)_mNR^6R^7$, $—N(R^5)(CH_2)_mNR^6R^7$ and $—R^3$;

$L^2$ is —O—, —NH— or a chemical bond;

$R^2$ is a C1-C6 alkyl, a C3-C14 cycloalkyl, a C6-C14 aryl, a 3-4 membered heterocycloalkyl,

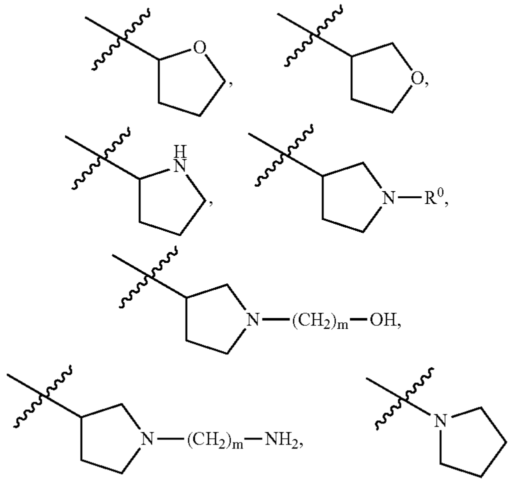

or a 6-11 membered heterocycloalkyl; wherein the alkyl, the cycloalkyl, the aryl, the heterocycloalkyl,

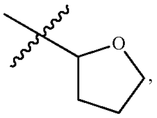
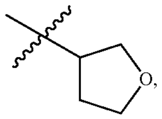
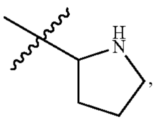
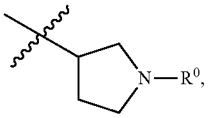
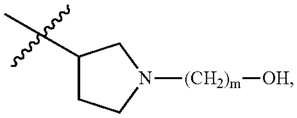
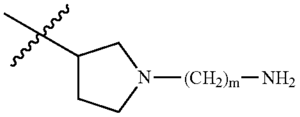
and
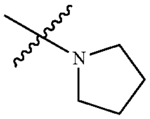

may be optionally substituted with one or more of the following groups: —H, a halogen, —$R^4$, —$(CH_2)_nOR^4$—, —$(CH_2)_nNR^4R^5$—, —$OR^4$, —$NR^4R^5$, —CN, —$C(O)NR^4R^5$, —$NR^5C(O)R^4$, —$NR^5S(O)_2R^4$, —$S(O)_pR^4$ and —$S(O)_2NR^4R^5$;

$R^3$ is a 3-11 membered heterocycloalkyl, wherein the heterocycloalkyl may be optionally substituted with one or more of the following groups: —H, —$CD_3$, —$R^4$, —$OR^4$ and —$NR^4R^5$;

$R^4$ and $R^5$ are each independently —H, a C1-C6 alkyl or a C3-C14 cycloalkyl;

$R^6$ and $R^7$ are each independently —H, a C1-C6 alkyl or a C3-C14 cycloalkyl, or $R^6$ and $R^7$ form a 3-11 membered heterocycloalkyl along with N atoms connected thereto, wherein the heterocycloalkyl may be optionally substituted with one or more of the following groups: —H, —$CD_3$, a halogen, —$R^4$ and —$OR^4$;

$R^0$ is a C1-C6 alkyl or a C3-C14 cycloalkyl; and p is an integer of 0, 1 or 2, n is an integer of 0, 1, 2 or 3, and m is an integer of 1, 2 or 3;

or

Y is

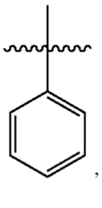
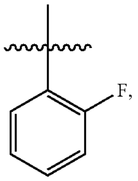
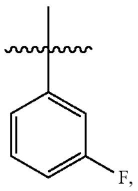
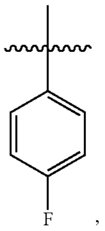

-continued

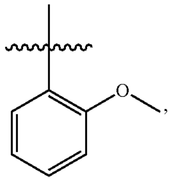
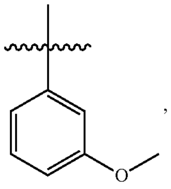
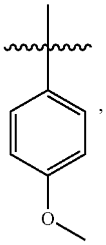
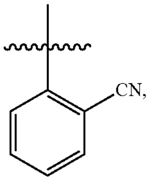
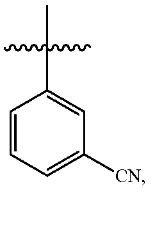
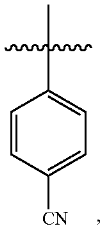
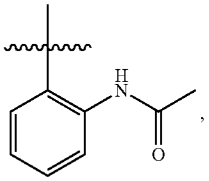
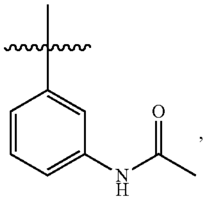
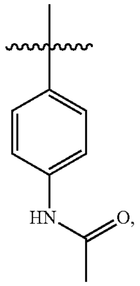
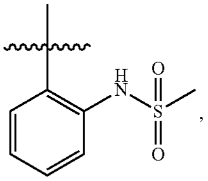
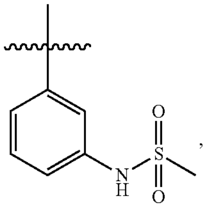
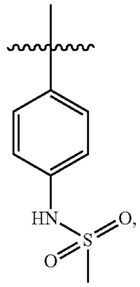
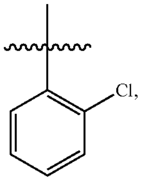
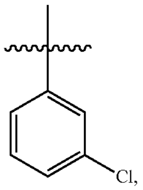
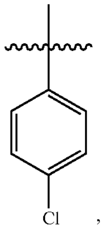
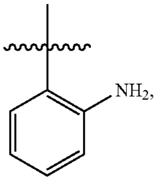
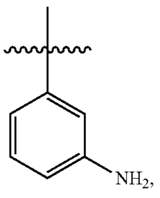
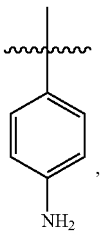
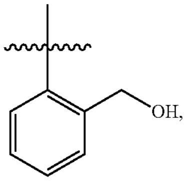

-continued
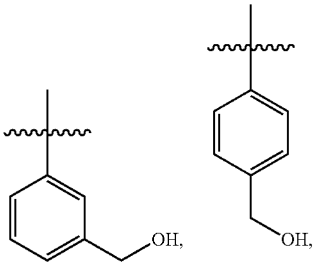
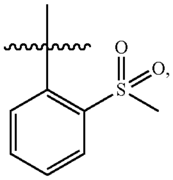
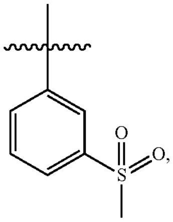
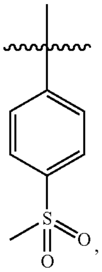
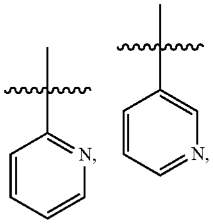
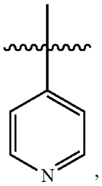,
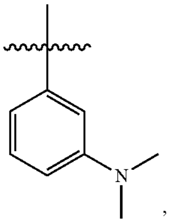,
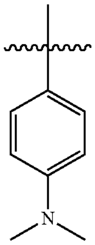,
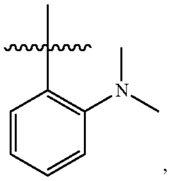,
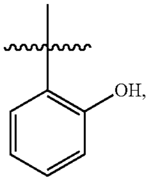
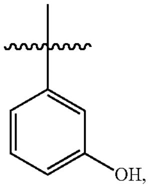
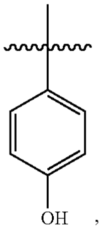,
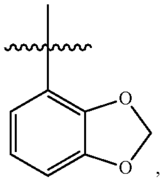,
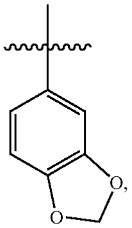
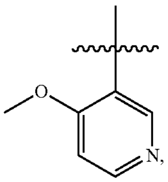
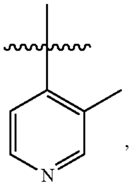,
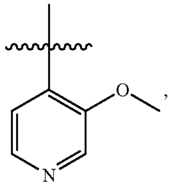
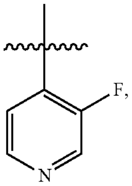
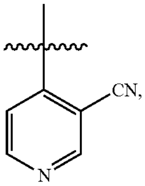
-continued
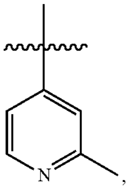,
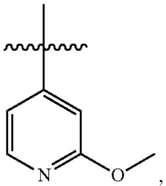,
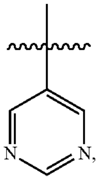
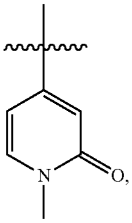
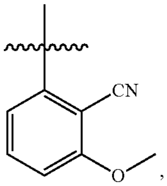,
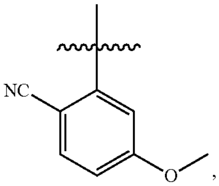,
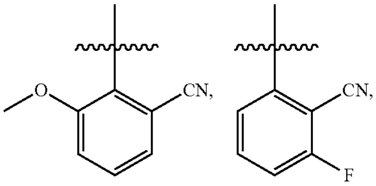
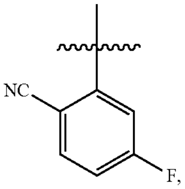
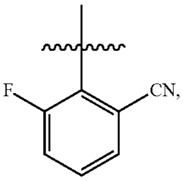
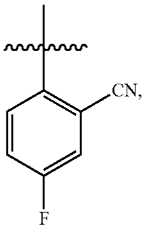
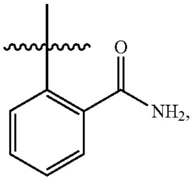
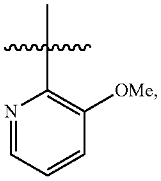
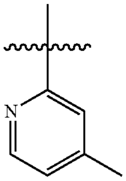,
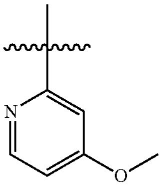,
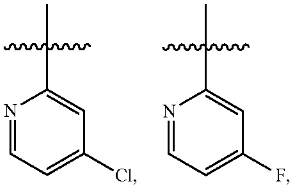
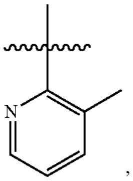,
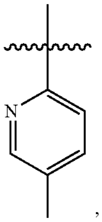,
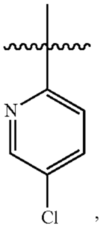,
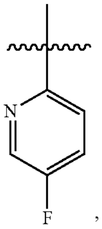,
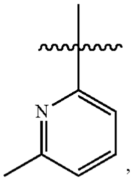,
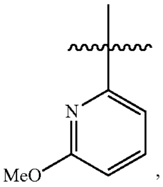, or -continued

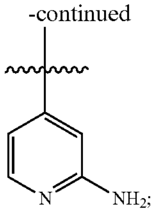

$L^1$ is —O— or —NH—;

X is a C6-C14 arylene or a 5-11 membered heteroarylene, wherein the arylene and the heteroarylene may be optionally substituted with one or more of the following groups: —H, a halogen, a C1-C6 alkyl, a C3-C6 cycloalkyl, a C1-C6 alkoxy and a C1-C6 haloalkoxy;

$R^1$ is —H, a halogen, $—(CH_2)_nNR^6R^7$, $—NR^6R^7$, $—O(CH_2)_mNR^6R^7$, $—N(R^5)(CH_2)_mNR^6R^7$, a C1-C6 alkoxy, a $—CH_2$-3-15 membered heterocycloalkyl or a 3-15 membered heterocycloalkyl, wherein the alkoxy and the heterocycloalkyl may be optionally substituted with one or more of the following groups: —H, $—R^4$, $—(CH_2)_nNR^6R^7$, $—NR^6R^7$, $—O(CH_2)_mNR^6R^7$, $—N(R^5)(CH_2)_mNR^6R^7$ and $—R^3$;

$L^2$ is —O—, —NH— or a chemical bond;

$R^2$ is a C1-C6 alkyl, a C3-C14 cycloalkyl, a C6-C14 aryl, a 3-4 membered heterocycloalkyl,

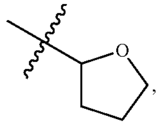, 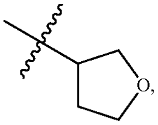

or a 6-11 membered heterocycloalkyl; wherein the alkyl, the cycloalkyl, the aryl, the heterocycloalkyl,

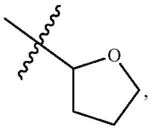, and 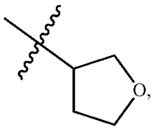

may be optionally substituted with one or more of the following groups: —H, a halogen, $—R^4$, $—(CH_2)_nOR^4—$, $—(CH_2)_nNR^4R^5—$, $—OR^4$, $—NR^4R^5$, —CN, $—C(O)NR^4R^5$, $—NR^5C(O)R^4$, $—NR^5S(O)_2R^4$, $—S(O)_pR^4$ and $—S(O)_2NR^4R^5$;

$R^3$ is a 3-11 membered heterocycloalkyl, wherein the heterocycloalkyl may be optionally substituted with one or more of the following groups: —H, $—CD_3$, $—R^4$, $—OR^4$ and $—NR^4R^5$;

$R^4$ and $R^5$ are each independently —H, a C1-C6 alkyl or a C3-C14 cycloalkyl;

$R^6$ and $R^7$ are each independently —H, a C1-C6 alkyl or a C3-C14 cycloalkyl, or $R^6$ and $R^7$ form a 3-11 membered heterocycloalkyl along with N atoms connected thereto, wherein the heterocycloalkyl may be optionally substituted with one or more of the following groups: —H, $—CD_3$, a halogen, $—R^4$ and $—OR^4$; and p is an integer of 0, 1 or 2, n is an integer of 0, 1, 2 or 3, and m is an integer of 1, 2 or 3.

2. The compound, or the isomer, the crystalline form, the pharmaceutically acceptable salt, the hydrate or the solvate thereof according to claim 1, wherein, in general formula (1), X is phenylene or a 6-membered heteroarylene, wherein the phenylene and the heteroarylene may be optionally substituted with one or more of the following groups: —H, —F, $—CH_3$, $—CH_2CH_3$, $—CH(CH_3)_2$,

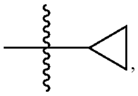, $—OCH_3$, $—OCF_2H$ and $—OCF_3$.

3. The compound, or the isomer, the crystalline form, the pharmaceutically acceptable salt, the hydrate or the solvate thereof according to claim 2, wherein, in general formula (1), X is:

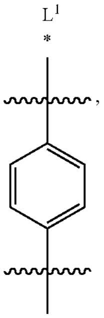, 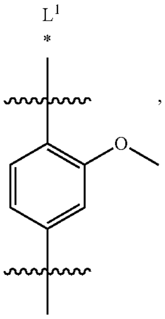, 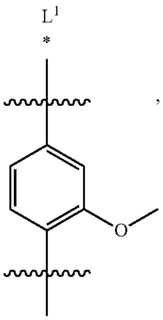,

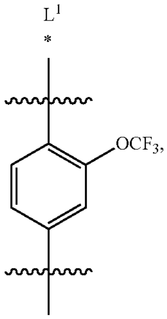 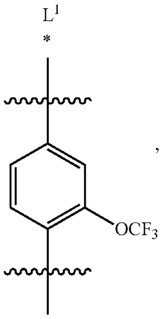, 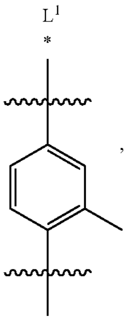,

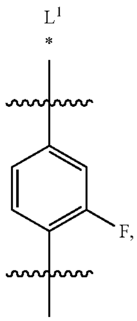 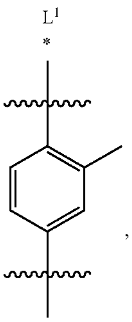, 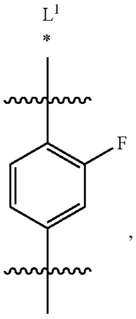,

-continued

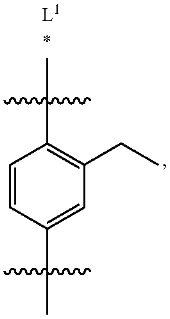,
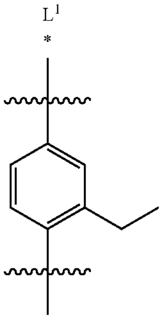,
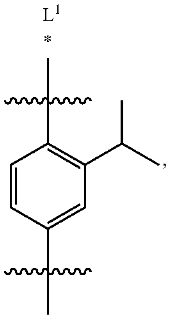,
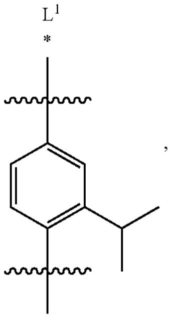,
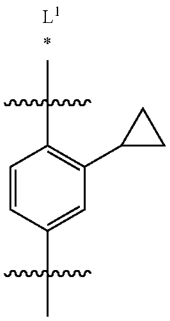,
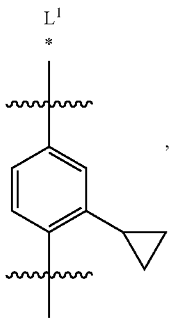,
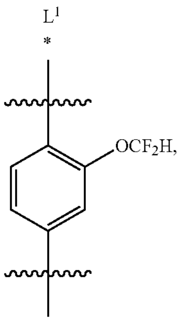
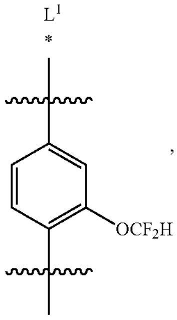,
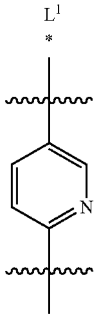 or 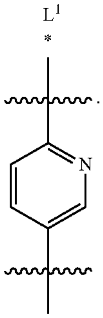.

4. The compound, or the isomer, the crystalline form, the pharmaceutically acceptable salt, the hydrate or the solvate thereof according to claim 1, wherein, in general formula (1), $R^1$ is: —H, —$N(CH_3)_2$, —$CH_2$-6-11 membered heterocycloalkyl or a 6-11 membered heterocycloalkyl, wherein the heterocycloalkyl is

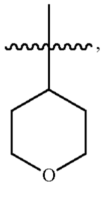,
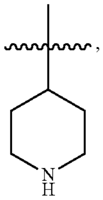,
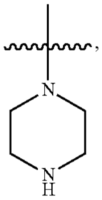,
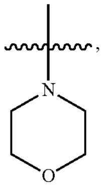,
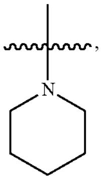,
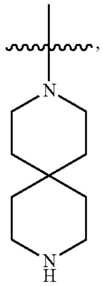,
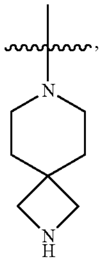,
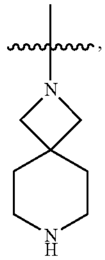,
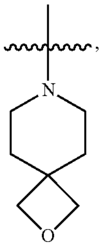,
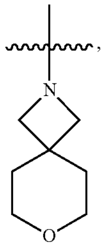,
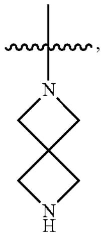,
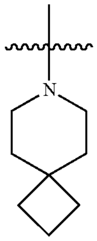 or 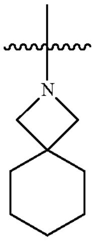

and may be optionally substituted with one or more of the following groups:

—H, —$CH_3$, 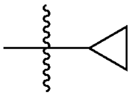, —$N(CH_3)_2$,
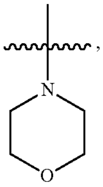,
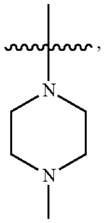,
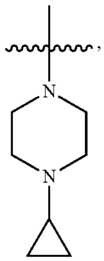,
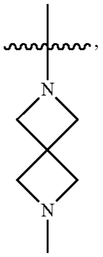, -continued

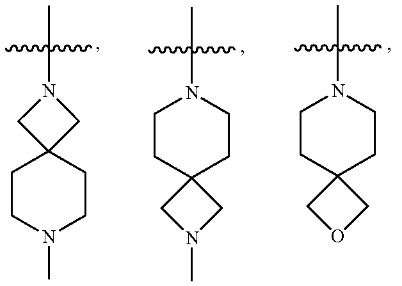

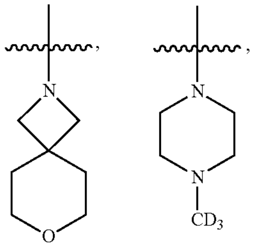

and —$CD_3$.

5. The compound, or the isomer, the crystalline form, the pharmaceutically acceptable salt, the hydrate or the solvate thereof according to claim 4, wherein, in general formula (1), $R^1$ is:

—H, —$N(CH_3)_2$.

—H, —$(N(CH_3)_2)$,

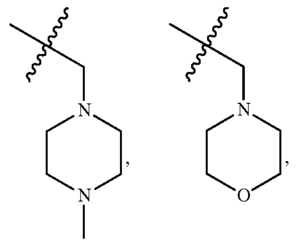

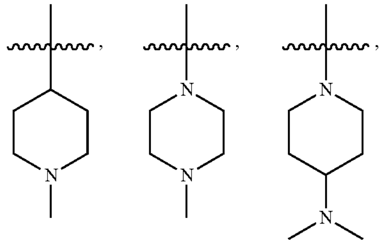

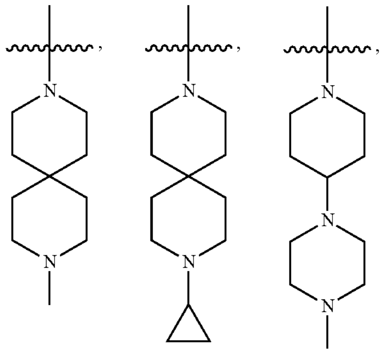

-continued

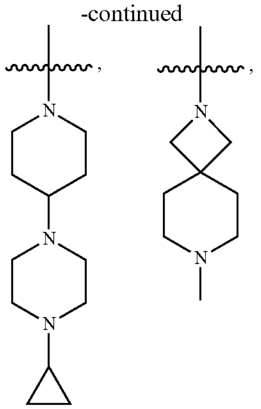

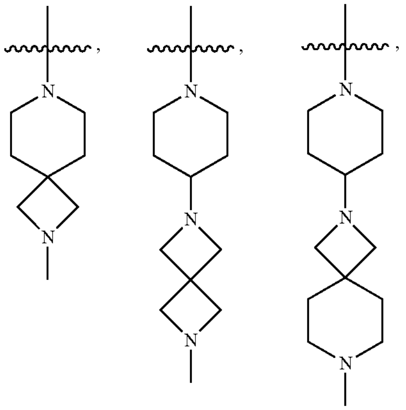

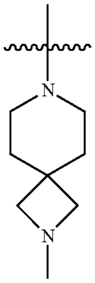

or

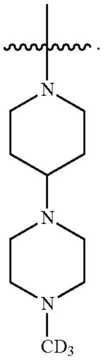

6. The compound, or the isomer, the crystalline form, the pharmaceutically acceptable salt, the hydrate or the solvate thereof according to claim 1, wherein, in general formula (1), when $L^2$ is —NH— and Y is

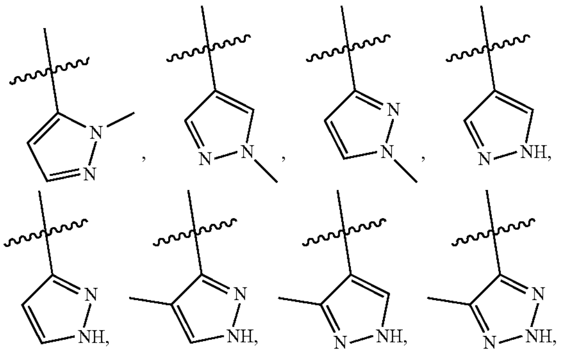

-continued
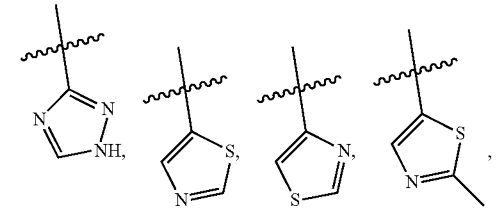
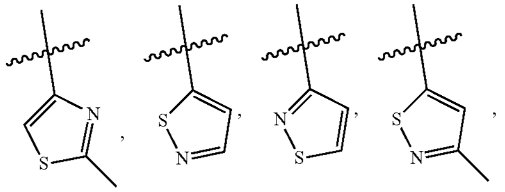
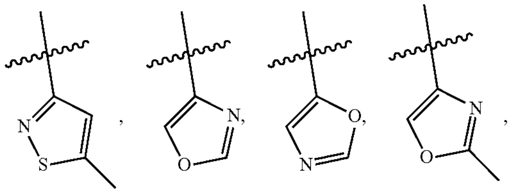
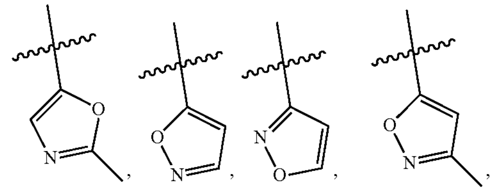
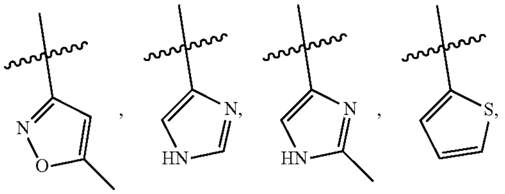
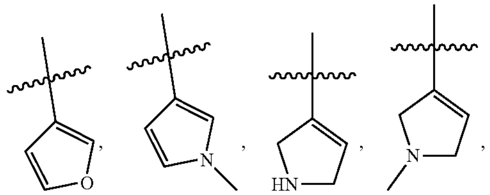
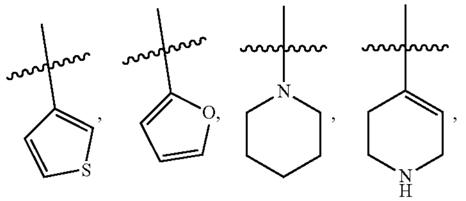
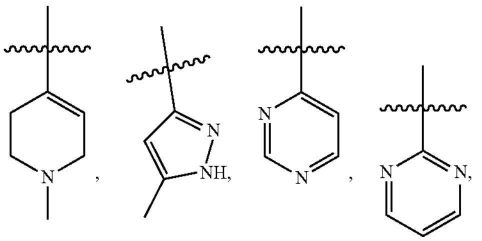
-continued
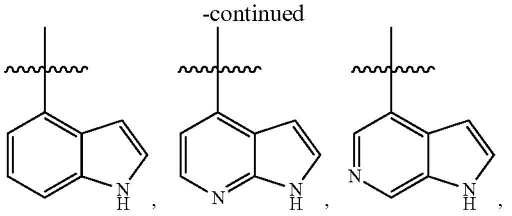
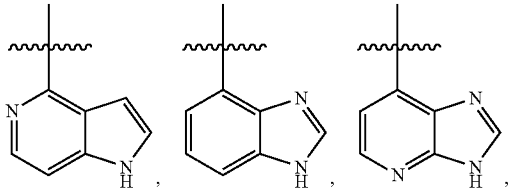
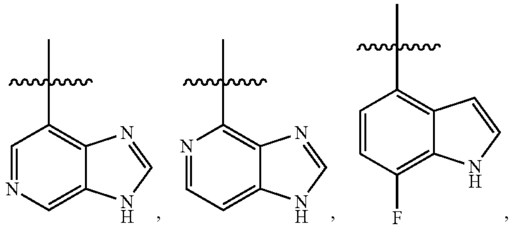
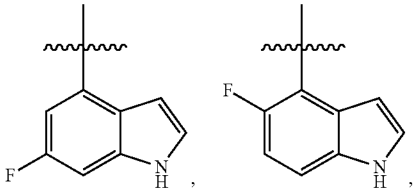
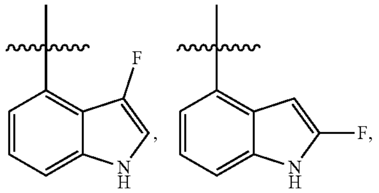
or
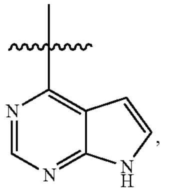
$R^2$ is:
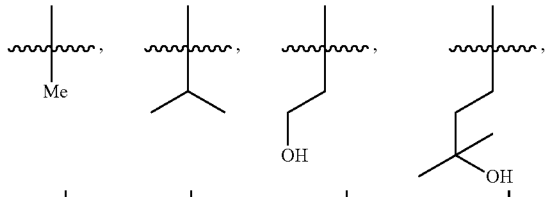
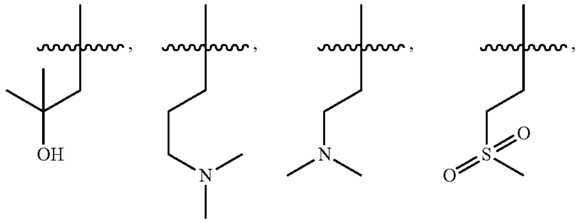

-continued
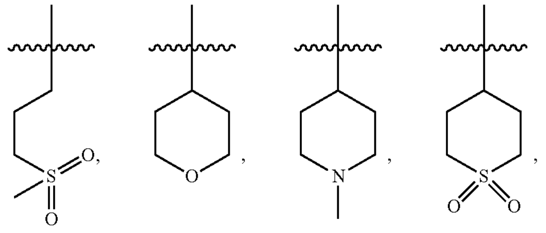
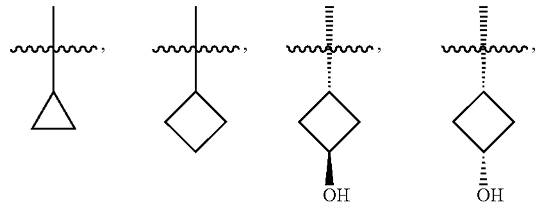
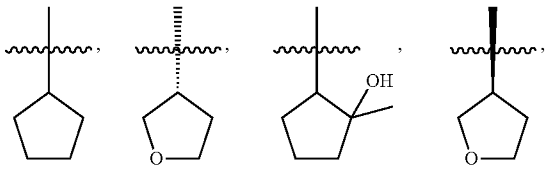
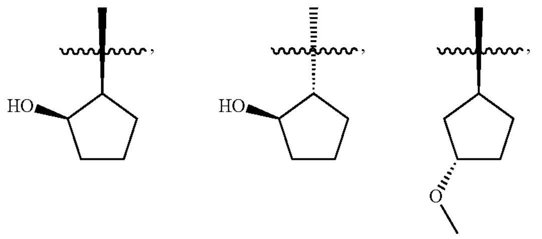
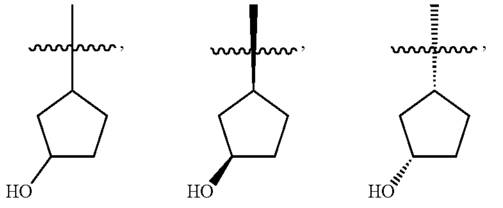
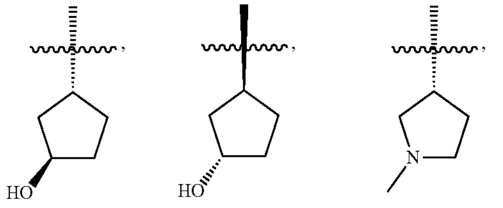
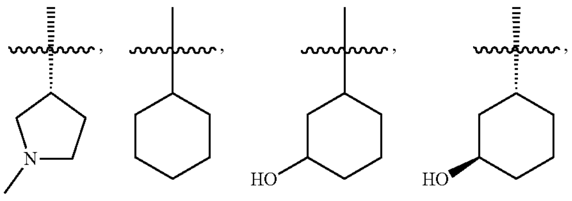
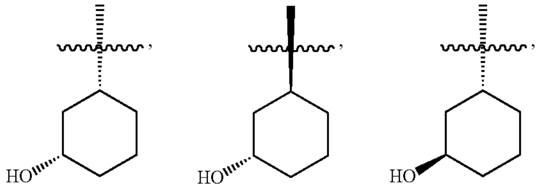
-continued
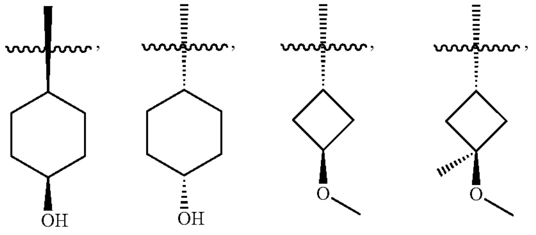
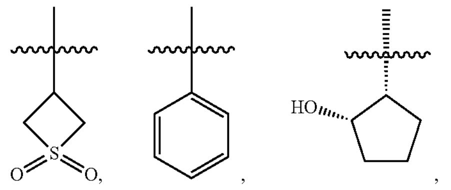
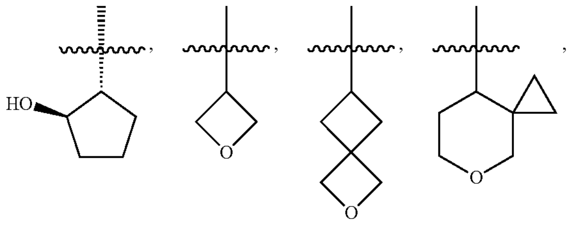
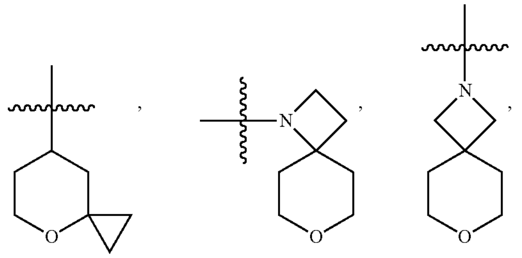
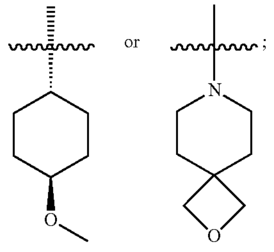
or
when $L^2$ is —NH— and Y is
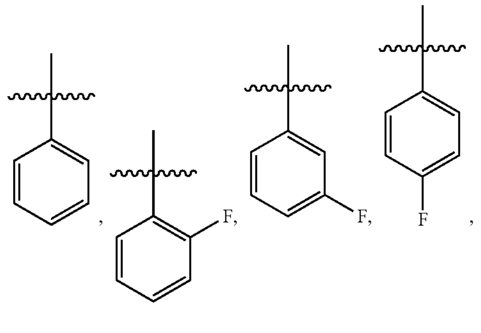

-continued
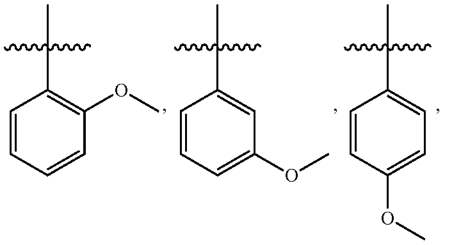
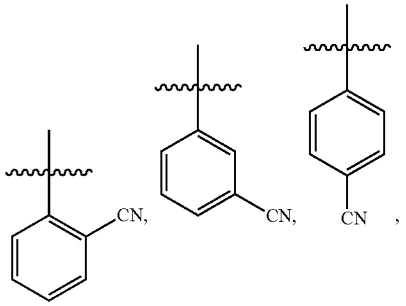
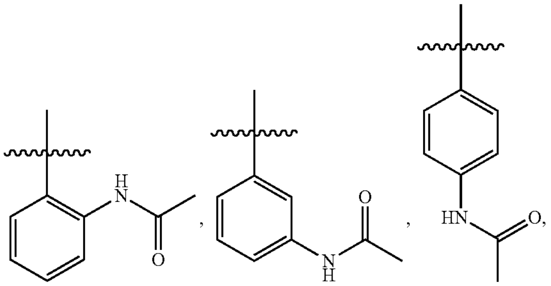
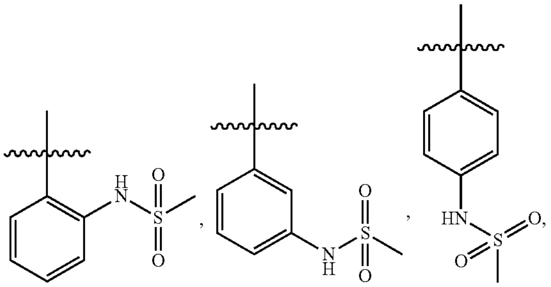
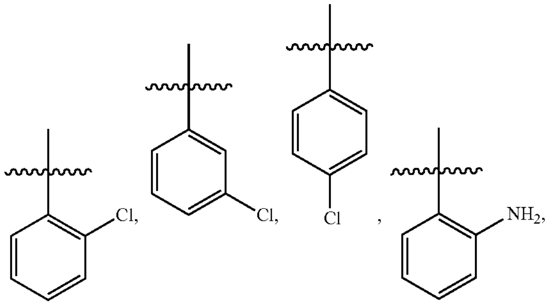
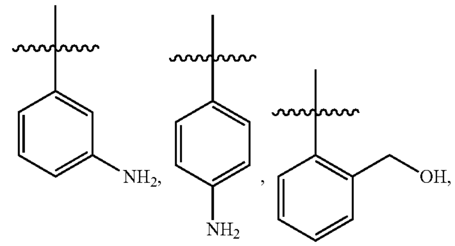
-continued
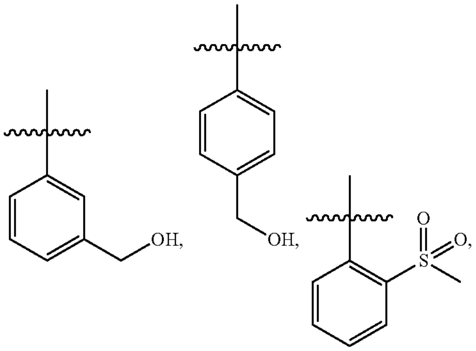
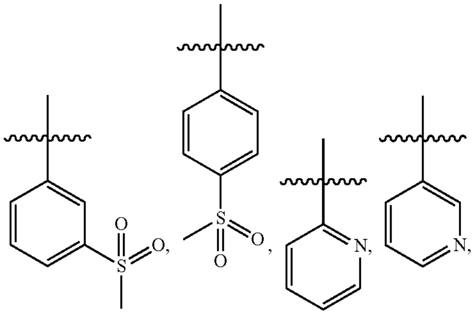
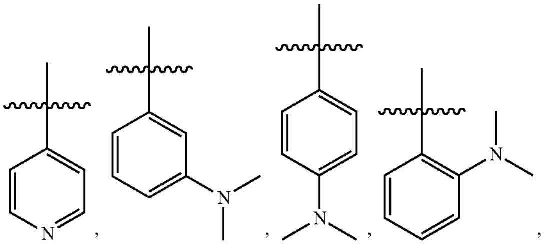
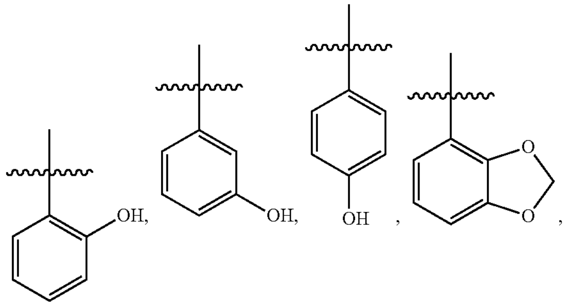
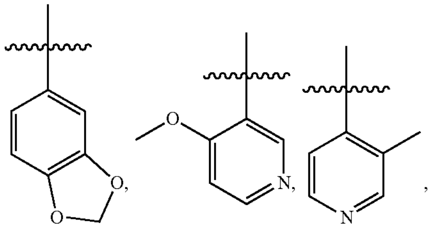
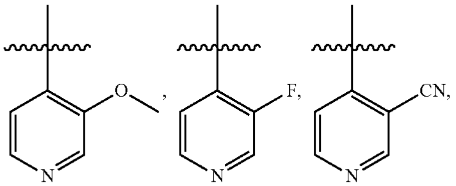

-continued
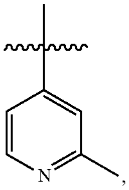, 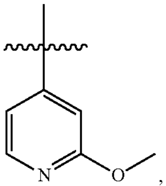, 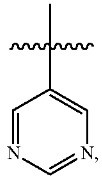, 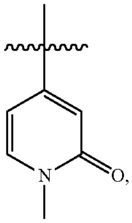
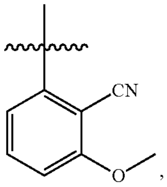, 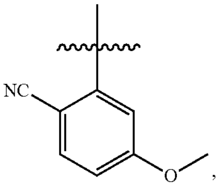,
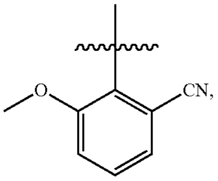 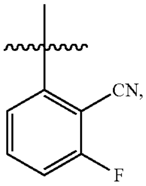 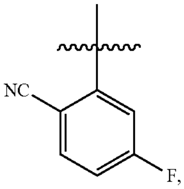
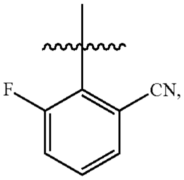 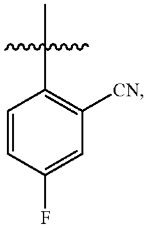
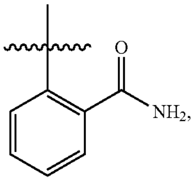 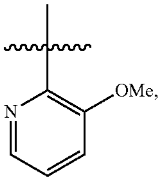
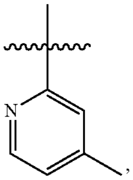, 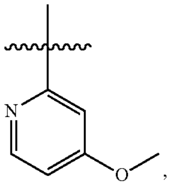,
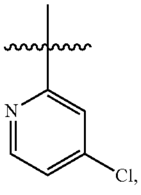 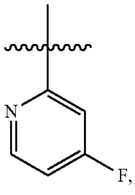 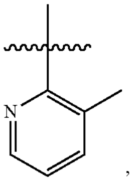, 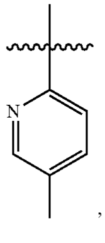,
-continued
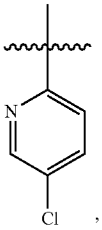, 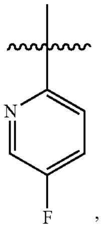, 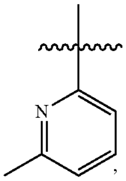,
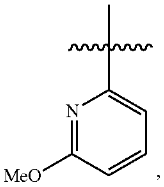, or 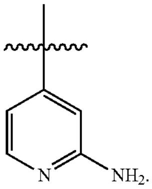
$R^2$ is:
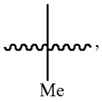, 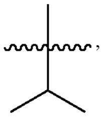, 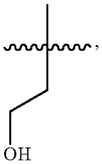, 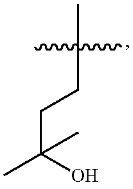,
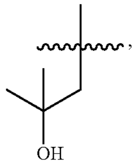, 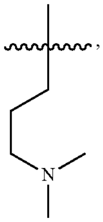, 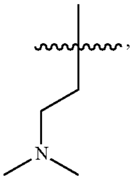,
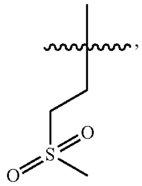, 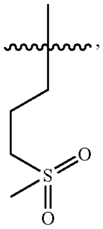, 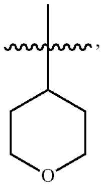, 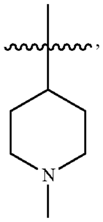,
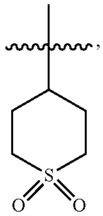, 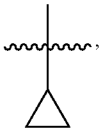, 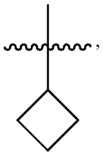, 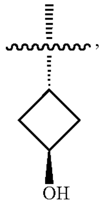,
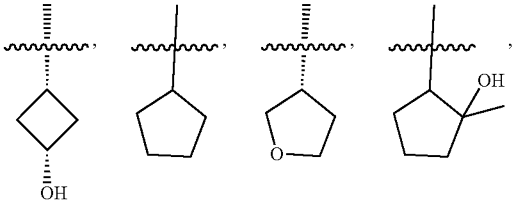

-continued

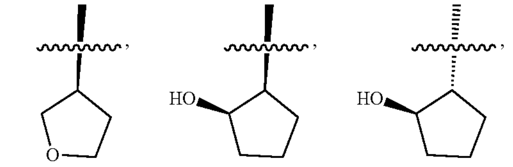

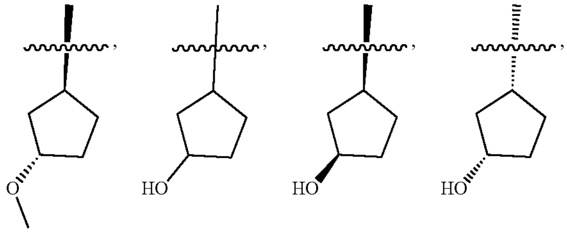

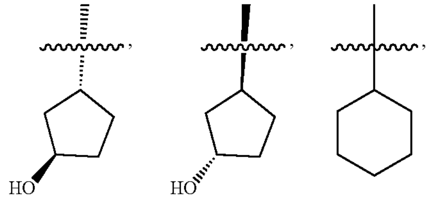

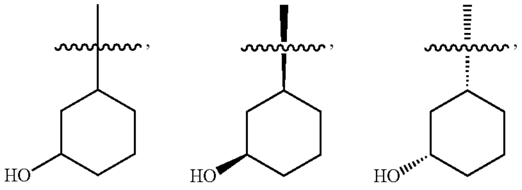

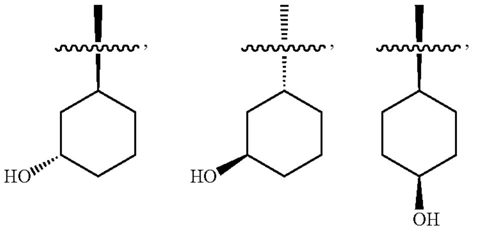

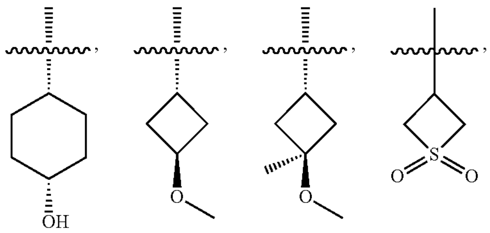

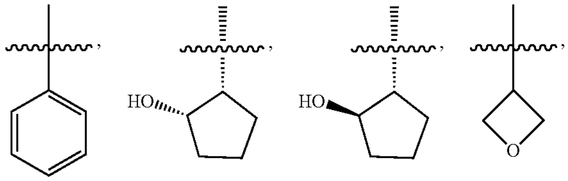

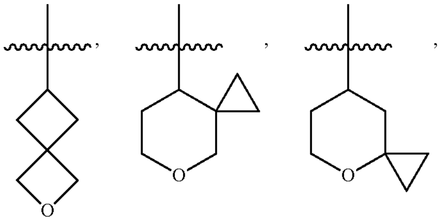

-continued

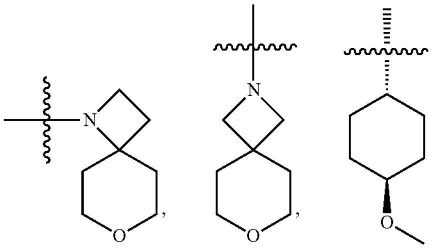

or

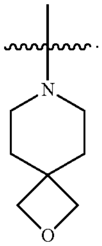

7. The compound, or the isomer, the crystalline form, the pharmaceutically acceptable salt, the hydrate or the solvate thereof according to claim 1, wherein, in general formula (1), when $L^2$ is —O—, $R^2$ is:

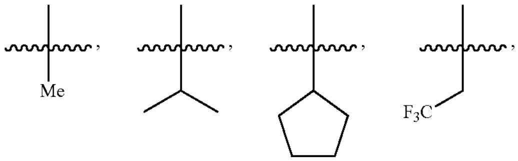

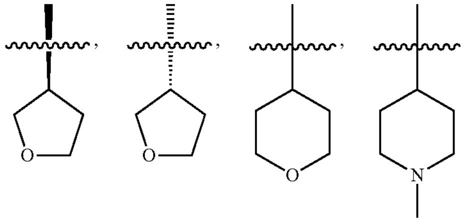

or

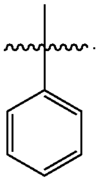

8. The compound, or the isomer, the crystalline form, the pharmaceutically acceptable salt, the hydrate or the solvate thereof according to claim 1, wherein, in general formula (1), when $L^2$ is a chemical bond, $R^2$ is:

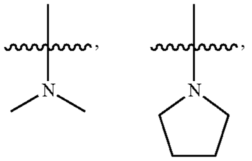

-continued
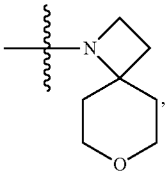
,
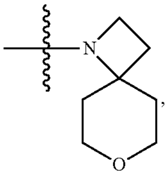
,
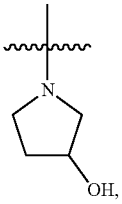
,
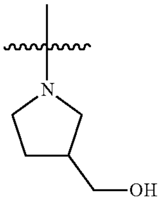
or
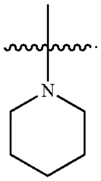
.
9. The compound, or the isomer, the crystalline form, the pharmaceutically acceptable salt, the hydrate or the solvate thereof according to claim 1, wherein the compound has one of the following structures:
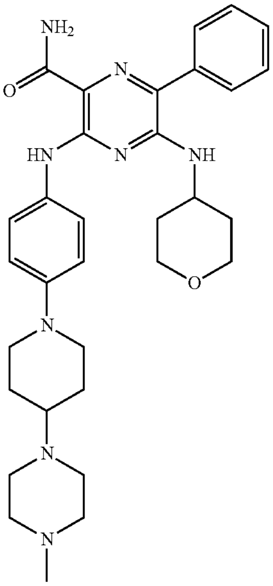
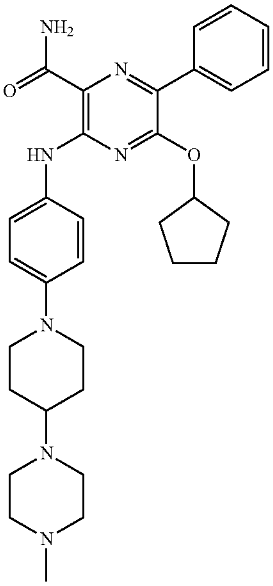
-continued
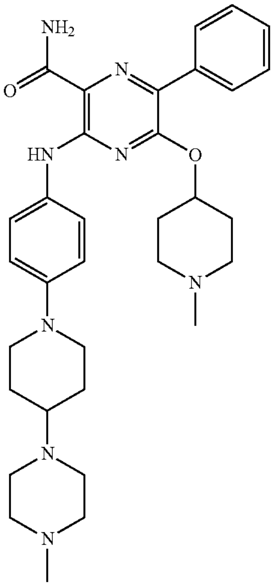
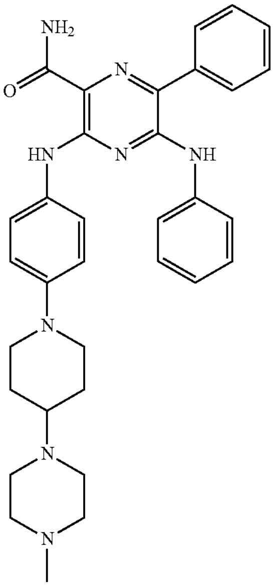
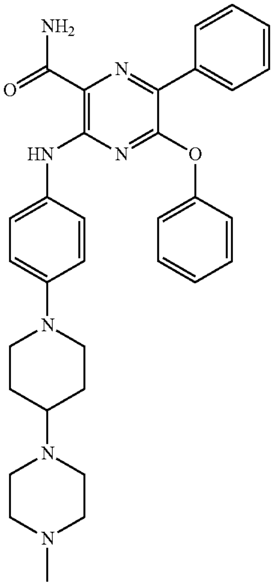
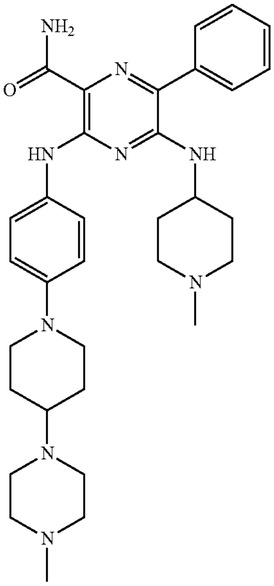

-continued
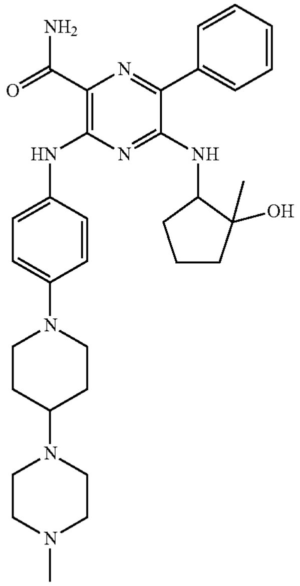
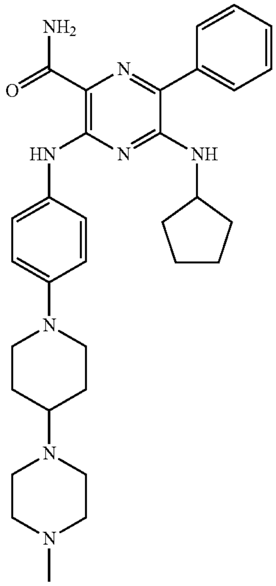
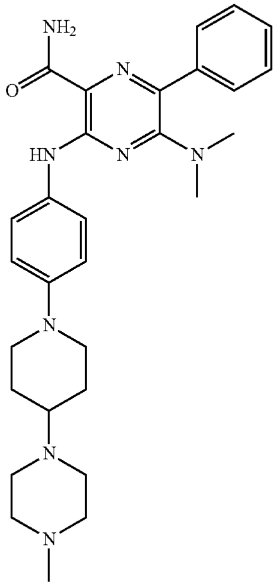
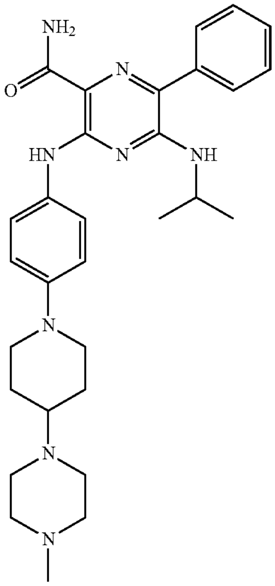
-continued
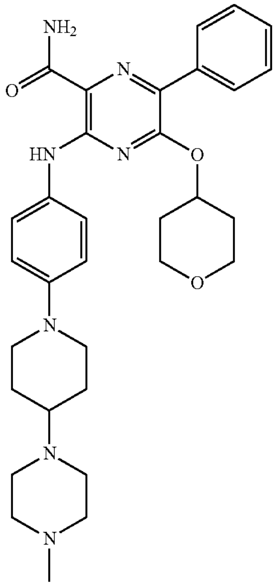
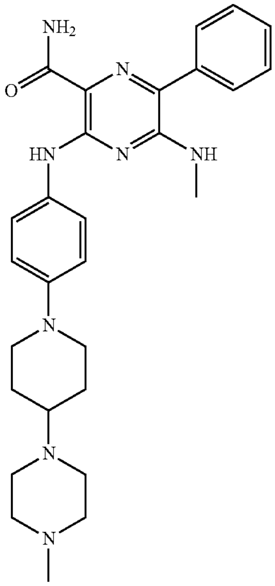
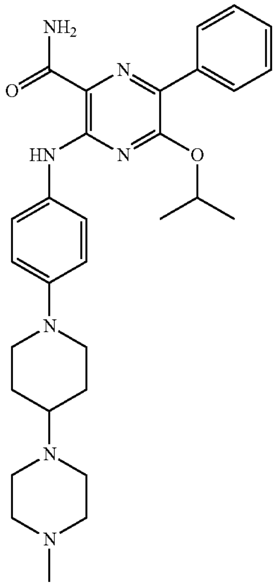
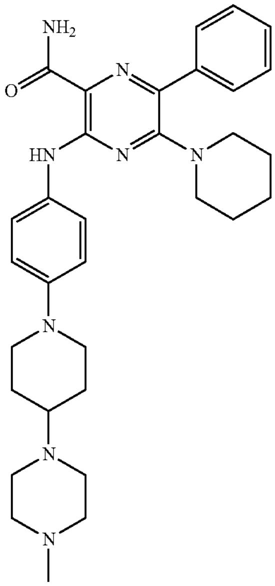

-continued
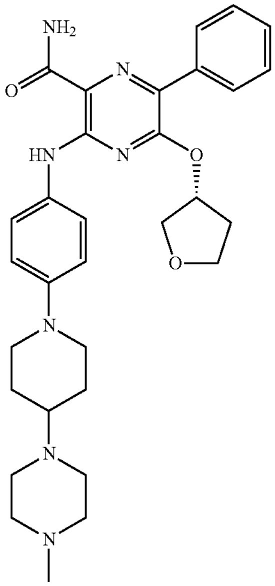
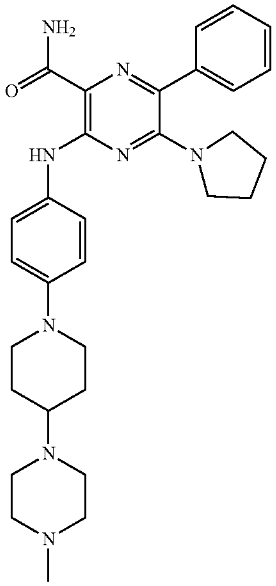
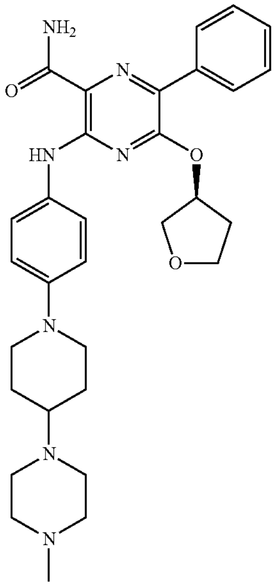
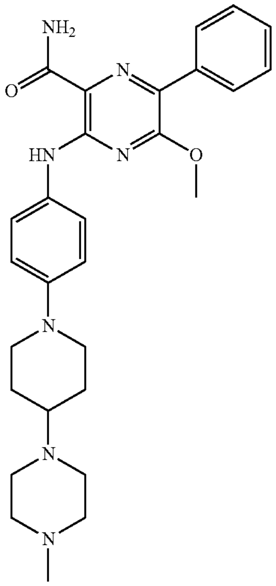
-continued
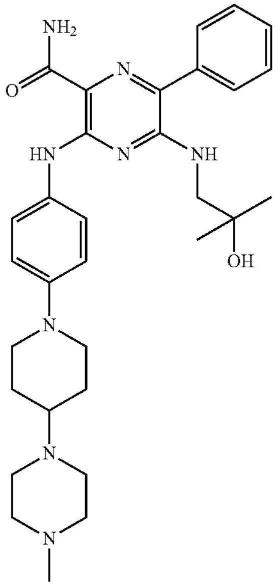
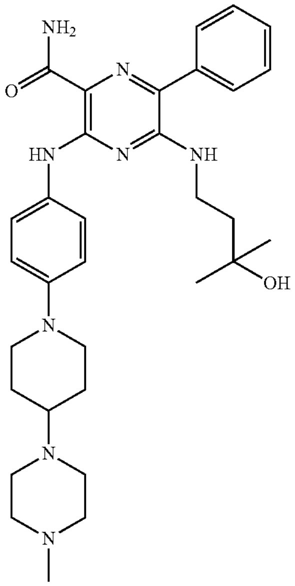
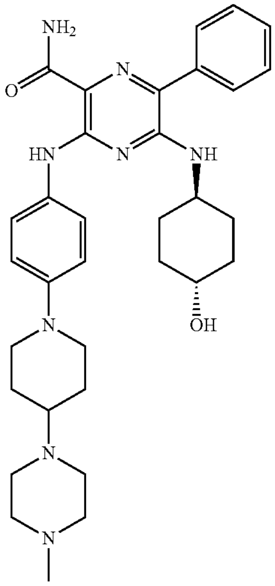
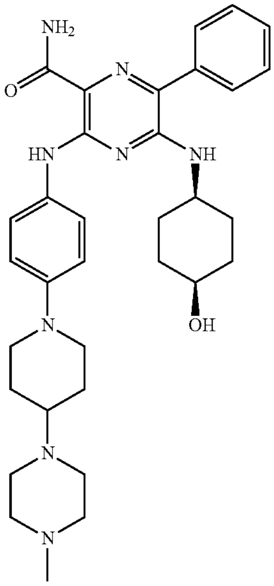

-continued
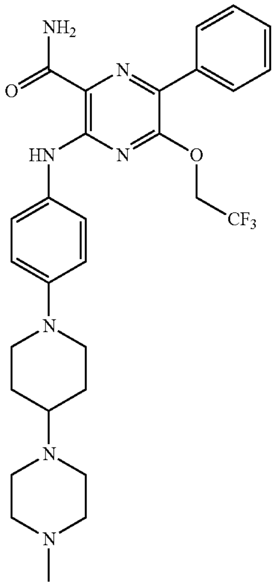
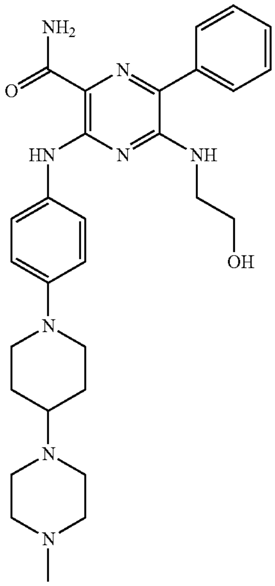
-continued
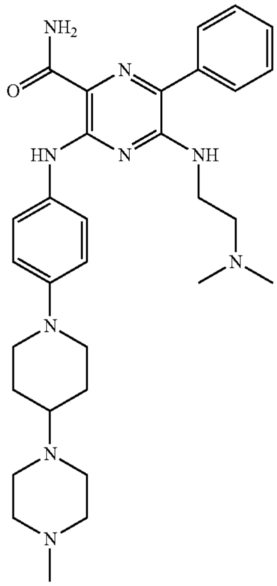
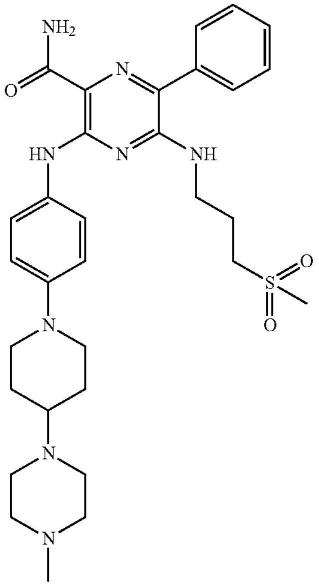
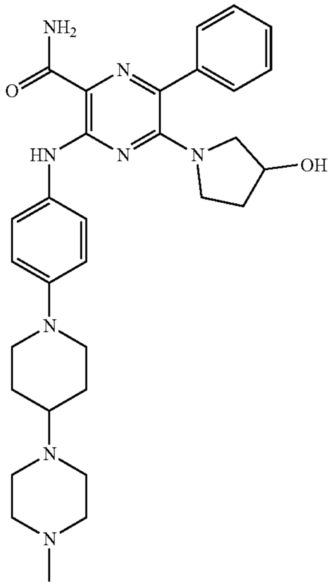

-continued
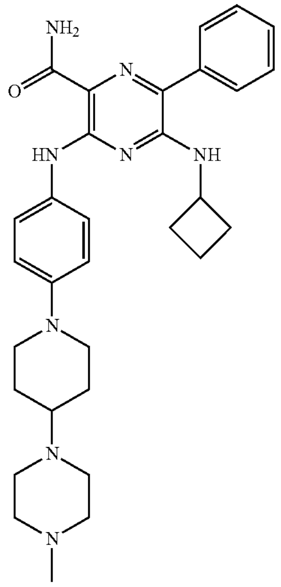
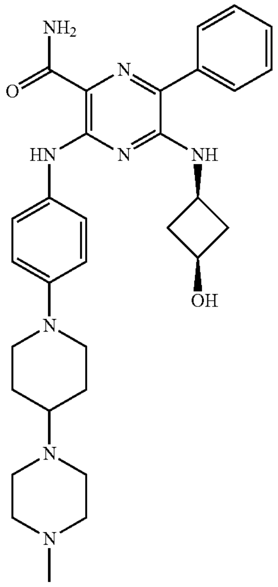
-continued
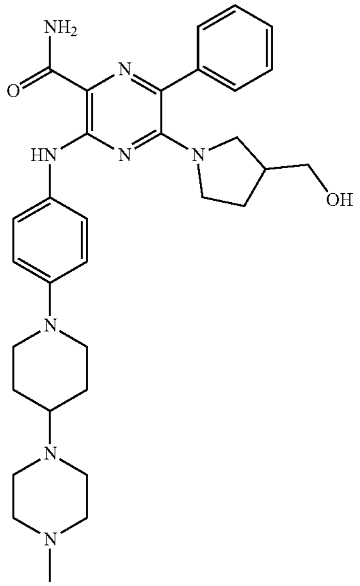
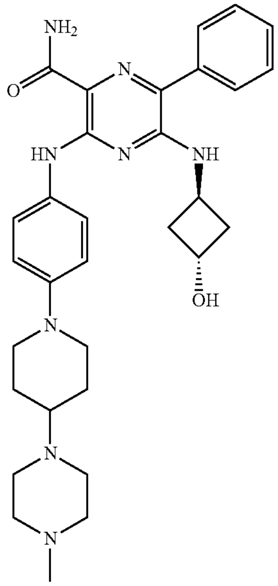
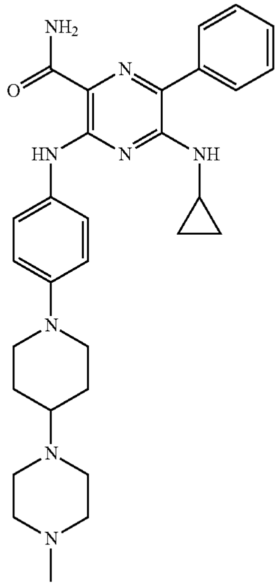
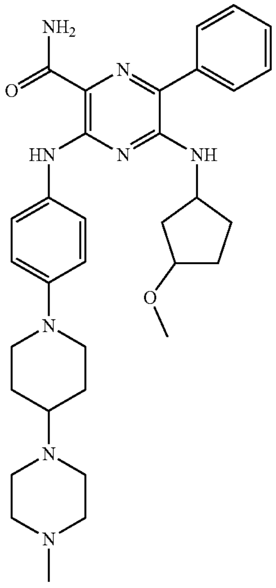
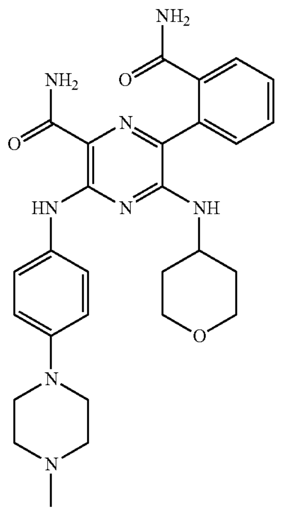

-continued
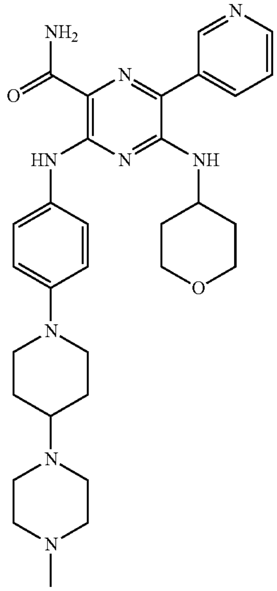
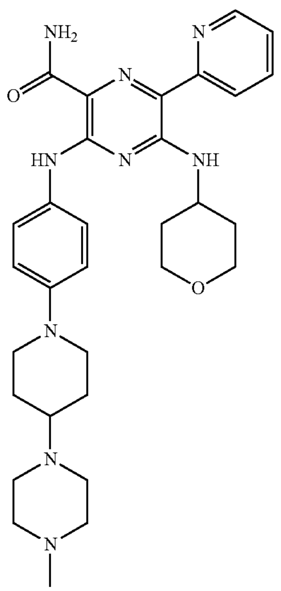
-continued
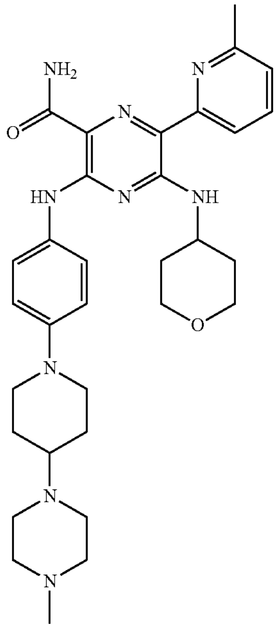
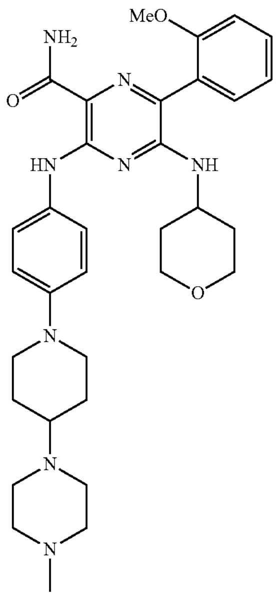
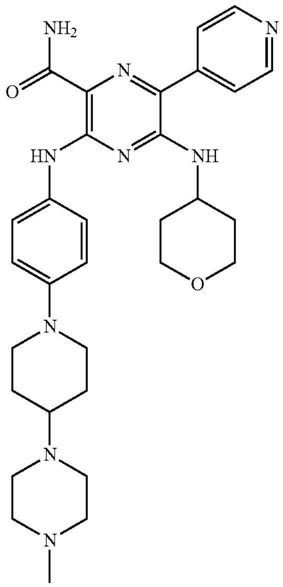
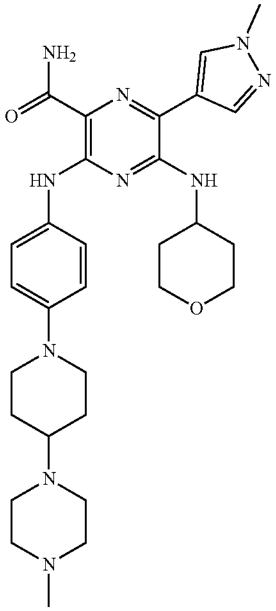
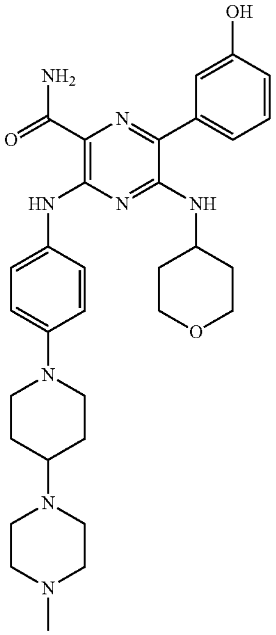
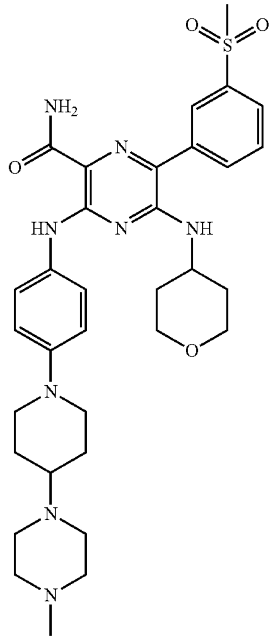

-continued
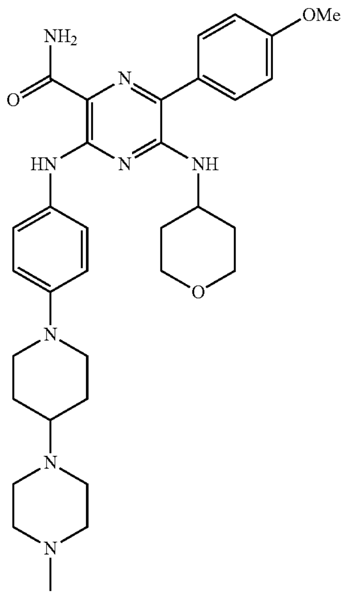
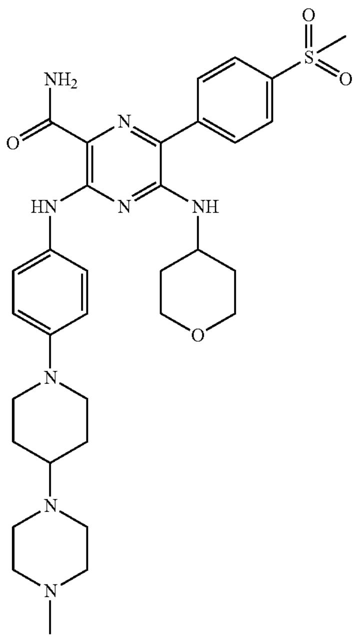
-continued
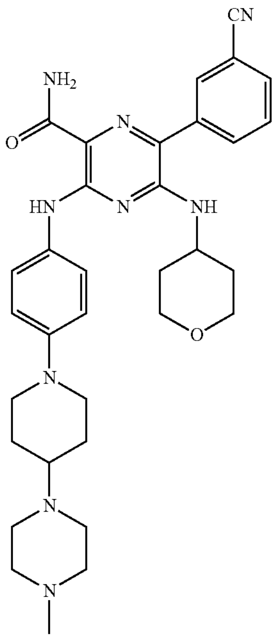
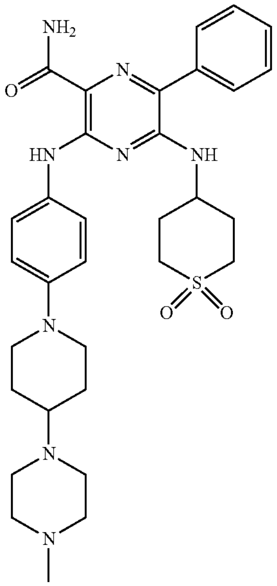
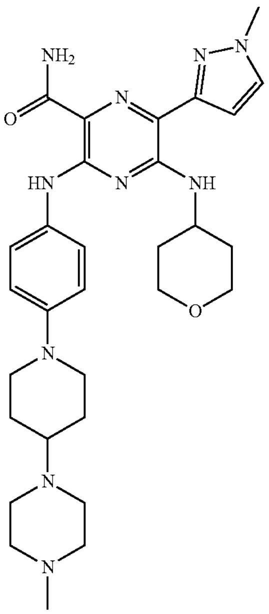
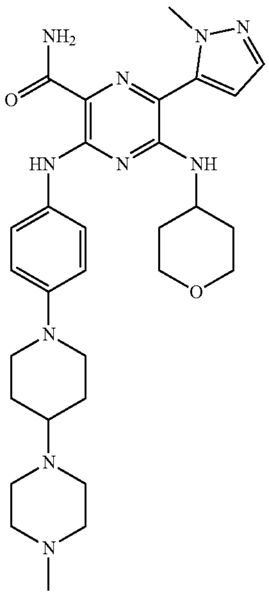

-continued
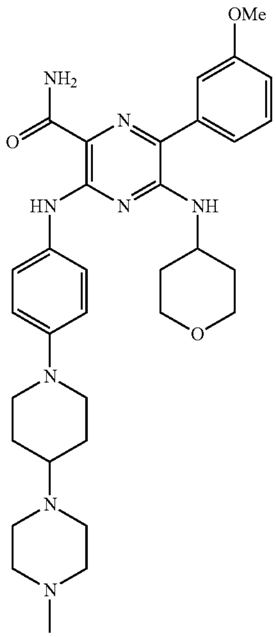
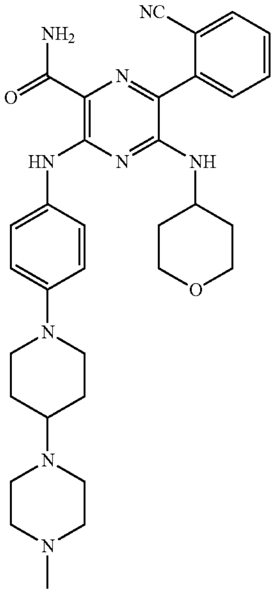
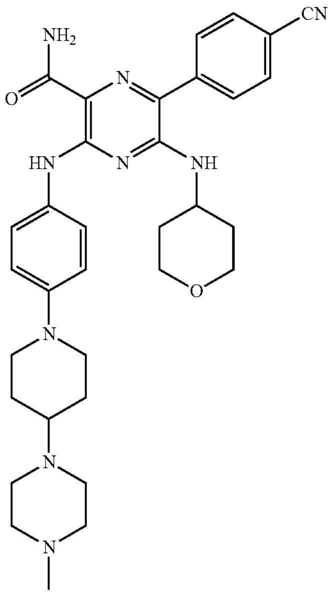
-continued
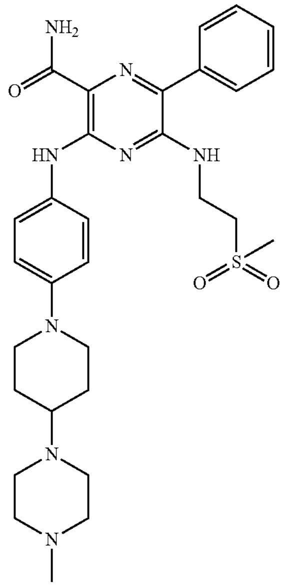
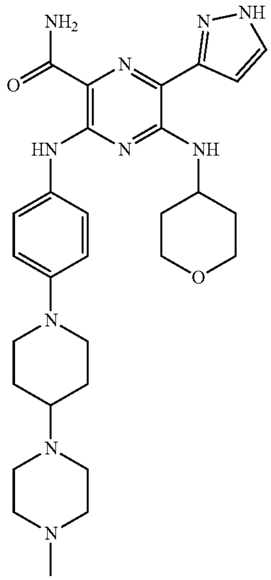
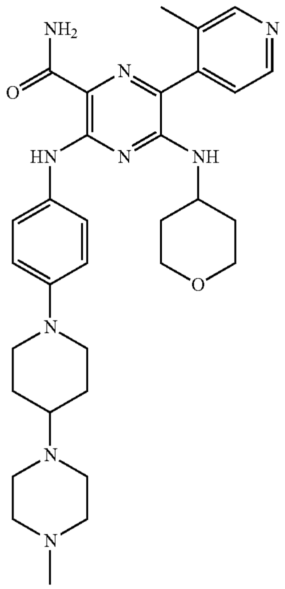
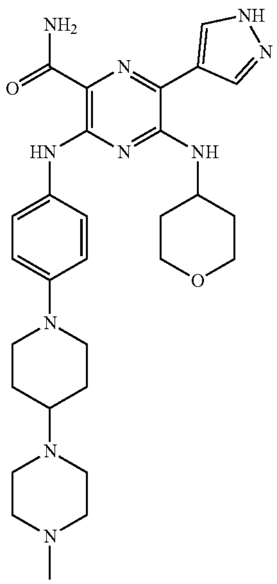

-continued
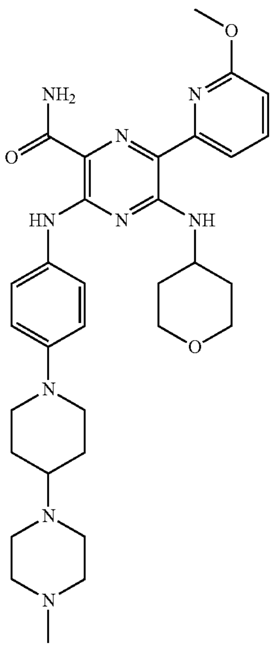
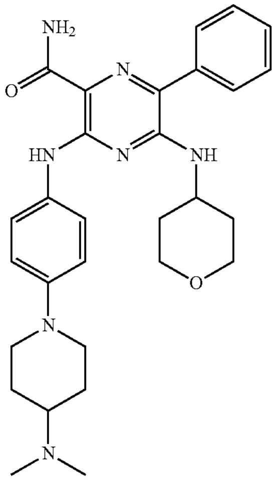
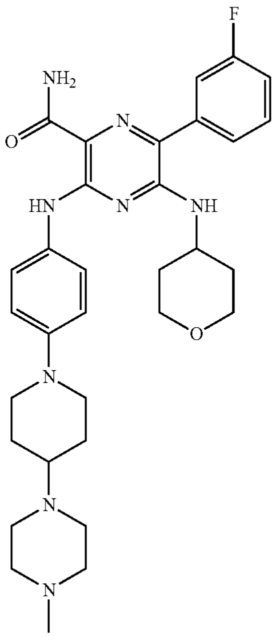
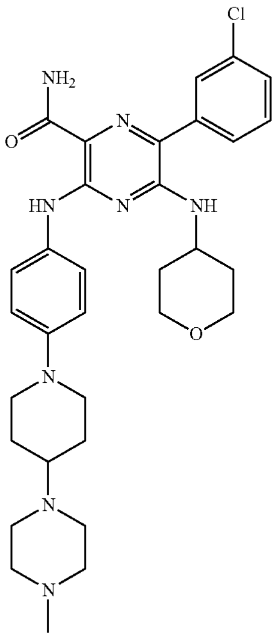
-continued
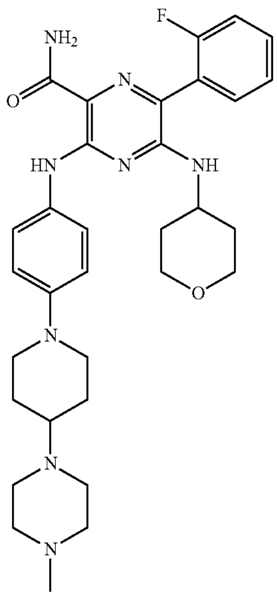
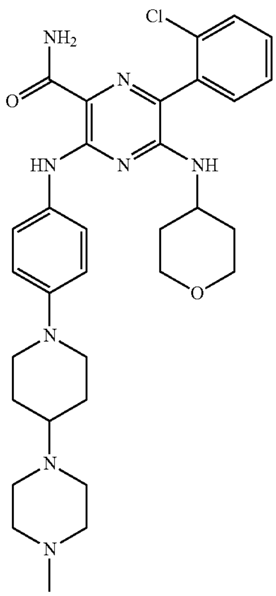
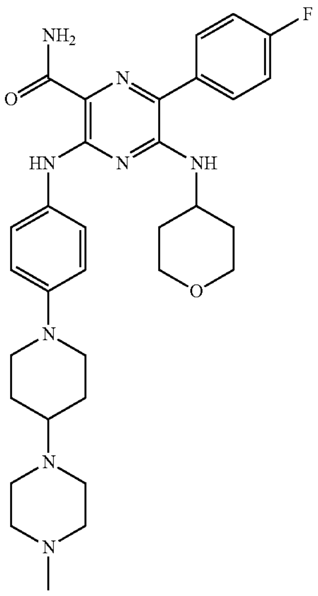

-continued
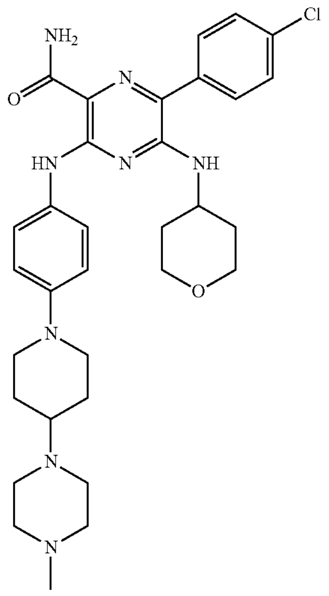
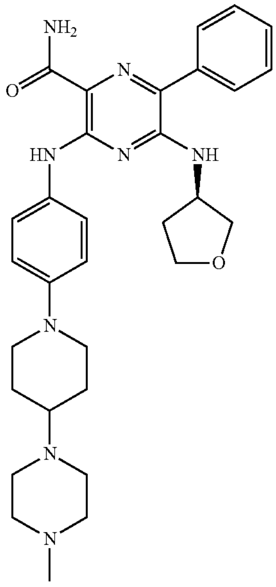
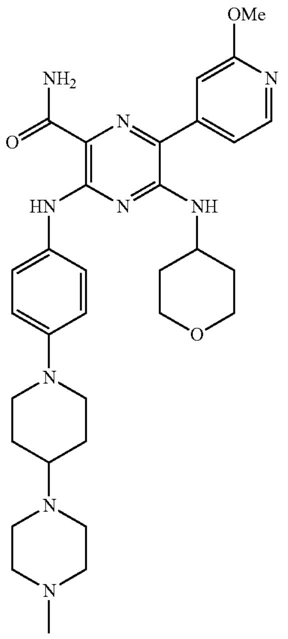
-continued
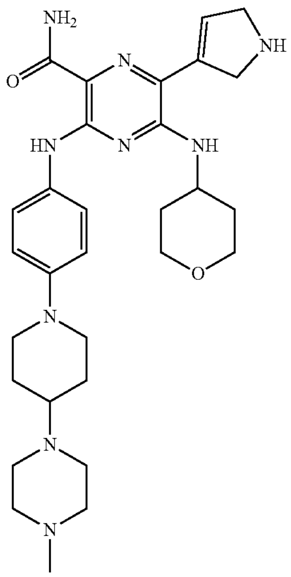
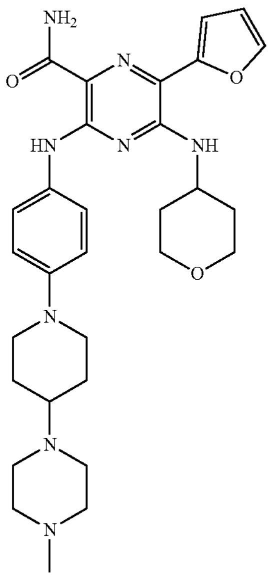
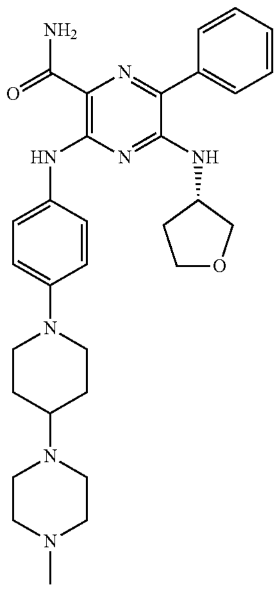
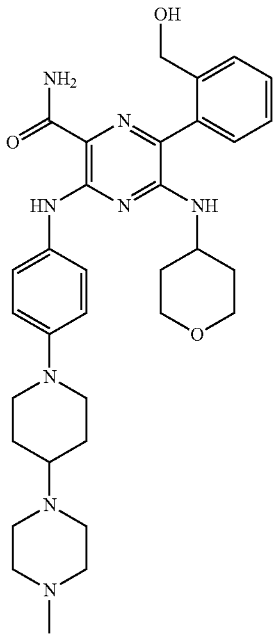

-continued
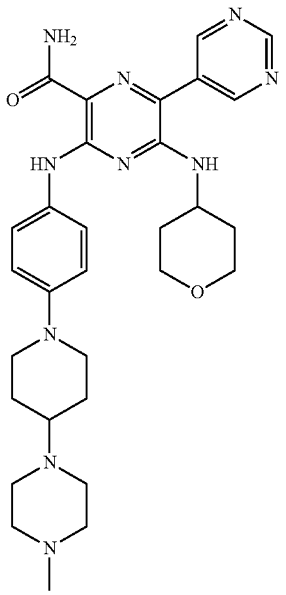
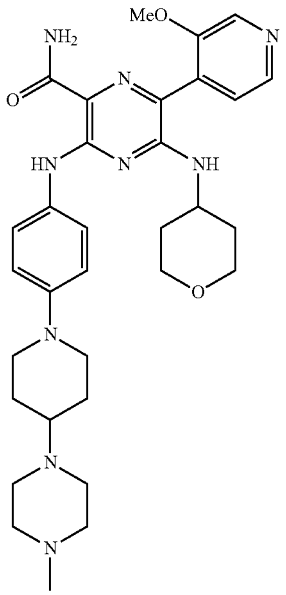
-continued
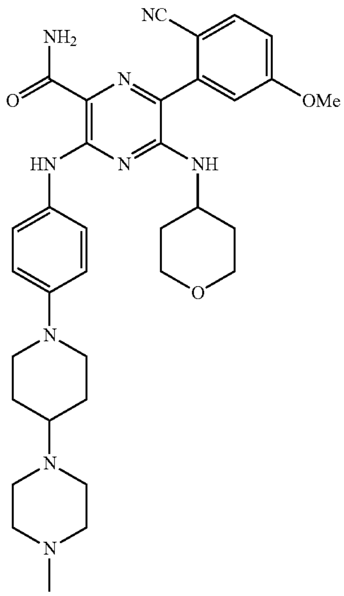
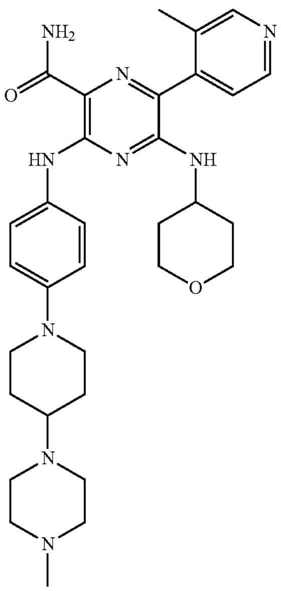
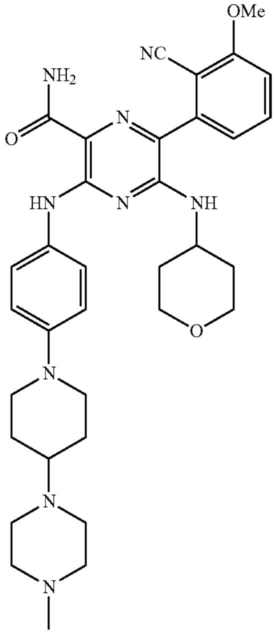
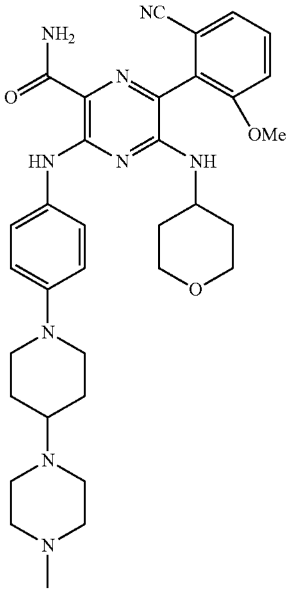
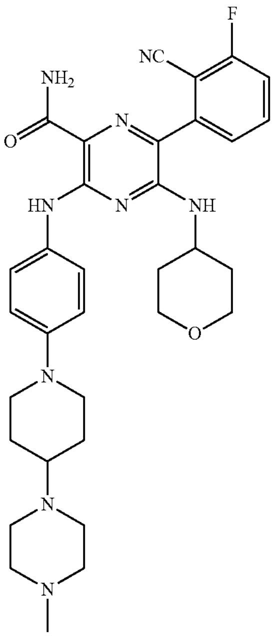

-continued
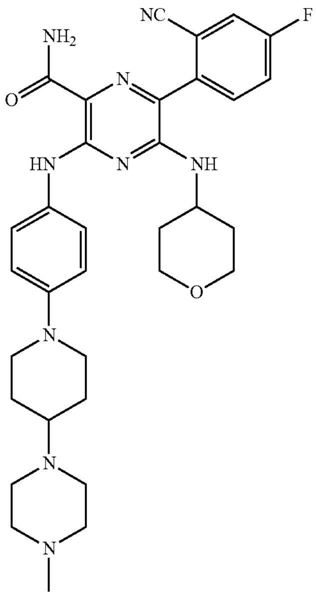
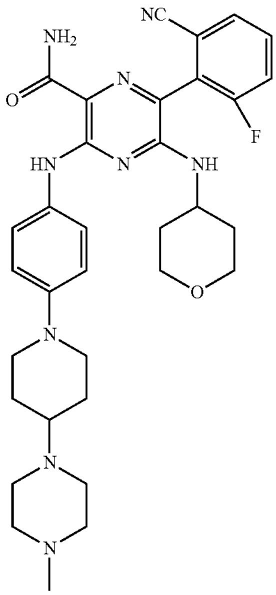
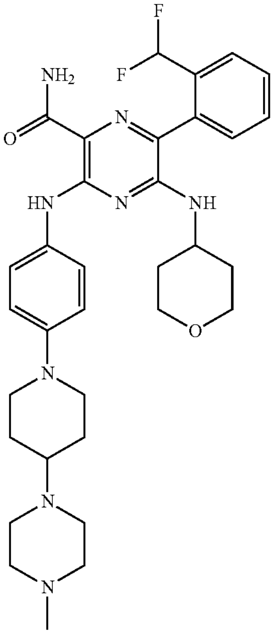
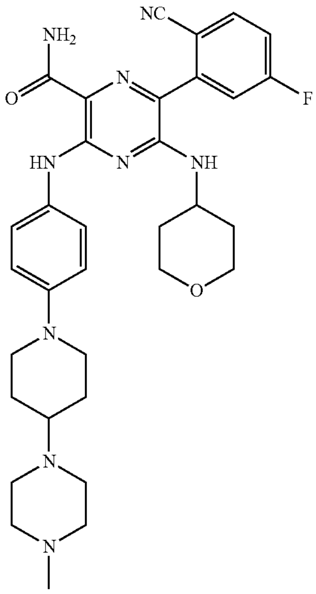
-continued
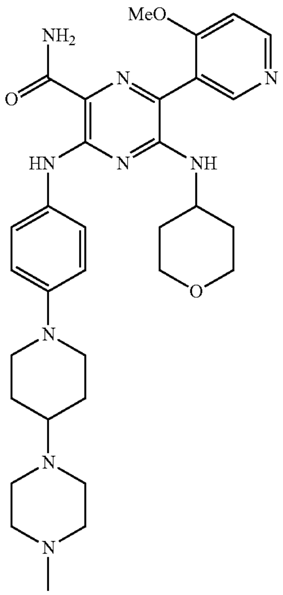

-continued
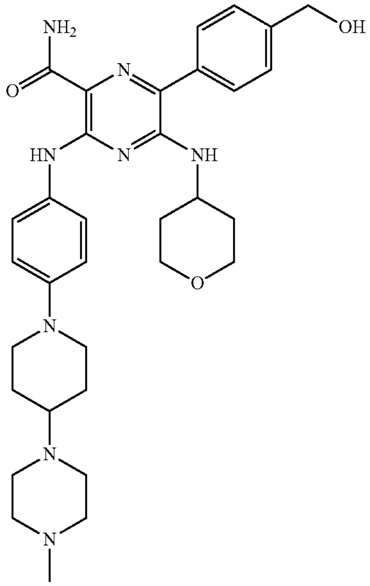
-continued
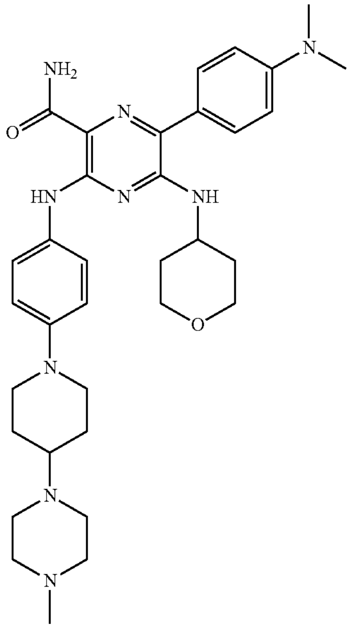
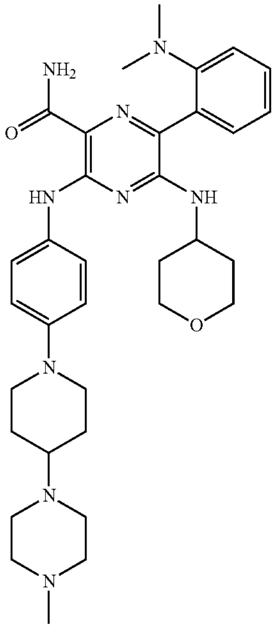
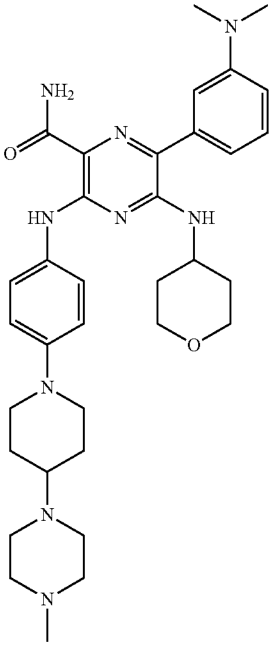
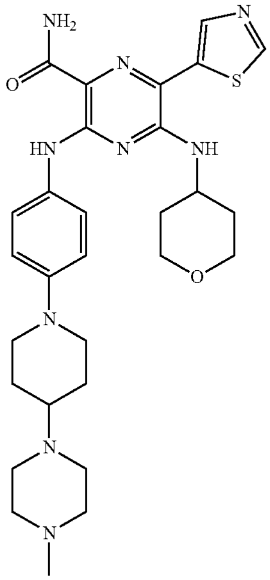

-continued
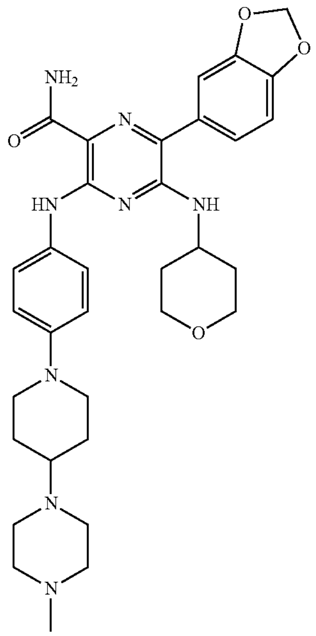
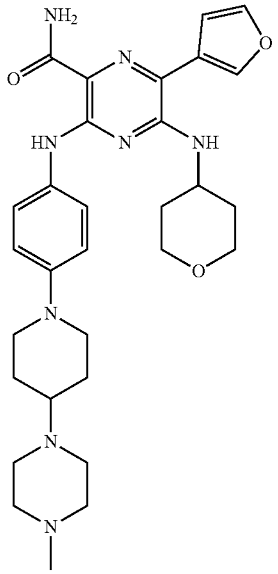
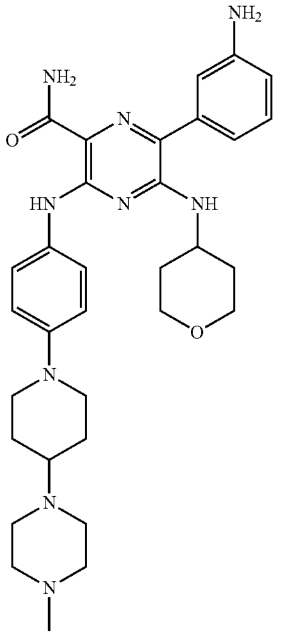
-continued
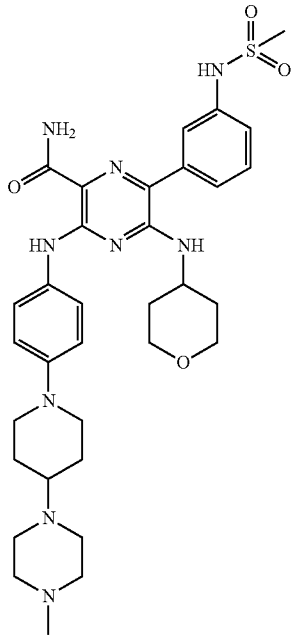
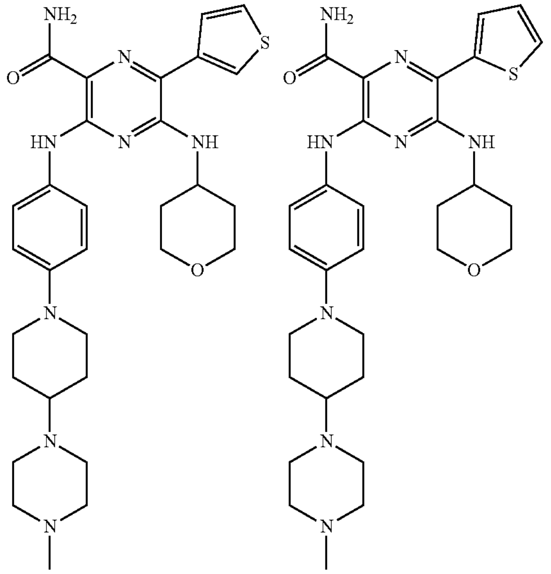

-continued
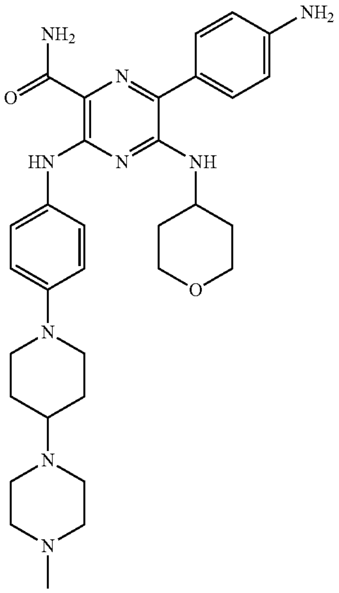
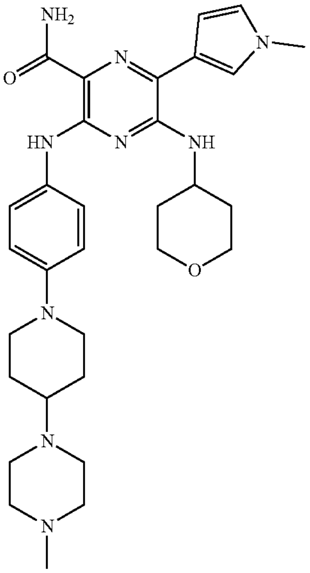
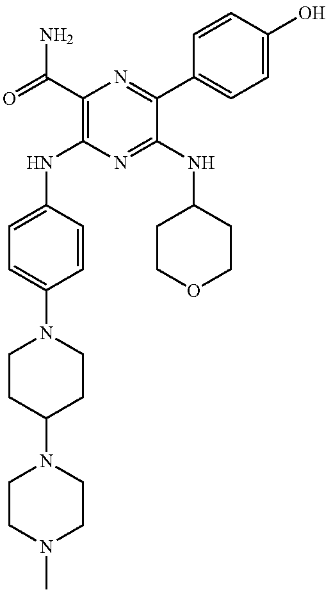
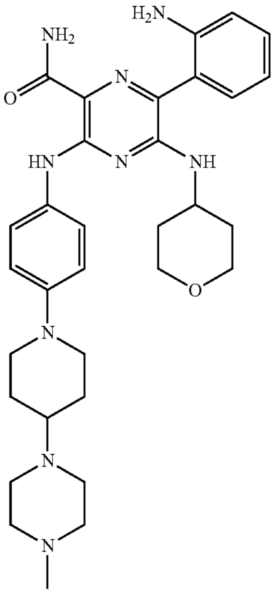
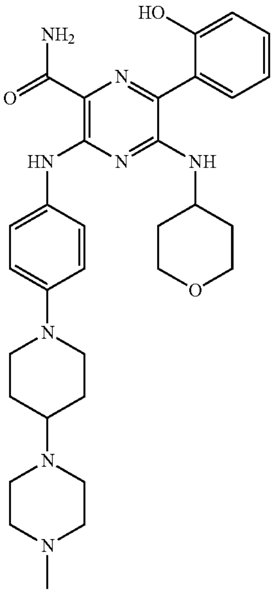

-continued
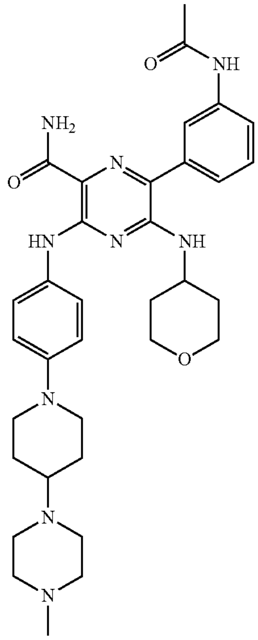
-continued
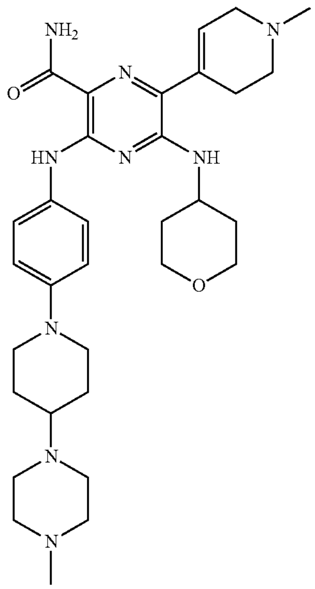
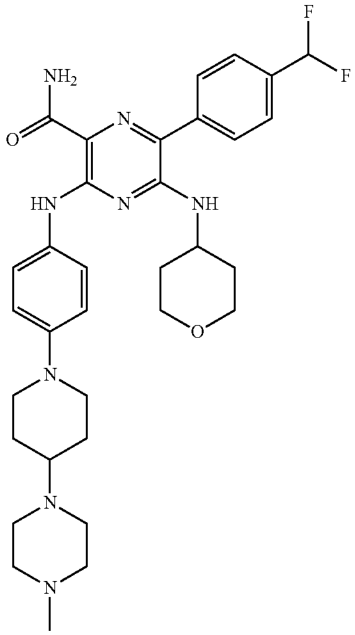
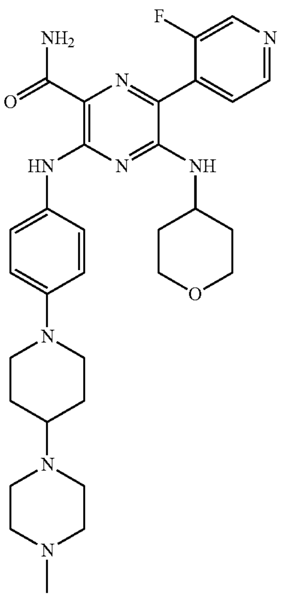
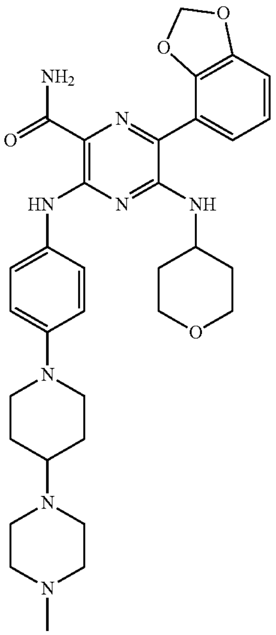

-continued
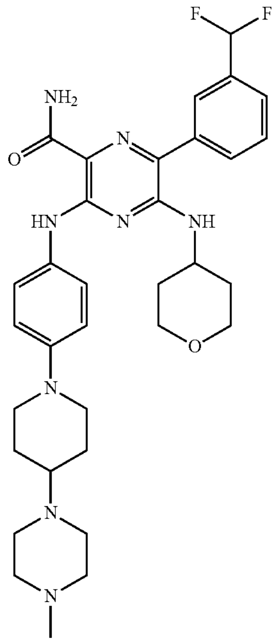
-continued
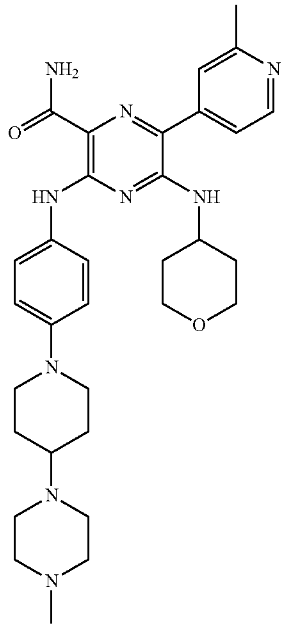
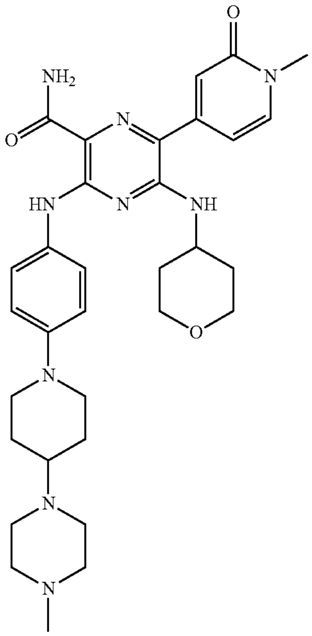
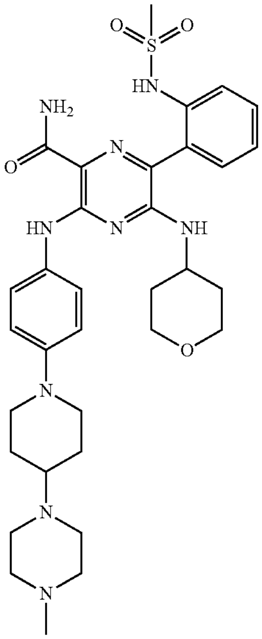
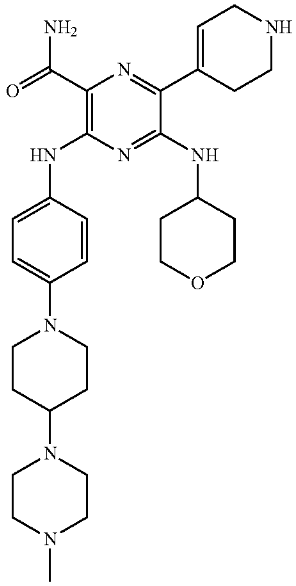

-continued
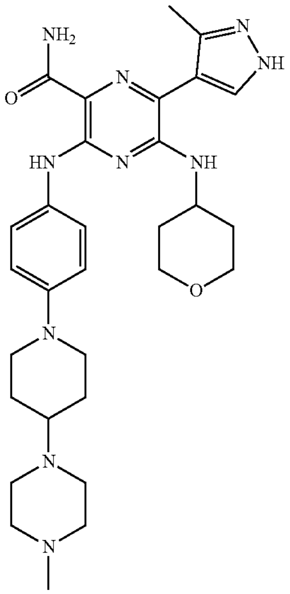
-continued
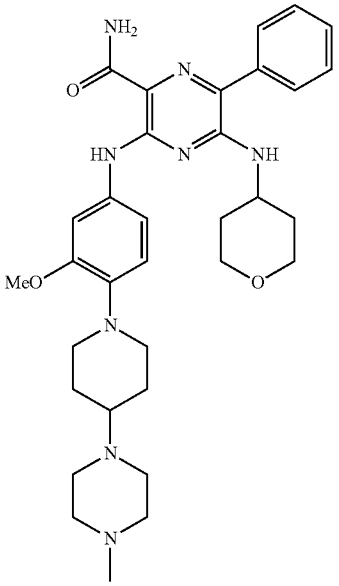
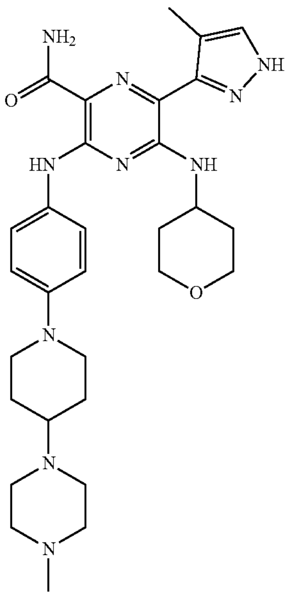
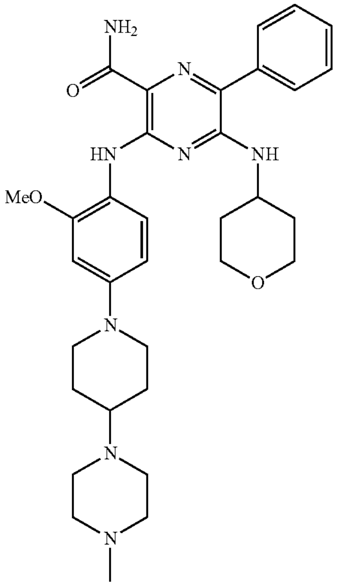

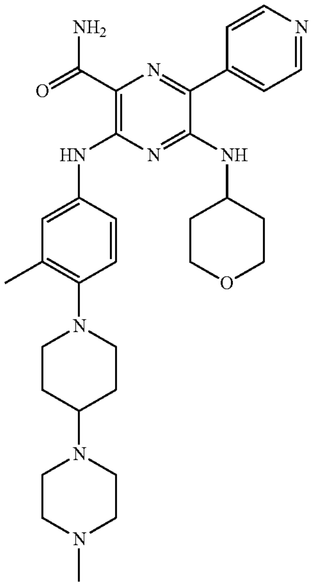
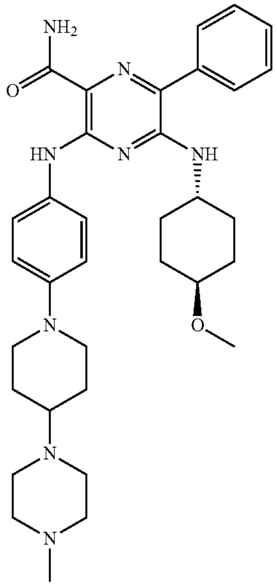
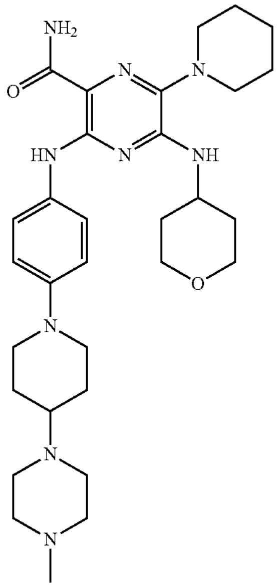
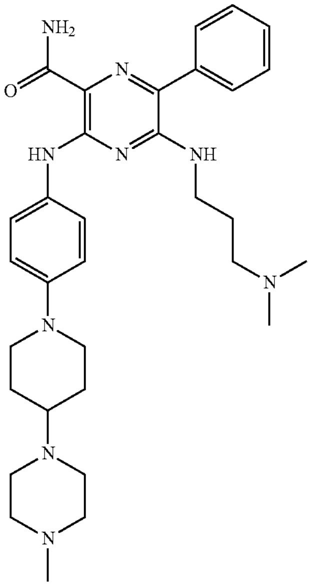
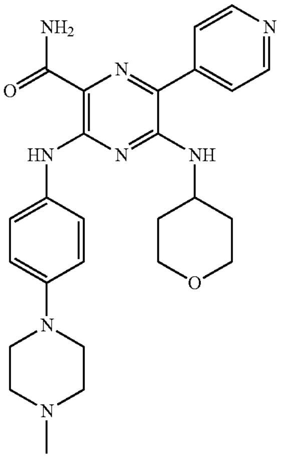

-continued
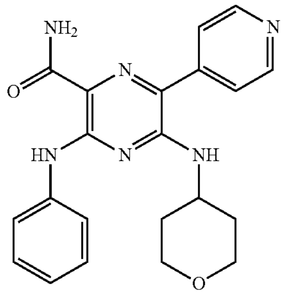
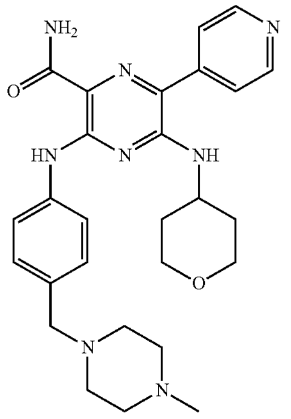
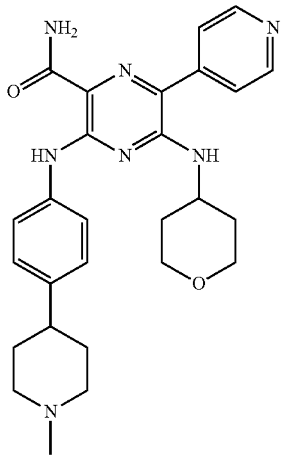
-continued
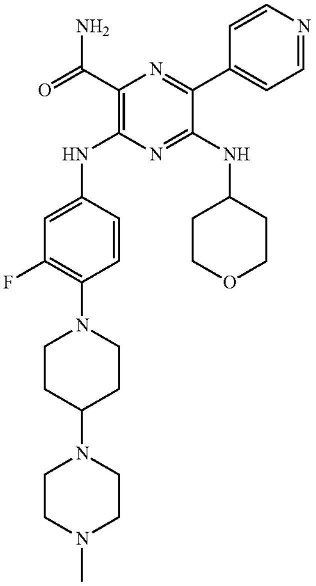
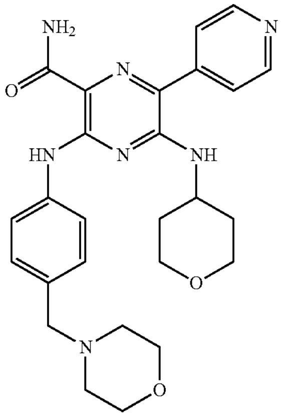
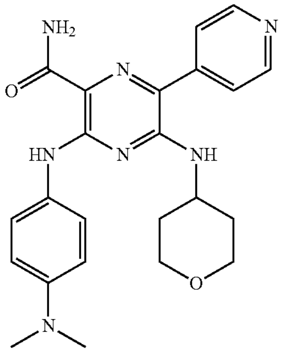

-continued
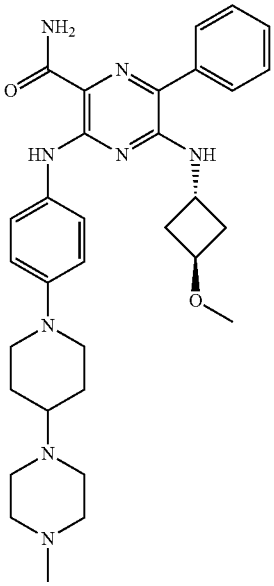
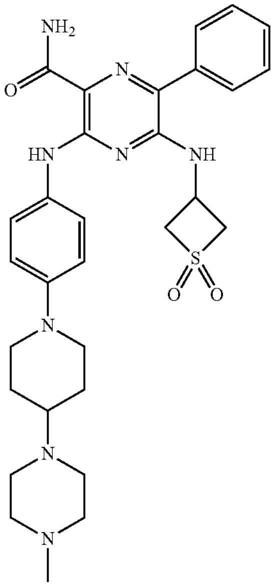
-continued
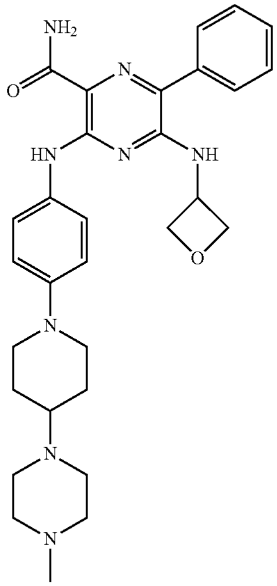
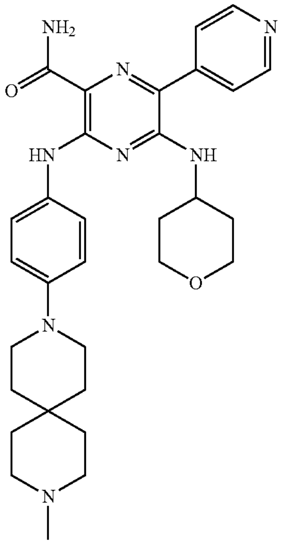
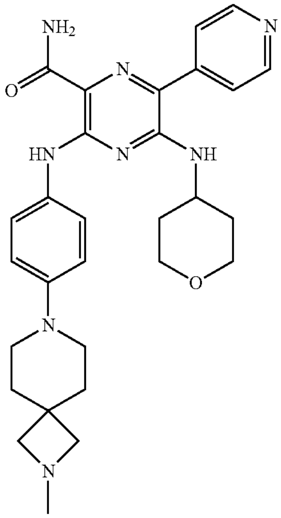

-continued
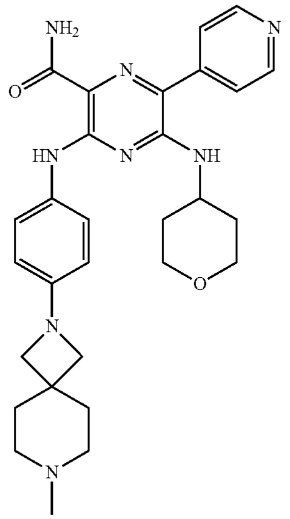
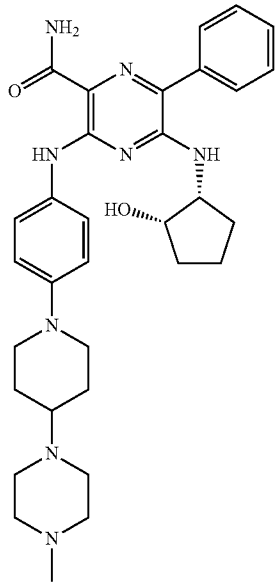
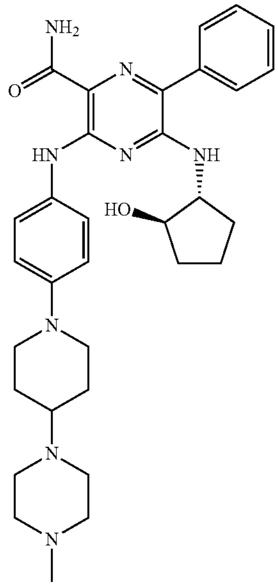
-continued
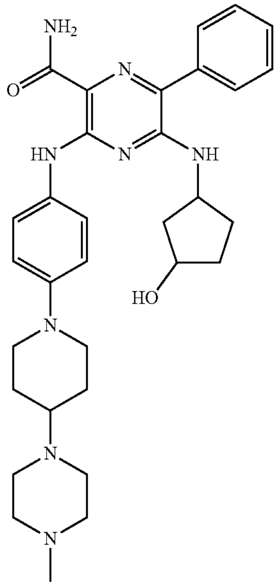
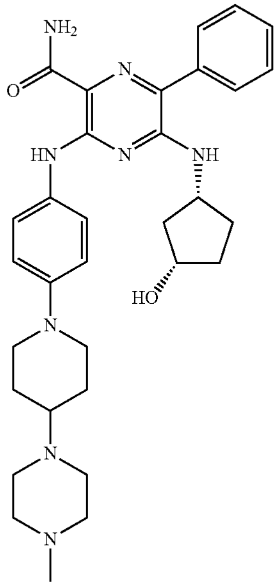

-continued
-continued
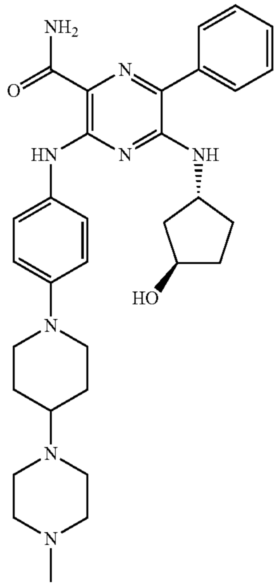
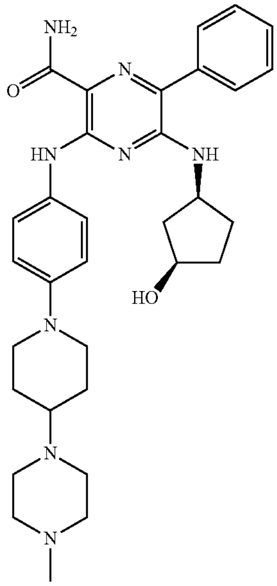
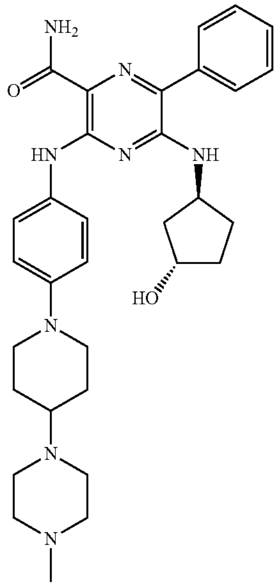
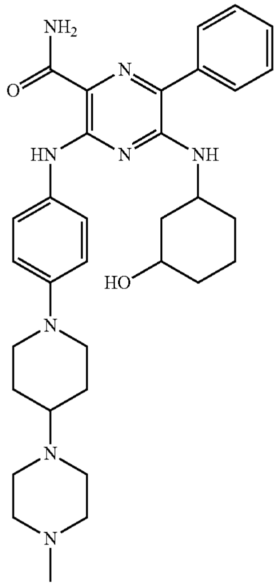

-continued
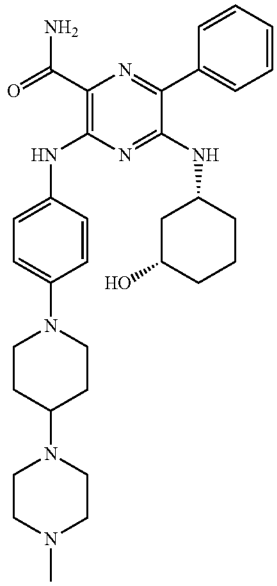
-continued
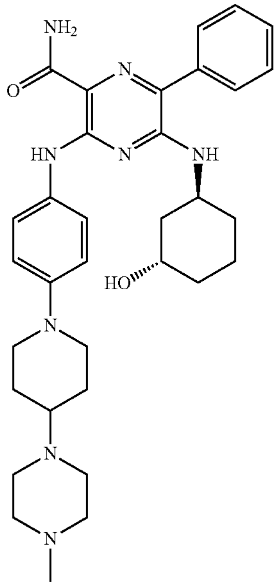
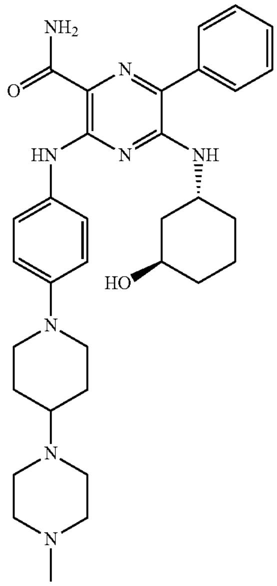
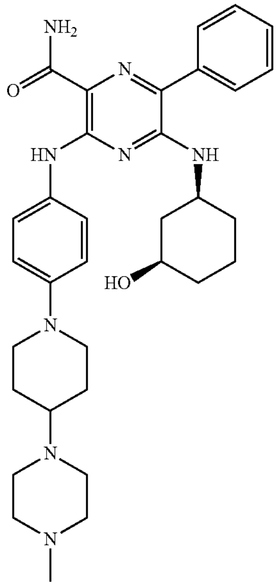

-continued
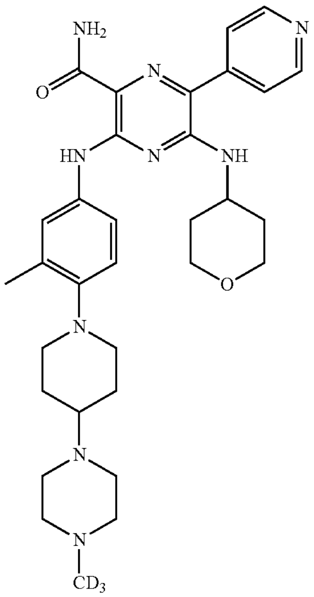
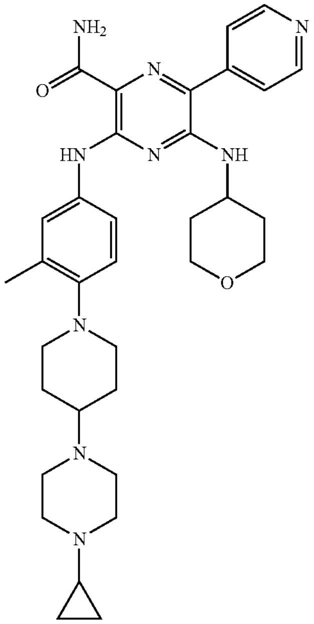
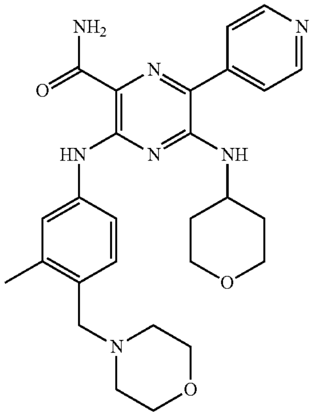
-continued
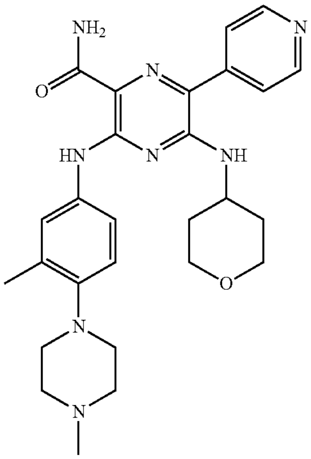
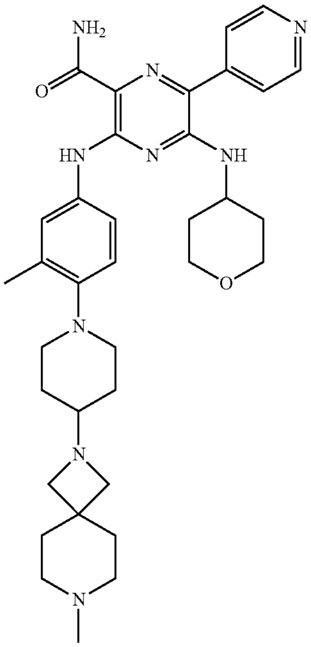

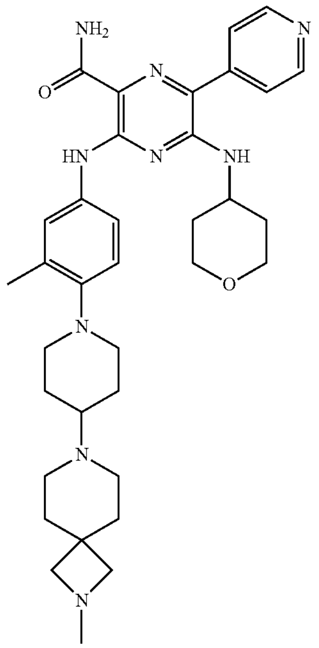
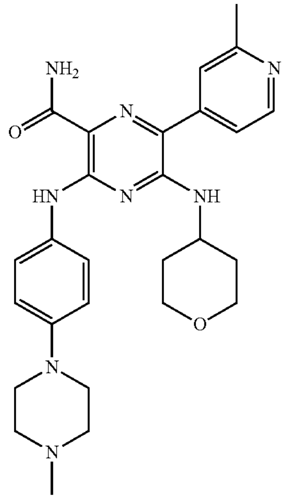
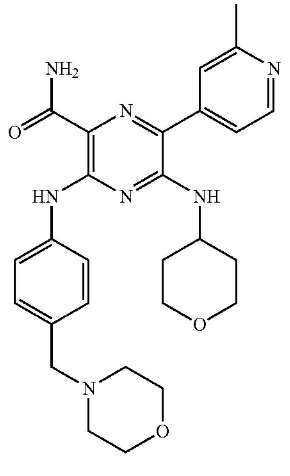
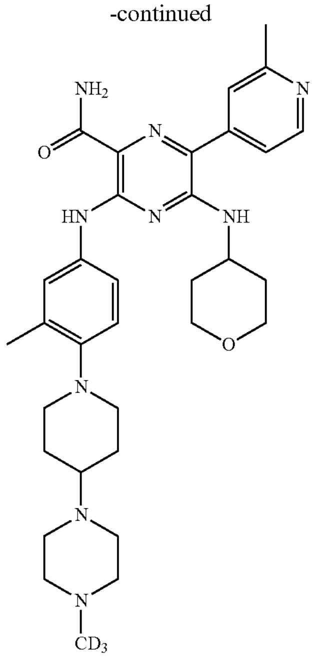
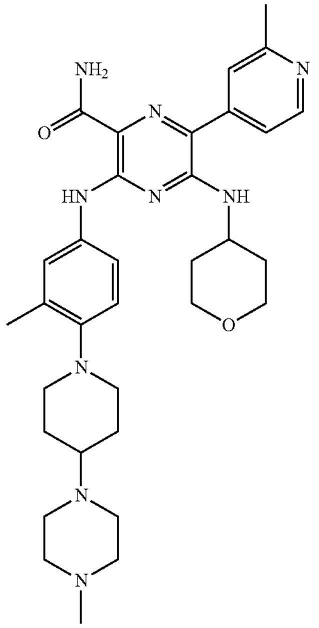

-continued
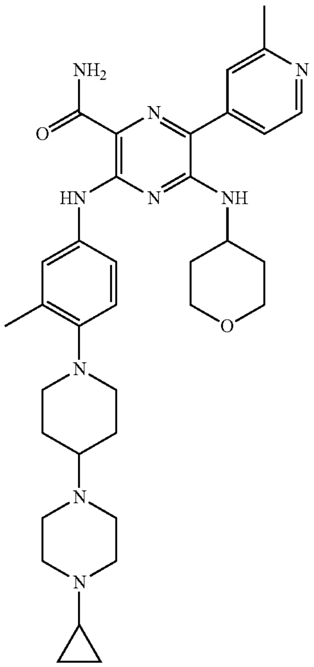
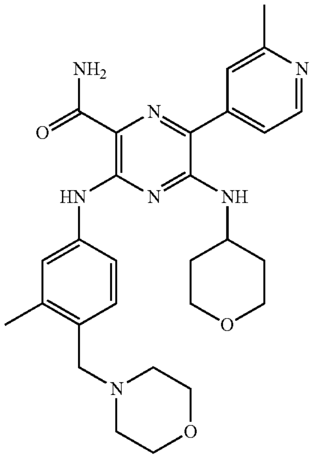
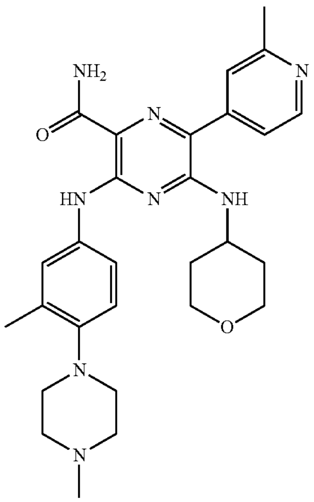
-continued
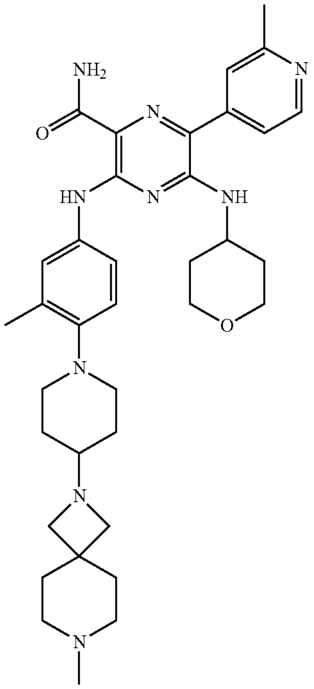
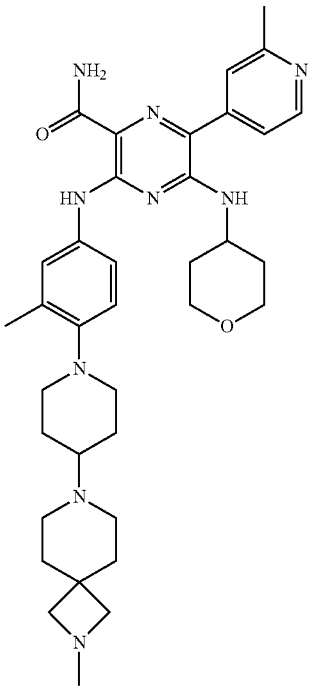

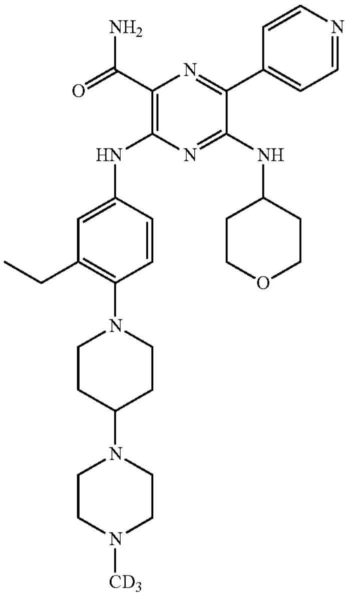
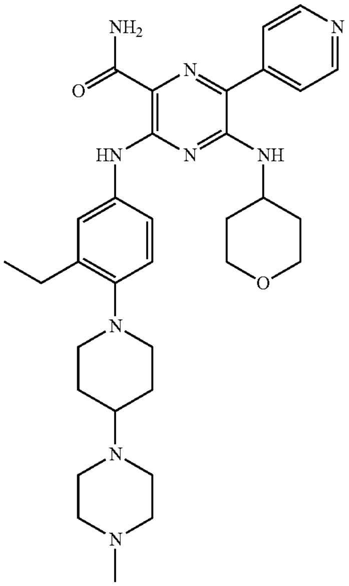
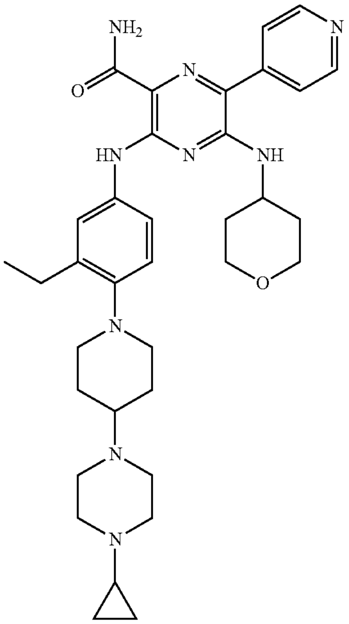
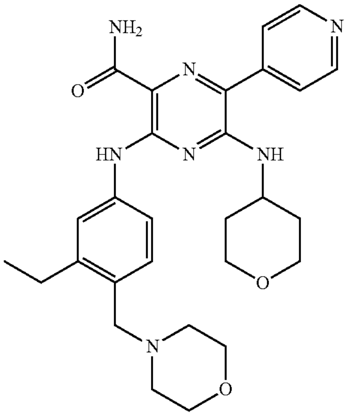
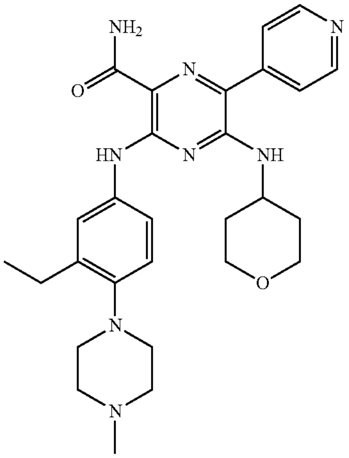

-continued
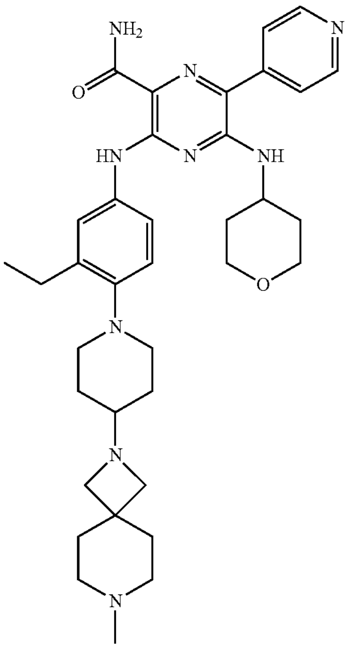
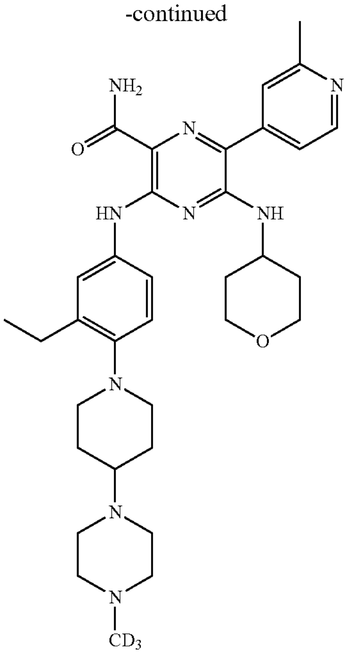
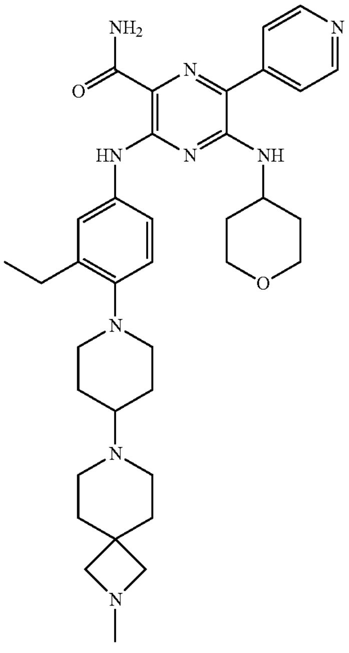
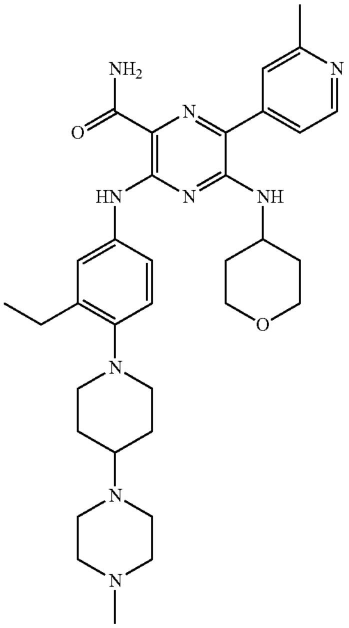
-continued

-continued
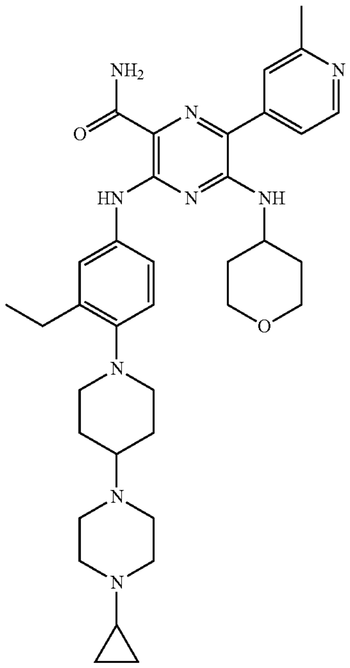
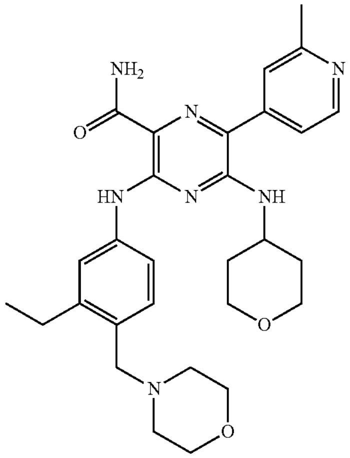
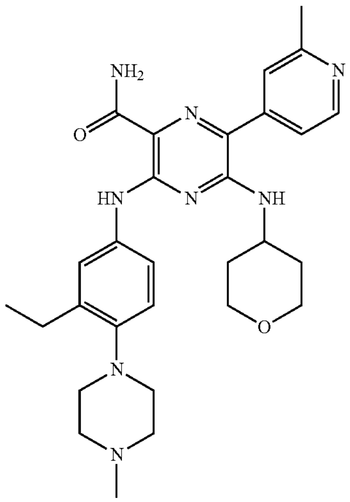
-continued
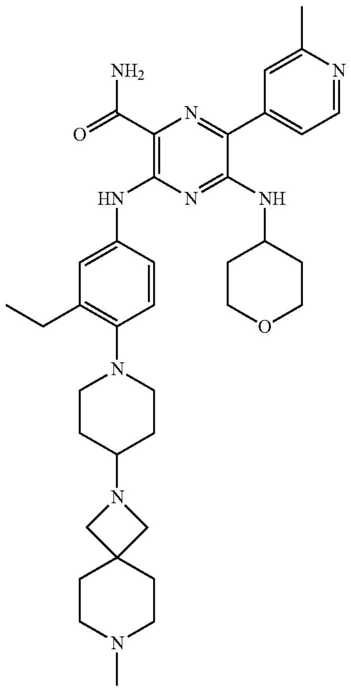
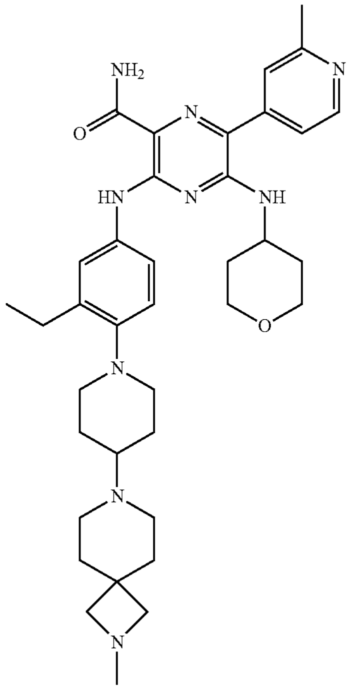

-continued
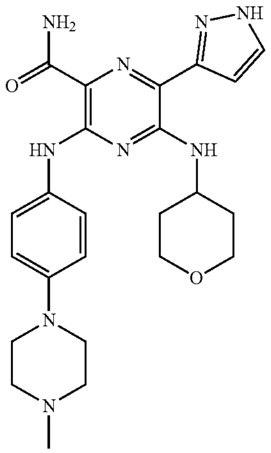
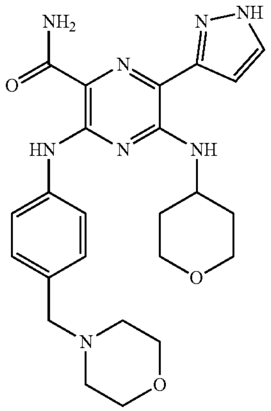
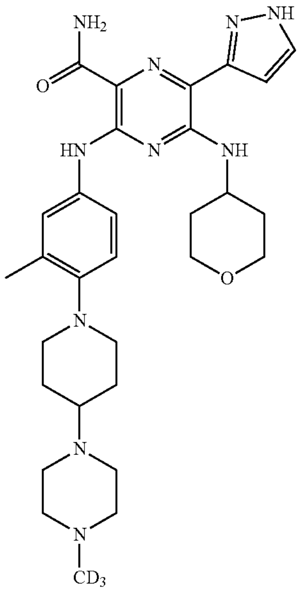
-continued
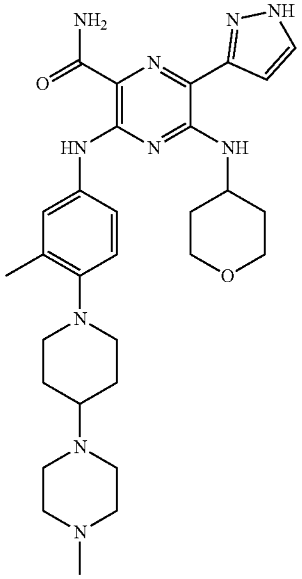
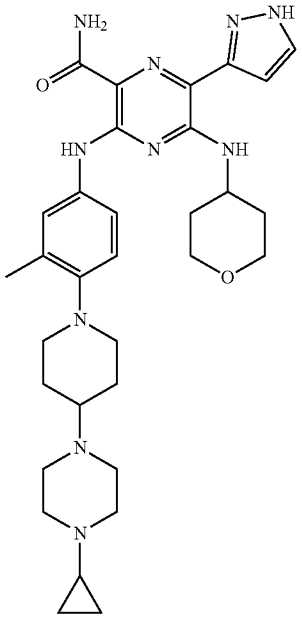
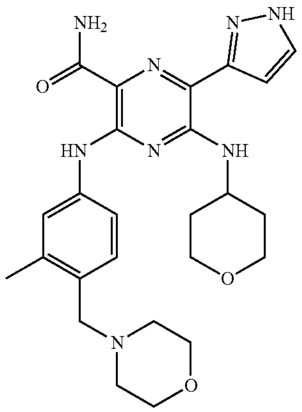

-continued
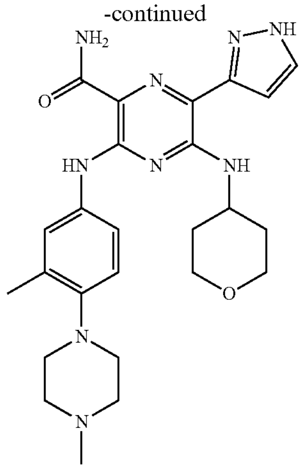
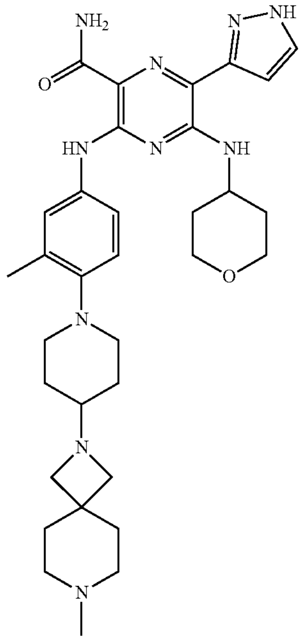
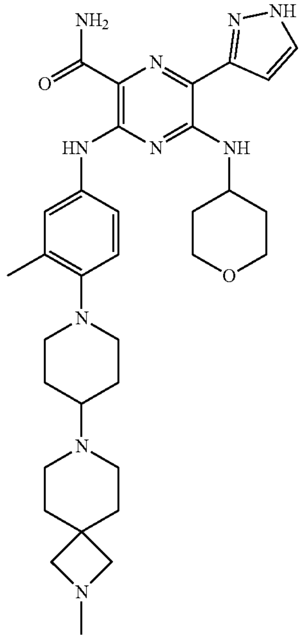
-continued
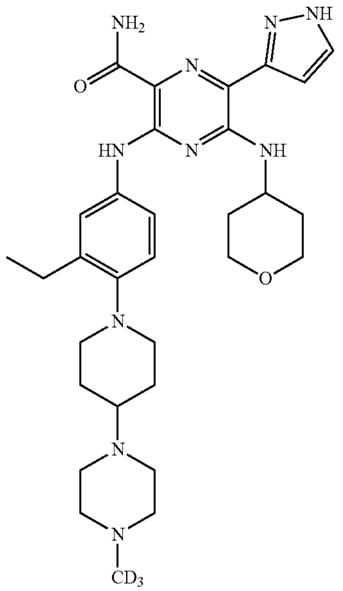
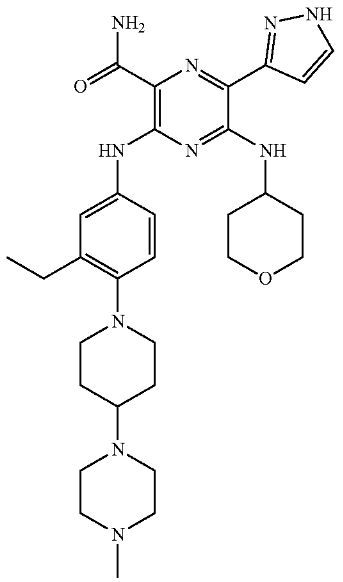

-continued
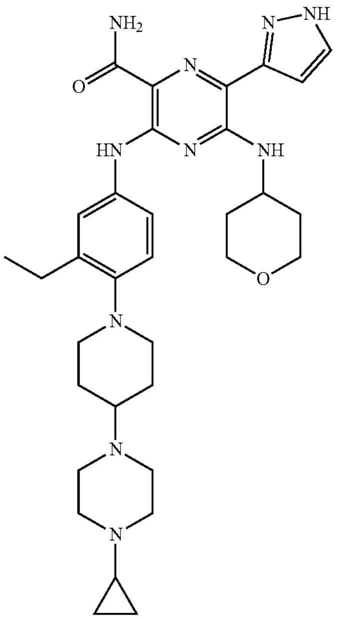
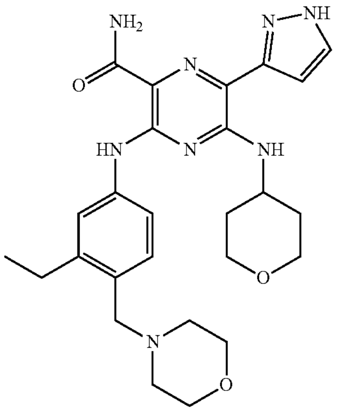
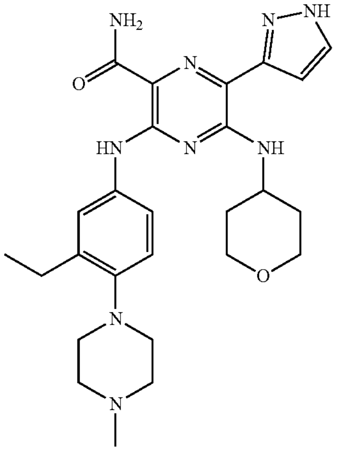
-continued
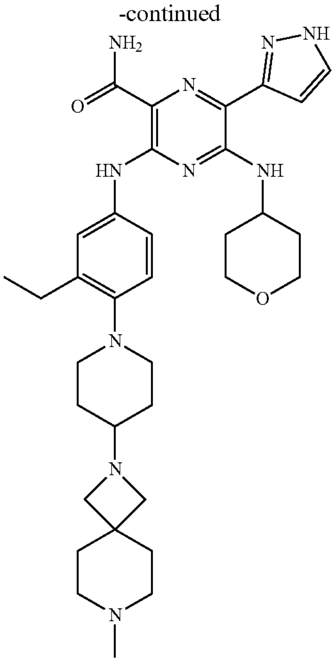
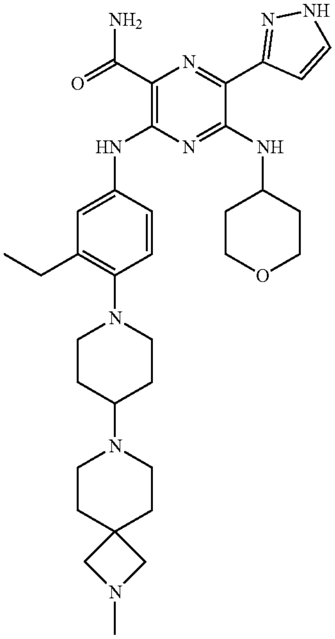
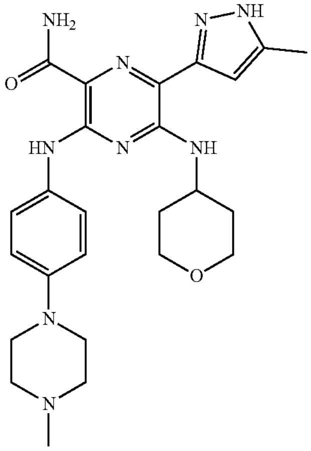

-continued
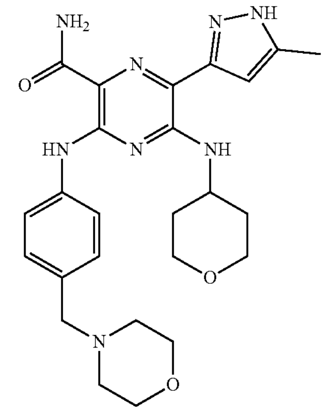
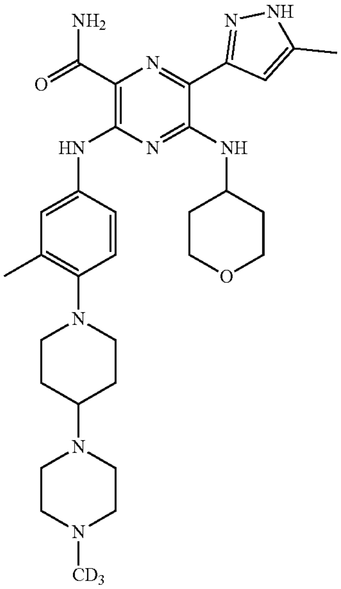
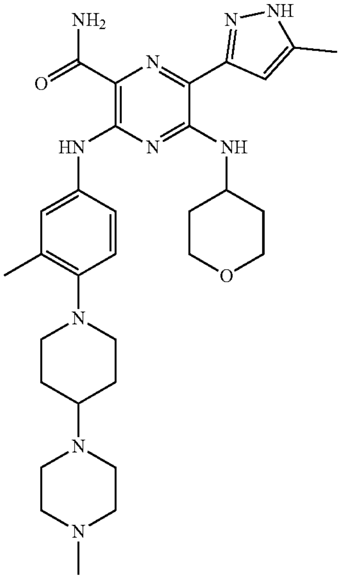
-continued
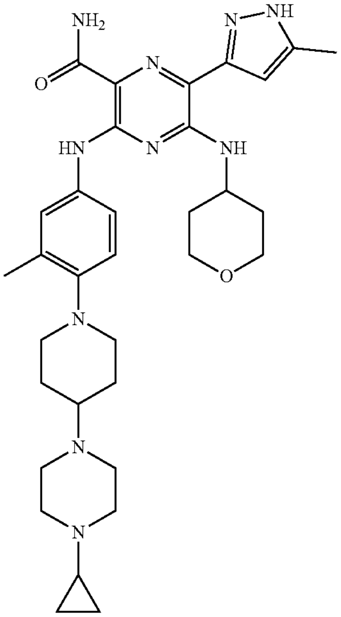
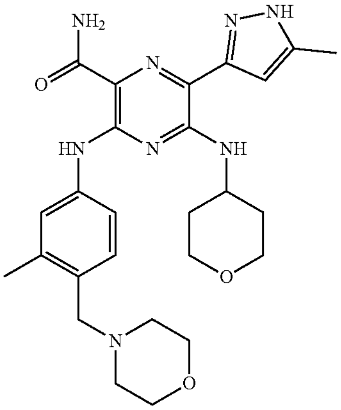
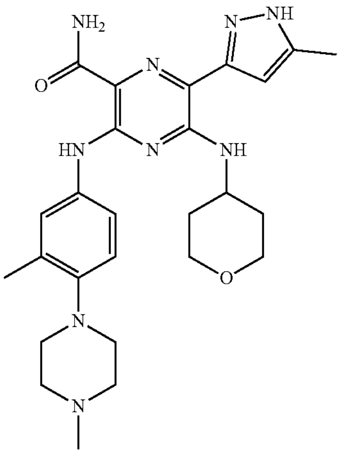

-continued
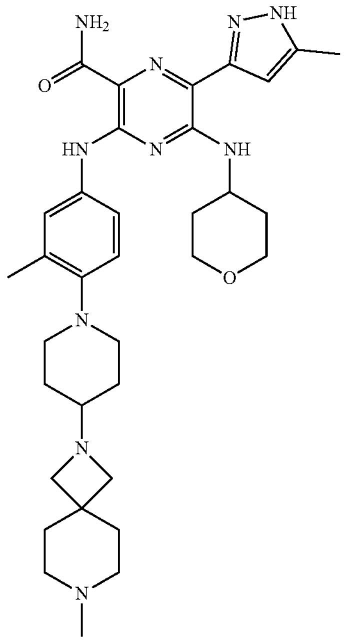
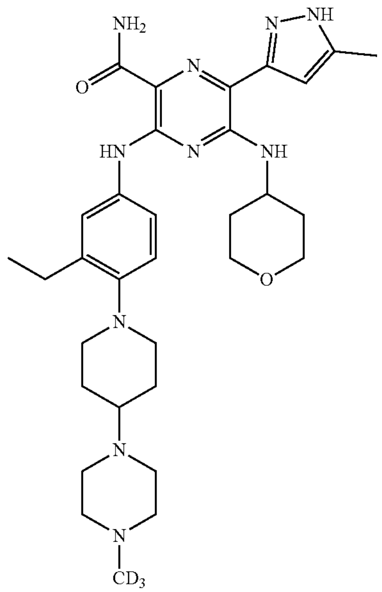
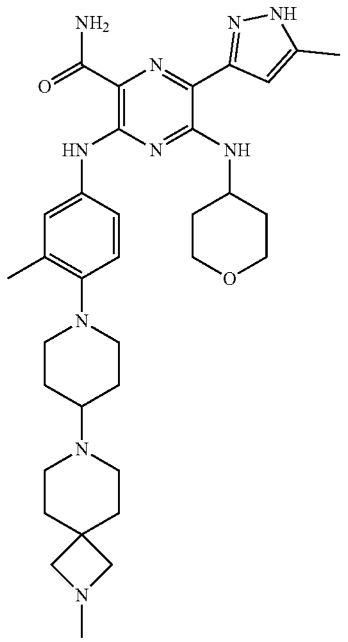
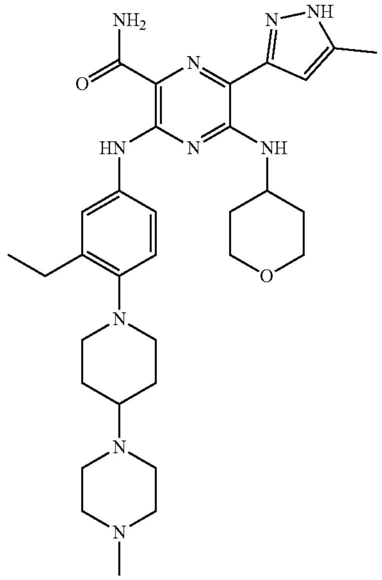

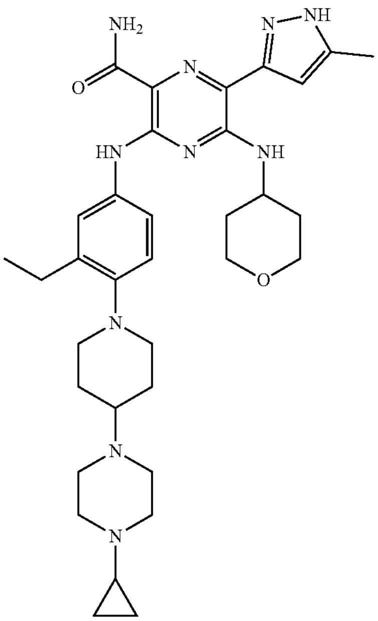
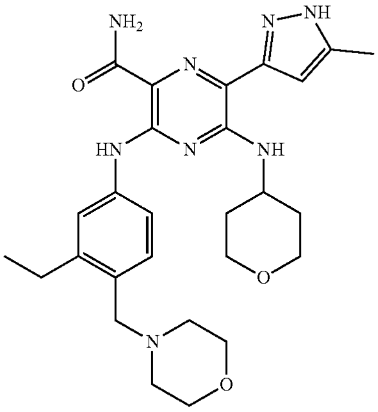
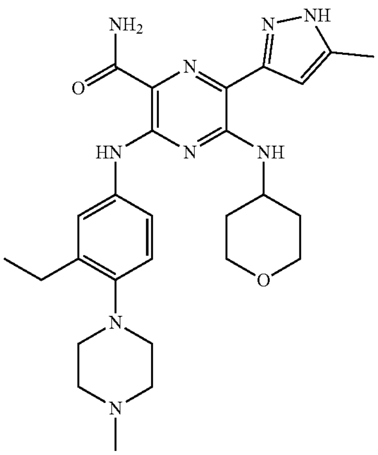
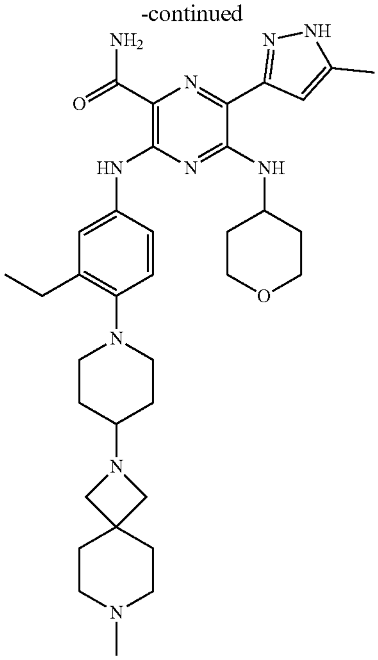
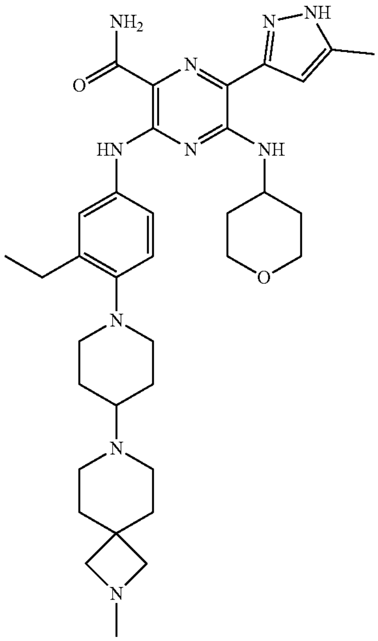

-continued
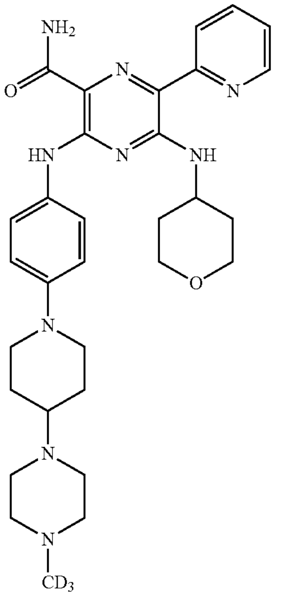
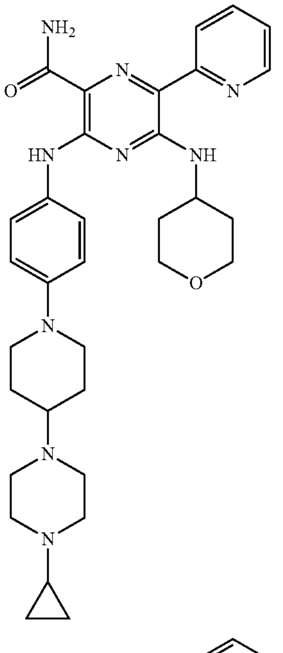
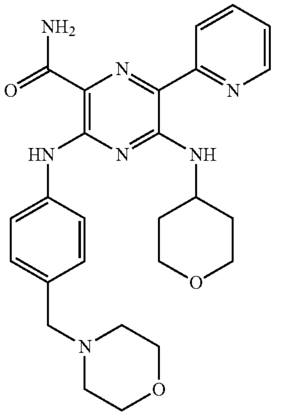
-continued
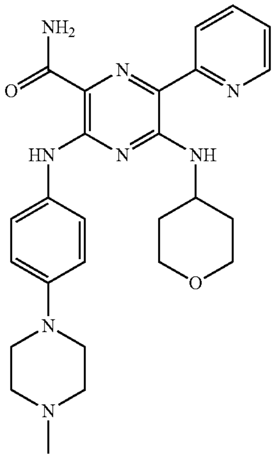
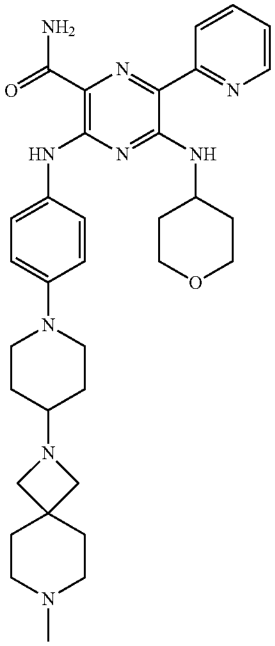

-continued
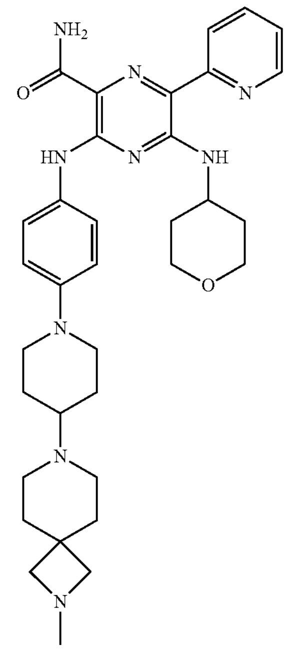
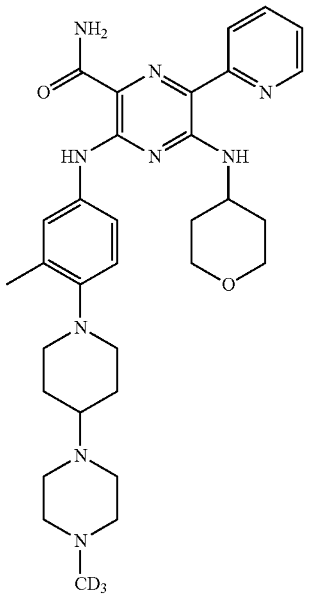
-continued
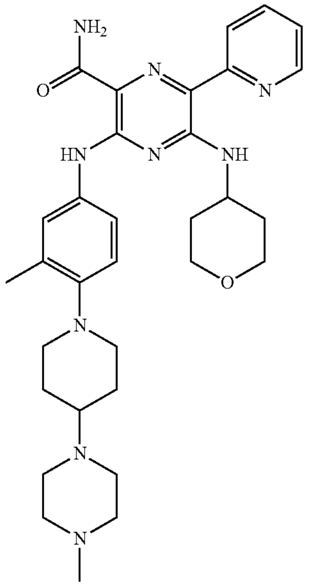
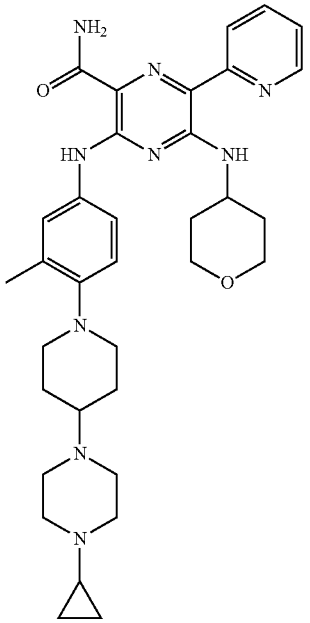
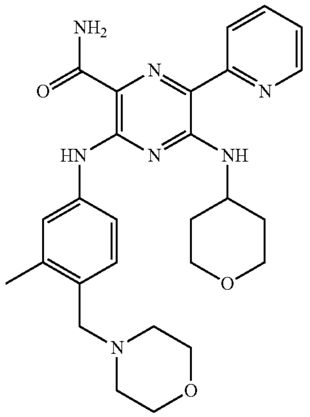

-continued
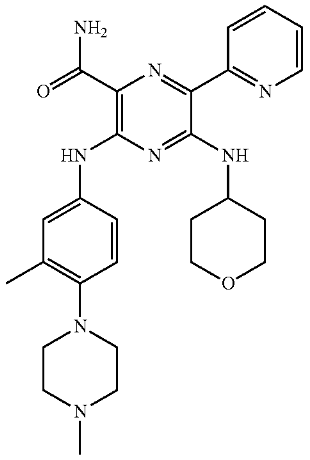
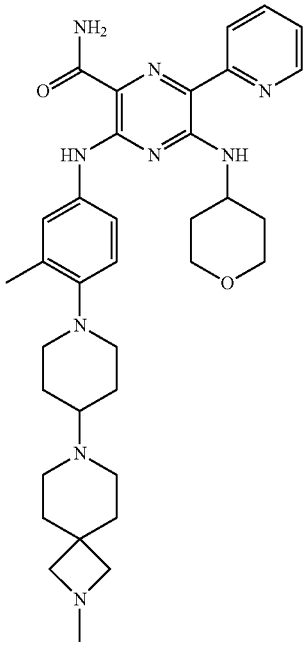
-continued
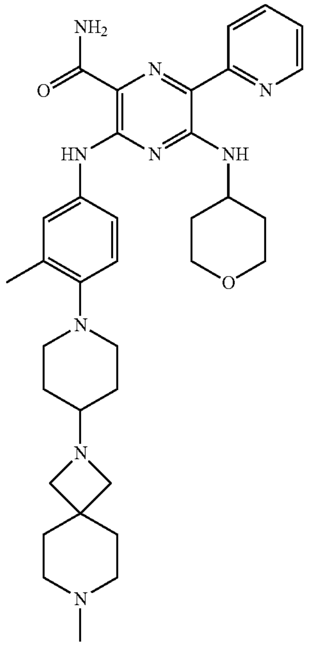
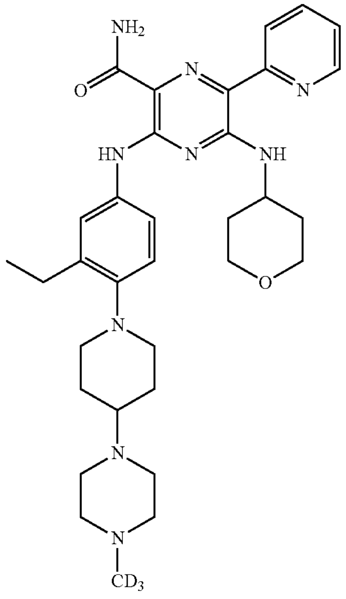

-continued
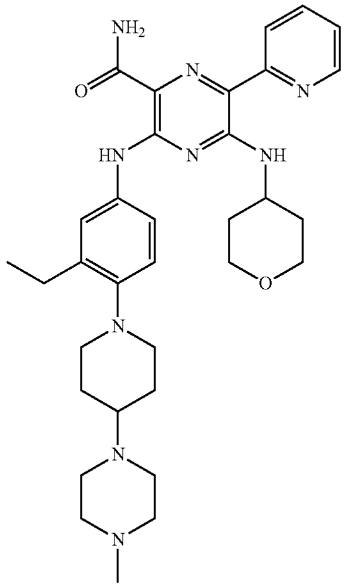
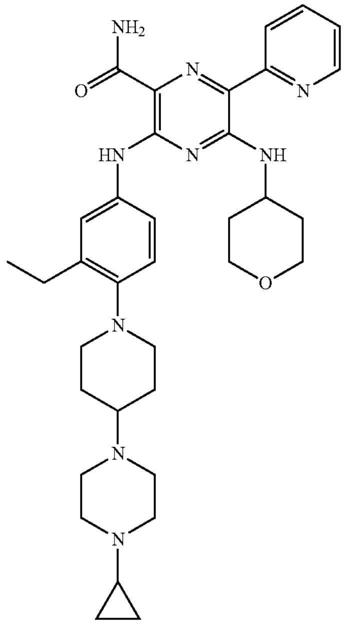
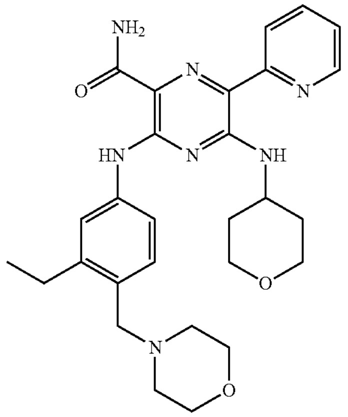
-continued
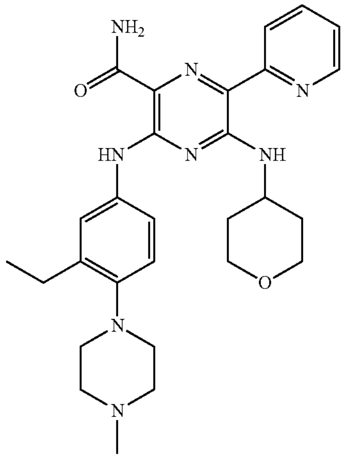
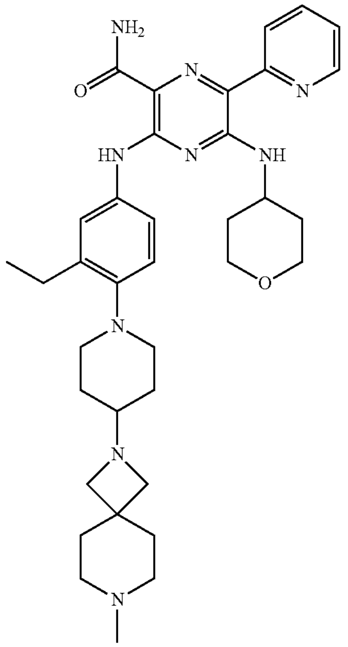

-continued
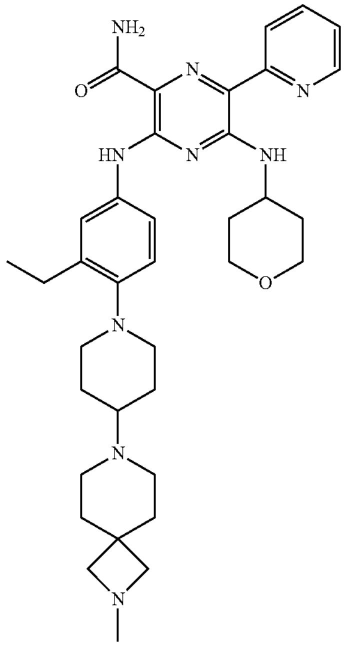
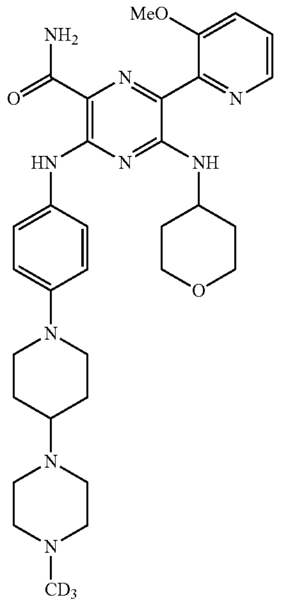
-continued
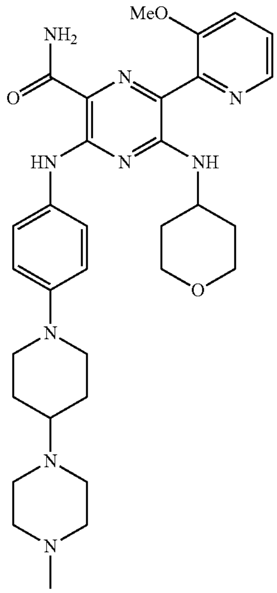
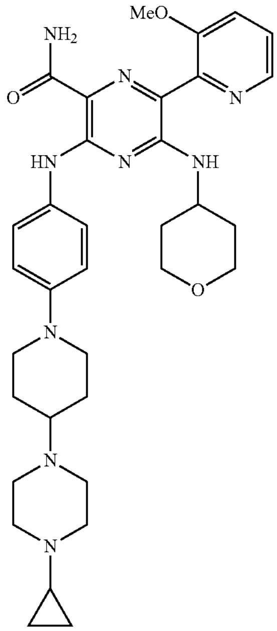
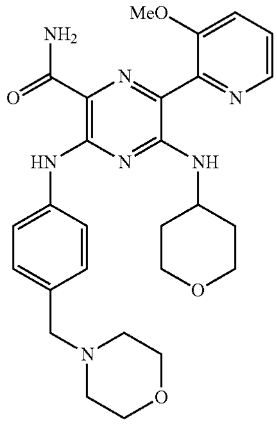

-continued
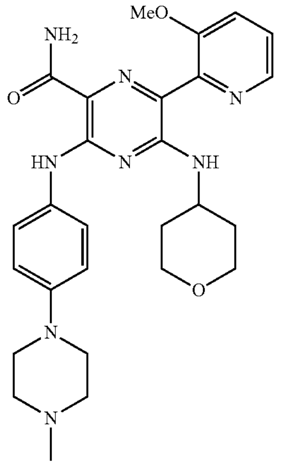
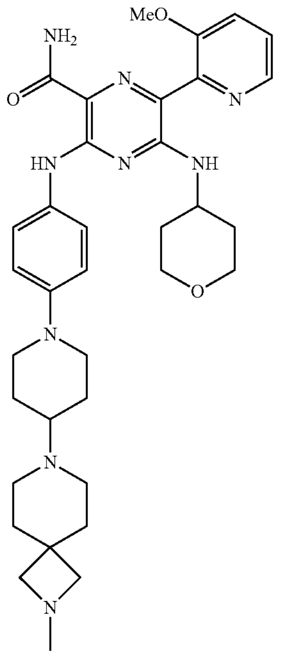
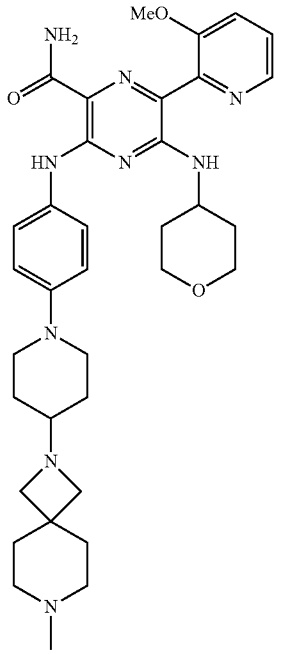
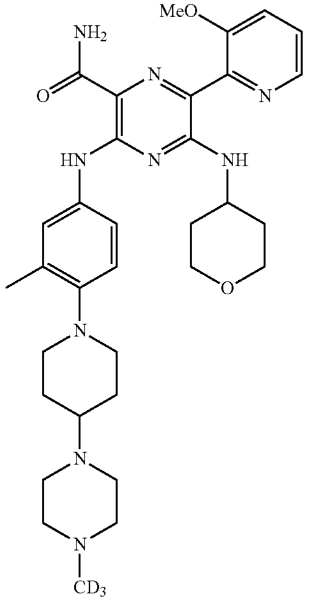

-continued
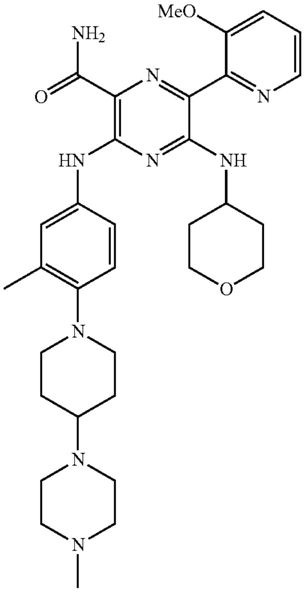
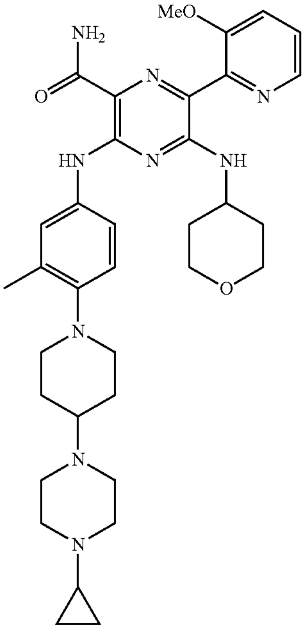
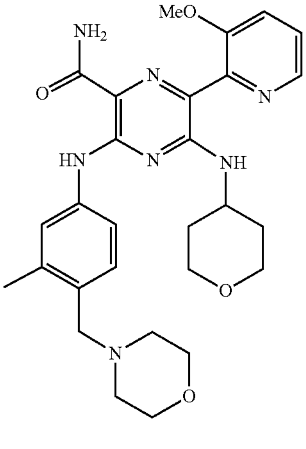
-continued
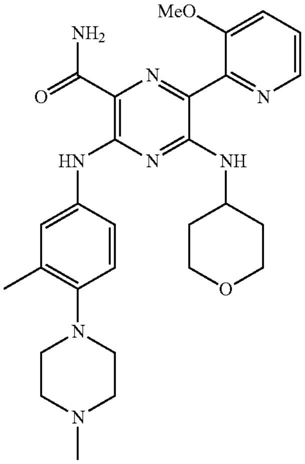
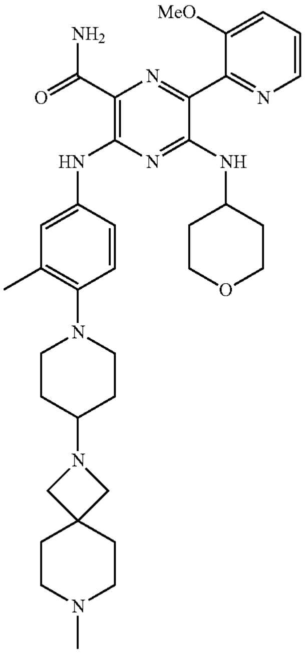

-continued
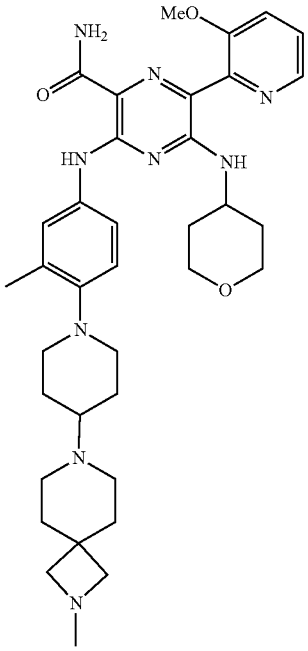
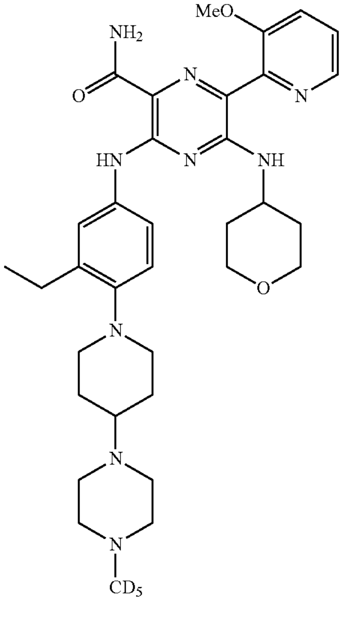
-continued
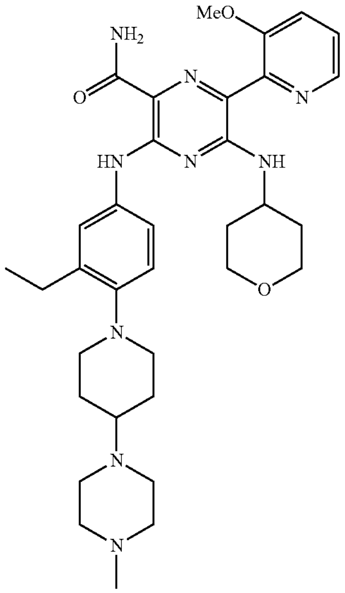
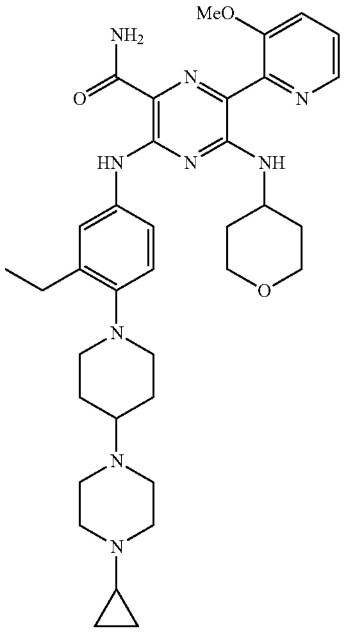
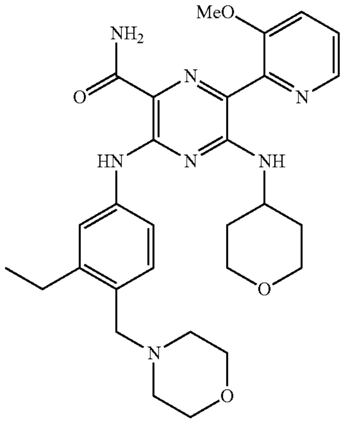

-continued
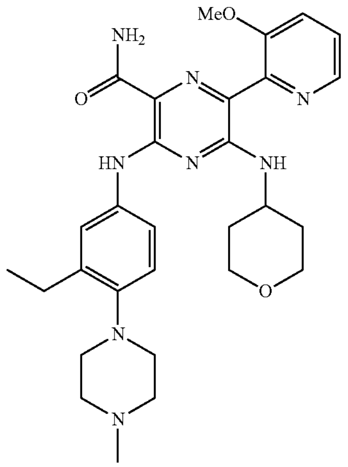
-continued
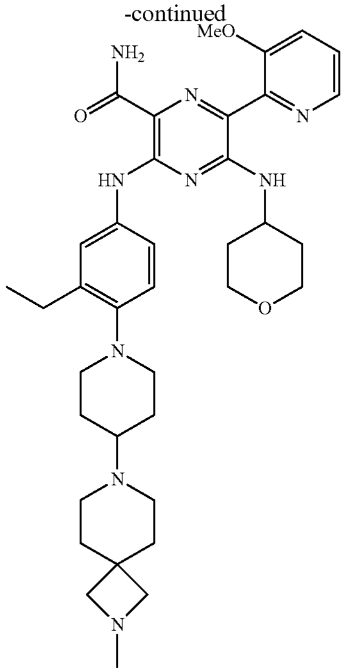
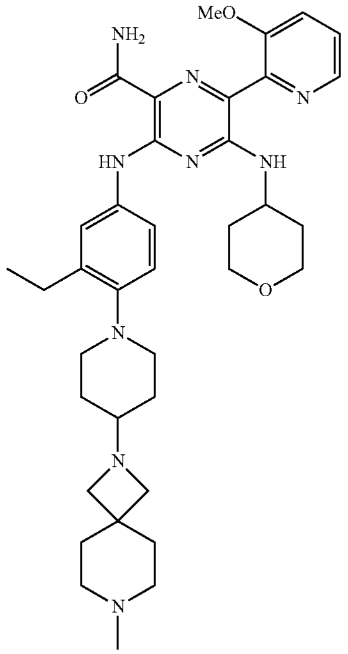
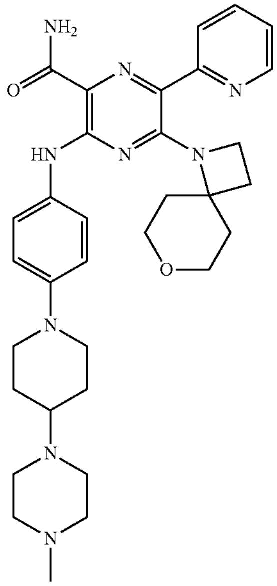

-continued
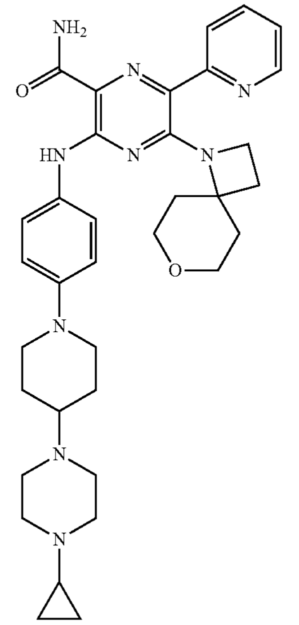
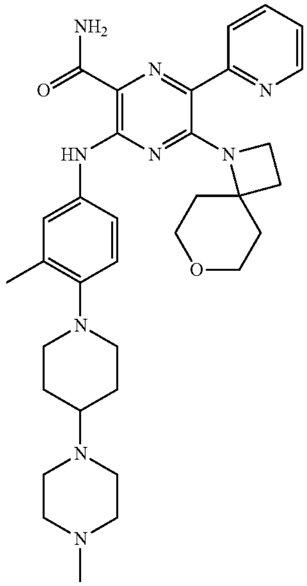
-continued
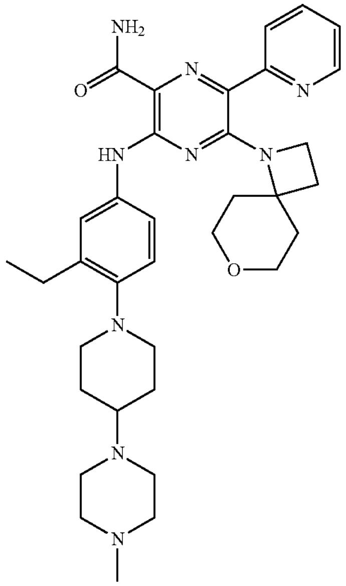
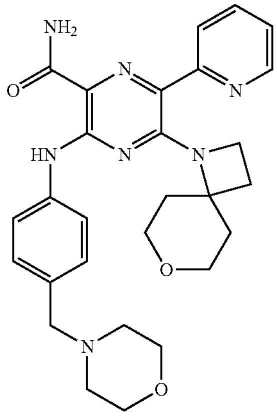
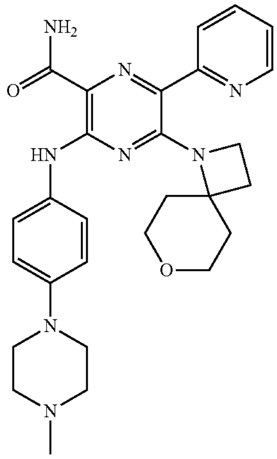

-continued
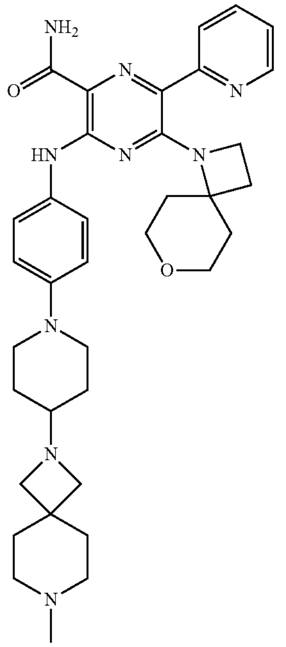
-continued
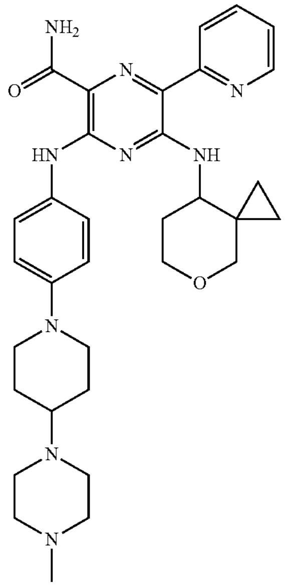
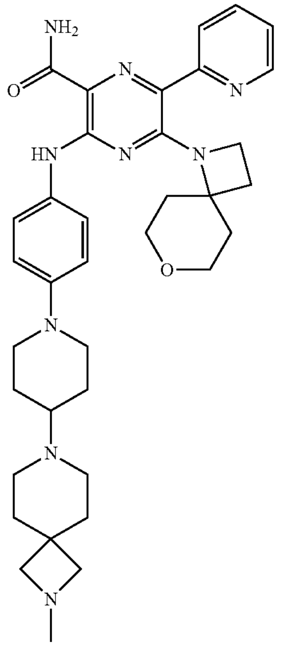
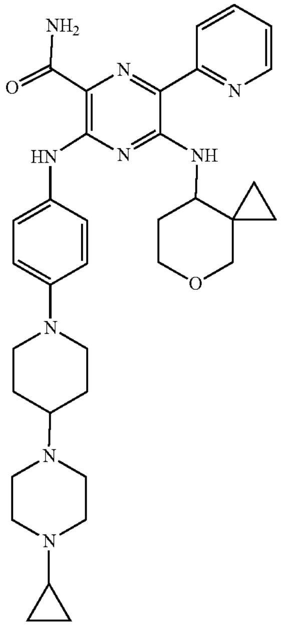

-continued
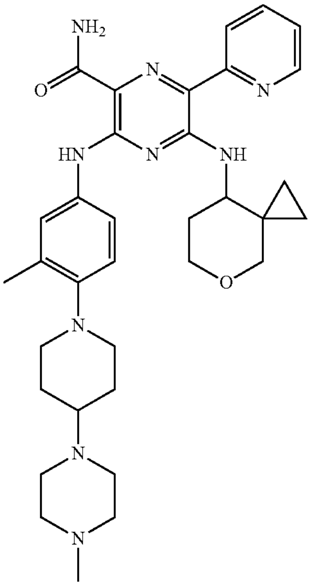
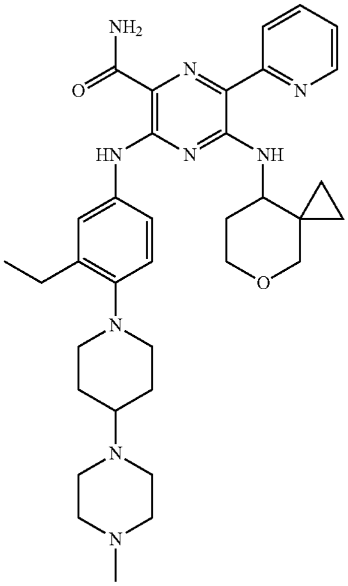
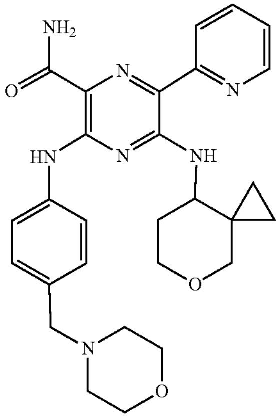
-continued
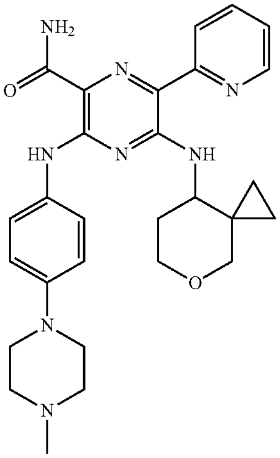
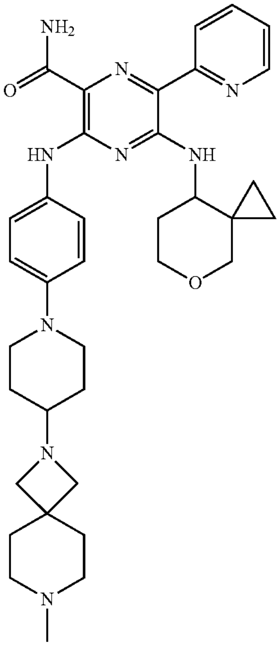

-continued
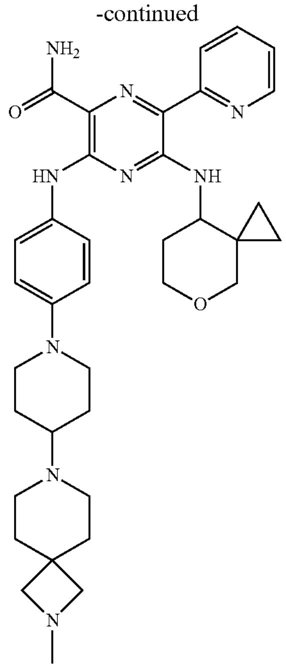
-continued
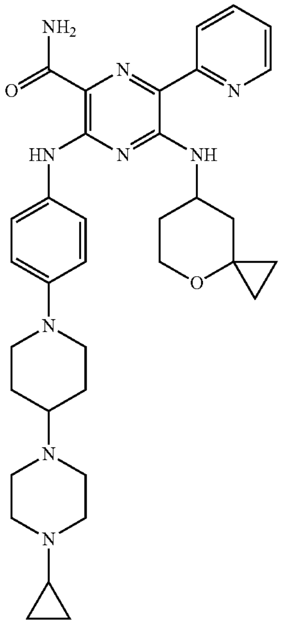
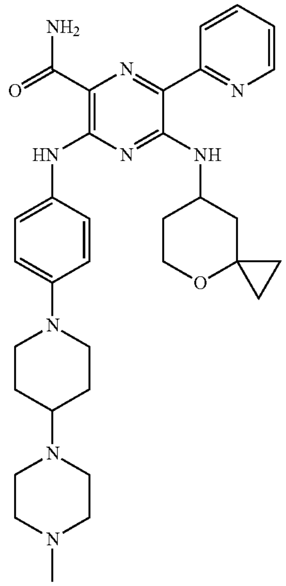
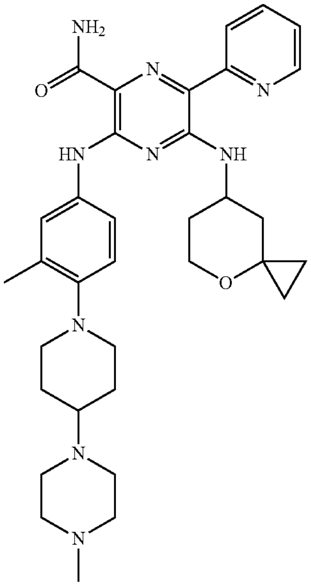

-continued
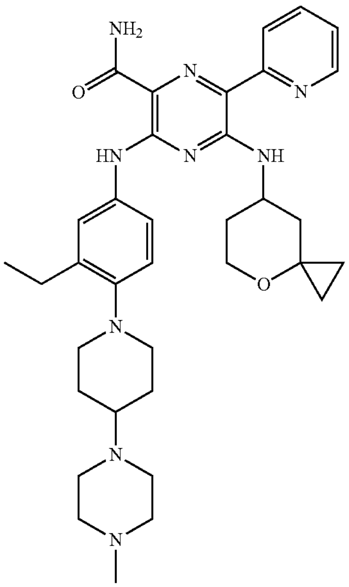
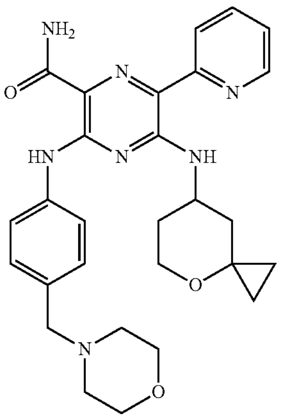
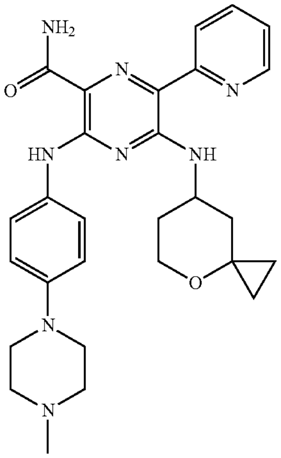
-continued
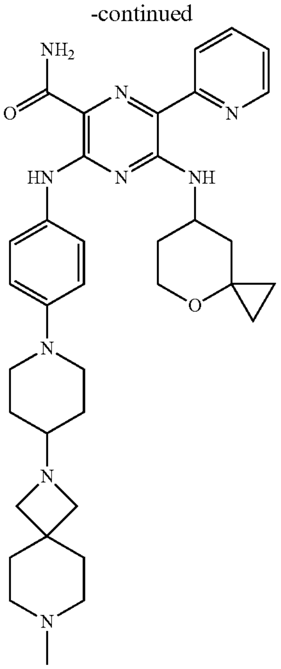
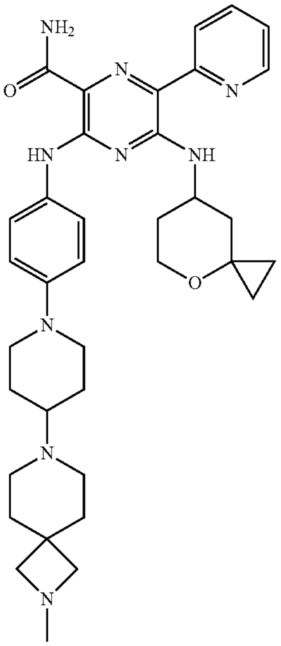

-continued
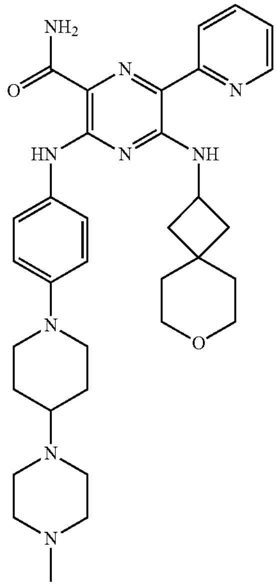
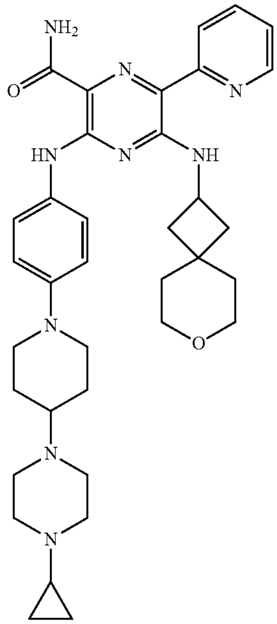
-continued
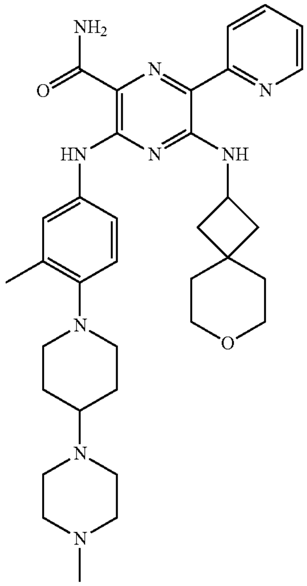
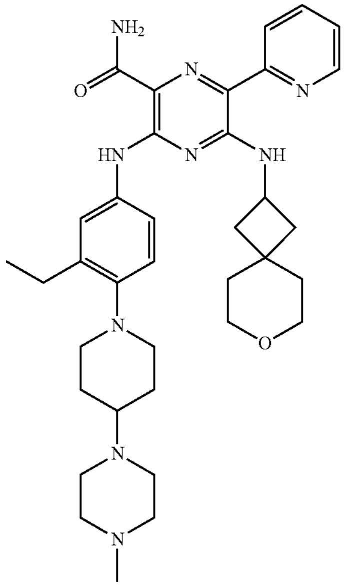
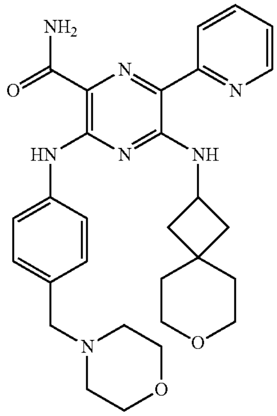

-continued
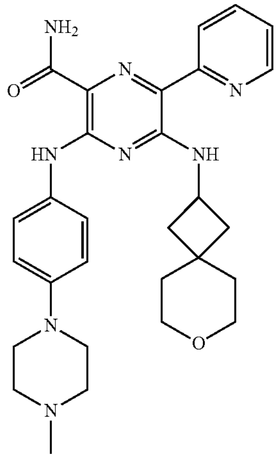
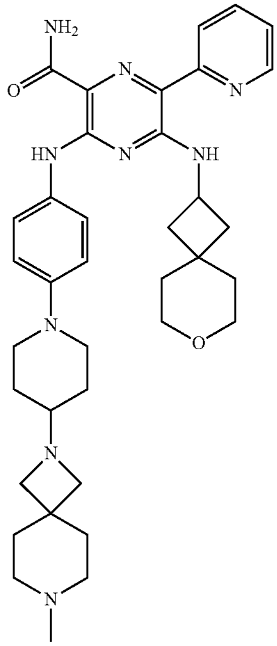
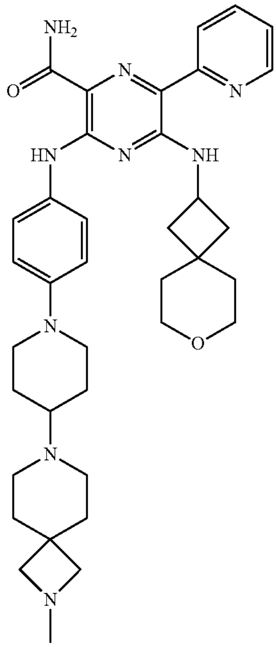
-continued
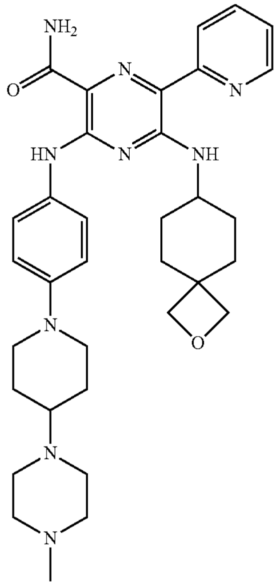

-continued
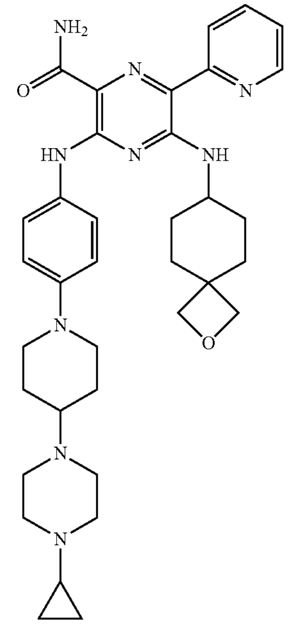
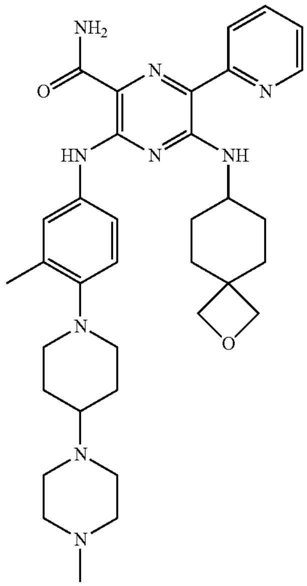
-continued
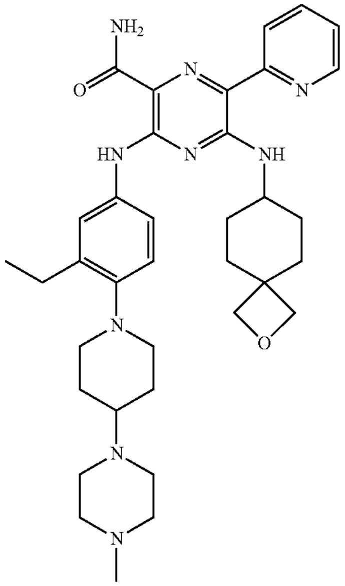
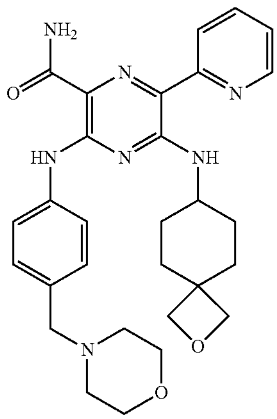
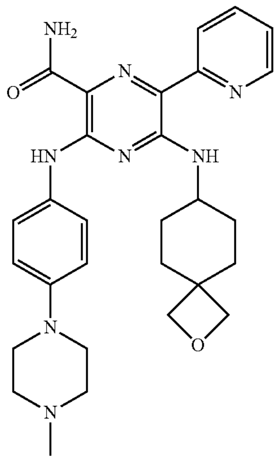

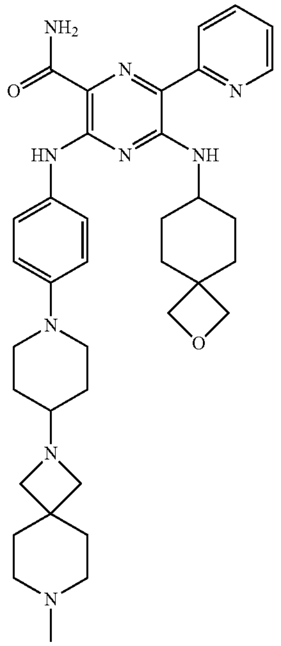
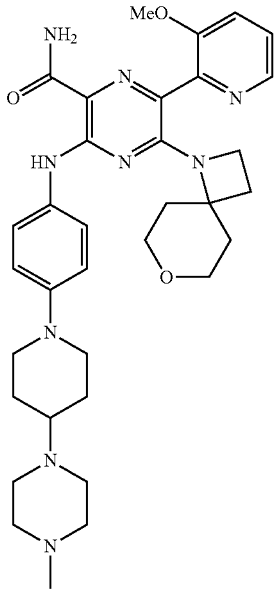
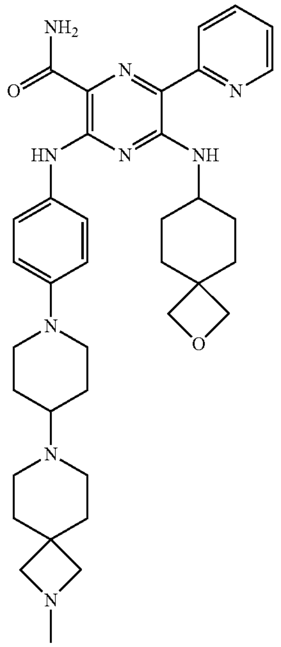
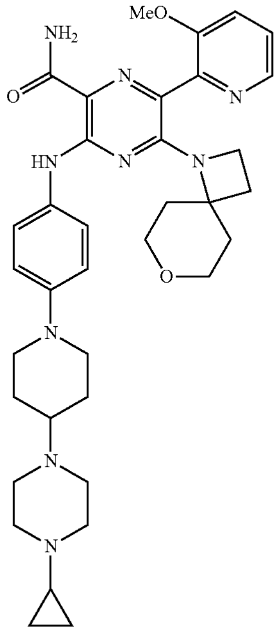

-continued
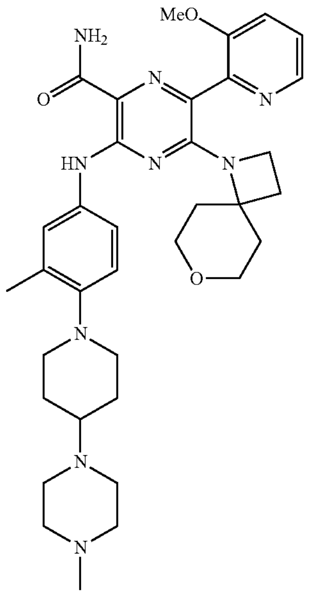
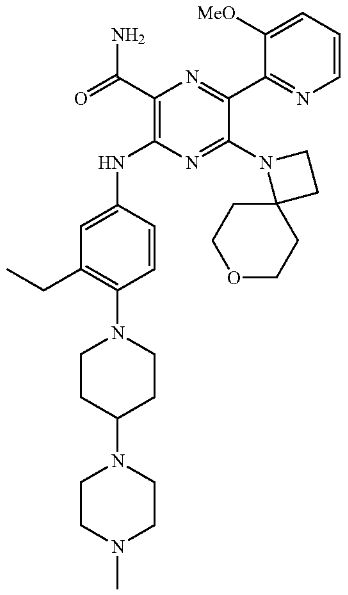
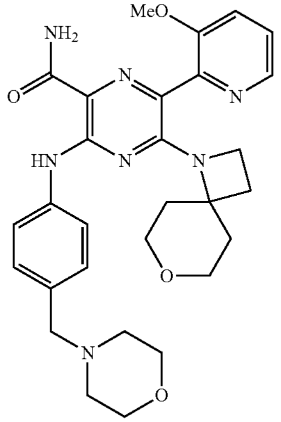
-continued
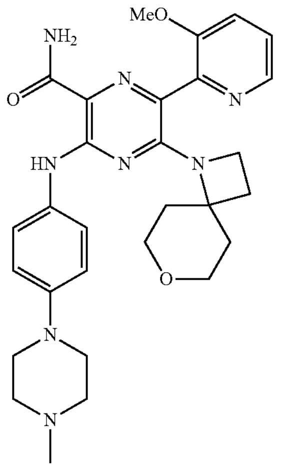
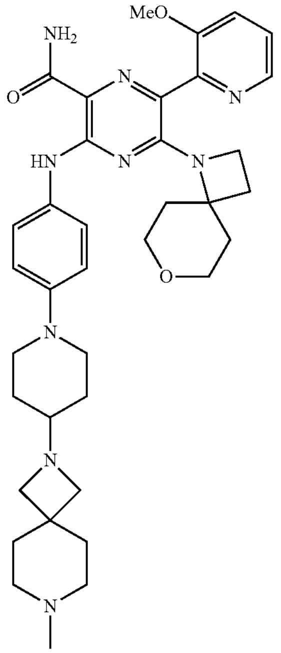

-continued
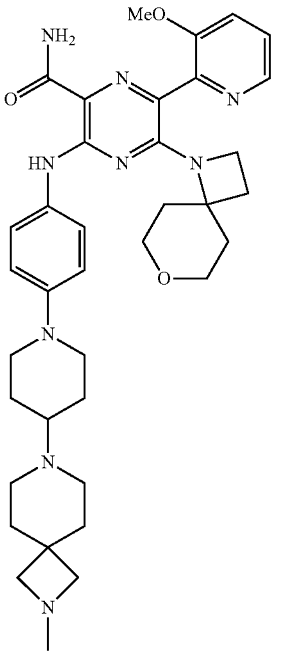
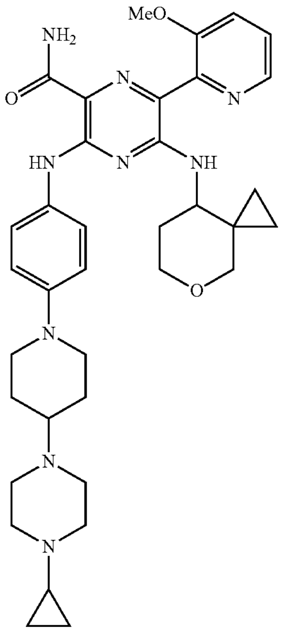
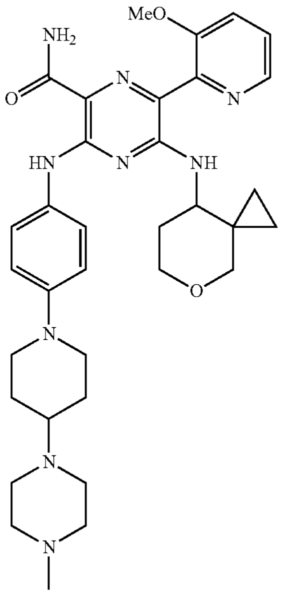
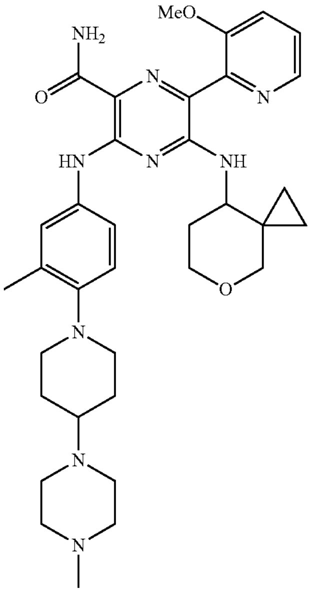

-continued
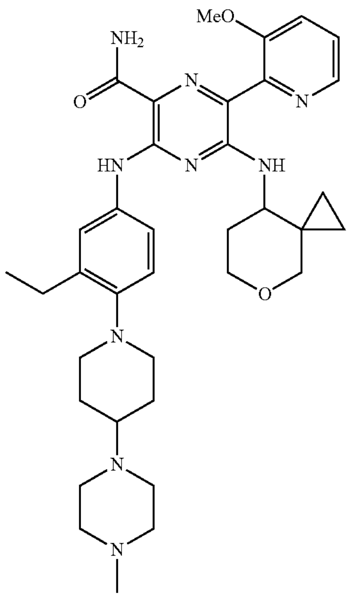
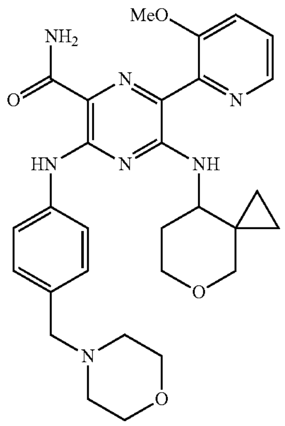
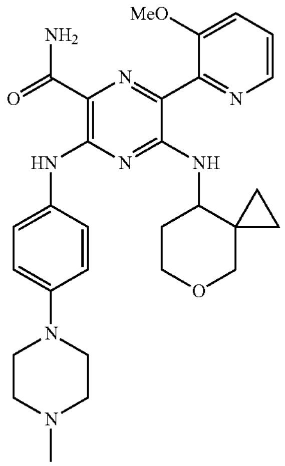
-continued
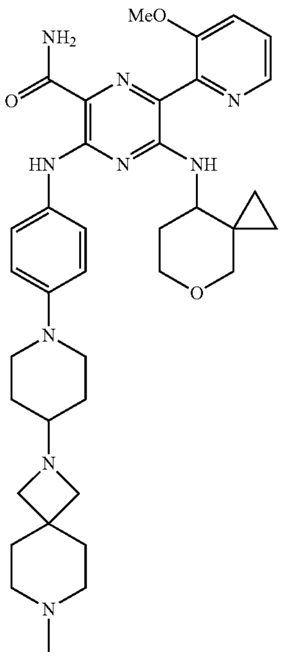
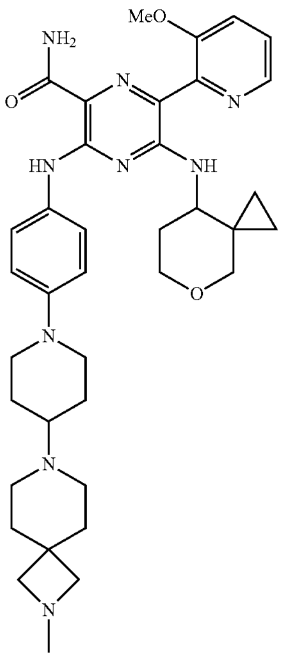

-continued
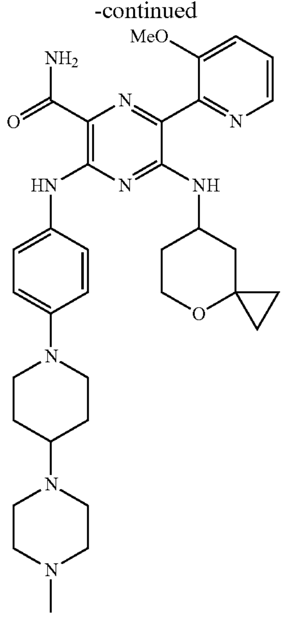
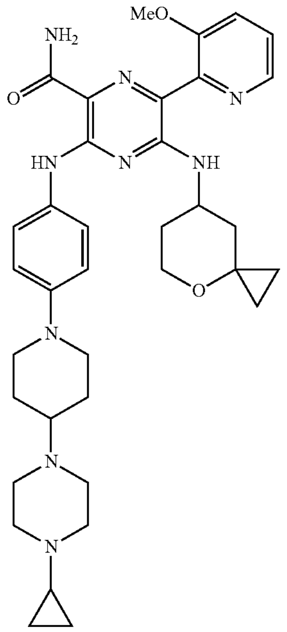
-continued
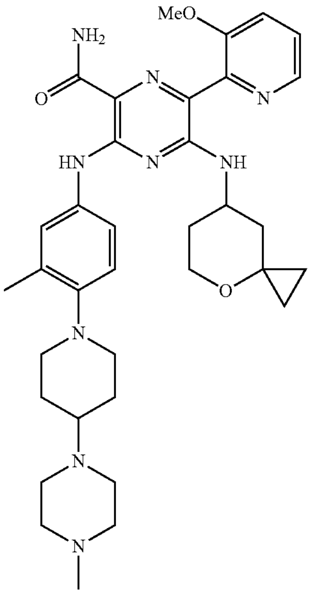
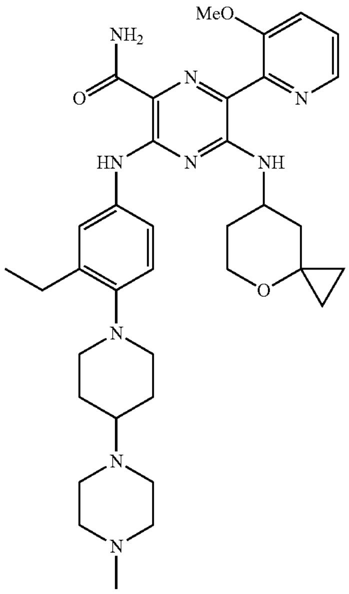
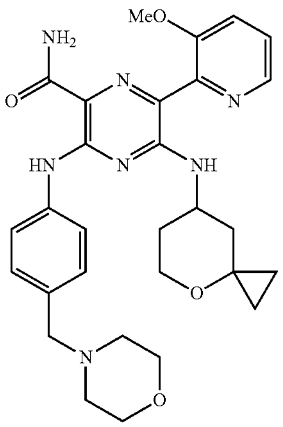

-continued
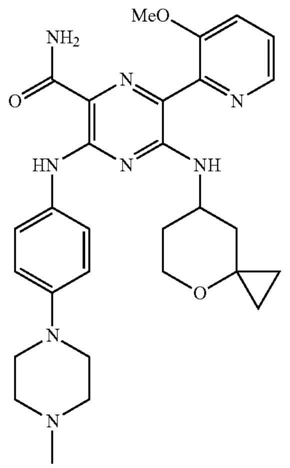
-continued
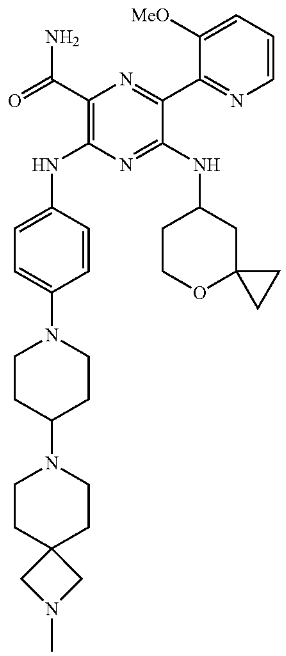
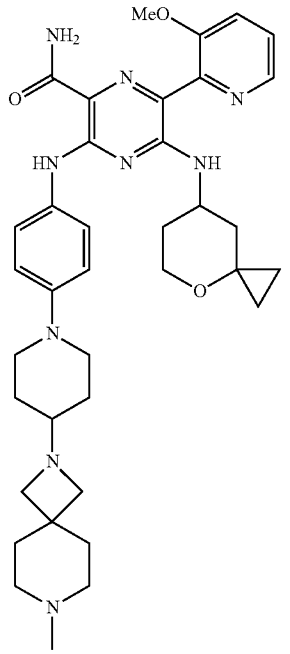
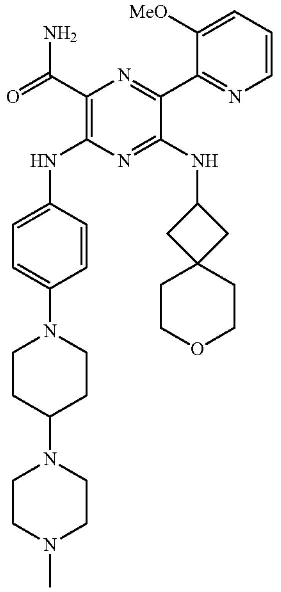

-continued
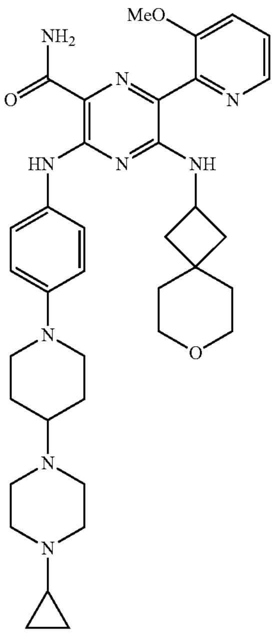
-continued
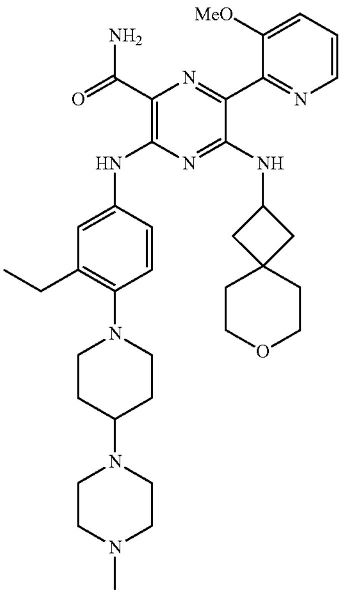
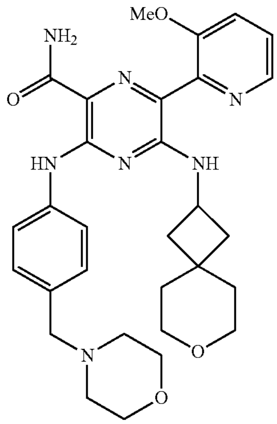
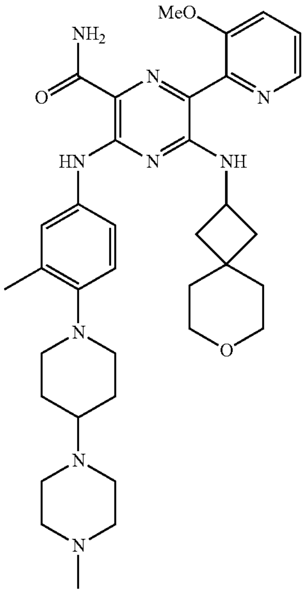
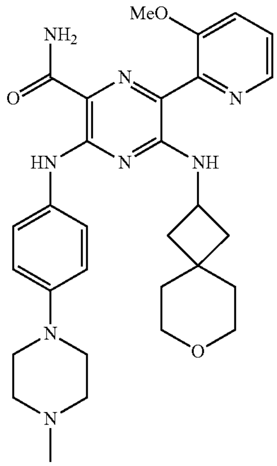

-continued
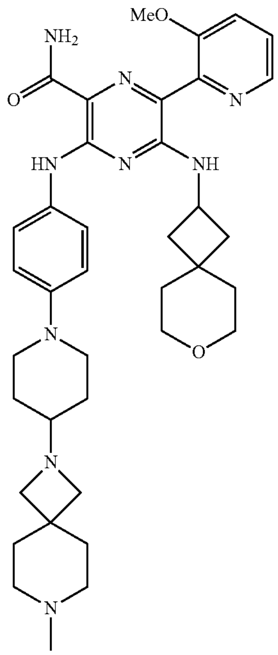
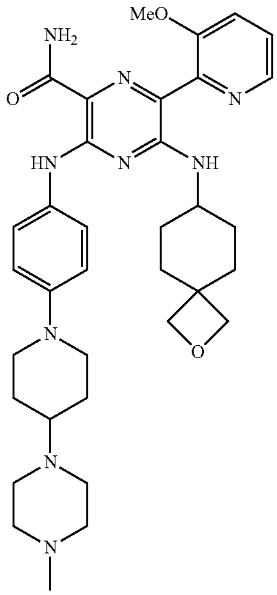
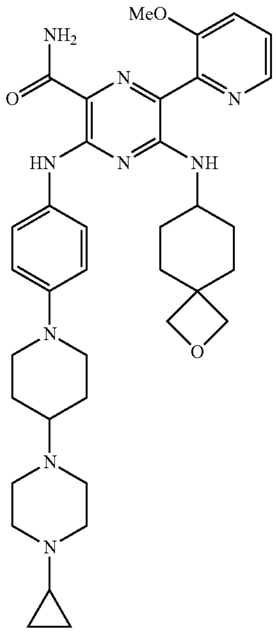
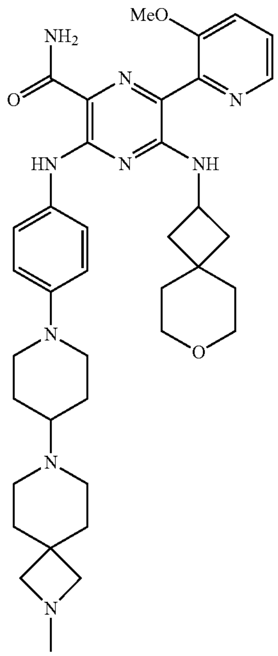
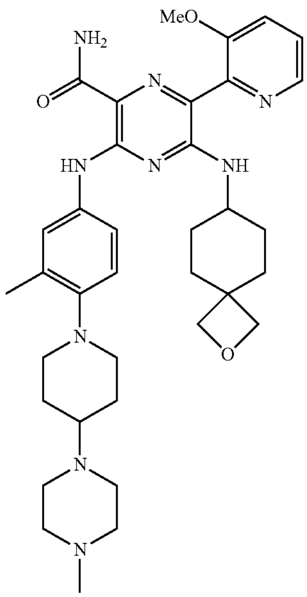

-continued
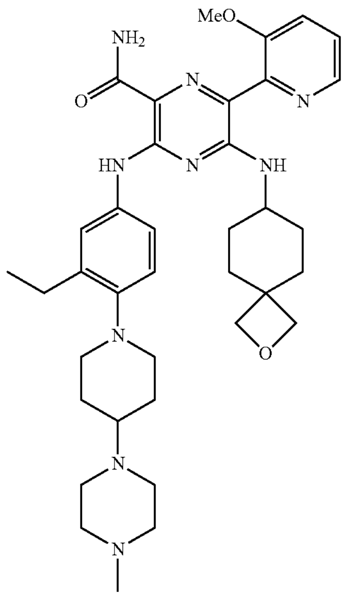
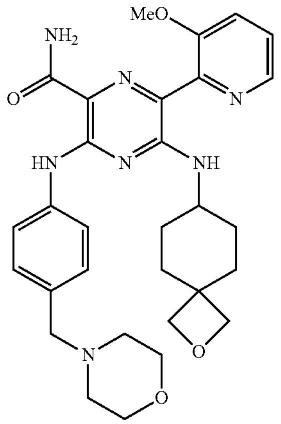
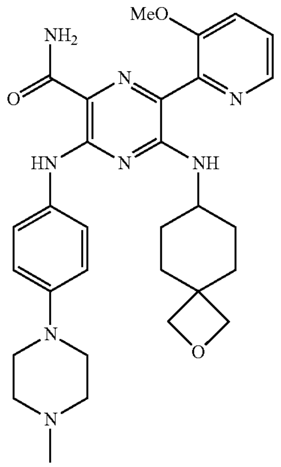
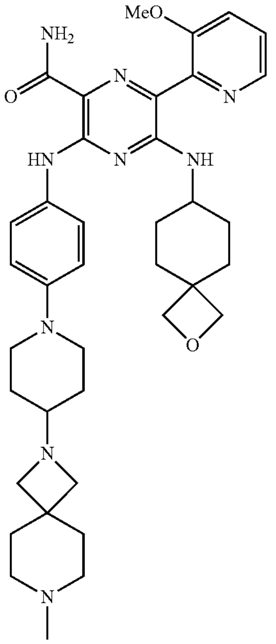
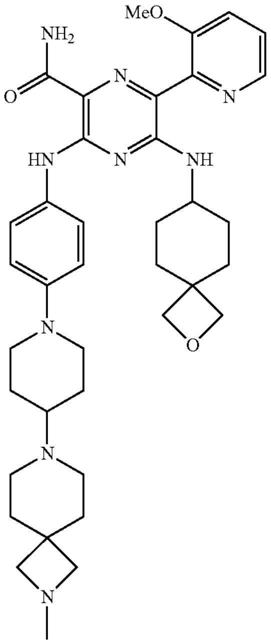
-continued
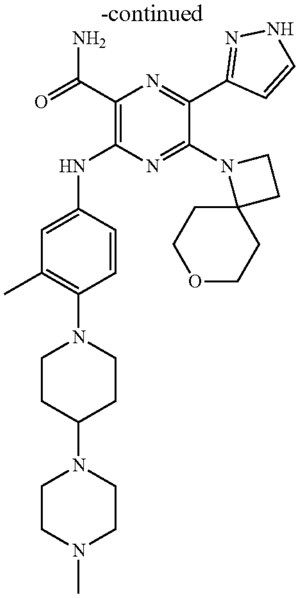
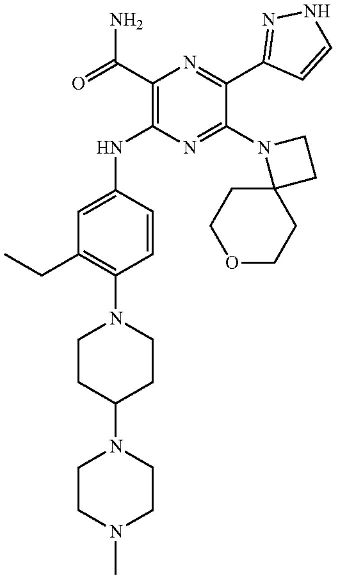
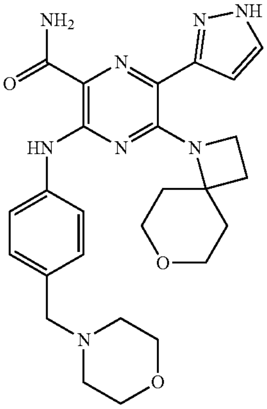
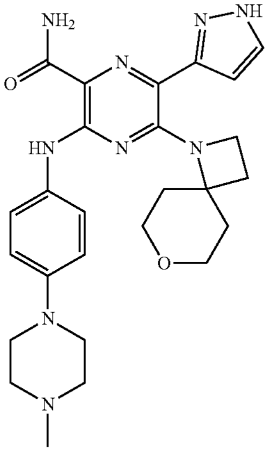

-continued
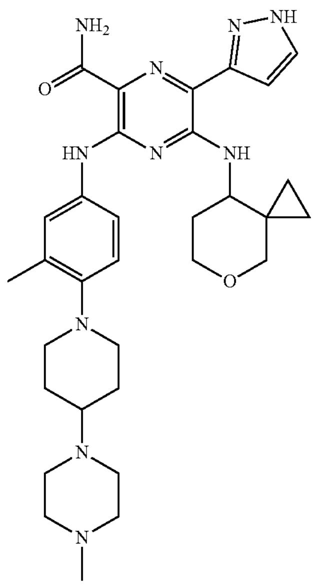
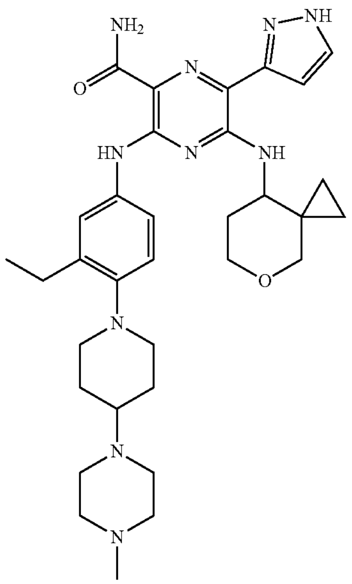
-continued
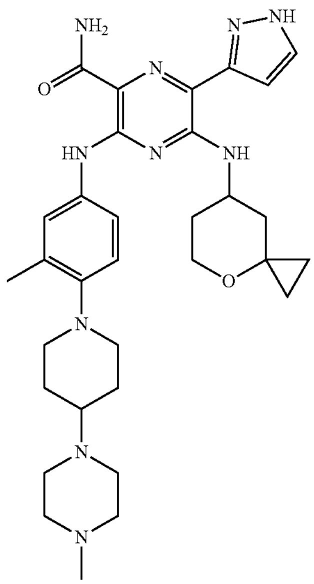
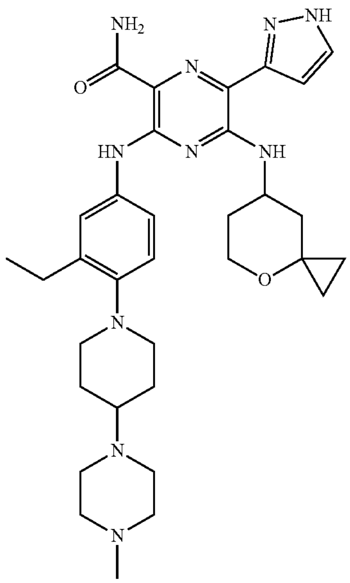
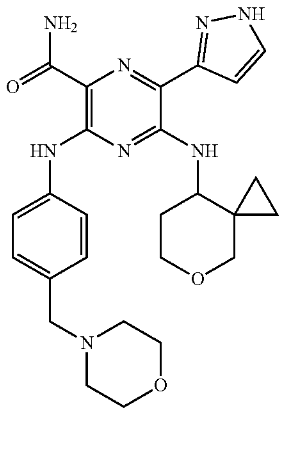
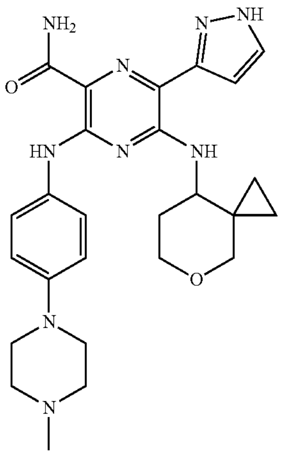
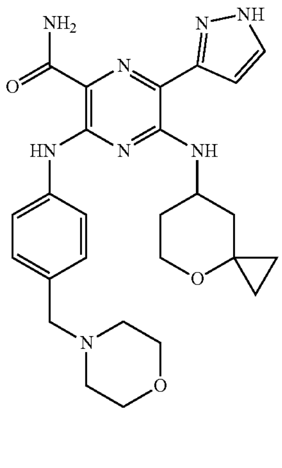
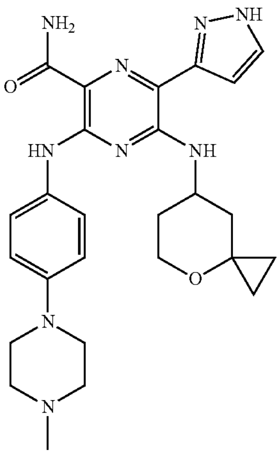

-continued
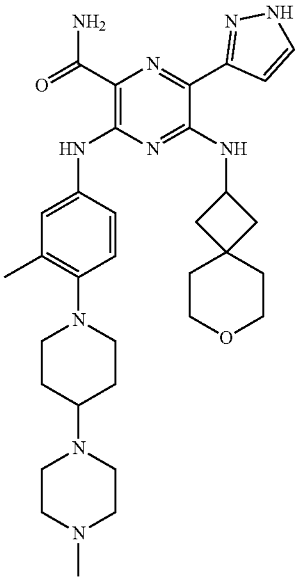
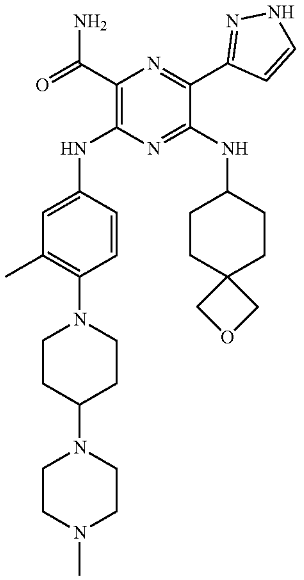
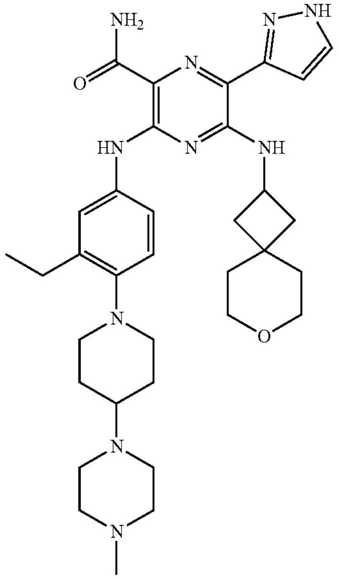
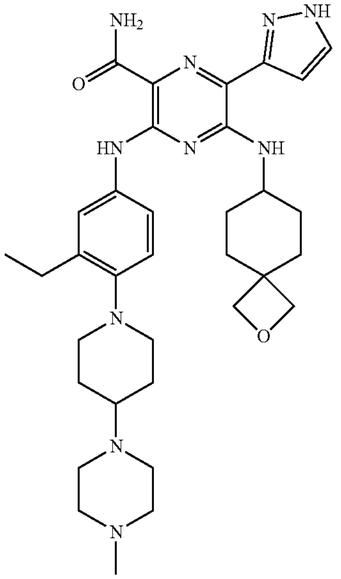
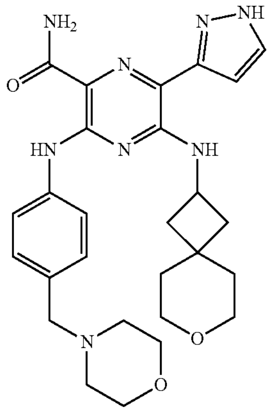
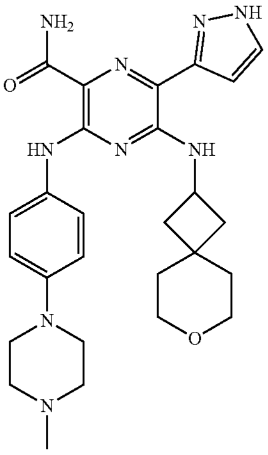
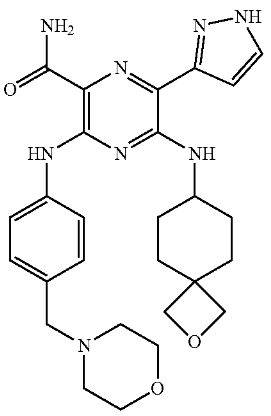
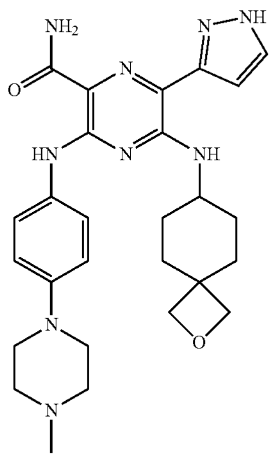
-continued -continued
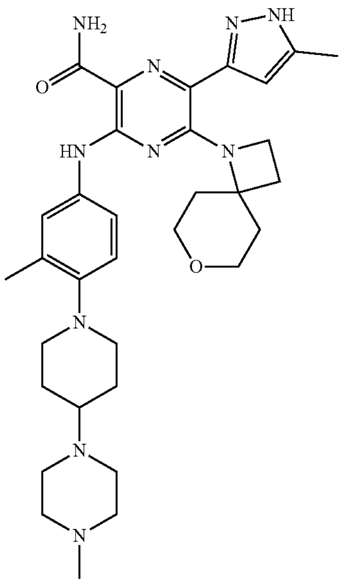
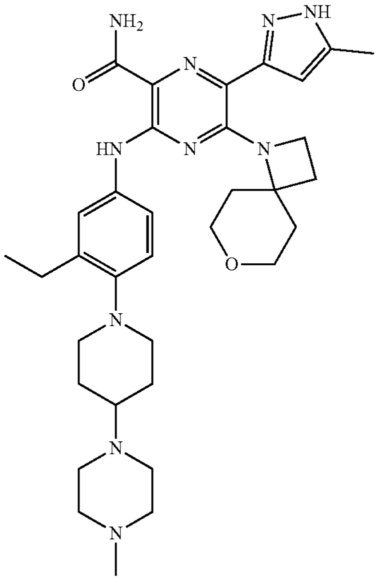
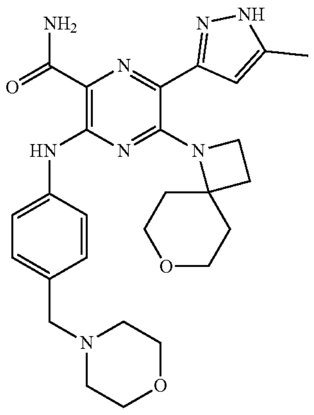
-continued
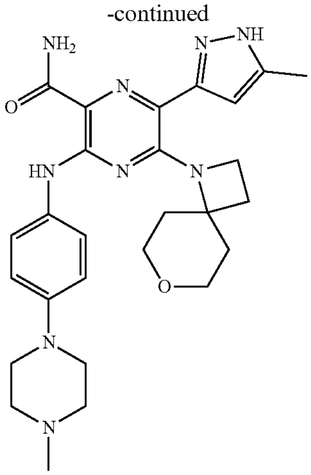
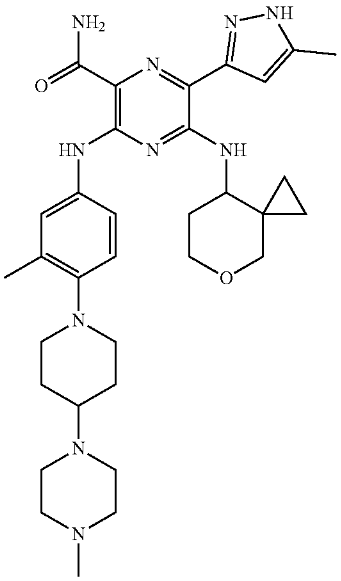
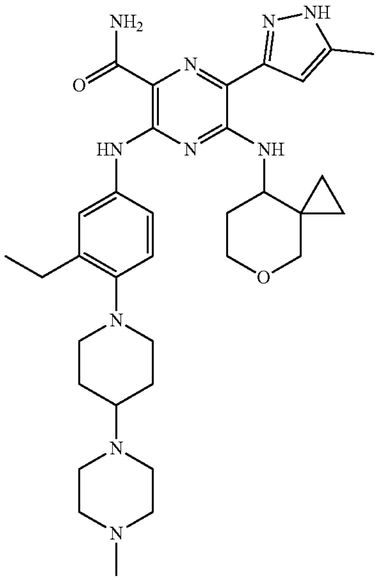

-continued
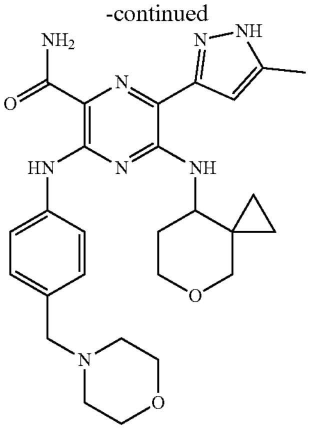
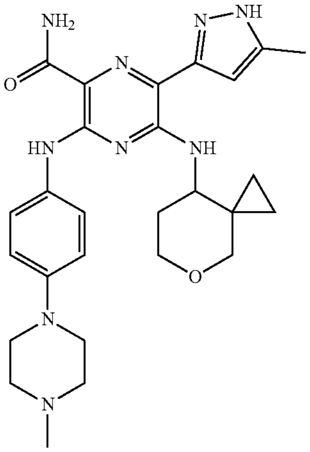
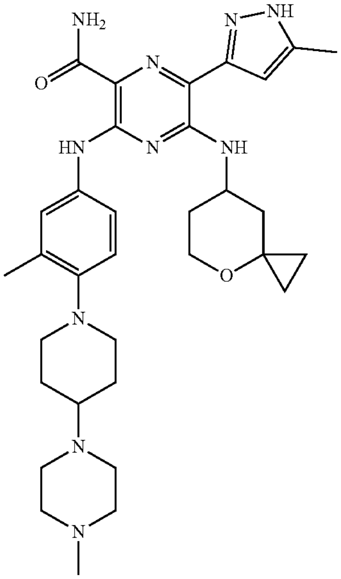
-continued
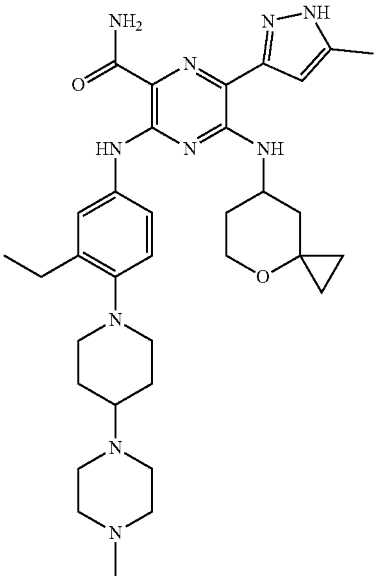
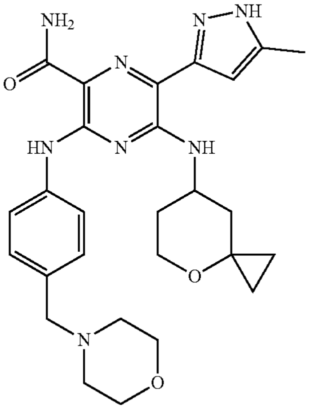
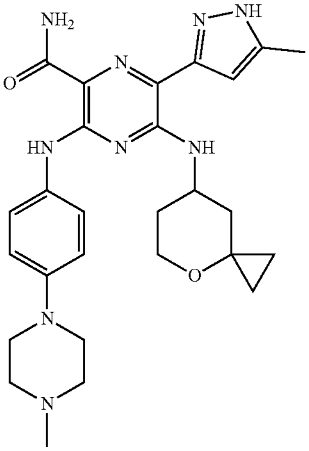

-continued
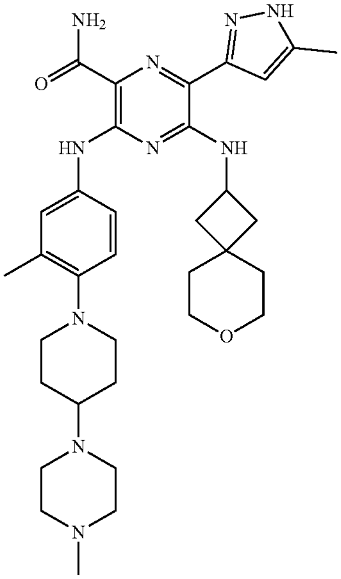
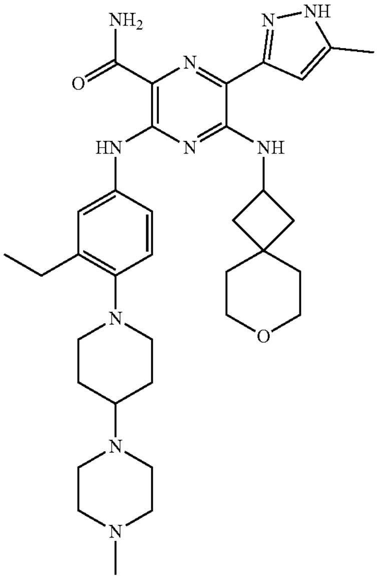
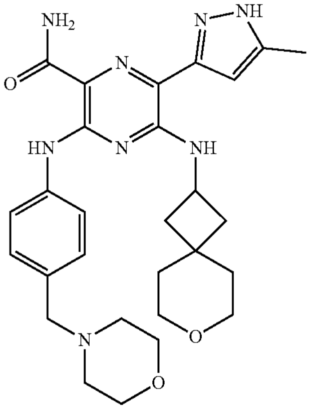
-continued
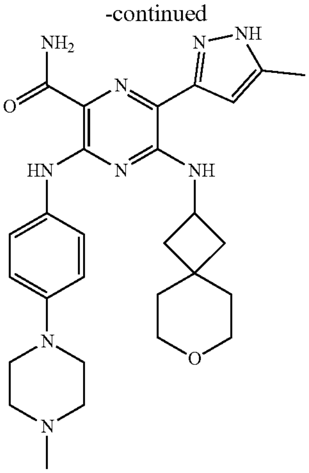
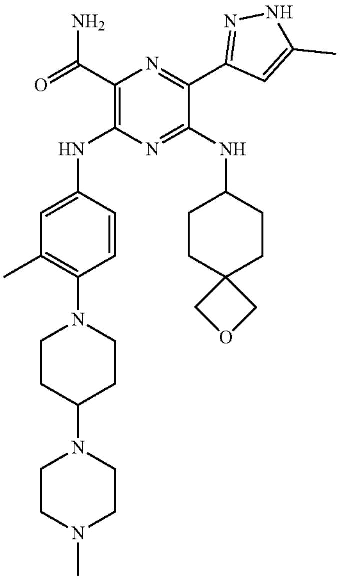
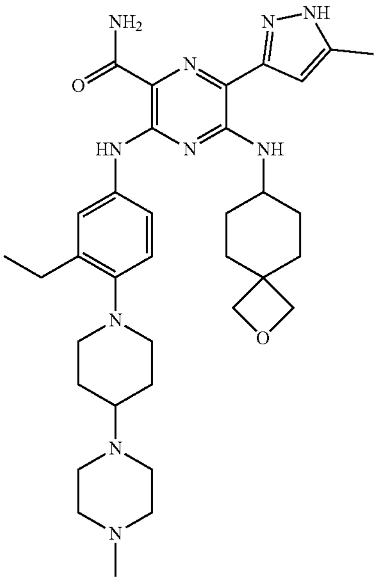

-continued
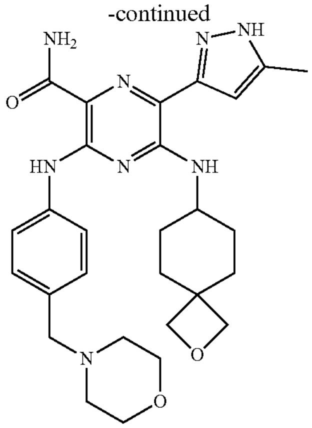
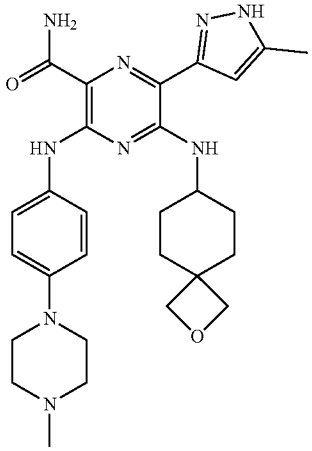
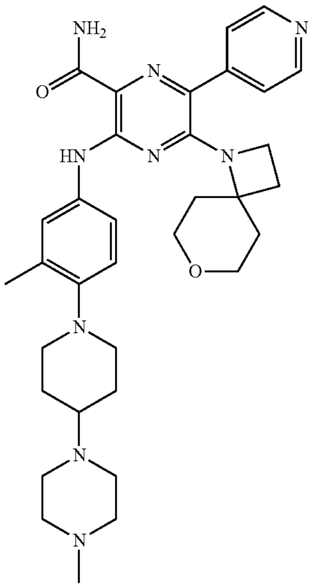
-continued
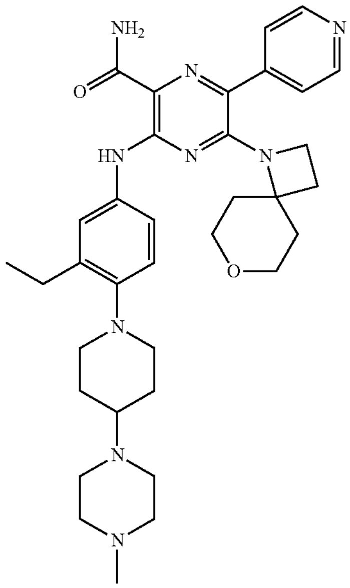
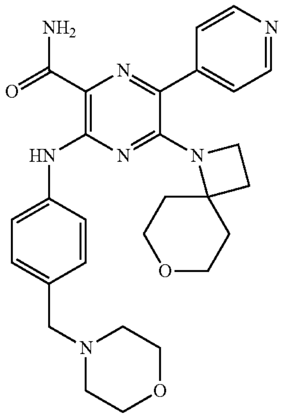
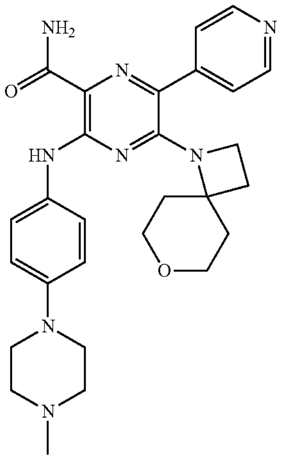
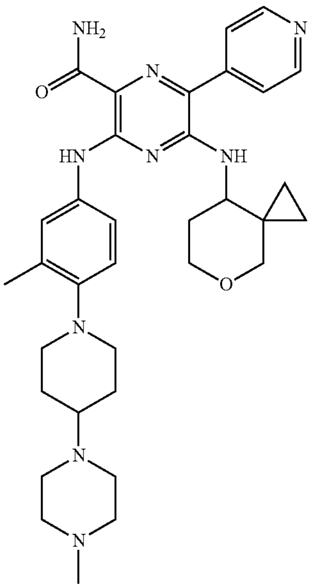

-continued
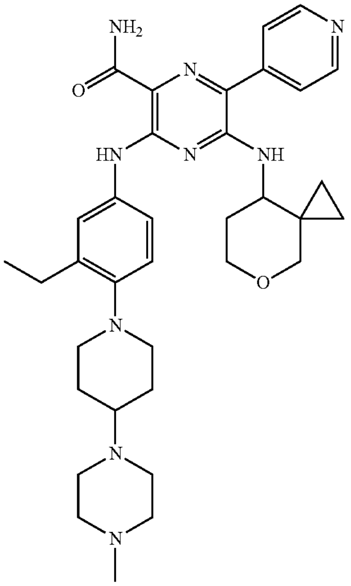
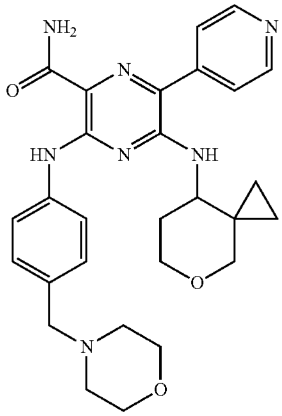
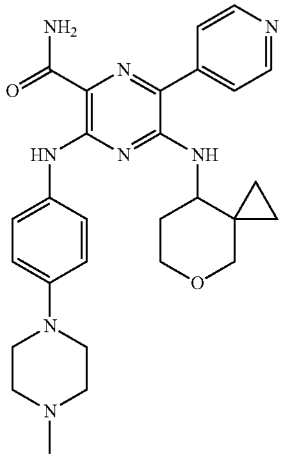
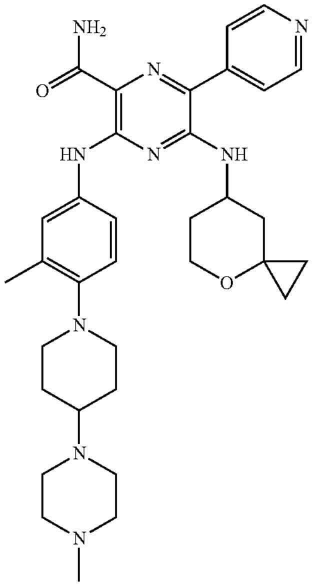
-continued
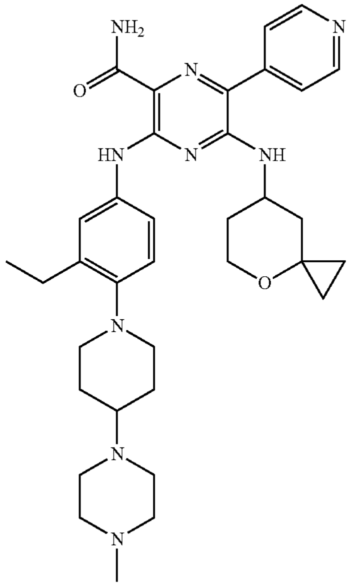
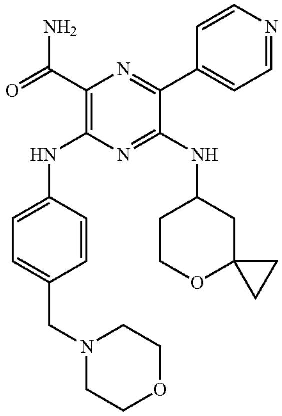
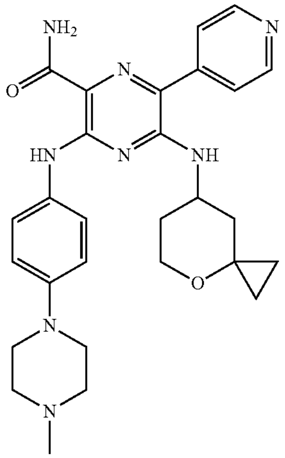
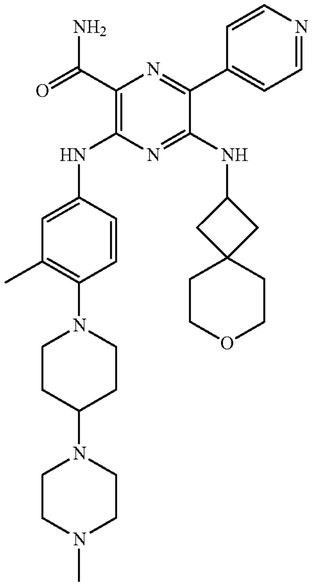

-continued
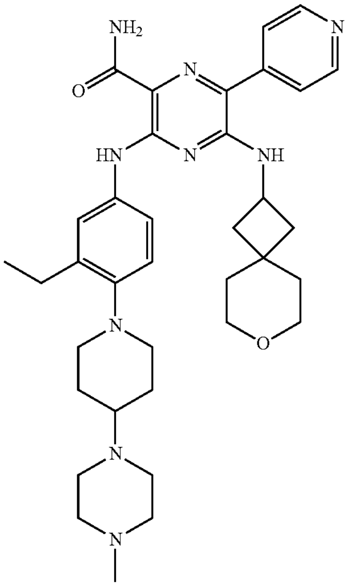
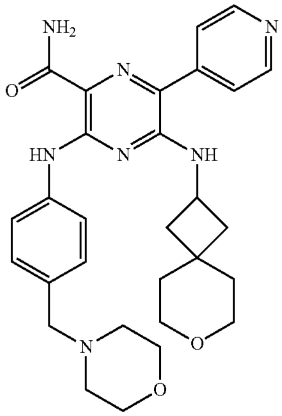
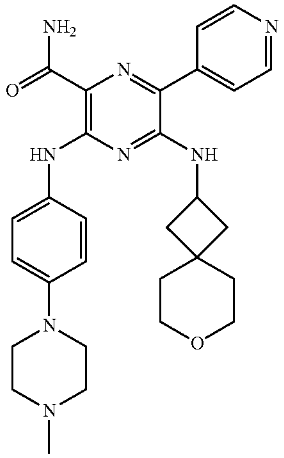
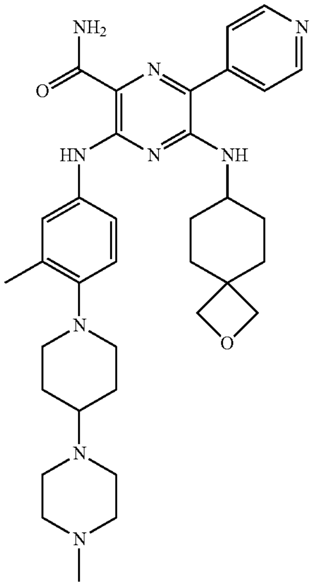
-continued
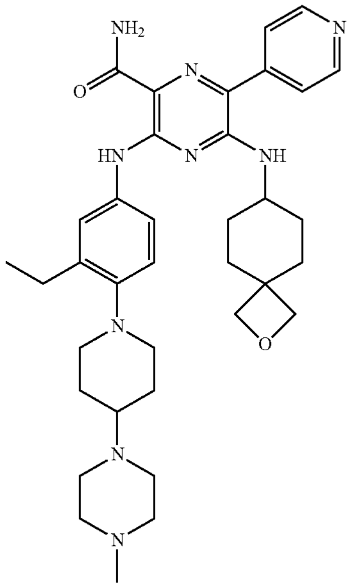
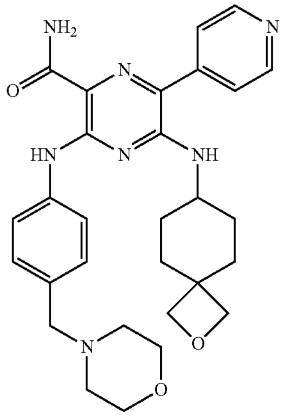
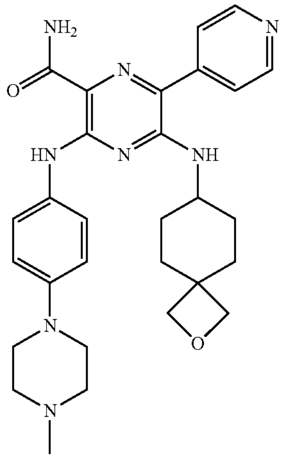
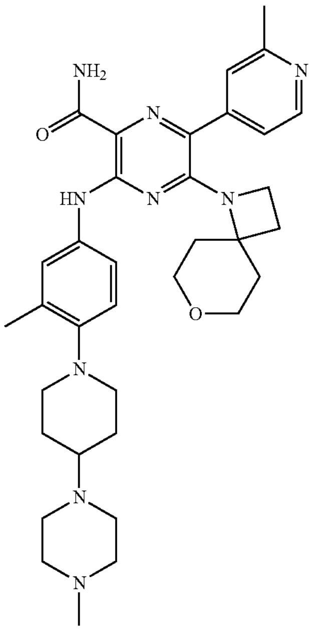

-continued
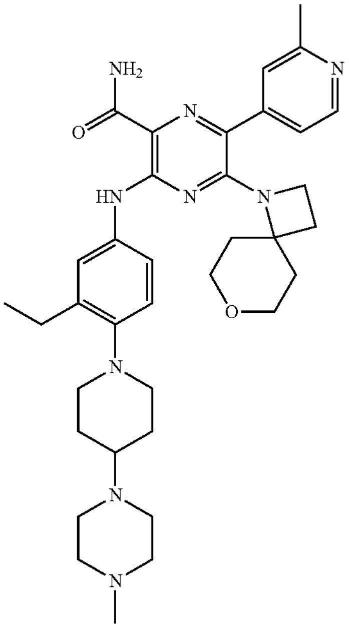
-continued
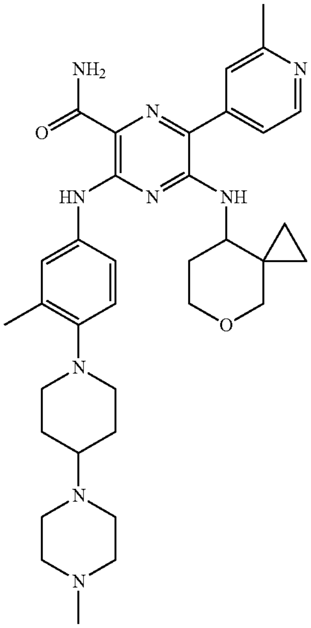
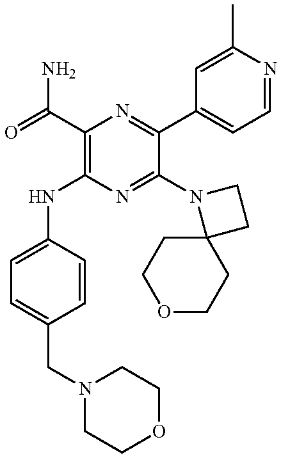
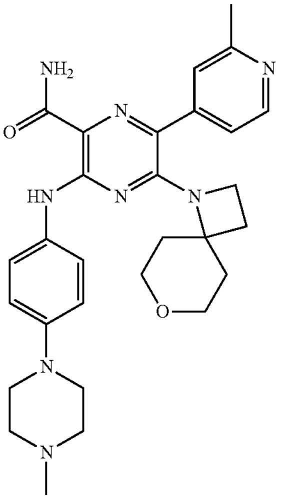
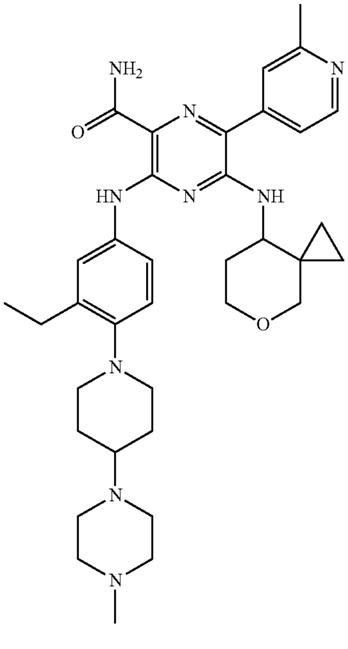

-continued
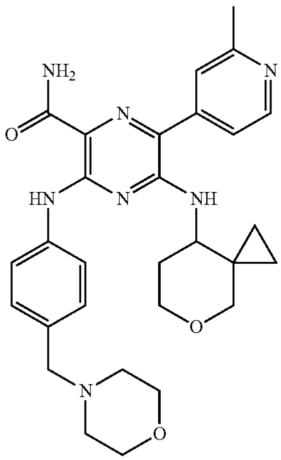
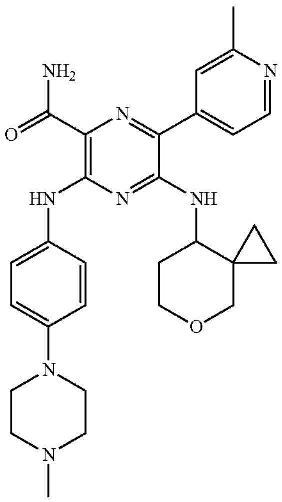
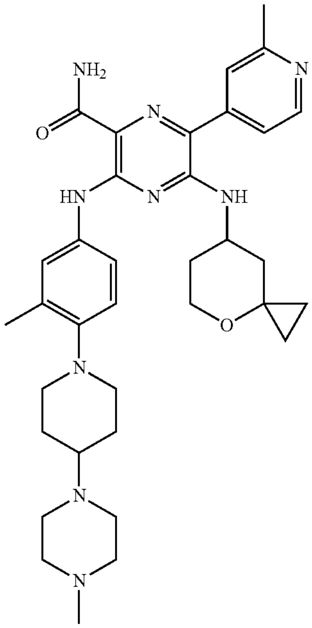
-continued
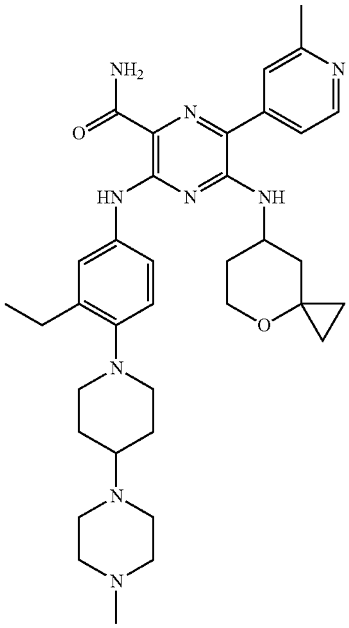
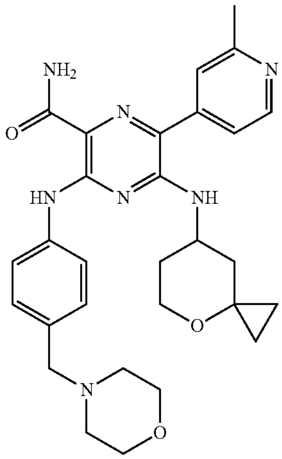
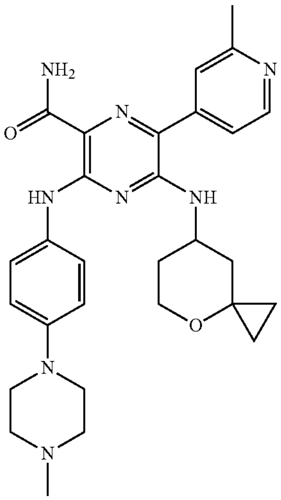

-continued
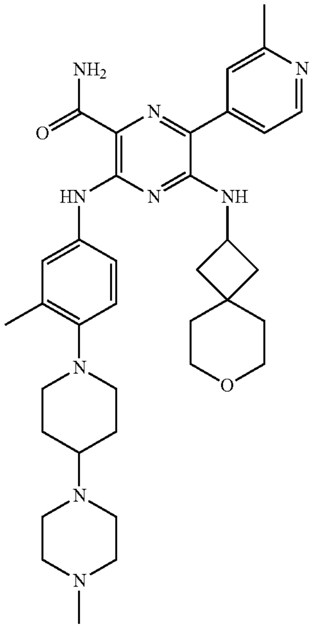
-continued
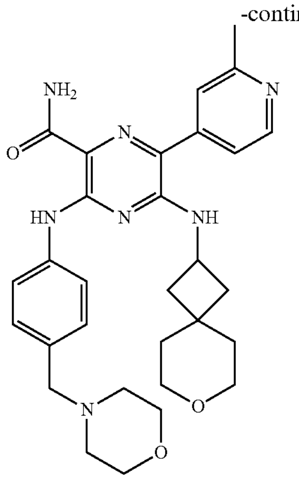
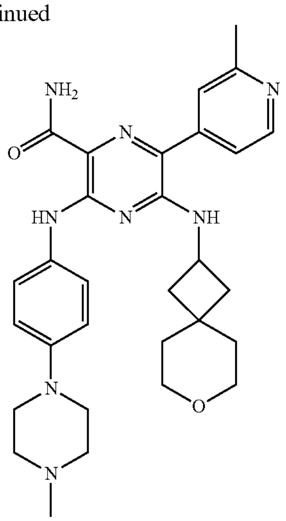
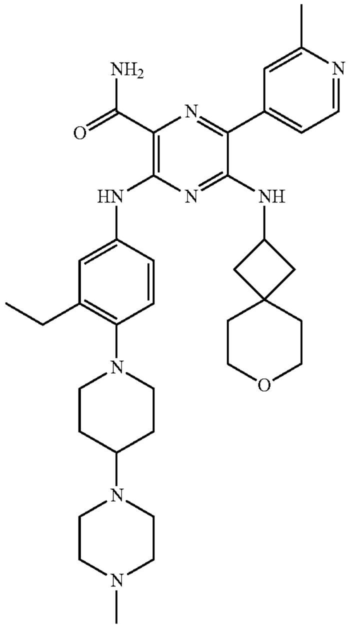
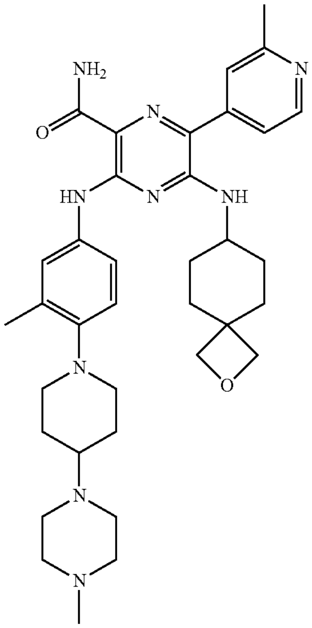

-continued
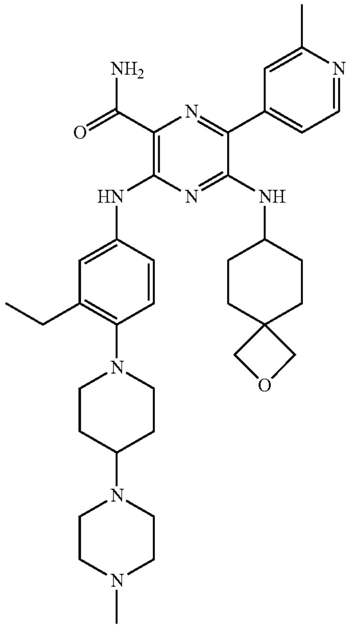
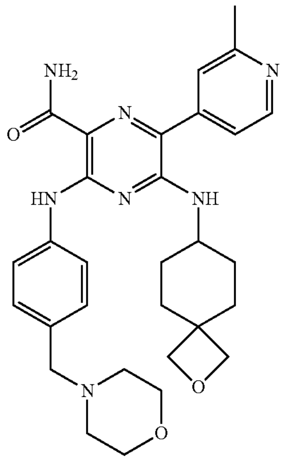
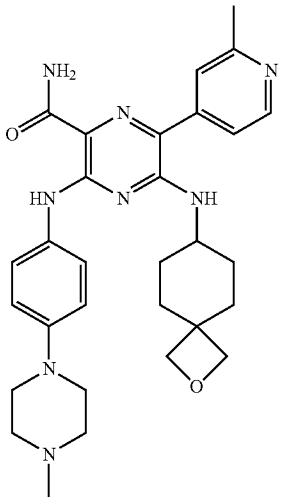
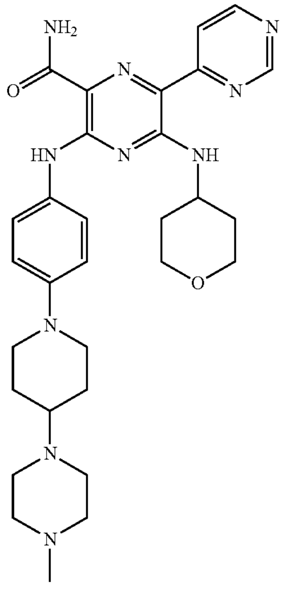
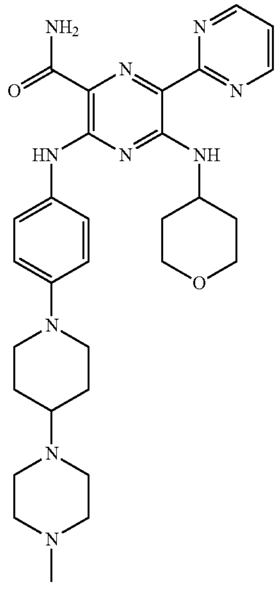
-continued
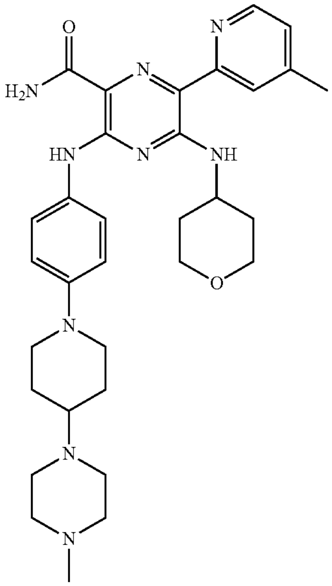
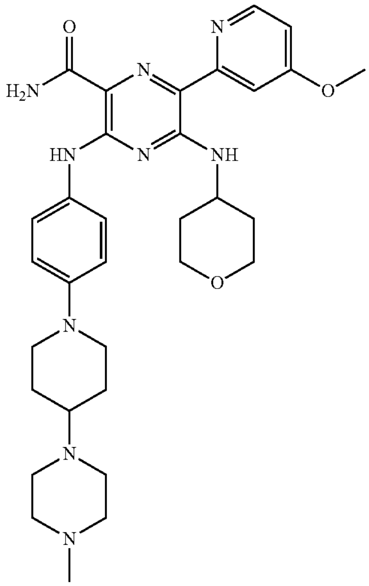

-continued
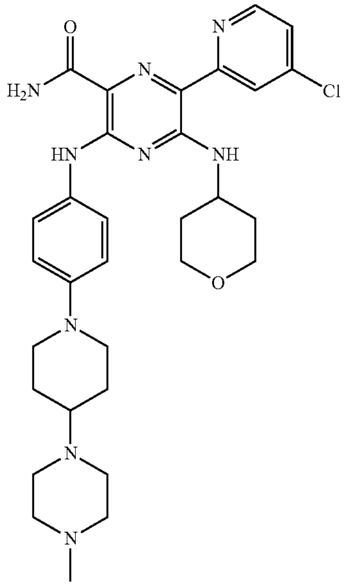
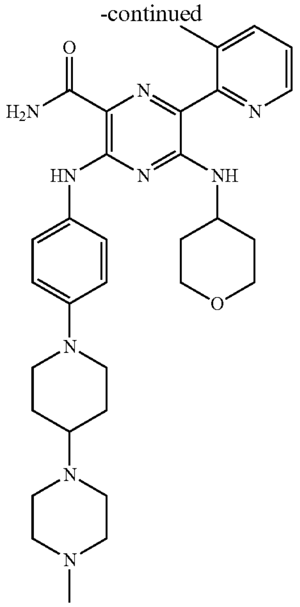
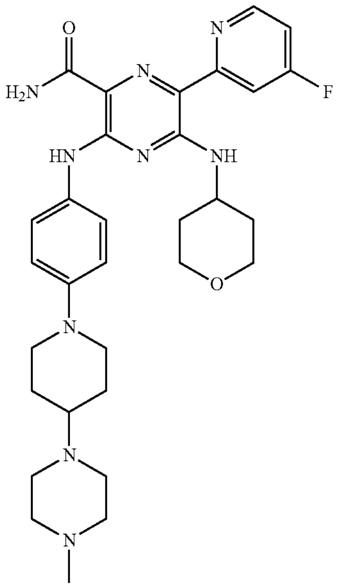
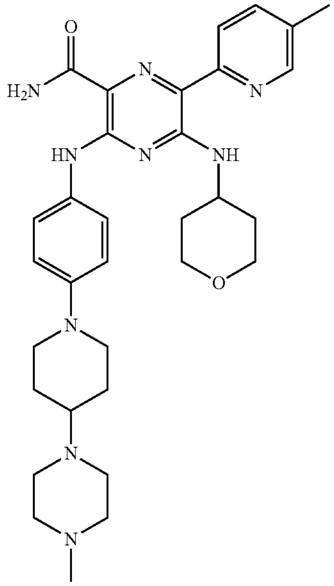
-continued

-continued
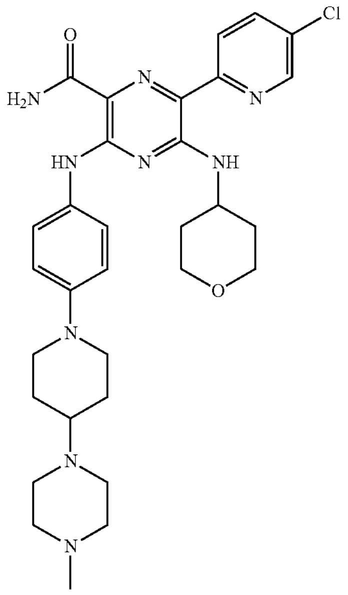
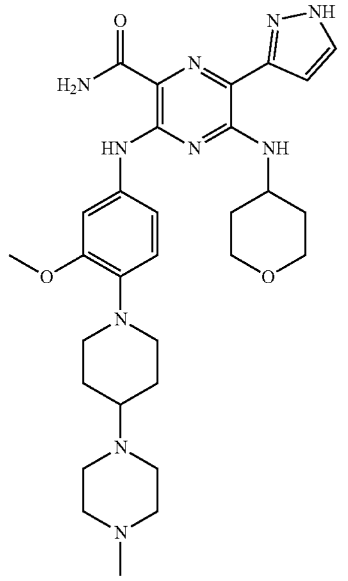
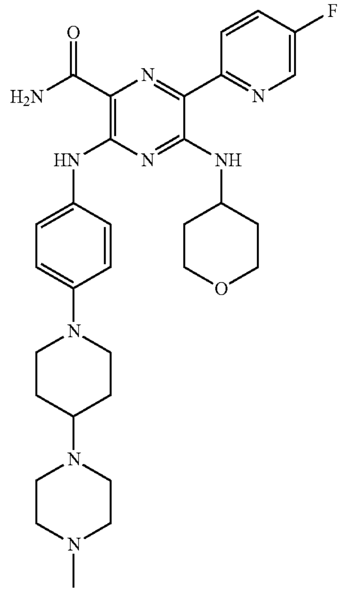
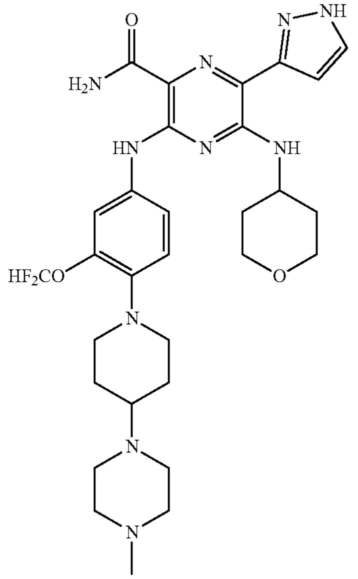

-continued
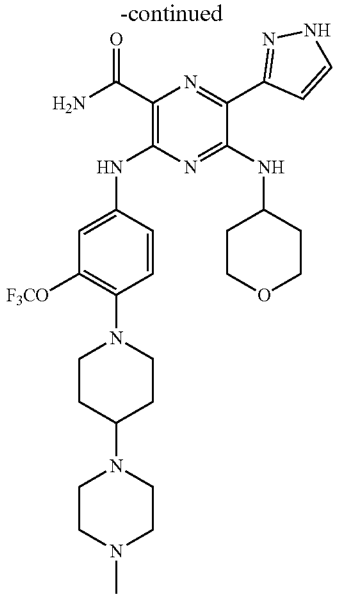
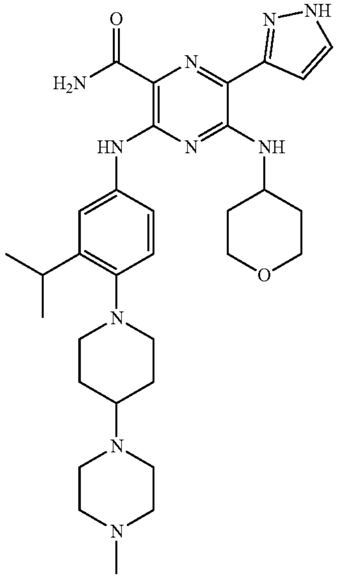
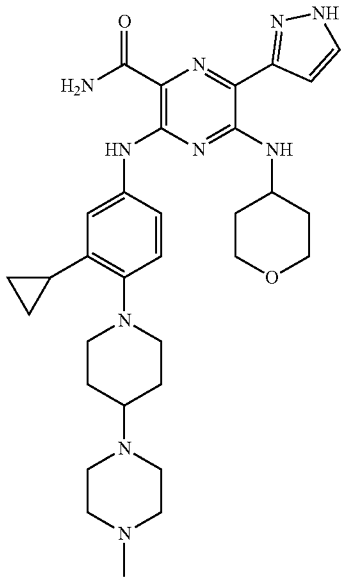
-continued
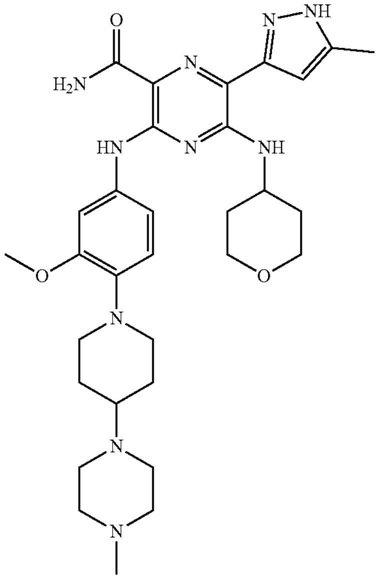
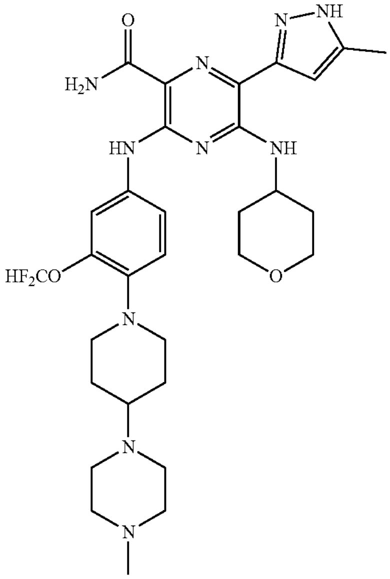

-continued
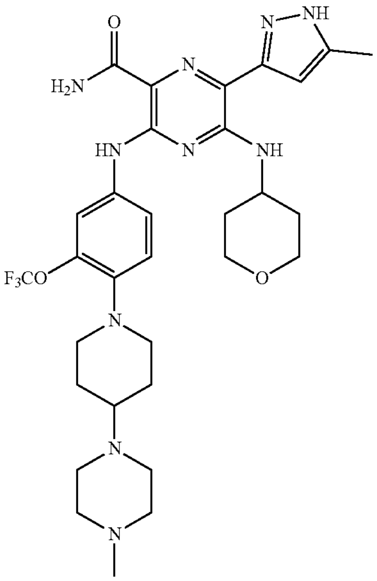
-continued
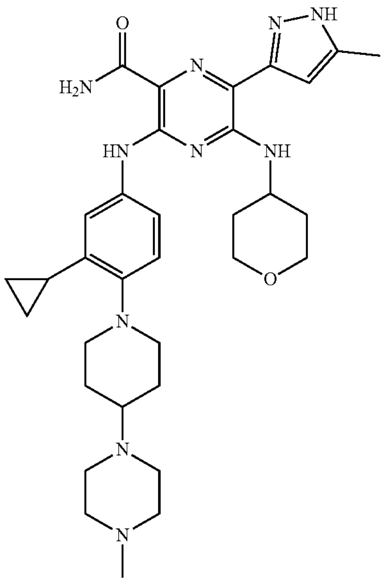
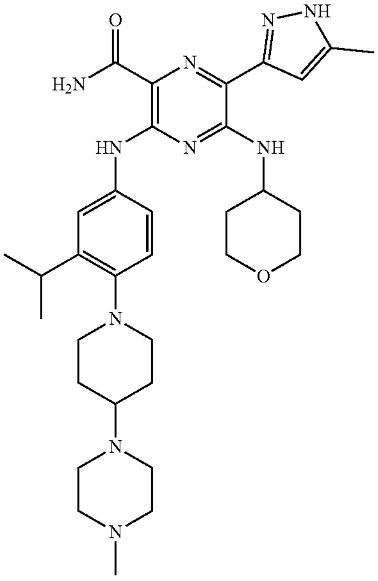
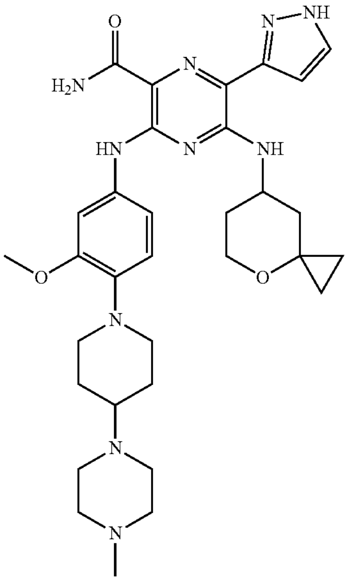

-continued
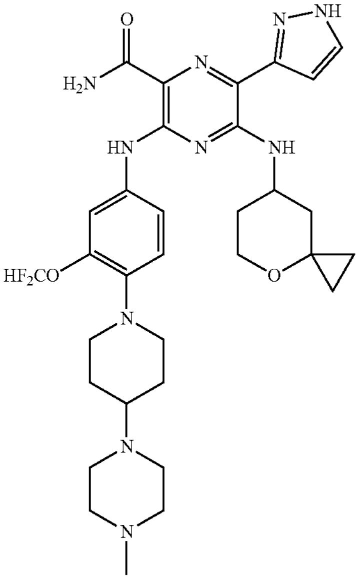
-continued
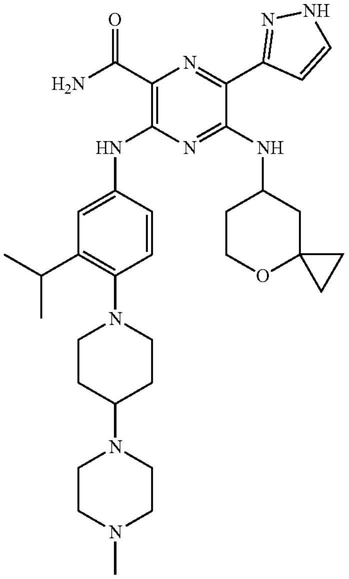
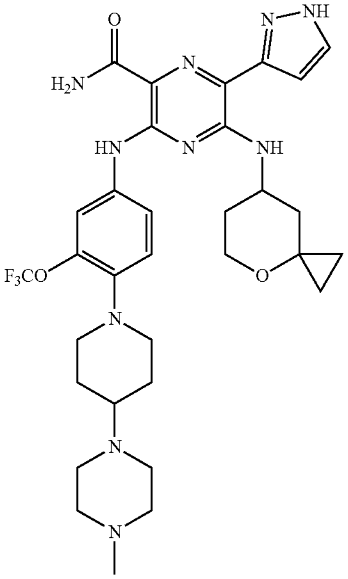
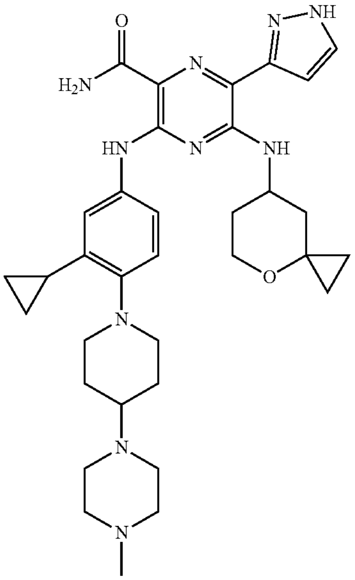

-continued
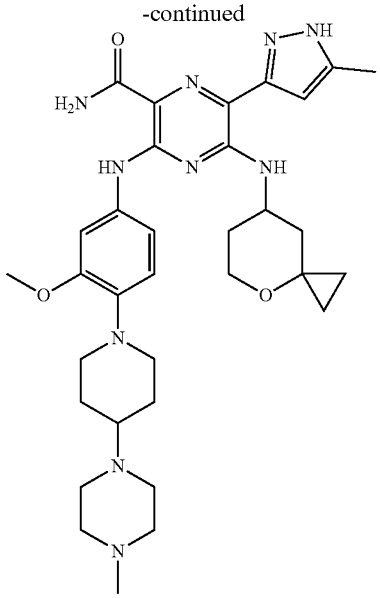
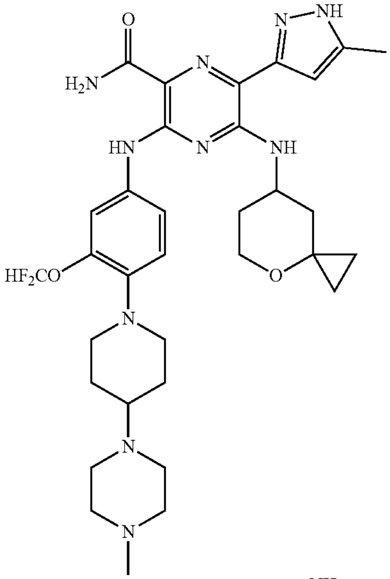
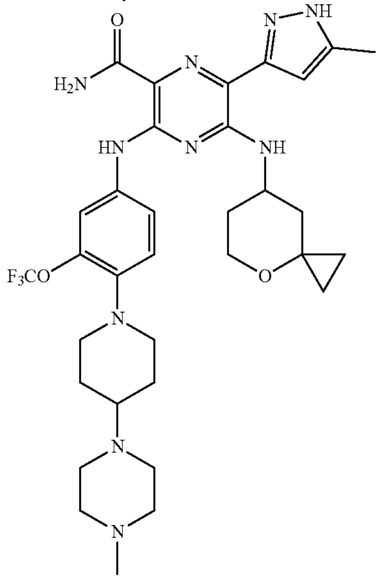
-continued
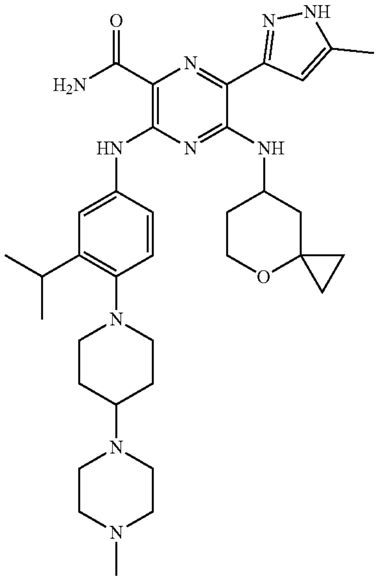
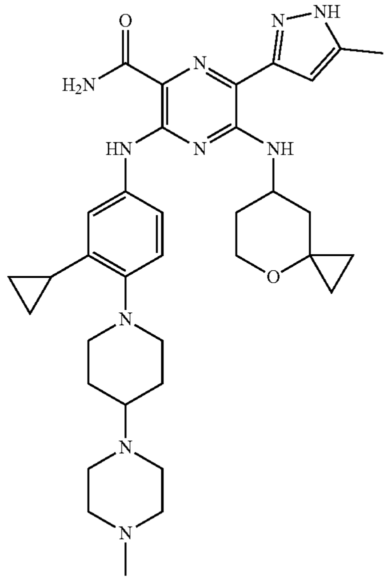

-continued
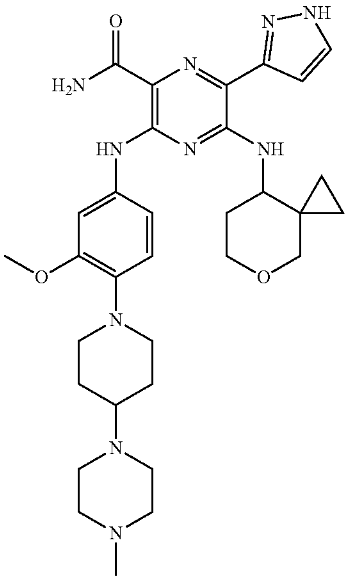
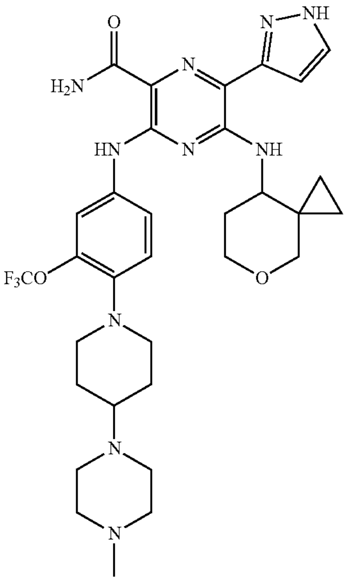
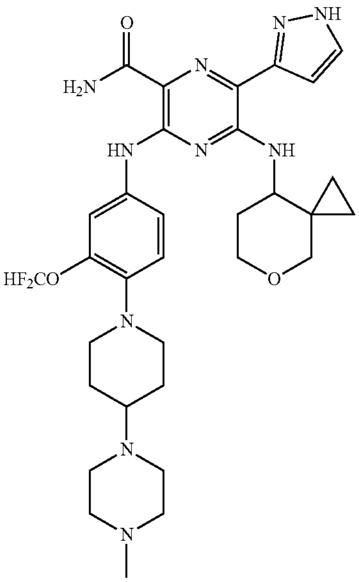
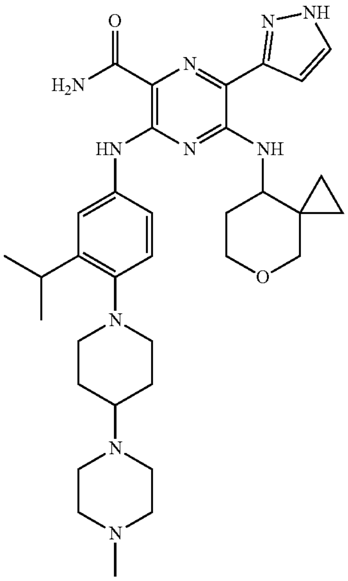
-continued

-continued
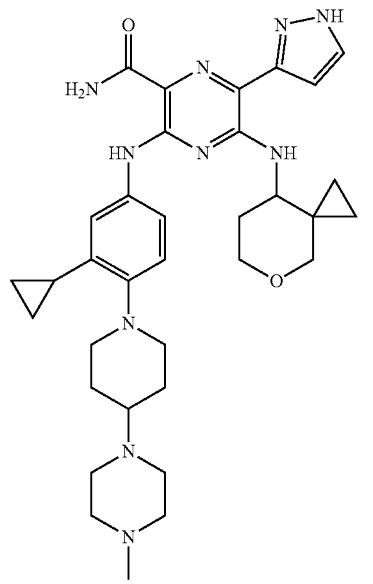
-continued
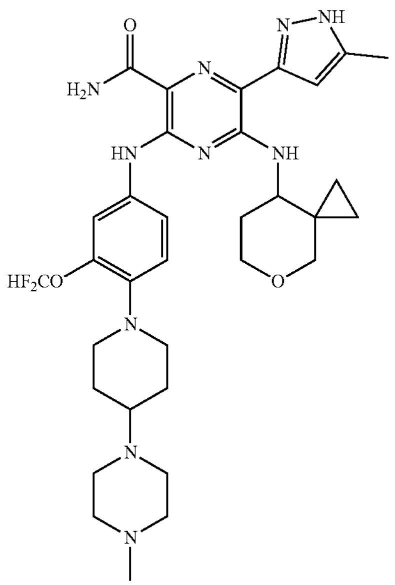
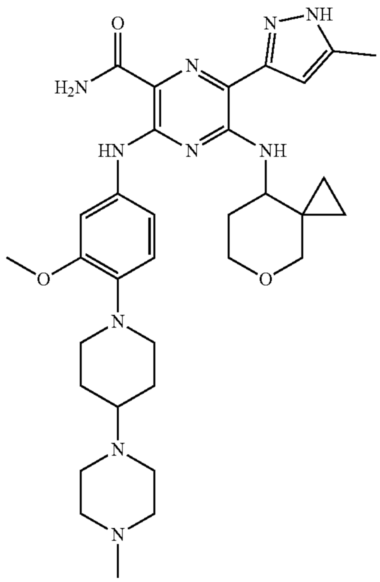
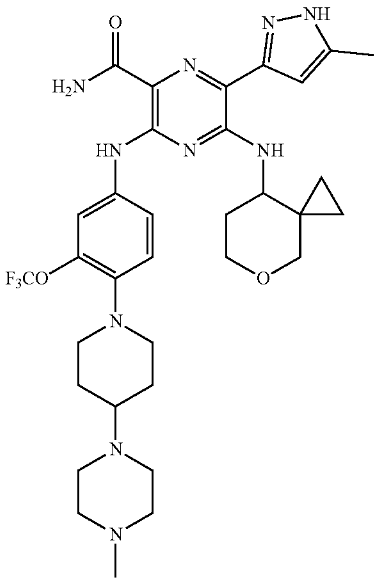

-continued
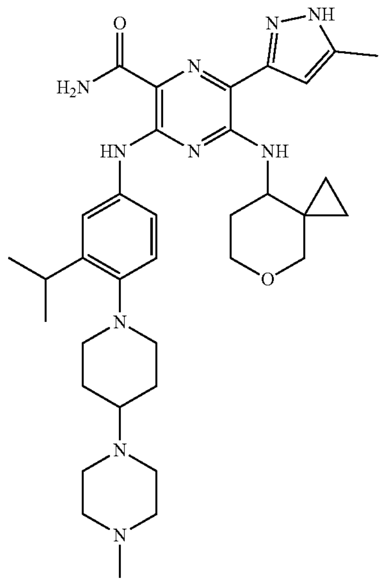
-continued
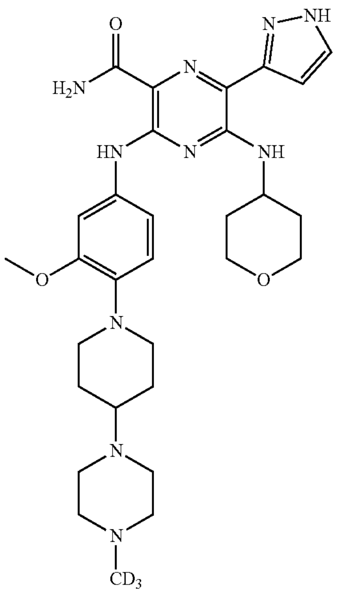
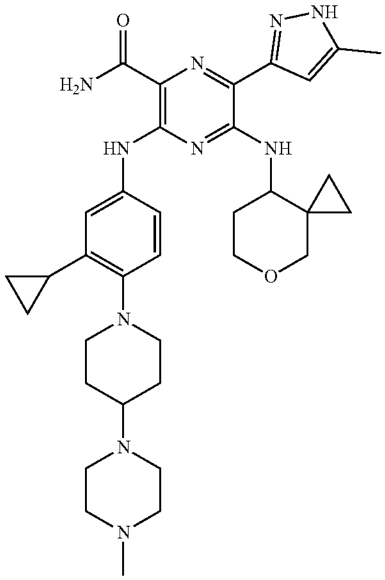
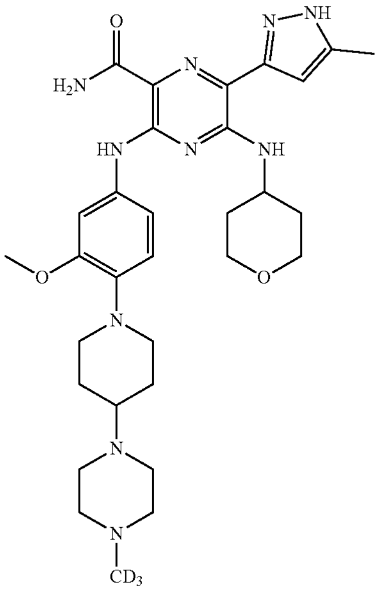

-continued
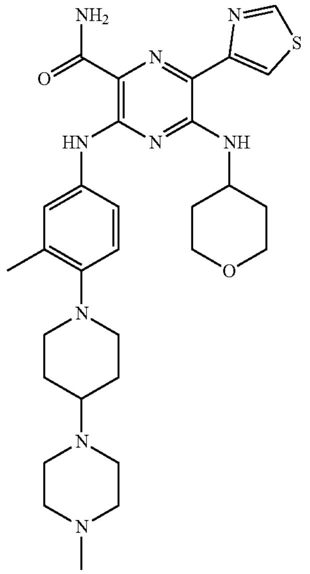
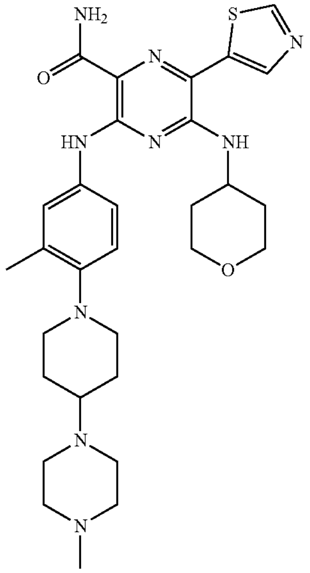
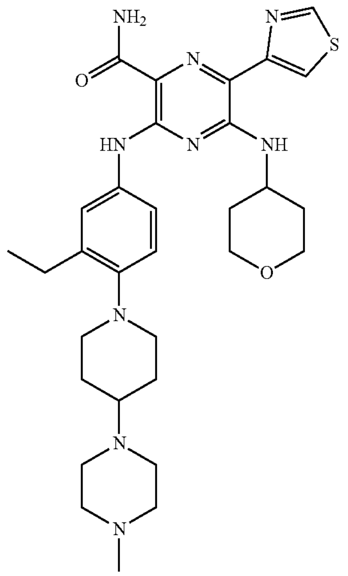
-continued
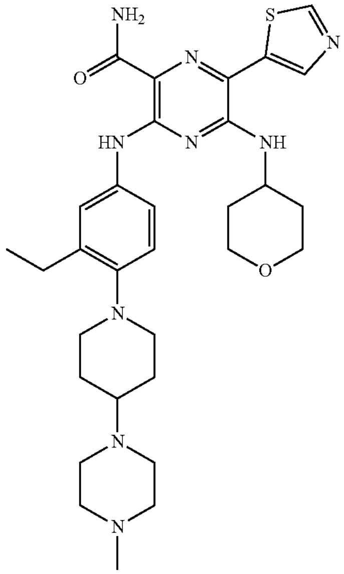
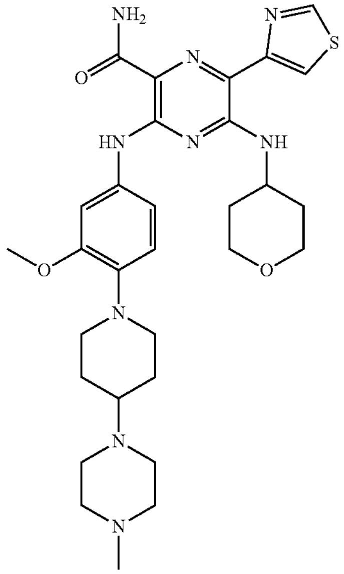
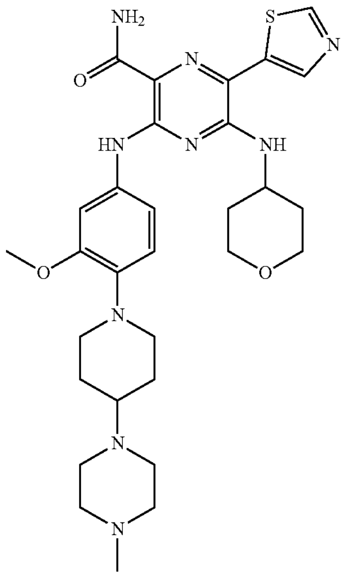

-continued
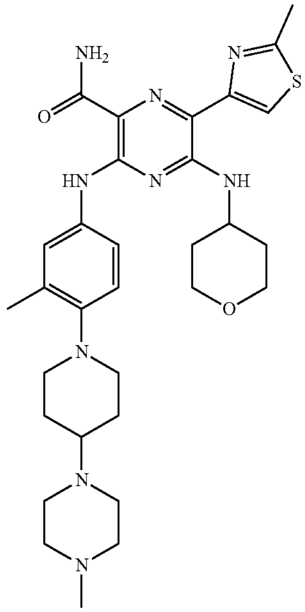
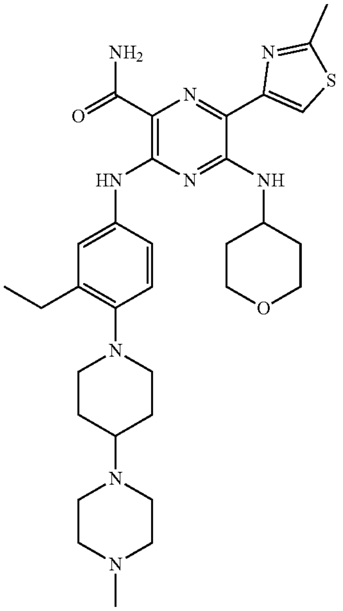
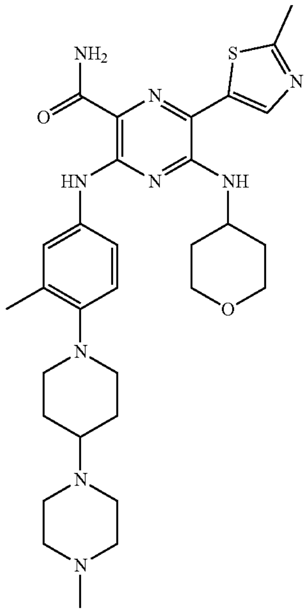
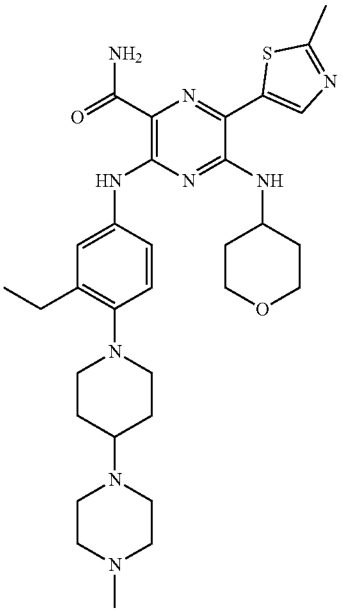

-continued
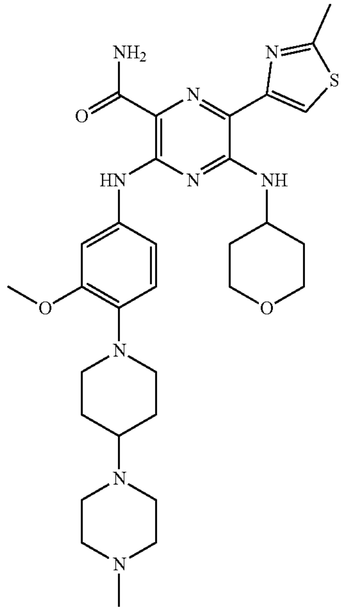
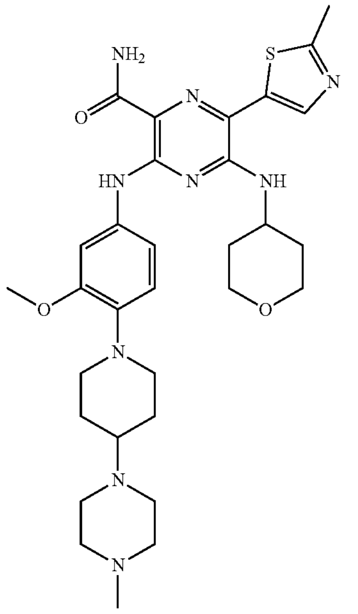
-continued
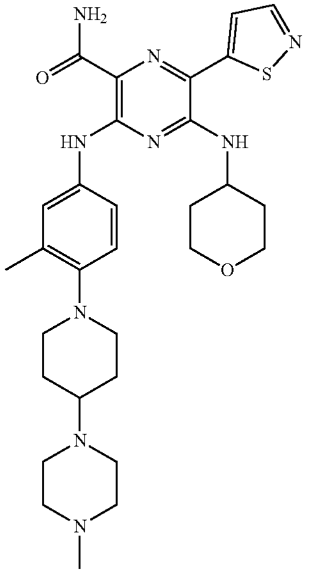
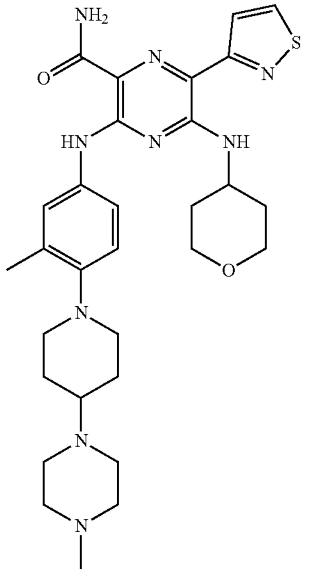
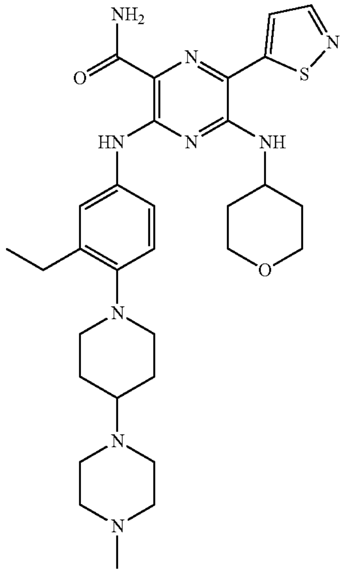

-continued
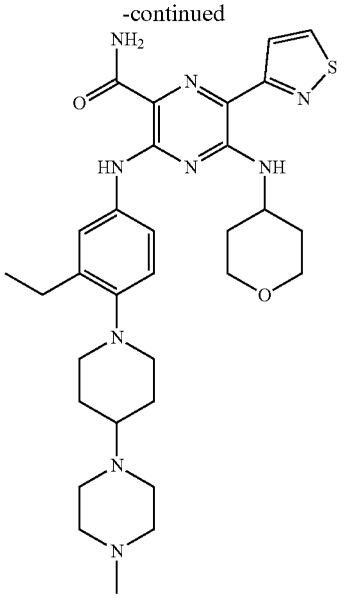
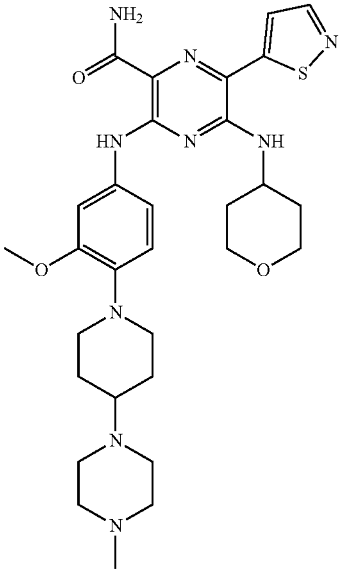
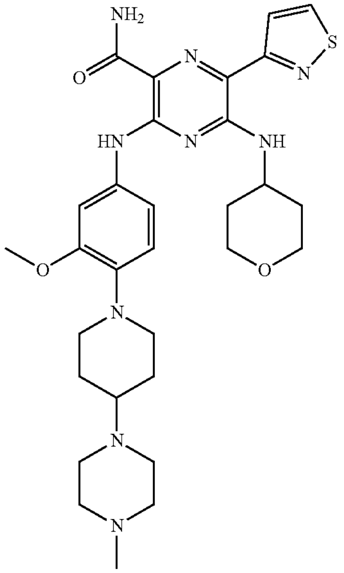
-continued
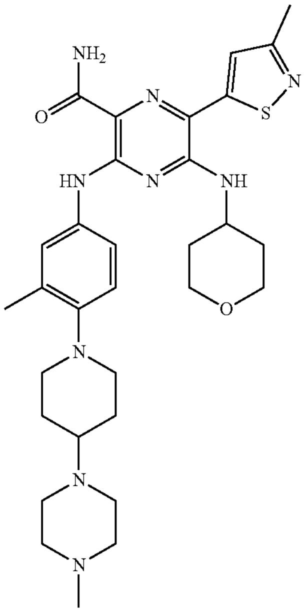
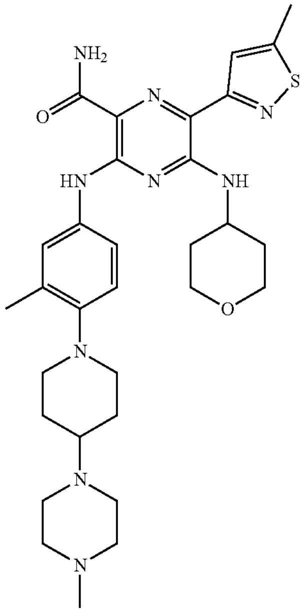

-continued
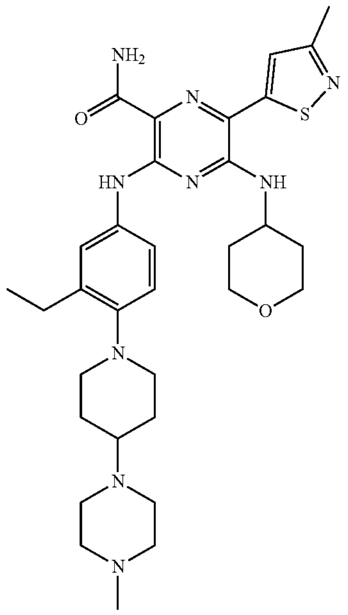
-continued
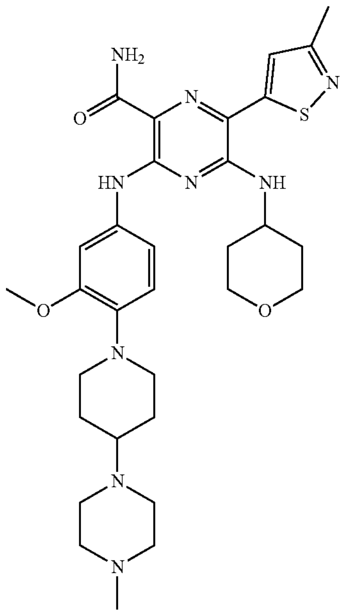
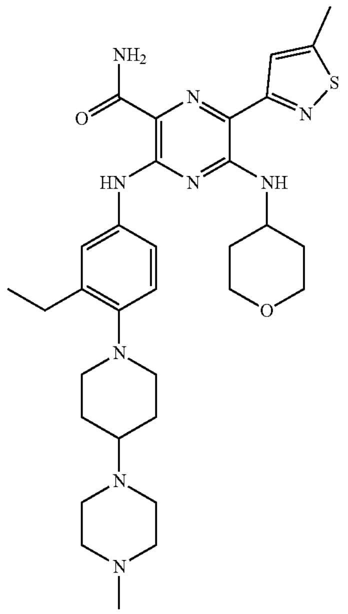
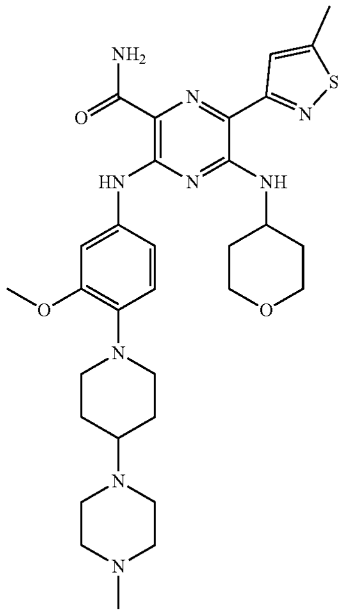

-continued
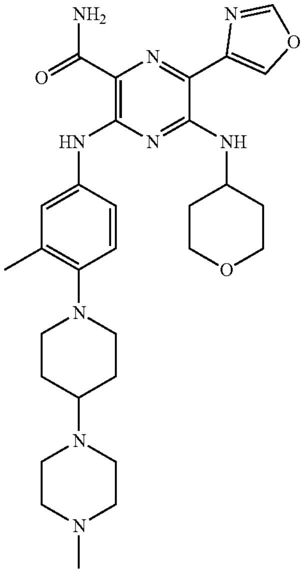
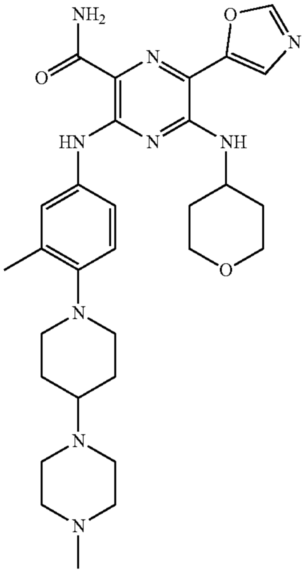
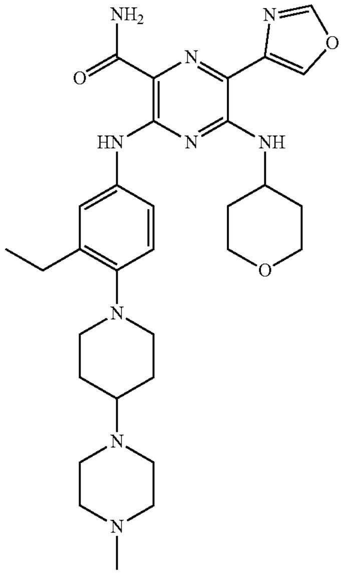
-continued
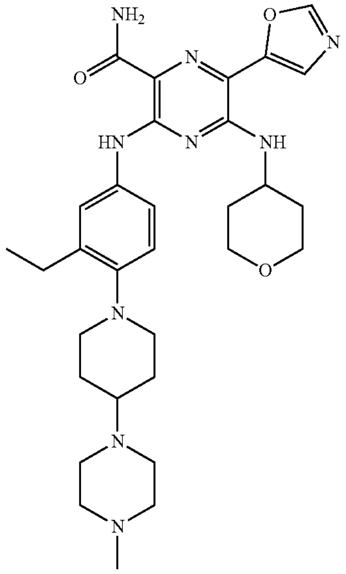
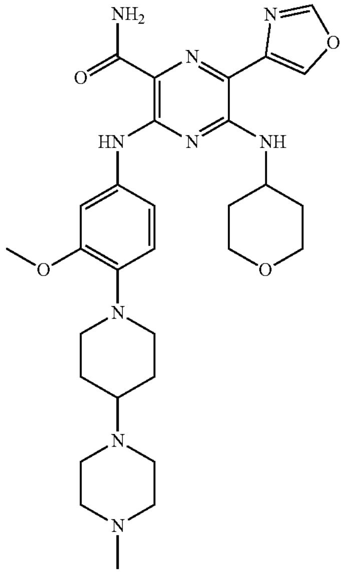
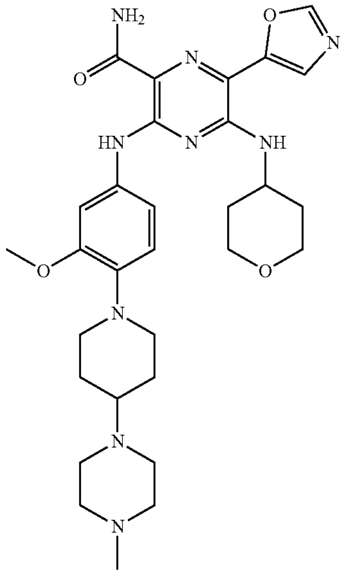

-continued
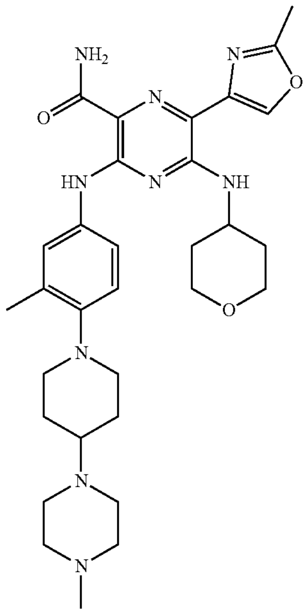
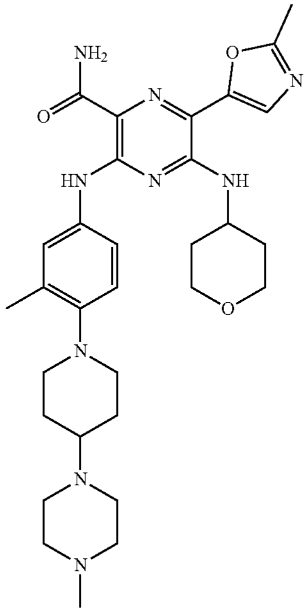
-continued
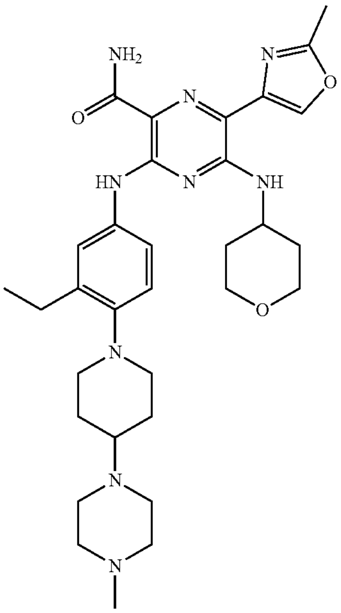
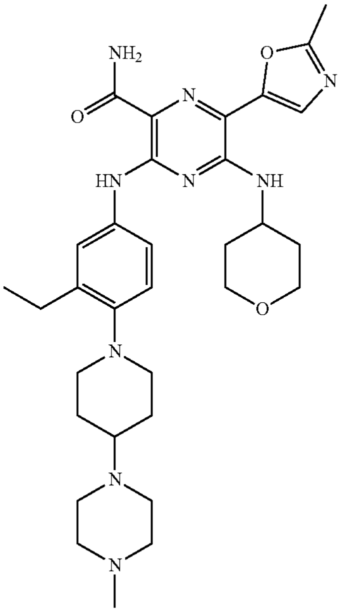

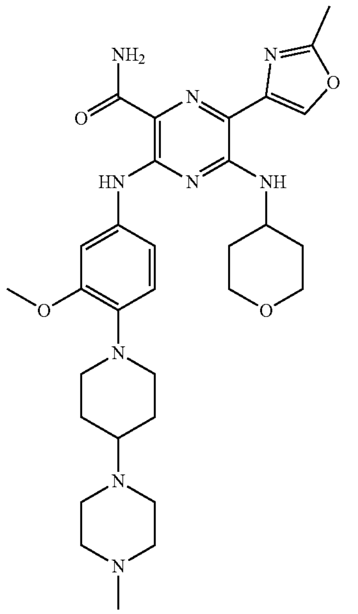
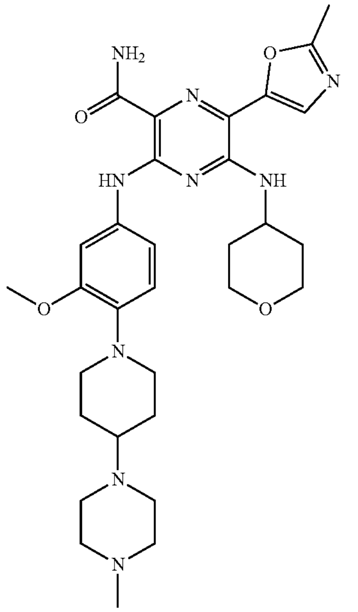
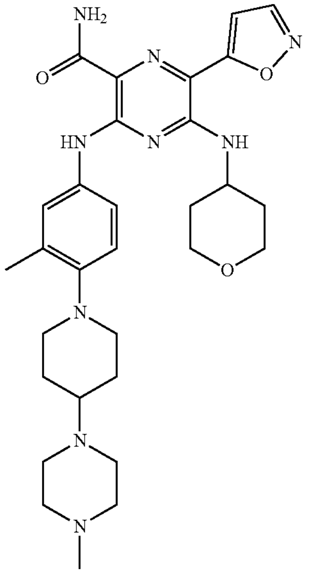
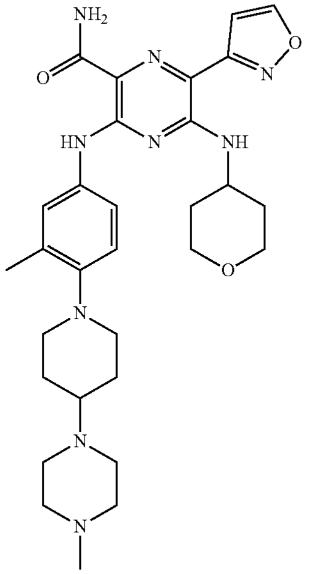
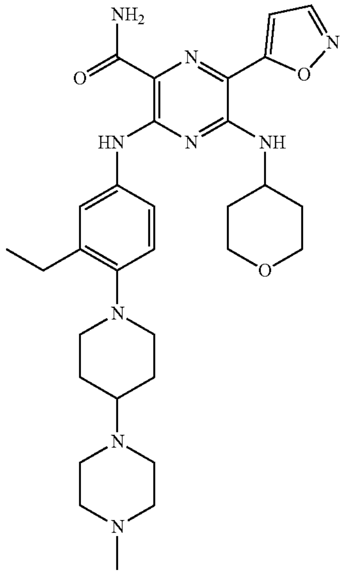

-continued
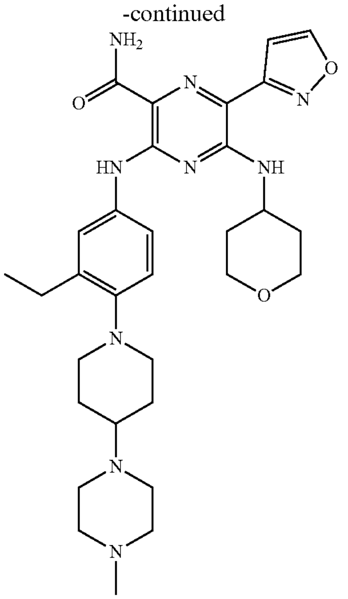
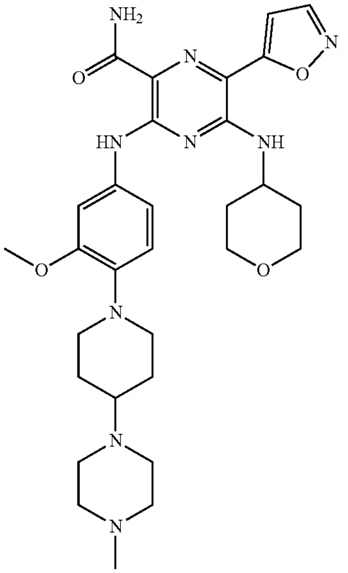
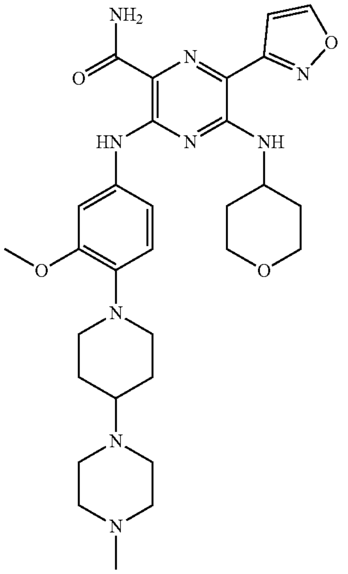
-continued
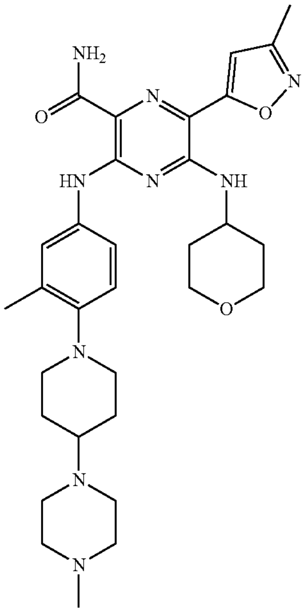
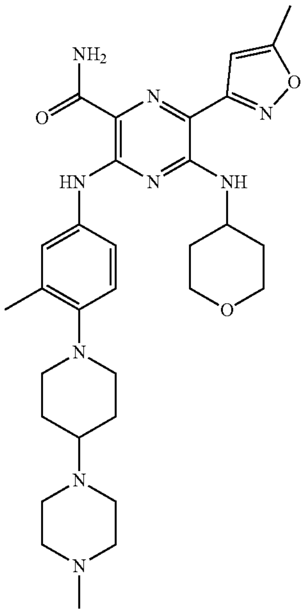

-continued
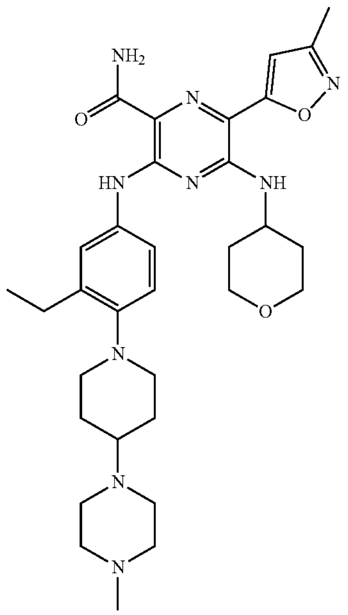
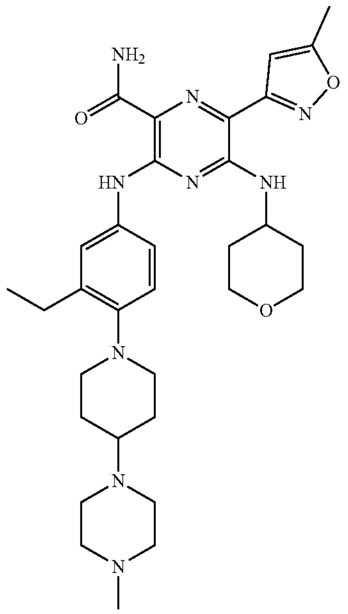
-continued
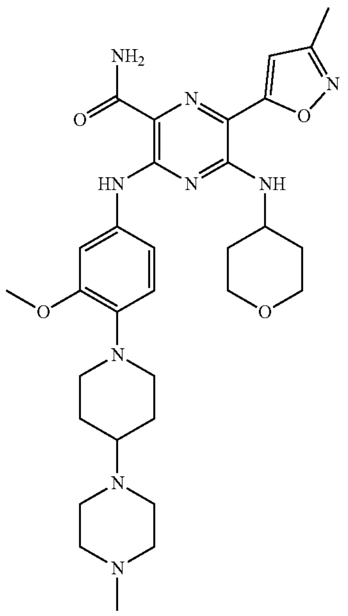
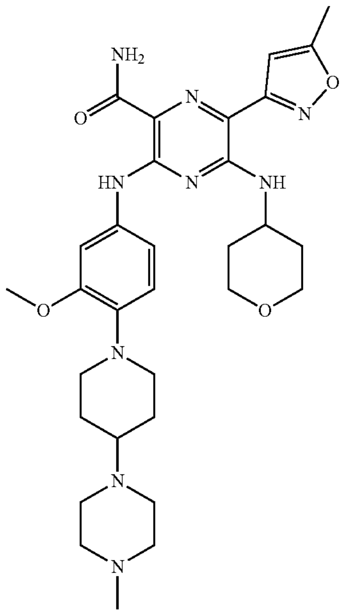

-continued
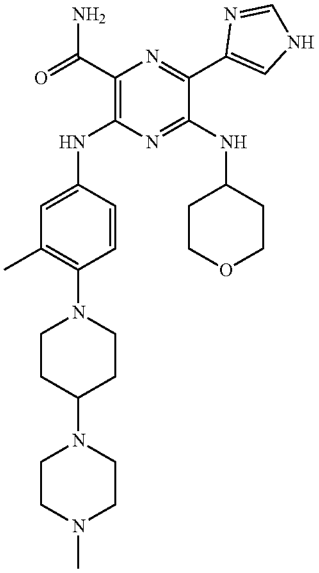
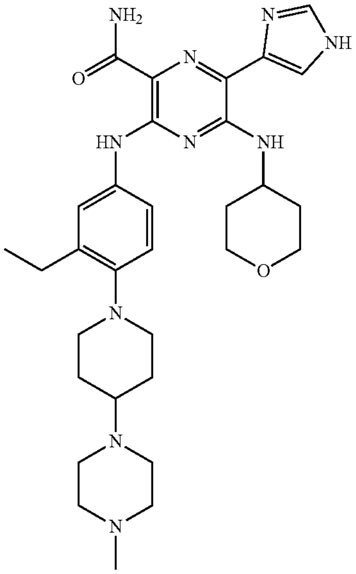
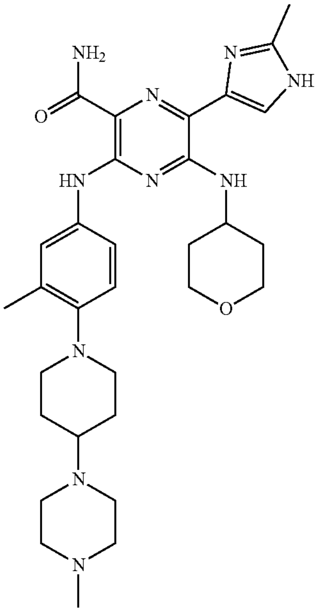
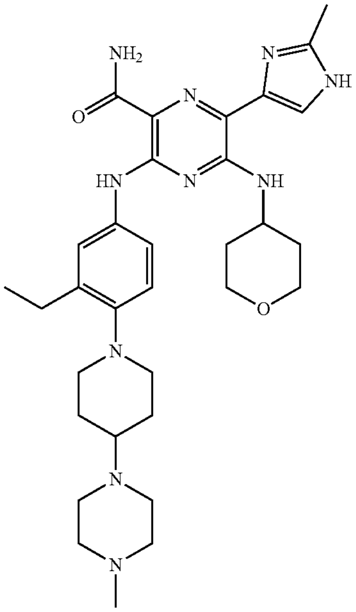
-continued

-continued
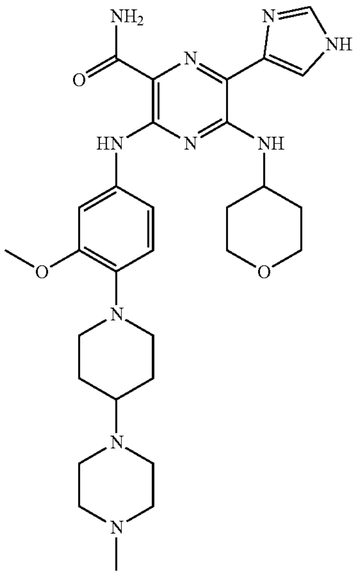
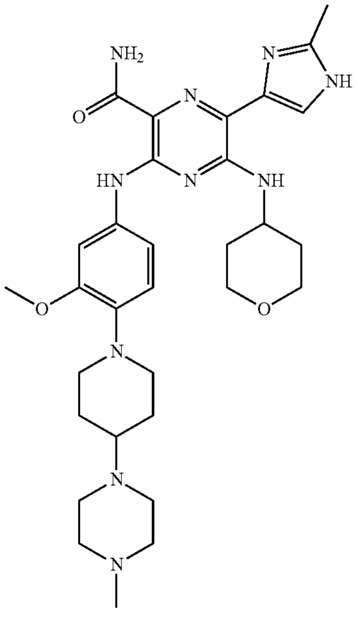
-continued
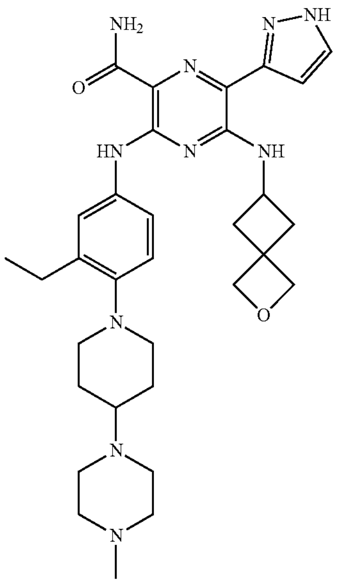
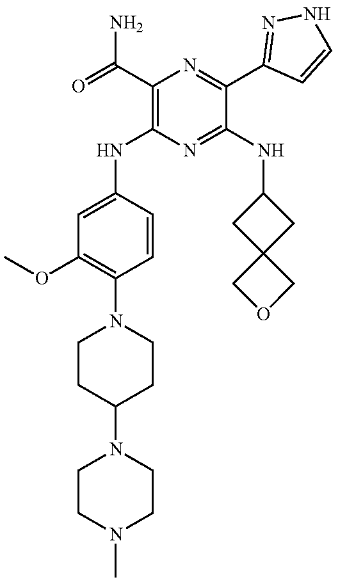

-continued
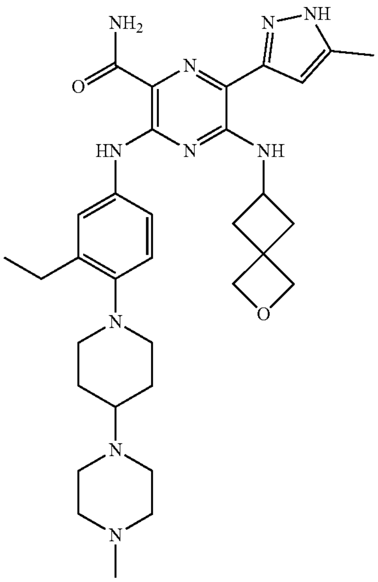
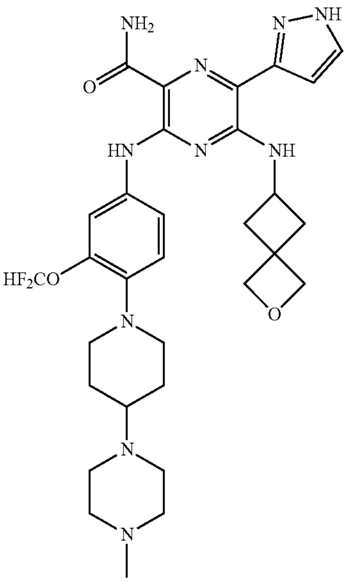
-continued
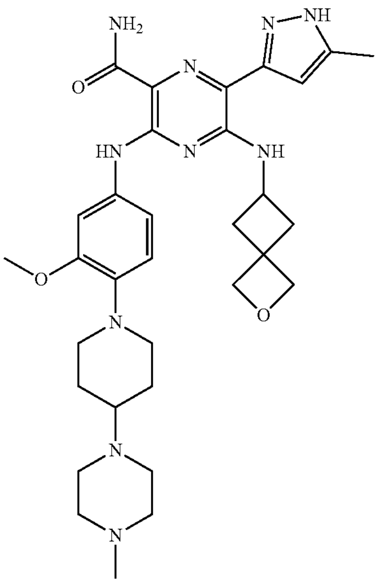
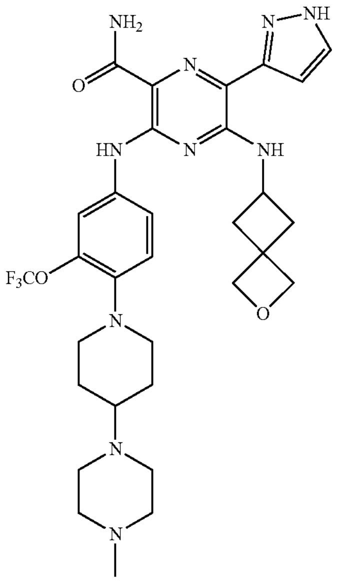

-continued
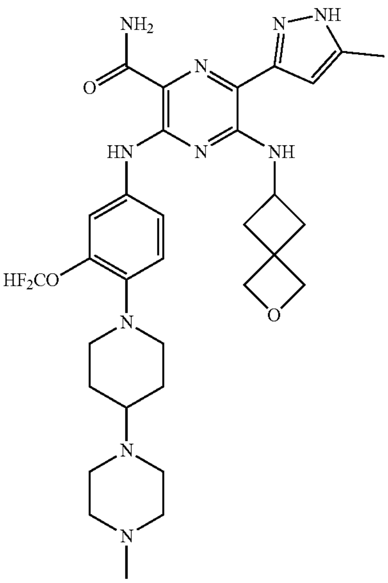
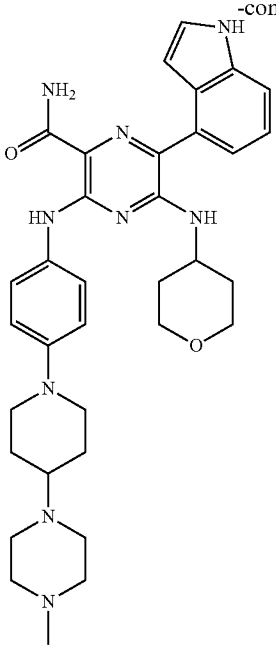
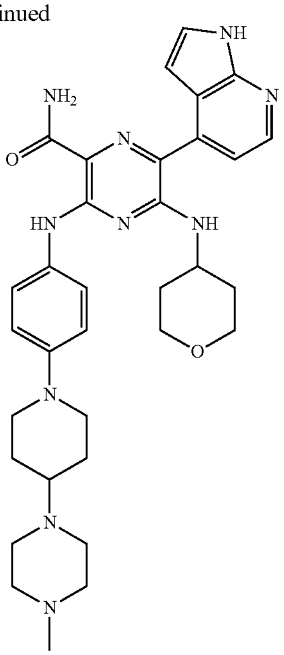
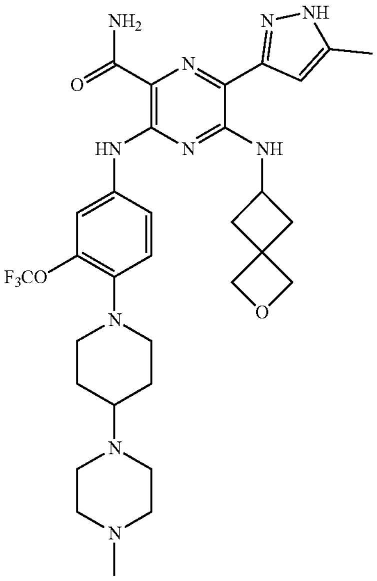
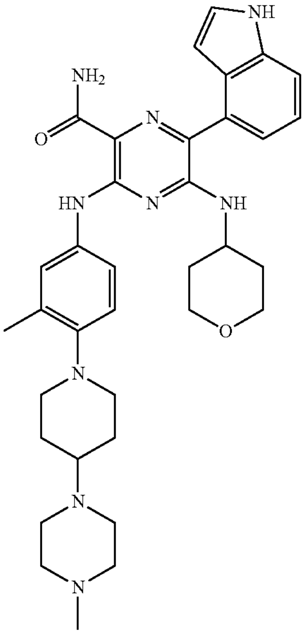

-continued
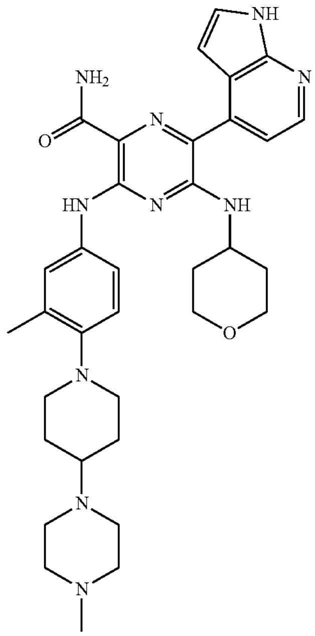
-continued
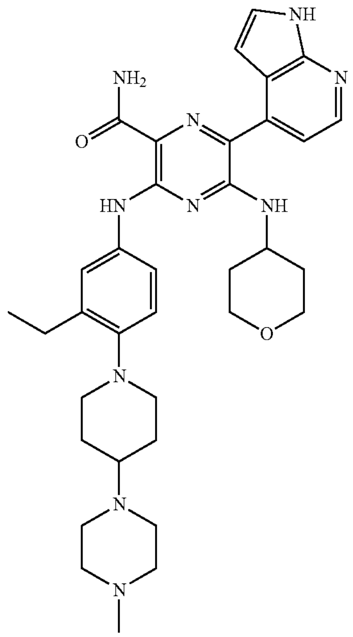
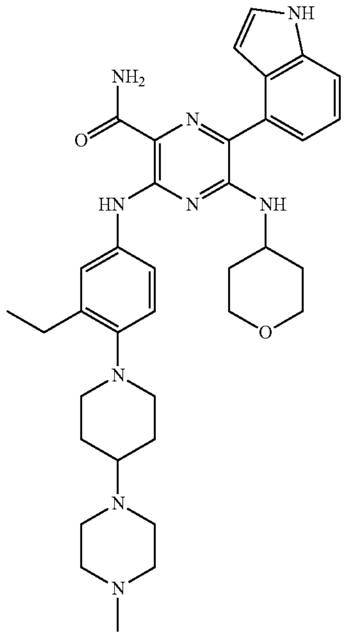
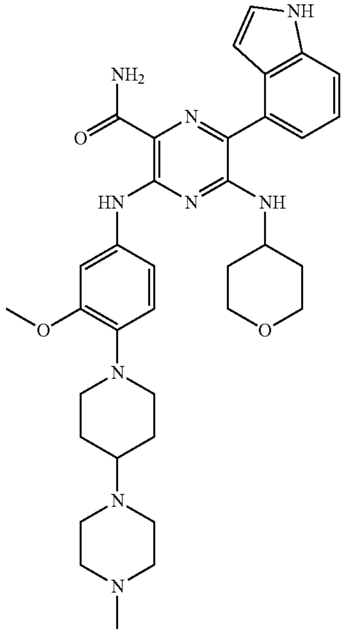

-continued
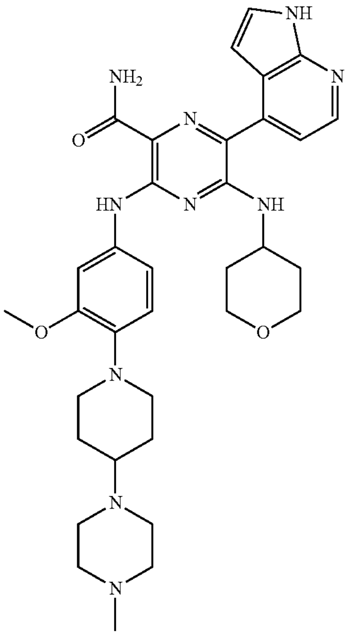
-continued
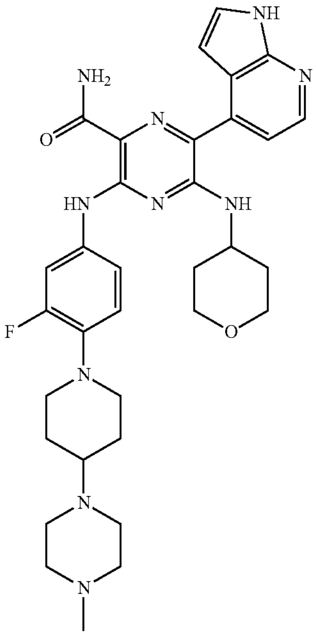
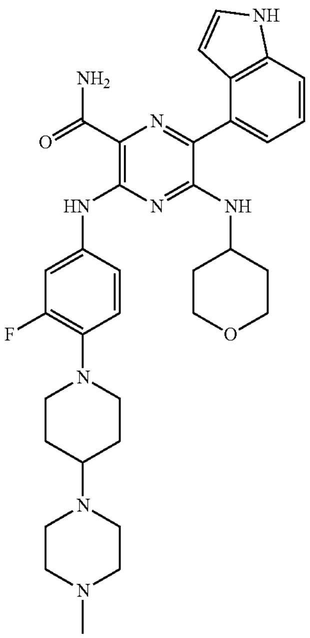
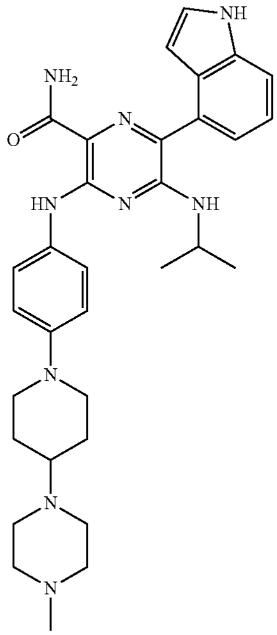
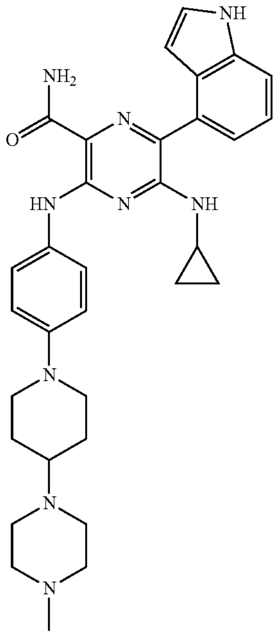

-continued
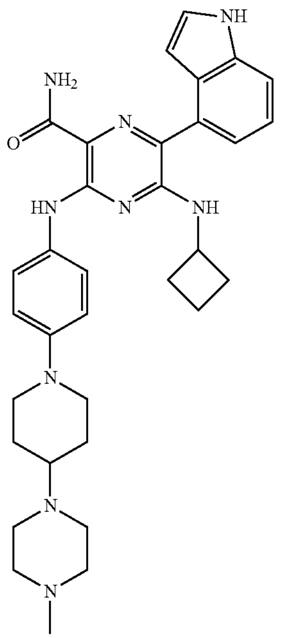
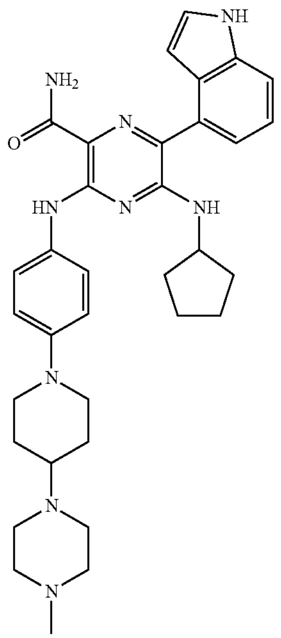
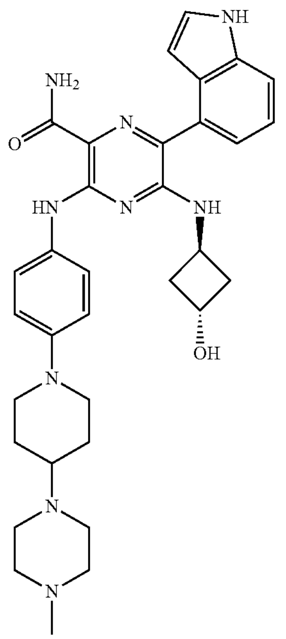
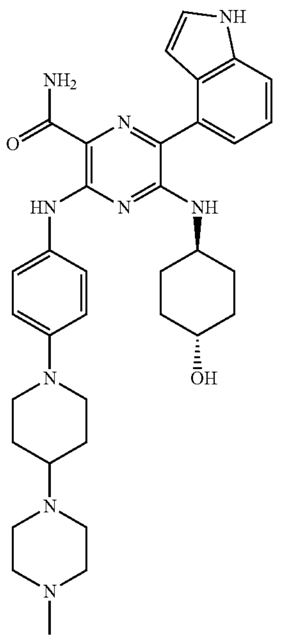
-continued
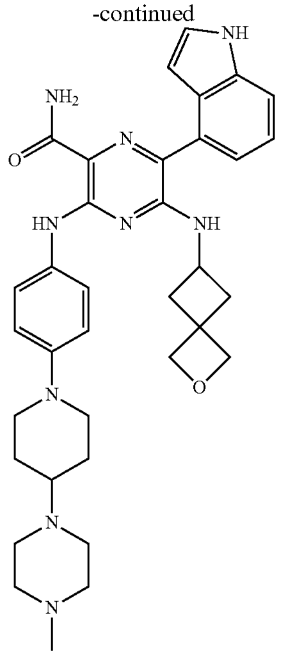
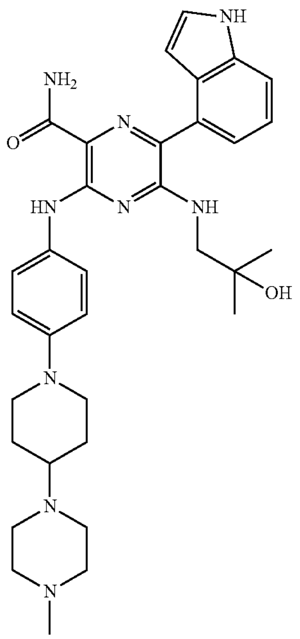

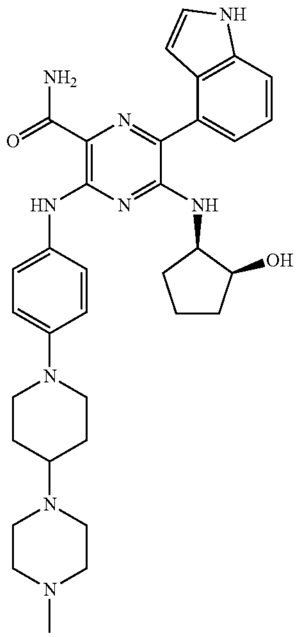
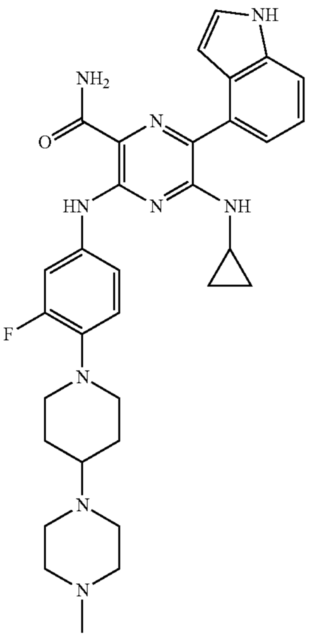
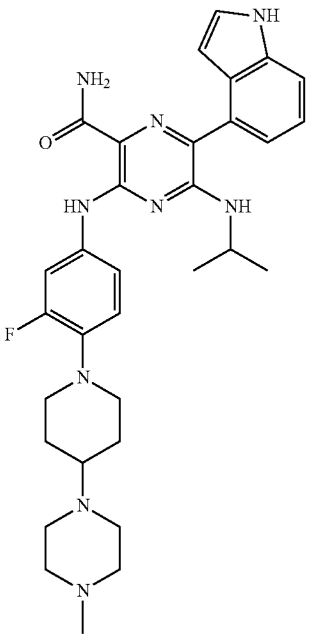
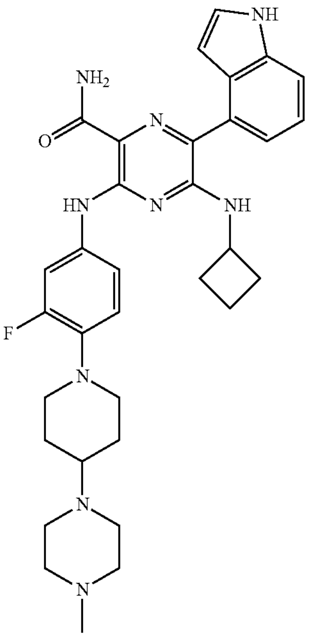

-continued
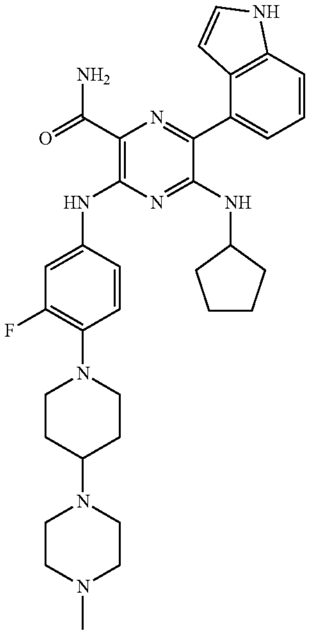
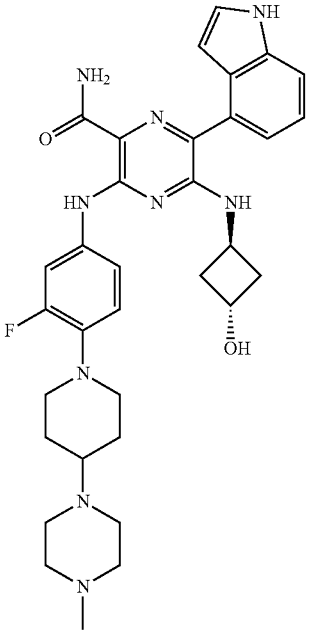
-continued
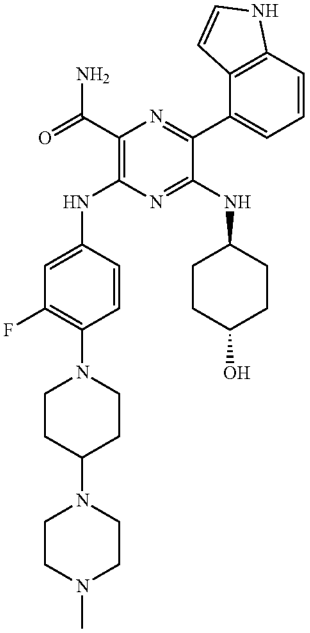
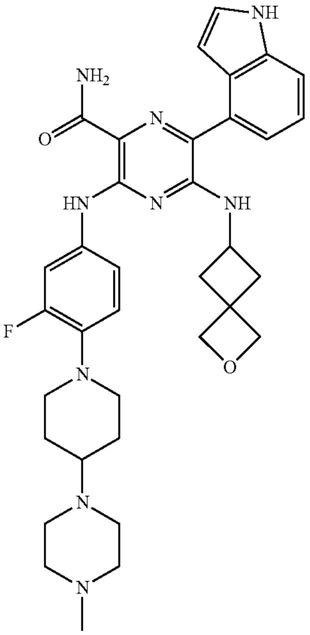

-continued
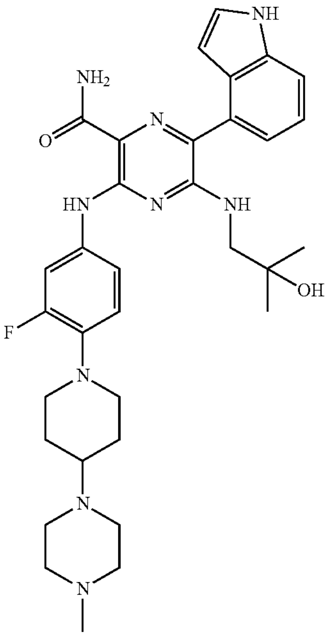
-continued
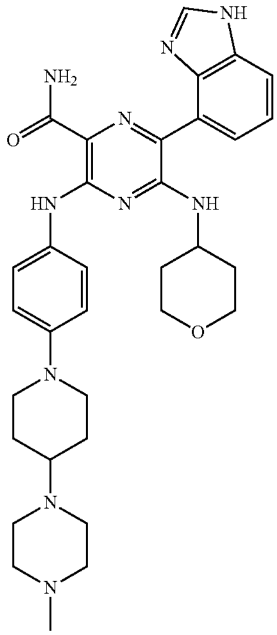
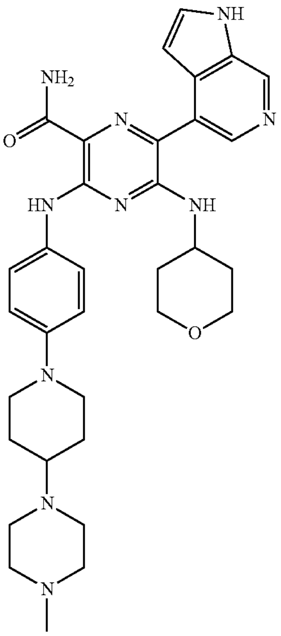
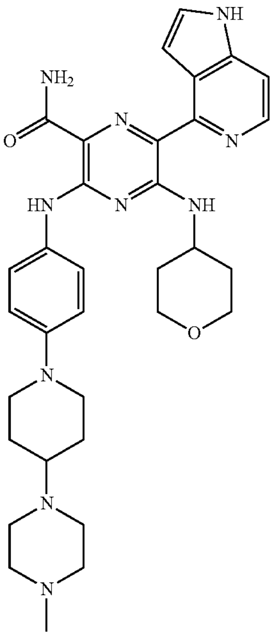
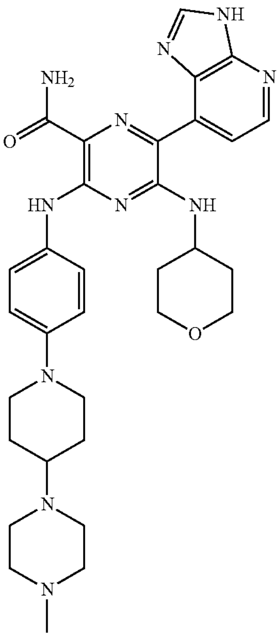
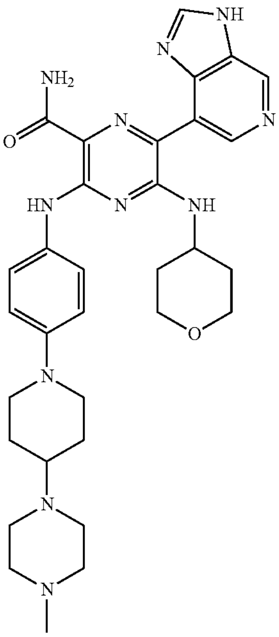

-continued
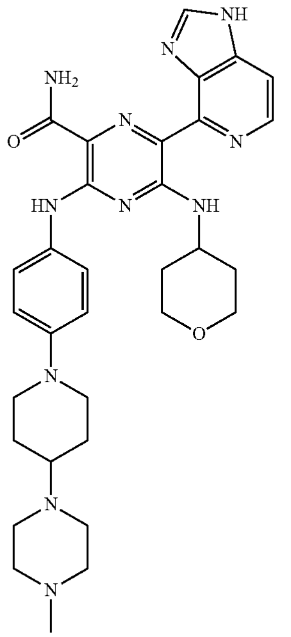
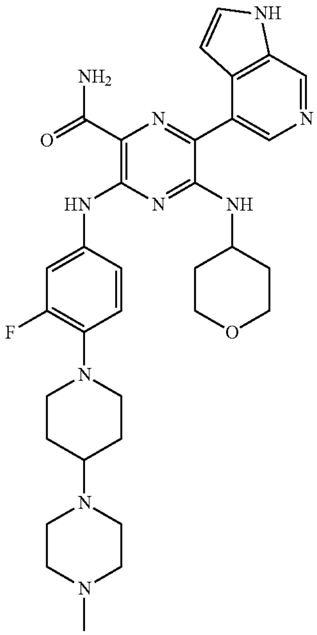
-continued
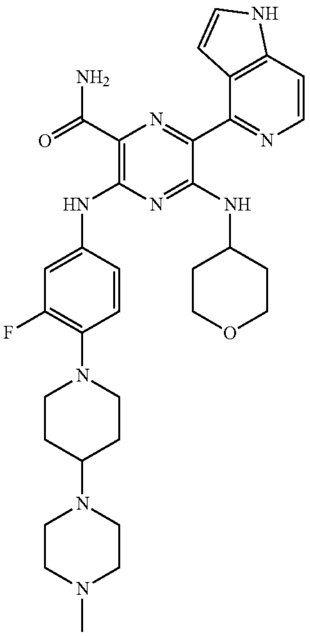
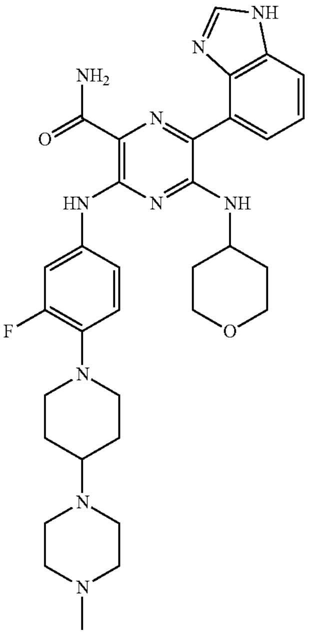

-continued
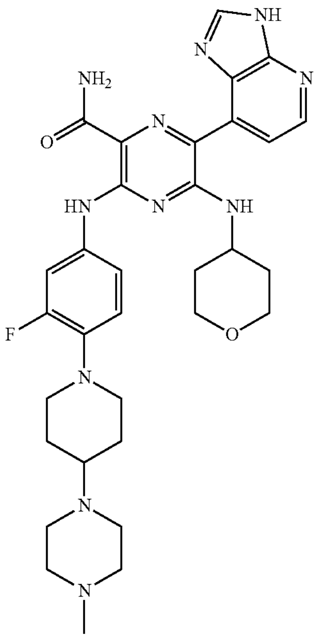
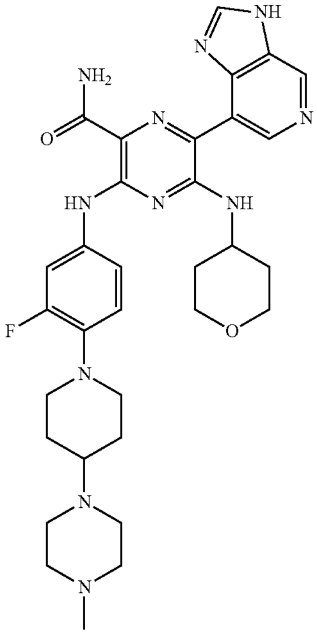
-continued
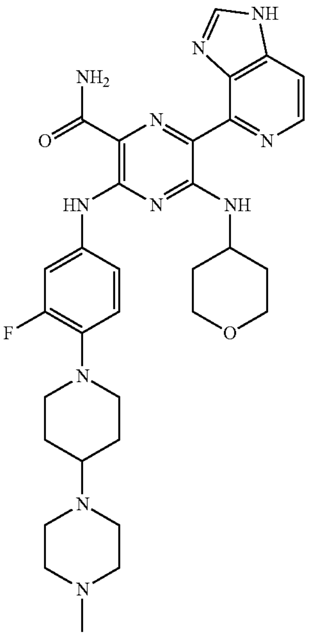
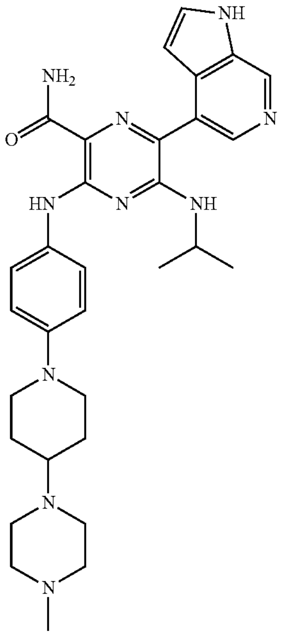
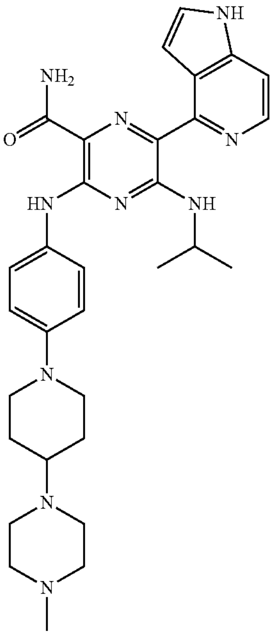

-continued
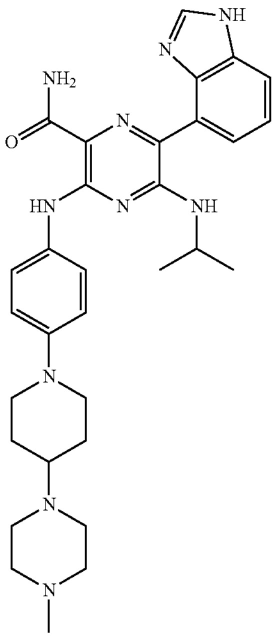
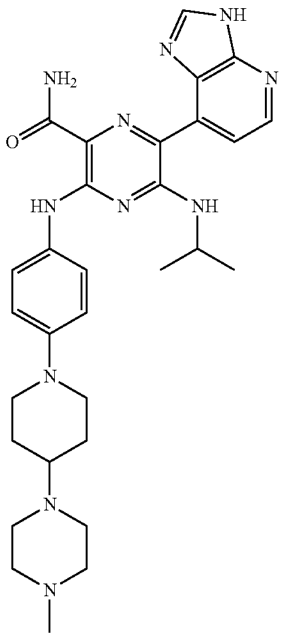
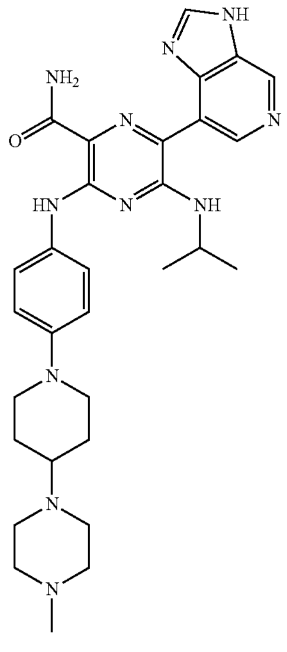
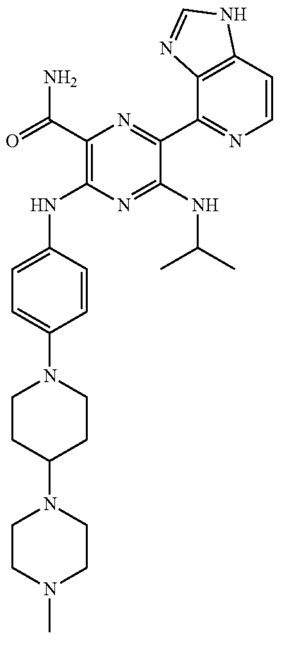
-continued
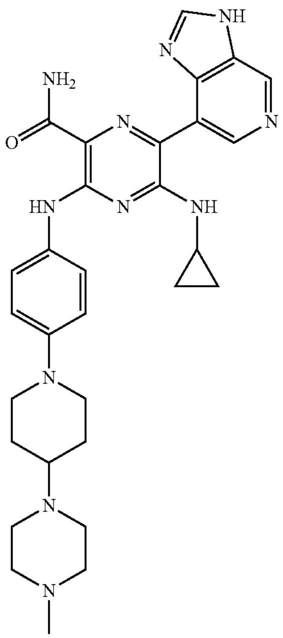
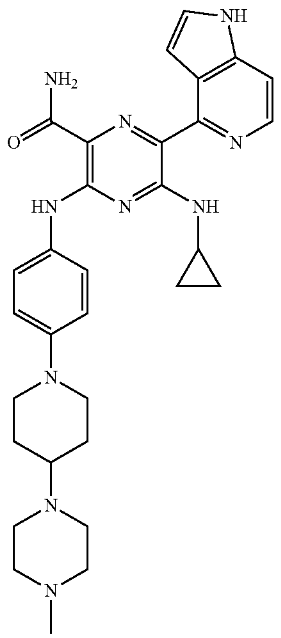
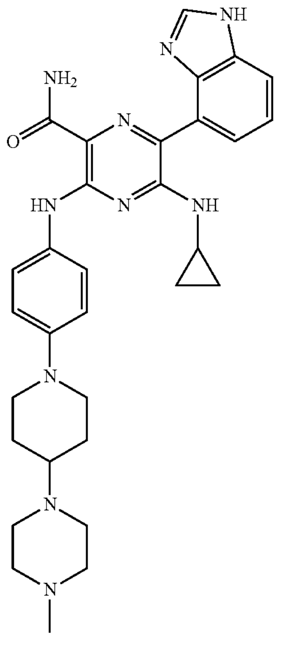
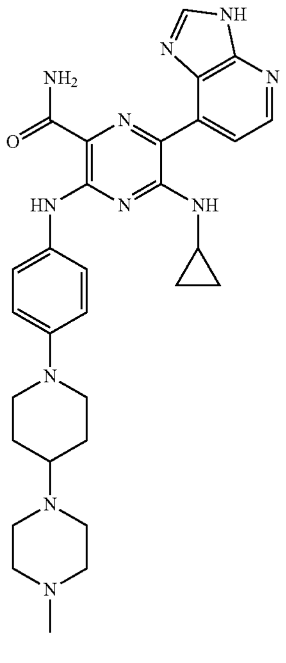

-continued
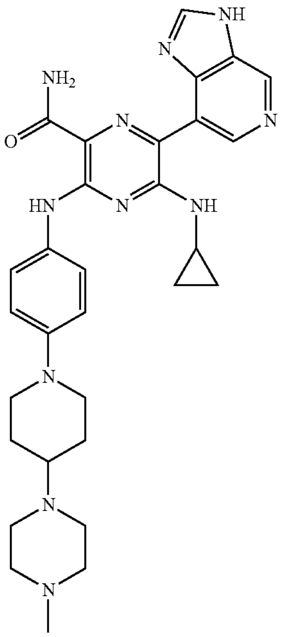
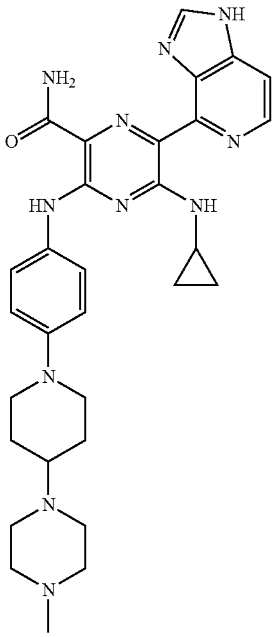
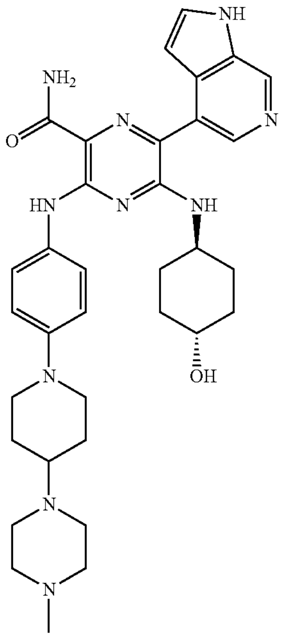
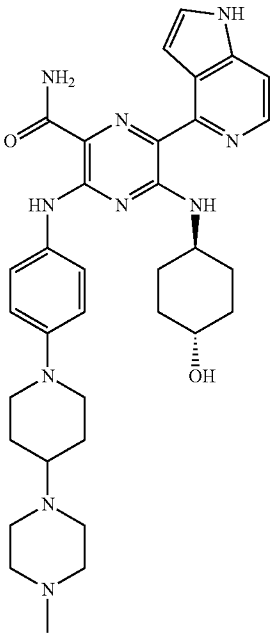
-continued
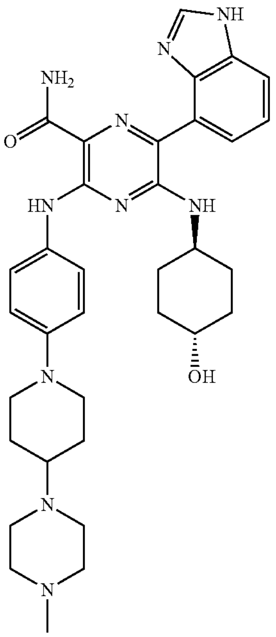
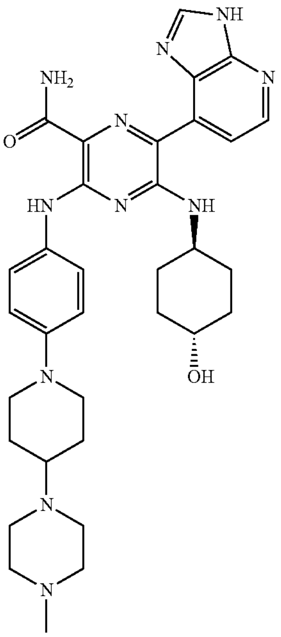
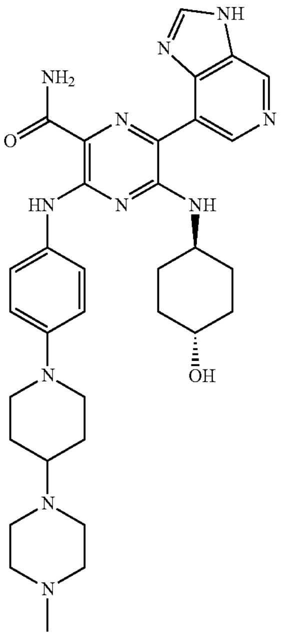
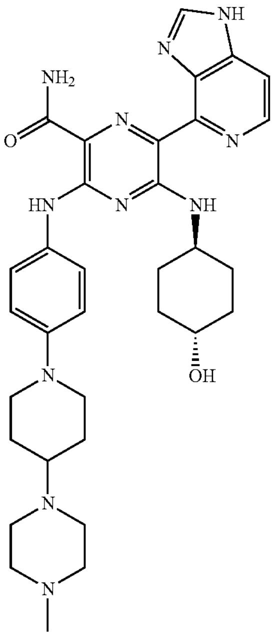

-continued
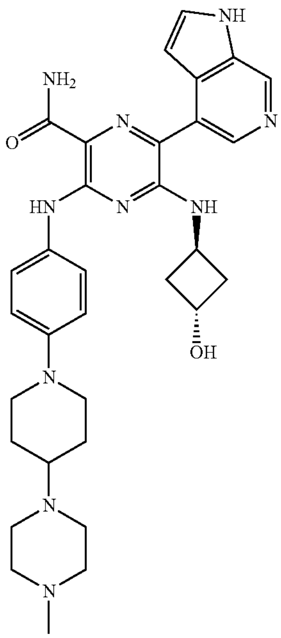
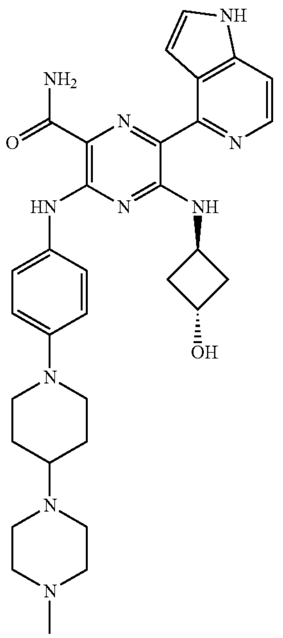
-continued
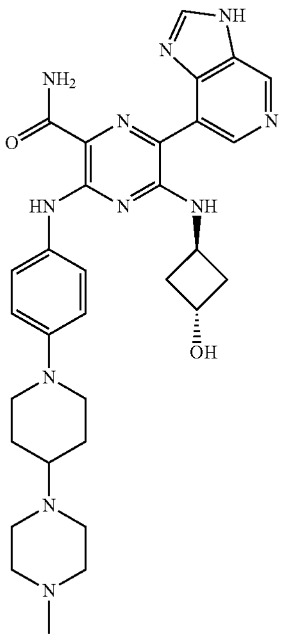
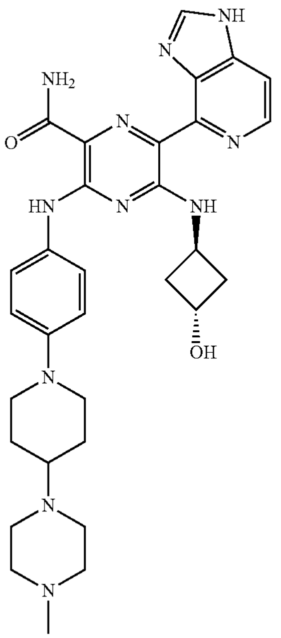
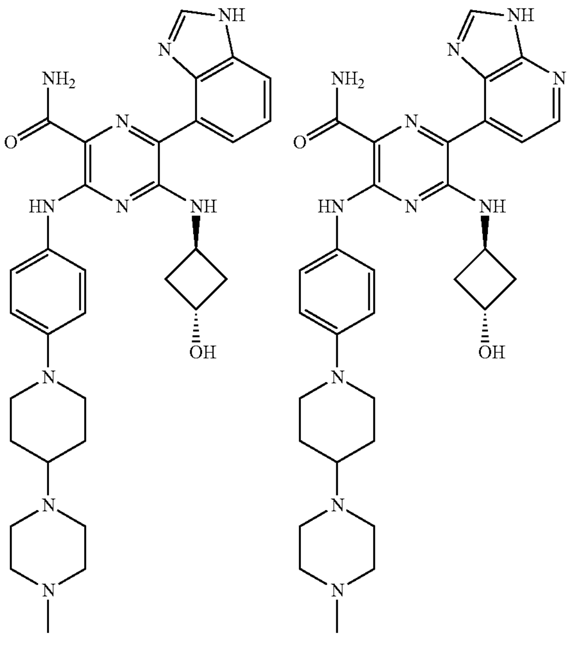
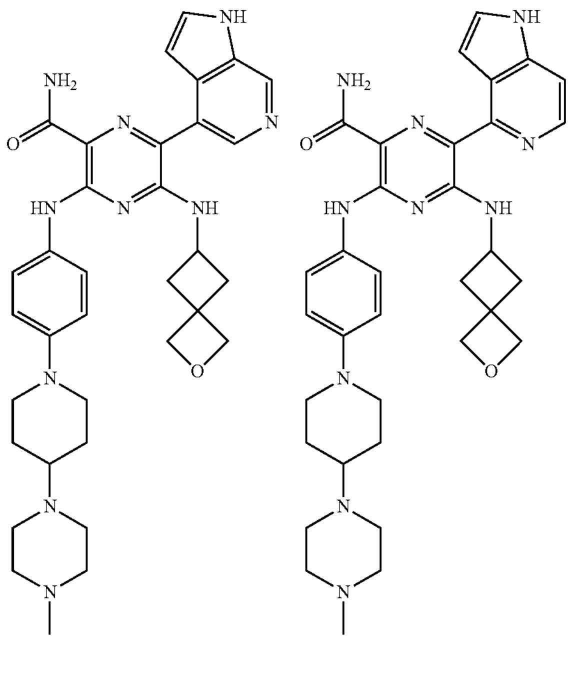

-continued
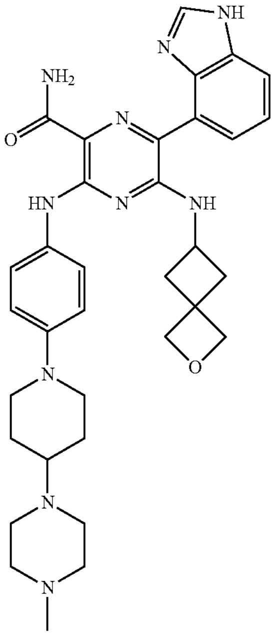
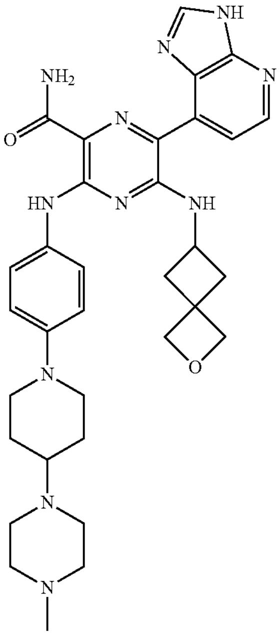
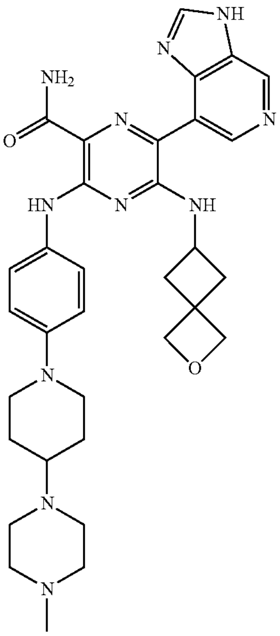
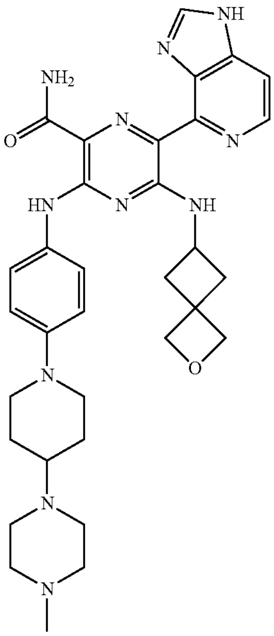
-continued
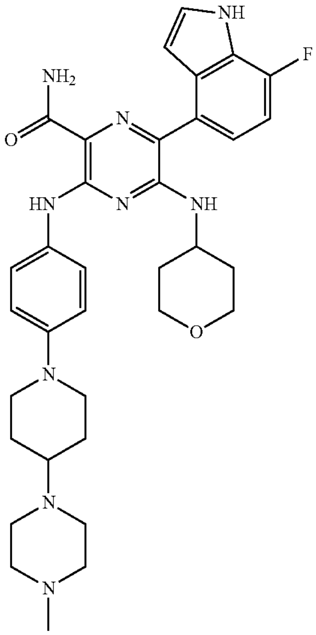
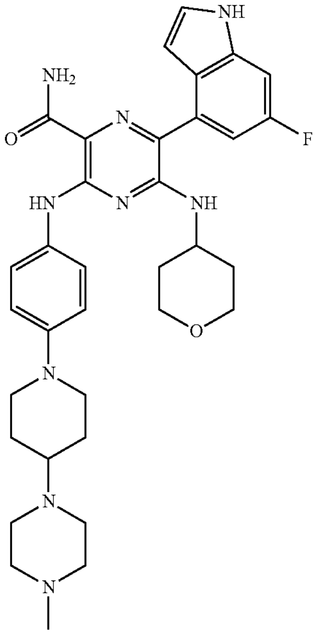

-continued
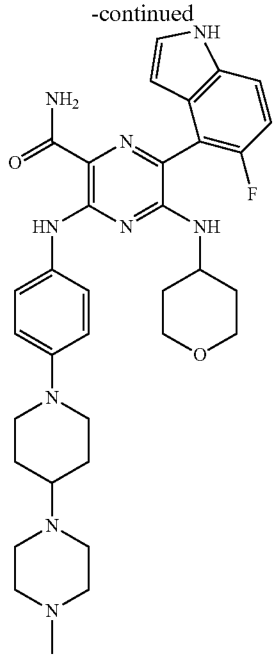
-continued
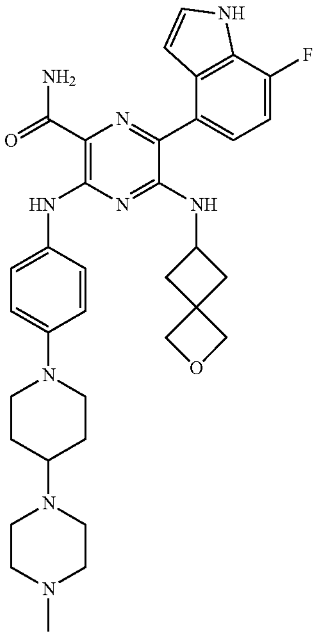
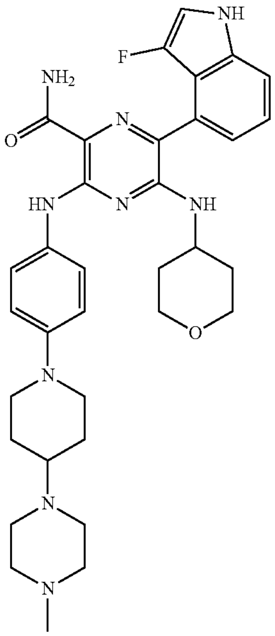
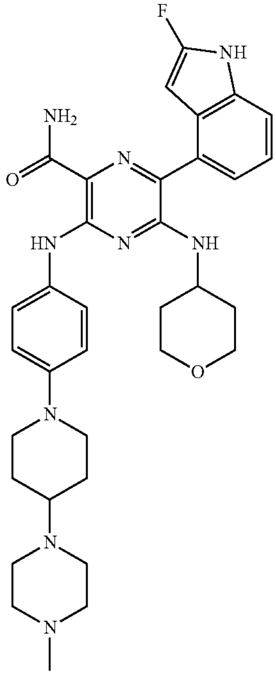
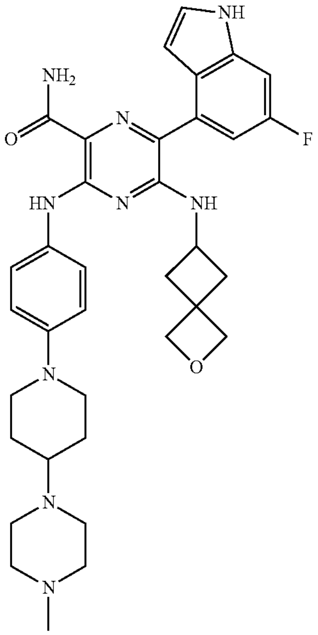

-continued
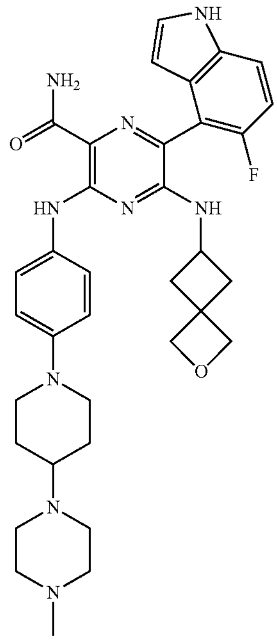
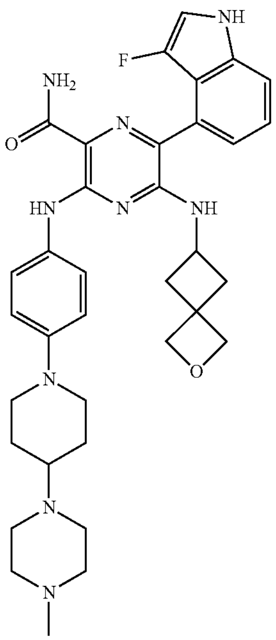
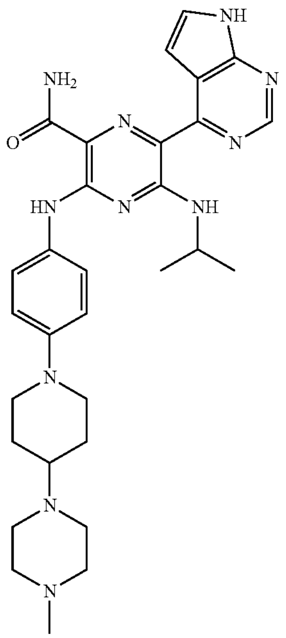
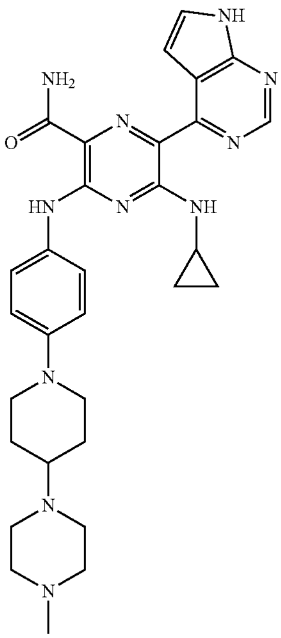
-continued
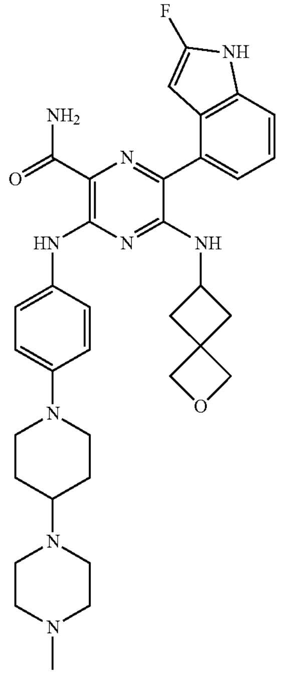
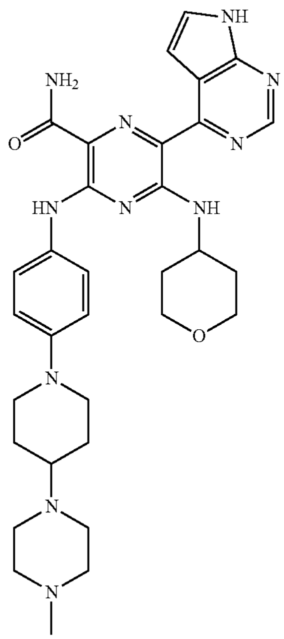
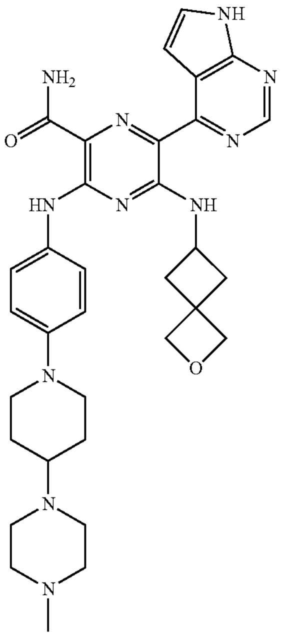
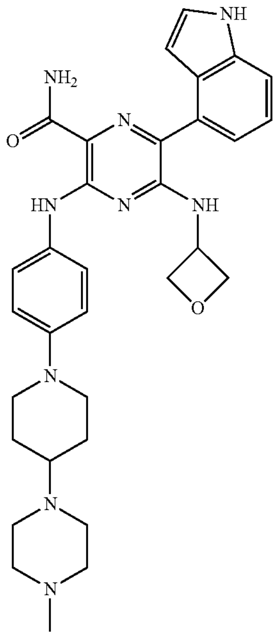

-continued
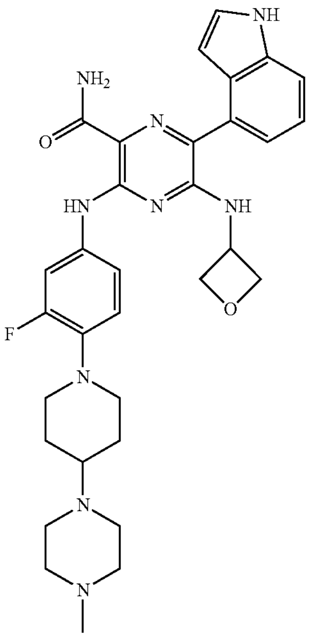
-continued
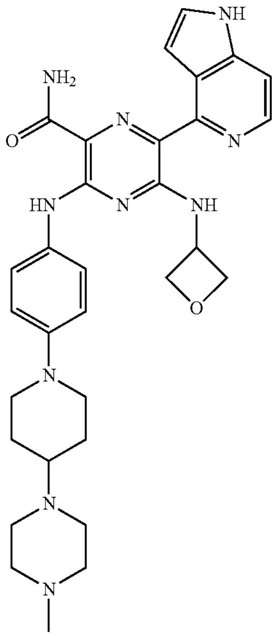
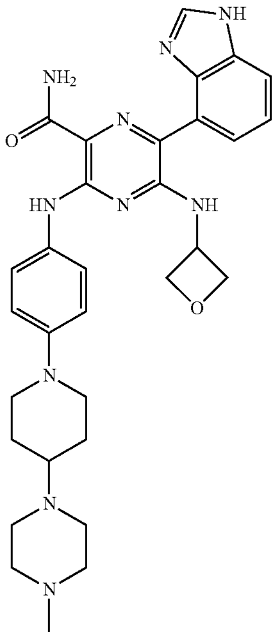
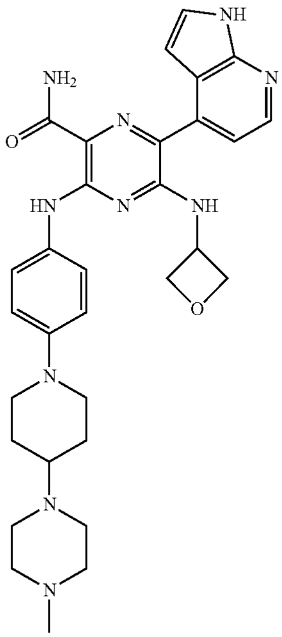
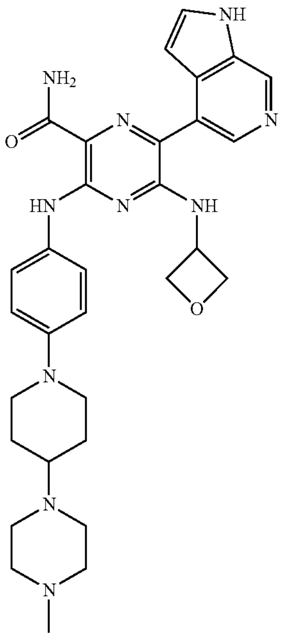
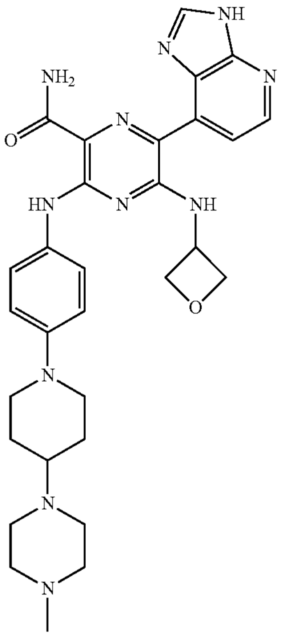
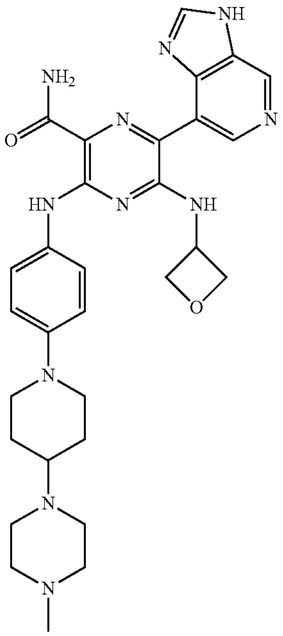

-continued
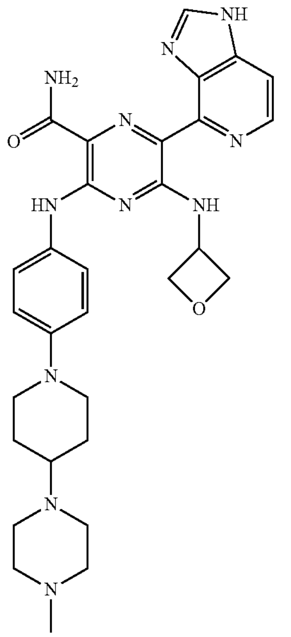
-continued
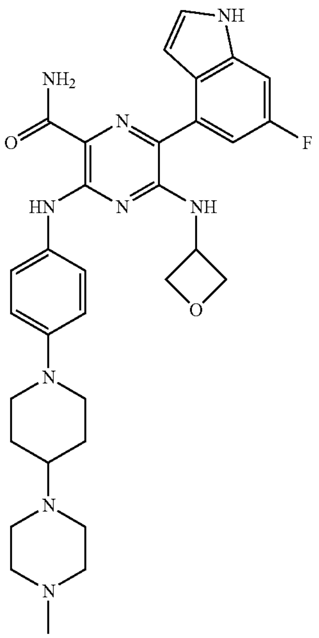
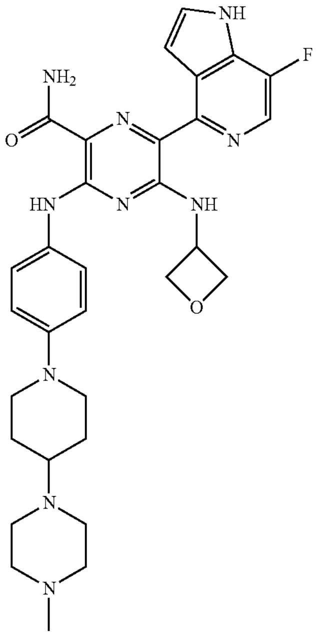
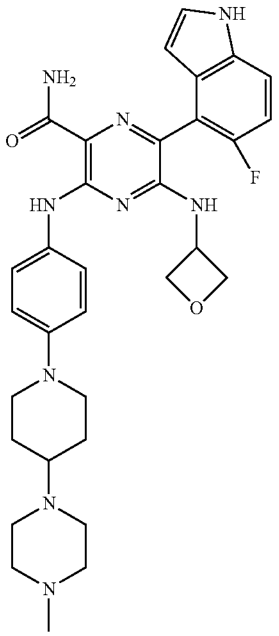
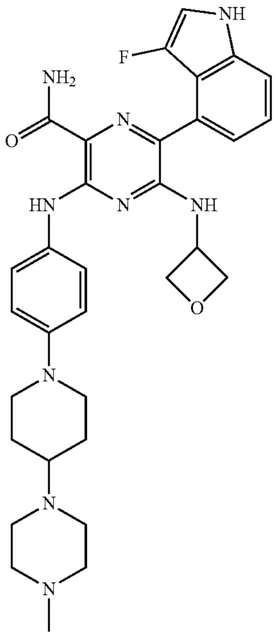

-continued
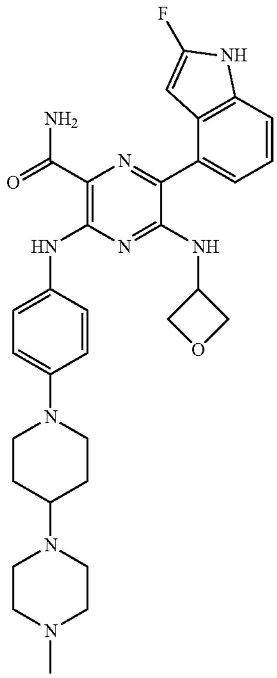
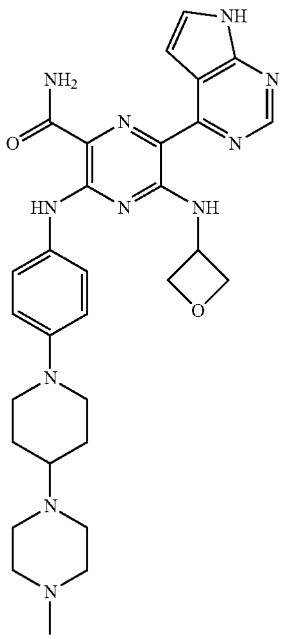
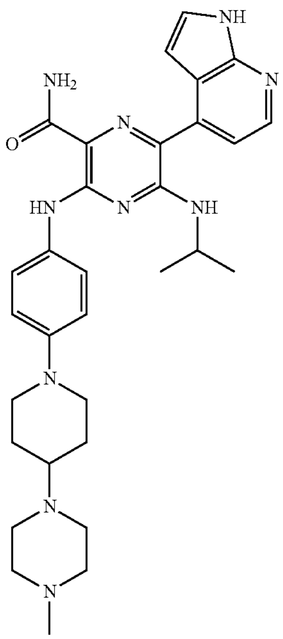
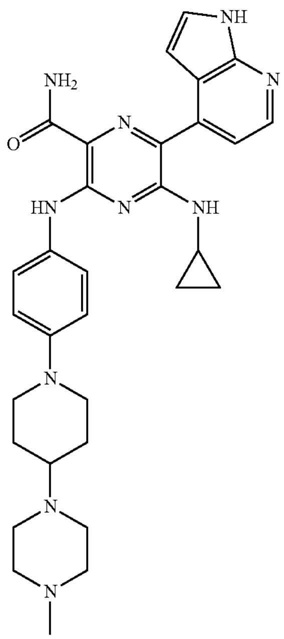
-continued
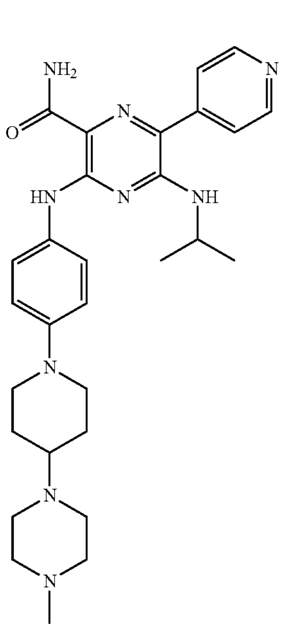
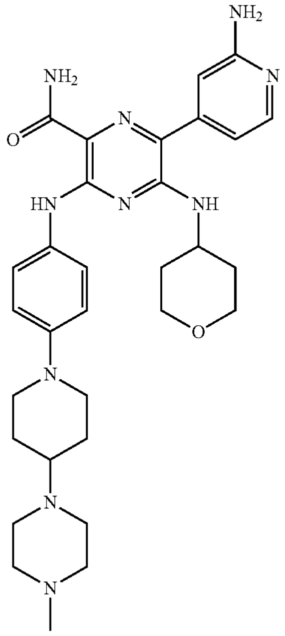
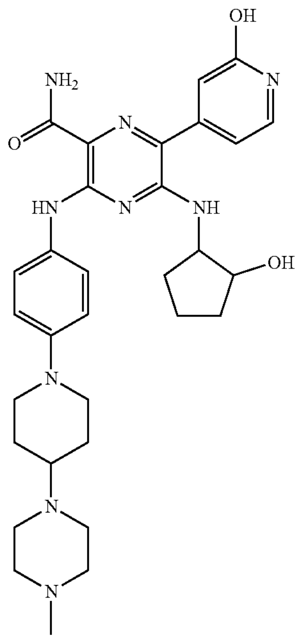

-continued
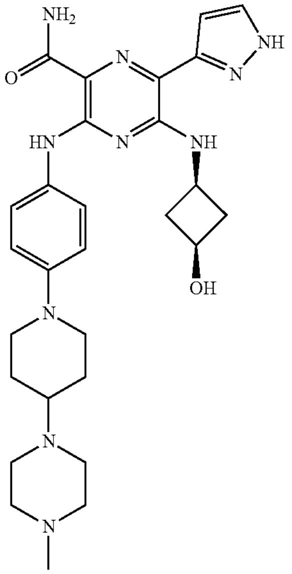
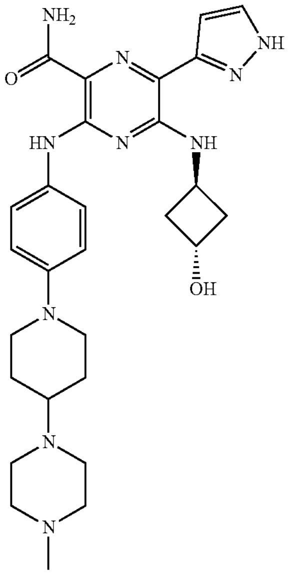
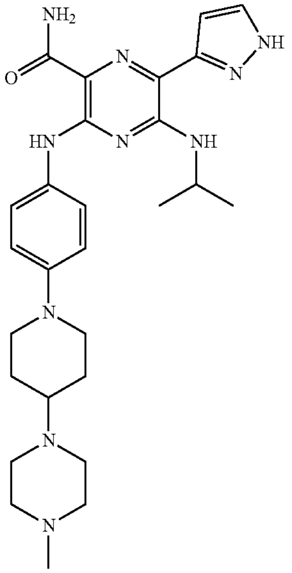
-continued
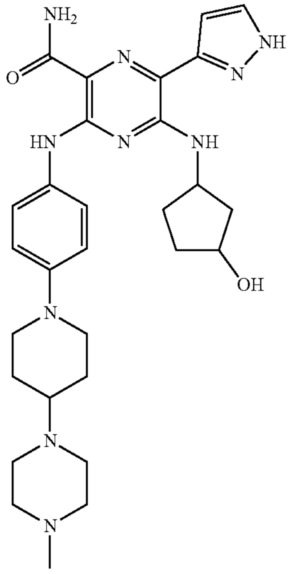
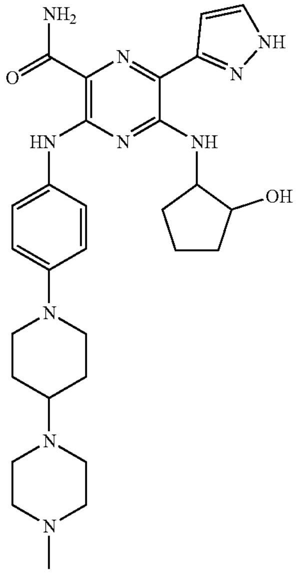
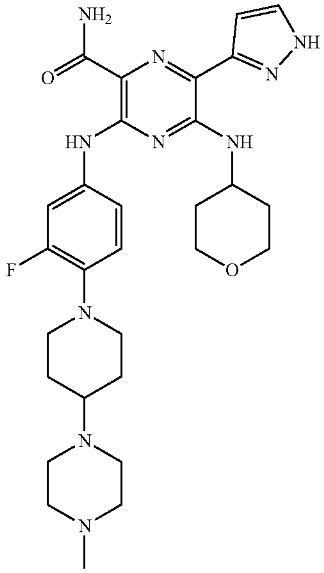

-continued
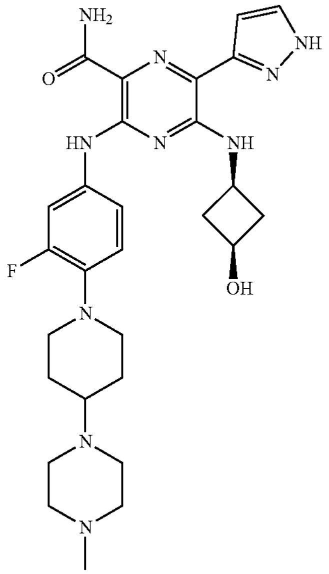
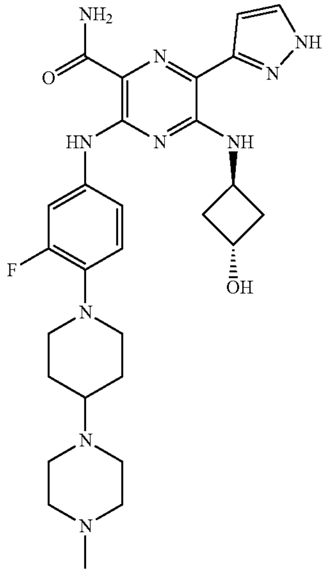
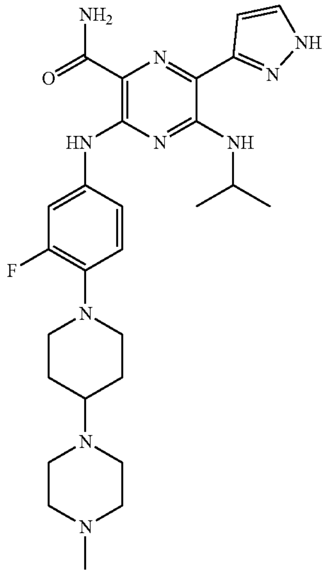
-continued
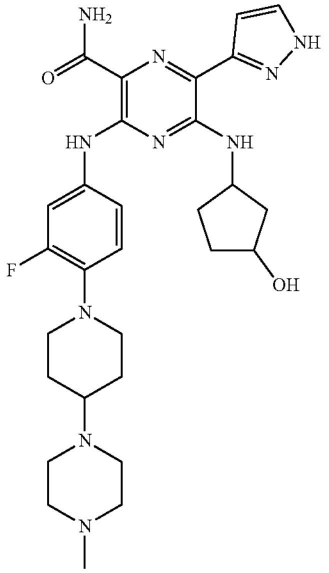
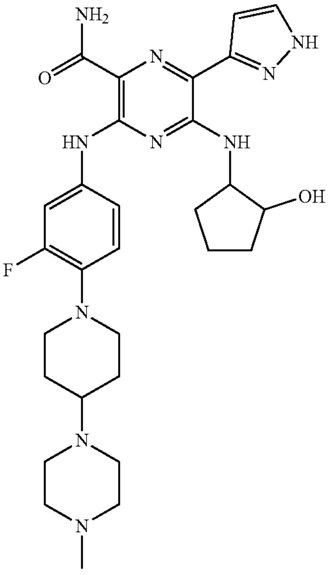
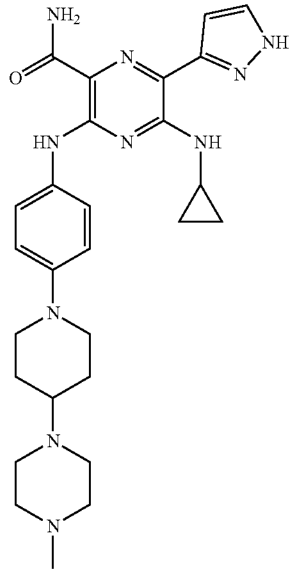

-continued
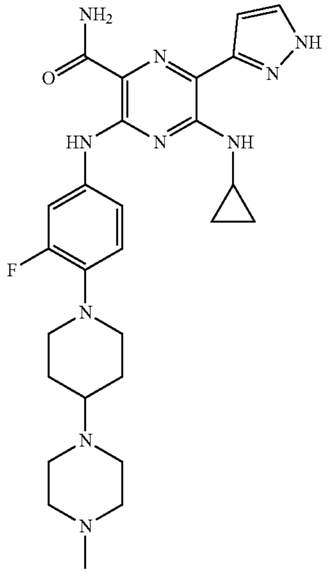
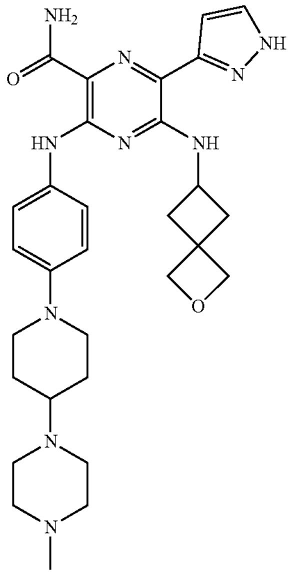
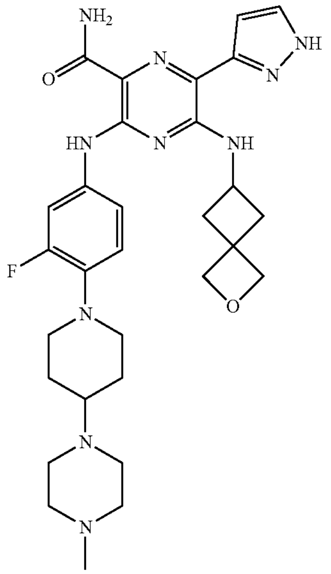
-continued
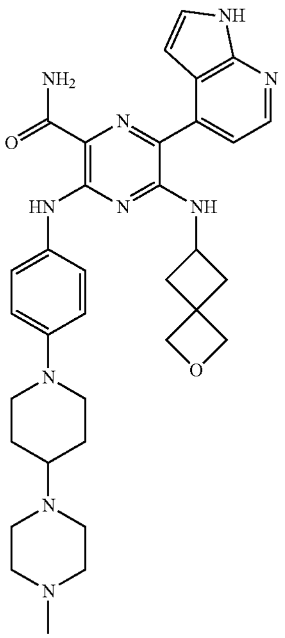
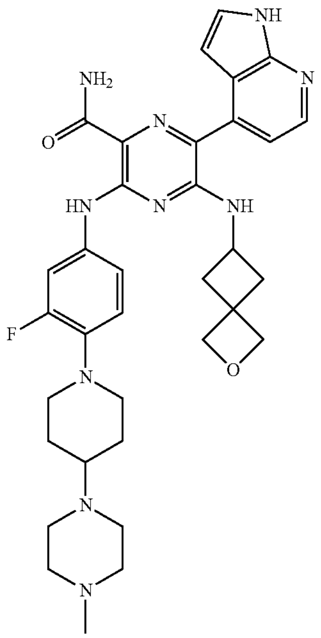

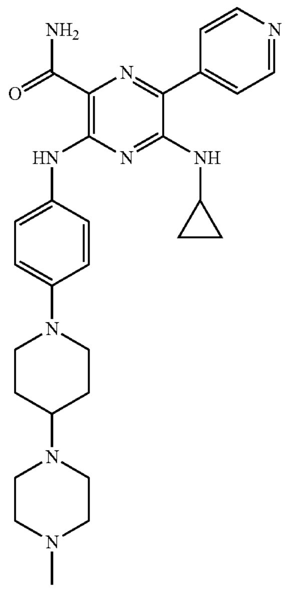
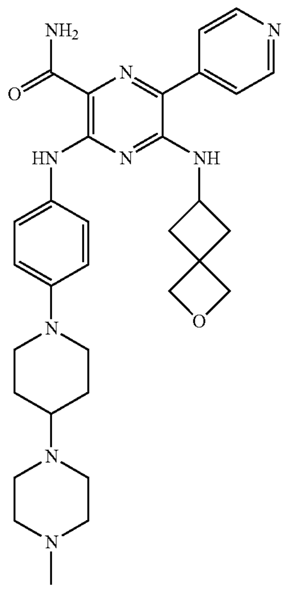
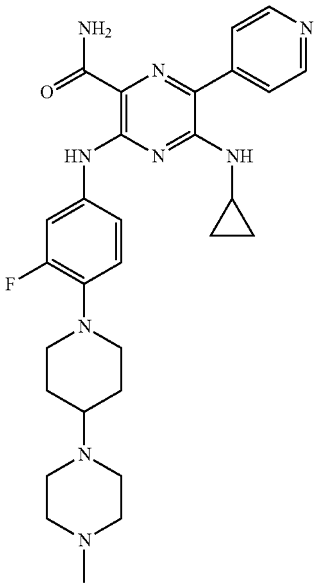
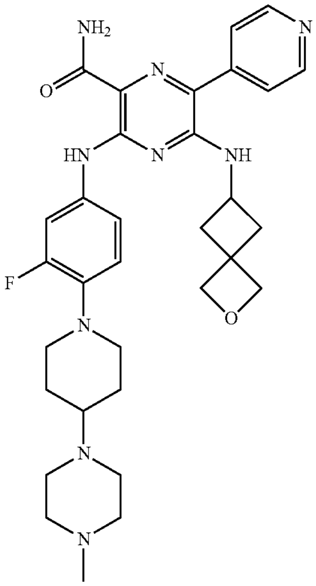

-continued
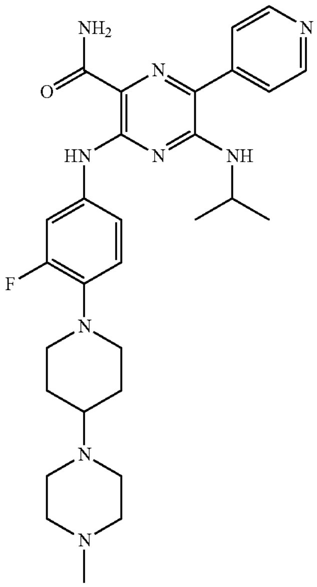
-continued
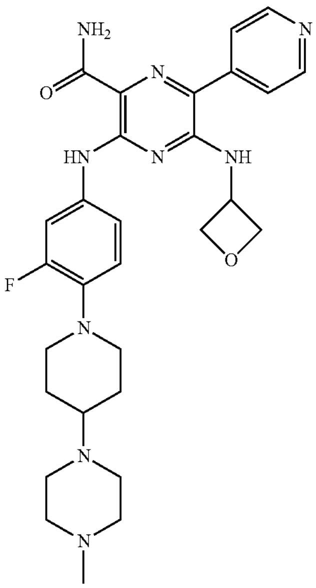
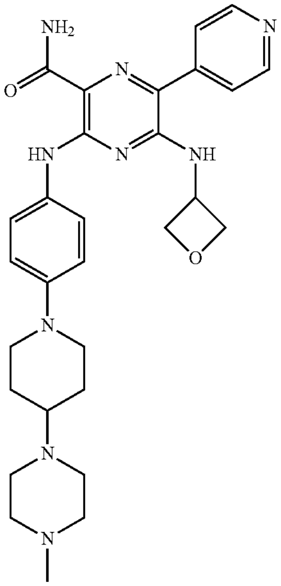
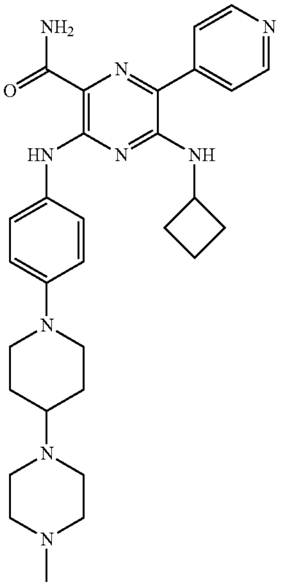

-continued
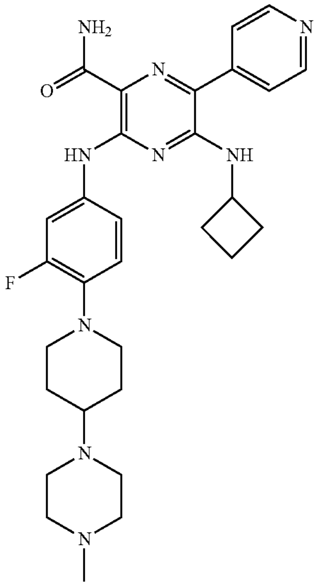
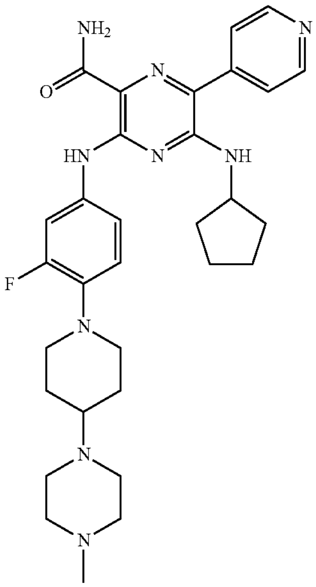
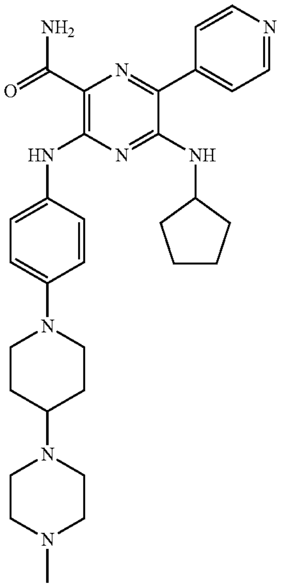
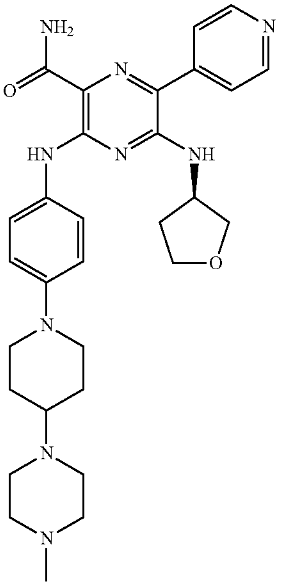

-continued

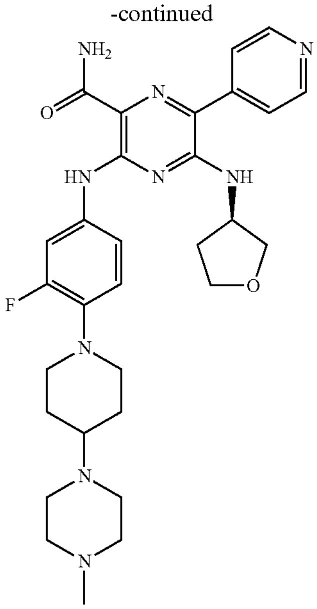

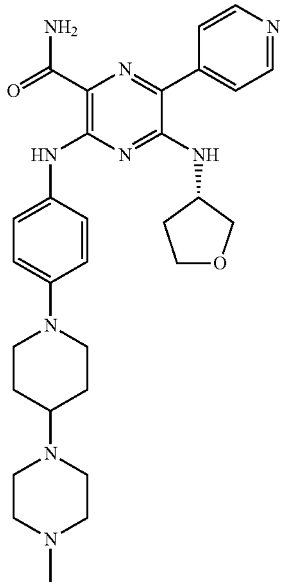

-continued

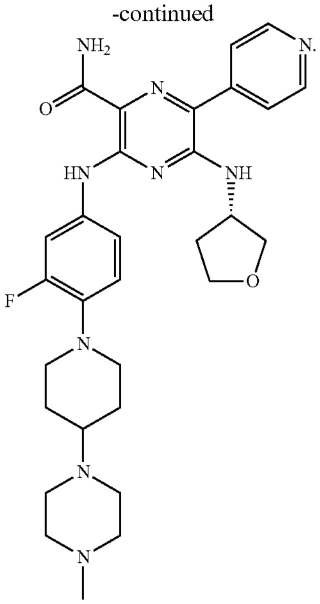

10. A pharmaceutical composition, comprising a pharmaceutically acceptable excipient or carrier, and the compound, or the isomer, the crystalline form, the pharmaceutically acceptable salt, the hydrate or the solvate thereof according to claim 1 as an active ingredient.

11. A method for treating, regulating and/or preventing a disease related to an EGFR mutant protein, comprising administering to a subject a therapeutically effective amount of the compound, or the isomer, the crystalline form, the pharmaceutically acceptable salt, the hydrate or the solvate thereof according to claim 1, wherein the disease is selected from lung cancer, brain cancer, breast cancer, and ovarian cancer.

* * * * *